US009884844B2

(12) United States Patent
Fang et al.

(10) Patent No.: US 9,884,844 B2
(45) Date of Patent: Feb. 6, 2018

(54) HETEROCYCLIC COMPOUNDS AND METHODS OF USE THEREOF

(71) Applicant: Sunovion Pharmaceuticals Inc., Marlborough, MA (US)

(72) Inventors: Qun Kevin Fang, Wellesley, MA (US); Una Campbell, Marlborough, MA (US); Kerry L. Spear, Concord, MA (US)

(73) Assignee: SUNOVION PHARMACEUTICALS, INC., Marlborough, MA (US)

( * ) Notice: Subject to any disclaimer, the term of this patent is extended or adjusted under 35 U.S.C. 154(b) by 48 days.

(21) Appl. No.: 14/758,681

(22) PCT Filed: Dec. 31, 2013

(86) PCT No.: PCT/US2013/078453
§ 371 (c)(1),
(2) Date: Jun. 30, 2015

(87) PCT Pub. No.: WO2014/106238
PCT Pub. Date: Jul. 3, 2014

(65) Prior Publication Data
US 2015/0336928 A1 Nov. 26, 2015

Related U.S. Application Data

(60) Provisional application No. 61/747,499, filed on Dec. 31, 2012.

(51) Int. Cl.
| | |
|---|---|
| *C07D 401/04* | (2006.01) |
| *C07D 491/113* | (2006.01) |
| *G01N 33/50* | (2006.01) |
| *C07D 401/14* | (2006.01) |
| *C07D 413/14* | (2006.01) |
| *C07D 487/10* | (2006.01) |
| *C07D 498/10* | (2006.01) |

(52) U.S. Cl.
CPC ......... *C07D 401/04* (2013.01); *C07D 401/14* (2013.01); *C07D 413/14* (2013.01); *C07D 487/10* (2013.01); *C07D 491/113* (2013.01); *C07D 498/10* (2013.01); *G01N 33/5038* (2013.01)

(58) Field of Classification Search
CPC .. C07D 401/04; C07D 401/14; C07D 413/14; C07D 487/10; C07D 491/113; C07D 498/10
USPC ............. 514/278, 296, 323; 546/15, 99, 201
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 7,566,728 B2 | 7/2009 | Teshima et al. | |
| 8,003,669 B2 | 8/2011 | Teshima et al. | |
| 8,101,647 B2 | 1/2012 | Chafeev et al. | |
| 8,173,813 B2* | 5/2012 | Maddaford | C07D 409/12 540/523 |
| 2003/0176693 A1 | 9/2003 | Tsushima et al. | |
| 2004/0152707 A1 | 8/2004 | Tulshian et al. | |
| 2005/0228023 A1* | 10/2005 | Zaveri | A61K 31/4439 514/323 |
| 2008/0234237 A1 | 9/2008 | Maddaford et al. | |
| 2009/0253727 A1 | 10/2009 | Goehring et al. | |
| 2014/0171466 A1* | 6/2014 | Zaveri | C07D 401/04 514/323 |

FOREIGN PATENT DOCUMENTS

| | | |
|---|---|---|
| EP | 1491212 A1 | 12/2004 |
| EP | 1918279 A2 | 5/2008 |
| WO | WO-2006/034338 A1 | 3/2006 |
| WO | WO-2007/050381 A2 | 5/2007 |
| WO | WO-2010/022055 A2 | 2/2010 |
| WO | WO-2010/098145 A1 | 9/2010 |
| WO | WO-2012/016697 A2 | 2/2012 |

OTHER PUBLICATIONS

Maddaford et al. "Preparation of tetrahydroquinolone . . . " CA 149:402219 (2008).*
Parrish et al. "A novel receptor . . . " CA142:103664 (2004).*
Takai et al. "Preparation of fused-ring . . . " CA156:284759 (2012).*
Zaveri et al. "A novel series . . . " J. Med. Chem. 47, p. 2973-2976 (2004).*
Zaveri et al. "Small molecule agonists . . . " AAPS Journal 7(2) p. E345-E352 (2005).*
PCT-206, p. 1-2 (2014).*
Bakshi, V. P. and Geyer, M. A., "Antagonism of phencyclidine-induced deficits in prepulse inhibition by the putative atypical antipsychotic olanzapine," Psychopharmacology, vol. 122, pp. 198-201 (1995).
Berge, S. M., et al., "Pharmaceutical Salts," Journal of Pharmaceutical Sciences, vol. 66, No. 1, pp. 1-19 (Jan. 1977).
Calo, G., et al., "Pharmacology of nociceptin and its receptor: a novel therapeutic target," British Journal of Pharmacology, vol. 129, pp. 1261-1283 (Apr. 2000).

(Continued)

*Primary Examiner* — Timothy R Rozof
(74) *Attorney, Agent, or Firm* — Heslin Rothenberg Farley & Mesiti P.C.; Nathan B. Davis

(57) ABSTRACT

Provided herein are heterocyclyl compounds, methods of their synthesis, pharmaceutical compositions comprising the compounds, and methods of their use. The compounds provided herein are useful for the treatment, prevention, and/or management of various neurological disorders, including but not limited to, psychosis and schizophrenia.

16 Claims, No Drawings

(56) References Cited

OTHER PUBLICATIONS

Carra, G., et al., "[(pF)Phe4,Arg14,Lys15]N/OFQ-NH2 (UFP-102), a Highly Potent and Selective Agonist of the Nociceptin/Orphanin FQ Receptor," J. Pharm and Exp. Therapeutics, vol. 312, No. 3, pp. 1114-1123 (2005).

Ciccocioppo, R., et al., "Attenuation of ethanol self-administration and of conditioned reinstatement of alcohol-seeking behaviour by the antiopioid peptide nociceptin/orphanin FQ in alcohol-preferring rats," Psychopharmacology (Berl)., vol. 172, No. 2, pp. 170-178 (Mar. 2004).

Database Registry, "Database assession No. 887440-76-8," Chemical Abstracts Service, XP002757016, 6 pages (Jun. 12, 2006).

Economidou, D., et al., "Effect of novel nociceptin/orphanin FQ-NOP receptor ligands on ethanol drinking in alcohol-preferring msP rats," Peptides, vol. 27, No. 12, pp. 3299-3306, 13 pages (Dec. 2006).

International Search Report and Written Opinion issued by the U.S. Patent and Trademark Office as International Searching Authority dated May 27, 2014, in the International application No. PCT/US13/78453 (18 pages).

Lin et al., "The Therapeutic Potential of Nociceptin/Orphanin FQ Receptor Agonists as Analgesics without Abuse Liability," ACS Chem. Neurosci., vol. 4, No. 2, pp. 214-224 (2013).

National Heart, Lung, and Blood Institute, Clinical Guidelines on the Identification, Evaluation, and Treatment of Overweight and Obesity in Adults, The Evidence Report, Washington, D.C., U.S. Department of Health and Human Services, NIH publication No. 98-4083, 262 pages (Sep. 1998).

Partial Supplementary European Search Report issued by the European Patent Office for Application No. 13867594.7 dated May 19, 2016 (10 pages).

Pauletti, G. M., et al., "Improvement of oral peptide bioavailability: Peptidomimetics and prodrug strategies," Adv. Drug. Delivery Rev., vol. 27, pp. 235-256 (1997).

Sakoori, K. and Murphy, N. P., "Central administration of nociceptin/orphanin FQ blocks the acquisition of conditioned place preference to morphine and cocaine, but not conditioned place aversion to naloxone in mice," Psychopharmacology, vol. 172, pp. 129-136 (2004).

Swerdlow, N. R., et al., "Seroquel Restores Sensorimotor Gating in Phencyclidine-Treated Rats," J. Pharm. Exp. Ther., vol. 279, No. 3, pp. 1290-1299 (1996).

Teshima, K., et al., "Nonphotic entrainment of the circadian body temperature rhythm by the selective ORL1 receptor agonist W-212393 in rats," British Journal of Pharmacology, vol. 146, Issue 1, pp. 33-40 (2005).

Thompson et al., "Structure of the nociceptin/orphanin FQ receptor in complex with a peptide mimetic," Nature, vol. 485, pp. 395-399 (May 17, 2012).

Toll, L., et al., "Comparison of the Antinociceptive and Antirewarding Profiles of Novel Bifunctional Nociceptin Receptor/μ-Opioid Receptor Ligands: Implications for Therapeutic Applications," Journal of Pharmacology and Experimental Therapeutics, vol. 331, No. 3, pp. 954-964 (Sep. 22, 2009).

Williams, M., et al., "Emerging Molecular Approaches to Pain Therapy," J. of Med. Chem., vol. 42, No. 9, pp. 1481-1500 (May 6, 1999).

Zaveri et al., "Small-Molecule Agonists and Antagonists of the Opioid Receptor-Like Receptor (ORL1, NOP); Ligand-Based Analysis of Structural Factors Influencing Intrinsic Activity at NOP," The AAPS Journal, vol. 7, No. 2, pp. E345-E352, (2005).

Zaveri, N., et al., "Designing Bifunctional NOP receptor-mu opioid receptor ligands from NOP receptor-selective scaffolds. Part I," Bioorg. Med. Chem. Lett., vol. 23, No. 11, pp. 3308-3313 (Jun. 1, 2013).

\* cited by examiner

HETEROCYCLIC COMPOUNDS AND METHODS OF USE THEREOF

CROSS-REFERENCE TO RELATED APPLICATIONS

This application is a national stage application of International Application No. PCT/US2013/078453 filed on Dec. 31, 2013, which claims the benefit of U.S. Provisional Application No. 61/747,499 filed on Dec. 31, 2012, the disclosures of each of which are hereby incorporated by reference in their entirety.

I. FIELD

Provided herein are heteroaryl compounds useful for treating various neurological disorders, including but not limited to, anxiety, depression, pain, sleep disorders and substance abuse/dependence, compositions comprising the compounds, and methods of use thereof.

II. BACKGROUND

Central nervous system/neurological disorders affect a wide range of the population with differing severity. CNS/neurological disorders can include, but are not limited to anxiety, depression, pain, sleep disorders and substance abuse/dependence. There remains a great need to effective treatment of these and various other CNS/neurological disorders.

The ORL-1 (orphan opioid receptor, now also known as NOP) G-protein coupled receptor, also known as the nociceptin receptor, was first reported in 1994, and was discovered based on its homology with the classic δ-, μ-, and κ-opioid receptors. The endogenous ligand of ORL-1 (NOP), known as nociceptin, a highly basic 17 amino acid peptide, was isolated from tissue extracts in 1995. Nociceptin plays an important role in the function of central nervous system such as learning, memory, anxiety and stress (Br. J. Pharmacol. 129, 1261-1283 (2000)).

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord.

Nociceptin binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia.

The Nociceptin receptor (NOPr) is a target for the treatment of pain and substance abuse. Nociceptin/orphanin FQ (N/OFQ), the endogenous peptide for NOPr, not only modulates opioid antinociceptin, but also potentially blocks the rewarding effects of several abused drugs, such as morphine, cocaine and amphetamine.

Substance abuse and dependence involves any of following classes of substances: alcohol, amphetamine, methamphetamine, *cannabis* (including marijuana, hashish), cocaine, hallucinogens (including LSD, mescaline, MDMA), nicotine, opioids (including morphine, heroin, codeine, methadone), phencyclidine, ketamine, barbiturates, benzodiazepines (including diazepam, triazolam), inhalants (including toluene, paint thinner).

It is known that nociceptin is effective in alcohol dependence (Ciccocioppo et al., Psychopharmacology (Berl). 141, 220-224, 1999; Ciccocioppo et al., Psychopharmacology (Berl) 172, 170-178, 2004; Martin-Fardon et al., NeuroReport. 11, 1939-1943, 2000), morphine or cocaine dependence (Sakoori et al., Psychopharmacology (Berl) 172, 129-136, 2004), methamphetamine dependence (Zhao et al., NeuroReport. 14, 2383-2385, 2003).

Therefore a small molecule ORL-1 receptor (NOP) agonist is expected to be effective in the prophylaxis or treatment of for substance abuse and dependence. However, first synthesized ORL-1 receptor agonist Ro64-6198 failed to decrease alcohol drinking, rather increase it at high dose (Economidou et al., Peptides 27, 3299-3306, 2006). This effect probably induced by its residual agonistic activity at μ-opioid receptors.

In view of the above, there remains a need for effective treatments of various neurological disorders, including but not limited to, anxiety, depression, pain, sleep disorders and substance abuse/dependence.

III. SUMMARY

Provided herein are compounds of formula (I), or pharmaceutically acceptable salts or stereoisomers thereof:

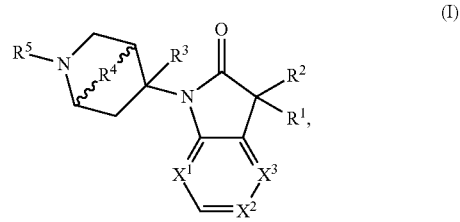

or a pharmaceutically acceptable salt thereof, wherein $X^1$, $X^2$, $X^3$, $R^1$, $R^2$, $R^3$, $R^4$, $R^5$, $R^6$, $R^7$, $R^8$ and $R^9$ are defined as described herein.

The compounds described herein are useful for treating various disorders, such as neurological disorders including, but not limited to, anxiety, depression, pain, sleep disorders and substance abuse/dependence.

Also provided herein are compositions and dosage forms, comprising a compound provided herein, and one or more pharmaceutically acceptable excipients. Compositions and dosage forms provided herein may further comprise one or more additional active ingredients.

Also provided herein are methods for the treatment, prevention, and/or management of various neurological disorders, including those of the central nervous system (CNS) using the compounds and compositions provided herein. In one embodiment, provided herein is a method of treating or managing one or more symptoms of a neurological disorder provided herein. Such neurological disorders include, but are not limited to, schizophrenia, psychosis, cognitive disorders, mood disorders, attention deficit disorders, and neurodegenerative diseases. In one embodiment, the disorders include, but are not limited to, neurological disorder, schizophrenia, schizophrenia-related disorder, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., bipolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, cognitive impairment associated with schizophrenia (CIAS), movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, Huntington's chorea, and premenstrual dysphoria.

In one embodiment, provided herein is a method of treating, preventing, and/or managing psychosis or schizophrenia. In one embodiment, provided herein is a method of treating or managing one or more symptoms of psychosis, schizophrenia or related disorders, including but not limited to, schizoaffective disorder, schizophreniform disorder, paraphrenia, paranoid personality disorder, schizoid personality disorder, and schizotypal personality disorder; a disease having a psychosis component, including but not limited to, Alzheimer's psychosis, Parkinson's psychosis, shared psychotic disorder, and substance-induced psychotic disorder; cognitive impairment, including but not limited to, cognitive impairment associated with schizophrenia, cognitive deficit in Alzheimer's disease, and cognitive deficit in Parkinson's disease; mood disorder, including but not limited to, bipolar disorder; attention deficit disorder, including but not limited to attention deficit hyperactive disorder; neurodegenerative disease, including but not limited to, Huntington's disease; or depression, including but not limited to, major depressive disorder, unipolar depression, and treatment resistant depression. In one embodiment, provided herein is a method of treating, preventing, and/or managing psychosis or schizophrenia a disorder provided herein elsewhere (e.g., a CNS disorder or a metabolic disorder), in a subject, such as a mammal, such as, e.g., human, rodent (such as, e.g., mice and rats), cat, dog, non-human primate, among others. In one embodiment, the method comprises contacting a compound provided herein with one or more receptors of the central nervous system. In one embodiment, the method comprises contacting a cell with a compound provided herein. In an exemplary embodiment, the cell is a brain cell, such as, e.g., a neuronal cell or a glial cell.

In one embodiment, provided herein is a method of treating, preventing, and/or managing pain comprising administering an effective amount of a compound of formula (I) or a composition comprising a compound of formula (I). In another embodiment, provided herein is a method of treating, preventing and/or managing substance abuse or dependence comprising administering an effective amount of a compound of formula (I) or a composition comprising a compound of formula (I).

In another embodiment, the compounds and compositions described herein modulate NOP (e.g., inhibit or activate). In another embodiment, the compounds and compositions described herein are used to treat an NOP-mediated disorder. Also described herein are pharmaceutical compositions comprising a compound described herein and methods of using such compositions to treat NOP mediated disorders. In another embodiment, the compounds and compositions described herein have greater NOP modulator activity compared to modulator activity (e.g., inhibitor or activator) against a μ-opioid receptor (e.g., 100,000:1, 50,000:1, 10,000:1, 5,000:1, 1,000:1, 500:1, 250:1, 100:1, 50:1, 25:1, 10:1, 5:1 or 2:1). In another embodiment, a compound or composition described herein has a modulator (e.g., inhibitor or activator) selectivity for NOP over a μ-opioid receptor over a range of activity levels (e.g., from 10,000 μM to 0.1 nM).

IV. DETAILED DESCRIPTION

Unless defined otherwise, all technical and scientific terms used herein have the same meaning as those commonly understood by one of ordinary skill in the art. In certain embodiments, abbreviations are as defined in *J. Org. Chem.* 2007, 72, 23A. All publications and patents referred to herein are incorporated by reference herein in their entireties.

Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may optionally be substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, and t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "cycloalkyl" refers to a monocyclic or multicyclic fully or partially saturated bridged or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, cycloalkyl also refers to bicyclic, tricyclic, or tetracyclic carbon rings, where the point of attachment is a fully or partially saturated bridged or non-bridged hydrocarbon ring, and the other ring(s) may be saturated, partially unsaturated, or aromatic. Examples of multicyclic cycloalkyl groups include 2,3-dihydoindyl, 1,2,3,4-tetrahydronaphthyl, and 1,2-dihydroacenaphthyl. In certain embodiments, cycloalkyl may be a bicyclic, tricyclic, or tetracyclic ring system, where the point of attachment is a fully or partially saturated bridged or non-bridged hydrocarbon ring, and one or more of the other ring(s) is/are saturated, partially unsaturated or aromatic and contains one or more heteroatoms independently selected from O, S, and N. In certain embodiments, the cycloalkyl is optionally substituted as described herein elsewhere. In certain embodiments, the ring carbon atoms may be optionally substituted with oxo, As used herein, and unless otherwise specified, the term "heteroalkyl" refers to a stable straight or branched chain, or cyclic hydrocarbon radical, or combinations thereof, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O, N and S can be placed at any interior position of the heteroalkyl group. In one embodiment, the heteroatom Si can be placed at any position of the heteroalkyl group (e.g., interior or terminal position), including the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms can be consecutive, such as, for example, —CH$_2$—NH—O—CH$_3$ and —CH$_2$—O—Si(CH$_3$)$_3$. In certain embodiments, the heteroalkyl is optionally substituted as described herein elsewhere.

As used herein, and unless otherwise specified, the term "alkoxyl" refers to a stable straight or branched chain, or cyclic hydrocarbon radical, or combinations thereof, consisting of the stated number of carbon atoms and from one or more, in one embodiment, one to three, O atoms. Examples of alkoxyl include, but are not limited to, —O—CH$_3$, —O—CF$_3$, —O—CH$_2$—CH$_3$, —O—CH$_2$—CH$_2$—CH$_3$, —O—CH—(CH$_3$)$_2$, and —O—CH$_2$—CH$_2$—O—CH$_3$. In one embodiment, the alkoxyl is optionally substituted as described herein elsewhere.

As used herein, and unless otherwise specified, the term "aminoalkyl" refers to a stable straight or branched chain, or cyclic hydrocarbon radical, or combinations thereof, consisting of the stated number of carbon atoms and from one or more, in one embodiment, one to three, N atoms. Examples of aminoalkyl include, but are not limited to, —NH—CH$_3$, —N(CH$_3$)$_2$, —NH—CH$_2$—CH$_3$, —N(CH$_3$)—CH$_2$—CH$_3$, —NH—CH—(CH$_3$)$_2$, —CH$_2$—CH$_2$—NH—CH$_3$, and —CH$_2$—CH$_2$—N(CH$_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where the point of attachment is an aromatic hydrocarbon ring, and the other ring(s) may be saturated, partially unsaturated, or aromatic hydrocarbon rings, for example, dihydronaphthyl, indenyl, indanyl, or tetrahydronaphthyl (tetralinyl). In certain embodiments, aryl may be a bicyclic, tricyclic, or tetracyclic ring system, where the point of attachment is an aromatic hydrocarbon ring, and one or more of the ring(s) is/are either (a) saturated, partially unsaturated or aromatic carbocyclic rings; or (b) saturated or partially unsaturated rings containing one or more heteroatoms independently selected from O, S, and N and in which the nitrogen or sulfur atoms may be optionally oxidized, the nitrogen atoms may be optionally quaternized, the ring carbon atoms may be optionally substituted with oxo. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. Example of aralkyl includes, but is not limited to, benzyl. In certain embodiments, both alkyl and aryl may be optionally substituted with one or more substituents as described herein elsewhere.

As used herein, and unless otherwise specified, the term "alkoxyalkyl" refers to a monovalent alkyl group substituted with an alkoxy moiety. Examples of alkoxyalkyl include, but are not limited to, —CH$_2$—OCH$_3$ and —CH$_2$CH$_2$—OCH$_3$. In certain embodiments, both alkyl and alkoxy may be optionally substituted with one or more substituents as described herein elsewhere.

As used herein, and unless otherwise specified, the term "cycloalkylalkyl" refers to a monovalent alkyl group substituted with cycloalkyl. In certain embodiments, both the alkyl and cycloalkyl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl refers to bicyclic, tricyclic, or tetracyclic rings wherein the point of attachment is (a) an aromatic ring which contains one or more heteroatoms independently selected from O, S, and N and in which the nitrogen or sulfur atoms may be optionally oxidized, the nitrogen atoms may be optionally quaternized, and the other ring(s) are saturated, partially saturated, or aromatic and may be carbocyclic or contain one or more heteroatoms independently selected from O, S, and N, and in which the nitrogen or sulfur atoms may be optionally oxidized, the nitrogen atoms may be optionally quaternized, the ring carbon atoms may be optionally substituted with oxo; or (b) the point of attachment is an aromatic carbocyclic ring and the other ring(s) are aromatic and contain one or more heteroatoms independently selected from O, S, and N, and in which the nitrogen or sulfur atoms may be optionally oxidized, and the nitrogen atoms may be optionally quaternized. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N, and the remaining ring atoms are carbon atoms, and in which the nitrogen or sulfur atoms may be optionally oxidized, the nitrogen atoms may be optionally quaternized, and the ring carbon atoms may be optionally substituted with oxo. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a bicyclic, tricyclic, or tetracyclic ring system, which may include a fused or bridged ring system, wherein the point of attachment is a non-aromatic (i.e. partially saturated or fully saturated) ring having one or more heteroatoms independently selected from O, S, and N, and in which the nitrogen or sulfur atoms may be optionally oxidized, the nitrogen atoms may be optionally quaternized, the ring carbon atoms may be optionally substituted with oxo, and the other ring(s) may be saturated, partially unsaturated, or aromatic ring(s) optionally having one or more heteroatoms independently selected from O, S, and N, and in which the nitrogen or sulfur atoms may be optionally oxidized, the nitrogen atoms may be optionally quaternized, and the ring carbon atoms may be optionally substituted with oxo. The heterocycloalkyl or heterocyclyl may be attached to the main structure at a heteroatom or a carbon atom of a non-aromatic heterocyclic ring which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

The term "combination treatment," as used herein, encompasses administration of two or more agents to a subject so that both agents and/or their metabolites are present in the subject at the same time. Combination treatment can include simultaneous administration in separate compositions, administration at different times in separate compositions, or administration in a composition in which both agents are present.

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—$NO_2$), oxo (═O), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(═N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(═N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(═N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(═N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids, such as acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate. In certain embodiments, a compound as disclosed herein may be provided as a solvate. In certain embodiments, a compound as disclosed herein may be provided as a hydrate.

As used herein, and unless otherwise specified, the term "stereoisomer" encompasses all enantiomerically/diastereomerically/stereomerically pure and enantiomerically/diastereomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess or diastereomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer or diastereomer and about 5% or less of the less preferred enantiomer or diastereomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In one embodiment, such symptoms are those known to a person of skill in the art to be associated with the disease or disorder being treated. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms associated with the disease or disorder. In one embodiment, such symptoms are those known to a person of skill in the art to be associated with the disease or disorder being prevented. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms associated with the disease or disorder. In one embodiment, such symptoms are those known to a person of skill in the art to be associated with the disease or disorder being managed. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression, bipolar disorder, manic conditions, and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, major depressive disorder, dysthymia, seasonal affective disorder, dementias, movement disorders, psychosis, alcoholism, post-traumatic stress disorder, and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the terms "psychosis," "schizophrenia," "obsessive-compulsive disorder," "substance abuse," "anxiety," "eating disorders," "migraine," and other CNS or neurological disorders described herein elsewhere are used herein in a manner consistent with their accepted meanings in the art. See, e.g., *Diagnostic and Statistical Manual of Mental Disorders, 4th* Ed., American Psychiatric Association (1997) (DSM-IV™).

As used herein, and unless otherwise specified, the term "seizure" refers to a neurological disorder and may be used interchangeably with "convulsion," although there are many types of seizure, some of which have subtle or mild symptoms instead of convulsions. In one embodiment, the term "seizure" as used herein is intended to encompass "convulsion." In some embodiments, seizures may be caused by disorganized and sudden electrical activity in the brain. In some embodiments, convulsions are a rapid and uncontrollable shaking during which the muscles contract and relax repeatedly. Unless otherwise specified, the terms "convulsion" and "seizure" are used herein in accordance with the accepted meanings as found in the *Diagnostic and Statistical Manual of Mental Disorders, 4th* Ed., American Psychiatric Association (1997) (DSM-IV™).

As used herein, and unless otherwise specified, the term "affective disorder" includes depression, attention deficit disorder, attention deficit disorder with hyperactivity, bipolar disorder, and manic disorder, and the like.

As used herein, and unless otherwise specified, the term "depression" includes all forms of depression, including, but not limited to, major depressive disorder (MDD) or unipolar depressive, bipolar disorder, dysthymia, seasonal affective disorder (SAD), and treatment resistant depression. "Major depressive disorder" is used herein interchangeably with "unipolar depression", "unipolar depressive disorder", and "major depression." "Depression" may also include any condition commonly associated with depression, such as all forms of fatigue (e.g., chronic fatigue syndrome) and cognitive deficits.

Unless otherwise specified, the terms "bipolar disorder" and "manic disorder" are used herein in accordance with the accepted meanings as found in the *Diagnostic and Statistical Manual of Mental Disorders, 4th* Ed., American Psychiatric Association (1997) (DSM-IV™).

Unless otherwise specified, the terms "attention deficit disorder" (ADD), and "attention deficit disorder with hyperactivity" (ADDH) or "attention deficit hyperactivity disorder" (ADHD), are used herein in accordance with the accepted meanings as found in the *Diagnostic and Statistical Manual of Mental Disorders, 4th* Ed., American Psychiatric Association (1997) (DSM-IV™).

As used herein, and unless otherwise specified, the term "pain" refers to an unpleasant sensory and emotional experience. Unless otherwise specified, the term "pain," as used herein, refers to all categories of pain, including pain that is described in terms of stimulus or nerve response, e.g., somatic pain (normal nerve response to a noxious stimulus) and neuropathic pain (abnormal response of an injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In one embodiment, the term "pain" includes pain resulting from dysfunction of the nervous system: organic pain states that share clinical features of neuropathic pain and possible common pathophysiology mechanisms, but are not initiated by an identifiable lesion in any part of the nervous system.

Unless otherwise specified, the term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

Unless otherwise specified, the term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, neuropathic cancer pain, HIV/AIDS induced pain, phantom limb pain, and complex regional pain syndrome. Unless otherwise specified, the term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "diabetic peripheral neuropathic pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "post-herpetic neuralgia", also called "postherpetic neuralgia" (PHN), refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "phantom limb pain" refers to pain appearing to come from where an amputated limb used to be. Phantom limb pain can also occur in limbs following paralysis (e.g., following spinal cord injury). "Phantom limb pain" is usually chronic in nature.

As used herein, and unless otherwise specified, the term "trigeminal neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "complex regional pain syndrome" (CRPS), formerly known as "reflex sympathetic dystrophy" (RSD), refers to a chronic pain condition whose key symptom is continuous, intense pain out of proportion to the severity of the injury, which gets worse rather than better over time. The term encompasses
type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, the term/phrase "substance abuse and dependence" includes abuse of and dependence on alcohol, amphetamine, methamphetamine, *cannabis* (including marijuana, hashish), cocaine, hallucinogens (including LSD, mescaline, MDMA), nicotine, opioids (including morphine, heroin, codeine, methadone), phencyclidine, ketamine, barbiturates, benzodiazepines (including diazepam, triazolam), inhalants (including toluene, paint thinner) and the like.

As used herein, and unless otherwise specified, the terms "overweight" and "obese" refer to adult persons 18 years or older having a greater than ideal body weight (e.g., greater than ideal body fat) that can be measured by the body mass index (BMI), which is generally correlated with total body fat and the relative risk of suffering from premature death or disability due to diseases as a consequence of the overweight or obese condition. BMI is calculated by weight in kilograms divided by height in meters squared (kg/m$^2$), or alternatively by weight in pounds, multiplied by 703, divided by height in inches squared (lbs×703/in$^2$). Overweight individuals typically have a BMI of between about 25 and about 29, whereas obese individuals typically have a BMI of about 30 or more (see, e.g., National Heart, Lung, and Blood Institute, Clinical Guidelines on the Identification, Evaluation, and Treatment of Overweight and Obesity in Adults, The Evidence Report, Washington, D.C., U.S. Department of Health and Human Services, NIH publication no. 98-4083, 1998). Other means for indicating excess body weight, excess body fat, and obesity include direct measure of body fat and/or waist-to-hip ratio measurements.

As used herein, and unless otherwise specified, the term "metabolic syndrome" is used according to its usual meaning in the art. The American Heart Association characterizes metabolic syndrome as having at least three or more of the following symptoms: 1) elevated waist circumference [>102 cm (40 inches) in men; >88 cm (35 inches) in women]; 2) elevated triglycerides [≤150 mg/dL (>1.695 mmol/L) or drug treatment for elevated triglycerides]; 3) reduced HDL cholesterol [<40 mg/dL (1.036 mmol/L) in men; <50 mg/dL (1.295 mmol/L) in women; or drug treatment for reduced HDL-C]; 4) elevated blood pressure [≥130/85 mmHg or drug treatment for hypertension]; and 5) elevated fasting glucose [≥110 mg/dL or drug treatment for elevated glucose]. According to the World Health Organization, metabolic syndrome includes individuals suffering from diabetes, impaired glucose tolerance, impaired fasting glucose, or insulin resistance plus two or more of the following symptoms: 1) high blood pressure [≥160/90 mmHg]; 2) hyperlipidemia [triglyceride concentration ≥150 mg/dL (1.695 mmol/L) and/or HDL cholesterol <35 mg/dL (0.9 mmol/L) in men and <39 mg/dL (1.0 mmol/L) in women]; 3) central obesity [waist-to-hip ratio of >0.90 for men and >0.85 for women and/or BMI >30 kg/m$^2$]; and 4) microalbuminuria [urinary albumin excretion rate ≥20 μg/min or an albumin-to-creatinine ratio ≥20 mg/kg).

Compounds

In one embodiment, provided herein is a compound of formula (I):

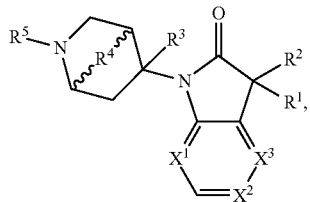

or a pharmaceutically acceptable salt thereof, wherein:
$X^1$, $X^2$ and $X^3$ are each independently —CH= or —N=;
$R^1$ is halo, hydroxyl, cyano, $C_{1-6}$ alkyl, $C_{1-6}$ alkenyl, $C_{1-6}$ haloalkyl, $C_{1-6}$ alkoxy, —O—C(O)—$C_{1-6}$ alkyl, —C(O)—O—$C_{1-6}$ alkyl, —C(O)—NR$^6$—$C_{1-6}$ alkyl, —NR$^6$—C(O)—$C_{1-6}$ alkyl, —$C_{1-6}$ alkyl-C(O)—NR$^6$—$C_{1-6}$ alkyl, —$C_{1-6}$ alkyl-NR$^6$—C(O)—$C_{1-6}$ alkyl, —$C_{1-6}$ alkyl-NR$^6$—C(O)—O—$C_{1-6}$ alkyl, —$C_{1-6}$ alkyl-C(O)—O—$C_{1-6}$ alkyl, —O—C(O)—NR$^6$—$C_{1-6}$ alkyl, $C_{3-7}$ cycloalkyl, $C_{3-7}$ cycloalkylalkyl, aryl, heteroaryl, aralkyl, heteroaralkyl, heterocyclyl or heterocyclylalkyl, wherein each alkyl, alkenyl, alkoxy, cycloalkyl, aryl, heteroaryl and heterocyclyl is substituted with 0-3 occurrences of R$^7$;

$R^2$ is hydrogen, halo, hydroxyl, $C_{1-6}$ alkyl, $C_{1-6}$ haloalkyl or $C_{1-6}$ alkoxy;

or alternatively, $R^1$ and $R^2$ taken together with the carbon atom to which they are attached form a cycloalkyl or heterocyclyl substituted with 0-3 occurrences of R$^7$;

or alternatively, $R^1$ and $R^2$ taken together with the carbon atom to which they are attached form a $C_{2-6}$ alkenyl substituted with R$^7$;

$R^3$ is hydrogen, hydroxyl, halo, $C_{1-6}$ alkyl, $C_{1-6}$ alkoxy, cyano, alkoxyalkyl or $C_{1-6}$ haloalkyl;

$R^4$ is absent, $C_{1-4}$ alkylene, —O— or —NR$^6$—, wherein each CH$_2$ of the $C_{1-4}$ alkylene may be replaced with —O— or —NR$^6$—;

$R^5$ is $C_{1-6}$ alkyl, $C_{1-6}$ alkoxy, $C_{1-6}$ haloalkyl, $C_{3-7}$ cycloalkyl, $C_{3-7}$ cycloalkylalkyl, aryl, aralkyl, heteroaryl, heteroaralkyl, heterocyclyl or heterocyclylalkyl, wherein each alkyl, cycloalkyl, cycloalkylalkyl, aryl, aralkyl, heteroaryl, heteroaralkyl, heterocyclyl and heterocyclylalkyl is substituted with 0-3 occurrences of R$^7$;

each R$^6$ is independently hydrogen or $C_{1-6}$ alkyl;

each R$^7$ is independently halo, cyano, N(R$^8$)$_2$, —C(O)—N(R$^8$)$_2$, hydroxyl, $C_{1-6}$ alkyl, $C_{1-6}$ alkoxy, $C_{3-7}$ cycloalkyl, aryl, aryloxy, heteroaryl, heteroaryloxy or heterocyclyl, wherein each alkyl, alkoxy, cycloalkyl, aryl, aryloxy, heteroaryl, heteroaryloxy or heterocyclyl is substituted with 0-3 occurrences of R$^9$;

each R$^8$ is independently hydrogen, $C_{1-6}$ alkyl, C(O)—$C_{1-6}$ alkyl, aryl, or benzyl;

or alternatively, two R$^8$ groups taken together with the nitrogen to which they are attached form a heterocyclyl; and each R$^9$ is independently halo, $C_{1-6}$ alkyl, $C_{1-6}$ alkoxy or $C_{1-6}$ haloalkyl.

In certain embodiments, $X^1$ is —CH=. In some embodiments, $X^2$ is —CH=. In some embodiments, $X^3$ is —CH=. In some embodiments, $X^1$, $X^2$ and $X^3$ are each —CH=. In some embodiments, at least one of $X^1$, $X^2$ and $X^3$ is —N=.

In certain embodiments, $R^1$ is —O—C(O)—$C_{1-6}$ alkyl (e.g., —O—C(O)—CH$_3$). In some embodiments, $R^1$ is —$C_{1-6}$ alkyl-C(O)—NR$^6$—$C_{1-6}$ alkyl (e.g., —CH$_2$—C(O)—NH—CH$_3$ or —CH$_2$—C(O)—N(CH$_3$)$_2$). In certain embodiments, $R^1$ is —O—C(O)—NR$^6$—$C_{1-6}$ alkyl (e.g., —O—C(O)—NH—CH$_3$).

In some embodiments, $R^1$ is $C_{1-6}$ alkyl substituted with 0-3 occurrences of R$^7$. In some embodiments, $R^1$ is $C_{1-6}$ alkyl substituted with 0 occurrences of R$^7$ (e.g., methyl). In some embodiments, $R^1$ is $C_{1-6}$ alkyl substituted with one occurrence of R$^7$. In some embodiments, $R^1$ is $C_{1-6}$ alkyl substituted with one occurrence of R$^7$, wherein R$^7$ is —C(O)—NH$_2$, $C_{1-6}$ alkoxy, heterocyclyl (e.g., oxazolidin-2-one), or heteroalkyl (e.g., triazole or oxazole), wherein each heterocyclyl and heteroaryl is substituted with 0-3 occurrences of R$^9$. In some embodiments, $R^1$ is $C_{1-6}$ alkyl substituted with two occurrences of R$^7$. In some embodiments, $R^1$ is $C_{1-6}$ alkyl substituted with two occurrences of R$^7$, wherein one R$^7$ is hydroxyl and one R$^7$ is —NH$_2$, or one R$^7$ is hydroxyl and one R$^7$ is —NH—CH$_3$, or one R$^7$ is hydroxyl and one R$^7$ is —N(CH$_3$)$_2$, or both occurrences of R$^7$ are hydroxyl.

In some embodiments, $R^2$ is hydrogen. In some embodiments, $R^2$ is halo, hydroxyl, $C_{1-6}$ alkyl, $C_{1-6}$ haloalkyl or $C_{1-6}$ alkoxy. In some embodiments, $R^2$ is hydroxyl. In some embodiments, $R^2$ is $C_{1-6}$ alkyl (e.g., methyl). In some embodiments, $R^2$ is halo (e.g., fluoro). In some embodiments, $R^2$ is $C_{1-6}$ alkoxy (e.g., methoxy).

In some embodiments, $R^1$ and $R^2$ are taken together with the carbon atom to which they are attached to form a cycloalkyl or heterocyclyl ring substituted by 0-3 occurrences of $R^7$. In some embodiments, $R^1$ and $R^2$ are taken together with the carbon atom to which they are attached to form a cycloalkyl substituted with 0-3 occurrences of $R^7$. In some embodiments, $R^1$ and $R^2$ are taken together with the carbon atom to which they are attached to form a cycloalkyl substituted with 1 occurrence of $R^7$, and $R^7$ is selected from —C(O)—NH$_2$, —C(O)—NH—CH$_3$, —C(O)—N(CH$_3$)$_2$, and $C_{1-6}$ alkyl. In some embodiments, $R^1$ and $R^2$ are taken together with the carbon atom to which they are attached to form a cycloalkyl substituted with 0 occurrences of $R^7$ (e.g., cyclopentyl).

In some embodiments, $R^1$ and $R^2$ are taken together with the carbon atom to which they are attached to form a heterocyclyl ring substituted with 0-3 occurrences of $R^7$. In some embodiments $R^1$ and $R^2$ are taken together with the carbon atom to which they are attached to form a heterocyclyl ring substituted with 0 occurrences of $R^7$ (e.g., imidazolin-2-one, oxazolidin-2-one, pyrrolidin-2-one or 1,3-dioxolan-2-one). In some embodiments, $R^1$ and $R^2$ are taken together with the carbon atom to which they are attached to form a heterocyclyl ring substituted with one occurrence of $R^7$ (e.g., 1-methylpyrrolidin-2-one, 1-methylimidazolidin-2-one or 3-methyloxazolidin-2-one).

In certain embodiments, $R^3$ is hydrogen. In certain embodiments, $R^4$ is absent. In certain embodiments, $R^3$ is hydrogen and $R^4$ is absent.

In certain embodiments, $R^5$ is aryl substituted with 0-3 occurrences of $R^7$. In some embodiments, $R^5$ is bicyclic aryl (e.g., naphthyl or 1,2,3,4-tetrahydronaphthyl) substituted with 0-3 occurrences of $R^7$. In some embodiments, $R^5$ is naphthyl substituted with 0-3 occurrences of $R^7$. In some embodiments, $R^5$ is naphthyl substituted with one occurrence of $R^7$ (e.g., 8-methylnaphthyl).

In certain embodiments, $R^5$ cycloalkyl substituted with 0-3 occurrences of $R^7$. In some embodiments, $R^5$ is 2,3-dihydroindenyl substituted with 0-3 occurrences of $R^7$. In some embodiments, $R^5$ is 2,3-dihydroindenyl substituted with 0 occurrences of $R^7$. In some embodiments, $R^5$ is 2,3-dihydroindenyl substituted with one occurrence of $R^7$ (e.g., 1-methyl-2,3-dihydroindenyl). In some embodiments, $R^5$ is 1,2,3,4-tetrahydronaphthyl substituted with 0-3 occurrences of $R^7$. In some embodiments, $R^5$ is 1,2,3,4-tetrahydronaphthyl substituted with 0 occurrences of $R^7$. In some embodiments, $R^5$ is 1,2,3,4-tetrahydronaphthyl substituted with one occurrence of $R^7$ (e.g., 1-methyl-1,2,3,4-tetrahydronaphthyl or 2-hydroxy-1,2,3,4-tetrahydronaphthyl).

In certain embodiments, $R^5$ is tricyclic cycloalkyl substituted with 0-3 occurrences of $R^7$. In some embodiments, $R^5$ is 1,2-dihydroacenaphthyl substituted with 0 occurrences of $R^7$. In some embodiments, $R^5$ is 1,2-dihydroacenaphthyl substituted with one occurrence of $R^7$ (e.g., 2-hydroxy-1,2-dihydroacenaphthyl, 3-methoxy-1,2-dihydroacenaphthyl, 1-methyl-1,2-dihydroacenaphthyl or 2-methyl-1,2-dihydroacenaphthyl). In some embodiments, $R^5$ is 1,2-dihydroacenaphthyl substituted with two occurrences of $R^7$ (e.g., 2,2-difluoro-1,2-dihydroacenaphthyl or 2-hydroxy-2-methyl-1,2-dihydroacenaphthyl).

In certain embodiments, $R^5$ is aralkyl (e.g., monocyclic aralkyl or bicyclic aralkyl) substituted with 0-3 occurrences of $R^7$. In some embodiments, $R^5$ is monocyclic aralkyl (e.g., benzyl) substituted with 0-3 occurrences of $R^7$. In some embodiments, $R^5$ is benzyl substituted with 0-3 occurrences of $R^7$. In some embodiments, $R^5$ is benzyl substituted with 0 occurrences of $R^7$. In some embodiments, $R^5$ is bicyclic aralkyl (e.g., napthalen-1-ylmethyl) substituted with 0-3 occurrences of $R^7$. In some embodiments, $R^5$ is napthalen-1-ylmethyl substituted with one occurrence of $R^7$ (e.g., (8-methylnapthalen-1-yl)methyl).

In certain embodiments, $R^5$ is $C_{1-6}$ alkyl substituted with 0-3 occurrences of $R^7$. In some embodiments, $R^5$ is $C_{1-6}$ alkyl (e.g., 4-methylpentyl) substituted with one occurrence of $R^7$. In some embodiments, $R^7$ is aryloxy substituted with 0-3 occurrences of $R^8$. In some embodiments, $R^7$ is aryloxy substituted with one occurrence of $R^8$ (e.g., 3-methoxyphenoxy). In some embodiments, $R^7$ is aryloxy substituted with two occurrences of $R^8$ (e.g., 2-chloro-5-methoxyphenoxy). In some embodiments, $R^5$ is represented by the following structures:

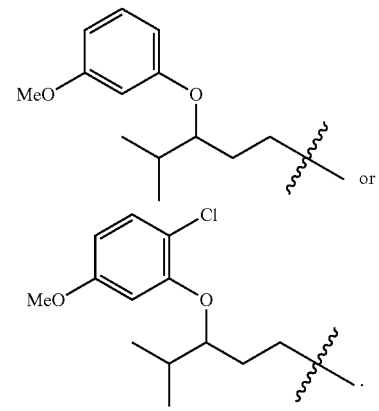

In certain embodiments, the compound of formula (I) is selected from a compound of formula (II):

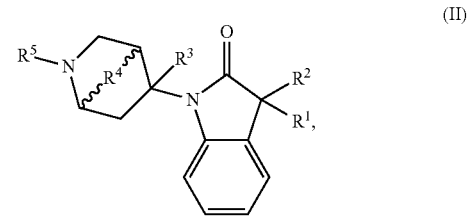

or a pharmaceutically acceptable salt thereof, wherein $R^1$, $R^2$, $R^3$, $R^4$, $R^5$, $R^6$, $R^7$, $R^8$ and $R^9$ are as defined for formula (I).

In certain embodiments, the compound of formula (I) or (II) is selected from a compound of formula (III):

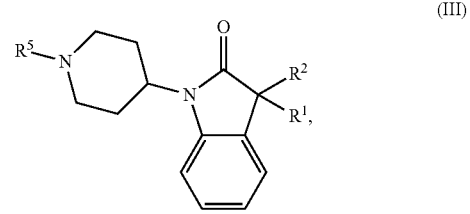

or a pharmaceutically acceptable salt thereof, wherein $R^1$, $R^2$, $R^5$, $R^6$, $R^7$, $R^8$ and $R^9$ are as defined for formula (I).

In certain embodiments, the compound of formula (I), (II) or (III) is selected from a compound of formula (IV):

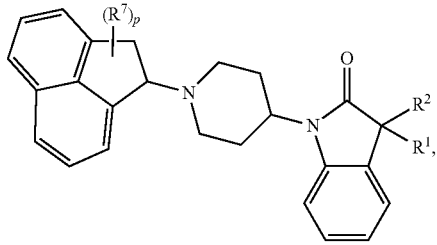
(IV)

or a pharmaceutically acceptable salt thereof, wherein p is 0-3 and $R^1$, $R^2$, $R^7$, $R^8$ and $R^9$ are as defined for formula (I).

In certain embodiments, the compound of formula (IV) is selected from a compound of formula (IVa):

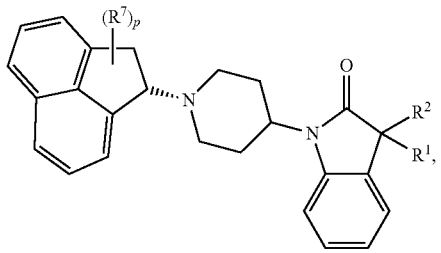
(IVa)

or a pharmaceutically acceptable salt thereof, wherein p is 0-3 and $R^1$, $R^2$, $R^7$, $R^8$ and $R^9$ are as defined for formula (I).

In certain embodiments, the compound of formula (IV) is selected from a compound of formula (IVb):

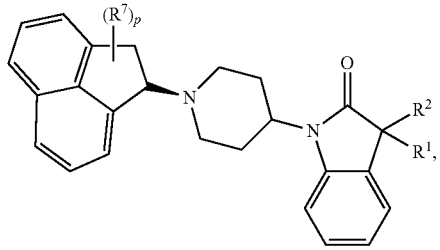
(IVb)

or a pharmaceutically acceptable salt thereof, wherein p is 0-3 and $R^1$, $R^2$, $R^7$, $R^8$ and $R^9$ are as defined for formula (I).

In certain embodiments, the compound of formula (I) is selected from a compound of formula (V):

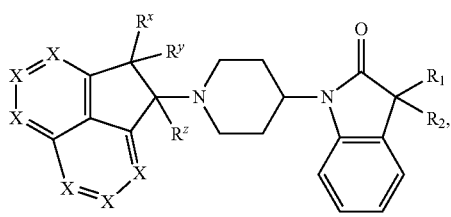
(V)

or a pharmaceutically acceptable salt thereof, wherein $R^1$, $R^2$, $R^7$, $R^8$ and $R^9$ are as defined for formula (I) and each X is independently —CH= or —N=; $R^x$ and $R^y$ are each independently hydrogen, fluoro, $C_{1-6}$ alkyl, $C_{1-6}$ alkoxy or hydroxyl and $R^z$ is hydrogen or $C_{1-6}$ alkyl. In some embodiments of compounds of formula (V), each X is —CH=.

In another embodiment, the compound is selected from any one of the compounds set forth in Table 1, or a pharmaceutically acceptable salt thereof

TABLE 1

| No. | Structure |
|---|---|
| 2 | 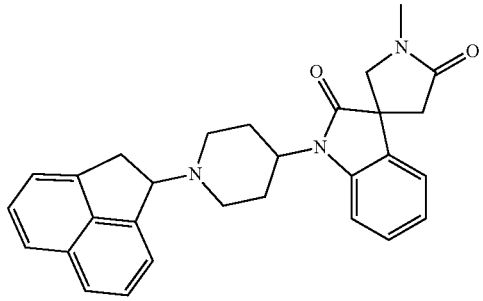 [SMILES: CN1CC2(CC1=O)C(=O)N(C1CCN(C3Cc4cccc5cccc3c45)CC1)c1ccccc12] |
| 3 | 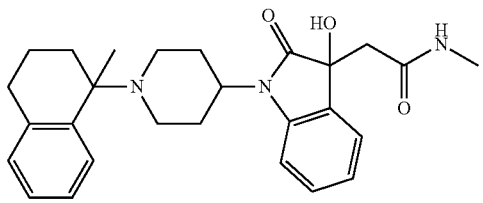 [SMILES: CNC(=O)CC1(O)C(=O)N(C2CCN(C3(C)CCCc4ccccc43)CC2)c2ccccc21] |

TABLE 1-continued
| No. | Structure |
|---|---|
| 4 | 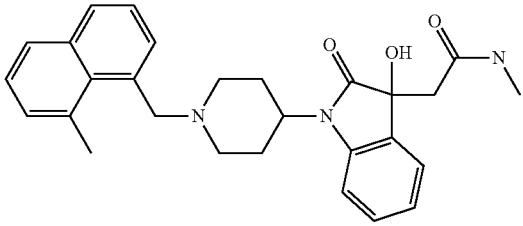 [SMILES: CNC(=O)CC1(O)C(=O)N(C2CCN(Cc3cccc4cccc(C)c34)CC2)c2ccccc21] |
| 5 | 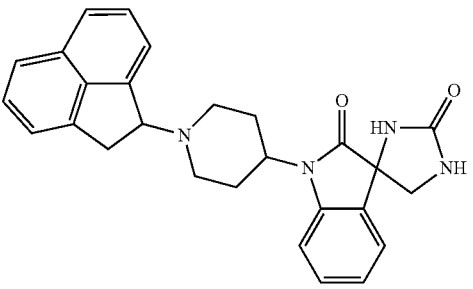 [SMILES: O=C1NCC2(N1)C(=O)N(C1CCN(C3Cc4cccc5cccc3c45)CC1)c1ccccc12] |
| 6 | 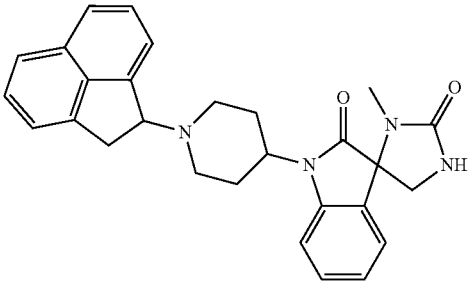 [SMILES: CN1C(=O)NCC12C(=O)N(C1CCN(C3Cc4cccc5cccc3c45)CC1)c1ccccc12] |
| 7 | 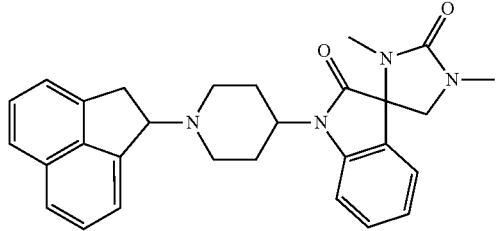 [SMILES: CN1CC2(C(=O)N(C3CCN(C4Cc5cccc6cccc4c56)CC3)c3ccccc32)N(C)C1=O] |
| 8 | 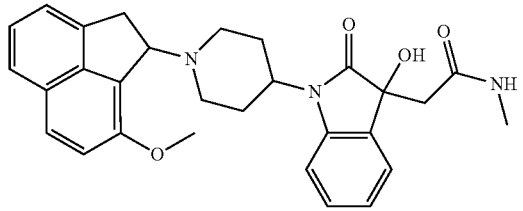 [SMILES: CNC(=O)CC1(O)C(=O)N(C2CCN(C3Cc4cccc5ccc(OC)c3c45)CC2)c2ccccc21] |
| 9 | 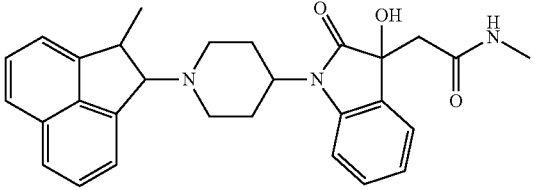 [SMILES: CNC(=O)CC1(O)C(=O)N(C2CCN(C3c4cccc5cccc(c45)C3C)CC2)c2ccccc21] |

TABLE 1-continued
| No. | Structure |
|---|---|
| 10 | 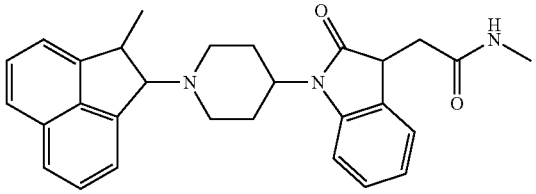 [SMILES: CNC(=O)CC1C(=O)N(C2CCN(C3c4cccc5cccc(c45)C3C)CC2)c2ccccc21] |
| 11 | 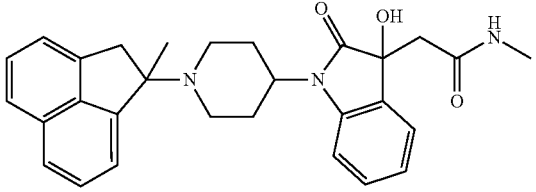 [SMILES: CNC(=O)CC1(O)C(=O)N(C2CCN(C3(C)Cc4cccc5cccc3c45)CC2)c2ccccc21] |
| 12 | 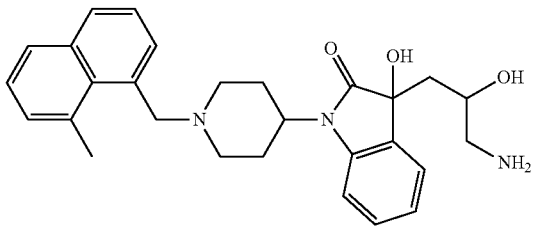 [SMILES: Cc1cccc2cccc(CN3CCC(N4C(=O)C(O)(CC(O)CN)c5ccccc54)CC3)c12] |
| 13 | 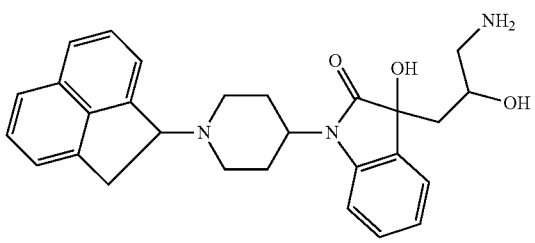 [SMILES: NCC(O)CC1(O)C(=O)N(C2CCN(C3Cc4cccc5cccc3c45)CC2)c2ccccc21] |
| 14 | 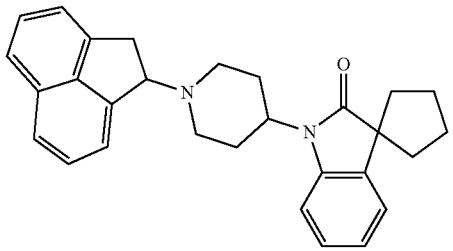 [SMILES: O=C1N(C2CCN(C3Cc4cccc5cccc3c45)CC2)c2ccccc2C12CCCC2] |
| 15 | 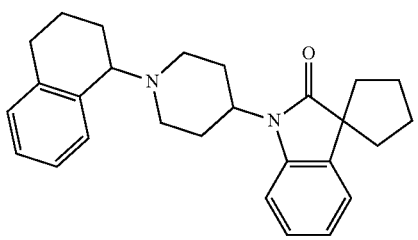 [SMILES: O=C1N(C2CCN(C3CCCc4ccccc43)CC2)c2ccccc2C12CCCC2] |
| 16 | 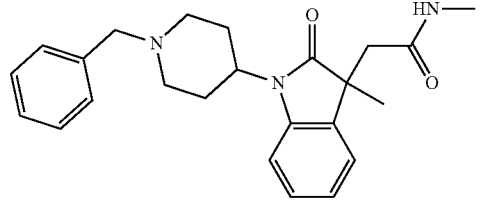 [SMILES: CNC(=O)CC1(C)C(=O)N(C2CCN(Cc3ccccc3)CC2)c2ccccc21] |

TABLE 1-continued

| No. | Structure |
|-----|-----------|
| 17  | 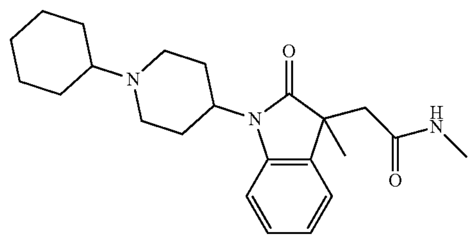 [SMILES: CNC(=O)CC1(C)C(=O)N(C2CCN(C3CCCCC3)CC2)c2ccccc21]          |
| 18  | 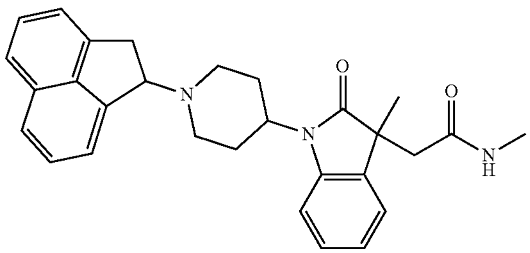 [SMILES: CNC(=O)CC1(C)C(=O)N(C2CCN(C3Cc4cccc5cccc3c45)CC2)c2ccccc21]          |
| 19  | 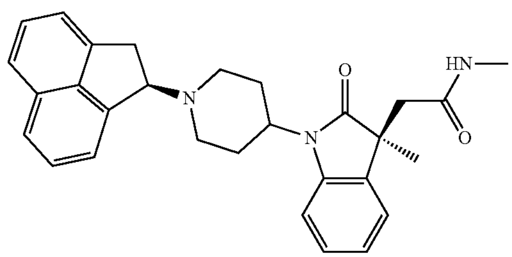 [SMILES: CNC(=O)C[C@]1(C)C(=O)N(C2CCN([C@@H]3Cc4cccc5cccc3c45)CC2)c2ccccc21]          |
| 20  | 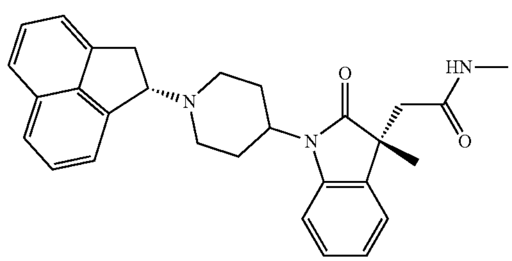 [SMILES: CNC(=O)C[C@@]1(C)C(=O)N(C2CCN([C@H]3Cc4cccc5cccc3c45)CC2)c2ccccc21]          |
| 21  | 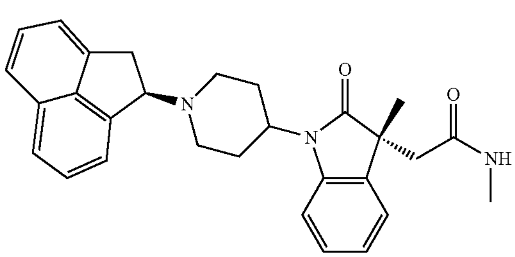 [SMILES: CNC(=O)C[C@@]1(C)C(=O)N(C2CCN([C@@H]3Cc4cccc5cccc3c45)CC2)c2ccccc21]          |
| 22  | 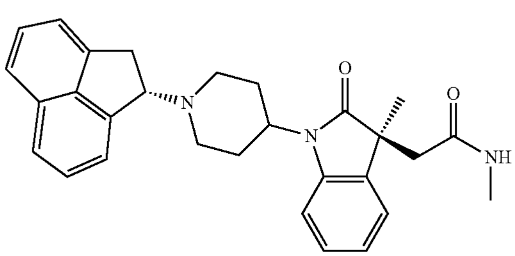 [SMILES: CNC(=O)C[C@]1(C)C(=O)N(C2CCN([C@H]3Cc4cccc5cccc3c45)CC2)c2ccccc21]          |

TABLE 1-continued

| No. | Structure |
|---|---|
| 23 | 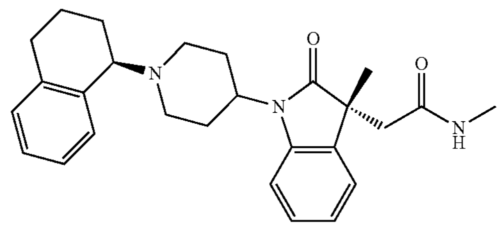 [SMILES: CNC(=O)C[C@@]1(C)C(=O)N(C2CCN([C@@H]3CCCc4ccccc43)CC2)c2ccccc21] |
| 24 | 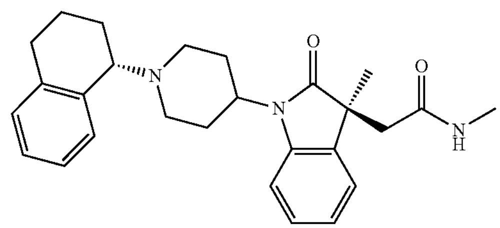 [SMILES: CNC(=O)C[C@]1(C)C(=O)N(C2CCN([C@H]3CCCc4ccccc43)CC2)c2ccccc21] |
| 25 | 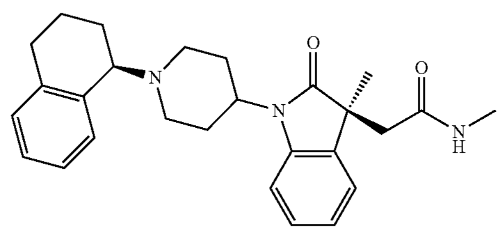 [SMILES: CNC(=O)C[C@]1(C)C(=O)N(C2CCN([C@@H]3CCCc4ccccc43)CC2)c2ccccc21] |
| 26 | 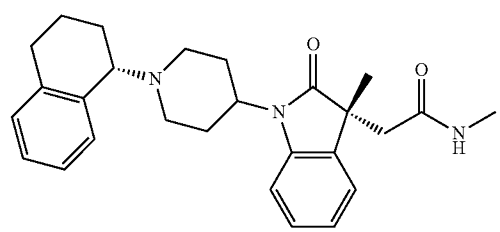 [SMILES: CNC(=O)C[C@@]1(C)C(=O)N(C2CCN([C@H]3CCCc4ccccc43)CC2)c2ccccc21] |
| 27 | 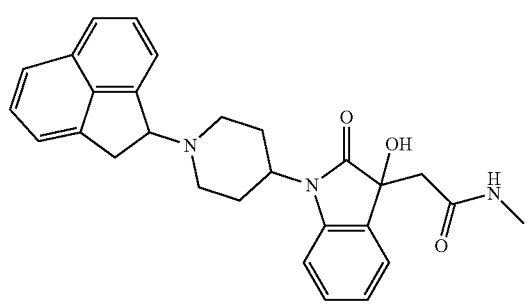 [SMILES: CNC(=O)CC1(O)C(=O)N(C2CCN(C3Cc4cccc5cccc3c45)CC2)c2ccccc21] |
| 28 | 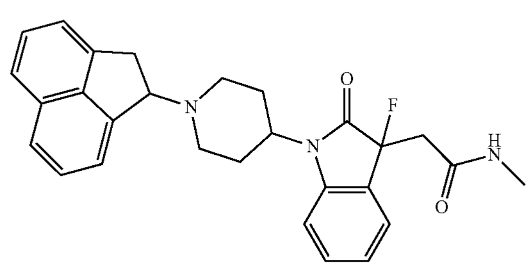 [SMILES: CNC(=O)CC1(F)C(=O)N(C2CCN(C3Cc4cccc5cccc3c45)CC2)c2ccccc21] |

TABLE 1-continued
| No. | Structure |
|---|---|
| 30 | 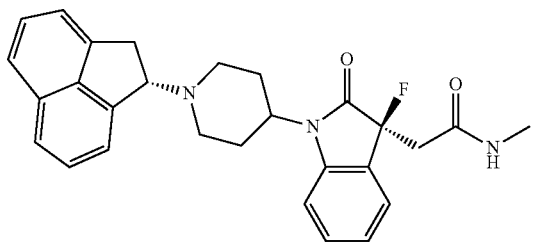 [SMILES: CNC(=O)C[C@@]1(F)C(=O)N(C2CCN([C@H]3Cc4cccc5cccc3c45)CC2)c2ccccc21] |
| 31 | 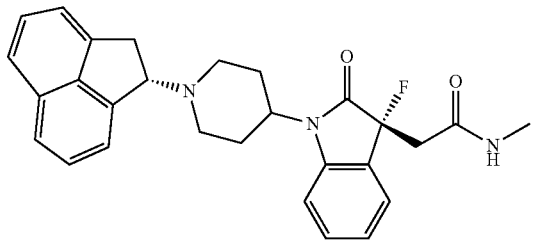 [SMILES: CNC(=O)C[C@]1(F)C(=O)N(C2CCN([C@H]3Cc4cccc5cccc3c45)CC2)c2ccccc21] |
| 32 | 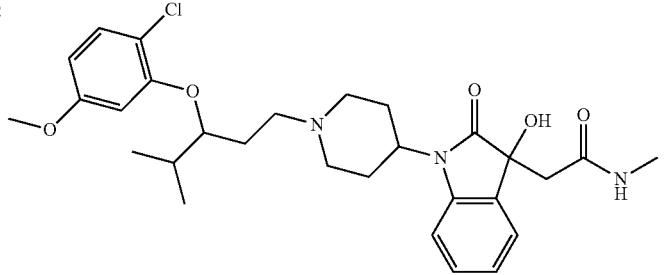 |
| 33 | 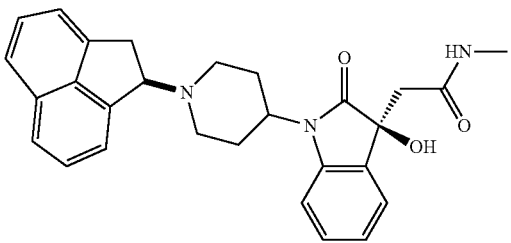 [SMILES: CNC(=O)C[C@@]1(O)C(=O)N(C2CCN([C@@H]3Cc4cccc5cccc3c45)CC2)c2ccccc21] |
| 34 | 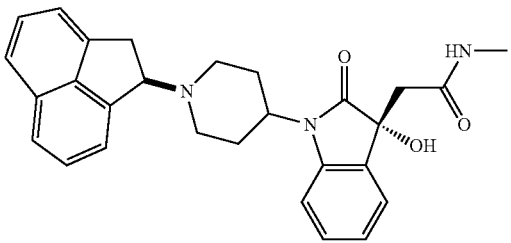 [SMILES: CNC(=O)C[C@]1(O)C(=O)N(C2CCN([C@@H]3Cc4cccc5cccc3c45)CC2)c2ccccc21] |
| 35 | 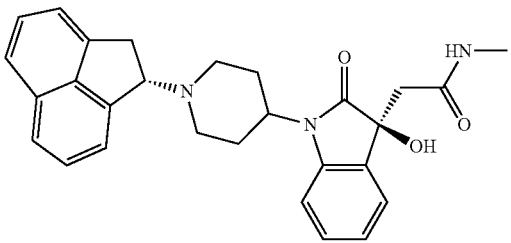 [SMILES: CNC(=O)C[C@@]1(O)C(=O)N(C2CCN([C@H]3Cc4cccc5cccc3c45)CC2)c2ccccc21] |

TABLE 1-continued

| No. | Structure |
|-----|-----------|
| 36  | 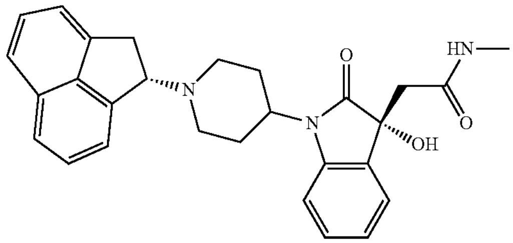 [SMILES: CNC(=O)C[C@]1(O)C(=O)N(C2CCN([C@H]3Cc4cccc5cccc3c45)CC2)c2ccccc21]          |
| 37  | 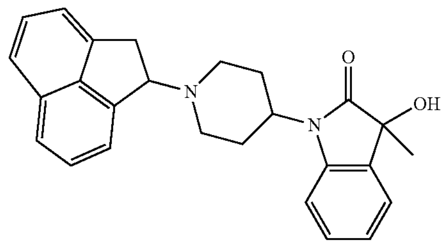 [SMILES: CC1(O)C(=O)N(C2CCN(C3Cc4cccc5cccc3c45)CC2)c2ccccc21]          |
| 38  | 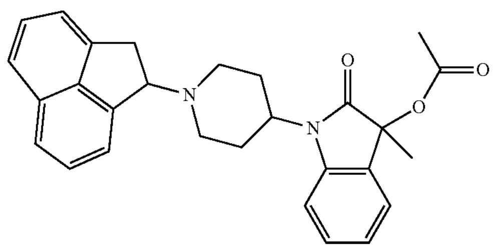 [SMILES: CC(=O)OC1(C)C(=O)N(C2CCN(C3Cc4cccc5cccc3c45)CC2)c2ccccc21]          |
| 39  | 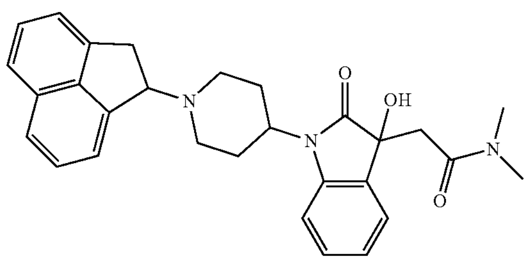 [SMILES: CN(C)C(=O)CC1(O)C(=O)N(C2CCN(C3Cc4cccc5cccc3c45)CC2)c2ccccc21]          |
| 40  | 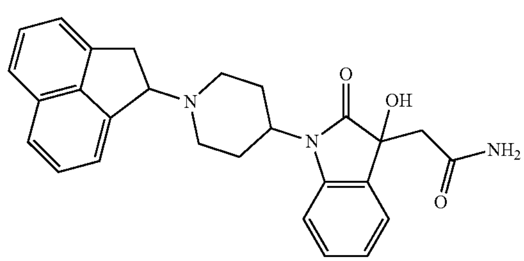 [SMILES: NC(=O)CC1(O)C(=O)N(C2CCN(C3Cc4cccc5cccc3c45)CC2)c2ccccc21]          |
| 41  | 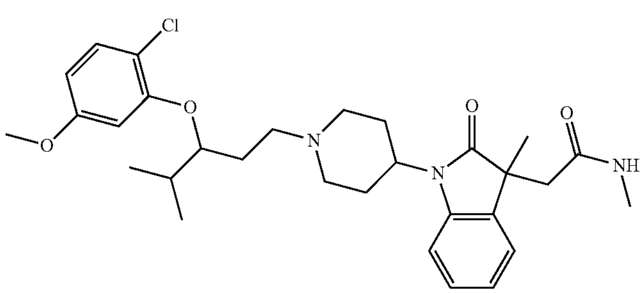          |

TABLE 1-continued
| No. | Structure |
|---|---|
| 42 | 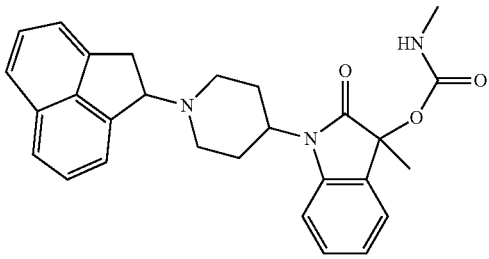 [SMILES: CNC(=O)OC1(C)C(=O)N(C2CCN(C3Cc4cccc5cccc3c45)CC2)c2ccccc21] |
| 43 | 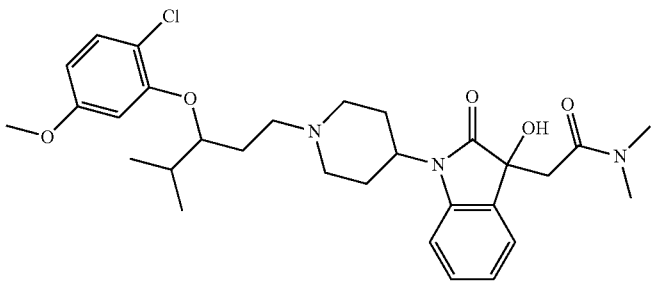 |
| 44 | 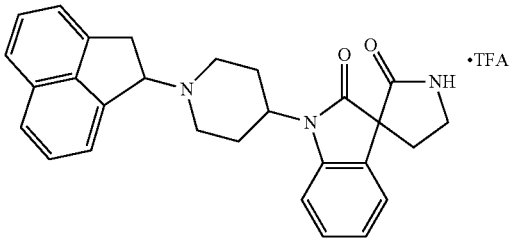 [SMILES: O=C1NCCC12C(=O)N(C1CCN(C3Cc4cccc5cccc3c45)CC1)c1ccccc12] |
| 45 | 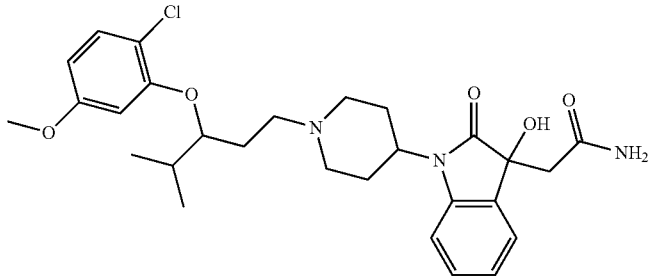 [SMILES: COc1ccc(Cl)c(OC(CCN2CCC(N3C(=O)C(O)(CC(N)=O)c4ccccc43)CC2)C(C)C)c1] |
| 46 | 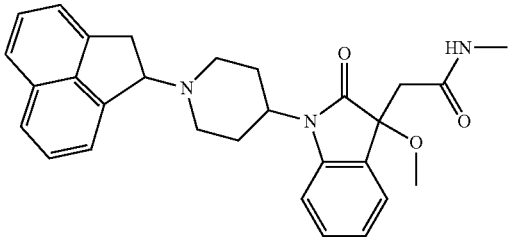 [SMILES: CNC(=O)CC1(OC)C(=O)N(C2CCN(C3Cc4cccc5cccc3c45)CC2)c2ccccc21] |
| 47 | 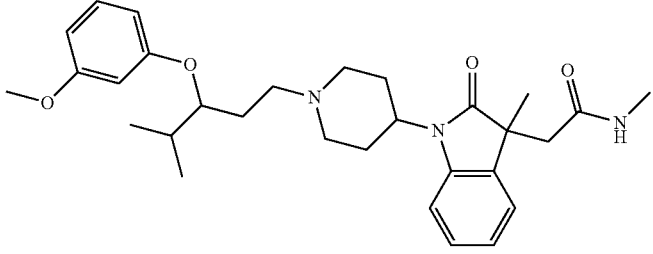 |

TABLE 1-continued
| No. | Structure |
|---|---|
| 48 | 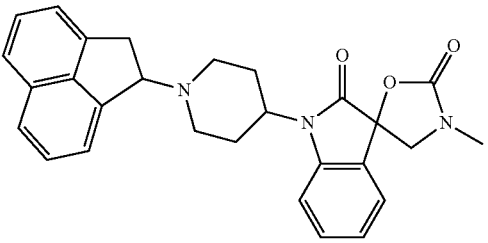 [SMILES: CN1CC2(OC1=O)C(=O)N(C1CCN(C3Cc4cccc5cccc3c45)CC1)c1ccccc12] |
| 49 | 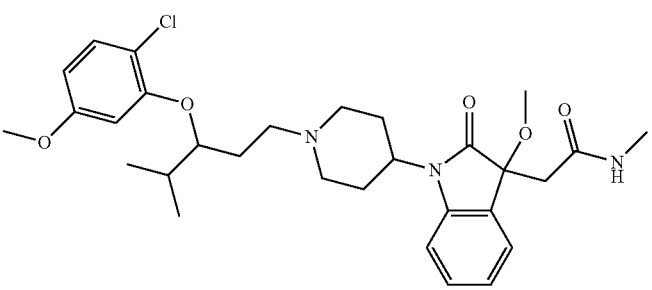 |
| 50 | 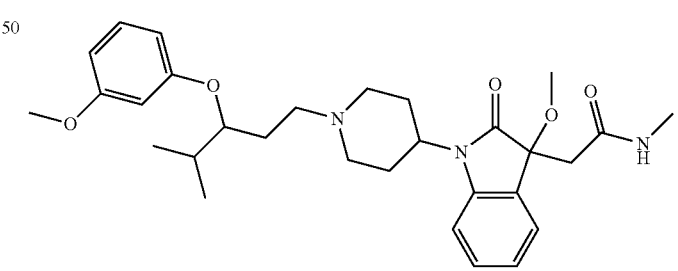 |
| 51 | 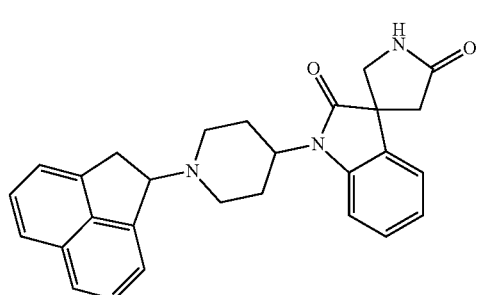 |
| 52 | 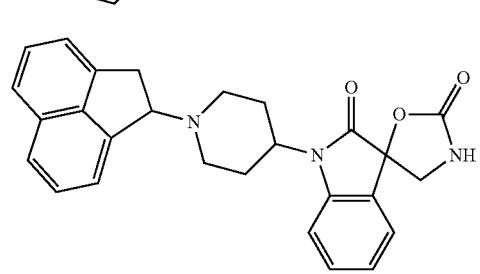 |
| 53 | 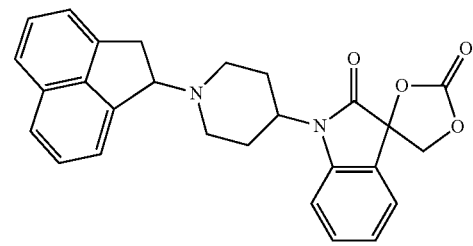 [SMILES: O=C1OCC2(O1)C(=O)N(C1CCN(C3Cc4cccc5cccc3c45)CC1)c1ccccc12] |

TABLE 1-continued
| No. | Structure |
|-----|-----------|
| 54 | 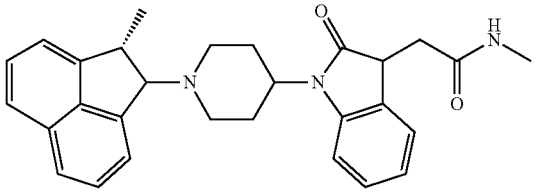 [SMILES: CNC(=O)CC1C(=O)N(C2CCN(C3c4cccc5cccc(c45)[C@@H]3C)CC2)c2ccccc21] |
| 55 | 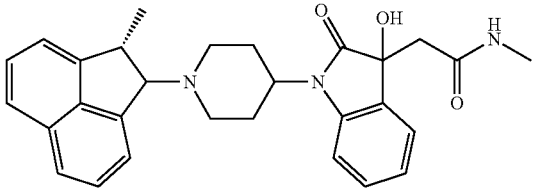 [SMILES: CNC(=O)CC1(O)C(=O)N(C2CCN(C3c4cccc5cccc(c45)[C@@H]3C)CC2)c2ccccc21] |
| 56 | 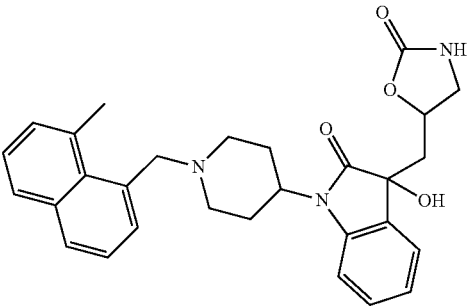 [SMILES: Cc1cccc2cccc(CN3CCC(N4C(=O)C(O)(CC5CNC(=O)O5)c5ccccc54)CC3)c12] |
| 57 | 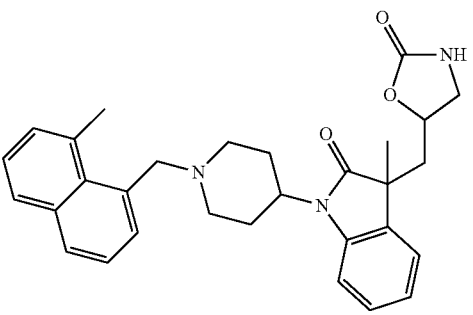 [SMILES: Cc1cccc2cccc(CN3CCC(N4C(=O)C(C)(CC5CNC(=O)O5)c5ccccc54)CC3)c12] |
| 58 | 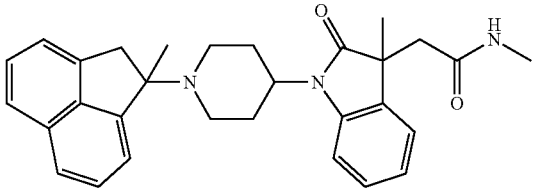 [SMILES: CNC(=O)CC1(C)C(=O)N(C2CCN(C3(C)Cc4cccc5cccc3c45)CC2)c2ccccc21] |
| 59 | 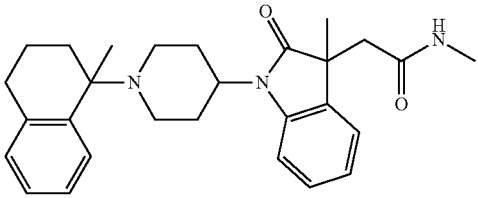 [SMILES: CNC(=O)CC1(C)C(=O)N(C2CCN(C3(C)CCCc4ccccc43)CC2)c2ccccc21] |

TABLE 1-continued
| No. | Structure |
|---|---|
| 60 | 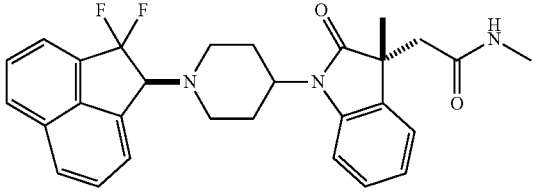 [SMILES: CNC(=O)C[C@@]1(C)C(=O)N(C2CCN([C@H]3c4cccc5cccc(c45)C3(F)F)CC2)c2ccccc21] |
| 61 | 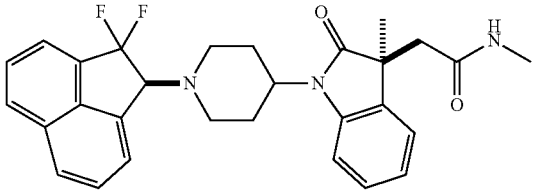 [SMILES: CNC(=O)C[C@]1(C)C(=O)N(C2CCN([C@H]3c4cccc5cccc(c45)C3(F)F)CC2)c2ccccc21] |
| 62 | 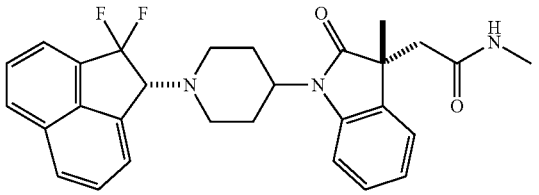 [SMILES: CNC(=O)C[C@@]1(C)C(=O)N(C2CCN([C@@H]3c4cccc5cccc(c45)C3(F)F)CC2)c2ccccc21] |
| 63 | 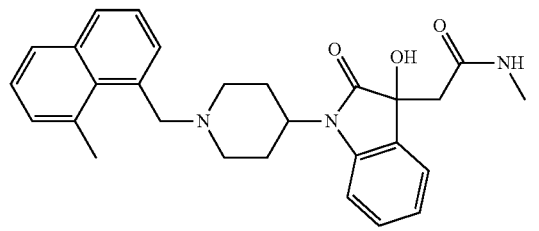 [SMILES: CNC(=O)CC1(O)C(=O)N(C2CCN(Cc3cccc4cccc(C)c34)CC2)c2ccccc21] |
| 64 | 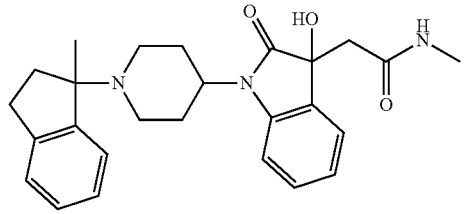 [SMILES: CNC(=O)CC1(O)C(=O)N(C2CCN(C3(C)CCc4ccccc43)CC2)c2ccccc21] |
| 65 | 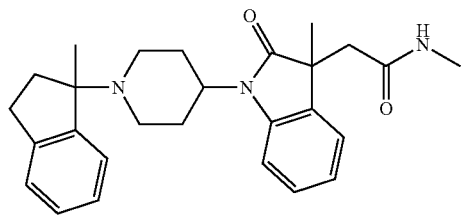 [SMILES: CNC(=O)CC1(C)C(=O)N(C2CCN(C3(C)CCc4ccccc43)CC2)c2ccccc21] |
| 66 | 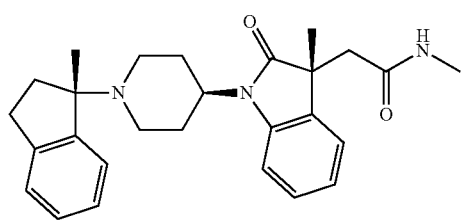 |

TABLE 1-continued

| No. | Structure |
| --- | --- |
| 67 | 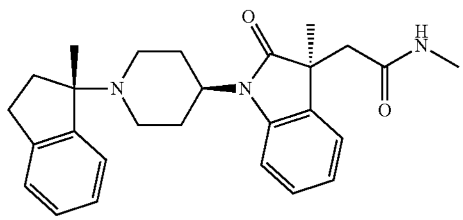 |
| 68 | 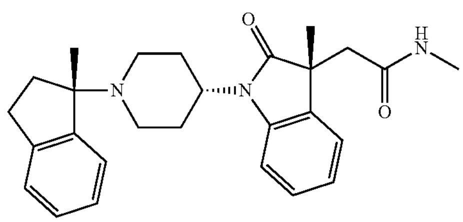 |
| 69 | 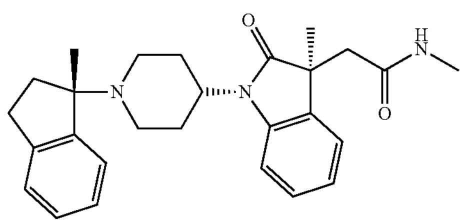 |
| 70 | 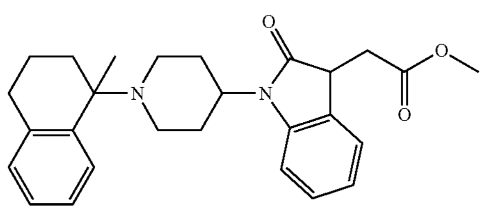 [SMILES: COC(=O)CC1C(=O)N(C2CCN(C3(C)CCCc4ccccc43)CC2)c2ccccc21] |
| 71 | 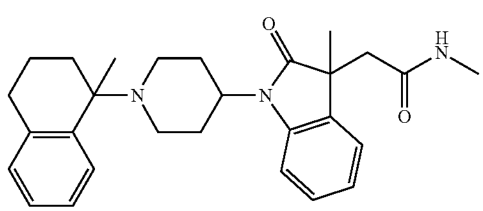 [SMILES: CNC(=O)CC1(C)C(=O)N(C2CCN(C3(C)CCCc4ccccc43)CC2)c2ccccc21] |
| 72 | 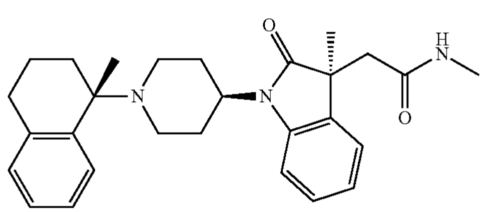 |
| 73 | 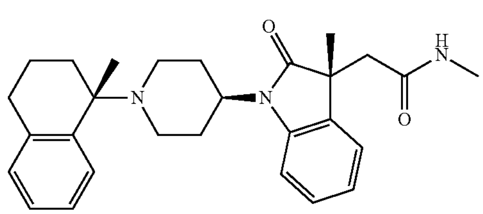 |

TABLE 1-continued
| No. | Structure |
|---|---|
| 74 | 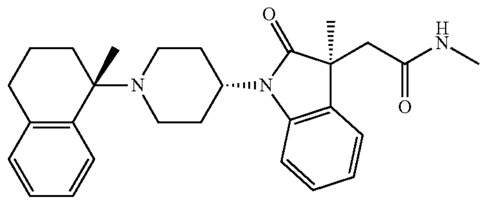 |
| 75 | 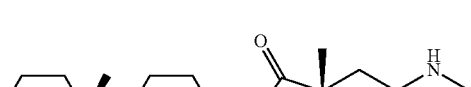 |
| 76 | 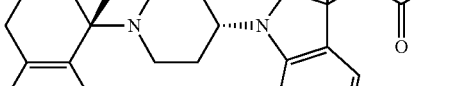 |
| 77 | 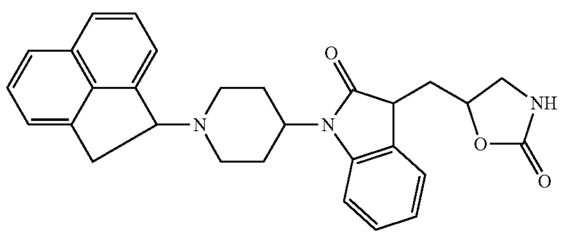 [SMILES: O=C1NCC(CC2C(=O)N(C3CCN(C4Cc5cccc6cccc4c56)CC3)c3ccccc32)O1] |
| 78 | 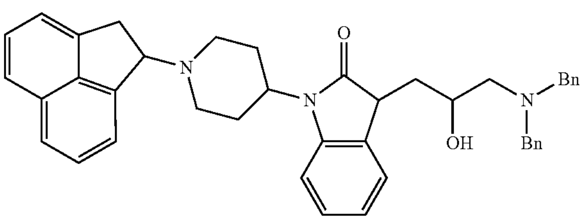 [SMILES: O=C1C(CC(O)CN(Cc2ccccc2)Cc2ccccc2)c2ccccc2N1C1CCN(C2Cc3cccc4cccc2c34)CC1] |
| 79 | 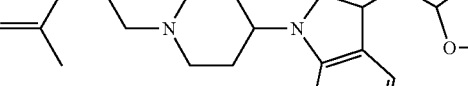 |
| 80 | 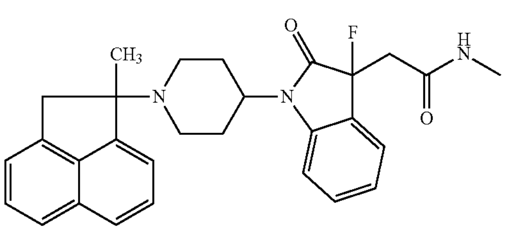 [SMILES: CNC(=O)CC1(F)C(=O)N(C2CCN(C3(C)Cc4cccc5cccc3c45)CC2)c2ccccc21] |

TABLE 1-continued

| No. | Structure |
|---|---|
| 86 | 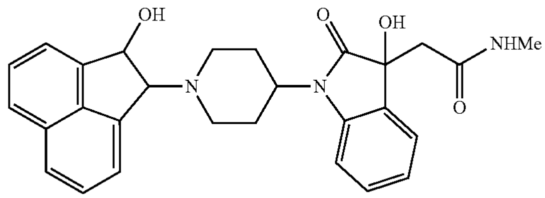 [SMILES: CNC(=O)CC1(O)C(=O)N(C2CCN(C3c4cccc5cccc(c45)C3O)CC2)c2ccccc21] |
| 87 | 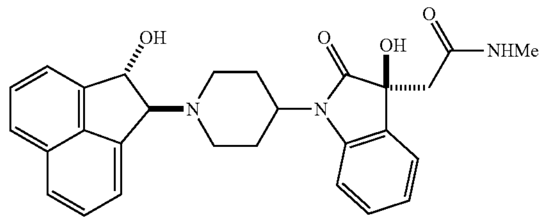 [SMILES: CNC(=O)C[C@@]1(O)C(=O)N(C2CCN([C@H]3c4cccc5cccc(c45)[C@@H]3O)CC2)c2ccccc21] |
| 88 | 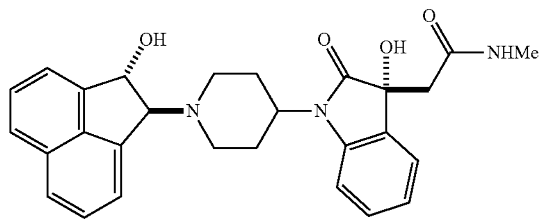 [SMILES: CNC(=O)C[C@]1(O)C(=O)N(C2CCN([C@H]3c4cccc5cccc(c45)[C@@H]3O)CC2)c2ccccc21] |
| 89 | 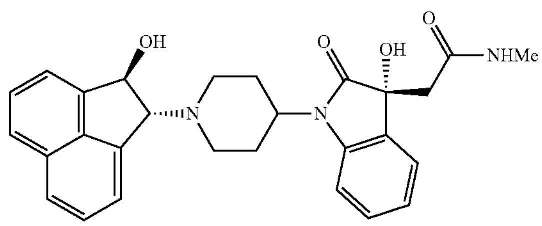 [SMILES: CNC(=O)C[C@]1(O)C(=O)N(C2CCN([C@@H]3c4cccc5cccc(c45)[C@H]3O)CC2)c2ccccc21] |
| 90 | 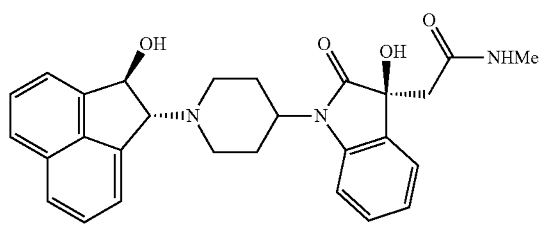 [SMILES: CNC(=O)C[C@@]1(O)C(=O)N(C2CCN([C@@H]3c4cccc5cccc(c45)[C@H]3O)CC2)c2ccccc21] |
| 91 | 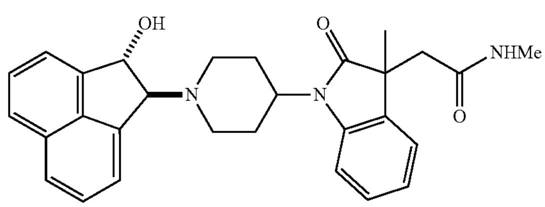 [SMILES: CNC(=O)CC1(C)C(=O)N(C2CCN([C@H]3c4cccc5cccc(c45)[C@@H]3O)CC2)c2ccccc21] |
| 93 | 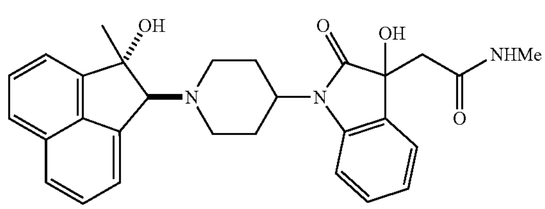 [SMILES: CNC(=O)CC1(O)C(=O)N(C2CCN([C@H]3c4cccc5cccc(c45)[C@]3(C)O)CC2)c2ccccc21] |

TABLE 1-continued
| No. | Structure |
|-----|-----------|
| 94 | 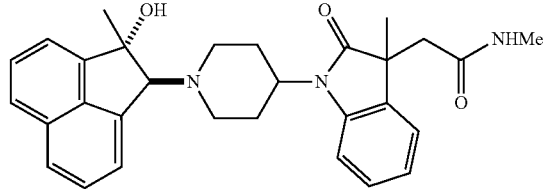 [SMILES: CNC(=O)CC1(C)C(=O)N(C2CCN([C@H]3c4cccc5cccc(c45)[C@]3(C)O)CC2)c2ccccc21] |
| 95 | 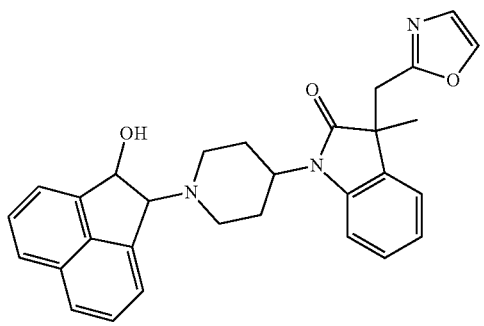 [SMILES: CC1(Cc2ncco2)C(=O)N(C2CCN(C3c4cccc5cccc(c45)C3O)CC2)c2ccccc21] |
| 96 | 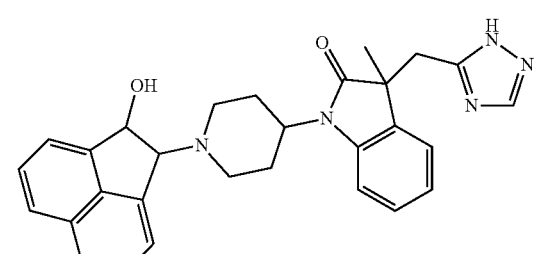 |
| 97 | 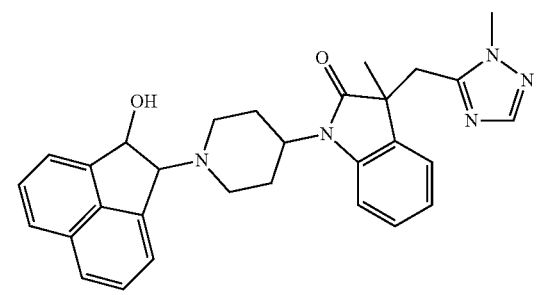 [SMILES: Cn1ncnc1CC1(C)C(=O)N(C2CCN(C3c4cccc5cccc(c45)C3O)CC2)c2ccccc21] |
| 98 | 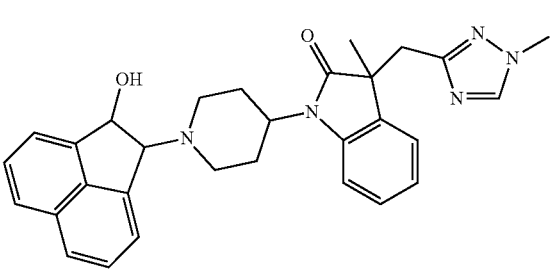 [SMILES: Cn1cnc(CC2(C)C(=O)N(C3CCN(C4c5cccc6cccc(c56)C4O)CC3)c3ccccc32)n1] |
| 99 | 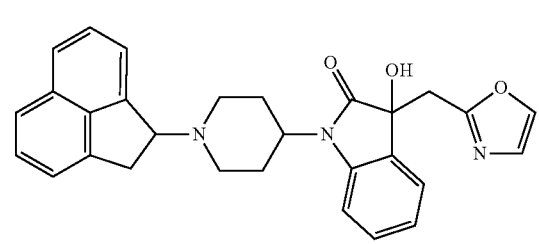 [SMILES: O=C1N(C2CCN(C3Cc4cccc5cccc3c45)CC2)c2ccccc2C1(O)Cc1ncco1] |

TABLE 1-continued
| No. | Structure |
|---|---|
| 100 | 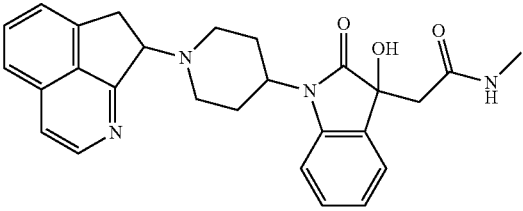 [SMILES: CNC(=O)CC1(O)C(=O)N(C2CCN(C3Cc4cccc5ccnc3c45)CC2)c2ccccc21] |
| 101 | 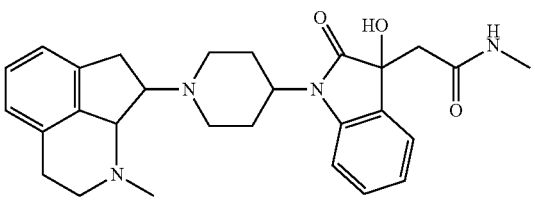 [SMILES: CNC(=O)CC1(O)C(=O)N(C2CCN(C3Cc4cccc5c4C3N(C)CC5)CC2)c2ccccc21] |
| 102 | 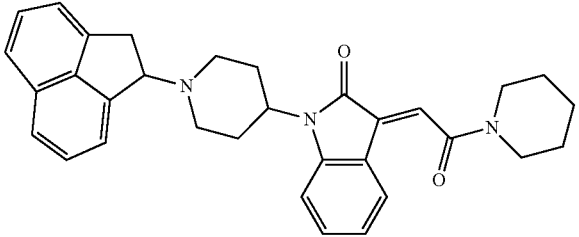 [SMILES: O=C(/C=C1/C(=O)N(C2CCN(C3Cc4cccc5cccc3c45)CC2)c2ccccc21)N1CCCCC1] |
| 104 | 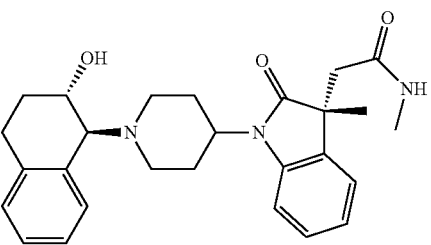 [SMILES: CNC(=O)C[C@@]1(C)C(=O)N(C2CCN([C@H]3c4ccccc4CC[C@@H]3O)CC2)c2ccccc21] |
| 105 | 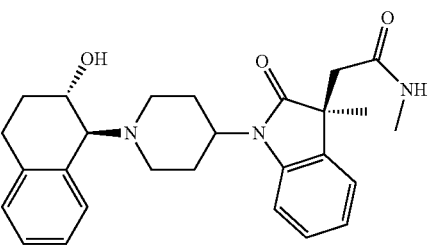 [SMILES: CNC(=O)C[C@]1(C)C(=O)N(C2CCN([C@H]3c4ccccc4CC[C@@H]3O)CC2)c2ccccc21] |
| 106 | 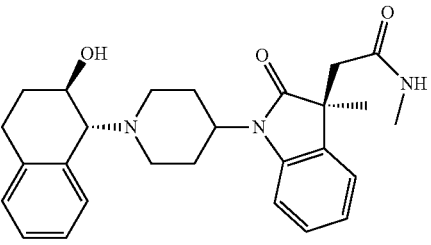 [SMILES: CNC(=O)C[C@]1(C)C(=O)N(C2CCN([C@@H]3c4ccccc4CC[C@H]3O)CC2)c2ccccc21] |

TABLE 1-continued
| No. | Structure |
|---|---|
| 107 | 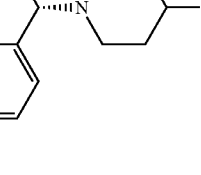 |
| 108 | 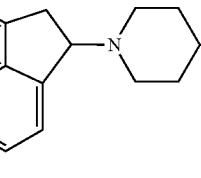 |
| 109 | 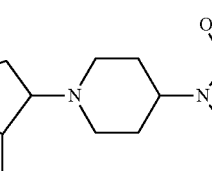 |
| 110 | 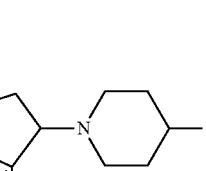 |
| 111 | 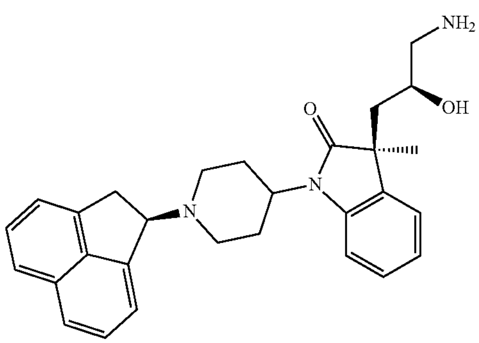 [SMILES: C[C@@]1(C[C@H](O)CN)C(=O)N(C2CCN([C@@H]3Cc4cccc5cccc3c45)CC2)c2ccccc21] |
| 112 | 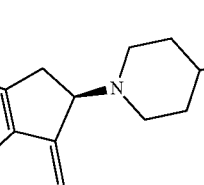 |

TABLE 1-continued
| No. | Structure |
|---|---|
| 113 | 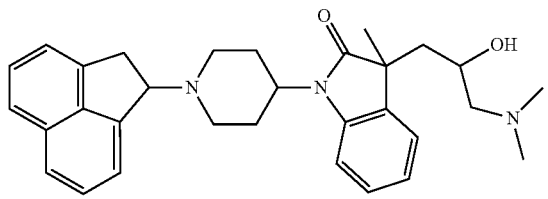 [SMILES: CN(C)CC(O)CC1(C)C(=O)N(C2CCN(C3Cc4cccc5cccc3c45)CC2)c2ccccc21] |
| 114 | 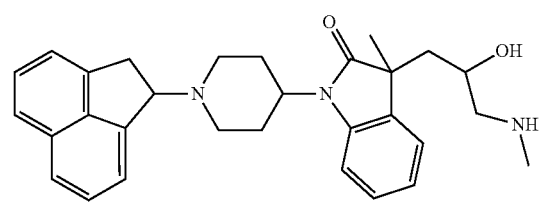 [SMILES: CNCC(O)CC1(C)C(=O)N(C2CCN(C3Cc4cccc5cccc3c45)CC2)c2ccccc21] |
| 115 | 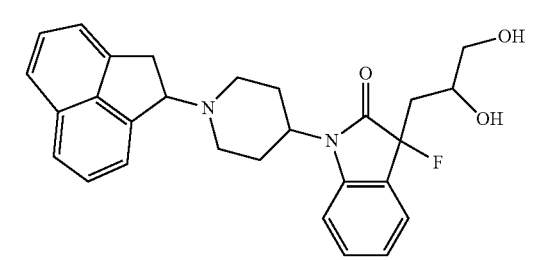 [SMILES: O=C1N(C2CCN(C3Cc4cccc5cccc3c45)CC2)c2ccccc2C1(F)CC(O)CO] |
| 118 | 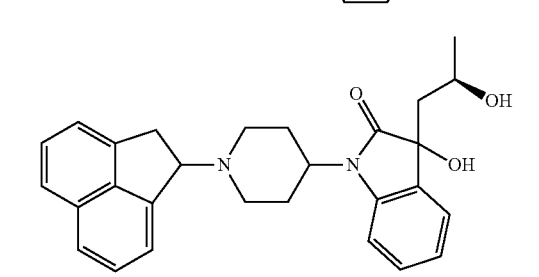 |
| 119 | 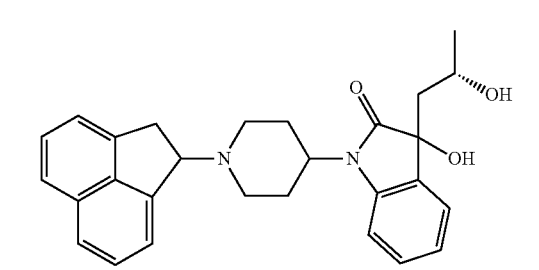 [SMILES: C[C@H](O)CC1(O)C(=O)N(C2CCN(C3Cc4cccc5cccc3c45)CC2)c2ccccc21] |
| 120 | 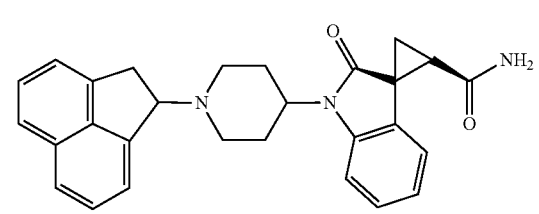 |
| 121 | 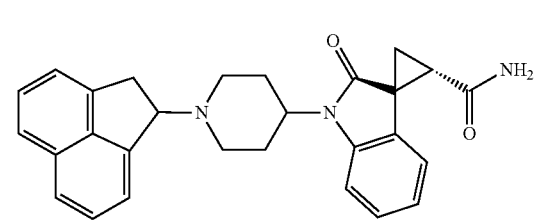 |

TABLE 1-continued

| No. | Structure |
|-----|-----------|
| 122 | 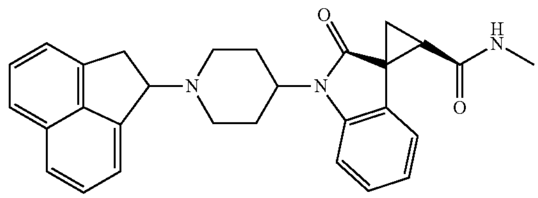 |
| 123 | 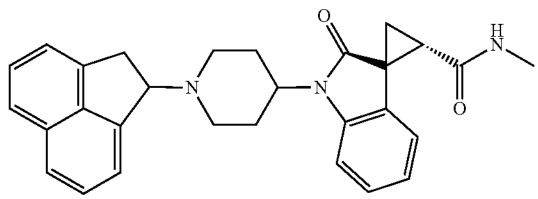 |
| 124 | 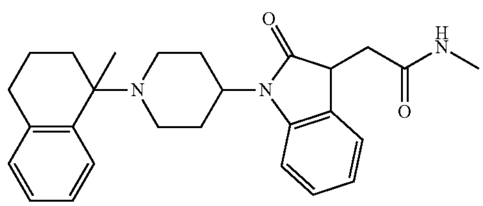 [SMILES: CNC(=O)CC1C(=O)N(C2CCN(C3(C)CCCc4ccccc43)CC2)c2ccccc21] |
| 125 | 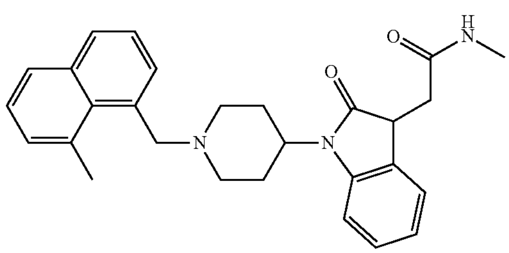 [SMILES: CNC(=O)CC1C(=O)N(C2CCN(Cc3cccc4cccc(C)c34)CC2)c2ccccc21] |
| 126 | 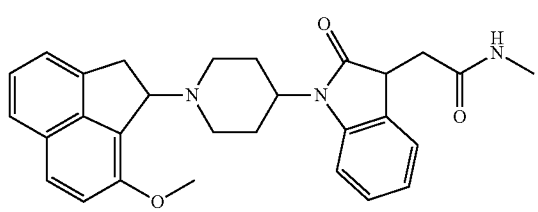 [SMILES: CNC(=O)CC1C(=O)N(C2CCN(C3Cc4cccc5ccc(OC)c3c45)CC2)c2ccccc21] |
| 127 | 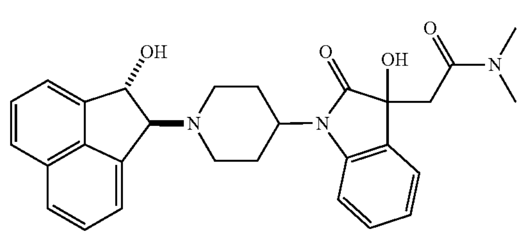 [SMILES: CN(C)C(=O)CC1(O)C(=O)N(C2CCN([C@H]3c4cccc5cccc(c45)[C@@H]3O)CC2)c2ccccc21] |
| 128 | 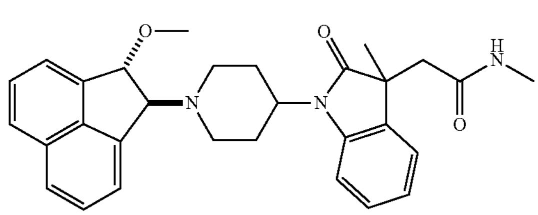 [SMILES: CNC(=O)CC1(C)C(=O)N(C2CCN([C@H]3c4cccc5cccc(c45)[C@@H]3OC)CC2)c2ccccc21] |

TABLE 1-continued

| No. | Structure |
|-----|-----------|
| 129 | 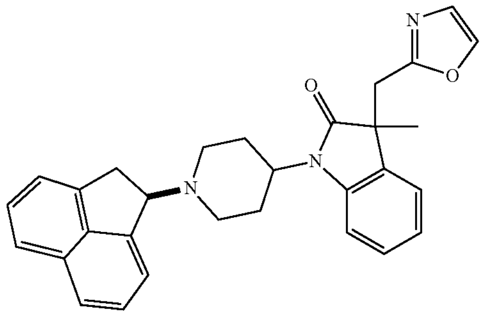 |
| 130 | 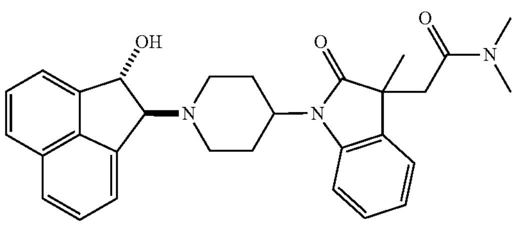 [SMILES: CN(C)C(=O)CC1(C)C(=O)N(C2CCN([C@H]3c4cccc5cccc(c45)[C@@H]3O)CC2)c2ccccc21] |
| 131 | 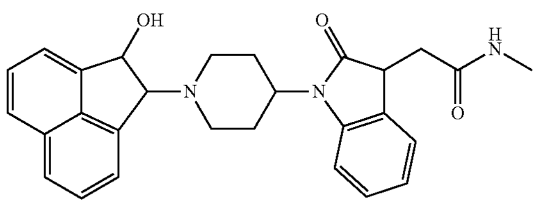 [SMILES: CNC(=O)CC1C(=O)N(C2CCN(C3c4cccc5cccc(c45)C3O)CC2)c2ccccc21] |
| 132 | 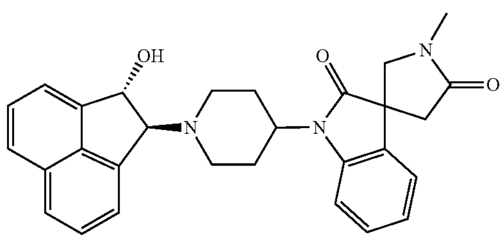 [SMILES: CN1CC2(CC1=O)C(=O)N(C1CCN([C@H]3c4cccc5cccc(c45)[C@@H]3O)CC1)c1ccccc12] |
| 133 | 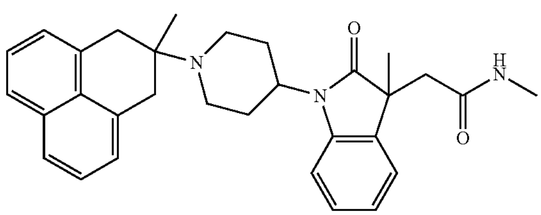 [SMILES: CNC(=O)CC1(C)C(=O)N(C2CCN(C3(C)Cc4cccc5cccc(c45)C3)CC2)c2ccccc21] |
| 134 | 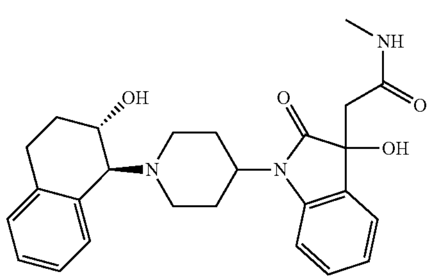 [SMILES: CNC(=O)CC1(O)C(=O)N(C2CCN([C@H]3c4ccccc4CC[C@@H]3O)CC2)c2ccccc21] |

TABLE 1-continued
| No. | Structure |
|---|---|
| 135 | 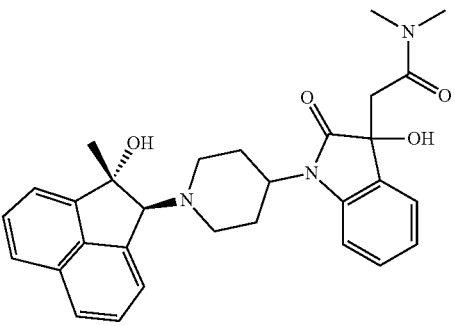 [SMILES: CN(C)C(=O)CC1(O)C(=O)N(C2CCN([C@H]3c4cccc5cccc(c45)[C@]3(C)O)CC2)c2ccccc21] |
| 136 | 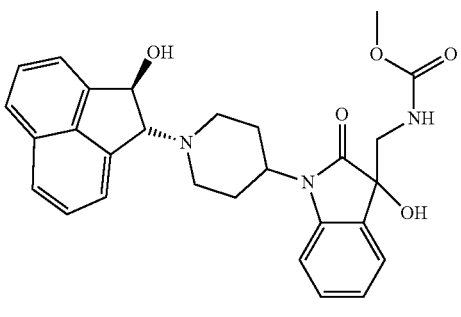 |
| 137 | 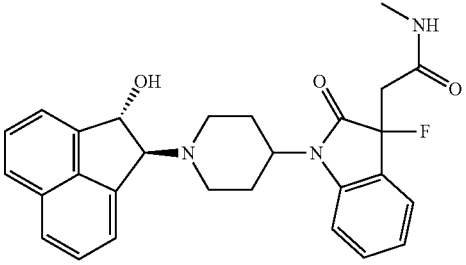 [SMILES: CNC(=O)CC1(F)C(=O)N(C2CCN([C@H]3c4cccc5cccc(c45)[C@@H]3O)CC2)c2ccccc21] |
| 138 | 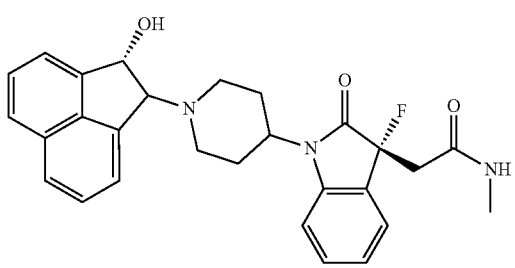 [SMILES: CNC(=O)C[C@]1(F)C(=O)N(C2CCN(C3c4cccc5cccc(c45)[C@@H]3O)CC2)c2ccccc21] |
| 139 | 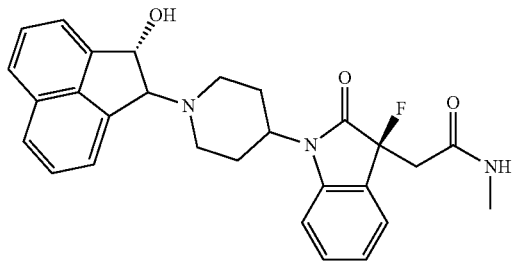 [SMILES: CNC(=O)C[C@@]1(F)C(=O)N(C2CCN(C3c4cccc5cccc(c45)[C@@H]3O)CC2)c2ccccc21] |

TABLE 1-continued
| No. | Structure |
|---|---|
| 140 | 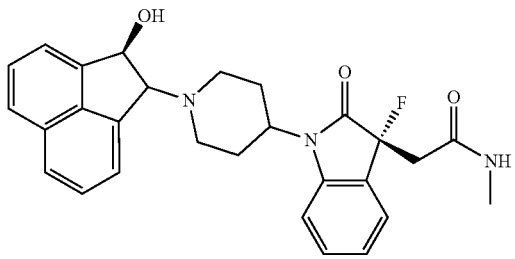 [SMILES: CNC(=O)C[C@]1(F)C(=O)N(C2CCN(C3c4cccc5cccc(c45)[C@H]3O)CC2)c2ccccc21] |
| 141 | 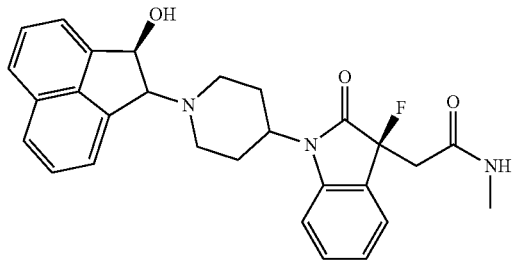 [SMILES: CNC(=O)C[C@@]1(F)C(=O)N(C2CCN(C3c4cccc5cccc(c45)[C@H]3O)CC2)c2ccccc21] |
| 142 | 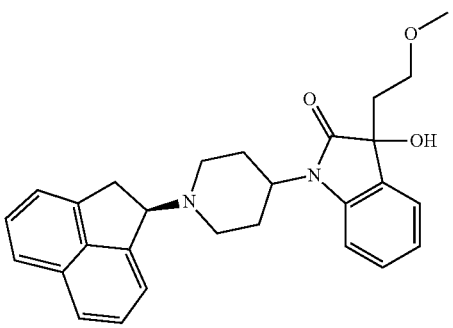 [SMILES: COCCC1(O)C(=O)N(C2CCN([C@@H]3Cc4cccc5cccc3c45)CC2)c2ccccc21] |
| 143 | 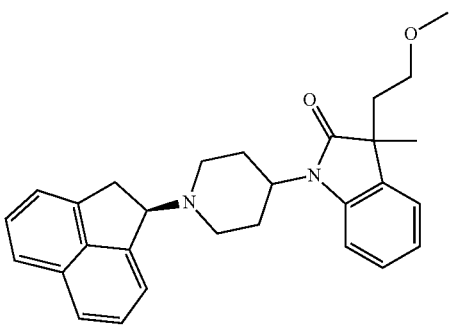 [SMILES: COCCC1(C)C(=O)N(C2CCN([C@@H]3Cc4cccc5cccc3c45)CC2)c2ccccc21] |
| 144 | 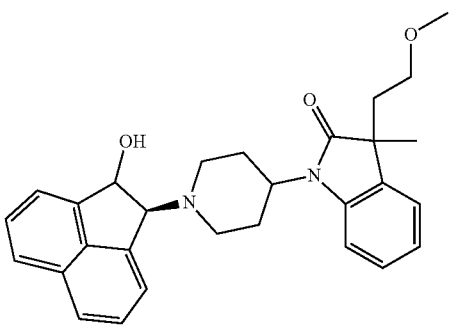 [SMILES: COCCC1(C)C(=O)N(C2CCN([C@H]3c4cccc5cccc(c45)C3O)CC2)c2ccccc21] |

TABLE 1-continued
| No. | Structure |
|---|---|
| 145 | 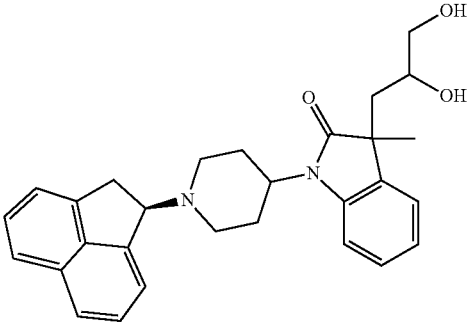 [SMILES: CC1(CC(O)CO)C(=O)N(C2CCN([C@@H]3Cc4cccc5cccc3c45)CC2)c2ccccc21] |
| 146 | 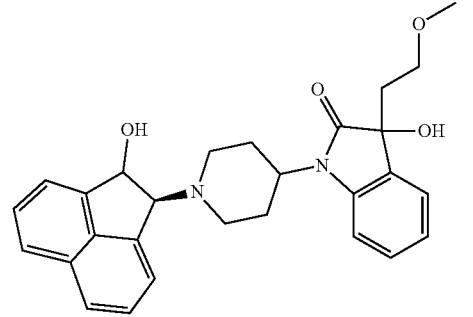 [SMILES: COCCC1(O)C(=O)N(C2CCN([C@H]3c4cccc5cccc(c45)C3O)CC2)c2ccccc21] |
| 147 | 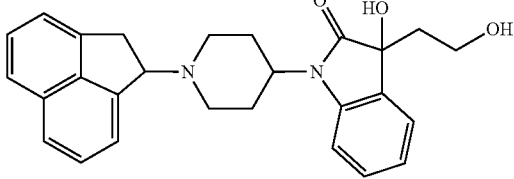 |
| 148 | 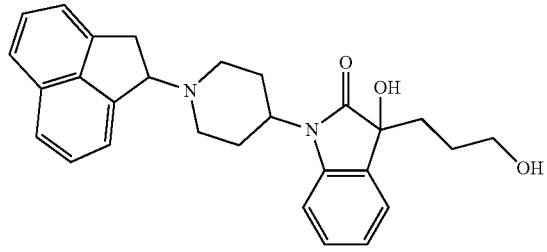 [SMILES: O=C1N(C2CCN(C3Cc4cccc5cccc3c45)CC2)c2ccccc2C1(O)CCCO] |
| 149 | 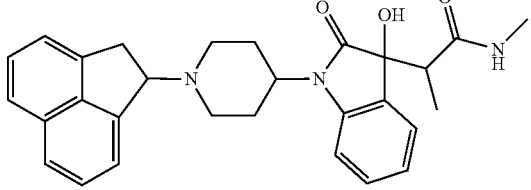 |
| 150 | 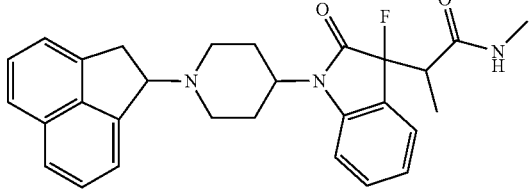 |

TABLE 1-continued
| No. | Structure |
|---|---|
| 151 | 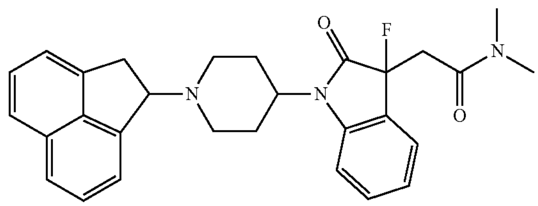 [SMILES: CN(C)C(=O)CC1(F)C(=O)N(C2CCN(C3Cc4cccc5cccc3c45)CC2)c2ccccc21] |
| 152 | 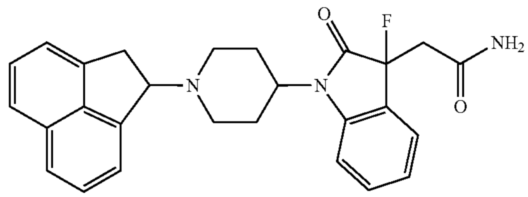 [SMILES: NC(=O)CC1(F)C(=O)N(C2CCN(C3Cc4cccc5cccc3c45)CC2)c2ccccc21] |
| 153 | 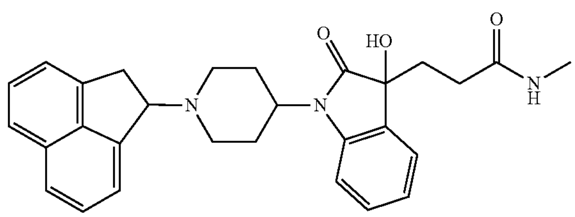 [SMILES: CNC(=O)CCC1(O)C(=O)N(C2CCN(C3Cc4cccc5cccc3c45)CC2)c2ccccc21] |
| 154 | 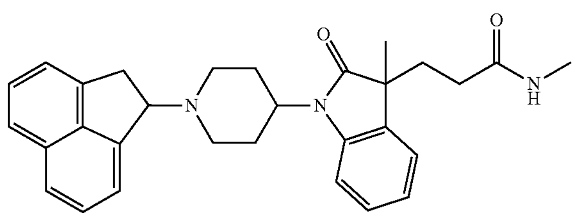 [SMILES: CNC(=O)CCC1(C)C(=O)N(C2CCN(C3Cc4cccc5cccc3c45)CC2)c2ccccc21] |
| 155 | 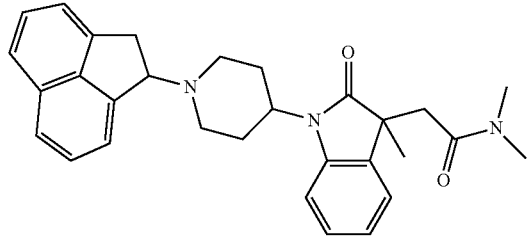 [SMILES: CN(C)C(=O)CC1(C)C(=O)N(C2CCN(C3Cc4cccc5cccc3c45)CC2)c2ccccc21] |
| 156 | 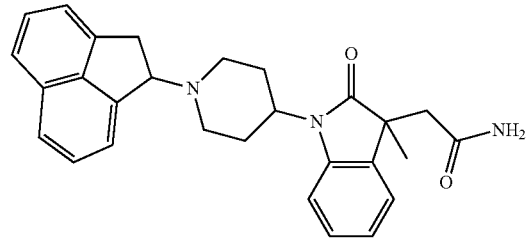 [SMILES: CC1(CC(N)=O)C(=O)N(C2CCN(C3Cc4cccc5cccc3c45)CC2)c2ccccc21] |

TABLE 1-continued
| No. | Structure |
|---|---|
| 157 | 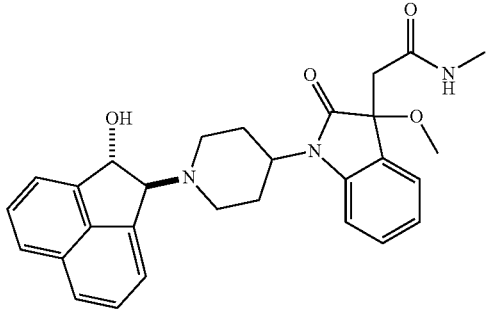 |
| 158 | 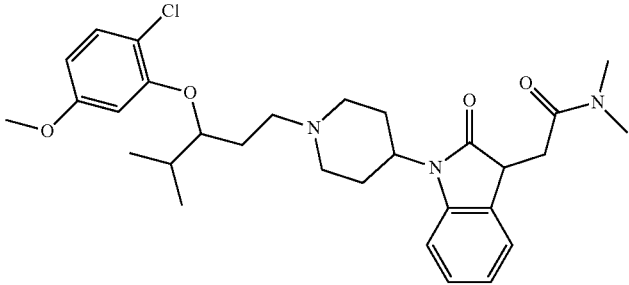 |
| 159 | 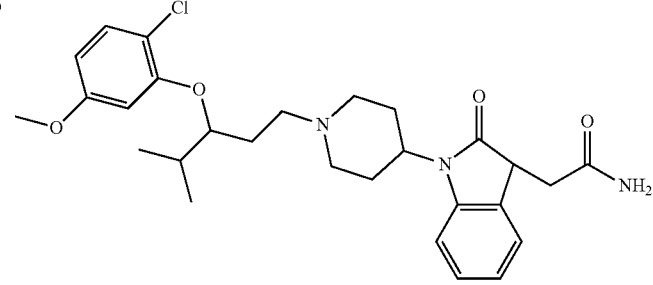 |
| 160 | 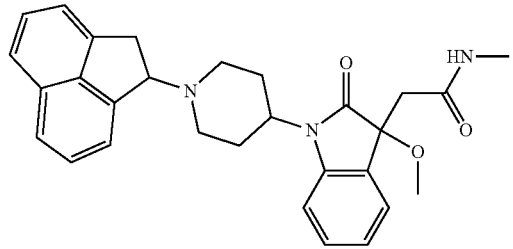 [SMILES: CNC(=O)CC1(OC)C(=O)N(C2CCN(C3Cc4cccc5cccc3c45)CC2)c2ccccc21] |
| 161 | 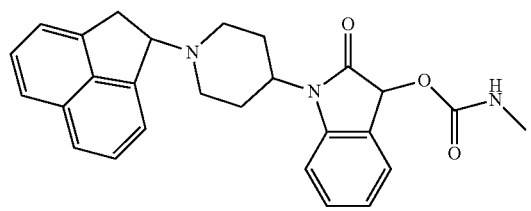 [SMILES: CNC(=O)OC1C(=O)N(C2CCN(C3Cc4cccc5cccc3c45)CC2)c2ccccc21] |

TABLE 1-continued
| No. | Structure |
|-----|-----------|
| 162 | 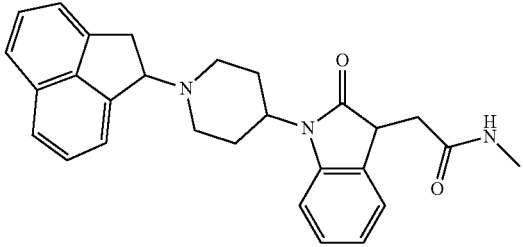 [SMILES: CNC(=O)CC1C(=O)N(C2CCN(C3Cc4cccc5cccc3c45)CC2)c2ccccc21] |
| 163 | 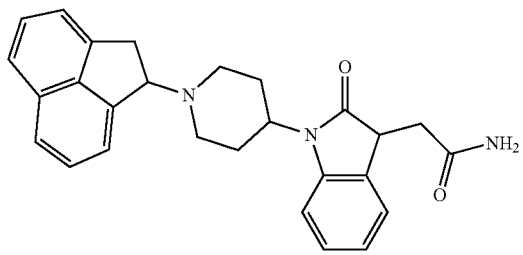 [SMILES: NC(=O)CC1C(=O)N(C2CCN(C3Cc4cccc5cccc3c45)CC2)c2ccccc21] |
| 164 | 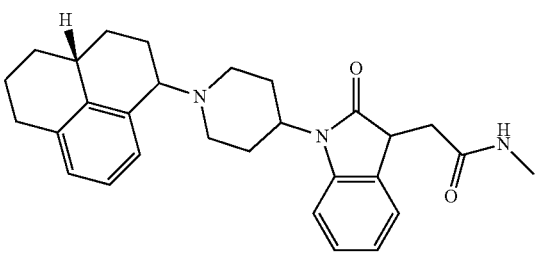 [SMILES: CNC(=O)CC1C(=O)N(C2CCN(C3CC[C@H]4CCCc5cccc3c54)CC2)c2ccccc21] |
| 165 | 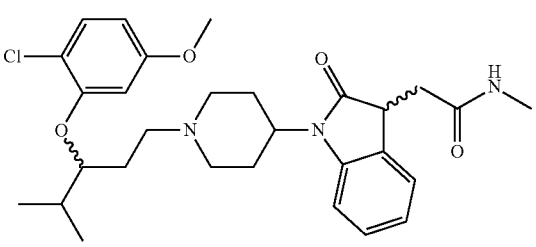 [SMILES: CNC(=O)CC1C(=O)N(C2CCN(CCC(Oc3cc(OC)ccc3Cl)C(C)C)CC2)c2ccccc21] |
| 166 | 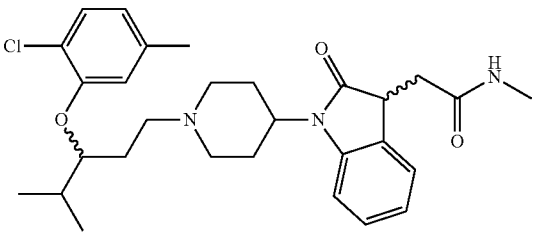 [SMILES: CNC(=O)CC1C(=O)N(C2CCN(CCC(Oc3cc(C)ccc3Cl)C(C)C)CC2)c2ccccc21] |
| 167 | 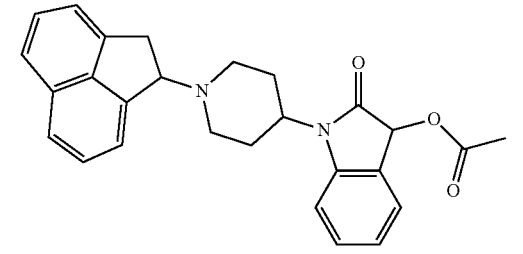 [SMILES: CC(=O)OC1C(=O)N(C2CCN(C3Cc4cccc5cccc3c45)CC2)c2ccccc21] |

TABLE 1-continued
| No. | Structure |
|---|---|
| 168 | 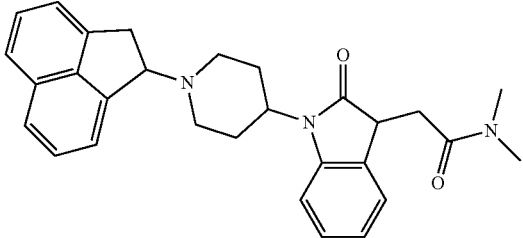 [SMILES: CN(C)C(=O)CC1C(=O)N(C2CCN(C3Cc4cccc5cccc3c45)CC2)c2ccccc21] |
| 169 | 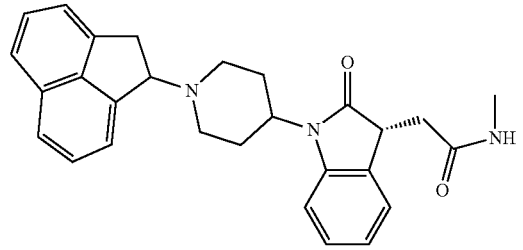 [SMILES: CNC(=O)C[C@H]1C(=O)N(C2CCN(C3Cc4cccc5cccc3c45)CC2)c2ccccc21] |
| 170 | 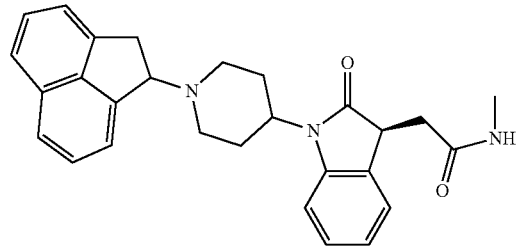 [SMILES: CNC(=O)C[C@@H]1C(=O)N(C2CCN(C3Cc4cccc5cccc3c45)CC2)c2ccccc21] |
| 171 | 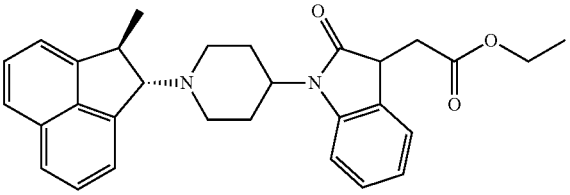 [SMILES: CCOC(=O)CC1C(=O)N(C2CCN([C@@H]3c4cccc5cccc(c45)[C@H]3C)CC2)c2ccccc21] |
| 172 | 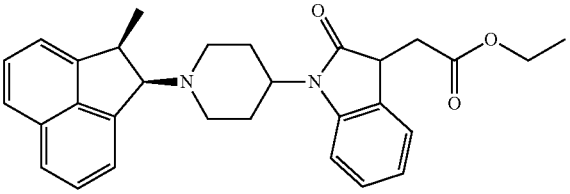 [SMILES: CCOC(=O)CC1C(=O)N(C2CCN([C@H]3c4cccc5cccc(c45)[C@H]3C)CC2)c2ccccc21] |
| 173 | 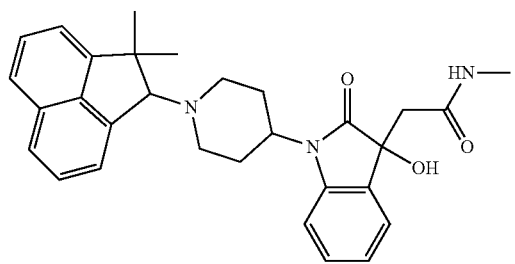 [SMILES: CNC(=O)CC1(O)C(=O)N(C2CCN(C3c4cccc5cccc(c45)C3(C)C)CC2)c2ccccc21] |

TABLE 1-continued

| No. | Structure |
|---|---|
| 174 | 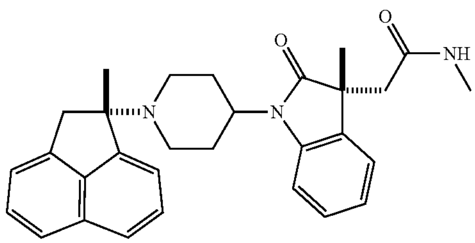 [SMILES: CNC(=O)C[C@@]1(C)C(=O)N(C2CCN([C@@]3(C)Cc4cccc5cccc3c45)CC2)c2ccccc21] |
| 175 | 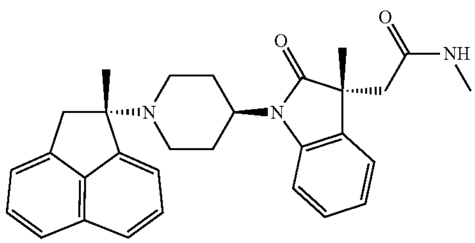 |
| 176 | 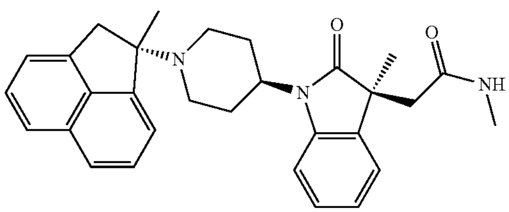 |
| 177 | 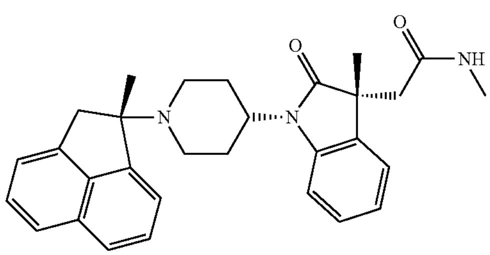 |
| 178 | 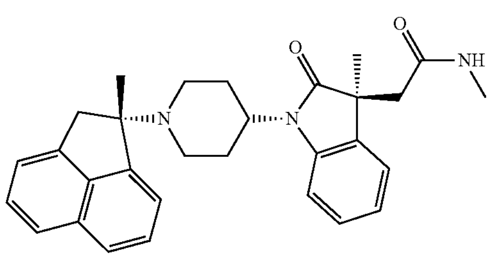 |
| 179 | 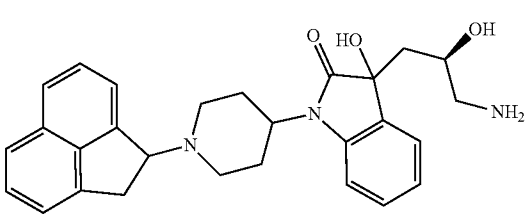 [SMILES: NC[C@H](O)CC1(O)C(=O)N(C2CCN(C3Cc4cccc5cccc3c45)CC2)c2ccccc21] |

TABLE 1-continued

| No. | Structure |
|---|---|
| 180 | 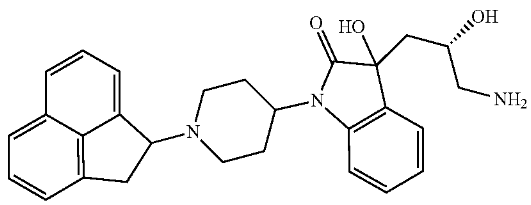 [SMILES: NC[C@@H](O)CC1(O)C(=O)N(C2CCN(C3Cc4cccc5cccc3c45)CC2)c2ccccc21] |

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it or mixtures thereof. Where the compound provided herein contains an alkenyl or alkenylene group, the compound may exist as one of or a mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contains, for example, an aromatic moiety. It follows that a single compound may exhibit more than one type of isomerism.

The compounds provided herein may be enantiomerically pure or diastereomerically pure, such as a single enantiomer or a single diastereomer, or be stereoisomeric mixtures, such as a mixture of enantiomers and/or diastereomers, e.g., a racemic or enantioenriched mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers or diastereomers include synthesis from a suitable optically pure precursor, asymmetric synthesis from achiral starting materials, or resolution of a stereomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, aspartic acid, L-aspartic acid, benzenesulfonic acid, benzoic acid, 4-acetamidobenzoic acid, boric acid, camphoric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, D-gluconic acid, glucuronic acid, D-glucuronic acid, glutamic acid, L-glutamic acid, α-oxoglutaric acid, glycolic acid, hippuric acid, hydrobromic acid, hydrochloric acid, hydroiodic acid, isoethonic acid; (+)-L-lactic acid, (±)-DL-lactic acid, lactobionic acid, lauric acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, pyroglutamic acid, pyroglutamic acid, L-pyroglutamic acid, saccharic acid, salicylic acid, 4-amino-salicylic acid, sebacic acid, stearic acid, succinic acid, sulfuric acid, tannic acid, tartaric acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, potassium carbonate, zinc hydroxide, sodium hydroxide, or ammonia; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Unless otherwise specified, the term "compound" referred to herein, such as, e.g., a compound of formula (I) is intended to encompass one or more of the following, a stereoisomer or a mixture of two or more stereoisomers, a solid form (e.g., a crystal form or an amorphous form) or a mixture of two or more solid forms thereof. In certain embodiments, the term "compound" referred to herein is intended to encompass a pharmaceutical acceptable form of the compound, including but not limited to, a free base, a stereoisomer or a mixture of two or more stereoisomers, a solid form (e.g., a crystal form or an amorphous form) or a mixture of two or more solid forms.

The compound provided herein may also be provided as a prodrug, which is a functional derivative of the compound, for example, of Formula (I) and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Treatment, Prevention, and/or Management

1. Assays

A method for identifying compounds or compositions that treat a variety of neurological disorders, e.g., by modulating NOP, comprises contacting a test cell with a compound or composition and assaying the modulation of NOP. The screening may be carried out in vitro or in vivo using an assay known to one of ordinary skill in the art. For example, some exemplary screening and in vivo assays are known for sleep disorders (See e.g., Br. J. Pharmacology, 146, 33-40 (2005), U.S. Pat. No. 8,003,669 and U.S. Pat. No. 7,566,728), pain (See e.g., WO 2012/016697 and ACS Chem. Neurosci. "The Therapeutic Potential of Nociceptin/Orphanin FQ Receptor Agonists as Analgesics without Abuse Liability" online (Accepted Oct. 24, 2012)), each of which is incorporated by reference herein in its entirety.

2. Treatment, Prevention and/or Management

In one embodiment, provided herein is a method for the treatment, prevention, and/or management of various disorders, including a disorder of the central nervous system, comprising administering a compound or a composition provided herein. In one embodiment, provided herein is a method for the treatment, prevention, and/or amelioration of one or more symptoms of a disorder (e.g., a CNS disorder), comprising administering a compound or a composition provided herein. In one embodiment, the disorders provided herein include, but are not limited to, schizophrenia, psychosis, cognitive disorders, mood disorders, depression, attention deficit disorders, and neurodegenerative diseases. In one embodiment, the disorders include, but are not limited to, neurological disorder, schizophrenia, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia. In one embodiment, the disorder provided herein is a disorder known in the art that affects the central nervous system (i.e., a CNS disorder).

In one embodiment, provided herein is a method of administering a compound provided herein in a disease model that is known in the art. In one embodiment, the disease model is an animal model. In one embodiment, provided herein is a method of administering the compound provided herein, or a pharmaceutically acceptable salt or stereoisomer thereof, in an animal model that is predictive of efficacy in the treatment of certain diseases in human. The method comprises administering a compound provided herein, or a pharmaceutically acceptable salt or stereoisomer thereof, in a subject. In one embodiment, the method comprises administering a therapeutically effective amount of a compound provided herein, or a pharmaceutically acceptable salt or stereoisomer thereof, in a subject. In one embodiment, the method comprises treatment of a test subject (e.g., a mouse or rat) with a compound provided herein, or a pharmaceutically acceptable salt or stereoisomer thereof. In one embodiment, the method comprises treatment of a test subject (e.g., a mouse or rat) with a compound provided herein, or a pharmaceutically acceptable salt or stereoisomer thereof, as well as a reference compound, either in separate animal groups (e.g., administer a reference compound in a control group and administer a compound provided herein in a test group) or in the same animal group (e.g., as combination therapy). In one embodiment, the in vivo activity of the compound provided herein is dose dependent.

In one embodiment, the compounds provided herein are active in animal models of psychosis such as Pre-Pulse Inhibition (PPI) and PCP-induced hyperlocomotion. These two models have been used in the development of several antipsychotics, including olanzapine (Bakshi and Geyer,

*Psychopharmacology* 1995, 122, 198-201) and quetapine (Swedlow et al., *J. Pharm. Exp. Ther.*, 1996, 279, 1290-99), and are predictive of efficacy in human psychotic patients. In one embodiment, compounds that are active in in vivo models of psychosis are further optimized to improve the potency in the in vivo assays and drug-like properties such as, e.g., solubility and lipophilicity. Given the exact molecular basis of certain diseases such as schizophrenia are poorly understood, this approach allows the use of predictive and well-validated animal models to develop compounds with established efficacy without focusing on specific molecular targets that may or may not translate to human efficacy in the clinic.

In one embodiment, provided herein is a method of treating, preventing, and/or managing various disorders, including, but not limited to, neurological disorders. In one embodiment, provided herein is a method of treating, preventing, and/or managing one or more symptoms of a neurological disorder. In one embodiment, the method comprises administering to a subject (e.g., human) a therapeutically or prophylactically effective amount of a composition or a compound provided herein or a pharmaceutically acceptable salt or stereoisomer thereof. In one embodiment, the subject is a human. In one embodiment, the subject is an animal. In one embodiment, the compounds provided herein are highly brain penetrable in the subject. In certain embodiments, the efficacious concentration of a compound provided herein is less than 10 nM, less than 100 nM, less than 1 µM, less than 10 µM, less than 100 µM, or less than 1 mM. In one embodiment, a compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of antipsychotic activity in humans. The phenotypic approach to develop antipsychotics has been used in psychopharmacology, with the antipsychotic chlorpromazine developed in this way. The phenotypic approach may also offer advantages over compounds developed by traditional in vitro based drug discovery approach, because the compounds developed using the phenotypic approach have established pharmaceutical properties and in vivo activity, rather than activity toward a given molecular target, which may be less predictive and lead to attrition at later stages of, for example, clinical development.

In one embodiment, provided herein is a method of treating, preventing, and/or managing a neurological disorder, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), psychoaffective disorder, aggression, delirium, Parkinson's psychosis, excitative psychosis, Tourette's syndrome, organic or NOS psychosis, seizure, agitation, post-traumatic stress disorder, behavior disorder, neurodegenerative disease, Alzheimer's disease, Parkinson's disease, dyskinesias, Huntington's disease, dementia, mood disorder, anxiety, affective disorders (e.g., depression, e.g., major depressive disorder and dysthymia; bipolar disorder, e.g., bipolar depressive disorder; manic disorder; seasonal affective disorder; and attention deficit disorder (ADD) and attention deficit hyperactivity disorder (ADHD)), obsessive-compulsive disorder, vertigo, epilepsy, pain (e.g., neuropathic pain, sensitization accompanying neuropathic pain, and inflammatory pain), fibromyalgia, migraine, cognitive impairment, cognitive impairment associated with schizophrenia (CIAS), movement disorder, restless leg syndrome (RLS), multiple sclerosis, sleep disorder, sleep apnea, narcolepsy, excessive daytime sleepiness, jet lag, drowsy side effect of medications, insomnia, substance abuse or dependency (e.g., nicotine, cocaine), addiction, eating disorder, sexual dysfunction, hypertension, emesis, Lesche-Nyhane disease, Wilson's disease, autism, obesity, undesirable weight retention or weight gain, metabolic syndrome, diabetes, non-insulin dependent diabetes, impaired glucose tolerance, or hyperglycemia, comprising administering to a subject an effective amount of a compound provided herein. In one embodiment, provided herein is a method of treating, preventing, and/or managing a disorder selected from schizophrenia, cognitive impairment associated with schizophrenia, cognitive impairment, psychosis, depression, and Huntington's disease, comprising administering to a subject an effective amount of a compound provided herein, or a pharmaceutically acceptable salt or stereoisomer thereof.

In one embodiment, provided herein is a method of treating, preventing, and/or managing a disorder related to psychosis, schizophrenia, ADHD, mood disorder or affective disorder such as depression and anxiety, comprising administering to a subject an effective amount of a compound provided herein.

In one embodiment, provided herein is a method of treating, preventing, and/or managing schizophrenia or a schizophrenia-related disorder, including but not limited to schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, and psychosis, comprising administering to a subject an effective amount of a compound provided herein. In one embodiment, the compounds provided herein treat, prevent, and/or ameliorate one or more positive symptoms of schizophrenia. In one embodiment, the compounds provided herein treat, prevent, and/or ameliorate one or more negative symptoms of schizophrenia. In one embodiment, the compounds provided herein treat, prevent, and/or ameliorate one or more cognitive symptoms of schizophrenia.

In one embodiment, provided herein is a method of treating, preventing, and/or managing a disease having a psychosis component, including but not limited to psychotic disorder, brief psychotic disorder, Alzheimer's psychosis, Parkinson's psychosis, shared psychotic disorder, substance-induced psychotic disorder (e.g., cocaine, alcohol, or amphetamine), psychotic disorder due to a general medical condition, psychoaffective disorder, aggression, delirium, excitative psychosis, Tourette's syndrome, manic disorder, organic psychosis, and NOS psychosis, comprising administering to a subject an effective amount of a compound provided herein.

In one embodiment, provided herein is a method of treating, preventing, and/or managing cognitive impairment, including but not limited to cognitive impairment associated with schizophrenia, cognitive deficit in Alzheimer's disease, cognitive deficit in Parkinson's disease, comprising administering to a subject an effective amount of a compound provided herein.

In one embodiment, provided herein is a method of treating, preventing, and/or managing mood disorder, bipolar disorder, anxiety, depression, major depressive disorder, unipolar depression, treatment resistant depression, dysthymia, affective disorder, seasonal affective disorder, or obsessive-compulsive disorder, comprising administering to a subject an effective amount of a compound provided herein.

In one embodiment, provided herein is a method of treating, preventing, and/or managing attention deficit disorder (ADD) or attention deficit hyperactivity disorder (ADHD), comprising administering to a subject an effective amount of a compound provided herein.

In one embodiment, provided herein is a method of treating, preventing, and/or managing a neurodegenerative disease, including but not limited to Huntington's disease, Alzheimer's disease, and Parkinson's disease, comprising administering to a subject an effective amount of a compound provided herein. In one embodiment, provided herein is a method of treating, preventing, and/or managing Huntington's disease, comprising administering to a subject an effective amount of a compound provided herein.

In one embodiment, provided herein is a method of treating, preventing, and/or managing agitation, posttraumatic stress disorder, or behavior disorder, comprising administering to a subject an effective amount of a compound provided herein.

In one embodiment, provided herein is a method of treating, preventing, and/or managing dementia, comprising administering to a subject an effective amount of a compound provided herein.

In one embodiment, provided herein is a method of treating, preventing, and/or managing vertigo, comprising administering to a subject an effective amount of a compound provided herein.

In one embodiment, provided herein is a method of treating, preventing, and/or managing pain, neuropathic pain, sensitization accompanying neuropathic pain, inflammatory pain, migraine or fibromyalgia, comprising administering to a subject an effective amount of a compound provided herein.

In one embodiment, provided herein is a method of treating, preventing, and/or managing movement disorder or restless leg syndrome (RLS), comprising administering to a subject an effective amount of a compound provided herein.

In one embodiment, provided herein is a method of treating, preventing, and/or managing multiple sclerosis, sleep disorder, substance abuse or dependency (e.g., nicotine, cocaine), addiction, eating disorder, or autism, comprising administering to a subject an effective amount of a compound provided herein.

In one embodiment, provided herein is a method of treating, preventing, and/or managing a disorder related to cognitive impairments, such as Alzheimer's disease, Parkinson's disease, schizophrenia, cognitive impairment associated with schizophrenia (CIAS), and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In another embodiment, provided herein is a method of treating, preventing, and/or managing a disorder associated with excessive daytime sleepiness, such as, narcolepsy, Parkinson's disease, multiple sclerosis, shift workers, jet lag, relief of side effects of other medications, and the like provided herein.

In one embodiment, provided herein is a method of treating, preventing, and/or managing an anxiety disorder, including but not limited to, panic and obsessive-compulsive disorder, comprising administering to a subject an effective amount of a compound provided herein. For example, without being limited by a particular theory, the compounds provided herein may have wake promoting effects.

In another embodiment, provided herein is a method of treating, preventing, and/or managing a sleeping disorder, such as insomnia, comprising administering to a subject an effective amount of a compound provided herein. In one embodiment, the psychotic disorders provided herein that can be treated, prevented, and/or managed using a compound or a pharmaceutical composition provided herein include, but are not limited to, schizophrenia, e.g., of the paranoid, disorganized, catatonic, undifferentiated, and/or residual type; schizophreniform disorder; schizoaffective disorder, e.g., of the delusional and/or depressive type; delusional disorder; substance-induced psychotic disorder, e.g., psychosis induced by alcohol, amphetamine, *cannabis*, cocaine, hallucinogens, inhalants, opioids, and/or phencyclidine; personality disorder of the paranoid type; and personality disorder of the schizoid type.

In one embodiment, the movement disorders provided herein that can be treated, prevented, and/or managed using a compound or a pharmaceutical composition provided herein include, but are not limited to, Huntington's disease, dyskinesia associated with dopamine agonist therapy, Parkinson's disease, restless leg syndrome, and essential tremor.

In one embodiment, other disorders provided herein that can be treated, prevented, and/or managed using a compound or a pharmaceutical composition provided herein include, but are not limited to, obsessive-compulsive disorder, Tourette's syndrome, and tic disorders.

In one embodiment, provided herein is a method of treating, preventing, and/or managing an anxiety disorder, including but not limited to, panic disorder, agoraphobia, specific phobia, social phobia, obsessive-compulsive disorder, post-traumatic stress disorder, acute stress disorder, and generalized anxiety disorder, comprising administering to a subject an effective amount of a compound provided herein.

In one embodiment, provided herein is a method of treating, preventing, and/or managing a drug addiction, including but not limited to, an alcohol, amphetamine, cocaine, and/or opiate addiction, comprising administering to a subject an effective amount of a compound provided herein. In one embodiment, the drug addiction provided herein represents an abnormal desire for a drug and is generally characterized by motivational disturbances such a compulsion to take the desired drug and episodes of intense drug craving.

In one embodiment, provided herein is a method of treating, preventing, and/or managing a disorder comprising a symptom of deficiency in attention and/or cognition, comprising administering to a subject an effective amount of a compound provided herein. In one embodiment, deficiency in attention and/or cognition provided herein may represent a subnormal functioning in one or more cognitive aspects, such as, e.g., memory, intellect, learning ability, and/or logic ability, in a particular subject relative to other subjects within the same general population and/or age group. In one embodiment, deficiency in attention and/or cognition provided herein may represent a reduction in a particular sub-population's functioning in one or more cognitive aspects, such as, e.g., in age-related cognitive decline.

In one embodiment, the disorders comprising a symptom of deficiency in attention and/or cognition provided herein that can be treated, prevented, and/or managed with a compound or a pharmaceutical composition provided herein, include, but are not limited to, dementia, e.g., dementia in Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, or AIDS-related dementia; delirium; amnestic disorder; post-traumatic stress disorder; mental retardation; learning disorder, e.g., reading disorder, mathematics disorder, or a disorder of written expression; attention-deficit/hyperactivity disorder; and age-related cognitive decline.

In one embodiment, provided herein is a method of treating, preventing, and/or managing a mood disorder or a mood episode, comprising administering to a subject an effective amount of a compound provided herein. In one embodiment, the mood disorders or mood episodes provided herein that can be treated, prevented, and/or managed with a compound or a pharmaceutical composition provided herein include, but are not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder.

In one embodiment, provided herein is a method of treating, preventing, and/or managing a neurodegenerative disorder or neurodegenerative condition, comprising administering to a subject an effective amount of a compound provided herein. In one embodiment, the neurodegenerative disorder or neurodegenerative condition provided herein that can be treated, prevented, and/or managed with a compound or a pharmaceutical composition provided herein represents a disorder or condition that is caused by the dysfunction and/or death of neurons in the central nervous system. The treatment of these disorders and conditions can be facilitated by administration of an agent which prevents the dysfunction or death of neurons at risk and/or enhances the function of damaged or healthy neurons to compensate for the loss of function caused by the dysfunction or death of at-risk neurons. In one embodiment, the neurodegenerative disorders or neurodegenerative conditions provided herein that can be treated, prevented, and/or managed with a compound or a pharmaceutical composition provided herein include, but are not limited to, Parkinson's disease; Huntington's disease; dementia, e.g., Alzheimer's disease, multi-infarct dementia, AIDS-related dementia, and Fronto temporal dementia; neurodegeneration associated with cerebral trauma; neurodegeneration associated with stroke; neurodegeneration associated with cerebral infarct; hypoglycemia-induced neurodegeneration; neurodegeneration associated with neurotoxin poisoning; and multi-system atrophy. In one embodiment, the neurodegenerative disorders or neurodegenerative conditions provided herein comprise neurodegeneration of striatal medium spiny neurons in a subject. In one embodiment, the neurodegenerative disorder or neurodegenerative condition is Huntington's disease.

In one embodiment, provided herein is a method of treating, preventing, and/or managing psychotic disorder, delusional disorder, drug induced psychosis, anxiety disorder, movement disorder, mood disorder, neurodegenerative disorder, or drug addiction, comprising administering to a subject an effective amount of a compound provided herein.

In one embodiment, provided herein is a method of treating, preventing, and/or managing a neurologic disorder, including but not limited to, dementia, Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, AIDS-related dementia, delirium, amnestic disorder, post-traumatic stress disorder, mental retardation, learning disorder, reading disorder, mathematics disorder, disorder of written expression, attention-deficit-hyperactivity disorder, age-related cognitive decline, major depressive episode of the mild, moderate or severe type, manic or mixed mood episode, hypomanic mood episode, depressive episode with atypical features, depressive episode with melancholic features, depressive episode with catatonic features, mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder comprising a delusional disorder or schizophrenia, bipolar disorder, bipolar I disorder, bipolar II disorder, cyclothymic disorder, Parkinson's disease, Huntington's disease, dementia, Alzheimer's disease, multi-infarct dementia, AIDS-related dementia, Fronto temporal dementia, neurodegeneration associated with cerebral trauma, neurodegeneration associated with stroke, neurodegeneration associated with cerebral infarct, hypoglycemia-induced neurodegeneration, neurodegeneration associated with neurotoxin poisoning, multi-system atrophy, schizophrenia of a paranoid, disorganized, catatonic, undifferentiated or residual type, schizophreniform disorder; schizoaffective disorder of the delusional type or the depressive type, delusional disorder, substance-induced psychotic disorder, psychosis induced by alcohol, amphetamine, *cannabis*, cocaine, hallucinogens, inhalants, opioids, or phencyclidine, personality disorder of the paranoid type, and personality disorder of the schizoid type, comprising administering to a subject an effective amount of a compound provided herein.

In one embodiment, provided herein is a method of treating, preventing, and/or managing a neurologic disorder, including but not limited to, psychotic disorders, delusional disorders, drug induced psychosis, anxiety disorders, movement disorders, mood disorders, neurodegenerative disorders, and drug addiction, comprising administering to a subject an effective amount of a compound provided herein.

In one embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In another embodiment, provided herein is a method of using the compounds provided herein as psycho-stimulants, which may lack the abuse liabilities generally associated with other classes of psycho-stimulants. Without being limited by a particular theory, the compounds provided herein may increase the levels of histamine, dopamine, norepinephrine, and/or acetylcholine in the prefrontal cortical area, which is consistent with their pro-cognitive effects and their wake promoting effects seen in animal models. For example, the compounds provided herein may increase dopamine in the frontal cortex but not the striatum. The compounds provided herein may not induce increased locomotor activity or sensitization that is associated with other psycho-stimulus.

In another embodiment, provided herein is a method of treating, preventing, and/or managing a disorder such as seizure, epilepsy, vertigo, and pain, comprising administering to a subject an effective amount of a compound provided herein. For example, without being limited by a particular theory, the compounds provided herein may be protective against pentylene-tetrazole (PTZ) and electrical-induced seizures. The compounds provided herein may increase the seizure threshold in humans. The compounds provided herein may decrease electrical discharge from afferent neurons in an inner ear preparation. Further, without being limited by a particular theory, the compounds provided herein may increase the threshold for neuropathic pain, which is shown in models such as the chronic constriction injure (CCI) model, herpes virus-induced model, and capsaicin-induced allodynia model. Therefore, in some embodiments, the compounds provided herein are employed for their analgesic effects to treat, prevent, and/or manage disorders involving pain and the sensitization that accompanies many neuropathic pain disorders.

In another embodiment, provided herein is a method of treating, preventing, and/or managing a movement disorder, such as Parkinson's disease, restless leg syndrome (RLS), and Huntington's disease, comprising administering to a subject an effective amount of a compound provided herein.

In some embodiments, a compound provided herein is active in at least one model, which can be used to measure the activity of the compound and estimate the efficacy in treating a neurological disorder. For example, when the model is for psychosis (e.g., PCP Hyperactivity Model or Prepulse Inhibition of Startle Model), a compound is active when the compound reduces PCP induced hyperactivity in mice by a statistically significant amount compared to a vehicle, or when the compound reverses the disruption of prepulse inhibition (PPI) induced by PCP in mice.

In other embodiments, provided herein is a method of effecting a therapeutic effect as described herein elsewhere. The method comprises administering to a subject (e.g., a mammal) a therapeutically effective amount of a compound or composition provided herein. The particular therapeutic effects may be measured using any model system known in the art and described herein, such as those involving an animal model of a disease.

In some embodiments, the neurological disorder is: depression (e.g., major depressive disorder or dysthymia); bipolar disorder, seasonal affective disorder; cognitive deficit; fibromyalgia; pain (e.g., neuropathic pain); sleep related disorder (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; post-traumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, epilepsy, disturbances of consciousness, coma, lowering of attention, speech disorder, Lennox syndrome, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction, overweight, metabolic syndrome, diabetes, non-insulin dependent diabetes, impaired glucose tolerance, and hyperglycemia.

In one embodiment, the neurological disorder is excessive daytime sleepiness. In another embodiment, the neurological disorder is a cognitive impairment. In another embodiment, the neurological disorder is a mood disorder. In another embodiment, the neurological disorder is an affective disorder. In another embodiment, the neurological disorder is a movement disorder. In another embodiment, the neurological disorder is schizophrenia. In another embodiment, the neurological disorder is an attention disorder. In another embodiment, the neurological disorder is an anxiety disorder. In another embodiment, the neurological disorder is seizure. In another embodiment, the neurological disorder is psychosis. In another embodiment, the neurological disorder is epilepsy. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a neurological disorder of the central nervous system, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compounds disclosed herein may be used in a combination treatment with one or more second active agents to treat, prevent, and/or manage disorders described herein. In one embodiment, the one or more second active agent is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is an antidepressant agent. In certain embodiments, the second active agent is selected from an SSRI, SNRI, and tricyclic antidepressants, agents useful in the treatment of Parkinson's disease and antipsychotics. Exemplary antipsychotics include, but are not limited to atypical antipsychotics such as amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, and zotepine. Exemplary antidepressants include, but are not limited to citalopram, excitalopram, fluoxetine, fluvoxamine, paroxetine, pimavanserin, loxapine, donepezil, rivastigmine, memantine, galantamine, tacrine, amphetamine, methylphenidate, atomoxetine, modafinil, sertraline, vilazodone, desvenlafaxine, fluoxetine, venlafaxine, duloxetine, milnacipran, vanlafaxine, mianserin, mirtazapine, atomoxetine, mazindol, reboxetine, viloxazine, bupropion, agomelatine, amitriptyline, clomipramine, doxepin, imipramine, timipramine, desipramine, nortriptyline, protriptyline, isocarboxazid, moclobemide, phenelzine, selegiline, tranylcypromine, buspirone, gepirone, nefazodone, tandospirone and trazodone. Exemplary treatments for Parkinson's disease include, but are not limited to carbidopa, levodopa, entacapone, bromocriptine, pergolide, pramipexole, ropinirole, rotogotine, tolcapone, selegiline, rasagiline, benzotropine, trihexylphenidyl and amantadine. In certain embodiments, the second active agent is a treatment for pain. Exemplary pain medications/treatments include, but are not limited to, non-opioid analgesics such as acetylsalicylic acid, choline magnesium trisalicylate, acetaminophen, ibuprofen, fenoprofen, diflusinal, and naproxen; and opioid analgesics, such as morphine, hydromorphone, methadone, levorphanol, fentanyl, oxycodone, and oxymorphone. Other such therapeutic agents may be a non-steroid anti-inflammatory agent, an antimigraine agent or a Cox-II inhibitor.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and/or magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise a second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

In one embodiment, pharmaceutical compositions and dosage forms described herein include one or more second active agents to treat, prevent, and/or manage disorders described herein. In one embodiment, the one or more second active agents are selected from antidepressants, agents useful in the treatment of Parkinson's disease and antipsychotics.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific example of a binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art (e.g., parenteral administration such as intravenous or intramuscular). Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's The Science and Practice of Pharmacy*, 21st Ed., Lippincott Williams & Wilkins (2005); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's The Science and Practice of Pharmacy*, 21st Ed., Lippincott Williams & Wilkins (2005).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

General Procedures for Compound Synthesis

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Sigma-Aldrich® in Sure-Seal® bottles and used as received. All solvents may be purified using standard methods known to those skilled in the art, unless otherwise indicated.

The reactions set forth below were done generally at ambient temperature, unless otherwise indicated. Unless otherwise specified, generally the reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., J. Org. Chem., 43: 2923 (1978)) was performed using, for example, silica gel 60 or various MPLC systems (such as Biotage® or ISCO® separation systems).

The compound structures in the examples below were confirmed by one or more of the following methods: proton nuclear magnetic resonance spectroscopy, mass spectroscopy, elemental microanalysis, and melting point. Proton nuclear magnetic resonance ($^1$H NMR) spectra were determined using a NMR spectrometer operating at a certain field strength. Chemical shifts are reported in parts per million (ppm, δ) downfield from an internal standard, such as TMS. Alternatively, $^1$H NMR spectra were referenced to signals from residual protons in deuterated solvents, for example, as follows: $CDCl_3$=7.25 ppm; DMSO-$d_6$=2.49 ppm; $C_6D_6$=7.16 ppm; $CD_3OD$=3.30 ppm. Peak multiplicities are designated, for example, as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

Example 1A: Preparation of Compound 1-8

Scheme 1:

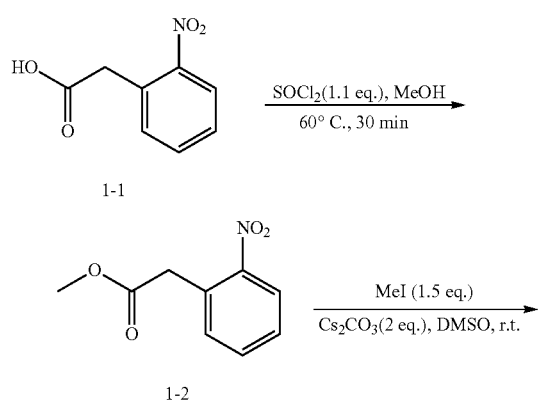

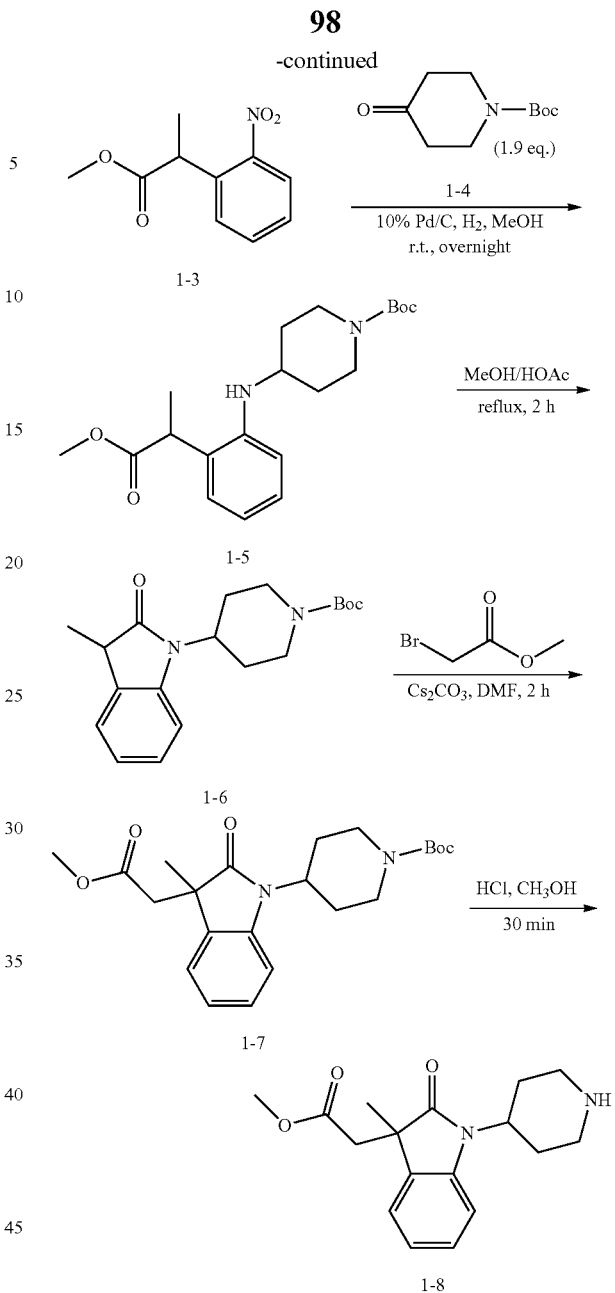

Preparation of Methyl 2-(2-nitrophenyl)acetate (Compound 1-2)

To a solution of Compound 1-1 (18.1 g, 100 mmol) in methanol (150 mL) at room temperature was added sulfurous dichloride ($SOCl_2$, 13.1 g, 110 mmol) dropwise. The mixture was heated to 60° C. and stirred for 30 minutes. The reaction mixture was concentrated to give a pale yellow oil, diluted with ethyl acetate (200 mL), washed with sodium bicarbonate (sat. aq., 150 mL×3), brine (100 mL×2), dried over anhydrous sodium sulfate, concentrated to give the desired product Compound 1-2 (19.1 g, yield: 98%) as a pale yellow oil. MS (ESI): m/z: 196[M+H]$^+$. $^1$H NMR (400 MHz, $CDCl_3$) δ: 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 3H).

Preparation of Methyl 2-(2-nitrophenyl)propanoate (Compound 1-3)

To a solution of 1-2 (19 g, 97 mmol) in methylsulfinylmethane (200 mL) was added iodomethane (20.7 g, 146 mmol) at room temperature. The mixture was stirred at room temperature for 30 minutes. Then to the mixture was added cesium carbonate (63 g, 195 mmol), and the mixture was stirred at room temperature for overnight. The mixture was poured into water (200 mL), diluted with ethyl acetate (200 mL), washed with water (200 mL×3), brine (200 mL×3), dried over anhydrous sodium sulfate, concentrated to give crude product which was purified on silica-gel (ethyl acetate in petrol ether 20%, v/v) to afford product Compound 1-3 (18.7 g, yield: 92%) as a colorless oil. MS (ESI): m/z: 210[M+H]$^+$. $^1$H NMR (400 MHz, CDCl$_3$) δ: 7.94 (dd, J=8.0, J=1.6 Hz, 1H), 7.63-7.59 (m, 1H), 7.49 (dd, J=7.6, J=1.6 Hz, 1H), 7.45-7.41 (m, 1H), 4.32 (q, J=7.2 Hz, 1H), 3.67 (s, 3H), 1.61 (d, J=7.2 Hz, 3H).

Preparation of tert-butyl 4-(2-(1-methoxy-1-oxopropan-2-yl)phenylamino) piperidine-1-carboxylate (Compound 1-5)

To a solution of Compound 1-3 (6 g, 28.7 mmol) in methanol (100 mL) was added tert-butyl 4-oxopiperidine-1-carboxylate iodomethane (10.85 g, 54.5 mmol) and palladium/active carbon catalyst (0.6 g) at room temperature. The mixture was stirred at room temperature for overnight under hydrogen atmosphere. The mixture was filtered. The filtrate was used for the next step without further purification. MS (ESI): m/z: 210[M+H]$^+$.

Preparation of tert-butyl 4-(3-methyl-2-oxoindolin-1-yl)piperidine-1-carboxylate (Compound 1-6)

To the mixture of Compound 1-5 in methanol from last step was added acetic acid (10 mL). The mixture was stirred at refluxing for 1 hour. The mixture was concentrated and the residue was poured into water (100 mL), adjusted pH 7 with sodium carbonate (aq). The mixture was extracted with ethyl acetate (150 mL×3), washed with brine (100 mL×2), dried over anhydrous sodium sulfate, concentrated to give the desired product Compound 1-6 which was purified on silica-gel (ethyl acetate in petrol ether 10%, v/v) (5.77 g, yield: 61%, two step) as a white solid. MS (ESI): m/z: 331[M+H]$^+$. $^1$H NMR (400 MHz, CDCl$_3$) δ: 7.26-7.21 (m, 1H), 7.05 (d, J=7.2, 1H), 7.49 (t, J=6.8 Hz, 1H), 4.45-4.38 (m, 1H), 4.31-4.27 (m, 1H), 3.41 (q, J=7.6 Hz, 1H), 2.83 (t, J=14.4 Hz, 2H), 2.37-2.27 (m, 2H), 1.73-1.67 (m, 2H), 1.50 (s, 9H), 1.47 (d, J=7.6 Hz, 3H).

Preparation of tert-butyl 4-(3-(2-methoxy-2-oxoethyl)-3-methyl-2-oxoindolin-1-yl) piperidine-1-carboxylate (Compound 1-7)

To the mixture of Compound 1-6 (5.77 g, 17.5 mmol) in N,N-dimethylformamide (100 mL) was added methyl 2-bromoacetate (2.94 g, 19.3 mmol). The mixture was stirred at room temperature for 30 minutes. Then to the mixture was added cesium carbonate (11.4 g, 35 mmol). The mixture was stirred at room temperature for 2 hours. The mixture was poured into water (100 mL), extracted with ethyl acetate (100 mL×3), washed with brine (100 mL×2), dried over anhydrous sodium sulfate, concentrated to give the desired product Compound 1-7 which was purified on silica-gel (ethyl acetate in petrol ether 10%, v/v) (3.8 g, yield: 54%) as a white solid. MS (ESI): m/z: 403[M+H]$^+$.

Preparation of methyl 2-(3-methyl-2-oxo-1-(piperidin-4-yl)indolin-3-yl)acetate (Compound 1-8)

The mixture of Compound 1-7 (3.8 g, 9.4 mmol) in hydrogen chloride/methanol (20 mL, 4 N) was stirred at room temperature for 30 minutes. The mixture was concentrated, adjusted pH 8 with sodium carbonate (aq). The mixture was extracted with ethyl acetate (100 mL×6), dried over anhydrous sodium sulfate, concentrated to give the desired product Compound 1-8 (2 g, yield: 70%) as a yellow solid. MS (ESI): m/z: 303[M+H]$^+$.

Example 1B: Preparation of Compound 16

Scheme 2:

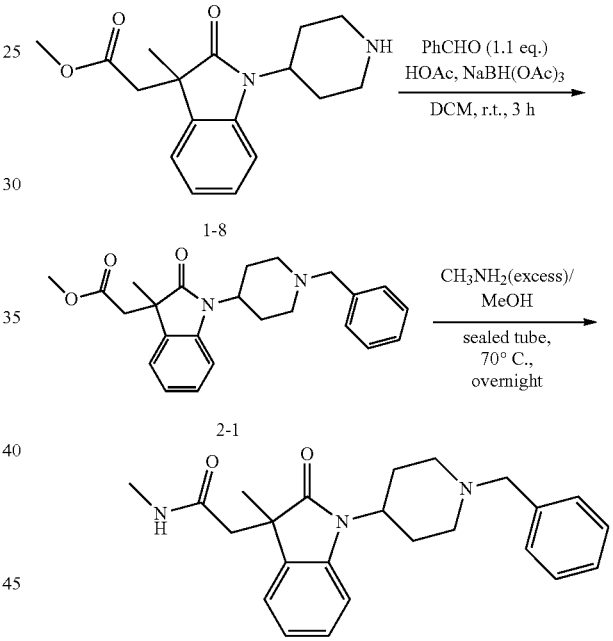

Preparation of methyl 2-(1-(1-benzylpiperidin-4-yl)-3-methyl-2-oxoindolin-3-yl)acetate (Compound 2-1)

To a solution of Compound 1-8 (302 mg, 1 mmol) in dichloromethane (10 mL) was added benzaldehyde (117 mg, 1.1 mmol). The mixture was stirred at room temperature for 1 hour. Then sodium triacetoxyborohydride (318 mg, 1.5 mmol) and acetic acid (1 drop) was added to the mixture. The resulting mixture was stirred at 35° C. for 2 hours. The mixture was diluted with dichloromethane, washed with water (10 mL×3) and brine (10 mL×2), dried over sodium sulfate, filtered and concentrated under reduced pressure to give the crude product (217 mg, 55%) as a brown oil which was used in the next step without further purification. MS (ESI): m/z: 393 [M+H]$^+$.

Preparation of 2-(1-(1-benzylpiperidin-4-yl)-3-methyl-2-oxoindolin-3-yl)-N-methylacetamide (Compound 16)

A mixture of Compound 2-1 (98 mg, 0.25 mmol) in methylamine (33% in methanol, 4 mL) in a sealed tube was stirred at 80° C. overnight. The mixture was cooled and concentrated under reduce pressure, and purified by prep-TLC (methanol in dichloromethane 10%, v/v) to give a white solid (48 mg, yield: 49%). MS (ESI): m/z: 392 [M+H]$^+$. $^1$H NMR (400 MHz, CDCl$_3$) δ: 7.38-7.32 (m, 4H), 7.29-7.27 (m, 1H), 7.26-7.22 (m, 2H), 7.16 (d, J=7.6 Hz, 1H), 7.07-7.03 (m, 1H), 4.27 (t, J=5.6 Hz, 1H), 3.56 (s, 2H), 3.04 (d, J=10.0 Hz, 2H), 2.79-2.75 (d, J=14.4 Hz, 1H), 2.66-2.61 (m, 4H), 2.49-2.47 (m, 2H), 2.17-2.15 (m, 2H), 1.70-1.68 (m, 2H), 1.40 (s, 3H).

Example 1C: Preparation of Compound 17

Scheme 3:

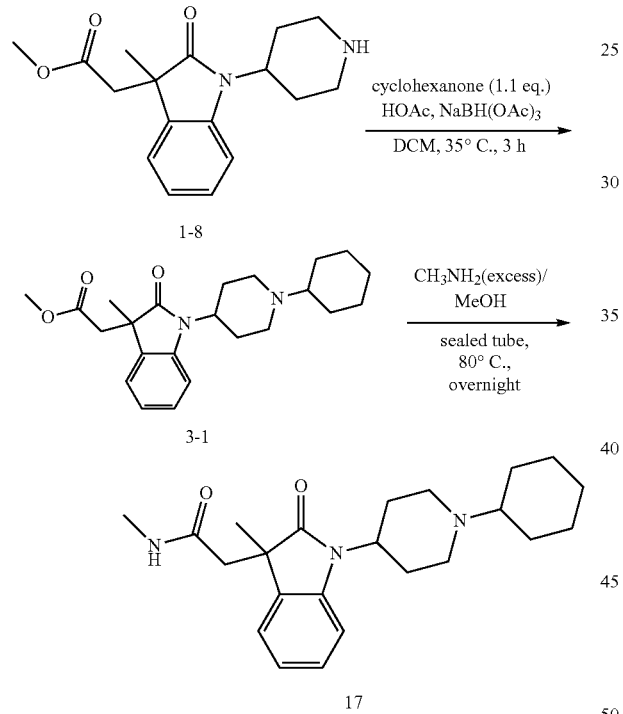

Preparation of 2-(1-(1-benzylpiperidin-4-yl)-3-methyl-2-oxoindolin-3-yl)-N-methylacetamide (Compound 3-1)

To a solution of Compound 1-8 (280 mg, 0.9 mmol) in dichloromethane (10 mL) was added cyclohexanone (98 mg, 1 mmol). The mixture was stirred at room temperature for 1 hour. Then sodium triacetoxyborohydride (286 mg, 1.35 mmol) and acetic acid (1 drop) was added to the mixture. The resulting mixture was stirred at 35° C. for 2 hours. The mixture was diluted with dichloromethane, washed with water (10 mL×3) and brine (10 mL×2), dried over sodium sulfate, filtered and concentrated under reduced pressure to give brown oil which was used in the next step without further purification. MS (ESI): m/z: 385 [M+H]$^+$.

Preparation of 2-(1-(1-cyclohexylpiperidin-4-yl)-3-methyl-2-oxoindolin-3-yl)-N-methylacetamide (Compound 17)

A mixture of Compound 3-1 (100 mg, 0.26 mmol) and methylamine (33% in methanol, 4 mL) in a sealed tube was stirred at 80° C. for overnight. The mixture was cooled and concentrated under reduce pressure, and purified by prep-TLC (methanol in dichloromethane 10%, v/v) to give a white solid (10 mg, yield: 10%). MS (ESI): m/z: 384 [M+H]$^+$. $^1$H NMR (400 MHz, MeOD) δ: 7.33 (d, J=8 Hz, 1H), 7.24 (m, 2H), 7.03 (t, J=7.6 Hz, 1H), 4.30-4.26 (m, 1H), 3.13 (d, J=8 Hz, 2H), 2.85~2.73 (m, 2H), 2.57~2.46 (m, 8H), 1.99~1.95 (m, 2H), 1.86~1.83 (m, 3H), 1.77~1.67 (m, 2H), 1.3~1.29 (m, 8H), 1.21~1.15 (m, 1H).

Example 1D: Preparation of Compounds 23, 24, 25 and 26

Scheme 4:

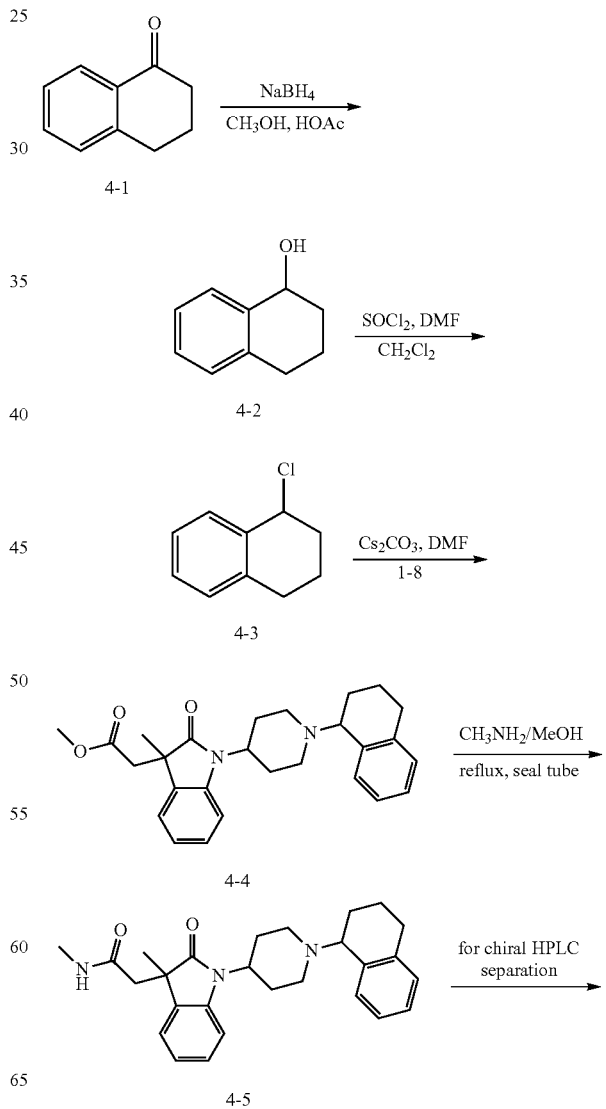

-continued

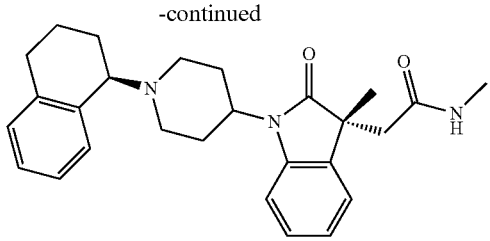

23

1st peak of 4

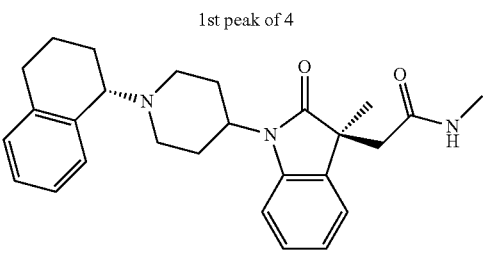

24

2nd peak of 4

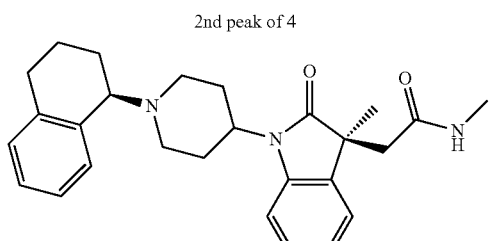

25

3rd peak of 4

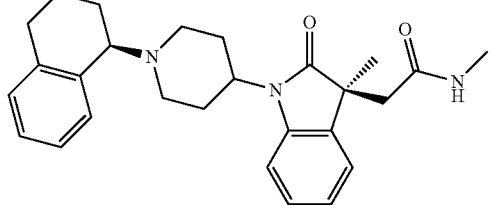

26

4th peak of 4

Preparation of 1,2,3,4-tetrahydronaphthalen-1-ol (Compound 4-2)

To a solution of Compound 4-1 (1.46 g, 10.0 mmol, 1.0 eq) in methanol (30 mL) was added sodium borohydride (760 mg, 20.0 mmol, 2.0 eq) at r.t. The mixture was stirred at r.t. for 3 h. Upon the completion, the mixture was concentrated in vacuo to give the residue, diluted in 50 mL of water, extracted with dichloromethane (50 mL), dried over anhydrous sodium sulfate and concentrated to give the product (1.36 g, colorless oil, purity: 88%, yield: 92%). MS (ESI): m/z: 131 [M−18+H]$^+$.

Preparation of 1-chloro-1,2,3,4-tetrahydronaphthalene (Compound 4-3)

To a solution of Compound 4-2 (140 mg, 1.0 mmol, 1.0 eq) and dimethyl formamide (2 drops, cat) in dichloromethane (20 mL) was added sulfurous dichloride (360 mg, 2.0 mmol, 2.0 eq) dropwise at −20° C. The mixture was stirred at this temperature for 2 h. Upon the completion, the mixture was concentrated in vacuo below 20° C. to give Compound 4-3 (160 mg crude as yellow solid used directly for next step). MS (ESI): m/z: 131 [M+H−36]$^+$.

Preparation of methyl 2-(3-methyl-2-oxo-1-(1-(1,2,3,4-tetrahydronaphthalen-1-yl) piperidin-4-yl)indolin-3-yl)acetate (Compound 4-4)

To a solution of 1-8 (150 mg, 0.5 mmol) and Compound 4-3 (250 mg crude, 1.5 mmol) in dimethyl formamide (20 mL) was added cesium carbonate (489 mg, 1.5 mmol). The mixture was stirred at 60° C. for overnight. The mixture was extracted with ethyl acetate (30 mL×3), washed with water (100 mL×3), brine (100 mL×2), dried over anhydrous sodium sulfate and concentrated. The residue was purified by prep. HPLC in 0.01% aqueous ammonia to give Compound 4-4 (80 mg, yield: 37%) as a white solid. MS (ESI): m/z: 433 [M+H]$^+$. $^1$H NMR (400 MHz, CDCl$_3$) δ: 7.83-7.80 (m, 1H), 7.31-7.26 (m, 1H), 7.24-7.12 (m, 4H), 7.01-7.00 (m, 2H), 4.32-4.25 (m, 1H), 3.93-3.89 (m, 1H), 3.42 (t, J=13.6 Hz, 3H), 3.06-3.00 (m, 2H), 2.88-2.59 (m, 6H), 2.39-2.33 (m, 1H), 2.28-2.22 (m, 1H), 2.03-2.00 (m, 2H), 1.86-1.80 (m, 1H), 1.73-1.63 (m, 3H), 1.36 (d, J=4.0 Hz, 3H).

Preparation of N-methyl-2-(3-methyl-2-oxo-1-(1-(1,2,3,4-tetrahydronaphthalen-1-yl)piperidin-4-yl)indolin-3-yl)acetamide (Compounds 23, 24, 25 and 26)

A mixture of Compound 4-4 (80 mg, 0.18 mmol) and methylamine (33% in methanol, 4 mL) in a sealed tube was stirred at 80° C. for overnight. The mixture was cooled and concentrated under reduce pressure. The residue was purified by prep. HPLC in 0.01% aqueous ammonia to give Compound 4-5 (51 mg, yield: 64%) as a white solid. The product (80 mg) was separated by Chiral-HPLC to give product Compound 23 (13 mg), Compound 24 (10 mg), Compound 25 (12 mg), and Compound 26 (20 mg). MS (ESI): m/z: 432 [M+H]$^+$. Compound 23: $^1$H NMR (400 MHz, CDCl$_3$) δ: 7.80 (d, J=7.6 Hz, 1H), 7.30-7.27 (m, 2H), 7.23-7.12 (m, 3H), 7.08-7.05 (m, 2H), 6.25 (br s, 1H), 4.27-4.20 (m, 1H), 3.91 (br s, 1H), 3.03-3.00 (m, 1H), 2.86-2.56 (m, 10H), 2.37-2.22 (m, 2H), 2.03-2.00 (m, 2H), 1.80-1.63 (m, 4H), 1.40 (s, 3H). Compound 24: $^1$H NMR (400 MHz, CDCl$_3$) δ: 7.80 (d, J=7.6 Hz, 1H), 7.30-7.28 (m, 2H), 7.22-7.12 (m, 3H), 7.09-7.05 (m, 2H), 6.24 (br s, 1H), 4.26-4.20 (m, 1H), 3.92 (br s, 1H), 3.05-3.01 (m, 1H), 2.85-2.61 (m, 10H), 2.40-2.22 (m, 2H), 2.02-2.00 (m, 2H), 1.82-1.67 (m, 4H), 1.41 (s, 3H). Compound 25: $^1$H NMR (400 MHz, CDCl$_3$) δ: 7.79 (d, J=7.2 Hz, 1H), 7.30-7.28 (m, 2H), 7.22-7.12 (m, 3H), 7.09-7.05 (m, 2H), 6.25 (br s, 1H), 4.27-4.20 (m, 1H), 3.91 (br s, 1H), 3.03-3.00 (m, 1H), 2.85-2.61 (m, 10H), 2.39-2.22 (m, 2H), 2.02-2.00 (m, 2H), 1.81-1.67 (m, 4H), 1.41 (s, 3H). Compound 26: $^1$H NMR (400 MHz, CDCl$_3$) δ: 7.80 (d, J=7.6 Hz, 1H), 7.30-7.28 (m, 2H), 7.23-7.12 (m, 3H), 7.08-7.05 (m, 2H), 6.25 (br s, 1H), 4.27-4.20 (m, 1H), 3.91 (br s, 1H), 3.03-3.00 (m, 1H), 2.86-2.62 (m, 10H), 2.36-2.21 (m, 2H), 2.02-2.00 (m, 2H), 1.80-1.64 (m, 4H), 1.40 (s, 3H).

Example 1E: Preparation of Compounds 19, 20, 21 and 22

Scheme 5:

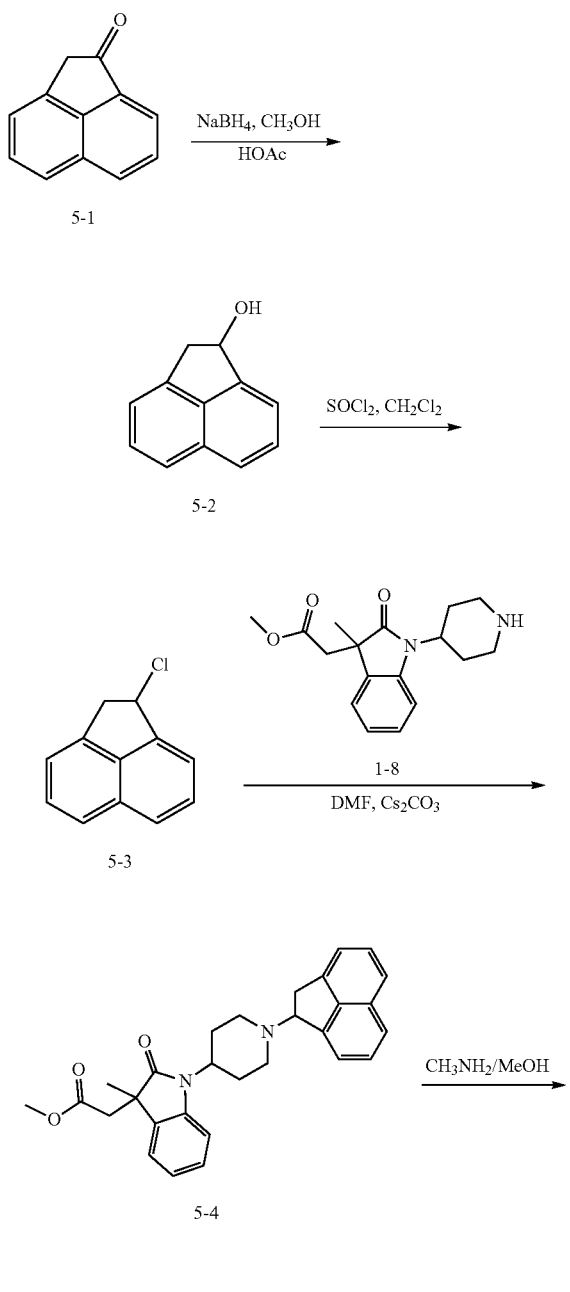


19

1st peak of the 4 peaks

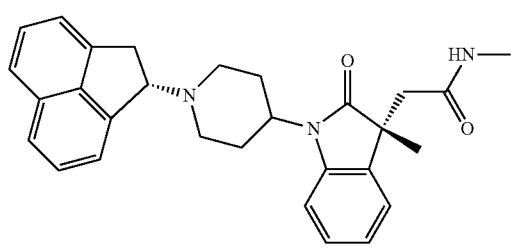

20

2nd peak of the 4 peaks

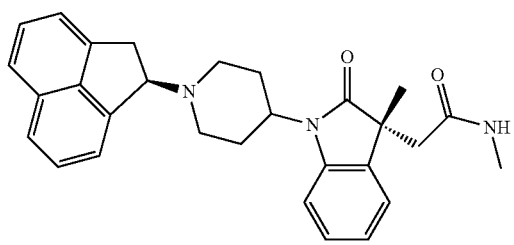

21

3rd peak of the 4 peaks

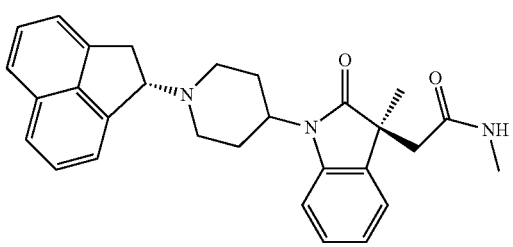

22

4th peak of the 4 peaks

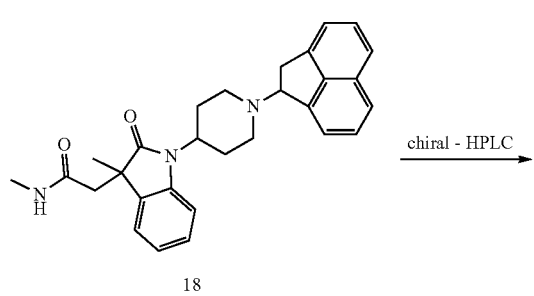

Preparation of 1,2-dihydroacenaphthylen-1-ol (Compound 5-2)

To a solution of Compound 5-1 (1.04 g, 6.2 mmol, 1.0 eq) in methanol (20 mL) was added sodium borohydride (470 mg, 12.4 mmol, 2.0 eq) at r.t. The mixture was stirred at r.t. for 2 h. Upon the completion, the mixture was concentrated in vacuo to give the residue, diluted in 50 mL of water, extracted with dichloromethane (50 mL), dried over anhydrous sodium sulfate and concentrated to give Compound 5-2 (920 mg, yield: 87%) as a light yellow solid. MS (ESI): m/z: 153 [M−18+H]$^+$.

Preparation of 1-chloro-1,2-dihydroacenaphthylene (Compound 5-3)

To a solution of Compound 5-2 (220 mg, 1.2 mmol, 1.0 eq) and dimethyl formamide (2 drops, cat) in dichloromethane (40 mL) was added sulfurous dichloride (456 mg, 2.4 mmol, 2.0 eq) dropwise at −20° C. The mixture was stirred at this temperature for 2 h. Upon the completion, the mixture was concentrated in vacuo below 20° C. to give 5-3 (270 mg, used directly for next step). MS (ESI): m/z: 153 [M−36+H]$^+$.

Preparation of methyl 2-(1-(1-(1,2-dihydroacenaphthylen-1-yl)piperidin-4-yl)-3-methyl-2-oxoindolin-3-yl)acetate (Compound 5-4)

To a solution of Compound 1-8 (250 mg, 0.83 mmol) and crude Compound 5-3 (469 mg crude, 1.5 mmol) in dimethyl formamide (20 mL) was added cesium carbonate (811 mg, 1.5 mmol). The mixture was stirred at 60° C. for overnight. The mixture was extracted with ethyl acetate (30 mL×3), washed with water (100 mL×3), brine (100 mL×2), dried over anhydrous sodium sulfate and concentrated. The residue was purified by prep. HPLC in 0.01% aqueous ammonia to give Compound 5-4 (150 mg, yield: 40%) as a white solid. MS (ESI): m/z: 455 [M+H]$^+$.

Preparation of 2-(1-(1-(1,2-dihydroacenaphthylen-1-yl)piperidin-4-yl)-3-methyl-2-oxoindolin-3-yl)-N-methylacetamide (Compounds 18, 19, 20, 21 and 22)

A mixture of Compound 5-4 (230 mg, 0.5 mmol) and methylamine (33% in methanol, 8 mL) in a sealed tube was stirred at 80° C. for overnight. The mixture was cooled and concentrated under reduce pressure. The residue was purified by prep. HPLC in 0.01% aqueous ammonia to give Compound 18 (180 mg, yield: 78%) as a white solid. The product (180 mg) was separated by Chiral-HPLC to give Compound 19 (12 mg), Compound 20 (10 mg), Compound 21 (11 mg), and Compound 22 (15 mg). MS (ESI): m/z: 454 [M+H]$^+$. Compound 18: $^1$H NMR (400 MHz, CDCl$_3$) δ: 7.72-7.69 (m, 1H), 7.63 (d, J=8.0 Hz, 2H), 7.54-7.52 (m, 2H), 7.48-7.45 (m, 1H), 7.30 (d, J=6.8 Hz, 1H), 7.27-7.23 (m, 3H), 7.20-7.18 (m, 1H), 7.05 (t, J=7.6 Hz, 1H), 6.20 (br s, 1H), 4.99 (t, J=5.6 Hz, 1H), 4.27-4.21 (m, 1H), 3.43 (d, J=5.2 Hz, 2H), 3.02 (d, J=12 Hz, 1H), 2.82-2.74 (m, 2H), 2.65-2.63 (m, 4H), 2.60-2.33 (m, 4H), 1.69-1.64 (m, 2H), 1.39 (s, 3H). Compound 19: $^1$H NMR (400 MHz, CDCl$_3$) δ: 7.73-7.70 (m, 1H), 7.64 (d, J=8.4 Hz, 2H), 7.55-7.52 (m, 2H), 7.49-7.46 (m, 1H), 7.31 (d, J=7.2 Hz, 1H), 7.28-7.24 (m, 3H), 7.07-7.03 (m, 1H), 6.19 (br s, 1H), 5.01 (t, J=5.6 Hz, 1H), 4.29-4.22 (m, 1H), 3.46 (d, J=5.2 Hz, 2H), 3.06-3.02 (m, 1H), 2.87-2.83 (m, 1H), 2.77 (d, J=14.4 Hz, 1H), 2.63 (d, J=4.4 Hz, 4H), 2.60-2.47 (m, 3H), 2.40-2.34 (m, 1H), 1.69 (t, J=14.0 Hz, 1H), 1.39 (s, 3H). Compound 20: $^1$H NMR (400 MHz, CDCl$_3$) δ: 7.73-7.69 (m, 1H), 7.64 (d, J=8.0 Hz, 2H), 7.55-7.52 (m, 2H), 7.49-7.45 (m, 1H), 7.31 (d, J=6.8 Hz, 1H), 7.27-7.20 (m, 3H), 7.07-7.03 (m, 1H), 6.19 (br s, 1H), 5.00 (t, J=6.4 Hz, 1H), 4.29-4.22 (m, 1H), 3.47 (d, J=5.2 Hz, 2H), 3.05-3.01 (m, 1H), 2.84-2.81 (m, 1H), 2.77 (d, J=14.8 Hz, 1H), 2.63 (d, J=19.2 Hz, 4H), 2.58-2.48 (m, 2H), 2.47-2.35 (m, 2H), 1.69 (t, J=13.2 Hz, 1H), 1.39 (s, 3H). Compound 21: $^1$H NMR (400 MHz, CDCl$_3$) δ: 7.71 (t, J=4.4 Hz, 1H), 7.64 (d, J=8.4 Hz, 2H), 7.54 (d, J=5.2 Hz, 2H), 7.49-7.45 (m, 1H), 7.30 (d, J=6.8 Hz, 1H), 7.26-7.19 (m, 3H), 7.07-7.03 (m, 1H), 6.20 (br s, 1H), 5.00 (t, J=5.6 Hz, 1H), 4.28-4.20 (m, 1H), 3.46 (d, J=5.6 Hz, 2H), 3.04-3.01 (m, 1H), 2.82-2.75 (m, 1H), 2.63 (d, J=20.0 Hz, 4H), 2.57-2.46 (m, 2H), 2.46-2.34 (m, 2H), 1.68 (t, J=15.6 Hz, 1H), 1.39 (s, 3H). 22: $^1$H NMR (400 MHz, CDCl$_3$) δ: 7.71 (t, J=4.4 Hz, 1H), 7.64 (d, J=8.4 Hz, 2H), 7.54 (d, J=5.2 Hz, 2H), 7.49-7.45 (m, 1H), 7.30 (d, J=6.8 Hz, 1H), 7.28-7.20 (m, 3H), 7.08-7.04 (m, 1H), 6.21 (br s, 1H), 5.00 (t, J=5.2 Hz, 1H), 4.28-4.21 (m, 1H), 3.45 (d, J=5.6 Hz, 2H), 3.02-3.00 (m, 1H), 2.85-2.82 (m, 1H), 2.76 (d, J=14.4 Hz, 1H), 2.62 (d, J=17.2 Hz, 4H), 2.57-2.46 (m, 3H), 2.40-2.33 (m, 1H), 1.69 (t, J=17.2 Hz, 1H), 1.39 (s, 3H).

Example 1F: Preparation of Compound 15

Scheme 6:

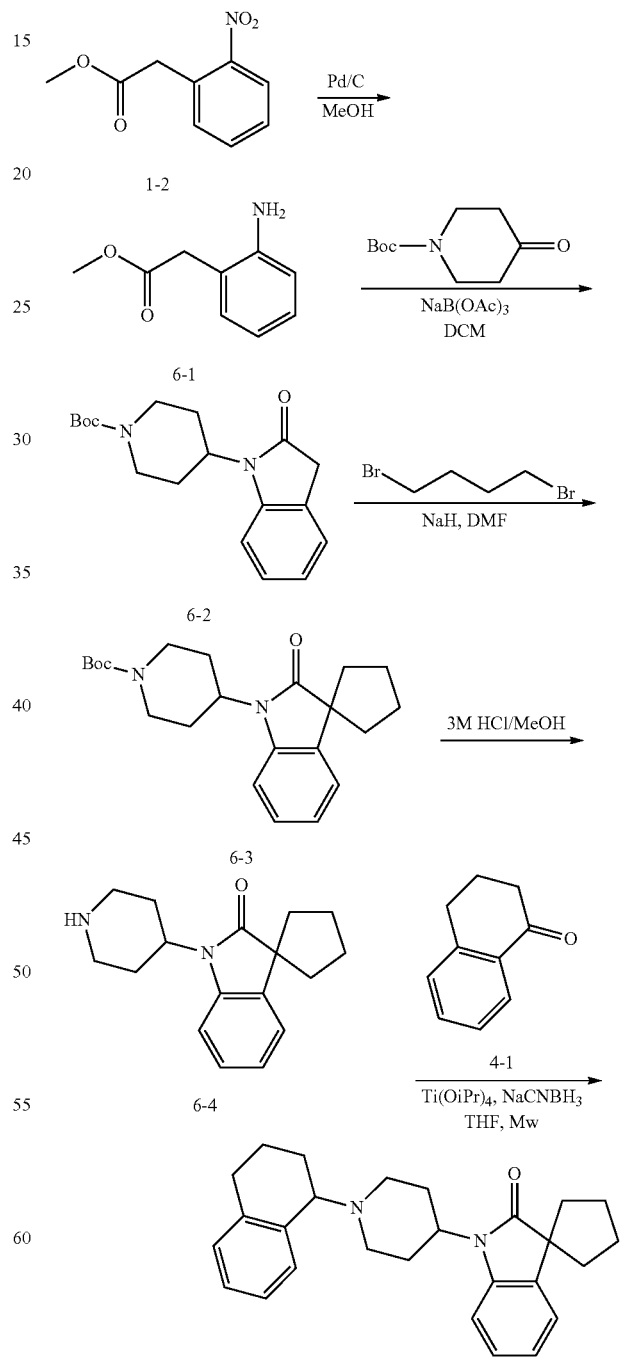

Preparation of methyl 2-(2-aminophenyl)acetate (Compound 6-1)

A mixture of Compound 1-2 (9.75 g, 50 mmol), 10% palladium/active carbon catalyst (dry, 530 mg, 5 mmol) in methanol (100 mL) was stirred under hydrogen atmosphere at room temperature for overnight. The reaction mixture was filtered to remove palladium/active carbon catalyst and the filtrate was concentrated to give Compound 6-1 (8.02 g, yield: 97%) as a pale yellow oil. MS (ESI): m/z: 166[M+H]$^+$. $^1$H NMR (400 MHz, DMSO-d$_6$) δ: 6.94 (m, 2H), 6.64 (d, 1H, J=8.0 Hz), 6.51 (m, 1H), 4.88 (s, 2H), 3.59 (s, 3H), 3.52 (s, 2H).

Preparation of tert-butyl 4-(2-oxoindolin-1-yl)piperidine-1-carboxylate (Compound 6-2)

A mixture of Compound 6-1 (3.30 g, 20 mmol), tert-butyl 4-oxopiperidine-1-carboxylate (4.38 g, 22 mmol), acetic acid (HOAc, 600 mg, 10 mmol) in dichloromethane (DCM, 80 mL) was stirred at room temperature for 2 h, then sodium triacetoxyborohydride (6.36 g, 30 mmol) was added in portions and heated to 40° C., stirred overnight. The reaction mixture was cooled to room temperature and diluted with dichloromethane (200 mL), washed with water (200 mL×2) and sodium bicarbonate (sat. aq., 200 mL×2), dried over anhydrous sodium sulfate, concentrated to give the crude product, purified by column chromatography on silica gel (ethyl acetate in petroleum ether, 5%, v/v) to give Compound 6-2 (2.65 g, yield: 42%) as a white solid. MS (ESI): m/z: 261[M+H−56]$^+$. $^1$H NMR (400 MHz, CDCl$_3$) δ: 7.24 (m, 2H), 7.01 (m, 2H), 4.41 (m, 1H), 4.28 (br s, 2H), 3.53 (s, 2H), 2.83 (br s, 2H), 2.32 (m, 2H), 1.70 (m, 2H), 1.50 (s, 9H).

Preparation of Compound 6-3

To a solution of tert-butyl 4-(2-oxoindolin-1-yl)piperidine-1-carboxylate (Compound 6-2, 1.68 g, 5.0 mmol) in tetrahydrofuran (30 mL) was added sodium hydride (1.0 g, 25 mmol) and 1,4-dibromobutane (1.3 g, 6.0 mmol) at 0° C. After stirred at room temperature for 2 hours, the mixture was neutralized with ammonium chloride (aq), extracted with ethyl acetate (50 mL×3). After cooled to room temperature, the mixture was filtered and the filtrate was concentrated. The organic layer was dried over anhydrous sodium sulfate, filtered and concentrated. The residue was purified on column chromatography eluting with ethyl acetate in petroleum ether (10%, v/v) to give Compound 6-3 as a white solid (400 mg, yield: 21%). MS (ESI): m/z: 315[M+H−56]$^+$.

Preparation of Compound 6-4

A solution of Compound 6-3 (370 mg, 1.0 mmol) in 3N hydrochloride in methyl alcohol (5 mL) was stirred at room temperature for 1 h. The mixture was concentrated to give crude Compound 6-4 as a yellow solid (270 mg, 100%). MS (ESI): m/z 271 [M+H]$^+$.

Preparation of Compound 15

To a solution of Compound 6-4 (135 mg, 0.5 mmol) and 3,4-dihydronaphthalen-1(2H)-one (73 mg, 0.5 mmol) in tetrahydrofuran (5 mL), was added titanium tetraisopropanolate (568 mg, 2.0 mmol). After stirred at 130° C. for 12 h under microwave condition, the mixture was cooled to room temperature. Sodium cyanoborohydride (126 mg, 2.0 mmol) was added to the mixture at room temperature. The mixture was stirred at 100° C. for 1 hour under microwave condition. The crude product was purified on column flash (40 g, 0.1% NH$_3$.H$_2$O) to give Compound 15 as a white solid (30 mg, 15%). MS (ESI): m/z 401 [M+H]$^+$. $^1$HNMR (400 MHz, DMSO-d$_6$), δ 7.72 (d, J=8.0 Hz, 1H), 7.31-7.27 (m, 2H), 7.22-7.19 (m, 2H), 7.13 (t, J=7.2 Hz, 1H), 7.09-7.02 (m, 1H), 4.10-4.09 (m, 1H), 3.90 (brs, 1H), 3.00-2.97 (m, 1H), 2.77-2.71 (m, 3H), 2.57-2.50 (m, 2H), 2.25-2.23 (m, 2H), 2.01-1.96 (m, 8H), 1.77-1.66 (m, 5H), 1.54-1.52 (m, 2H).

Example 1G: Preparation of Compound 14

Scheme 7:

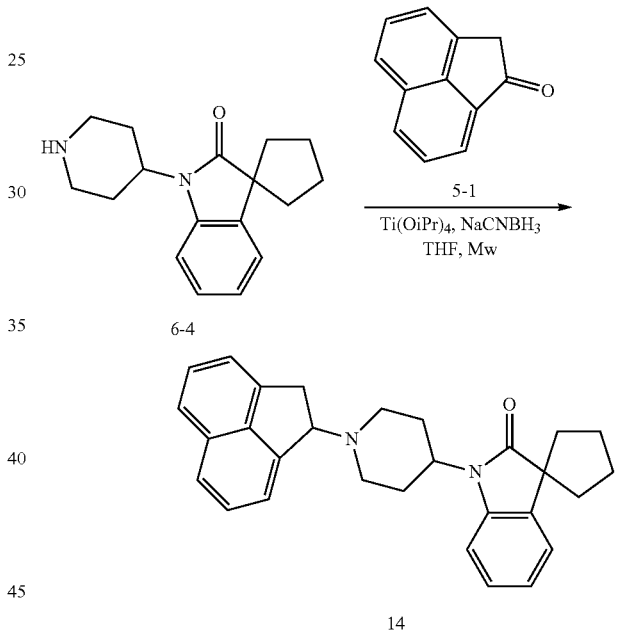

To a solution of Compound 6-4 (135 mg, 0.5 mmol) and acenaphthylen-1(2H)-one (84 mg, 0.5 mmol) in tetrahydrofuran (5 mL), was added titanium tetraisopropanolate (568 mg, 2.0 mmol). After stirred at 130° C. for 12 h under microwave condition, the mixture was cooled to room temperature. Sodium cyanoborohydride (126 mg, 2.0 mmol) was added to the mixture at room temperature. The mixture was stirred at 100° C. for 1 hour under microwave condition. The crude product was purified on column flash (40 g, 0.1% NH$_3$.H$_2$O) to give Compound 14 as a gray solid (30 mg, 15%). MS (ESI): m/z 423[M+H]$^+$. $^1$HNMR (400 MHz, DMSO-d$_6$), δ 7.70-7.67 (m, 1H), 7.62 (d, J=8.0 Hz, 1H), 7.53-7.52 (m, 2H), 7.45 (dd, J=7.2, 8.4 Hz, 1H), 7.29 (d, J=6.8 Hz, 1H), 7.21-7.17 (m, 3H), 7.02-6.98 (m, 1H), 4.96 (t, J=5.4 Hz, 1H), 4.31-4.24 (m, 1H), 3.42-3.40 (m, 2H), 3.01-2.98 (m, 1H), 2.77-2.75 (m, 1H), 2.54-2.34 (m, 4H), 2.15-2.01 (m, 4H), 1.99-1.92 (m, 2H), 1.83-1.78 (m, 2H), 1.69-1.60 (m, 2H).

Example 2A: Preparation Compound 1

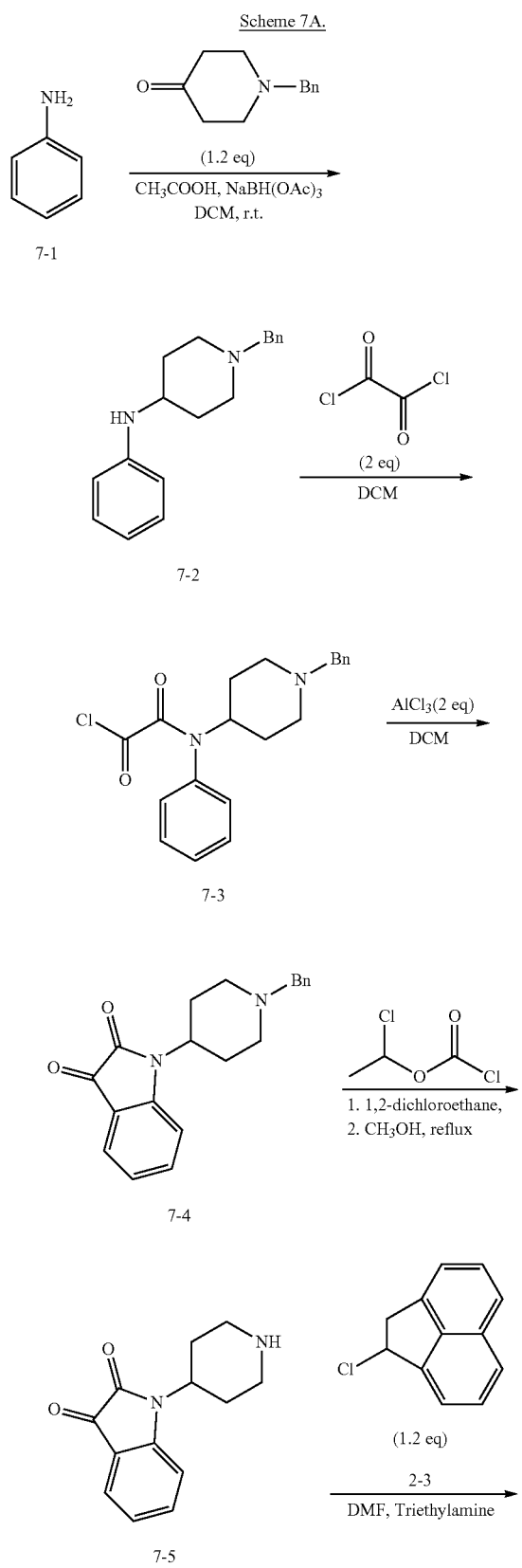

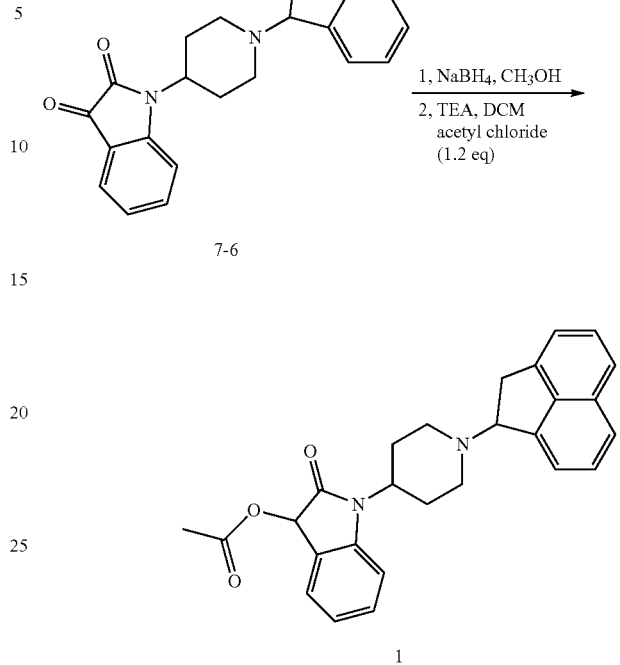

Preparation of 1-benzyl-N-phenylpiperidin-4-amine (Compound 7-2)

To a solution of aniline (Compound 7-1, 3.72 g, 40 mmol) in dichloromethane (50 mL), was added 1-benzylpiperidin-4-one (7.94 g, 42 mmol) and acetic acid (240 mg, 4 mmol). After stirred at room temperature for 2 h, sodium triacetoxyborohydride (12.72 g, 60 mmol) was added. The reaction mixture was stirred for another 1 h, then diluted with water (50 mL), neutralized to pH 7 with sodium bicarbonate, extracted with dichloromethane (100 ml×2). The combined organic layer was washed with brine (100 ml×2), dried over anhydrous sodium sulfate and concentrated to give 1-benzyl-N-phenylpiperidin-4-amine (Compound 7-2, 9.49 g, yield: 89%) as a white solid. MS (ESI): m/z: 267[M+H]$^+$.

Preparation of 2-((1-benzylpiperidin-4-yl)(phenyl)amino)-2-oxoacetyl chloride (Compound 7-3)

To a solution of oxalyl chloride (9.14 g, 72 mmol) in dichloromethane (50 mL) at room temperature, was added a solution of (1-benzyl-N-phenylpiperidin-4-amine (Compound 7-2, 9.49 g, 36 mmol) in dichloromethane (30 mL) slowly. After stirred for 2 h, dichloromethane and oxalyl chloride were removed in vacuo. The residue (Compound 7-3) was directly used for next step as dark green oil. MS (ESI): m/z: 353[M+H]$^+$.

Preparation of 1-(1-benzylpiperidin-4-yl)indoline-2,3-dione (Compound 7-4)

To a mixture of 2-((1-benzylpiperidin-4-yl)(phenyl)amino)-2-oxoacetyl chloride (12.8 g, 36 mmol) in dichloromethane (50 mL) at room temperature, was added anhydrous aluminum chloride (9.58 g, 72 mmol). The mixture was stirred at 40° C. for 2 h and then poured onto ice water, neutralized to pH 7 with sodium bicarbonate, filtered. The filtrate was extracted with dichloromethane (100 mL×2). The combined organic layer was dried over anhydrous sodium sulfate, evaporated. The residue was purified by silica gel chromatography (chloromethane:methanol=20:1) to afford 1-(1-benzyl-piperidin-4-yl)indoline-2,3-dione (Compound 7-4, 5.15 g, yield: 45%). MS (ESI): m/z: 321[M+H]$^+$. $^1$H NMR (400 MHz, CDCl$_3$) δ: 7.60-7.55 (m, 2H), 7.43-7.28 (m, 6H), 7.24-7.18 (m, 1H), 7.10 (t, J=6.8 Hz, 1H), 4.21 (m, 1H), 3.57 (s, 2H), 3.05 (d, J=9.2 Hz, 2H), 2.46-2.43 (m, 2H), 2.17-2.14 (m, 2H), 2.32 (m, 2H), 1.75 (dd, J=1.2, 12.0 Hz, 2H).

Preparation of 1-(piperidin-4-yl)indoline-2,3-dione (Compound 7-5)

A mixture of 1-(1-benzylpiperidin-4-yl)indoline-2,3-dione (Compound 7-4, 5.15 g, 16 mmol) and 2-chloroethyl chloroformate (2.74 g, 19 mmol) in 1,2-dichloroethane (50 mL) was stirred at 90° C. for 16 h, then concentrated in vacuo. The residue was diluted in with methanol (50 mL) and concentrated hydrochloric acid (5 mL), and heated 80° C. for 5 h, evaporated. The residue was diluted with chloromethane (50 mL), and neutralized to pH 7 with triethylamine, concentrated, and then purified by silica chromatography (dichloromethane:methanol=10:1) to give 1-(piperidin-4-yl)indoline-2,3-dione (Compound 7-5, 2.15 g, yield: 58%) as a yellow solid. MS (ESI): m/z: 231 [M+H]$^+$.

Preparation of 1-(1-(1,2-dihydroacenaphthylen-1-yl) piperidin-4-yl)indoline-2,3-dione (Compound 7-6)

To a mixture of 1-(piperidin-4-yl)indoline-2,3-dione (Compound 7-5, 1.38 g, 6 mmol) and 1-chloro-1,2-dihydroacenaphthylene (1.35 g, 7.2 mmol) in N,N-Dimethylformamide (5 mL), was added triethylamine (1.21 g, 12 mmol). The mixture was stirred at 50° C. for 13 h in seal tube, then diluted with H$_2$O (10 mL), extracted with ethyl acetate (30 ml×3). The combined organic layer was washed with brine, dried and concentrated. The residue was purified by silica gel chromatography (dichloromethane:methanol=20:1) to afford 1-(1-(1,2-dihydroacenaphthylen-1-yl)piperidin-4-yl) indoline-2,3-dione (Compound 7-6, 800 mg, yield: 35%) as a yellow solid. MS(ESI):m/z: 383[M+H]$^+$. $^1$H NMR (400 MHz, CDCl$_3$) δ: 7.72 (m, 1H), 7.65-7.59 (m, 2H), 7.57-7.45 (m, 4H), 7.30 (d, J=7.2 Hz, 1H), 7.21 (d, J=8.4 Hz, 4H), 7.09 (t, J=7.6 Hz, 1H), 4.97 (t, J=5.2 Hz, 1H), 4.22-4.14 (m, 1H), 3.49-3.37 (m, 2H), 3.01 (d, J=11.6 Hz, 2H), 2.82 (m, 1H), 2.57-2.32 (m, 4H), 1.78-1.74 (m, 2H).

Preparation of 1-(1-(1,2-dihydroacenaphthylen-1-yl) piperidin-4-yl)-2-oxoindolin-3-yl acetate (Compound 1)

To a solution of 1-(1-(1,2-dihydroacenaphthylen-1-yl) piperidin-4-yl)indoline-2,3-dione (Compound 7-6, 170 mg, 0.45 mmol) in methanol (5 mL) at room temperature, was added sodium borohydride (34 mg, 0.9 mmol) under argon condition. After stirred for 15 minutes, methanol was removed in vacuo. The residue was diluted with dichloromethane (5 mL) and triethylamine (90 mg, 0.9 mmol), cooled to 0° C. Acetyl chloride (42 mg, 0.54 mmol) was added slowly, then the mixture was stirred for 5 h, diluted with H$_2$O (10 mL), extracted with dichloromethane (20 mL×3). The combined organic layer was dried over anhydrous sodium sulfate and concentrated. The residue was purified by silica chromatography (dichloromethane:methanol=20:1) to give 1-(1-(1,2-dihydroacenaphthylen-1-yl)piperidin-4-yl)-2-oxoindolin-3-yl acetate (Compound 1, 20 mg, yield: 11%) as a light yellow solid. MS (ESI): m/z: 427[M+H]$^+$. $^1$H NMR (400 MHz, CDCl$_3$) δ: 7.71 (d, J=6.4 Hz, 1H), 7.63 (d, J=8.0 Hz, 1H), 7.56-7.52 (m, 2H), 7.47 (t, J=7.6 Hz, 1H), 7.36-7.29 (m, 3H), 7.18 (d, J=8.0 Hz, 1H), 7.04 (t, J=7.2 Hz, 1H), 5.88 (d, J=4.4 Hz, 1H), 4.98 (t, J=5.2 Hz, 1H), 4.20 (m, 1H), 3.42 (d, J=4.4 Hz, 2H), 2.99 (s, 1H), 2.78 (m, 1H), 2.54-2.34 (m, 4H), 2.18 (s, 3H), 1.72 (m, 2H).

Example 2B: Preparation of 1-(1-(1,2-dihydroacenaphthylen-1-yl)piperidin-4-yl)-2-oxoindolin-3-yl methylcarbamate (Compound 7-7)

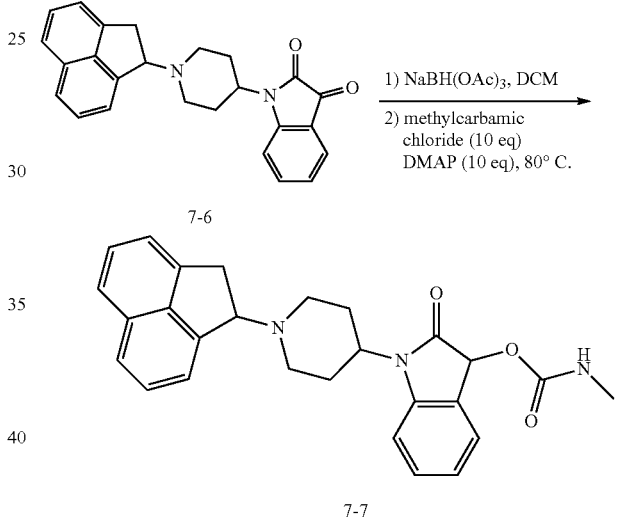

Scheme 7B.

To a solution of 1-(1-(1,2-dihydroacenaphthylen-1-yl) piperidin-4-yl)indoline-2,3-dione (Compound 7-6, 80 mg, 0.24 mmol) in dry dichloromethane (2 ml) was added sodium triacetoxyhydroborate (80 mg, 0.38 mmol). The mixture was stirred at room temperature under argon for 2 hours and concentrated. The residue was added N,N-dimethylpyridin-4-amine (306 mg, 2.5 mmol) and methylcarbamic chloride (234 mg, 2.5 mmol) and stirred in a sealed tube at 80° C. under argon overnight. The resulting mixture was diluted with dichloromethane and purified with pre-TLC twice (dichloromethane/methanol=30:1 and 20:1) to give a crude product, which was purified with pre-HPLC to give Compound 7-7 (5.2 mg, yield: 4.7%) as a white solid. MS (ESI): m/z: 442 [M+H]$^+$. $^1$H NMR (400 MHz, CDCl$_3$) δ: 7.71-7.69 (m, 1H), 7.63 (d, J=8 Hz, 1H), 7.55-7.50 (m, 2H), 7.48-7.41 (m, 2H), 7.33-7.29 (m, 2H), 7.18-7.16 (m, 1H), 7.03 (t, J=7.6 Hz, 1H), 5.82 (d, J=4.8 Hz, 1H), 4.97 (m, 1H), 4.84-4.83 (m, 1H), 4.25-4.19 (m, 1H), 3.41 (s, 1H), 3.00 (m, 1H), 2.84 (d, J=8 Hz, 1H), 2.79 (m, 1H), 2.57-2.34 (m, 4H), 1.70-1.65 (m, 2H).

Example 2C: Preparation of 1-(1-(1,2-dihydroace-naphthylen-1-yl)piperidin-4-yl)-3-hydroxy-3-methylindolin-2-one (Compound 37)

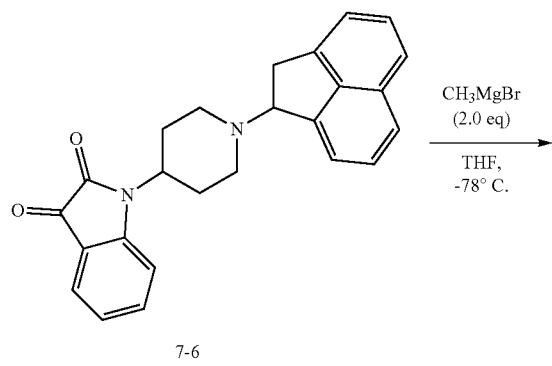

Example 2D: Preparation of 1-(1-(1,2-dihydroace-naphthylen-1-yl)piperidin-4-yl)-3-methyl-2-oxoindolin-3-yl acetate (Compound 38)

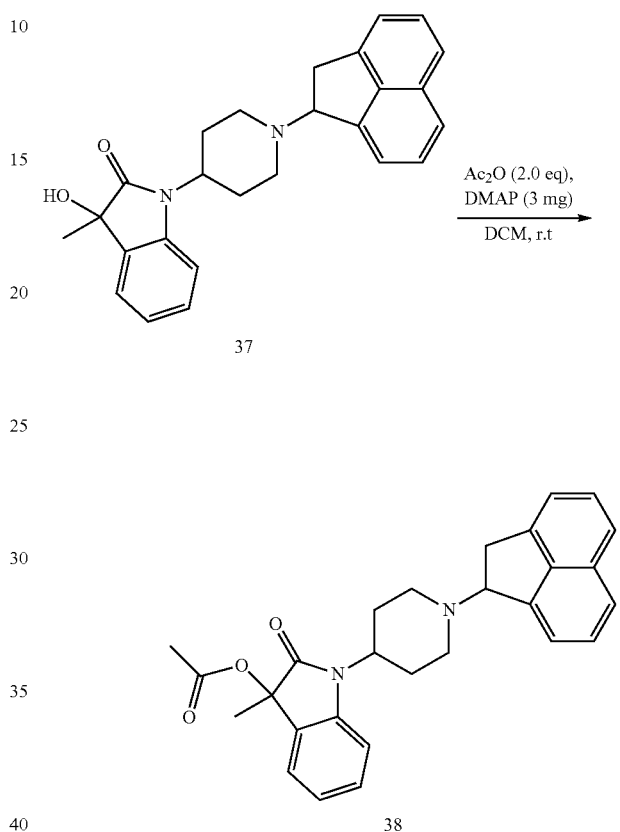

To a solution of 1-(1-(1,2-dihydroacenaphthylen-1-yl)piperidin-4-yl)indoline-2,3-dione (Compound 7-6, 382 mg, 1 mmol) in tetrahydrofuran (10 mL) at −78° C., methyl magnesium bromide (3M in tetrahydrofuran) (0.7 mL, 2 mmol) was added. The mixture was stirred for 5 hours at −78° C. for 5 hours, and then quenched by saturated ammonium chloride solution, extracted with ethyl acetate (50 mL). The organic layer was concentrated and the residue was purified by flash chromatography on silica gel (dichloromethane:methanol=15:1) to give 1-(1-(1,2-dihydroacenaphthylen-1-yl) piperidin-4-yl)-3-hydroxy-3-methylindolin-2-one (Compound 37, 120 mg, yield: 30%) as a yellow solid. MS (ESI): m/z: 399 [M+H]$^+$. $^1$H NMR (400 MHz, CDCl$_3$) δ: 7.71 (t, J=4.4 Hz, 1H), 7.63 (d, J=8.0 Hz, 1H), 7.54 (m, 2H), 7.46 (t, J=7.6 Hz, 1H), 7.42 (d, J=7.2 Hz, 1H), 7.30 (m, 2H), 7.22 (m, 1H), 7.08 (t, J=7.6 Hz, 1H), 4.95 (m, 1H), 4.21 (t, J=16.0 Hz, 1H), 3.42 (d, J=4.4 Hz, 2H), 3.21 (s, 1H), 2.98 (s, 1H), 2.79 (s, 1H), 2.55-2.29 (m, 4H), 1.66 (m, 2H), 1.57 (s, 3H)

A mixture of 1-(1-(1,2-dihydroacenaphthylen-1-yl) piperidin-4-yl)-3-hydroxy-3-methylindolin-2-one (Compound 37, 20 mg, 0.05 mmol), acetic anhydride (10 mg, 0.1 mmol) and DMAP (2 mg, 0.01 mmol) in dichloromethane (2 mL) was stirred room temperature. Then the mixture was diluted with water, extracted with dichloromethane (10 mL). The organic layer was washed with brine, dried over sodium sulfate, and concentrated in vacuo. The residue was purified by flash chromatography on silica gel (dichloromethane:methanol=15:1) to give 1-(1-(1,2-dihydroacenaphthylen-1-yl)piperidin-4-yl)-3-methyl-2-oxoindolin-3-yl acetate (Compound 38, 14 mg, yield: 64%). MS (ESI): m/z: 441 [M+H]$^+$. $^1$H NMR (400 MHz, CDCl$_3$) δ: 7.70 (m, 1H), 7.63 (d, J=8.0 Hz, 1H), 7.52 (m, 2H), 7.47 (t, J=7.6 Hz, 1H), 7.29 (m, 2H), 7.22 (m, 2H), 7.03 (t, J=7.2 Hz, 1H), 4.98 (s, 1H), 4.23 (m, 1H), 3.42 (m, 2H), 3.04-2.74 (m, 2H), 2.58-2.32 (m, 4H), 2.02 (s, 3H), 1.78 (m, 2H), 1.57 (s, 3H).

Example 2E: Preparation of 1-(1-(1,2-dihydroacenaphthylen-1-yl)piperidin-4-yl)-3-methyl-2-oxoindolin-3-yl methylcarbamate (Compound 42)

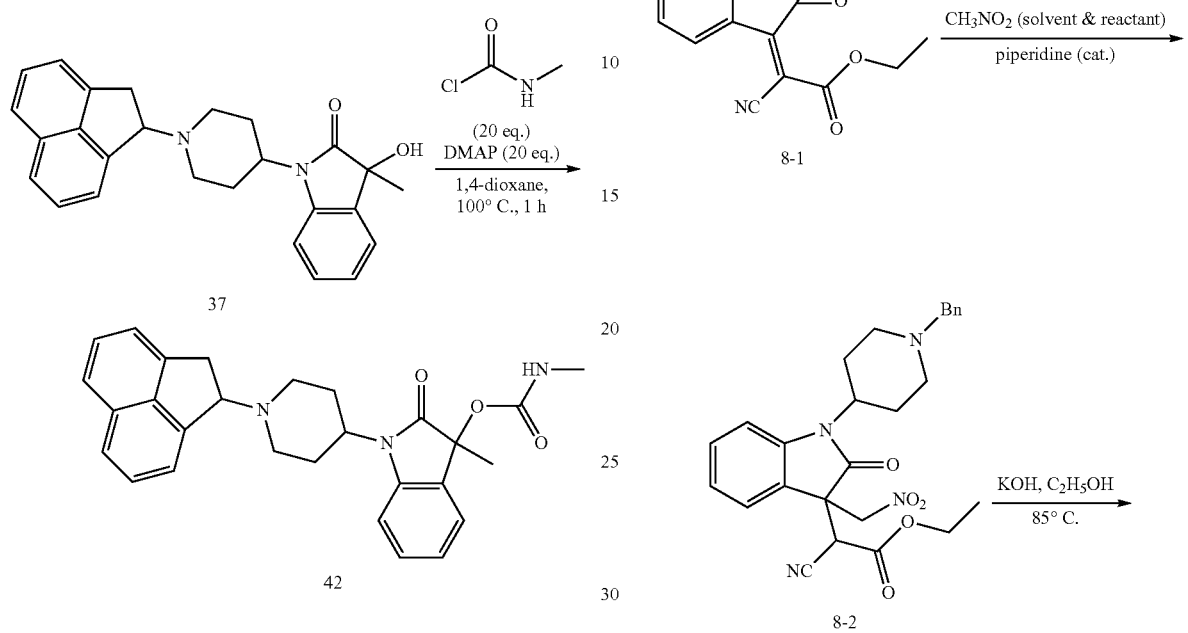

A mixture of methylcarbamic chloride (95 mg, 1 mmol) and DMAP (122 mg, 1 mmol) in seal tube was stirred at 80° C. for 1 hour. Then a solution of 1-(1-(1,2-dihydro acenaphthylen-1-yl)piperidin-4-yl)-3-hydroxy-3-methylindolin-2-one (Compound 37, 20 mg, 0.05 mmol) in 1,4-dioxane (5 mL) was added to the mixture. After addition, the mixture was stirred for 1 hour at 100° C., then filtered. The filtrate was purified by prep-HPLC to give 1-(1-(1,2-dihydroacenaphthylen-1-yl) piperidin-4-yl)-3-methyl-2-oxoindolin-3-ylmethylcarbamate (Compound 42, 8 mg, yield: 36%) as a white solid. MS (ESI): m/z: 456 [M+H]$^+$. $^1$H NMR (400 MHz, CDCl$_3$) δ: 7.72 (m, 1H), 7.67 (d, J=8.0 Hz, 1H), 7.55-7.46 (m, 3H), 7.31 (m, 2H), 7.26 (m, 2H), 7.03 (t, J=7.6 Hz, 1H), 5.00 (s, 1H), 4.73 (m, 1H), 4.28 (m, 1H), 3.46 (s, 2H), 3.07-2.83 (m, 2H), 2.67 (m, 3H), 2.42-2.32 (m, 4H), 1.75 (m, 2H), 1.54 (s, 3H).

Example 2F: Preparation of Compounds 2 and 51

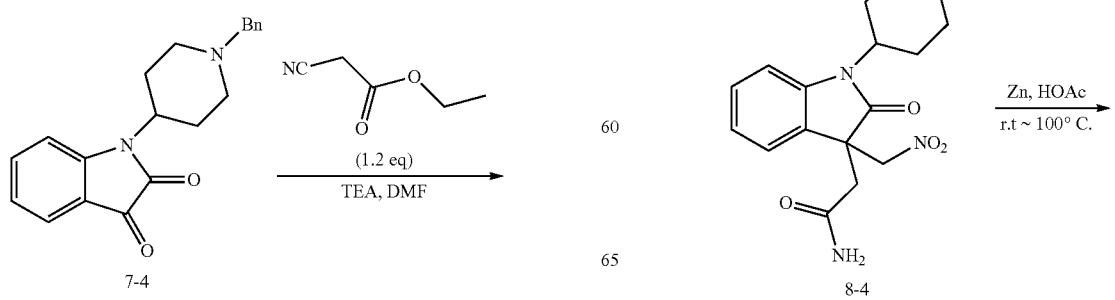

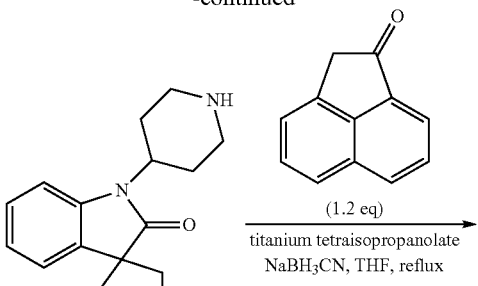

8-5

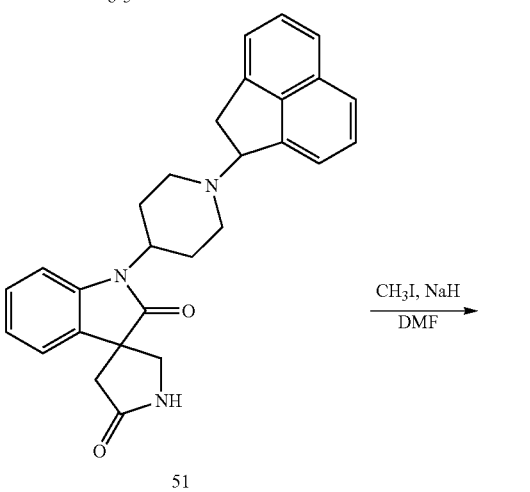

51

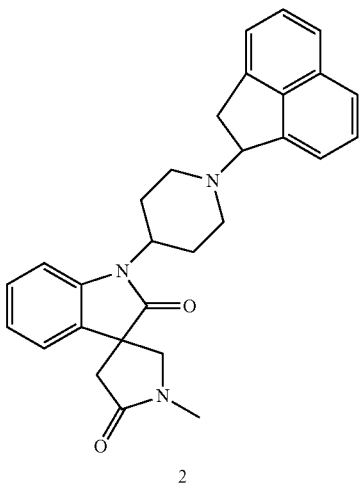

2

Preparation of (Z)-ethyl 2-(1-(1-benzylpiperidin-4-yl)-2-oxoindolin-3-ylidene)-2-cyanoacetate (Compound 8-1)

A mixture of 1-(1-benzylpiperidin-4-yl) indoline-2,3-dione (Compound 7-4, 16.0 g, 50 mmol), ethyl 2-cyanoacetate (6.78 g, 60 mmol) and triethylamine (10.1 g, 100 mmol) in N,N-dimethylformamide (30 mL) was stirred at 50° C. for 3 hours, then it was diluted with water (20 mL), extracted with ethyl acetate (100 mL×2). The combined organic layers were washed with brine (3 times), dried over sodium sulfate, and concentrated in vacuo to give crude (Z)-ethyl 2-(1-(1-benzylpiperidin-4-yl)-2-oxoin-dolin-3-ylidene)-2-cyanoacetate (Compound 8-1, 23.6 g, yield: 100%) as a black oil and it was directly used for next step. MS (ESI): m/z: 416[M+H]$^+$.

Preparation of (ethyl 2-(1-(1-benzylpiperidin-4-yl)-3-(nitromethyl)-2-oxoindolin-3-yl)-2-cyanoacetate (Compound 8-2)

To a solution of (Z)-ethyl 2-(1-(1-benzylpiperidin-4-yl)-2-oxoindolin-3-ylidene)-2-cyanoacetate (Compound 8-1, 20.75 g, 50 mmol) in nitromethane (20 mL), was added piperidine (8.5 g, 100 mmol). The reaction mixture was stirred for 2 hours, then nitromethane was removed under reduced pressure, and the residue was purified by flash column chromatography on silica gel (ethyl acetate: petroleum ether=1:3) to give (ethyl 2-(1-(1-benzylpiperidin-4-yl)-3-(nitromethyl)-2-oxoindolin-3-yl)-2-cyanoacetate (Compound 8-2, 11.98 g, yield: 50%) to give a black oil. MS (ESI): m/z: 477[M+H]$^+$.

Preparation of 2-(1-(1-benzylpiperidin-4-yl)-3-(nitromethyl)-2-oxoindolin-3-yl) acetonitrile (Compound 8-3)

A mixture of (ethyl 2-(1-(1-benzylpiperidin-4-yl)-3-(nitromethyl)-2-oxoindolin-3-yl)-2-cyanoacetate (Compound 8-2, 4.5 g, 9.45 mmol), and potassium hydroxide (1.06 g, mmol) in ethanol (20 mL) and water (2 mL) was stirred at 85° C. for 2 hours. Ethanol was removed under reduced pressure and the residue was extracted with ethyl acetate (50 mL×2). The organic layer was dried over sodium sulfate, and concentrated in vacuo, and purified by flash column chromatography on silica gel (ethyl acetate: petroleum ether=1:3) to give 2-(1-(1-benzylpiperidin-4-yl)-3-(nitromethyl)-2-oxoindolin-3-yl)acetonitrile (Compound 8-3, 1.07 g, yield: 28%) as a yellow solid. MS (ESI): m/z: 405[M+H]$^+$. $^1$H NMR (400 MHz, CDCl$_3$) δ: 7.57 (m, 1H), 7.40-7.21 (m, 9H), 7.10 (t, J=7.6 Hz, 1H), 5.29 (q, J=14.0 Hz, 2H), 4.12 (m, 1H), 3.53 (s, 2H), 3.23 (d, J=16.8 Hz, 1H), 3.10 (d, J=16.4 Hz, 1H), 2.95 (d, J=10.8 Hz, 2H), 2.45-2.37 (m, 2H), 2.15-2.07 (m, 2H), 1.65-1.62 (m, 2H).

Preparation of 2-(1-(1-benzylpiperidin-4-yl)-3-(nitromethyl)-2-oxoindolin-3-yl) acetamide (Compound 8-4)

To a mixture of 2-(1-(1-benzylpiperidin-4-yl)-3-(nitromethyl)-2-oxoindolin-3-yl)-acetonitrile (Compound 8-3, 1.07 g, 2.65 mmol) in tetrahydrofuran (6 mL) and water 1.5 mL) at room temperature, was added acetamide (1.56 g, 26.5 mmol) and palladium chloride (94 mg, 0.53 mmol). The reaction mixture was stirred 40° C. for 16 hours, then extracted with ethyl acetate (50 mL×3). The combined organic layer was washed with brine, dried over sodium sulfate and concentrated in vacuo to give crude 2-(1-(1-benzylpiperidin-4-yl)-3-(nitromethyl)-2-oxoindolin-3-yl) acetamide (Compound 8-4, 814 mg, yield: 73%) as a yellow solid. MS (ESI): m/z: 423[M+H]$^+$. $^1$H NMR (400 MHz, CDCl$_3$) δ: 7.40-7.37 (m, 5H), 7.31-7.25 (m, 3H), 7.17 (d, J=8.4 Hz, 1H), 7.01 (t, J=7.2 Hz, 1H), 6.83 (brs, 1H), 5.37 (d, J=14.4 Hz, 1H), 5.09 (d, J=13.6 Hz, 1H), 4.11 (m, 1H), 3.54 (s, 2H), 2.96 (t, J=5.2 Hz, 2H), 2.69 (d, J=15.2 Hz, 1H), 2.52 (d, J=15.2 Hz, 1H), 2.39-2.34 (m, 2H), 2.08-2.14 (m, 2H), 1.67-1.61 (m, 2H).

Preparation of Compound 8-5

To a solution of 2-(1-(1-benzylpiperidin-4-yl)-3-(nitromethyl)-2-oxoindolin-3-yl)-acetamide (Compound 8-4, 814 mg, 1.9 mmol) in acetic acid (20 mL) at 0° C., Zinc (1.24 g, 19 mmol) was added in portions. The mixture was heated to 100° C. and stirred for 2 hours. Acetic acid was removed in vacuo, and the residue was purified by flash column chromatography on silica gel (dichloromethane:methanol=4:10 to afford Compound 8-5 (539 mg, yield: 98%) as a yellow solid. MS (ESI): m/z: 286[M+H]$^+$.

Preparation of Compound 51

A mixture of Compound 8-5 (450 mg, 1.58 mmol), acenaphthylen-1(2H)-one (317 mg, 1.89 mmol) and titanium tetraisopropanolate (2.24 g, 7.89 mmol) in dry toluene (10 mL) was stirred 100° C. for 2 hours, then sodium cyanoborohydride (466 mg, 7.89 mmol) was added. After stirred for another 1 hour, the mixture was diluted with water (20 mL), filtered. The solid was washed with ethyl acetate (100 mL) and ammonium hydroxide (20 mL). The organic layer was dried over sodium sulfate, then concentrated in vacuo and the residue was purified by flash column chromatography (dichloromethane:methanol=20:1) to give Compound 51 (120 mg, yield: 17%) as a light yellow solid. MS (ESI): m/z: 438[M+H]$^+$. $^1$H NMR (400 MHz, CDCl$_3$) δ: 7.66 (m, 1H), 7.58 (d, J=8.4 Hz, 1H), 7.48 (d, J=8.0 Hz, 2H), 7.41 (t, J=6.8 Hz, 1H), 7.32 (d, J=7.2 Hz, 1H), 7.26-7.23 (m, 2H), 7.18 (d, J=7.6 Hz, 1H), 7.02 (t, J=7.2 Hz, 1H), 6.40 (brs, 1H), 4.92 (t, J=5.6 Hz, 1H), 4.19 (t, J=8.0 Hz, 1H), 3.76 (d, J=9.6 Hz, 1H), 3.38 (m, 3H), 2.95 (d, J=10.4 Hz, 1H), 2.88 (d, J=17.2 Hz, 1H), 2.74 (m, 1H), 2.52-2.29 (m, 5H), 1.66-1.58 (m, 2H).

Preparation of Compound 2

To a solution of Compound 51 (44 mg, 0.1 mmol) in N,N-dimethylformamide (2 mL), was added sodium hydride (60% in mineral oil, 5 mg, 2 mmol) at room temperature. After the mixture was stirred at 10 minutes, iodomethane (21 mg, 0.15 mmol) was added, then stirred for another 1 hour. water (10 mL) was added, and the mixture was extracted with ethyl acetate (20 mL×3). The combined organic layer was washed with brine (3 times), dried over sodium sulfate, and concentrated in vacuo. The residue was purified by reverse phase chromatography to give Compound 2 (20 mg, yield: 44%) as a white solid. MS (ESI): m/z: 452 (M+H)$^+$. $^1$H NMR (400 MHz, CDCl$_3$) δ: 7.73-7.68 (m, 1H), 7.63 (d, J=8.4 Hz, 1H), 7.55-7.52 (m, 2H), 7.46 (t, J=7.6 Hz, 1H), 7.31-7.22 (m, 4H), 7.06 (t, J=7.2 Hz, 1H), 4.98 (d, J=5.2 Hz, 1H), 4.25 (m, 1H), 3.79 (d, J=9.2 Hz, 1H), 3.43 (t, J=5.2 Hz, 2H), 3.38 (t, J=10.0 Hz, 1H), 3.13-2.96 (m, 5H), 2.79 (t, J=6.8 Hz, 1H), 2.58-2.33 (m, 5H), 1.71 (m, 2H).

Example 3: Preparation of Compound 32

Scheme 9.

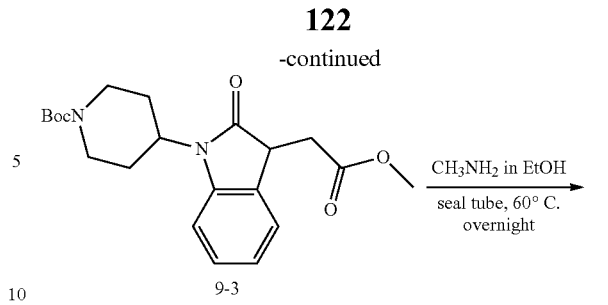

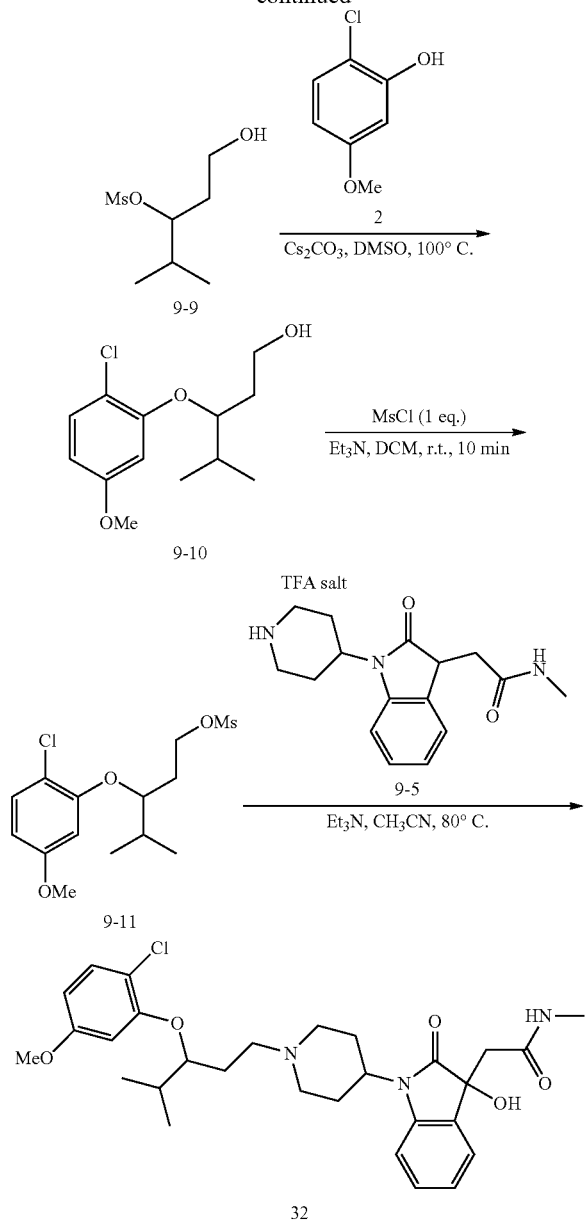

NMR (400 MHz, CDCl$_3$) δ: 7.17 (d, 1H, J=8.8 Hz), 6.58 (d, 1H, J=2.8 Hz), 6.44 (dd, 1H, J=8.8, 2.8 Hz), 5.58 (bs, 1H), 3.76 (s, 3H).

Preparation of tert-butyl 4-(3-(2-(methylamino)-2-oxoethyl)-2-oxoindolin-1-yl)piperidine-1-carboxylate (Compound 9-4)

A suspension of tert-butyl 4-(3-(2-methoxy-2-oxoethyl)-2-oxoindolin-1-yl) piperidine-1-carboxylate (Compound 9-3, 5.82 g, 15 mmol) in methanamine (33 wt. % solution in ethanol, 18 mL) was stirred in a seal tube at 60° C. overnight. The reaction mixture was evaporated to dryness and purified by flash column chromatography on silica gel (ethyl acetate/petroleum ether, 1/15-1/10-1/5 v/v) to give the desired product tert-butyl 4-(3-(2-(methylamino)-2-oxoethyl)-2-oxoindolin-1-yl)piperidine-1-carboxylate (Compound 9-4, 4.00 g, yield: 69%) as a pale yellow solid. MS (ESI): m/z: 388[M+H]$^+$, 332[M+H−56]$^+$.

Preparation of N-methyl-2-(2-oxo-1-(piperidin-4-yl) indolin-3-yl)acetamide (Compound 9-5)

A mixture of tert-butyl 4-(3-(2-(methylamino)-2-oxoethyl)-2-oxoindolin-1-yl) piperidine-1-carboxylate (Compound 9-4, 4.00 g, 10.3 mmol), trifluoroacetic acid (5.70 g, 50 mmol), in dichloromethane (DCM, 20 mL) was stirred at room temperature for 1 h. The reaction mixture was concentrated to remove trifluoroacetic acid and dichloromethane to give the crude product N-methyl-2-(2-oxo-1-(piperidin-4-yl) indolin-3-yl)acetamide TFA salt (Compound 9-5, 4.10 g, yield: 99%) as a pale yellow syrup. MS (ESI): m/z: 288[M+H]$^+$.

Preparation of methyl 3-hydroxy-4-methylpentanoate (Compound 9-7)

Sodium borohydride (NaBH$_4$, 1.90 g, 50 mmol) was added to a solution of methyl 4-methyl-3-oxopentanoate (Compound 9-6, 14.4 g, 100 mmol) in methanol (MeOH, 150 mL), the mixture was stirred for 1 hour at room temperature and evaporated to dryness and diluted with ethyl acetate (300 mL) and water (200 mL), stirred for 5 minutes and washed with brine (300 mL×3), dried over anhydrous sodium sulfate, concentrated to give the desired product methyl 3-hydroxy-4-methylpentanoate (Compound 9-7, 12.5 g, yield: 86%) as a pale yellow oil. MS (ESI): m/z: 147[M+H]$^+$, 169[M+H+23]$^+$. $^1$H NMR (400 MHz, CDCl$_3$) δ: 3.79 (m, 1H), 3.72 (s, 3H), 2.93 (d, 1H, J=4.0 Hz), 2.38-2.54 (m, 2H), 1.70 (m, 1H), 0.95 (d, 3H, J=6.8 Hz), 0.92 (d, 3H, J=6.8 Hz).

Preparation of methyl 4-methyl-3-(methylsulfonyloxy)pentanoate (Compound 9-8)

Methanesulfonyl chloride (MsCl, 15.6 g, 137 mmol) was added dropwise to a solution of methyl 3-hydroxy-4-methylpentanoate (Compound 9-7, 20.0 g, 137 mmol), triethylamine (TEA, 20.8 g, 206 mmol) in dichloromethane (DCM, 200 mL) at 0° C. and the mixture was stirred for 4 hours at room temperature. The mixture was diluted with dichloromethane (DCM, 200 mL) and washed with water (350 mL×3), dried over anhydrous sodium sulfate, concentrated to give the desired product 4-methyl-3-(methylsulfonyloxy) pentanoate (Compound 9-8, 18.0 g, yield: 60%) as a pale yellow oil. MS (ESI): m/z: 247[M+H+23]$^+$. $^1$H NMR (400

Preparation of 2-chloro-5-methoxyphenol (Compound 9-2)

To a solution of 3-methoxyphenol (Compound 9-1, 37.2 g, 300 mmol) in diethyl ether (Et$_2$O, 300 mL) at 0° C. was added sulfuryl chloride (SO$_2$Cl$_2$, 48.6 g, 360 mmol) dropwise. The mixture was warmed to room temperature and stirred for 2 hours. The reaction mixture was diluted with ethyl acetate (300 mL) and water (200 mL), stirred for 5 minutes and washed with sodium bicarbonate (sat. aq., 250 mL×3), brine (300 mL×2), dried over anhydrous sodium sulfate, concentrated to give the crude product, purified by flash column chromatography on silica gel (ethyl acetate/ petroleum ether, 1/30-1/20 v/v) to give the desired product 2-chloro-5-methoxyphenol (Compound 9-2, 16.0 g, yield: 34%) as a pale yellow oil. MS (ESI): m/z: 159[M+H]$^+$. $^1$H MHz, CDCl$_3$) δ: 4.96 (m, 1H), 3.72 (s, 3H), 3.04 (s, 3H), 2.59-2.76 (m, 2H), 2.14 (m, 1H), 1.01 (d, 3H, J=6.8 Hz), 0.97 (d, 3H, J=7.2 Hz).

Preparation of 1-hydroxy-4-methylpentan-3-yl methanesulfonate (Compound 9-9)

Lithium aluminum hydride (LiAlH$_4$, 380 mg, 10 mmol) was added in portions to a solution of 4-methyl-3-(methylsulfonyloxy)pentanoate (Compound 9-8, 2.24 g, 10 mmol) in dry tetrahydrofuran (THF, 40 mL) at 0° C. and the mixture was stirred for 1 hour at room temperature. The reaction mixture was poured to a mixture of sodium sulfate (Na$_2$SO$_4$, 5 g) in water (100 mL) and stirred for 10 minutes, filtered, the filtrate was extracted with ethyl acetate (100 mL×4), combined organic phase was washed with water (250 mL×3), dried over anhydrous sodium sulfate, concentrated to give the desired product 1-hydroxy-4-methylpentan-3-yl methanesulfonate (Compound 9-9, 1.58 g, yield: 81%) as a pale yellow oil. MS (ESI): m/z: 219[M+H+23]$^+$. $^1$H NMR (400 MHz, CDCl$_3$) δ: 4.81 (m, 1H), 3.78 (m, 2H), 3.07 (s, 3H), 2.06 (m, 2H), 1.85 (m, 2H), 1.01 (d, 3H, J=7.2 Hz), 0.97 (d, 3H, J=6.8 Hz).

Preparation of 3-(2-chloro-5-methoxyphenoxy)-4-methylpentan-1-ol (Compound 9-10)

A mixture of 1-hydroxy-4-methylpentan-3-yl methanesulfonate (Compound 9-9, 1.0 g, 5.1 mmol), 2-chloro-5-methoxyphenol (Compound 9-2, 806 mg, 51 mmol), cesium carbonate (Cs$_2$CO$_3$, 3.33 g, 102 mmol) in dimethyl sulfoxide (DMSO, 20 mL) was heated to 100° C. and stirred overnight. The reaction mixture was cooled to room temperature and diluted with ethyl acetate (100 mL) and water (100 mL), stirred for 5 minutes and washed with brine (100 mL×4), dried over anhydrous sodium sulfate, concentrated to give the crude product, purified by flash column chromatography on silica gel (ethyl acetate/petroleum ether, 1/10-1/5 v/v) to give the desired product 3-(2-chloro-5-methoxyphenoxy)-4-methylpentan-1-ol (Compound 9-10, 220 mg, yield: 17%) as a brown oil. MS (ESI): m/z: 259[M+H]$^+$, 281[M+H+23]$^+$. $^1$H NMR (400 MHz, CDCl$_3$) δ: 7.22 (d, 1H, J=8.8 Hz), 6.62 (d, 1H, J=2.4 Hz), 6.41 (dd, 1H, J=8.8, 2.8 Hz), 4.37 (m, 1H), 3.80 (m, 2H), 3.77 (s, 3H), 1.85-2.10 (m, 4H), 0.97 (d, 3H, J=6.8 Hz), 0.92 (d, 3H, J=6.8 Hz).

Preparation of 3-(2-chloro-5-methoxyphenoxy)-4-methylpentyl methanesulfonate (Compound 9-11)

Methanesulfonyl chloride (MsCl, 1.38 g, 12 mmol) was added dropwise to a solution of 3-(2-chloro-5-methoxyphenoxy)-4-methylpentan-1-ol (Compound 9-10, 3.10 g, 12 mmol), triethylamine (TEA, 2.42 g, 24 mmol) in dichloromethane (DCM, 40 mL) at 0° C. and the mixture was stirred for 10 minutes at room temperature. The mixture was diluted with dichloromethane (DCM, 100 mL) and washed with water (100 mL×3), dried over anhydrous sodium sulfate, concentrated to give the desired product 3-(2-chloro-5-methoxyphenoxy)-4-methylpentyl methanesulfonate (Compound 9-11, 3.50 g, yield: 87%) as a pale yellow oil. MS (ESI): m/z: 359[M+H+23]$^+$. $^1$H NMR (400 MHz, CDCl$_3$) δ: 7.23 (d, 1H, J=8.8 Hz), 6.55 (d, 1H, J=2.4 Hz), 6.44 (dd, 1H, J=8.8, 2.4 Hz), 4.41 (m, 1H), 4.33 (m, 2H), 3.78 (s, 3H), 2.88 (s, 3H), 2.09 (m, 3H), 1.01 (d, 3H, J=6.8 Hz), 0.98 (d, 3H, J=6.8 Hz).

Preparation of 3-(2-chloro-5-methoxyphenoxy)-4-methylpentan-1-ol (Compound 32)

A mixture of 3-(2-chloro-5-methoxyphenoxy)-4-methylpentyl methanesulfonate (Compound 9-11, 168 mg, 0.5 mmol), N-methyl-2-(2-oxo-1-(piperidin-4-yl)indolin-3-yl)acetamide TFA salt (Compound 9-2, 200 mg, 0.5 mmol), N,N-diisopropylethylamine (DIPEA, 129 mg, 1.0 mmol) in acetonitrile (CH$_3$CN, 5 mL) was heated to 80° C. and stirred overnight. The reaction mixture was cooled to room temperature and evaporated to remove acetonitrile, the residue was diluted with ethyl acetate (20 mL) and washed with water (15 mL×2), and brine (20 mL×1), dried over anhydrous sodium sulfate, concentrated to give the crude product, purified by Pre-TLC (CH$_3$OH/DCM, 1/15 v/v) to give the desired product 3-(2-chloro-5-methoxyphenoxy)-4-methylpentan-1-ol (Compound 32, 20 mg, yield: 7%) as a pale yellow solid. MS (ESI): m/z: 544[M+H]$^+$. $^1$H NMR (400 MHz, CDCl$_3$) δ: 7.38 (d, 1H, J=6.8 Hz), 7.18-7.31 (m, 3H), 7.05 (t, 1H, J=7.2 Hz), 6.76 (d, 1H, J=2.4 Hz), 6.40 (dd, 1H, J=8.8, 2.0 Hz), 6.02 (bs, 1H), 4.25 (m, 2H), 3.78 (d, 3H, J=8.0 Hz), 3.11 (m, 1H), 2.97 (m, 1H), 2.85 (d, 3H, J=4.8 Hz), 2.73 (d, 1H, J=14.8 Hz), 2.40-2.60 (m, 5H), 1.95-2.20 (m, 3H), 1.87 (m, 2H), 1.69 (m, 2H), 1.01 (d, 3H, J=7.2 Hz), 0.98 (d, 3H, J=7.2 Hz).

Example 4: Preparation of Compounds 41 and 47

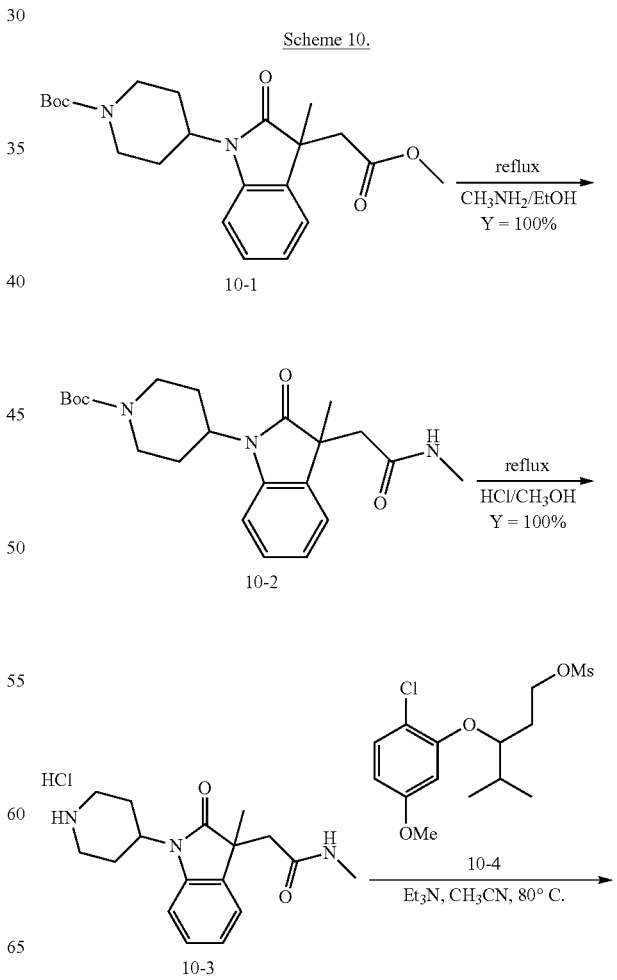

-continued

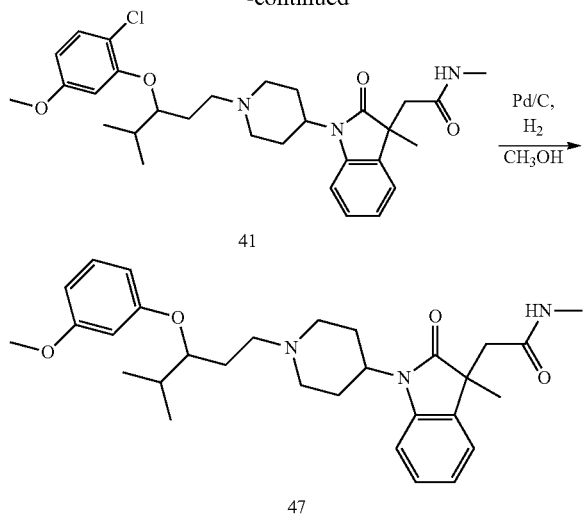

Preparation of tert-butyl 4-(3-methyl-3-(2-(methylamino)-2-oxoethyl)-2-oxoindolin-1-yl)piperidine-1-carboxylate (Compound 10-2)

A suspension of tert-butyl 4-(3-(2-methoxy-2-oxoethyl)-3-methyl-2-oxoindolin-1-yl)piperidine-1-carboxylate (Compound 10-1, 2 g, 5 mmol) in methanamine (33 wt. % solution in ethanol, 15 mL) was stirred in a seal tube at 80° C. overnight. The reaction mixture was evaporated to dryness to afford the product (2 g, 100%) as an yellow oil which was used for the next step without further purification. MS (ESI): m/z: 402[M+H]$^+$, 346[M+H−56]$^+$.

Preparation of N-methyl-2-(3-methyl-2-oxo-1-(piperidin-4-yl)indolin-3-yl)acetamide (Compound 10-3)

A mixture of tert-butyl 4-(3-methyl-3-(2-(methylamino)-2-oxoethyl)-2-oxoindolin-1-yl)piperidine-1-carboxylate (Compound 10-2, 2 g, 5 mmol) in HCl/CH$_3$OH (2.5 M, 15 mL) was stirred at refluxing for 1 h. The reaction mixture was concentrated to remove the solvent to give the crude product N-methyl-2-(3-methyl-2-oxo-1-(piperidin-4-yl)indolin-3-yl)acetamide HCl salt (Compound 10-3, 1.9 g, yield: 100%) as a white solid. MS (ESI): m/z: 302[M+H]$^+$.

Preparation of 2-(1-(1-(3-(2-chloro-5-methoxyphenoxy)-4-methylpentyl)piperidin-4-yl)-3-methyl-2-oxoindolin-3-yl)-N-methylacetamide (Compound 41)

A mixture of 3-(2-chloro-5-methoxyphenoxy)-4-methylpentyl methanesulfonate (Compound 10-4, 168 mg, 0.5 mmol), N-methyl-2-(3-methyl-2-oxo-1-(piperidin-4-yl)indolin-3-yl)acetamide HCl salt (Compound 10-3, 200 mg, 0.6 mmol), N,N-diisopropylethylamine (DIPEA, 129 mg, 1.0 mmol) in acetonitrile (CH$_3$CN, 5 mL) was heated to 80° C. and stirred overnight. The reaction mixture was cooled to room temperature and evaporated to remove acetonitrile, the residue was diluted with ethyl acetate (20 mL) and washed with water (15 mL×2), and brine (20 mL×1), dried over anhydrous sodium sulfate, concentrated to give the crude product, purified by column flash (40 g, NH$_3$.H$_2$O, 0.1%) to give the product 2-(1-(1-(3-(2-chloro-5-methoxyphenoxy)-4-methylpentyl)piperidin-4-yl)-3-methyl-2-oxoindolin-3-yl)-N-methylacetamide (Compound 41, 135 mg, yield: 50%) as a white solid. MS (ESI): m/z: 542[M+H]$^+$. $^1$H NMR (400 MHz, CDCl$_3$) δ: 7.24 (d, J=8.8 Hz, 2H), 7.17-7.20 (m, 1H), 7.06 (t, J=7.6 Hz, 1H,), 6.79 (dd, J=2.4 Hz, J=12.0 Hz, 1H,), 6.41 (dd, J=2.4 Hz, J=8.4 Hz, 1H), 6.21 (brs, 1H), 4.25-4.33 (m, 2H), 3.78 (d, J=2.4 Hz, 3H), 3.10 (d, J=13.2 Hz, 1H), 2.94 (d, J=12.0 Hz, 1H), 2.79 (dd, J=3.2 Hz, J=14.0 Hz, 1H), 2.66 (d, J=4.8 Hz, 3H), 2.62-2.65 (m, 1H), 2.39-2.58 (m, 4H), 1.96-2.16 (m, 3H), 1.86 (m, 2H), 1.67-1.73 (m, 2H), 1.4 (s, 3H), 1.00 (t, J=8.0 Hz, 6H).

Preparation of 2-(1-(1-(3-(3-methoxyphenoxy)-4-methylpentyl)piperidin-4-yl)-3-methyl-2-oxoindolin-3-yl)-N-methylacetamide (Compound 47)

To a solution of 2-(1-(1-(3-(2-chloro-5-methoxyphenoxy)-4-methylpentyl)piperidin-4-yl)-3-methyl-2-oxoindolin-3-yl)-N-methylacetamide (Compound 41, 50 mg, 0.09 mmol) in methanol (3 mL) was added Pd/C (10 mg). The mixture was stirred at room temperature for overnight under N$_2$ atmosphere. The mixture was filtered and the filtrate was concentrated to afford the crude product which was purified by Pre-TLC to give the pure product 2-(1-(1-(3-(3-methoxyphenoxy)-4-methylpentyl)piperidin-4-yl)-3-methyl-2-oxoindolin-3-yl)-N-methylacetamide (Compound 47, 8 mg, 17%) as a white solid. MS (ESI): m/z: 508[M+H]$^+$. $^1$H NMR (400 MHz, DMSO-d$_6$) δ: 7.59-7.63 (m, 1H), 7.14-7.23 (m, 3H), 7.05 (d, J=8.4 Hz, 1H,), 6.93 (t, J=7.6 Hz, 1H,), 6.57-6.61 (m, 1H), 6.53-6.56 (m, 1H), 6.48 (dd, J=2.4 Hz, J=8.4 Hz, 1H), 4.26-4.30 (m, 1H), 4.02-4.09 (m, 1H), 3.72 (s, 3H), 3.00 (d, J=10.4 Hz, 1H), 2.86 (d, J=10.8 Hz, 1H), 2.69 (d, J=15.2 Hz, 1H), 2.57 (d, J=15.2 Hz, 1H), 2.27-2.40 (m, 7H), 1.89-2.05 (m, 3H), 1.79 (m, 2H), 1.58-1.66 (m, 2H), 1.17 (s, 3H), 0.92 (q, J=6.8 Hz, 6H).

Example 5: Preparation of Compounds 27 and 28

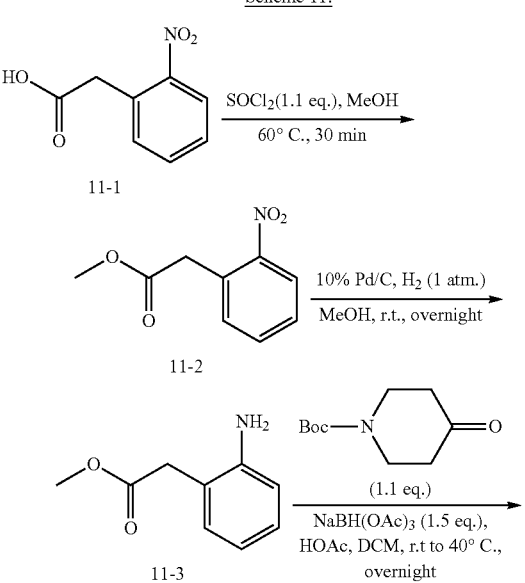

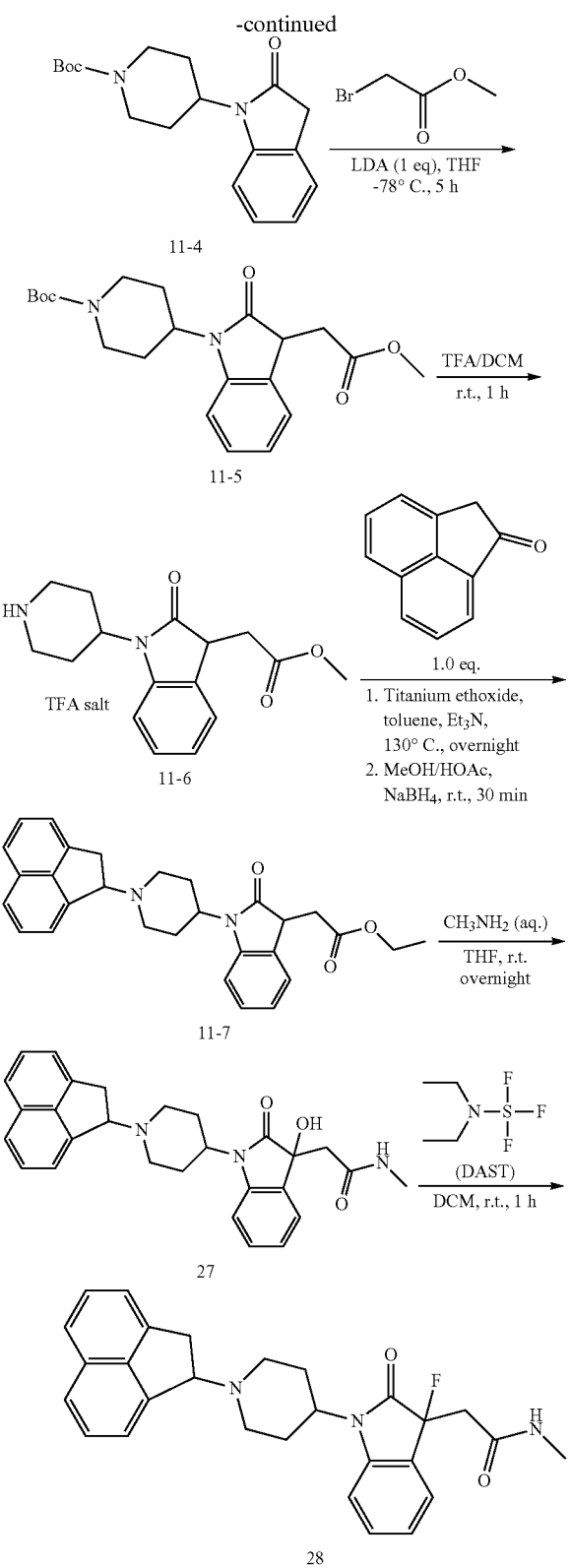

Preparation of methyl 2-(2-nitrophenyl)acetate (Compound 11-2)

To a solution of 2-(2-nitrophenyl)acetic acid (Compound 11-1, 18.1 g, 100 mmol) in methanol (150 mL) at room temperature was added sulfurous dichloride (SOCl$_2$, 13.1 g, 110 mmol) dropwise. The mixture was heated to 60° C. and stirred for 30 minutes. The reaction mixture was concentrated to give a pale yellow oil, diluted with ethyl acetate (200 mL), washed with sodium bicarbonate (sat. aq., 150 mL×3), brine (100 mL×2), dried over anhydrous sodium sulfate, concentrated to give the desired product methyl 2-(2-nitrophenyl)acetate (Compound 11-2, 19.1 g, yield: 98%) as a pale yellow oil. MS (ESI): m/z: 196[M+H]$^+$. $^1$H NMR (400 MHz, CDCl$_3$) δ: 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 1H).

Preparation of methyl 2-(2-aminophenyl)acetate (Compound 11-3)

A mixture of methyl 2-(2-nitrophenyl)acetate (Compound 11-2, 9.75 g, 50 mmol), 10% palladium/active carbon catalyst (dry, 530 mg, 5 mmol) in methanol (100 mL) was stirred under H$_2$ (1 atm.) at room temperature overnight. The reaction mixture was filtered to remove palladium/active carbon catalyst and the filtrate was concentrated to give the desired product methyl 2-(2-aminophenyl)acetate (Compound 11-3, 8.02 g, yield: 97%) as a pale yellow oil. MS (ESI): m/z: 166[M+H]$^+$. $^1$H NMR (400 MHz, DMSO-d6) δ: 6.94 (m, 2H), 6.64 (d, 1H, J=8.0 Hz), 6.51 (m, 1H), 4.88 (s, 2H), 3.59 (s, 3H), 3.52 (s, 2H).

Preparation of tert-butyl 4-(2-oxoindolin-1-yl)piperidine-1-carboxylate (Compound 11-4)

A mixture of methyl 2-(2-aminophenyl)acetate (Compound 11-3, 3.30 g, 20 mmol), tert-butyl 4-oxopiperidine-1-carboxylate (4.38 g, 22 mmol), acetic acid (HOAc, 600 mg, 10 mmol) in dichloromethane (DCM, 80 mL) was stirred at room temperature for 2 h, then sodium triacetoxyborohydride (NaBH(OAc)$_3$, 6.36 g, 30 mmol) was added in portions and heated to 40° C., stirred overnight. The reaction mixture was cooled to room temperature and diluted with dichloromethane (DCM, 200 mL), washed with water (200 mL×2) and sodium bicarbonate (sat. aq., 200 mL×2), dried over anhydrous sodium sulfate, concentrated to give the crude product, purified by flash column chromatography on silica gel (ethyl acetate/petroleum ether, 1/20-1/15-1/10 v/v) to give the desired product tert-butyl 4-(2-oxoindolin-1-yl)piperidine-1-carboxylate (Compound 11-4, 2.65 g, yield: 42%) as a pale yellow solid. MS (ESI): m/z: 261[M+H−56]$^+$. $^1$H NMR (400 MHz, CDCl$_3$) δ: 7.24 (m, 2H), 7.01 (m, 2H), 4.41 (m, 1H), 4.28 (br s, 2H), 3.53 (s, 2H), 2.83 (br s, 2H), 2.32 (m, 2H), 1.70 (m, 2H), 1.50 (s, 9H).

Preparation of tert-butyl 4-(3-(2-methoxy-2-oxoethyl)-2-oxoindolin-1-yl)piperidine-1-carboxylate (Compound 11-5)

A solution of tert-butyl 4-(2-oxoindolin-1-yl)piperidine-1-carboxylate (Compound 11-4, 3.16 g, 10 mmol) in dry tetrahydrofuran (THF, 100 mL) was cooled to −78° C. by dry ice-acetone bath and lithium diisopropylamide (2 M in THF, 5 mL, 10 mmol) was added dropwise over 10 minutes, stirred for 1 hour at −78° C. A solution of methyl 2-bromoacetate (1.53 g, 10 mmol) in dry tetrahydrofuran (10 mL) was added dropwise over 5 minutes. The reaction mixture was stirred for 4 hours at −78° C., quenched with ammonium chloride (sat. aq., 10 mL) at −78° C., and added acetic acid (HOAc, 1 mL) to make the reaction mixture neutral (pH=7), extracted with ethyl acetate (150 mL×3), combined organic layer was washed with brine (300 mL×2), dried over anhydrous sodium sulfate, concentrated to give the crude product, purified by flash column chromatography on silica gel (ethyl acetate/petroleum ether, 1/15-1/10 v/v) to give the desired product tert-butyl 4-(3-(2-methoxy-2-oxoethyl)-2-oxoindolin-1-yl)piperidine-1-carboxylate (Compound 11-5, 1.98 g, yield: 51%) as a pale yellow solid. MS (ESI): m/z: 333[M+H−56]$^+$. $^1$H NMR (400 MHz, CDCl$_3$) δ: 7.24 (m, 2H), 7.01 (m, 2H), 4.39 (m, 1H), 4.30 (d, 2H, J=12.8 Hz), 3.73 (m, 1H), 3.65 (s, 3H), 3.06 (dd, 1H, J=4.4, 12.8 Hz), 2.84 (m, 3H), 2.34 (m, 2H), 1.73 (d, 2H, J=12.8 Hz), 1.50 (s, 9H).

Preparation of methyl 2-(2-oxo-1-(piperidin-4-yl)indolin-3-yl)acetate TFA salt (Compound 11-6)

Trifluoroacetic acid (TFA, 5.70 g, 50 mmol) was added to a solution of tert-butyl 4-(3-(2-methoxy-2-oxoethyl)-2-oxoindolin-1-yl)piperidine-1-carboxylate (Compound 11-5, 3.88 g, 10 mmol) in dry dichloromethane (DCM, 100 mL), the mixture was stirred for 1 hour at room temperature and concentrated to remove solvent to give crude desired product methyl 2-(2-oxo-1-(piperidin-4-yl)indolin-3-yl)acetate TFA salt (Compound 11-6, 3.90 g, yield: 97%) as a pale yellow syrup. MS (ESI): m/z: 289[M+H]$^+$.

Preparation of ethyl 2-(1-(1-(1,2-dihydroacenaphthylen-1-yl)piperidin-4-yl)-2-oxoindolin-3-yl)acetate (Compound 11-7)

Methyl 2-(2-oxo-1-(piperidin-4-yl)indolin-3-yl)acetate TFA salt (Compound 11-6, 4.02 g, 10 mmol) was dissolved in dry toluene (100 mL), triethylamine (3.03 g, 30 mmol) was added and stirred for 15 minutes, acenaphthylen-1(2H)-one (2.01 g, 12 mmol) and titanium ethoxide was (4.56 g, 20 mmol) was added, the mixture was heated to 130° C. and stirred overnight. The reaction mixture was cooled to room temperature and diluted with ethyl acetate (300 mL) and water (200 mL), stirred for 10 minutes and filtered, the filtrate was extracted with ethyl acetate (250 mL×3), combined organic layer was washed with brine (400 mL×2), dried over anhydrous sodium sulfate, concentrated to give the crude product (4.70 g, yield>100%) and dissolved in methanol (40 mL), added acetic acid (HOAc, 2 drops), sodium borohydride (NaBH$_4$, 760 mg, 20 mmol) was added in portions, stirred for 30 minutes, concentrated to dryness, diluted with ethyl acetate (200 mL) and washed with water (100 mL×1), brine (100 mL×2), dried over anhydrous sodium sulfate, concentrated to give the crude product, purified by flash column chromatography on silica gel (methanol/dichloromethane, 1/150-1/100-1/80 v/v) to give the desired product ethyl 2-(1-(1-(1,2-dihydroacenaphthylen-1-yl)piperidin-4-yl)-2-oxoindolin-3-yl)acetate (Compound 11-7, 1.63 g, yield: 36%) as a pale yellow solid. MS (ESI): m/z: 455[M+H]$^+$. $^1$H NMR (400 MHz, CDCl$_3$) δ: 7.70 (m, 1H), 7.63 (m, 1H), 7.54 (m, 2H), 7.47 (m, 1H), 7.25 (m, 4H), 7.00 (m, 1H), 4.98 (s, 1H), 4.28 (m, 1H), 4.10 (m, 2H), 3.73 (t, 1H, J=6.4 Hz), 3.42 (d, 2H, J=6.4 Hz), 3.02 (m, 2H), 2.80 (m, 2H), 2.46 (m, 4H), 1.69 (m, 2H), 1.18 (m, 3H).

Preparation of 2-(1-(1-(1,2-dihydroacenaphthylen-1-yl)piperidin-4-yl)-3-hydroxy-2-oxoindolin-3-yl)-N-methylacetamide (Compound 27)

To a solution of ethyl 2-(1-(1-(1,2-dihydroacenaphthylen-1-yl)piperidin-4-yl)-2-oxoindolin-3-yl)acetate (Compound 11-7, 454 mg, 1.0 mmol) in tetrahydrofuran (THF, 5 mL) was added methylamine (40% w/w aqueous solution, 2 mL). The mixture was stirred overnight at room temperature and purified by reversed phase chromatography (methanamine/water=0%-45%, added 0.05% NH$_3$.H$_2$O) to give the desired product 2-(1-(1-(1,2-dihydroacenaphthylen-1-yl)piperidin-4-yl)-3-hydroxy-2-oxoindolin-3-yl)-N-methylacetamide (Compound 27, 218 mg, yield: 48%) as a pale yellow solid. MS (ESI): m/z: 456[M+H]$^+$. $^1$H NMR (400 MHz, CDCl$_3$) δ: 7.70 (m, 1H), 7.63 (m, 1H), 7.50 (m, 3H), 7.38 (m, 1H), 7.29 (m, 2H), 7.17 (m, 1H), 7.05 (m, 1H), 5.92 (d, 1H, J=4.4 Hz), 5.70 (br s, 1H), 4.96 (t, 1H, J=5.2 Hz), 4.18 (m, 1H), 3.41 (d, 2H, J=5.2 Hz), 2.97 (d, 1H, J=11.6 Hz), 2.85 (d, 3H, J=5.2 Hz), 2.74 (m, 2H), 2.49 (m, 3H), 2.32 (m, 2H), 1.67 (m, 2H).

Preparation of 2-(1-(1-(1,2-dihydroacenaphthylen-1-yl)piperidin-4-yl)-3-fluoro-2-oxoindolin-3-yl)-N-methylacetamide (Compound 28)

To a solution of 2-(1-(1-(1,2-dihydroacenaphthylen-1-yl)piperidin-4-yl)-3-hydroxy-2-oxoindolin-3-yl)-N-methylacetamide (Compound 27, 80 mg, 0.18 mmol) in dry dichloromethane (DCM, 2 mL) was added diethylaminosulfur trifluoride (32 mg, 0.20 mmol). The mixture was stirred at room temperature for 1 hour and concentrated to dryness and purified by reversed phase chromatography (methanamine/water=0%-70%, added 0.05% NH$_3$.H$_2$O) to give the desired product 2-(1-(1-(1,2-dihydroacenaphthylen-1-yl)piperidin-4-yl)-3-fluoro-2-oxoindolin-3-yl)-N-methylacetamide (Compound 28, 45 mg, yield: 56%) as a pale yellow solid. MS (ESI): m/z: 458[M+H]$^+$. $^1$H NMR (400 MHz, CDCl$_3$) δ: 7.70 (m, 1H), 7.63 (m, 1H), 7.54 (m, 2H), 7.45 (m, 2H), 7.37 (m, 1H), 7.29 (m, 1H), 7.17 (m, 1H), 7.09 (m, 1H), 6.26 (br s, 1H), 4.98 (s, 1H), 4.15 (m, 1H), 3.42 (s, 1H), 3.03 (m, 3H), 2.79 (m, 1H), 2.75 (d, 3H, J=4.8 Hz), 2.43 (m, 4H), 1.73 (m, 2H). $^{19}$F NMR (400 MHz, CDCl$_3$) δ: −154.28 (m, 1F). Compound 28 was separated by chiral HPLC to yield Compound 30 and Compound 31.

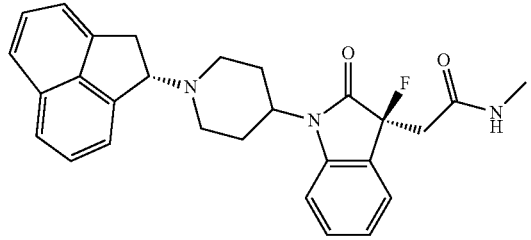

Compound 30

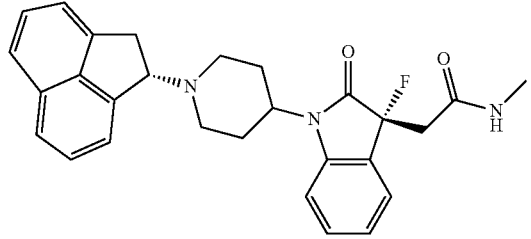

Compound 31

Example 6: Chiral Resolution of Compound 27

Compound 27 was subjected to Chiral-HPLC separation to give Compound 33, Compound 34, Compound 35 and Compound 36.

Compound 33

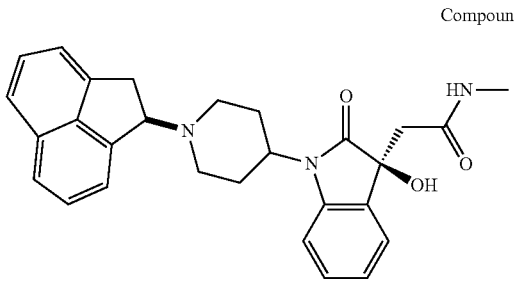

Compound 34

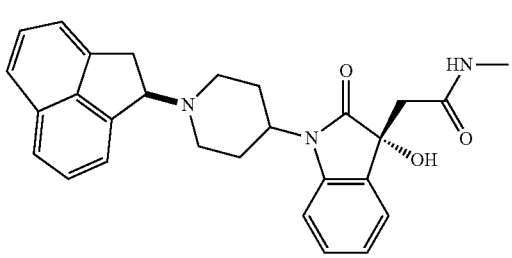

Compound 35

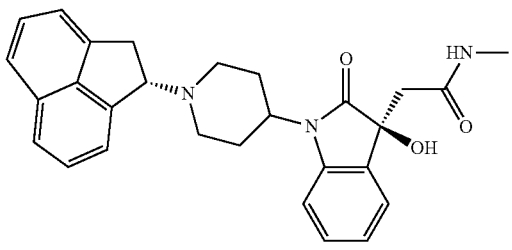

Compound 36

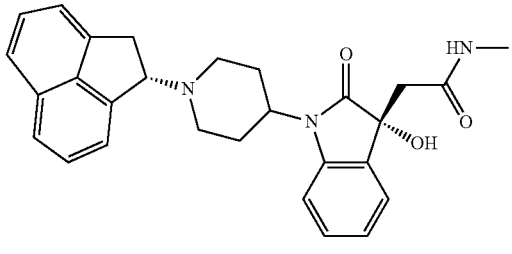

Example 7A: Preparation of Compound 40

Scheme 13A.

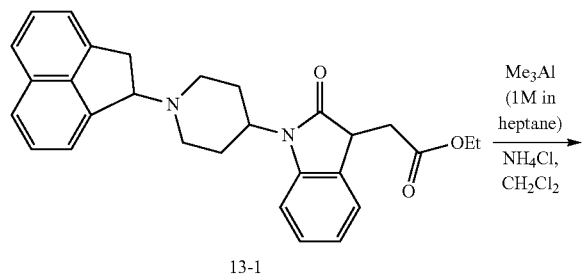

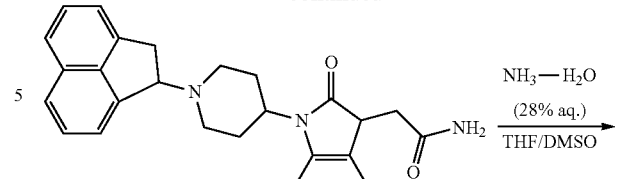

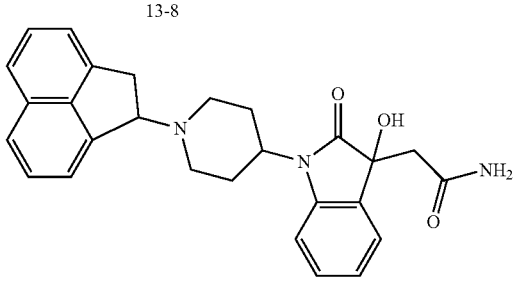

Preparation of 2-(1-(1-(1,2-dihydroacenaphthylen-1-yl)piperidin-4-yl)-2-oxoindolin-3-yl)acetamide (Compound 13-8)

Trimethylaluminum (1M in heptane, 1.0 mL, 1.0 mmol) was added dropwise to a suspension of ammonium chloride (54 mg, 1.0 mmol) in dry dichloromethane (4 mL) at 0° C., the mixture was stirred at room temperature for 1 hour. This aluminum amine complex solution (2.5 mL, about 0.5 mmol) was added to a solution of ethyl 2-(1-(1-(1,2-dihydroacenaphthylen-1-yl)piperidin-4-yl)-2-oxoindolin-3-yl) acetate (Compound 13-1, 20 mg, 0.04 mmol) in dry dichloromethane (0.5 mL), the mixture was stirred in a seal tube overnight and diluted with dichloromethane (10 mL) and water (10 mL), stirred for 10 minutes and filtered, the residue was washed with dichloromethane (5 mL×3) and methanol (1 mL×2), filtrate was extracted with dichloromethane (20 mL×3), combined organic layer was washed with brine (30 mL×2), dried over anhydrous sodium sulfate, concentrated to give crude product and purified by pre-TLC (methanol/dichloromethane, 1/10 v/v) to give the desired product 2-(1-(1-(1,2-dihydroacenaphthylen-1-yl)piperidin-4-yl)-2-oxoindolin-3-yl)acetamide (Compound 13-8, 8 mg, yield: 40%) as a pale yellow solid. MS (ESI): m/z: 426 [M+H]$^+$, 873 [2M+Na]$^+$. $^1$H NMR (400 MHz, CDCl$_3$) δ: 7.70 (m, 1H), 7.63 (m, 1H), 7.54 (m, 2H), 7.47 (m, 1H), 7.30 (m, 3H), 7.20 (m, 1H), 7.04 (m, 1H), 6.53 (br s, 1H), 5.43 (br s, 1H), 4.99 (s, 1H), 4.26 (t, 1H, J=12.0 Hz), 3.81 (t, 1H, J=6.4 Hz), 3.43 (d, 2H, J=2.8 Hz), 3.01 (m, 1H), 2.89 (dd, 1H, $^1$J=16.0 Hz, $^2$J=6.4 Hz), 2.32-2.54 (m, 5H), 1.70 (m, 2H).

Preparation of 2-(1-(1-(1,2-dihydroacenaphthylen-1-yl)piperidin-4-yl)-3-hydroxy-2-oxoindolin-3-yl)acetamide (Compound 40)

To a solution of 2-(1-(1-(1,2-dihydroacenaphthylen-1-yl)piperidin-4-yl)-2-oxoindolin-3-yl)acetamide (Compound 13-8, 36 mg (LC-MS purity: 76%), 0.08 mmol) in tetrahydrofuran/dimethyl sulfoxide (THF/DMSO, 1 mL/1 mL) was added ammonium hydroxide (28% w/w aqueous solution, 2 mL). The mixture was stirred overnight at room temperature and diluted with dichloromethane (15 mL), washed with brine (10 mL×3), organic layer was dried over anhydrous sodium sulfate, concentrated to give crude product and purified by pre-TLC (methanol/dichloromethane, 1/8 v/v) to give the desired product 2-(1-(1-(1,2-dihydroacenaphthylen-1-yl)piperidin-4-yl)-3-hydroxy-2-oxoindolin-3-yl)acetamide (Compound 40, 7 mg, yield: 19%) as a pale yellow solid. MS (ESI): m/z: 442[M+H]$^+$. $^1$H NMR (400 MHz, CDCl$_3$) δ: 7.70 (m, 1H), 7.63 (m, 1H), 7.53 (m, 2H), 7.47 (m, 2H), 7.30 (m, 2H), 7.18 (m, 1H), 7.05 (m, 1H), 6.18 (br s, 1H), 5.72 (br s, 1H), 4.96 (t, 1H, J=4.8 Hz), 4.17 (m, 1H), 3.42 (d, 2H, J=5.2 Hz), 2.97 (d, 1H, J=10.4 Hz), 2.80 (m, 2H), 2.30-2.61 (m, 5H), 1.67 (m, 2H).

Example 7B: Preparation of Compound 39

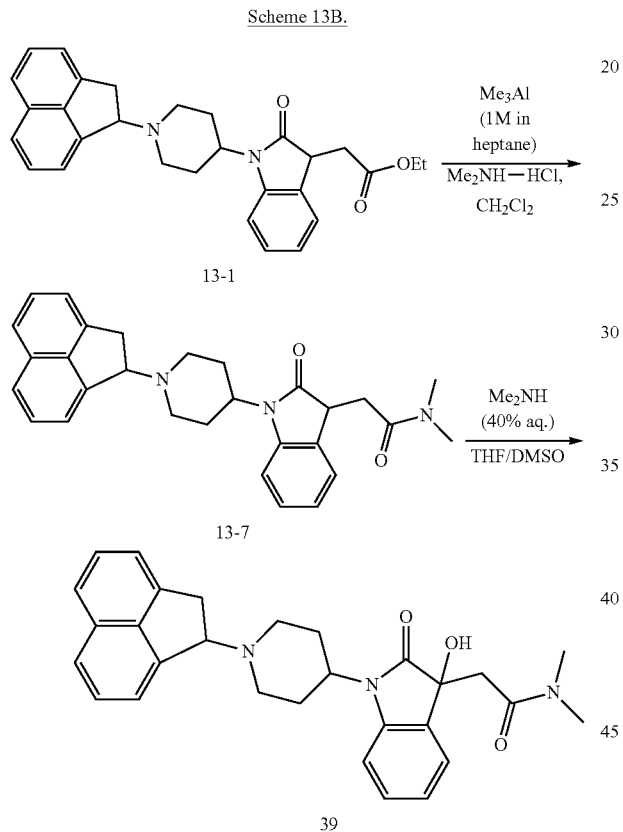

Preparation of 2-(1-(1-(1,2-dihydroacenaphthylen-1-yl)piperidin-4-yl)-2-oxoindolin-3-yl)-N,N-dimethylacetamide (Compound 13-7)

Trimethylaluminum (1 M in heptane, 1.0 mL, 1.0 mmol) was added dropwise to a suspension of dimethylamine hydrochloride (82 mg, 1.0 mmol) in dry dichloromethane (4 mL) at 0° C., the mixture was stirred at room temperature for 1 hour. This aluminum amine complex solution (2.5 mL, about 0.5 mmol) was added to a solution of ethyl 2-(1-(1-(1,2-dihydroacenaphthylen-1-yl)piperidin-4-yl)-2-oxoindolin-3-yl)acetate (Compound 13-1, 20 mg, 0.04 mmol) in dry dichloromethane (0.5 mL), the mixture was stirred in a seal tube overnight and diluted with dichloromethane (10 mL) and water (10 mL), stirred for 10 minutes and filtered, the residue was washed with dichloromethane (5 mL×3) and methanol (1 mL×2), filtrate was extracted with dichloromethane (20 mL×3), combined organic layer was washed with brine (30 mL×2), dried over anhydrous sodium sulfate, concentrated to give crude product and purified by pre-TLC (methanol/dichloromethane, 1/15 v/v) to give the desired product 2-(1-(1-(1,2-dihydroacenaphthylen-1-yl)piperidin-4-yl)-2-oxoindolin-3-yl)-N,N-dimethylacetamide (Compound 13-7, 11 mg, yield: 55%) as a pale yellow solid. MS (ESI): m/z: 454 [M+H]$^+$, 929 [2M+Na]$^+$. $^1$H NMR (400 MHz, CDCl$_3$) δ: 7.70 (m, 1H), 7.63 (m, 1H), 7.54 (m, 2H), 7.46 (m, 1H), 7.36 (m, 1H), 7.30 (m, 1H), 7.21 (m, 2H), 7.00 (m, 1H), 4.99 (t, 1H, J=4.8 Hz), 4.29 (m, 1H), 3.92 (m, 1H), 3.43 (d, 2H, J=4.4 Hz), 3.01-3.13 (m, 2H), 2.98 (s, 6H), 2.80 (m, 1H), 2.32-2.68 (m, 5H), 1.70 (m, 2H).

Preparation of 2-(1-(1-(1,2-dihydroacenaphthylen-1-yl)piperidin-4-yl)-3-hydroxy-2-oxoindolin-3-yl)-N,N-dimethylacetamide (Compound 39)

To a solution of 2-(1-(1-(1,2-dihydroacenaphthylen-1-yl)piperidin-4-yl)-2-oxoindolin-3-yl)-N,N-dimethylacetamide (Compound 13-7, 130 mg (LC-MS purity: 80%), 0.29 mmol) in tetrahydrofuran and dimethyl sulfoxide (THF/DMSO, 1.5 mL/1.5 mL) was added dimethylamine (40% w/w aqueous solution, 2 mL). The mixture was stirred overnight at room temperature and diluted with dichloromethane (15 mL), washed with brine (10 mL×3), organic layer was dried over anhydrous sodium sulfate, concentrated to give crude product and purified by pre-TLC (methanol/dichloromethane, 1/10 v/v) to give the desired product 2-(1-(1-(1,2-dihydroacenaphthylen-1-yl)piperidin-4-yl)-3-hydroxy-2-oxoindolin-3-yl)-N,N-dimethylacetamide (Compound 39, 29 mg, yield: 21%) as a pale yellow solid. MS (ESI): m/z: 470[M+H]$^+$, 961 [2M+Na]$^+$. $^1$H NMR (400 MHz, CDCl$_3$) δ: 7.72 (m, 1H), 7.62 (m, 1H), 7.53 (m, 3H), 7.46 (m, 1H), 7.29 (m, 2H), 7.18 (m, 1H), 7.04 (m, 1H), 6.50 (br s, 1H), 4.97 (t, 1H, J=5.2 Hz), 4.22 (m, 1H), 3.41 (d, 2H, J=5.6 Hz), 3.00 (s, 3H), 2.93 (m, 2H), 2.91 (s, 3H), 2.80 (m, 1H), 2.30-2.61 (m, 5H), 1.70 (m, 2H).

Example 7C: Preparation of Compound 43

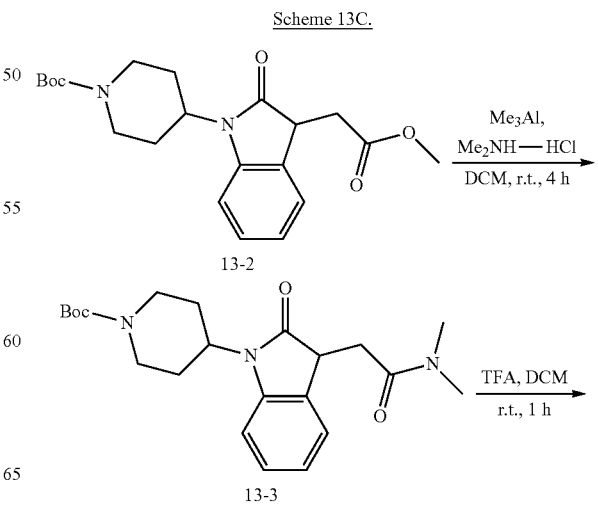

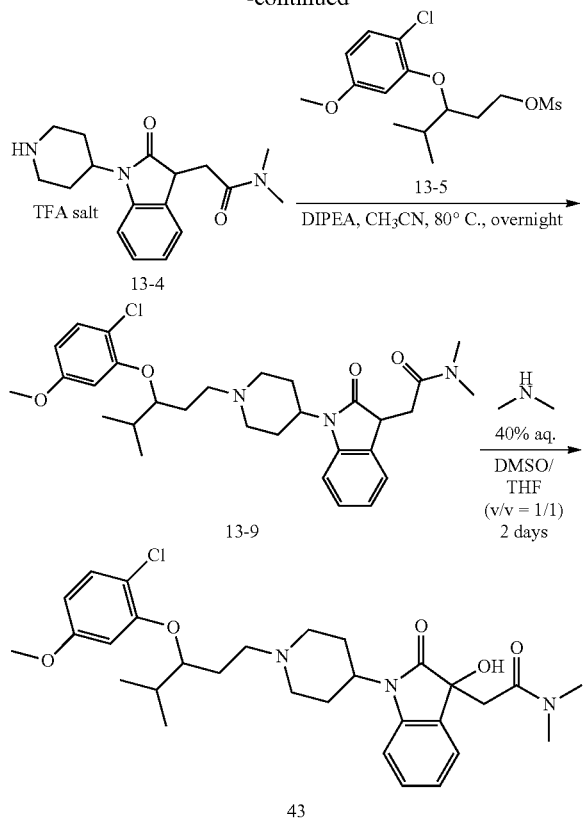

Preparation of tert-butyl 4-(3-(2-(dimethylamino)-2-oxoethyl)-2-oxoindolin-1-yl)piperidine-1-carboxylate (Compound 13-3)

Trimethylaluminum (1 M in heptane, 2.0 mL, 2.0 mmol) was added dropwise to a suspension of dimethylamine hydrochloride (164 mg, 2.0 mmol) in dry dichloromethane (8 mL) at 0° C., the mixture was stirred at room temperature for 1 hour. This aluminum amine complex solution (10 mL, about 2 mmol) was added to a solution of tert-butyl 4-(3-(2-methoxy-2-oxoethyl)-2-oxoindolin-1-yl)piperidine-1-carboxylate (Compound 13-2, 388 mg, 1.0 mmol) in dry dichloromethane (1 mL), the mixture was stirred in a seal tube for 4 hours and diluted with dichloromethane (25 mL) and water (20 mL), stirred for 10 minutes and filtered, the residue was washed with dichloromethane (10 mL×3) and methanol (1 mL×3), filtrate was extracted with dichloromethane (30 mL×3), combined organic layer was washed with brine (30 mL×2), dried over anhydrous sodium sulfate, concentrated to give crude product and purified by pre-TLC (methanol/dichloromethane, 1/20 v/v) to give the desired product tert-butyl 4-(3-(2-(dimethylamino)-2-oxoethyl)-2-oxoindolin-1-yl)piperidine-1-carboxylate (Compound 13-3, 240 mg, yield: 60%) as a pale yellow solid. MS (ESI): m/z: 402 [M+H]$^+$. $^1$H NMR (400 MHz, CDCl$_3$) δ: 7.36 (d, 1H, J=7.2 Hz), 7.22 (m, 1H), 7.00 (m, 2H), 4.20-4.44 (m, 3H), 3.90 (dd, 1H, $^1$J=8.8, $^2$J=2.4 Hz), 3.11 (dd, 1H, $^1$J=16.8, $^2$J=3.2 Hz), 3.00 (s, 3H), 2.98 (s, 3H), 2.80 (m, 2H), 2.71 (m, 1H), 2.34 (m, 2H), 1.73 (m, 2H).

Preparation of N,N-dimethyl-2-(2-oxo-1-(piperidin-4-yl)indolin-3-yl)acetamide TFA salt (Compound 13-4)

A mixture of tert-butyl 4-(3-(2-(dimethylamino)-2-oxoethyl)-2-oxoindolin-1-yl)piperidine-1-carboxylate (Compound 13-3, 240 mg, 0.6 mmol), trifluoroacetic acid (684 mg, 6 mmol), in dichloromethane (DCM, 3.5 mL) was stirred at room temperature for 1 h. The reaction mixture was concentrated to remove trifluoroacetic acid and dichloromethane to give the crude product N,N-dimethyl-2-(2-oxo-1-(piperidin-4-yl)indolin-3-yl)acetamide TFA salt (Compound 13-4, 245 mg, yield: 98%) as a pale yellow syrup. MS (ESI): m/z: 302[M+H]$^+$.

Preparation of 2-(1-(1-(3-(2-chloro-5-methoxyphenoxy)-4-methylpentyl)piperidin-4-yl)-2-oxoindolin-3-yl)-N,N-dimethylacetamide (Compound 13-9)

A mixture of 3-(2-chloro-5-methoxyphenoxy)-4-methylpentyl methanesulfonate (Compound 13-5, 300 mg, 0.89 mmol), N,N-dimethyl-2-(2-oxo-1-(piperidin-4-yl)indolin-3-yl)acetamide TFA salt (Compound 13-4, 245 mg, 0.59 mmol), N,N-diisopropylethylamine (DIPEA, 152 mg, 1.0 mmol) in acetonitrile (CH$_3$CN, 5 mL) was heated to 80° C. and stirred overnight. The reaction mixture was cooled to room temperature and evaporated to remove acetonitrile, the residue was diluted with ethyl acetate (20 mL) and washed with water (15 mL×2), and brine (20 mL×1), dried over anhydrous sodium sulfate, concentrated to give the crude product, purified by Pre-TLC (CH$_3$OH/DCM, 1/15 v/v) to give the desired product and purified by Pre-HPLC (CH$_3$CN/H$_2$O, added 0.05% TFA) to give the desired product (evaporated to removed CH$_3$CN, extracted with dichloromethane, washed with saturated NaHCO$_3$) (Compound 13-9, 100 mg, yield: 31%) as a pale yellow solid. MS (ESI): m/z: 542[M+H]$^+$. $^1$H NMR (400 MHz, CDCl$_3$) δ: 7.36 (d, 1H, J=8.0 Hz), 7.18-7.25 (m, 3H), 6.99 (m, 1H), 6.78 (m, 1H), 6.40 (dd, 1H, $^1$J=8.8, $^2$J=2.8 Hz), 4.25-4.36 (m, 2H), 3.91 (m, 1H), 3.76 (d, 3H, J=2.4 Hz), 3.11 (m, 2H), 2.99 (s, 6H), 2.92 (m, 1H), 2.40-2.70 (m, 5H), 1.95-2.20 (m, 3H), 1.87 (m, 2H), 1.69 (m, 2H), 1.01 (d, 3H, J=7.2 Hz), 0.98 (d, 3H, J=7.2 Hz).

Preparation of 2-(1-(1-(3-(2-chloro-5-methoxyphenoxy)-4-methylpentyl)piperidin-4-yl)-3-hydroxy-2-oxoindolin-3-yl)-N,N-dimethylacetamide (Compound 43)

To a solution of 2-(1-(1-(3-(2-chloro-5-methoxyphenoxy)-4-methylpentyl)piperidin-4-yl)-2-oxoindolin-3-yl)-N,N-dimethylacetamide (Compound 13-9, 90 mg (LC-MS purity: 99%), 0.17 mmol) in tetrahydrofuran/dimethyl sulfoxide (THF/DMSO, 1.5 mL/1.5 mL) was added dimethylamine (40% w/w aqueous solution, 2 mL). The mixture was stirred 2 days at room temperature and diluted with dichloromethane (15 mL), washed with brine (10 mL×3), organic layer was dried over anhydrous sodium sulfate, concentrated to give crude product and purified by pre-TLC (methanol/dichloromethane, 1/12 v/v) to give the desired product 2-(1-(1-(3-(2-chloro-5-methoxyphenoxy)-4-methylpentyl)piperidin-4-yl)-3-hydroxy-2-oxoindolin-3-yl)-N,N-dimethylacetamide (Compound 43, 38 mg, yield: 40%) as a pale yellow solid. MS (ESI): m/z: 558[M+H]$^+$. $^1$H NMR (400 MHz, CDCl$_3$) δ: 7.51 (d, 1H, J=7.6 Hz), 7.15-7.30 (m, 3H), 7.04 (m, 1H), 6.78 (m, 1H), 6.40 (dd, 1H, J=8.8, 2.4 Hz), 4.25-4.29 (m, 2H), 3.76 (d, 3H, J=7.6 Hz), 3.11 (m, 1H), 3.01 (s, 3H), 2.98 (m, 1H), 2.89 (s, 3H), 2.40-2.64 (m, 5H), 1.95-2.20 (m, 3H), 1.89 (m, 2H), 1.68 (m, 2H), 1.01 (d, 3H, J=7.2 Hz), 0.98 (d, 3H, J=7.2 Hz).

Example 7D: Preparation of Compound 45

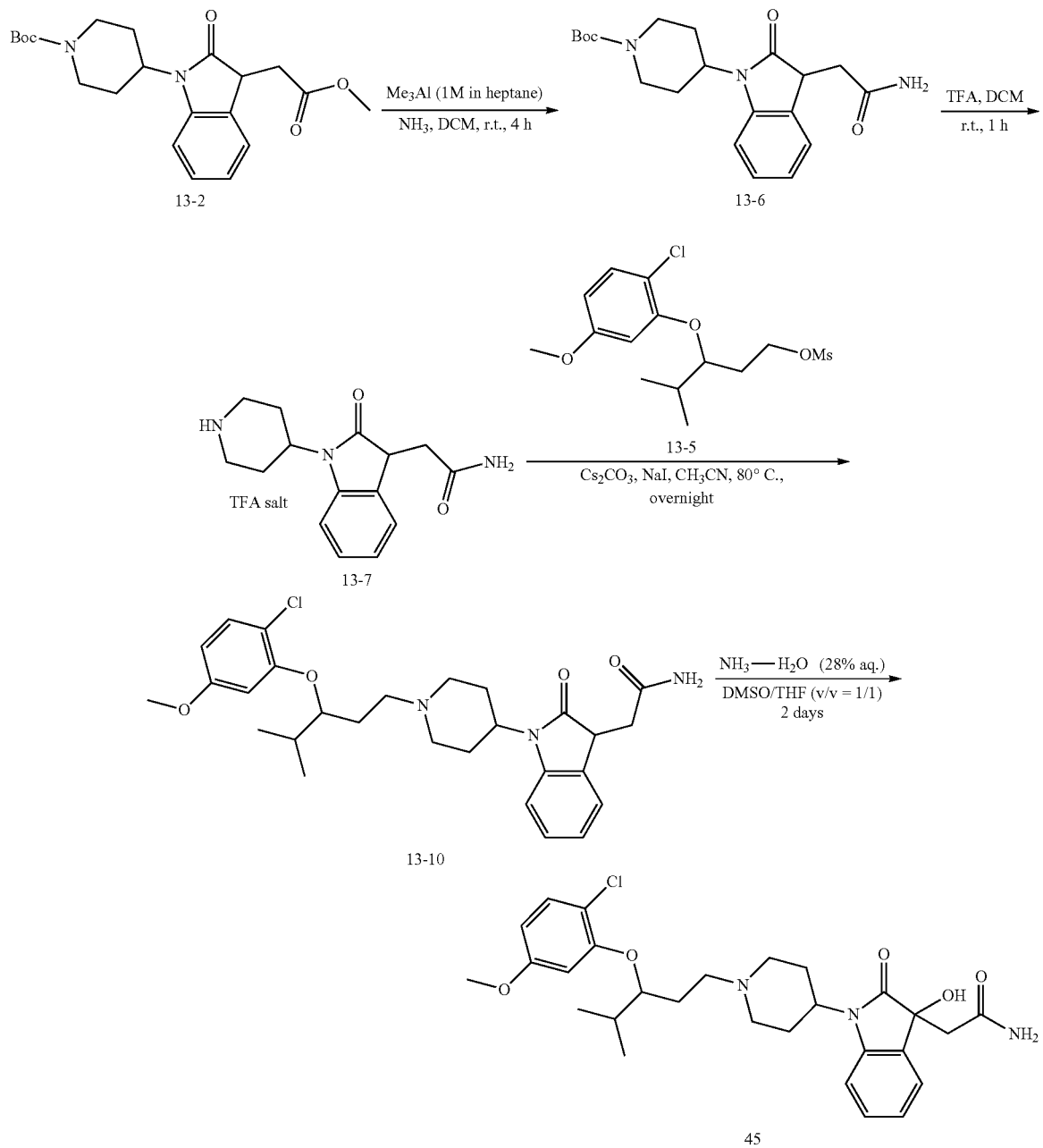

Scheme 13C.

Preparation of tert-butyl 4-(3-(2-amino-2-oxoethyl)-2-oxoindolin-1-yl)piperidine-1-carboxylate (Compound 13-6)

To a solution of trimethylaluminum (1 M in heptane, 2.0 mL, 2.0 mmol) in dry dichloromethane (5 mL) was charged ammonia for 5 minutes. The resulting mixture was stirred at room temperature for 1 hour. This aluminum amine complex solution (7 mL, about 2 mmol) was added to a solution of tert-butyl 4-(3-(2-methoxy-2-oxoethyl)-2-oxoindolin-1-yl)piperidine-1-carboxylate (Compound 13-2, 388 mg, 1.0 mmol) in dry dichloromethane (1 mL), the mixture was stirred in a seal tube for 4 hours and diluted with dichloromethane (25 mL) and water (20 mL), stirred for 10 minutes and filtered, the residue was washed with dichloromethane (10 mL×3) and methanol (1 mL×3). The filtrate was extracted with dichloromethane (30 mL×3). The combined organic layer was washed with brine (30 mL×2), dried over anhydrous sodium sulfate, concentrated to give the crude tert-butyl 4-(3-(2-amino-2-oxoethyl)-2-oxoindolin-1-yl)piperidine-1-carboxylate (Compound 13-6, 350 mg, yield: 94%) as a pale yellow solid. MS (ESI): m/z: 374 [M+H]$^+$.

Preparation of 2-(2-oxo-1-(piperidin-4-yl)indolin-3-yl)acetamide TFA salt (Compound 13-7)

A mixture of tert-butyl 4-(3-(2-amino-2-oxoethyl)-2-oxoindolin-1-yl)piperidine-1-carboxylate (Compound 13-6, 350 mg, 0.94 mmol), trifluoroacetic acid (1.07 g, 9.4 mmol), in dichloromethane (5 mL) was stirred at room temperature for 1 h. The reaction mixture was concentrated to remove trifluoroacetic acid and dichloromethane to give the crude product 2-(2-oxo-1-(piperidin-4-yl)indolin-3-yl)acetamide TFA salt (Compound 13-7, 490 mg, yield: 97%) as a pale yellow syrup. MS (ESI): m/z: 274 [M+H]$^+$.

Preparation of 2-(1-(1-(3-(2-chloro-5-methoxyphenoxy)-4-methylpentyl)piperidin-4-yl)-2-oxoindolin-3-yl)acetamide (Compound 13-10)

A mixture of 3-(2-chloro-5-methoxyphenoxy)-4-methylpentyl methanesulfonate (Compound 13-5, 487 mg, 1.45 mmol), 2-(2-oxo-1-(piperidin-4-yl)indolin-3-yl)acetamide TFA salt (Compound 13-7, 490 mg, 0.97 mmol), cesium carbonate (632 mg, 1.94 mmol) sodium iodide (30 mg, 0.2 mmol) in acetonitrile (15 mL) was stirred at 80° C. overnight. The reaction mixture was cooled to room temperature and evaporated to remove acetonitrile, the residue was diluted with ethyl acetate (20 mL) and washed with water (15 mL×2), and brine (20 mL×1), dried over anhydrous sodium sulfate, concentrated to give the crude product, purified by HPLC (CH$_3$CN/H$_2$O, added 0.01% NH$_3$—H$_2$O) to give the desired product (Compound 13-10, 164 mg, yield: 28%) as a white solid. MS (ESI): m/z: 514 [M+H]$^+$.
$^1$H NMR (400 MHz, CDCl$_3$) δ: 7.33 (d, 1H, J=7.6 Hz), 7.2-87.17 (m, 3H), 7.05 (t, 1H, J=7.2 Hz), 6.79 (m, 1H), 6.54 (br s, 1H), 6.41 (dd, 1H, $^1$J=8.8, $^2$J=2.4 Hz), 5.50 (m, 1H), 4.34-4.25 (m, 2H), 3.82 (t, 1H, J=6.4 Hz), 3.77 (s, 3H), 3.09 (d, 1H, J=11.2 Hz), 2.95-2.88 (m, 2H), 2.68-2.55 (m, 1H), 2.38 (m, 4H), 2.15-1.97 (m, 3H), 1.88-1.81 (m, 2H), 1.73-1.62 (m, 2H), 1.01 (d, 3H, J=7.2 Hz), 0.99 (d, 3H, J=7.2 Hz).

Preparation of 2-(1-(1-(3-(2-chloro-5-methoxyphenoxy)-4-methylpentyl)piperidin-4-yl)-3-hydroxy-2-oxoindolin-3-yl)acetamide (Compound 45)

To a solution of 2-(1-(1-(3-(2-chloro-5-methoxyphenoxy)-4-methylpentyl)piperidin-4-yl)-2-oxoindolin-3-yl)-N,N-dimethylacetamide (Compound 13-10, 100 mg, 0.19 mmol) in tetrahydrofuran/dimethyl sulfoxide (THF/DMSO, 1.5 mL/1.5 mL) was added dimethylamine (28% w/w aqueous solution, 2 mL). The mixture was stirred 2 days at room temperature and diluted with dichloromethane (15 mL), washed with brine (10 mL×3), organic layer was dried over anhydrous sodium sulfate, concentrated to give crude product and purified by pre-TLC (methanol/dichloromethane, 1/10 v/v) to give the desired product 2-(1-(1-(3-(2-chloro-5-methoxyphenoxy)-4-methylpentyl)piperidin-4-yl)-3-hydroxy-2-oxoindolin-3-yl)acetamide (Compound 45, 25 mg, yield: 24%) as a white solid. MS (ESI): m/z: 530 [M+H]$^+$.
$^1$H NMR (400 MHz, MeOD) δ: 7.37 (d, 1H, 7.2 Hz), 7.26 (t, 1H, 7.6 Hz), 7.20-7.16 (m, 2H), 7.02 (t, 1H, 7.2 Hz), 6.72 (m, 1H), 6.45 (dd, 1H, $^1$J=8.8, $^2$J=3.6 Hz), 4.31 (m, 1H), 4.16 (m, 1H), 3.73 (s, 3H), 3.27 (m, 1H), 3.08 (d, 1H, J=11.2 Hz), 2.97 (d, 1H, J=11.6 Hz), 2.92-2.83 (m, 2H), 2.53-2.41 (m, 4H), 2.16-2.07 (m, 2H), 1.98-1.84 (m, 3H), 1.73-1.68 (m, 2H), 1.00 (d, 3H, J=6.8 Hz), 0.97 (d, 3H, J=6.8 Hz).

Example 8A: Preparation of Compound 52

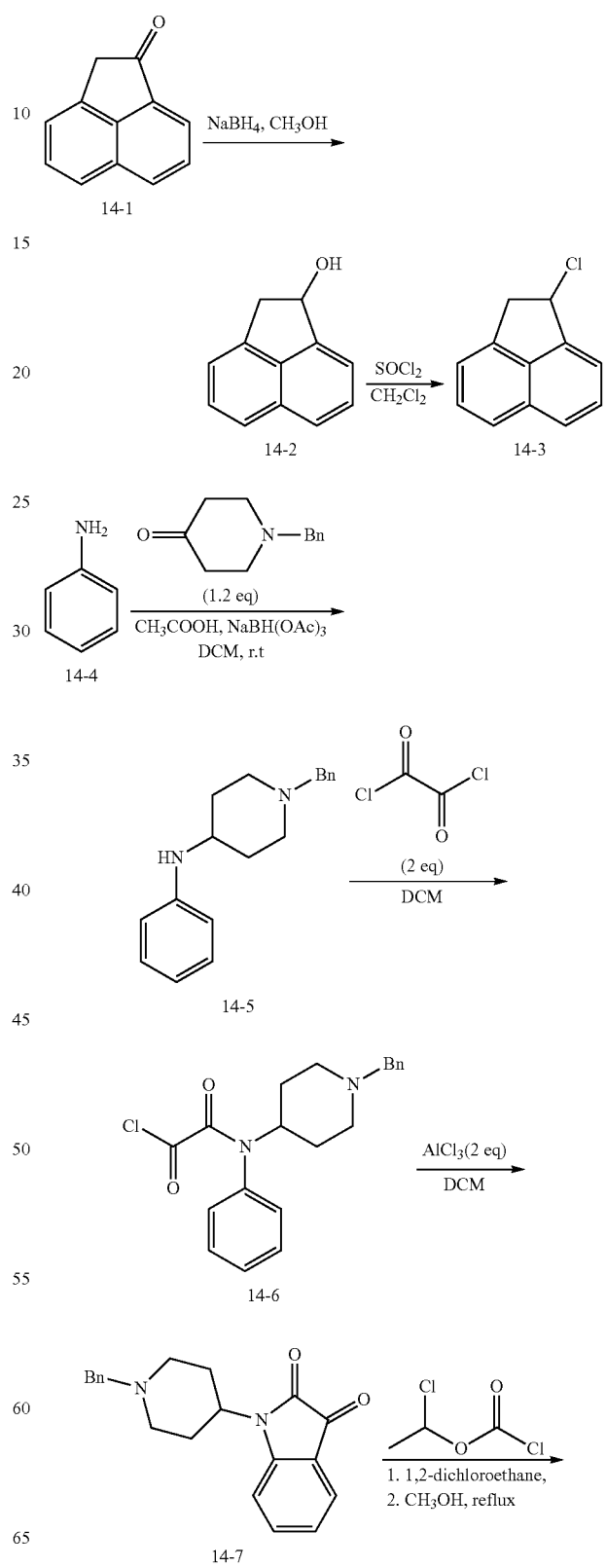

Scheme 14A.

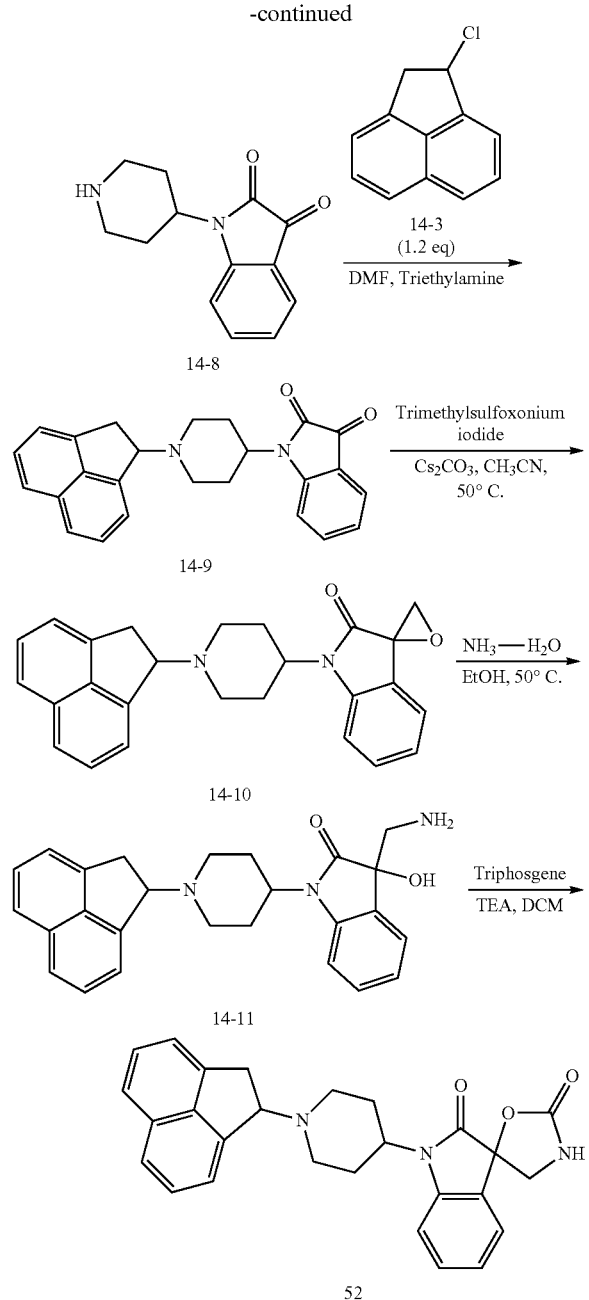

Preparation of 1,2-Dihydroacenaphthylen-1-ol (Compound 14-2)

To a solution of acenaphthylen-1(2H)-one (Compound 14-1, 1.04 g, 6.2 mmol) in methanol (20 mL) was added sodium borohydride (470 mg, 12.4 mmol) at room temperature. The mixture was stirred at room temperature for 2 hours. Upon the completion, the mixture was concentrated in vacuo. The residue was diluted with water (50 mL), extracted with dichloromethane (50 mL), dried over anhydrous sodium sulfate and concentrated to afford 1,2-dihydroacenaphthylen-1-ol (Compound 14-2, 920 mg, yield: 87%) as a light yellow solid. MS (ESI): m/z: 153 [M+H−H$_2$O]$^+$.

Preparation of 1-Chloro-1,2-dihydroacenaphthylene (Compound 14-3)

To a solution of 1,2-dihydroacenaphthylen-1-ol (Compound 14-2, 220 mg, 1.2 mmol) and N,N-Dimethylformamide (2 drops) in dichloromethane (40 mL) was added sulfurous dichloride (456 mg, 2.4 mmol) dropwise at −20° C. The mixture was stirred at this temperature for 2 hours. Upon the completion, the mixture was concentrated in vacuo below 20° C. to afford crude 1-chloro-1,2-dihydroacenaphthylene (Compound 14-3, 270 mg) as brown oil which was used for next step directly. MS (ESI): m/z: 153 [M+H−HCl]$^+$.

Preparation of 1-Benzyl-N-phenylpiperidin-4-amine (Compound 14-5)

To a solution of aniline (Compound 14-4, 3.72 g, 40 mmol) in dichloromethane (50 mL) was added 1-benzylpiperidin-4-one (7.94 g, 42 mmol) and acetic acid (240 mg, 4 mmol). The mixture was stirred at room temperature for 2 hours and then sodium triacetoxyborohydride (12.72 g, 60 mmol) was added. The reaction mixture was stirred for another 1 hour, diluted with water (50 mL), neutralized to pH=7 with sodium bicarbonate, extracted with dichloromethane (100 mL×2). The combined organic layer was washed with brine (100 mL×2), dried over anhydrous sodium sulfate and concentrated to afford 1-benzyl-N-phenylpiperidin-4-amine (Compound 14-5, 9.49 g, yield: 89%) as a white solid. MS (ESI): m/z: 267 [M+H]$^+$.

Preparation of 2-((1-Benzylpiperidin-4-yl)(phenyl)amino)-2-oxoacetyl chloride (Compound 14-6)

To a solution of oxalyl chloride (9.14 g, 72 mmol) in dichloromethane (50 mL) at room temperature was added a solution of (1-benzyl-N-phenylpiperidin-4-amine (Compound 14-5, 9.49 g, 36 mmol) in dichloromethane (30 mL) slowly. After the mixture was stirred for 2 hours, dichloromethane and oxalyl chloride were removed in vacuo to afford Compound 14-3 as dark green oil which was used for next step without further purification. MS (ESI): m/z: 353 [M+H]$^+$.

Preparation of 1-(1-Benzylpiperidin-4-yl)indoline-2,3-dione (Compound 14-7)

To a mixture of 2-((1-benzylpiperidin-4-yl)(phenyl)amino)-2-oxoacetyl chloride (12.8 g, 36 mmol) in dichloromethane (50 mL) at room temperature was added anhydrous aluminum chloride (9.58 g, 72 mmol). The mixture was stirred at 40° C. for 2 hours and then poured into ice water. The resulting mixture was neutralized to pH=7 with sodium bicarbonate, and then filtrated. The filtrate was extracted with dichloromethane (100 mL×2). The combined organic layer was dried over anhydrous sodium sulfate and evaporated. The residue was purified by flash column chromatography on silica gel (chloromethane:methanol=20:1) to afford 1-(1-benzyl-piperidin-4-yl)indoline-2,3-dione (Compound 14-7, 5.15 g, yield: 45%) as a white solid. MS (ESI): m/z: 321 [M+H]$^+$. $^1$H NMR (400 MHz, CDCl$_3$) δ: 7.60-7.55 (m, 2H), 7.43-7.28 (m, 6H), 7.24-7.18 (m, 1H), 7.10 (t, J=6.8 Hz, 1H), 4.21 (m, 1H), 3.57 (s, 2H), 3.05 (d, J=9.2 Hz, 2H), 2.46-2.43 (m, 2H), 2.17-2.14 (m, 2H), 2.32 (m, 2H), 1.75 (dd, $^1$J=1.2 Hz, $^2$J=12.0 Hz, 2H).

Preparation of 1-(Piperidin-4-yl)indoline-2,3-dione (Compound 14-8)

A mixture of 1-(1-benzylpiperidin-4-yl)indoline-2,3-dione (Compound 14-7, 5.15 g, 16 mmol) and 2-chloroethyl chloroformate (2.74 g, 19 mmol) in 1,2-dichloroethane (50 mL) was stirred at 90° C. for 16 hours. The mixture was cooled and concentrated in vacuo. The residue was diluted with methanol (50 mL) and concentrated hydrochloric acid (5 mL) was added. The resulting mixture was heated to 80° C. for 5 hours, and then concentrated. The residue was diluted with dichloromethane (50 mL), neutralized to pH=7 with triethylamine, concentrated, and then purified by flash column chromatography on silica gel (dichloromethane:methanol=10:1) to afford 1-(piperidin-4-yl)indoline-2,3-dione (Compound 14-8, 2.15 g, yield: 58%) as a yellow solid. MS (ESI): m/z: 231 [M+H]$^+$.

Preparation of 1-(1-(1,2-Dihydroacenaphthylen-1-yl)piperidin-4-yl)indoline-2,3-dione (Compound 14-9)

To a mixture of 1-(piperidin-4-yl)indoline-2,3-dione (Compound 14-8, 1.38 g, 6 mmol) and 1-chloro-1,2-dihydroacenaphthylene (1.35 g, 7.2 mmol) in N,N-dimethylformamide (5 mL) was added triethylamine (1.21 g, 12 mmol). The mixture was stirred at 50° C. for 13 hours in a sealed tube. The resulting mixture was diluted with water (10 mL), extracted with ethyl acetate (30 mL×3). The combined organic layer was washed with brine, dried over sodium sulfate and concentrated. The residue was purified by flash column chromatography on silica gel (dichloromethane:methanol=20:1) to afford 1-(1-(1,2-dihydroacenaphthylen-1-yl)piperidin-4-yl) indoline-2,3-dione (Compound 14-9, 800 mg, yield: 35%) as a yellow solid. MS(ESI): m/z: 383 [M+H]$^+$. $^1$H NMR (400 MHz, CDCl$_3$) δ: 7.72 (m, 1H), 7.65-7.59 (m, 2H), 7.57-7.45 (m, 4H), 7.30 (d, J=7.2 Hz, 1H), 7.21 (d, J=8.4 Hz, 4H), 7.09 (t, J=7.6 Hz, 1H), 4.97 (t, J=5.2 Hz, 1H), 4.22-4.14 (m, 1H), 3.49-3.37 (m, 2H), 3.01 (d, J=11.6 Hz, 1H), 2.82 (m, 1H), 2.57-2.32 (m, 4H), 1.78-1.74 (m, 2H).

Preparation of 1-(1-(1,2-Dihydroacenaphthylen-1-yl)piperidin-4-yl)spiro[indolin-3,2'-oxiran]-2-one (Compound 14-10)

A mixture of trimethylsulfoxonium iodide (2.86 g, 13 mmol) and Cesium carbonate (8.52 g, 26 mmol) in acetonitrile (20 mL) was stirred at 50° C. for 1 hour under a nitrogen atmosphere. To the mixture, a solution of 1-(1-(1,2-dihydroacenaphthylen-1-yl)piperidin-4-yl)indoline-2,3-dione (Compound 14-9, 5.00 g, 13 mmol) in acetonitrile was added slowly. The resulting mixture was stirred at 50° C. for 5 hours. The resulting mixture was cooled and concentrated. The residue was diluted with dichloromethane, washed with brine (100 mL×3), dried over sodium sulfate and concentrated. The residue was purified by flash column chromatography on silica gel (petroleum ether:ethyl acetate=4:1) to afford 1-(1-(1,2-dihydroacenaphthylen-1-yl)piperidin-4-yl)spiro[indolin-3,2'-oxiran]-2-one (Compound 14-10, 3.30 mg, yield: 64%) as a yellow solid. MS (ESI): m/z: 397 [M+H]$^+$.

Preparation of 3-(Aminomethyl)-1-(1-(1,2-dihydroacenaphthylen-1-yl)piperidin-4-yl)-3-hydroxyindolin-2-one (Compound 14-11)

A mixture of 1-(1-(1,2-dihydroacenaphthylen-1-yl)piperidin-4-yl)spiro[indolin-3,2'-oxiran]-2-one (Compound 14-10, 2.20 g, 5.56 mmol) in ethanol (20 mL) and ammonium hydroxide (20 mL) was stirred at 50° C. for 2 hours. After completion, the solvent was removed to give crude 3-(aminomethyl)-1-(1-(1,2-dihydroacenaphthylen-1-yl)piperidin-4-yl)-3-hydroxyindolin-2-one (Compound 14-11, 2.30 g, used for next step directly) as a yellow solid. MS (ESI): m/z: 414 [M+H]$^+$.

Preparation of 1-(1-(1,2-Dihydroacenaphthylen-1-yl)piperidin-4-yl)spiro[indoline-3,5'-oxazolidine]-2,2'-dione (Compound 52)

To a solution of 3-(aminomethyl)-1-(1-(1,2-dihydroacenaphthylen-1-yl)piperidin-4-yl)-3-hydroxyindolin-2-one (Compound 14-11, 128 mg, 0.31 mmol), triethylamine (63 mg, 0.62 mmol) in dichloromethane (10 mL) at 0° C. was added triphosgene (34 mg, 0.11 mmol). The mixture was stirred at 0° C. for 10 minutes and then at room temperature for 1 hour. The resulting mixture was quenched by saturated sodium bicarbonate solution and concentrated. The residue was purified by pre-TLC (dichloromethane:methanol=40:1) to give the desired product 1-(1-(1,2-dihydroacenaphthylen-1-yl)piperidin-4-yl)spiro[indoline-3,5'-oxazolidine]-2,2'-dione (Compound 52, 20 mg, yield: 15%) as a white solid. MS (ESI): m/z: 440 [M+H]$^+$. $^1$H NMR (400 MHz, CDCl$_3$) δ: 8.09 (br s, 1H), 7.74 (d, J=8.0 Hz, 1H), 7.66 (d, J=8.0 Hz, 1H), 7.56 (t, J=6.8 Hz, 2H), 7.51-7.46 (m, 2H), 7.43 (t, J=8.0 Hz, 1H), 7.33 (d, J=6.4 Hz, 1H), 7.25 (d, J=8.0 Hz, 1H), 7.13 (t, J=7.6 Hz, 1H), 4.96 (t, J=6.0 Hz, 1H), 4.03-3.96 (m, 1H), 3.38-3.37 (m, 1H), 3.67 (dd, $^1$J=22 Hz, $^2$J=9.6 Hz, 1H), 2.95-2.93 (m, 1H), 2.59-2.54 (m, 1H), 2.44-2.36 (m, 2H), 2.33-2.22 (m, 2H), 1.69-1.57 (m, 2H).

Example 8B: Preparation of Compound 48

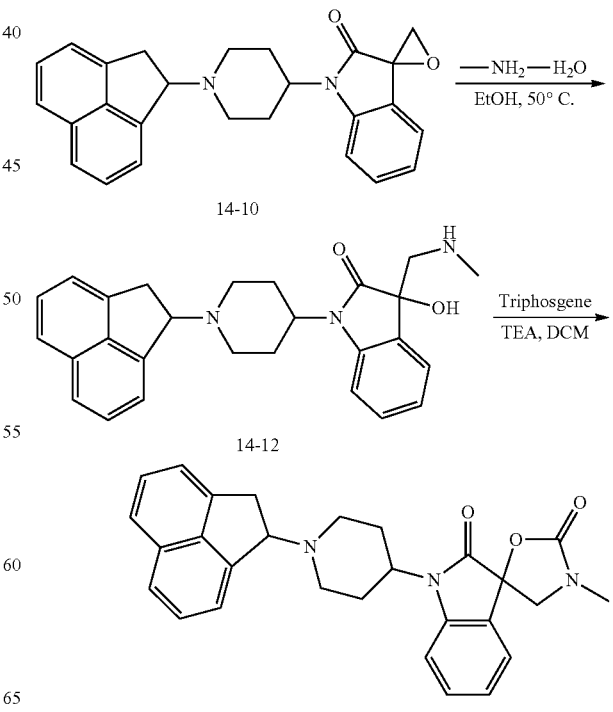

Scheme 14B.

14-10

14-12

48

Preparation of 1-(1-(1,2-Dihydroacenaphthylen-1-yl)piperidin-4-yl)-3-hydroxy-3-((methylamino)methyl)indolin-2-one (Compound 14-12)

A mixture of 1-(1-(1,2-dihydroacenaphthylen-1-yl)piperidin-4-yl)spiro[indoline-3,2'-oxiran]-2-one (Compound 14-10, 300 mg, 0.75 mmol) in ethanol (20 mL) and methylamine (28% in water, 20 mL) was stirred at 50° C. for 2 hours. After completion, the solvent was removed to give crude 1-(1-(1,2-dihydroacenaphthylen-1-yl)piperidin-4-yl)-3-hydroxy-3-((methylamino)methyl)indolin-2-one (Compound 14-12, 320 mg, used for next step directly) as a yellow solid. MS (ESI): m/z: 428 [M+H]$^+$.

Preparation of 1-(1-(1,2-Dihydroacenaphthylen-1-yl)piperidin-4-yl)-3'-methylspiro[indoline-3,5'-oxazolidine]-2,2'-dione (Compound 48)

To a solution of 1-(1-(1,2-dihydroacenaphthylen-1-yl)piperidin-4-yl)-3-hydroxy-3-((methylamino)methyl)indolin-2-one (Compound 14-12, 80 mg, 0.18 mmol), triethylamine (38 mg, 0.37 mmol) in dichloromethane (10 mL) at 0° C. was added triphosgene (20 mg, 0.06 mmol). The mixture was stirred at 0° C. for 10 minutes and then at room temperature for 1 hour. The resulting mixture was quenched by saturated sodium bicarbonate solution and concentrated. The residue was purified by pre-TLC (dichloromethane:methanol=40:1) to give the desired product 1-(1-(1,2-dihydroacenaphthylen-1-yl)piperidin-4-yl)-3'-methylspiro[indoline-3,5'-oxazolidine]-2,2'-dione (Compound 48, 36 mg, yield: 43%) as a white solid. MS (ESI): m/z: 454 [M+H]$^+$. $^1$H NMR (400 MHz, CDCl$_3$) δ: 7.73-7.70 (m, 1H), 7.63 (d, J=8.0 Hz, 1H), 7.55-7.52 (m, 2H), 7.46 (t, J=7.2 Hz, 1H), 7.41-7.36 (m, 2H), 7.29 (d, J=6.8 Hz, 1H), 7.21 (d, J=8.0 Hz, 1H), 7.10 (t, J=7.6 Hz, 1H), 4.97 (t, J=4.8 Hz, 1H), 4.19-4.14 (m, 1H), 3.82 (d, J=9.2 Hz, 1H), 3.65 (d, J=8.8 Hz, 1H), 3.43 (d, J=4.8 Hz, 1H), 3.00 (m, 1H), 2.83-2.79 (m, 1H), 2.54-2.33 (m, 4H), 1.71-1.68 (m, 2H).

Example 8C: Preparation of Compound 53

Scheme 14C.

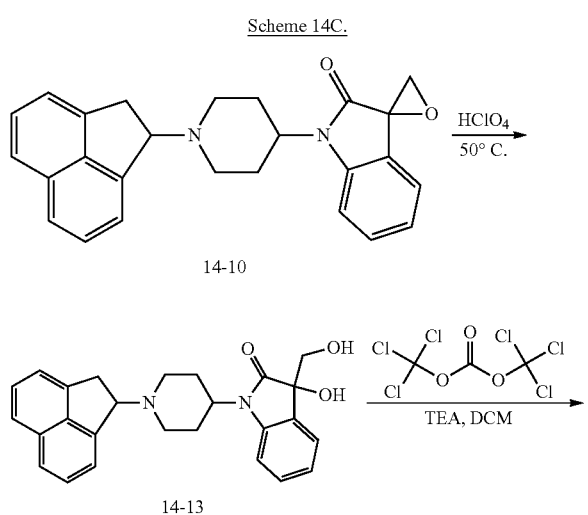

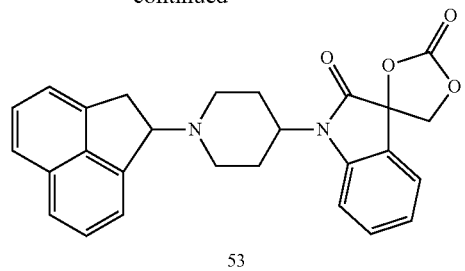

53

Preparation of 1-(1-(1,2-Dihydroacenaphthylen-1-yl)piperidin-4-yl)-3-hydroxy-3-(hydroxymethyl)indolin-2-one (Compound 14-13)

To a solution of 1-(1-(1,2-dihydroacenaphthylen-1-yl)piperidin-4-yl)spiro[indoline-3,2'-oxiran]-2-one (Compound 14-10, 0.3 g, 0.75 mmol) in 1,4-dioxane (5.0 mL) and water (3.0 mL) was added perchloric acid (0.5 mL, 8.3 mmol) dropwise at 50° C. The reaction mixture was stirred at 50° C. for 2 hours. After completion, the reaction mixture was neutralized to pH=7 with sodium bicarbonate, extracted with dichloromethane (30 mL×2). The combined organic layer was washed with brine (30 mL×2), dried over anhydrous sodium sulfate and concentrated to give the crude 1-(1-(1,2-dihydroacenaphthylen-1-yl)piperidin-4-yl)-3-hydroxy-3-(hydroxymethyl)indolin-2-one (Compound 14-13, 260 mg, yield: 74%) which was used directly without further purification. MS (ESI): m/z: 415 [M+H]$^+$.

Preparation of 1'-(1-(1,2-Dihydroacenaphthylen-1-yl)piperidin-4-yl)spiro[[1,3]dioxolane-4,3'-indoline]-2,2'-dione (Compound 53)

To a solution of 1-(1-(1,2-dihydroacenaphthylen-1-yl)piperidin-4-yl)-3-hydroxy-3-(hydroxymethyl)indolin-2-one (Compound 14-13, 50 mg, 0.12 mmol), triethylamine (24 mg, 0.24 mmol) in dichloromethane (3 mL) at 0° C. was added triphosgene (90 mg, 0.3 mmol). The mixture was stirred at 0° C. for 10 minutes and then at room temperature for 1 hour. The resulting mixture was quenched by saturated sodium bicarbonate solution and concentrated. The residue was purified by pre-TLC (dichloromethane:methanol=50:1) to give the desired product (Compound 53, 6 mg, yield: 11%) as a white solid. MS (ESI): m/z: 441 [M+H]$^+$. $^1$H NMR (400 MHz, CDCl$_3$) δ: 7.71 (d, J=7.6 Hz, 1H), 7.64 (d, J=8.0 Hz, 1H), 7.56-7.52 (m, 2H), 7.49-7.45 (m, 2H), 7.39 (t, J=8.0 Hz, 1H), 7.30 (d, J=7.2 Hz, 1H), 7.20 (d, J=8.4 Hz, 1H), 7.13 (t, J=7.6 Hz, 1H), 4.98 (t, J=4.8 Hz, 1H), 4.17 (m, 1H), 3.94 (d, J=8.8 Hz, 1H), 3.73 (d, J=9.2 Hz, 1H), 3.43 (d, J=3.2 Hz, 1H), 3.01 (m, 1H), 2.80 (m, 1H), 2.53-2.34 (m, 4H), 1.73-1.67 (m, 2H).

Example 8D: Preparation of Compound 5

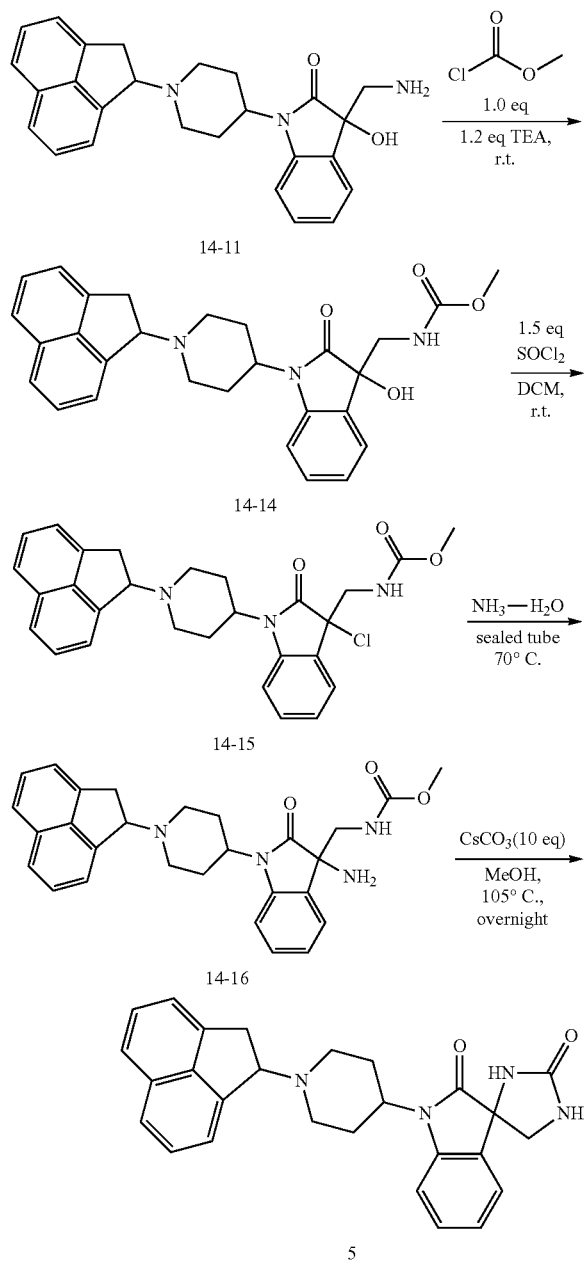

Preparation of Methyl(1-(1-(1,2-dihydroacenaphth-ylen-1-yl)piperidin-4-yl)-3-hydroxy-2-oxoindolin-3-yl)methylcarbamate (Compound 14-14)

To a solution of 3-(aminomethyl)-1-(1-(1,2-dihydroacenaphthylen-1-yl)piperidin-4-yl)-3-hydroxyindolin-2-one (Compound 14-11, 2.30 g, 5.57 mmol) in dichloromethane (80 mL) was added methyl carbonochloridate (0.785 g, 8.35 mmol) and then triethylamine (1.55 mL, 11.14 mmol) dropwise at 25° C. The mixture was stirred at 25° C. for 2 hours. After completion, the solvent was removed. The residue was purified by flash column chromatography on silica gel (dichloromethane:methanol=60:1) to afford methyl(1-(1-(1,2-dihydroacenaphthylen-1-yl)piperidin-4-yl)-3-hydroxy-2-oxoindolin-3-yl)methylcarbamate (Compound 14-14, 2.09 g, yield: 88%) as brown oil. MS (ESI): m/z: 472 [M+H]$^+$.

Preparation of Methyl(3-chloro-1-(1-(1,2-dihydroacenaphthylen-1-yl)piperidin-4-yl)-2-oxoindolin-3-yl)methylcarbamate (Compound 14-15)

To a solution of methyl(1-(1-(1,2-dihydroacenaphthylen-1-yl)piperidin-4-yl)-3-hydroxy-2-oxoindolin-3-yl)methylcarbamate (Compound 14-14, 0.68 g, 1.44 mmol) in dichloromethane (40 mL), was added thionyl chloride (0.26 mL, 3.6 mmol) dropwise at 25° C. The mixture was stirred at room temperature for 2 hours. After completion, the solvent was removed to give the crude methyl(3-chloro-1-(1-(1,2-dihydroacenaphthylen-1-yl)piperidin-4-yl)-2-oxoindolin-3-yl)methylcarbamate (Compound 14-15) as brown oil, which was used directly without further purification. MS (ESI): m/z: 490 [M+H]$^+$.

Preparation of Methyl(3-chloro-1-(1-(1,2-dihydroacenaphthylen-1-yl)piperidin-4-yl)-2-oxoindolin-3-yl)methylcarbamate (Compound 14-16)

The crude product of methyl(3-chloro-1-(1-(1,2-dihydroacenaphthylen-1-yl)piperidin-4-yl)-2-oxoindolin-3-yl)methylcarbamate (Compound 14-15) obtained in the above were dissolved in 28% ammonium hydroxide solution (45 mL) at 25° C. The mixture was stirred at 70° C. for 3.0 hours. After completion, the solvent was removed to give crude methyl(3-chloro-1-(1-(1,2-dihydroacenaphthylen-1-yl)piperidin-4-yl)-2-oxoindolin-3-yl)methylcarbamate (Compound 14-16) as brown oil, which was used directly without further purification. MS (ESI): m/z: 471 [M+H]$^+$.

Preparation of 1'-(1-(1,2-Dihydroacenaphthylen-1-yl)piperidin-4-yl)spiro[imidazolidine-4,3'-indoline]-2,2'-dione (Compound 5)

To a solution of methyl(3-chloro-1-(1-(1,2-dihydroacenaphthylen-1-yl)piperidin-4-yl)-2-oxoindolin-3-yl)methylcarbamate (Compound 14-16, 70 mg, 0.15 mmol) in methanol (18 mL) was added cesium carbonate (489 mg, 1.5 mmol) in one portion at room temperature. The mixture was stirred in a sealed tube at 105° C. for 4.0 h. After completion, the solid was filtered off and the solvent was removed to give the crude product, which was purified by pre-HPLC to afford 1'-(1-(1,2-dihydroacenaphthylen-1-yl)piperidin-4-yl)spiro[imidazolidine-4,3'-indoline]-2,2'-dione (Compound 5, 21 mg, yield: 33%) as a white solid. MS (ESI): m/z: 453 [M+H]$^+$. $^1$H NMR (400 MHz, CDCl$_3$) δ: 7.73 (d, J=8.0 Hz, 1H), 7.63 (t, J=8.8 Hz, 2H), 7.55 (t, J=8.0 Hz, 1H), 7.45-7.51 (m, 2H), 7.28-7.40 (m, 3H), 7.15 (t, J=7.6 Hz, 1H), 5.03 (q, J=3.3 Hz, 1H), 4.15 (tt, $^1$J=3.8 Hz, $^2$J=12.3 Hz, 1H), 3.73 (d, J=9.1 Hz, 1H), 3.57 (d, J=9.1 Hz, 1H), 3.47-3.54 (m, 2H), 3.08 (d, J=11.2 Hz, 1H), 2.79 (d, J=10.1 Hz, 1H), 2.39-2.66 (m, 4H), 1.64-1.78 (m, 2H).

Example 8E: Preparation of Compound 6

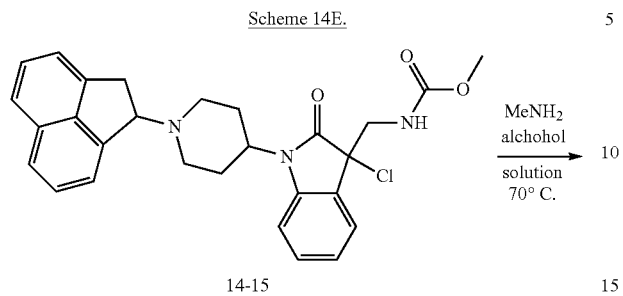

Scheme 14E.

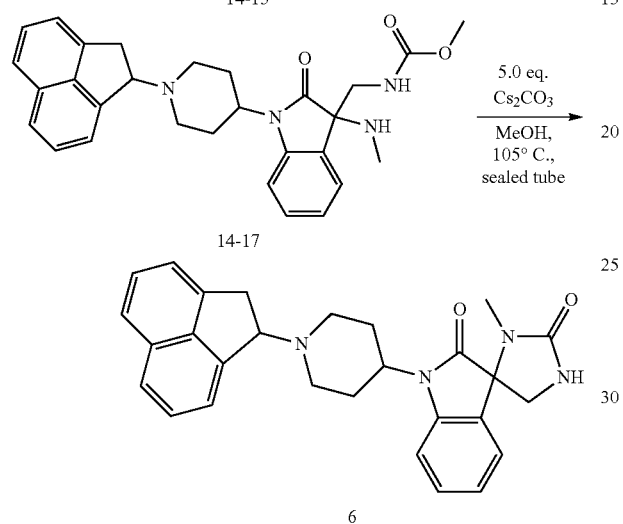

Preparation of Methyl(1-(1-(1,2-dihydroacenaphthylen-1-yl)piperidin-4-yl)-3-(methylamino)-2-oxoindolin-3-yl)methylcarbamate (Compound 14-17)

The crude product of methyl(3-chloro-1-(1-(1,2-dihydroacenaphthylen-1-yl)piperidin-4-yl)-2-oxoindolin-3-yl)methylcarbamate (Compound 14-15) obtained in the above was dissolved in 31% methylamine alcohol solution (45 mL) at 25° C. The mixture was stirred at 70° C. for 3.0 hours. After completion, the solvent was removed to give crude methyl(1-(1-(1,2-dihydroacenaphthylen-1-yl)piperidin-4-yl)-3-(methylamino)-2-oxoindolin-3-yl)methylcarbamate (Compound 14-17) as brown oil, which was used directly without further purification. MS (ESI): m/z: 485 [M+H]$^+$.

Preparation of 1'-(1-(1,2-Dihydroacenaphthylen-1-yl)piperidin-4-yl)-3-methylspiro[imidazolidine-4,3'-indoline]-2,2'-dione (Compound 6)

To a solution of methyl(1-(1-(1,2-dihydroacenaphthylen-1-yl)piperidin-4-yl)-3-(methylamino)-2-oxoindolin-3-yl)methylcarbamate (Compound 14-17, the crude obtained in the above) in methanol (18 mL) was added cesium carbonate (1.17 g, 3.6 mmol) in one portion at room temperature. The mixture was stirred in a sealed tube at 105° C. for 4.0 h. After completion, the solid was filtered off and the solvent was removed to give the crude product, which was purified by pre-HPLC to afford 1'-(1-(1,2-dihydroacenaphthylen-1-yl)piperidin-4-yl)-3-methylspiro[imidazolidine-4,3'-indoline]-2,2'-dione (Compound 6, 50 mg, yield of three steps: 7.6%) as a white solid. MS (ESI): m/z: 453 [M+H]$^+$. $^1$H NMR (400 MHz, CDCl$_3$) δ: 7.71 (d, J=6.5 Hz, 1H), 7.64 (d, J=8.3 Hz, 1H), 7.50-7.57 (m, 2H), 7.47 (t, J=7.5 Hz, 1H), 7.33-7.42 (m, 2H), 7.30 (d, J=6.8 Hz, 1H), 7.23 (d, J=7.9 Hz, 1H), 7.12 (t, J=7.5 Hz, 1H), 4.96-5.03 (m, 1H), 4.73 (s, 1H), 4.25 (t, J=11.6 Hz, 1H), 3.75 (dd, $^1$J=1.2 Hz, $^2$J=8.8 Hz, 1H), 3.48 (d, J=8.5 Hz, 1H), 3.43 (d, J=2.9 Hz, 2H), 3.02 (t, J=11.0 Hz, 1H), 2.81 (t, J=10.8 Hz, 1H), 2.28-2.63 (m, 7H), 1.60-1.74 (m, 2H).

Example 8F: Preparation of Compound 7

Scheme 14F.

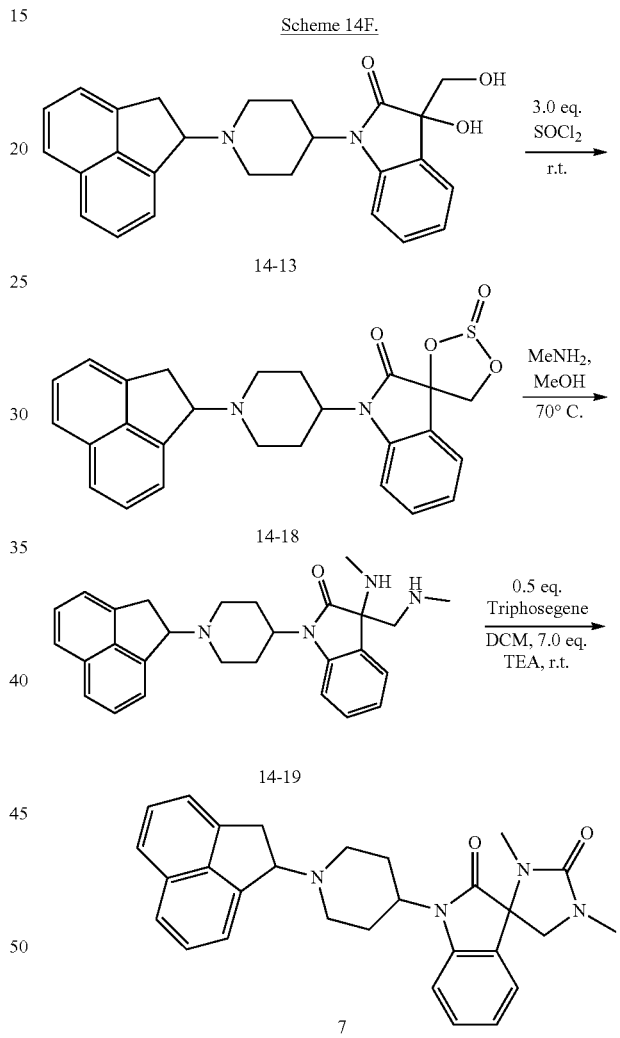

Preparation of Compound 14-18

To a solution of 1-(1-(1,2-dihydroacenaphthylen-1-yl)piperidin-4-yl)-3-hydroxy-3-(hydroxymethyl)indolin-2-one (Compound 14-13, the crude obtained in the above) in dichloromethane (20 mL) was added thionyl chloride (0.17 mL, 2.4 mmol) dropwise at 25° C. The mixture was stirred at room temperature for 2 hours. After completion, the solvent was removed to give the crude product, which was used directly without further purification. MS (ESI): m/z: 461 [M+H]$^+$.

Preparation of 1-(1-(1,2-Dihydroacenaphthylen-1-yl)piperidin-4-yl)-3-(methylamino)-3-((methylamino)methyl)indolin-2-one (Compound 14-19)

Compound 14-18 (crude obtained in the above procedure) was dissolved in 31% methylamine alcohol solution (30 mL) at 25° C. The mixture was stirred at 70° C. for 3.0 hours. After completion, the solvent was removed to give the crude 1-(1-(1,2-dihydroacenaphthylen-1-yl)piperidin-4-yl)-3-(methylamino)-3-((methylamino)methyl)indolin-2-one (Compound 14-19) as brown oil, which was used directly for next step without further purification. MS (ESI): m/z: 441 [M+H]⁺.

Preparation of 1'-(1-(1,2-Dihydroacenaphthylen-1-yl)piperidin-4-yl)-1,3-dimethylspiro[imidazolidine-4,3'-indoline]-2,2'-dione (Compound 7)

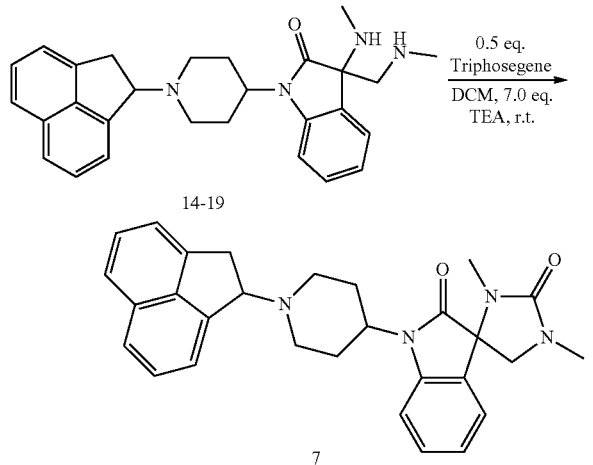

To a solution of 1-(1-(1,2-dihydroacenaphthylen-1-yl)piperidin-4-yl)-3-(methylamino)-3-((methylamino)methyl)indolin-2-one (Compound 14-19, crude product obtained in the above) in dichloromethane (30 mL) was added triphosgene (111 mg, 0.375 mmol) in one portion and then triethylamine (5.25 mmol, 0.72 mL) dropwise at 25° C. The mixture was stirred at 25° C. for 2 hours. After completion, the reaction was quenched with saturated sodium bicarbonate solution to pH=7. The organic layer was washed with brine (15 mL×3), dried over anhydrous sodium sulfate and concentrated to give the crude product, which was purified by pre-HPLC to give the 1'-(1-(1,2-dihydroacenaphthylen-1-yl)piperidin-4-yl)-1,3-dimethylspiro[imidazolidine-4,3'-indoline]-2,2'-dione (Compound 7, 70 mg, yield of three steps: 19.8%) as a white solid. MS (ESI): m/z: 467 [M−41]⁺.
¹H NMR (400 MHz, CDCl₃) δ: 7.71 (d, J=7.4 Hz, 1H), 7.64 (d, J=8.1 Hz, 1H), 7.50-7.57 (m, 2H), 7.47 (t, J=7.8 Hz, 1H), 7.27-7.38 (m, 3H), 7.22 (d, J=7.6 Hz, 1H), 7.10 (t, J=7.5 Hz, 1H), 4.96-5.03 (m, 1H), 4.24 (t, J=11.2 Hz, 1H), 3.59 (d, J=8.9 Hz, 1H), 3.42 (d, J=3.5 Hz, 2H), 3.37 (d, J=9.0 Hz, 1H), 3.01 (t, J=10.6 Hz, 1H), 2.89 (s, 3H), 2.79 (t, J=11.0 Hz, 1H), 2.26-2.63 (m, 7H), 1.58-1.75 (m, 2H).

Example 8G: Preparation of Compound 44

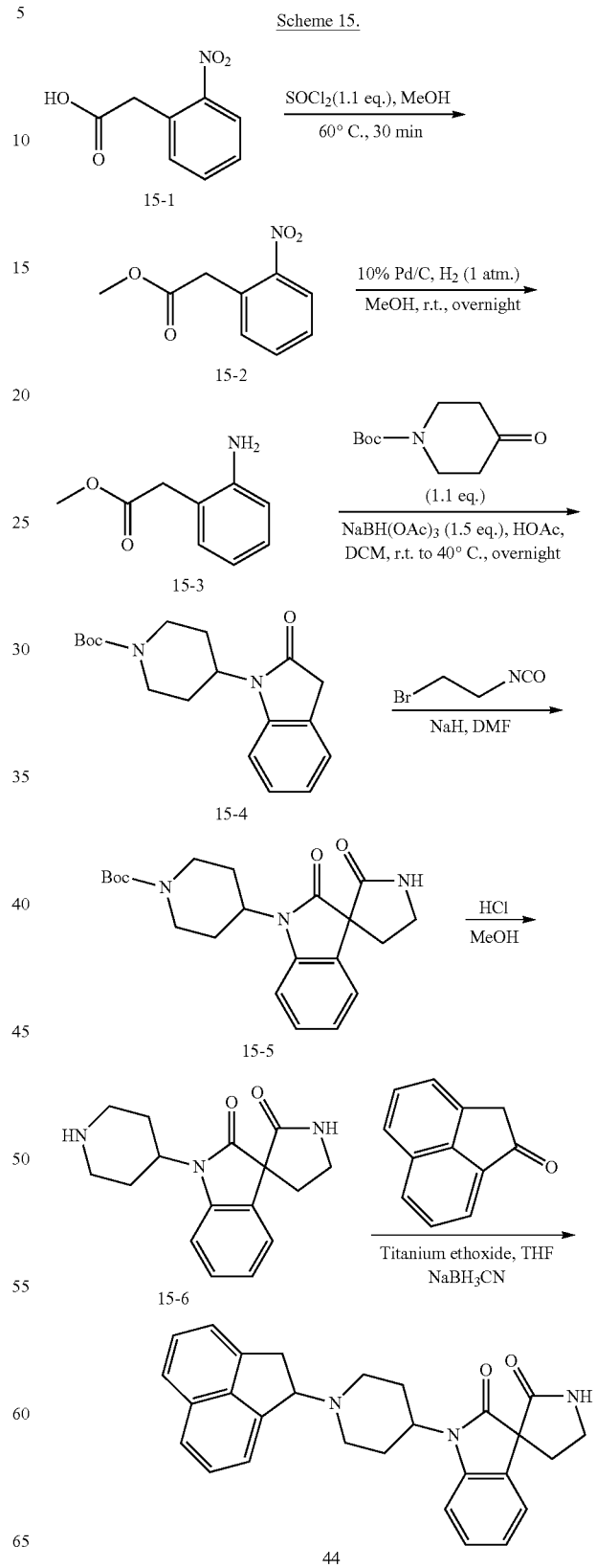

Preparation of Methyl 2-(2-nitrophenyl)acetate (15-2)

To a solution of 2-(2-nitrophenyl)acetic acid (Compound 15-1, 18.1 g, 100 mmol) in methanol (150 mL) at room temperature was added sulfurous dichloride (13.1 g, 110 mmol) dropwise. The mixture was heated to 60° C. and stirred for 30 minutes. The reaction mixture was concentrated to give a pale yellow oil, diluted with ethyl acetate (200 mL), washed with saturated sodium bicarbonate solution (150 mL×3) and brine (100 mL×2), dried over anhydrous sodium sulfate, concentrated to give the desired product methyl 2-(2-nitrophenyl)acetate (Compound 15-2, 19.1 g, yield: 98%) as pale yellow oil. MS (ESI): m/z: 196 [M+H]$^+$. $^1$H NMR (400 MHz, CDCl$_3$) δ: 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 1H).

Preparation of Methyl 2-(2-aminophenyl)acetate (Compound 15-3)

A mixture of methyl 2-(2-nitrophenyl)acetate (Compound 15-2, 9.75 g, 50 mmol), palladium on activated carbon (10% Pd, dry, 530 mg, 5 mmol) in methanol (100 mL) was stirred under hydrogen (1 atm.) at room temperature overnight. The reaction mixture was filtered to remove palladium on activated carbon and the filtrate was concentrated to give the desired product methyl 2-(2-aminophenyl)acetate (Compound 15-3, 8.02 g, yield: 97%) as a pale yellow oil. MS (ESI): m/z: 166 [M+H]$^+$. $^1$H NMR (400 MHz, DMSO-d$^6$) δ: 6.94 (m, 2H), 6.64 (d, 1H, J=8.0 Hz), 6.51 (m, 1H), 4.88 (s, 2H), 3.59 (s, 3H), 3.52 (s, 2H).

Preparation of Tert-butyl 4-(2-oxoindolin-1-yl)piperidine-1-carboxylate (Compound 15-4)

A mixture of methyl 2-(2-aminophenyl)acetate (Compound 15-3, 3.30 g, 20 mmol), tert-butyl 4-oxopiperidine-1-carboxylate (4.38 g, 22 mmol), acetic acid (600 mg, 10 mmol) in dichloromethane (80 mL) was stirred at room temperature for 2 hours, then sodium triacetoxyborohydride (6.36 g, 30 mmol) was added in portions and heated to 40° C. and stirred overnight. The reaction mixture was cooled to room temperature and diluted with dichloromethane (200 mL), washed with water (200 mL×2) and saturated sodium bicarbonate solution (200 mL×2), dried over anhydrous sodium sulfate, concentrated to give the crude product, which was purified by flash column chromatography on silica gel (petroleum ether:ethyl acetate=1:20-1:15-1:10) to give the desired product tert-butyl 4-(2-oxoindolin-1-yl)piperidine-1-carboxylate (Compound 15-4, 2.65 g, yield: 42%) as a pale yellow solid. MS (ESI): m/z: 261 [M+H−56]$^+$. $^1$H NMR (400 MHz, CDCl$_3$) δ: 7.24 (m, 2H), 7.01 (m, 2H), 4.41 (m, 1H), 4.28 (br s, 2H), 3.53 (s, 2H), 2.83 (br s, 2H), 2.32 (m, 2H), 1.70 (m, 2H), 1.50 (s, 9H).

Preparation of Tert-butyl 4-(2,2'-dioxospiro[indoline-3,3'-pyrrolidine]-1-yl)piperidine-1-carboxylate (Compound 15-5)

To a solution of tert-butyl 4-(2-oxoindolin-1-yl)piperidine-1-carboxylate (Compound 15-4, 1 g, 3.1 mmol) in N,N-dimethylformamide (10 mL) was added sodium hydride (60% in oil, 130 mg, 3.1 mmol). The mixture was stirred at room temperature for 10 minutes. 2-Bromoethyl isocyanate (470 mg, 3.1 mmol) was added. The mixture was stirred at room temperature for another 20 minutes. Ethyl acetate was added and the resulting mixture was washed with brine (20 mL×6), dried over anhydrous sodium sulfate and concentrated. The residue was purified by flash column chromatography on silica gel (dichloromethane:methanol=80:1) to give the desired product tert-butyl 4-(2,2'-dioxospiro[indoline-3,3'-pyrrolidine]-1-yl)piperidine-1-carboxylate (Compound 15-5, 726 mg, yield: 60%) as a yellow solid. MS (ESI): m/z: 386 [M−41]$^+$. $^1$H NMR (400 MHz, CDCl$_3$) δ: 8.60 (br s, 1H), 7.47-7.43 (m, 1H), 7.08-6.97 (m, 3H), 4.72 (t, J=8.0 Hz, 2H), 4.58-4.52 (m, 1H), 4.32 (m, 2H), 3.87 (t, J=8.4 Hz, 2H), 2.86 (m, 2H), 2.46-2.35 (m, 2H), 1.74-1.65 (m, 2H), 1.50 (s, 9H).

Preparation of 1-(Piperidin-4-yl)spiro[indoline-3,3'-pyrrolidine]-2,2'-dione (Compound 15-6)

A mixture of tert-butyl 4-(2,2'-dioxospiro[indoline-3,3'-pyrrolidine]-1-yl)piperidine-1-carboxylate (Compound 15-5, 500 mg, 1.3 mmol) in methanol with hydrogen chloride (10 mL) was stirred at room temperature for 2 hours. The mixture was concentrated and purified by reverse phase chromatography (acetonitrile in water 22% v/v, 0.01% ammonium hydroxide) to give the desired product 1-(piperidin-4-yl)spiro[indoline-3,3'-pyrrolidine]-2,2'-dione (Compound 15-6, 361 mg, yield: 97%) as a white solid. MS (ESI): m/z: 286 [M+H]$^+$.

Preparation of 1-(1-(1,2-Dihydroacenaphthylen-1-yl)piperidin-4-yl)spiro[indoline-3,3'-pyrrolidine]-2,2'-dione (Compound 44)

A mixture of 1-(piperidin-4-yl)spiro[indoline-3,3'-pyrrolidine]-2,2'-dione (Compound 15-6, 150 mg, 0.39 mmol), acenaphthylen-1-(2H)-one (66 mg, 0.39 mmol) and titanium ethoxide (444 mg, 1.95 mmol) in tetrahydrofuran (15 mL) was stirred at 120° C. for 12 hours under a nitrogen atmosphere with microwave machine. Sodium cyanoborohydride (123 mg 1.95 mmol) was added. The mixture was stirred at 100° C. for 1 hour with microwave machine. The resulting mixture was diluted with dichloromethane and water, filtrated and separated. The organic layer was concentrated and purified by reverse phase chromatography (acetonitrile in water 45% v/v, 0.01% trifluoroacetic acid) to give the desired product 1-(1-(1,2-dihydroacenaphthylen-1-yl)piperidin-4-yl)spiro[indoline-3,3'-pyrrolidine]-2,2'-dione (Compound 44, 46 mg, yield: 20%) as a white solid. MS (ESI): m/z: 438 [M+H]$^+$. $^1$H NMR (400 MHz, CDCl$_3$) δ: 7.87 (d, J=8.4 Hz, 1H), 7.75 (d, J=7.2 Hz, 1H), 7.68 (d, J=8.4 Hz, 1H), 7.61 (d, J=7.6 Hz, 1H), 7.51 (d, J=7.2 Hz, 1H), 7.40 (d, J=6.8 Hz, 1H), 7.30 (d, J=7.2 Hz, 1H), 7.03 (d, J=7.6 Hz, 1H), 6.89-6.82 (m, 2H), 5.51-5.50 (m, 1H), 4.66 (t, J=8.0 Hz, 1H), 4.49-4.43 (m, 1H), 3.85-3.73 (m, 4H), 3.52-3.49 (m, 1H), 3.40-3.33 (m, 1H), 3.28-3.21 (m, 1H), 3.03-2.97 (m, 1H), 2.85-2.76 (m, 2H), 1.86-1.82 (m, 2H).

Example 9A: Preparation of Compound 46

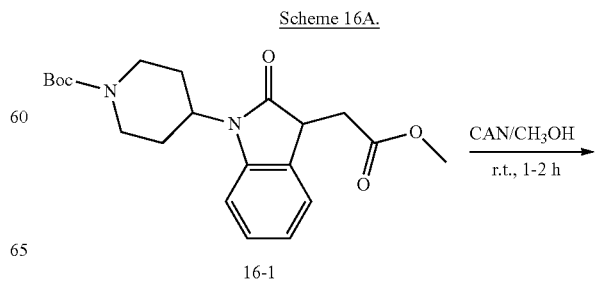

Scheme 16A.

16-1

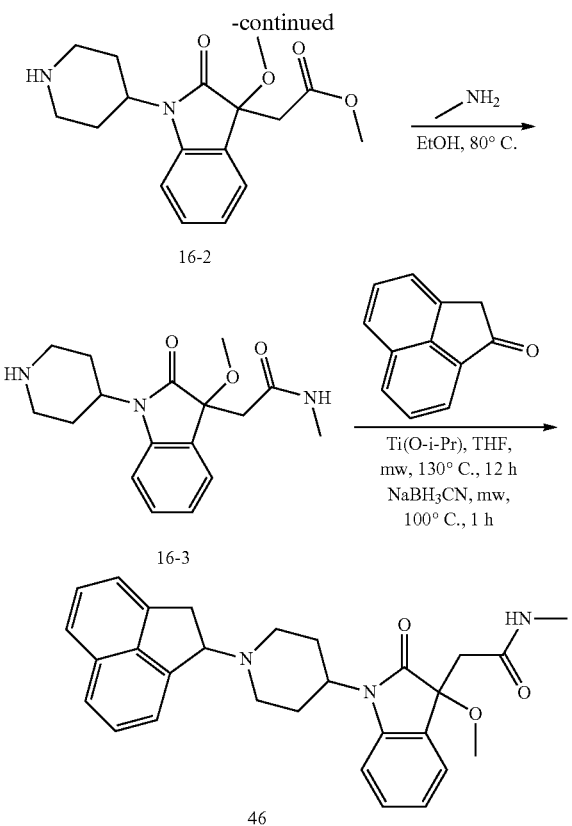

Preparation of methyl 2-(3-methoxy-2-oxo-1-(piperidin-4-yl)indolin-3-yl)acetate (Compound 16-2)

A suspension of tert-butyl 4-(3-(2-methoxy-2-oxoethyl)-2-oxoindolin-1-yl)piperidine-1-carboxylate (621 mg, 1.6 mmol) in methanol (13 mL) was stirred at room temperature. Ammonium cerium(IV) nitrate (1.75 g, 3.2 mmol) was added by portions. The mixture was exothermic mildly. The mixture was stirred at room temperature for 1 hour. The color of the solution turned to orange from red gradually. The solvent was concentrated in vacuum. The residue was basified with saturated sodium bicarbonate solution (30 mL). Dichloromethane (30 mL) was added and then stirred at room temperature for 5 minutes. The solid was removed by filtration. The separated aqueous layer was extracted with dichloromethane (30 mL×2). The organic layer was washed with brine (30 mL), dried over sodium sulfate, filtered and then concentrated in vacuum. The crude Compound 16-2 was obtained as a pale yellow oil (1 g) and then used for the next step without further purification. MS: m/z 319 [M+1]$^+$, $^1$H NMR (400 MHz, CDCl$_3$), δ 7.32-7.33 (m, 2H), 7.17-7.19 (m, 1H), 7.06-7.10 (m, 1H), 4.38 (t, 1H), 3.45 (s, 3H), 3.27-3.30 (m, 2H), 3.20 (d, J=16.0 Hz, 1H), 3.06 (d, J=16.0 Hz, 1H), 2.98 (s, 3H), 2.80-2.81 (m, 2H), 2.35-2.43 (m, 2H), 1.75-1.84 (m, 2H).

Preparation of 2-(3-methoxy-2-oxo-1-(piperidin-4-yl)indolin-3-yl)-N-methylacetamide (Compound 16-3)

A solution of methyl 2-(3-methoxy-2-oxo-1-(piperidin-4-yl)indolin-3-yl)acetate (Compound 16-2, 1 g, 1.6 mmol) in methylamine/ethanol (20 mL, 35%) was heated to 80 degrees in a sealed tube and stirred for 2 hours. The mixture was concentrated in vacuum. The crude product was purified by reverse phase to give the product 2-(3-methoxy-2-oxo-1-(piperidin-4-yl)indolin-3-yl)-N-methylacetamide (Compound 16-3, 290 mg, 57%, acetonitrile/water (ammonium) =28%) as a pink solid. MS: m/z 318 [M+1]$^+$, $^1$H NMR (400 MHz, CDCl$_3$) δ 7.29-7.34 (m, 2H), 7.06-7.17 (m, 2H), 6.67 (brs, 1H), 4.28-4.34 (m, 1H), 3.20-3.26 (m, 2H), 3.03 (s, 3H), 2.86 (d, J=14.8 Hz, 1H), 2.81 (d, J=4.8 Hz, 3H), 2.70-2.78 (m, 2H), 2.68 (d, J=14.8 Hz, 1H), 2.30-2.42 (m, 2H), 1.71-1.75 (m, 2H).

Preparation of 2-(1-(1-(1,2-dihydroacenaphthylen-1-yl)piperidin-4-yl)-3-methoxy-2-oxoindolin-3-yl)-N-methylacetamide (Compound 46)

A solution of 2-(3-methoxy-2-oxo-1-(piperidin-4-yl)indolin-3-yl)-N-methylacetamide (Compound 16-3, 100 mg, 0.32 mmol) in tetrahydrofuran (5 mL) was added acenaphthylen-1(2H)-one (106 mg, 0.63 mmol), Titanium tetraisopropanolate (444 mg, 1.58 mmol). The mixture was heated to 130° C. with microwave and stirred for 12 hours. Then the cold reaction mixture was added sodium cyanoborohydride (60 mg, 0.96 mmol) and irritated with microwave to 100° C. for 1 hour. Then the reaction mixture was diluted with water (10 mL) and extracted with ethyl acetate (10 mL×3). The combined extracts were washed with brine and dried over sodium sulfate. Filtered and the filtrate was concentrated to give the crude product. Purified by pre-TLC (dichloromethane/methanol=10/1) to give 50 mg (33%) of Compound 46 as a yellow solid: m/z 470.1[M+1]$^+$, $^1$H NMR (400 MHz, CDCl$_3$) δ 7.72-7.69 (m, 1H), 7.65-7.62 (m, 1H), 7.56-7.45 (m, 3H), 7.36-7.26 (m, 3H), 7.21-7.19 (m, 1H), 7.11-7.07 (m, 1H), 6.71-6.68 (m, 1H), 4.98 (t, J=5.6 Hz, 1H), 4.25-4.19 (m, 1H), 3.42 (d, J=5.2 Hz, 2H), 3.07-2.97 (m, 4H), 2.87-2.79 (m, 5H), 2.65 (d, J=14.8 Hz, 1H), 2.57-2.35 (m, 4H), 1.73-1.63 (m, 2H).

Example 9B: Preparation of 2-(1-(1-(3-(2-chloro-5-methoxyphenoxy)-4-methylpentyl)piperidin-4-yl)-3-methoxy-2-oxoindolin-3-yl)-N-methylacetamide (Compound 49)

Scheme 16B.

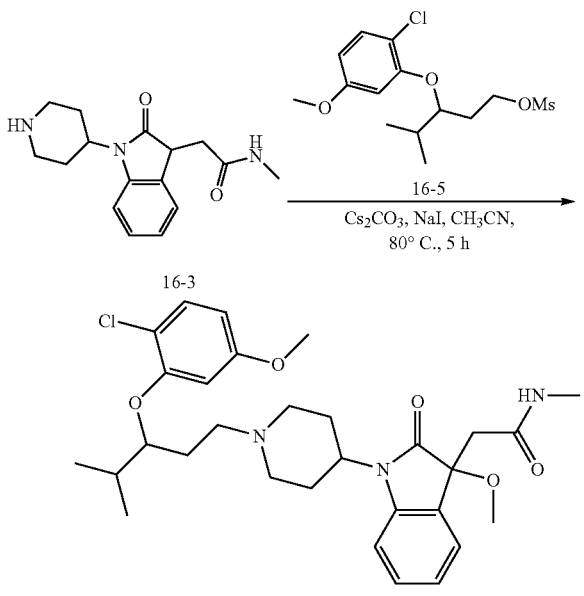

A mixture of 2-(3-methoxy-2-oxo-1-(piperidin-4-yl)indolin-3-yl)-N-methylacetamide (Compound 16-3, 100 mg, 0.31 mmol), 3-(2-chloro-5-methoxyphenoxy)-4-methylpentyl methanesulfonate (Compound 16-5, 106 mg, 0.31 mmol), Cesium carbonate (205 mg, 0.63 mmol), Sodium iodide (5 mg, 0.03 mmol) in acetonitrile (10 ml) was stirred at 80° C. for 5 hours. The mixture was cooled and concentrated to remove acetonitrile. The residue was diluted with ethyl acetate (20 ml) and washed with water (15 mL×2), and brine (20 mL), dried over anhydrous sodium sulfate and concentrated. The crude product was purified by Pre-TLC (methanol/dichloromethane, 1/15 v/v) and Pre-HPLC to give Compound 49 as a white solid (25 mg, yield: 14%). MS (ESI): m/z: 558[M+H]⁺. ¹H NMR (400 MHz, CDCl3) δ: 7.34-7.16 (m, 4H), 7.09 (t, J=7.6 Hz, 1H), 6.78 (dd, J=6.8 Hz, J=2.8 Hz, 1H), 6.68 (brs, 1H), 6.41 (dd, J=8.8 Hz, J=2.8 Hz, 1H), 4.27 (m, 2H), 3.77 (s, 3H), 3.09 (d, J=11.2 Hz, 1H), 3.02 (s, 3H), 2.93 d, J=10.8 Hz, 1H), 2.88-2.84 (m, 1H), 2.82-2.80 (m, 3H), 2.69-2.64 (m, 1H), 2.55-2.43 (m, 4H), 2.13-2.01 (m, 2H), 2.00-1.97 (m, 1H), 1.86-1.83 (m, 2H), 1.68-1.64 (m, 2H), 1.00 (t, J=7.6 Hz, 6H).

Example 9C: Preparation of 2-(3-methoxy-1-(1-(3-(3-methoxyphenoxy)-4-methylpentyl)piperidin-4-yl)-2-oxoindolin-3-yl)-N-methylacetamide (Compound 50)

Scheme 16C.

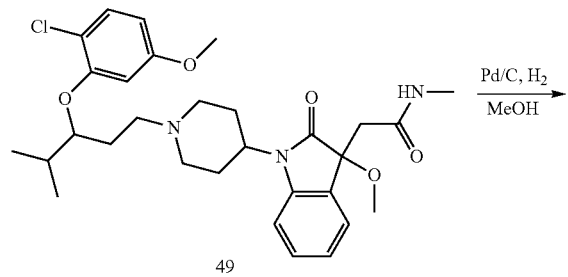

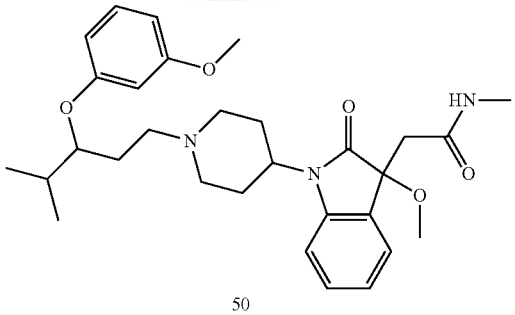

A mixture of 2-(1-(1-(3-(2-chloro-5-methoxyphenoxy)-4-methylpentyl)piperidin-4-yl)-3-methoxy-2-oxoindolin-3-yl)-N-methylacetamide (Compound 49, 18 mg, 0.03 mmol) and Palladium on activated carbon 10% Pd (dry, 3 mg, 0.03 mmol) in methanol (3 mL) was stirred under hydrogen at room temperature overnight. The mixture was filtrated and the filtrate was concentrated and purified by pre-HPLC to give 2-(3-methoxy-1-(1-(3-(3-methoxyphenoxy)-4-methylpentyl)piperidin-4-yl)-2-oxoindolin-3-yl)-N-methylacetamide (Compound 50, 15 mg, yield: 89%) as a pale yellow solid. MS (ESI): m/z: 524[M+H]⁺. ¹H NMR (400 MHz, CDCl₃) δ: 7.34-7.28 (m, 2H), 7.18-7.14 (m, 2H), 7.09 (t, J=7.6 Hz, 1H), 6.66 (brs, 1H), 6.57-6.55 (m, 2H), 6.49-6.47 (m, 1H), 4.25-4.17 (m, 2H), 3.78 (s, 3H), 3.09-3.05 (m, 1H), 3.01 (s, 3H), 2.97-2.95 (m, 1H), 2.87-2.81 (m, 4H), 2.69-2.64 (m, 1H), 2.48-2.41 (m, 4H), 2.11-1.98 (m, 3H), 1.81-1.80 (m, 2H), 1.72-1.65 (m, 2H), 0.97 (t, J=6.8 Hz, 6H).

Example 10A: Preparation of Compounds 3 and 59

Scheme 17.

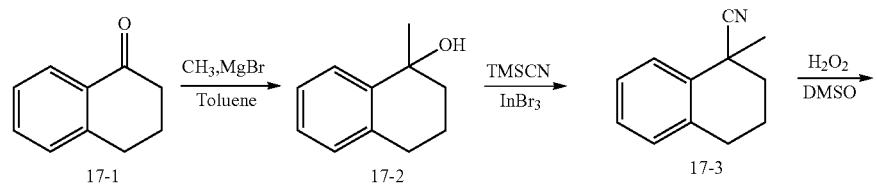

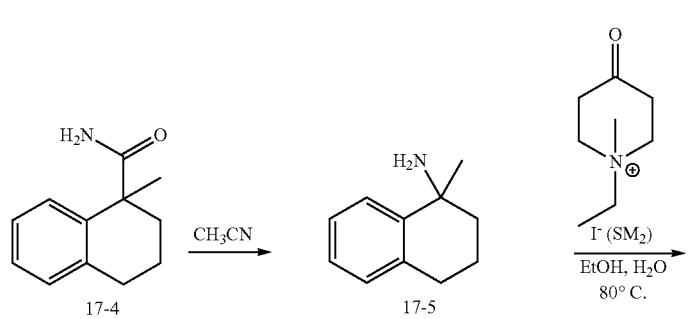

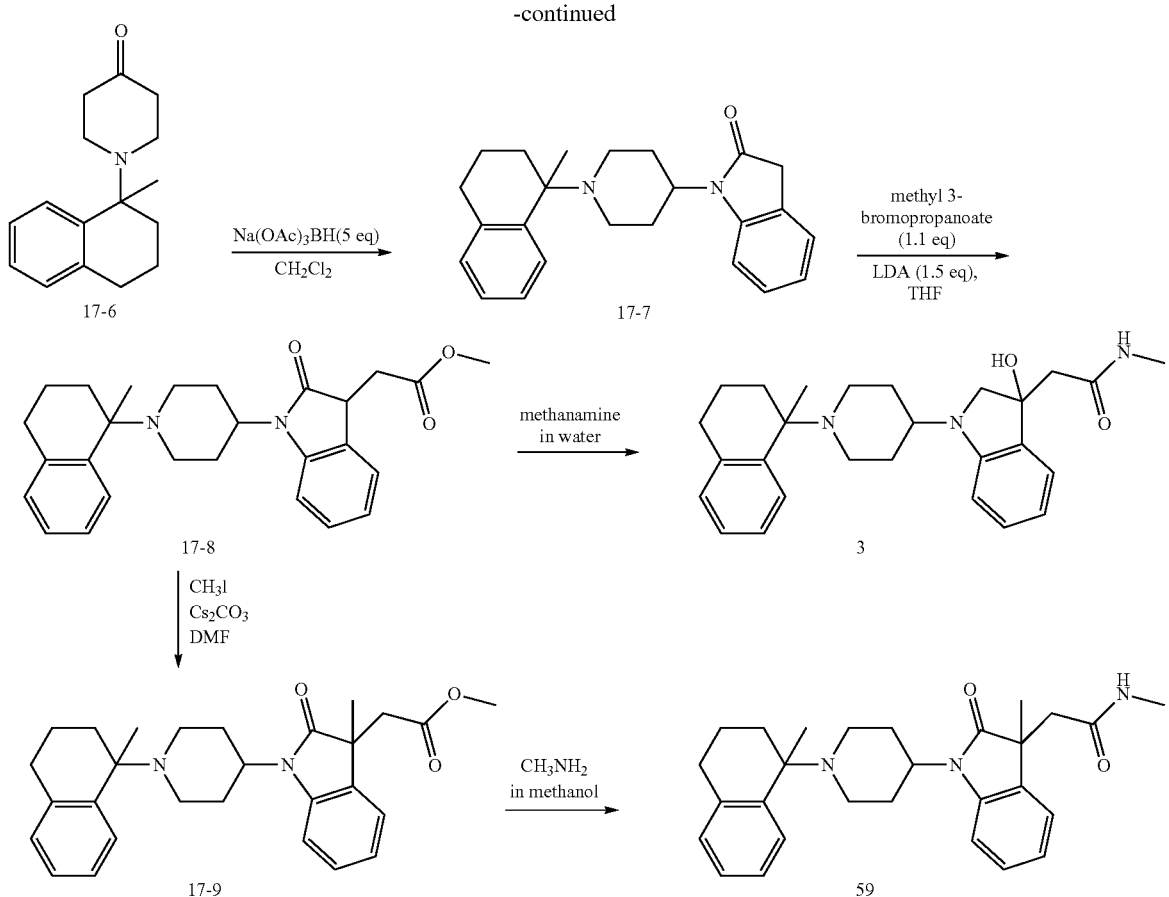

Synthesis of 1-methyl-1,2,3,4-tetrahydronaphthalen-1-ol (Compound 17-2)

A solution of 14.6 g (0.1 mol) of α-tetralone in anhydrous ether (200 ml) was added over 30 min to a solution of 60 mL (0.2 mol) of 3.0M methyl magnesium bromide in ether under nitrogen whilst stirring magnetically. After completion of the addition, the reaction was heated to reflux for 30 mins, allowed to cool, then quenched with 120 mL of saturated ammonium chloride solution. The ether layer was decanted from an off white solid, washed with water (400 mL), then with saturated sodium chloride solution, dried by sodium sulfate and evaporated in vacuo to get the crude product, the crude product was purified by recrystallization in ethyl acetate and petroleum ether to get Compound 17-2 (11 g white solid, yield 68%, purity: 99%, 214 nm). MS (ESI): m/z 145[M−OH]$^+$.

Synthesis of 1-methyl-1,2,3,4-tetrahydronaphthalene-1-carbonitrile (Compound 17-3)

To a 250 mL Schlenk tube equipped with a teflon-coated magnetic stirred bar were added InBr3 (1.77 g, 0.005 mol), dichloromethane (60 mL) and trimethylsilane carbonitrile (9.9 g, 0.1 mol) sequentially under argon atmosphere. Compound 17-2 (8.1 g, 0.05 mol) in dichloromethane (30 mL) was then introduced to the reaction system dropwise with a syringe. The mixture was stirred at room temperature for 30 mins. The resulting yellow solution was evaporated under vacuum and the residue was submitted to flash column chromatography separation on silica gel with petroleum ether/ethyl acetate (10:1) as eluent to afford Compound 17-3 (5.13 g, yield: 60%). MS (ESI): m/z 145 [M−CN]$^+$.

Synthesis of 1-methyl-1,2,3,4-tetrahydronaphthalene-1-carboxamide (Compound 17-4)

To a solution of Compound 17-3 (5 g, 29.2 mmol) and potassium carbonate (12.1 g, 88 mmol) dissolved in dimethyl sulfoxide (15 mL) was added hydrogen peroxide (292 mmol, 17 mL) at room temperature. The reaction mixture was stirred at ambient temperature for 2 h. After the reaction completed, the reaction mixture was partitioned between ethyl acetate (50 mL) and brine (40 mL). The aqueous layer was extracted with ethyl acetate (3×80 mL) and the combined organic phased were concentrated to give the crude product which can be purified by recrystallization in ethyl acetate and petroleum ether to get Compound 17-4 (3.5 g white solid, yield 64%, purity: 99%, 214 nm). MS (ESI): m/z 190[M+H]$^+$

Synthesis of 1-methyl-1,2,3,4-tetrahydronaphthalen-1-amine (Compound 17-5)

To a solution of Compound 17-4 (1.89 g, 10 mmol) in a mixture of acetonitrile and water (80 mL, 1:1) was added [Bis(trifluoroacetoxy)iodo]benzene (6.45 g, 15 mmol) in some portions at 0° C. Then the mixture was stirred at room temperature for overnight, and alkalized with saturated sodium bicarbonate solution. The aqueous layer was extracted with ethyl acetate (3×80 mL) and the combined organic phase was concentrated to give a black oil. The black oil was purified by flash chromatography to get Compound 17-5 (1.0 g, black oil, yield: 62%, purity: 90%, 214 nm). MS (ESI): m/z 145 [M−NH$_2$]$^+$ Synthesis of 1-(1-methyl-1,2,3,4-tetrahydronaphthalen-1-yl)piperidin-4-one (Compound 17-6)

To a mixture of Compound 17-5 (1 g, 6.2 mmol) and potassium carbonate (214 mg, 1.55 mmol) in ethanol (3 mL) was added 1-ethyl-1-methyl-4-oxopiperidin-1-ium iodide (4.1 g, 15.5 mmol) that was dissolved in water (2 mL) at 80° C. Then the mixture was stirred at 80° C. for 6 h, and the reaction was cooled to room temperature and extracted with ethyl acetate (3×80 mL). The combined organic phase was concentrated and purified by silica gel chromatography (eluted from petroleum ether to petroleum ether:ethyl acetate=10:1) to give Compound 17-6 (680 mg, yield: 45%) as a pale yellow oil. ESI MS (m/z): 262[M+H$_2$O+H]$^+$ Synthesis of 1-(1-(1-methyl-1,2,3,4-tetrahydronaphthalen-1-yl) piperidin-4-yl) indolin-2-one (Compound 17-7)

To a solution of Compound 17-6 (486 mg, 2 mmol) and methyl 2-(2-aminophenyl)acetate (996 mg, 6 mmol) in dichloromethane (20 mL) was added acetic acid (150.0 mg, 2.5 mmol). The mixture was stirred for 1.5 h at room temperature. Sodium triacetoxyborohydride (1.27 g, 6 mmol) was added into the mixture and stirred for 2 h at room temperature. Then the reaction mixture was heated to 30° C. and stirred overnight. The mixture was washed with sat. sodium carbonate (30 mL), brine (20 mL×2). The organic layer were dried over anhydrous sodium sulfate and evaporated in vacuum to afford the crude product. The crude product was purified by chromatography silica gel (ethyl acetate:petroleum ether=1:5 to 1:2) to obtain Compound 17-7 (500 mg, yield 69%) as a pale yellow solid. MS (ESI): m/z 361 [M+H]$^+$ Synthesis of methyl 2-(1-(1-(1-methyl-1,2,3,4-tetrahydronaphthalen-1-yl) piperidin-4-yl)-2-oxoindolin-3-yl)acetate (Compound 17-8)

To a solution of Compound 17-7 (180 mg, 0.5 mmol) in tetrahydrofuran (8 mL) was added lithium diisopropylamide (0.375 mL, 0.75 mmol) at −78° C. over 30 mins. A solution of methyl 2-bromoacetate (84.15 mg, 0.55 mmol) in 1 mL of tetrahydrofuran was added into the mixture at −78° C. The reaction mixture was stirred for 6 h at −78° C. Then sat. ammonium chloride (20 mL) was added slowly and stirred for 10 min at 0° C., sequentially EtOAc (30 mL) was added. The organic layer were separated and washed with solution of sat. Ammonium chloride (15 mL×2). The organic layer were dried over anhydrous sodium sulfate and evaporated in vacuum to afford crude Compound 17-8. Crude product was used for next step without further purification.

Preparation of Compound 3

The solution of Compound 17-8 (crude product from the previous step) in methylamine in water (28%-30%, 10 mL) was stirred at room temperature for overnight. After removed the solvent, the residue was purified by PREP-HPLC to get Compound 3 as white solid (10 mg, purity: 100%, yield 4.5% over the two step). ESI-MS (m/z): 448 [M+H]$^+$.

1H-NMR (400 MHZ, CDCl$_3$): δ 7.73-7.71 (d, J=7.2 Hz, 1H), 7.41-7.32 (m, 2H), 7.21-7.03 (m, 5H), 5.88 (brs, 1H), 5.63 (d, J=19.6 Hz, 1H) 4.17-4.16 (m, 1H), 3.35-3.34 (m, 1H) 2.89-2.87 (m, 3H) 2.77-2.71 (m, 3H) 2.64-2.62 (m, 1H), 2.50-2.38 (m, 3H), 2.27-2.20 (m, 2H), 2.02-1.91 (m, 2H), 1.79-1.78 (m, 2H) 1.65-1.58 (m, 1H) 1.52-1.42 (m, 1H), 1.26 (s, 3H)

Synthesis of methyl 2-(3-methyl-1-(1-(1-methyl-1,2,3,4-tetrahydronaphthalen-1-yl)piperidin-4-yl)-2-oxoindolin-3-yl)acetate (Compound 17-9)

A mixture of Compound 17-8 (216 mg, purity: 55%), cesium carbonate (489 mg, 1.5 mmol) and iodomethane (213 mg, 1.5 mmol) was stirred at R.T. for 3 h. Upon the completion, the mixture was purified by PREP-TLC (petroleum ether:ethyl acetate=1:5) to get Compound 17-9 (60 mg, yield: 54%, purity: 214 nm 93%) as a white solid. MS (ESI): m/z 447[M+1]$^+$ Preparation of Compound 59

The solution of Compound 17-9 (60 mg, 0.13 mmol) in methylamine methanol (5 mL) was stirred at 90° C. in microwave for 2 hrs. After removed the solvent, the residue was purified by PREP-HPLC to get Compound 59 as white solid (11 mg, purity 100%, yield 18%).

ESIMS (m/z): 446 [M+H]$^+$. 1H-NMR (400 MHZ, CDCl$_3$): δ 7.77-7.75 (m, 1H), 7.32-7.28 (m, 2H), 7.22-7.18 (m, 2H), 7.14-7.04 (m, 3H), 6.30 (brs, 1H), 4.25-4.18 (m, 1H), 3.38 (d, J=10 Hz, 1H) 2.83-2.74 (m, 3H) 2.72-2.58 (m, 5H) 2.52-2.39 (m, 2H), 2.36-2.27 (m, 2H), 2.14-2.09 (m, 2H), 1.89-1.79 (m, 2H), 1.75-1.56 (m, 2H), 1.50-1.40 (m, 6H).

Example 10B: Preparation of Compound 4

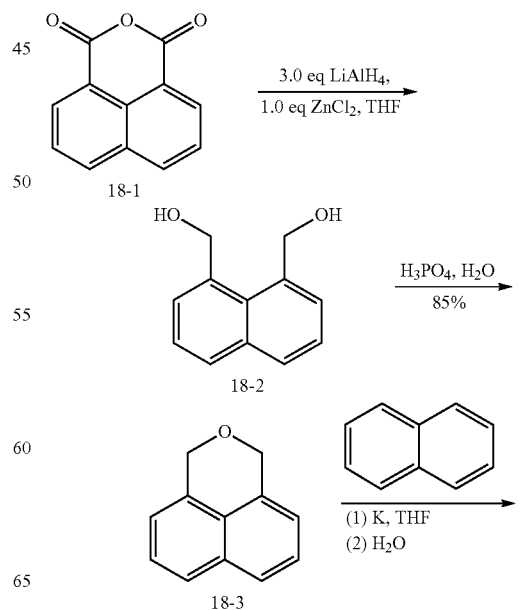

Scheme 18.

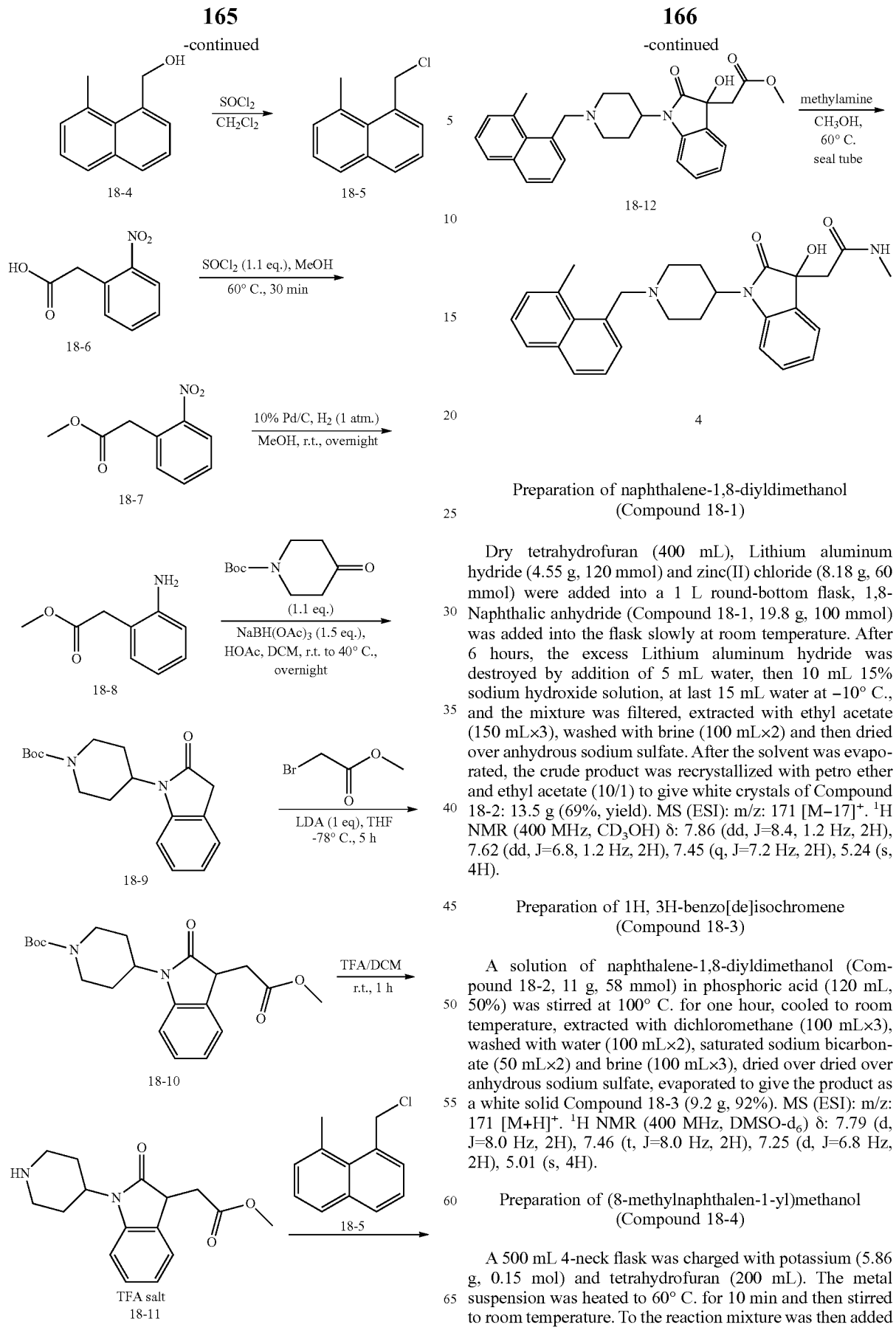

Preparation of naphthalene-1,8-diyldimethanol (Compound 18-1)

Dry tetrahydrofuran (400 mL), Lithium aluminum hydride (4.55 g, 120 mmol) and zinc(II) chloride (8.18 g, 60 mmol) were added into a 1 L round-bottom flask, 1,8-Naphthalic anhydride (Compound 18-1, 19.8 g, 100 mmol) was added into the flask slowly at room temperature. After 6 hours, the excess Lithium aluminum hydride was destroyed by addition of 5 mL water, then 10 mL 15% sodium hydroxide solution, at last 15 mL water at −10° C., and the mixture was filtered, extracted with ethyl acetate (150 mL×3), washed with brine (100 mL×2) and then dried over anhydrous sodium sulfate. After the solvent was evaporated, the crude product was recrystallized with petro ether and ethyl acetate (10/1) to give white crystals of Compound 18-2: 13.5 g (69%, yield). MS (ESI): m/z: 171 [M−17]$^+$. $^1$H NMR (400 MHz, CD$_3$OH) δ: 7.86 (dd, J=8.4, 1.2 Hz, 2H), 7.62 (dd, J=6.8, 1.2 Hz, 2H), 7.45 (q, J=7.2 Hz, 2H), 5.24 (s, 4H).

Preparation of 1H, 3H-benzo[de]isochromene (Compound 18-3)

A solution of naphthalene-1,8-diyldimethanol (Compound 18-2, 11 g, 58 mmol) in phosphoric acid (120 mL, 50%) was stirred at 100° C. for one hour, cooled to room temperature, extracted with dichloromethane (100 mL×3), washed with water (100 mL×2), saturated sodium bicarbonate (50 mL×2) and brine (100 mL×3), dried over dried over anhydrous sodium sulfate, evaporated to give the product as a white solid Compound 18-3 (9.2 g, 92%). MS (ESI): m/z: 171 [M+H]$^+$. $^1$H NMR (400 MHz, DMSO-d$_6$) δ: 7.79 (d, J=8.0 Hz, 2H), 7.46 (t, J=8.0 Hz, 2H), 7.25 (d, J=6.8 Hz, 2H), 5.01 (s, 4H).

Preparation of (8-methylnaphthalen-1-yl)methanol (Compound 18-4)

A 500 mL 4-neck flask was charged with potassium (5.86 g, 0.15 mol) and tetrahydrofuran (200 mL). The metal suspension was heated to 60° C. for 10 min and then stirred to room temperature. To the reaction mixture was then added naphthalene (0.4 g, 3 mmol), the suspension was stirred at room temperature for 10 min and then cooled to −20° C. to afford a blue suspension. A solution of 1H, 3H-benzo[de]isochromene (Compound 18-3, 5.1 g, 30 mmol) in tetrahydrofuran (100 mL) was slowly added via the addition funnel, with addition controlled so that the reaction mixture did not exceed −15° C. After stirred for 5 hours at −15° C., the suspension was removed from the cooling bath, warmed with stirring to 0° C., and then allowed to stand without stirring. The solution was decanted and the residual potassium was carefully decomposed with isopropyl alcohol. The decanted solution was carefully treated with water (10 mL). The mixture was extracted with ethyl acetate (100 mL×3), washed with brine (100 mL×2) and dried over anhydrous sodium sulfate, evaporated to give the crude product which was purified on silica gel (ethyl acetate in petro ether, 10% v/v) to give the product as a white solid Compound 18-4 (3 g, 58%). MS (ESI): none, $^1$H NMR (400 MHz, DMSO-d$_6$) δ: 7.81 (dd, J=8.0 Hz, J=1.2 Hz, 1H), 7.75 (dd, J=7.6 Hz, J=1.6 Hz, 1H), 7.59 (d, J=6.8 Hz, 1H), 7.42 (t, J=7.6 Hz, 1H), 7.37-7.31 (m, 2H), 5.28 (t, J=5.6 Hz, 1H), 5.05 (d, J=5.6 Hz, 2H), 2.94 (s, 3H).

Preparation of 1-(chloromethyl)-8-methylnaphthalene (Compound 18-5)

To a solution of compound (8-methylnaphthalen-1-yl)methanol (Compound 18-4, 52 mg, 0.3 mmol) in dichloromethane (2 mL) was added sulfurous dichloride (72 mg, 0.6 mmol) dropwise at 0° C. The reaction mixture was stirred at 0° C. for 1 hr. The mixture was evaporated at 10° C. The crude Compound 18-5 was used without further purification.

Preparation of methyl 2-(2-nitrophenyl)acetate (Compound 18-7)

To a solution of 2-(2-nitrophenyl)acetic acid (Compound 18-6, 18.1 g, 100 mmol) in methanol (150 ml) at room temperature was added sulfurous dichloride (SOCl$_2$, 13.1 g, 110 mmol) dropwise. The mixture was heated to 60° C. and stirred for 30 minutes. The reaction mixture was concentrated to give a pale yellow oil, diluted with ethyl acetate (200 mL), washed with NaHCO$_3$ (sat. aq., 150 mL×3), brine (100 mL×2), dried over anhydrous sodium sulfate, concentrated to give the desired product methyl 2-(2-nitrophenyl)acetate (Compound 18-7, 19.1 g, yield: 98%) as a pale yellow oil. MS (ESI): m/z: 196[M+H]$^+$. $^1$H NMR (400 MHz, CDCl$_3$) δ: 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 1H).

Preparation of methyl 2-(2-aminophenyl)acetate (Compound 18-8)

A mixture of methyl 2-(2-nitrophenyl)acetate (Compound 18-7, 9.75 g, 50 mmol), 10% Pd/C (dry, 530 mg, 5 mmol) in methanol (100 ml) was stirred under H$_2$ (1 atm.) at room temperature overnight. The reaction mixture was filtered to remove Pd/C and the filtrate was concentrated to give the desired product methyl 2-(2-aminophenyl)acetate (Compound 18-8, 8.02 g, yield: 97%) as a pale yellow oil. MS (ESI): m/z: 166[M+H]$^+$. $^1$H NMR (400 MHz, DMSO-d6) δ: 6.94 (m, 2H), 6.64 (d, 1H, J=8.0 Hz), 6.51 (m, 1H), 4.88 (s, 2H), 3.59 (s, 3H), 3.52 (s, 2H).

Preparation of tert-butyl 4-(2-oxoindolin-1-yl)piperidine-1-carboxylate (Compound 18-9)

A mixture of methyl 2-(2-aminophenyl)acetate (Compound 18-8, 3.30 g, 20 mmol), tert-butyl 4-oxopiperidine-1-carboxylate (4.38 g, 22 mmol), acetic acid (HOAc, 600 mg, 10 mmol) in dichloromethane (80 ml) was stirred at room temperature for 2 h, then sodium triacetoxyborohydride (6.36 g, 30 mmol) was added in portions and heated to 40° C., stirred overnight. The reaction mixture was cooled to room temperature and diluted with dichloromethane (200 ml), washed with water (200 mL×2) and sodium bicarbonate (sat. aq., 200 mL×2), dried over anhydrous sodium sulfate, concentrated to give the crude product, purified by flash column chromatography on silica gel (ethyl acetate in petroleum ether, 1/20-1/15-1/10 v/v) to give the desired product tert-butyl 4-(2-oxoindolin-1-yl)piperidine-1-carboxylate (Compound 18-9, 2.65 g, yield: 42%) as a pale yellow solid. MS (ESI): m/z: 261[M+H−56]$^+$. $^1$H NMR (400 MHz, CDCl$_3$) δ: 7.24 (m, 2H), 7.01 (m, 2H), 4.41 (m, 1H), 4.28 (brs, 2H), 3.53 (s, 2H), 2.83 (brs, 2H), 2.32 (m, 2H), 1.70 (m, 2H), 1.50 (s, 9H).

Preparation of tert-butyl 4-(3-(2-methoxy-2-oxoethyl)-2-oxoindolin-1-yl)piperidine-1-carboxylate (Compound 18-10)

A solution of tert-butyl 4-(2-oxoindolin-1-yl)piperidine-1-carboxylate (Compound 18-9, 3.16 g, 10 mmol) in dry tetrahydrofuran (100 ml) was cooled to −78° C. by dry ice-acetone bath and lithium diisopropylamide (2 M in tetrahydrofuran, 5 mL, 10 mmol) was added dropwise over 10 minutes, stirred for 1 hour at −78° C. A solution of methyl 2-bromoacetate (1.53 g, 10 mmol) in dry tetrahydrofuran (10 mL) was added dropwise over 5 minutes. The reaction mixture was stirred for 4 hours at −78° C., quenched with ammonium chloride (sat. aq., 10 mL) at −78° C., and added acetic acid (1 mL) to make the reaction mixture neutral (pH=7), extracted with ethyl acetate (150 mL×3), combined organic layer was washed with brine (300 mL×2), dried over anhydrous sodium sulfate, concentrated to give the crude product, purified by flash column chromatography on silica gel (ethyl acetate in petroleum ether, 1/15-1/10, v/v) to give the desired product tert-butyl 4-(3-(2-methoxy-2-oxoethyl)-2-oxoindolin-1-yl)piperidine-1-carboxylate (Compound 18-10, 1.98 g, yield: 51%) as a pale yellow solid. MS (ESI): m/z: 333[M+H−56]$^+$. $^1$H NMR (400 MHz, CDCl$_3$) δ: 7.24 (m, 2H), 7.01 (m, 2H), 4.39 (m, 1H), 4.30 (d, 2H, J=12.8 Hz), 3.73 (m, 1H), 3.65 (s, 3H), 3.06 (dd, 1H, J=4.4, 12.8 Hz), 2.84 (m, 3H), 2.34 (m, 2H), 1.73 (d, 2H, J=12.8 Hz), 1.50 (s, 9H).

Preparation of methyl 2-(2-oxo-1-(piperidin-4-yl)indolin-3-yl)acetate TFA salt (Compound 18-11)

Trifluoroacetic acid (5.70 g, 50 mmol) was added to a solution of tert-butyl 4-(3-(2-methoxy-2-oxoethyl)-2-oxoindolin-1-yl)piperidine-1-carboxylate (Compound 18-10, 3.88 g, 10 mmol) in dry dichloromethane (100 ml), the mixture was stirred for 1 hour at room temperature and concentrated to remove solvent to give crude desired product methyl 2-(2-oxo-1-(piperidin-4-yl)indolin-3-yl)acetate TFA salt (Compound 18-11, 3.90 g, yield: 97%) as a pale yellow syrup. MS (ESI): m/z: 289[M+H]$^+$.

Preparation of methyl 2-(3-hydroxy-1-(1-((8-methylnaphthalen-1-yl)methyl)piperidin-4-yl)-2-oxoindolin-3-yl)acetate (Compound 18-12)

To a solution of compound methyl 2-(2-oxo-1-(piperidin-4-yl)indolin-3-yl)acetate of 2,2,2-trifluoroacetic acid salt (Compound 18-11, 80 mg, 0.2 mmol) in N,N-dimethylformamide (3 mL) was added triethylamine (91 mg, 0.9 mmol) carefully. The mixture was stirred at room temperature for 10 min. Then to the mixture was added sodium iodide (5 mg, 0.03 mmol) and a solution of 1-(chloromethyl)-8-methylnaphthalene (Compound 18-5, 58 mg, crude). The reaction mixture was stirred at room temperature for overnight. The mixture was poured into ice-water, extracted with dichloromethane (10 mL×3), washed with brine (20 mL×3), dried and concentrated to give the crude product which was purified by TLC. (16 mg, yield 12%, as a white solid) MS (ESI): m/z: 459[M+H]$^+$.

Preparation of 2-(3-hydroxy-1-(1-((8-methylnaphthalen-1-yl)methyl)piperidin-4-yl)-2-oxoindolin-3-yl)-N-methylacetamide (Compound 4)

A solution of methyl 2-(3-hydroxy-1-(1-((8-methylnaphthalen-1-yl)methyl)piperidin-4-yl)-2-oxoindolin-3-yl)acetate (Compound 18-12, 16 mg, 0.1 mmol) in methylamine/ethanol (2 mL, 35%) was heated to 80 degrees in a sealed tube and stirred for 2 hours. The mixture was concentrated in vacuum. The crude product was purified by TLC to give the product 2-(3-hydroxy-1-(1-((8-methylnaphthalen-1-yl)methyl)piperidin-4-yl)-2-oxoindolin-3-yl)-N-methylacetamide (Compound 4, 7 mg, 44%) as a pale yellow solid. MS: m/z 458 [M+l]$^+$, $^1$H NMR (400 MHz, CDCl$_3$) δ: 7.79 (dd, J=2.0 Hz, J=7.2 Hz, 1H), 7.72 (t, J=4.4 Hz, 1H), 7.37-7.33 (m, 5H), 7.23 (dd, J=0.8 Hz, J=7.6 Hz, 1H), 7.00-7.04 (m, 2H), 5.92 (q, J=4.6 Hz, 1H), 5.63 (br s, 1H), 4.27-4.19 (m, 1H), 3.99 (q, J=13.6 Hz, 2H), 3.12 (s, 3H), 3.02 (d, J=10.2 Hz, 2H), 2.84 (d, J=4.9 Hz, 3H), 2.70 (d, J=14.6 Hz, 1H), 2.47 (d, J=14.9 Hz, 1H), 2.26-2.42 (m, 2H), 2.07-2.22 (m, 2H), 1.59-1.70 (m, 2H).

Example 11A: Preparation of Compounds 19-11 and 56

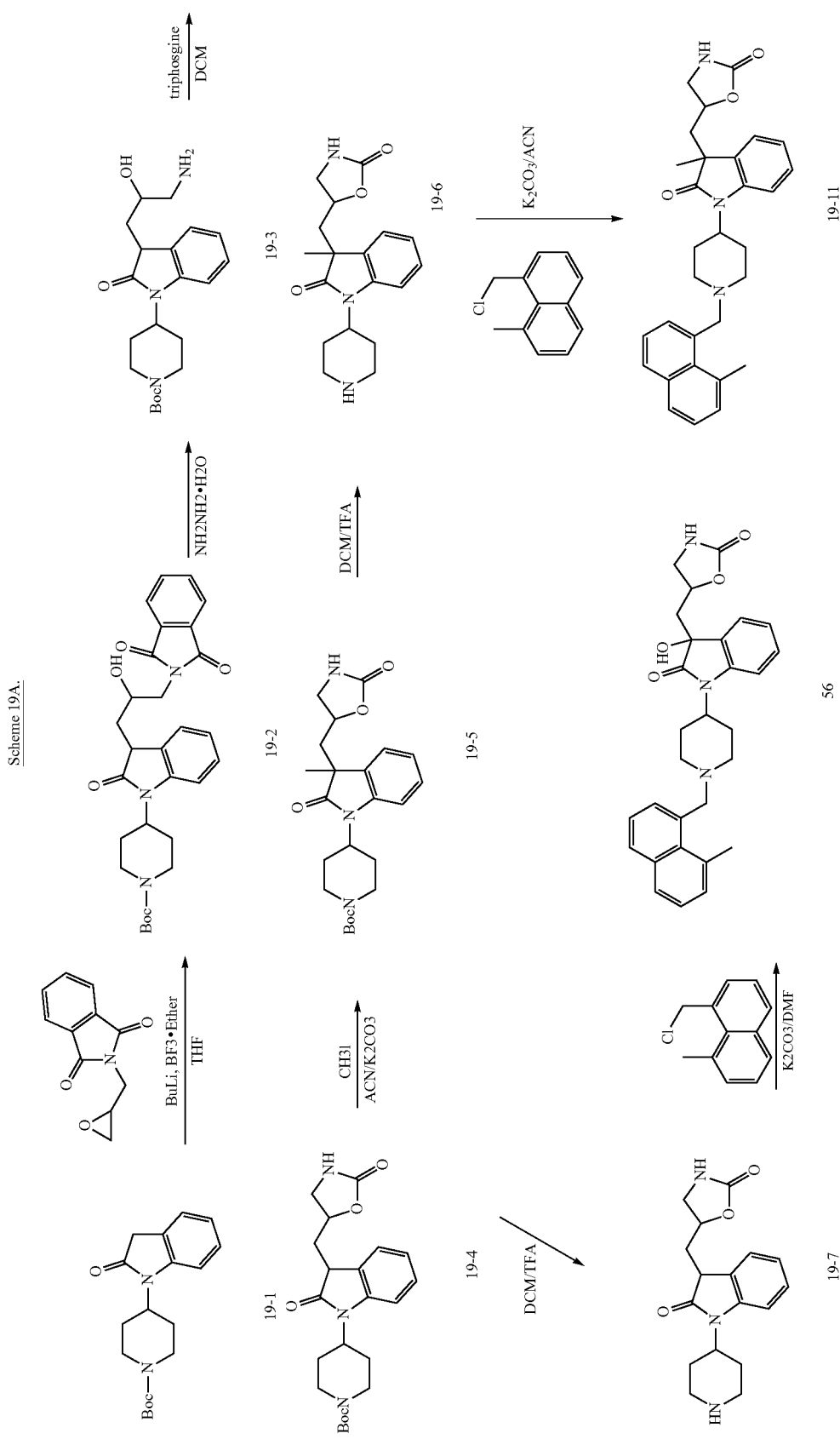
Scheme 19A.

Preparation of Compound 19-2

Compound 19-1 (1.58 g, 5 mmol, 1.0 eq) was dissolved in THF (5 mL) and the system was cooled to −78° C. Then BuLi (2.5 M in hexane, 3 mL, 7.5 mmol) was dropped and the mixture was stirred for 10 min followed with addition of $BF_3 \cdot Et_2O$ (1.06 g, 7.5 mmol). The mixture was stirred for 15 min, then 2-(oxiran-2-ylmethyl)isoindoline-1,3-dione (1.02 g, 5.00 mmol) solution in THF (5 mL) was dropped within 5 min. Then the mixture was stirred at −78° C. for another 2 h and allowed to warm to room temperature overnight. The reaction was quenched with aq. NH4Cl and extracted with ethyl acetate for three times (20 mL×3). The combined organic layers were dried with Na2SO4. After filtered and condensed, the residue was purified with silicon column (200-300 m, petrol:ethyl ester=2:1, Rf=0.2). Compound 19-2 (600 mg, 23%) was obtained as solid. ESI/MS: 420 (M−100+1).

Preparation of Compound 19-3

Compound 19-2 (0.60 g, 1.15 mmol) was dissolved in ethanol (5 mL) and hydrazine (85%, 1.0 mL) was charged, the mixture was stirred at room temperature for 2 h, monitored by LCMS. The reaction was purified with reverse phase column (TFA 0.1%, acetonitrile:$H_2O$=1:4) and Compound 19-3 (400 mg, 88%) was obtained as solid after lyophilized. ESI/MS: 390 (M+1).

Preparation of Compound 19-4

Compound 19-3 (0.40 g, 1.03 mmol) was dissolved in DCM (5 mL) and TEA (0.31 g, 3.09 mL) was charged. The system was cooled to 0° C. and triphosgene (101 mg, 0.34 mmol) was charged. The mixture was stirred for 2 h, monitored by LCMS and 19-3 disappeared. The reaction was quenched with NaHCO3 solution and extracted with DCM. After condensed and the residue was purified with reverse phase column (TFA 0.1%, acetonitrile:$H_2O$=1:3) and Compound 19-4 (200 mg, 47%) was obtained as solid after lyophilized. ESI/MS: 316 (M−100+1).

Preparation of Compound 19-5

A mixture of Compound 19-4 (0.10 g, 0.24 mmol, 1.0 equiv.), $K_2CO_3$ (0.066 g, 0.48 mmol) and acetonitrile (5 mL) was stirred at room temperature, then $CH_3I$ (0.07 g, 0.48 mmol) was charged. The mixture was stirred at RT for 12 h. Then LCMS indicated that it was completed. The solution was quenched with water and extracted with ethyl acetate (10 mL×3). The combined organic layer was washed with water and dried with anhydrous $Na_2SO_4$. After condensed, the crude Compound 19-5 (80 mg, 77%) was obtained and used for next without further purification. ESI/MS: 330 (M−100+1).

Preparation of Compound 19-6

A mixture of Compound 19-5 (80.0 mg, 0.18 mmol, 1.0 equiv.), TFA (0.5 mL) and DCM (3.0 mL) was stirred at room temperature for 2 h. Then LCMS indicated that it is completed. The solution was quenched with aq. $NaHCO_3$ and extracted with ethyl acetate (10 mL×3). The combined organic layer was washed with water and dried with anhydrous $Na_2SO_4$. After concentrated, the crude Compound 19-6 (40 mg, 66%) was obtained and used for next step without further purification. ESI/MS: 330 (M+1).

Preparation of Compound 19-11

A solution of Compound 19-6 (40.00 mg, 0.12 mmol, 1.0 equiv.) in acetonitrile (5 mL) was mixed with $K_2CO_3$ (42.0 mg) and stirred at room temperature for 12 h. Then LCMS indicated that the reaction was completed. Quenched with water and extracted with ethyl acetate (10 mL×3), the combined organic layers were dried with $Na_2SO_4$. After filtered and condensed, the residue was purified with reverse phase column (TFA 0.1%, Acetonitrile:$H_2O$=1:3), and Compound 19-11 (15 mg, 26%) was obtained. ESI/MS: 484 (M+1). 1H NMR (400 MHz, MEOD): 8.12 (m, 1H), 7.91 (m, 1H), 7.75 (m, 1H), 7.49-7.60 (m, 3H), 7.21-7.34 (m, 2H), 7.12-7.19 (m, 2H), 5.06 (s, 2H), 4.52-4.88 (m, 2H), 3.61-3.64 (m, 2H), 3.29-3.40 (m, 3H), 3.10-3.15 (m, 1H), 2.99 (s, 3H), 2.71-2.78 (m, 2H), 2.05-2.40 (m, H), 1.80-1.85 (m, 3H).

Preparation of Compound 19-7

A mixture of Compound 19-4 (100 mg, 0.24 mmol, 1.0 equiv.), TFA (0.5 mL) and DCM (3.0 mL) was stirred at room temperature for 2 h. Then LCMS indicated that it was completed. The solution was quenched with $NaHCO_3$ solution and extracted with ethyl acetate (10 mL×3), The combined organic layer was washed with water and dried with anhydrous $Na_2SO_4$. After condensed, the crude (60 mg, 79%) was obtained and used for next step without further purification. ESI/MS: 316 (M+1).

Preparation of Compound 56

A solution of Compound 19-7 (31.5 mg, 0.10 mmol, 1.0 equiv.) and 1-(chloromethyl)-8-methylnaphthalene (18.8 mg, 0.10 mmol) in DMF (3 mL) were mixed with $K_2CO_3$ (13.8 mg, 0.10 mmol) and stirred at room temperature for 12 h. Then LCMS indicated that the reaction was completed. Quenched with water and extracted with ethyl acetate (10 mL×3), the combined organic layers were dried with $Na_2SO_4$. After filtered and condensed, the residue was purified with reverse phase column (TFA 0.1%, Acetonitrile: $H_2O$=3:10), and Compound 56 (8.0 mg, 16%) was obtained. ESI/MS: 486 (M+1). $^1$H NMR (400 MHz, MEOD): 7.99-8.01 (m, 1H), 7.76-7.78 (m, 1H), 7.62-7.63 (m, 1H), 7.41-7.49 (m, 1H), 7.36-7.39 (m, 2H), 7.22-7.32 (m, 2H), 7.01-7.06 (m, 2H), 4.97 (s, 2H), 4.31-4.35 (m, 1H), 3.96-3.98 (m, 1H), 3.42-3.53 (m, 3H), 3.32-3.39 (m, 2H), 3.02-3.06 (m, 1H), 2.87 (s, 3H), 2.59-2.68 (m, 2H), 2.17-2.43 (m, 2H), 1.87-2.03 (m, 2H).

Example 11B: Preparation of Compounds 12 and 13

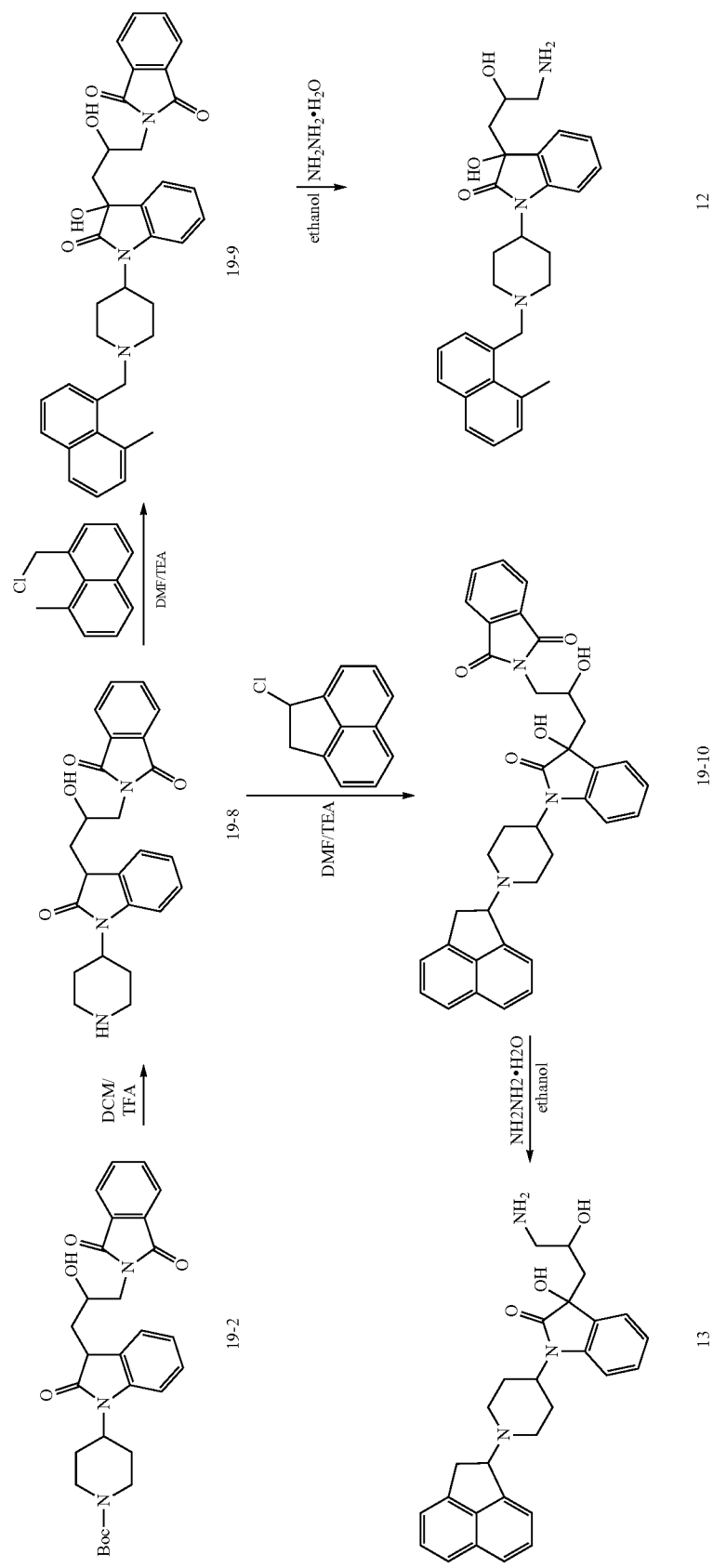

Preparation of Compound 19-8

A mixture of Compound 19-2 (620 mg, 1.19 mmol, 1.0 equiv.), TFA (1.0 mL) and DCM (5.0 mL) was stirred at room temperature for 2 h. Then LCMS indicated that it was completed. The solution was quenched with NaHCO₃ solution and extracted with ethyl acetate (50 mL×3). The combined organic layer was washed with water and dried with anhydrous $Na_2SO_4$. After condensed, the crude Compound 19-8 (387 mg, 77%) was obtained and used for next without further purification. ESI/MS: 420 (M+1).

Preparation of Compound 19-9

A solution of Compound 19-8 (100 mg, 0.24 mmol, 1.0 equiv.) and 1-(chloromethyl)-8-methylnaphthalene (45 mg, 0.24 mmol) in DMF (3 mL) were mixed with TEA (101 mg, 1.00 mmol) and stirred at room temperature for 12 h. Then LCMS indicated that the reaction was completed. The reaction solution was purified with reverse phase column (TFA 0.1%, Acetonitrile:H₂O=1:3) and Compound 19-9 (30 mg, 21%) was obtained. ESI/MS: 590 (M+1).

Preparation of Compound 12

Compound 19-9 (30.0 mg, 0.05 mmol) was dissolved in ethanol (2 mL) and hydrazine (85%, 0.5 mL) was charged. The mixture was stirred at room temperature for 2 h, monitored by LCMS. The reaction was completed. The reaction was purified with reverse phase column (TFA 0.1%, acetonitrile:H₂O=3:10) and Compound 12 (12 mg, 52%) was obtained as solid after lyophilized. ESI/MS: 460 (M+1). 1H NMR (400 MHz, MEOD, δ): 8.05-8.09 (m, 1H), 7.85-7.87 (m, 1H), 7.72-7.74 (m, 1H), 7.50-7.57 (m, 1H), 7.41-7.49 (m, 2H), 7.33-7.39 (m, 1H), 7.29-7.31 (m, 1H), 7.08-7.18 (m, 2H), 5.08 (s, 2H), 4.35-4.46 (m, 1H), 3.58-3.60 (m, 2H), 3.34-3.37 (m, 2H), 2.93-3.12 (m, 1H), 2.97 (s, 3H), 2.66-2.79 (m, 3H), 2.16-2.20 (m, 1H), 1.87-2.07 (m, 3H), 1.25-1.27 (m, 1H).

Preparation of Compound 19-10

A solution of Compound 19-8 (100 mg, 0.24 mmol, 1.0 equiv.) and 1-chloro-1,2-dihydroacenaphthylene (135 mg, 0.72 mmol) in DMF (3 mL) were mixed with TEA (101 mg, 1.00 mmol) and stirred at room temperature for 12 h. Then LCMS indicated that the reaction was completed. The reaction solution was purified with reverse phase column (TFA 0.1%, Acetonitrile:H₂O=1:3) and Compound 19-10 (36 mg, 25%) was obtained. ESI/MS: 588 (M+1).

Preparation of Compound 13

Compound 19-10 (36.0 mg, 0.06 mmol) was dissolved in ethanol (2 mL) and hydrazine (85%, 0.5 mL) was charged, the mixture was stirred at room temperature for 2 h, monitored by LCMS and the reaction was completed. The reaction was purified with reverse phase column (TFA 0.1%, acetonitrile:H₂O=3:10) and Compound 13 (11 mg, 40%) was obtained as a solid after lyophilization. ESI/MS: 458 (M+1). 1H NMR (400 MHz, MEOD): 7.94-7.96 (m, 1H), 7.87-7.89 (m, 1H), 7.76-7.78 (m, 1H), 7.67-7.71 (m, 1H), 7.57-7.61 (m, 1H), 7.48-7.49 (m, 1H), 7.39-7.43 (m, 1H), 7.32-7.35 (m, 1H), 7.23-7.26 (m, 1H), 7.09-7.14 (m, 1H), 5.59-5.60 (m, 1H), 4.39-4.81 (m, 1H), 3.87 (m, 2H), 3.30-3.43 (m, 1H), 3.24-3.28 (m, 1H), 3.11-3.13 (m, 1H), 3.05-3.08 (m, 1H), 2.93-2.97 (m, 2H), 2.71-2.87 (m, 3H), 2.17-2.23 (m, 1H), 1.87-2.08 (m, 3H), 1.25-1.26 (m, 1H).

Compound 13 was purified by chiral HPLC to yield Compound 179 and Compound 180.

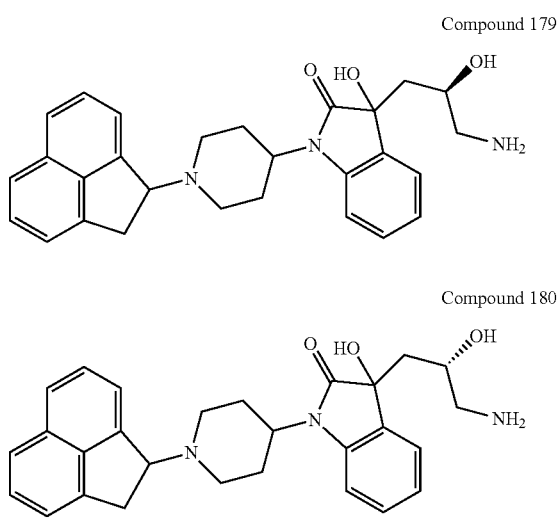

Compound 179

Compound 180

Example 12A: Preparation of Compound 8

Scheme 20.

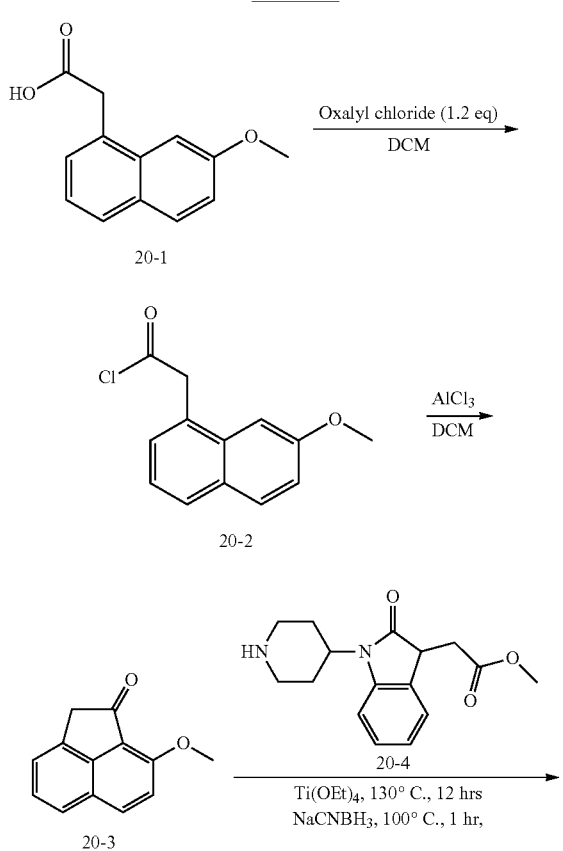

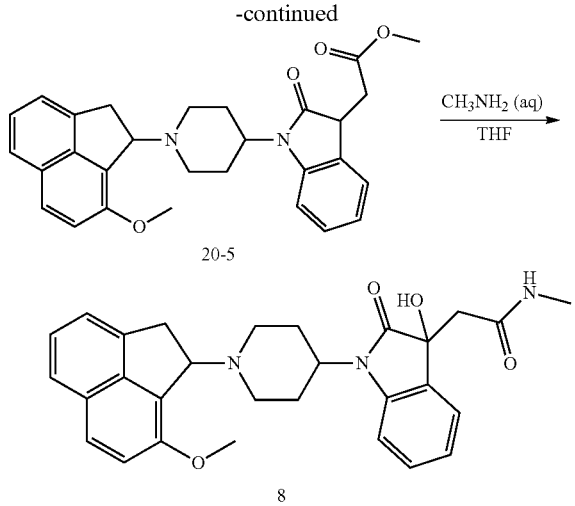

Preparation of 8-methoxyacenaphthylen-1(2H)-one (Compound 20-3)

A solution of 2-(7-methoxynaphthalen-1-yl)acetic acid (Compound 20-1) (1 g, 4.63 mmol) in dichloromethane (20 mL) at 0° C. was added oxalyl chloride (700 mg, 5.56 mmol) dropwise. The mixture was stirred at 0° C. for 0.5 h, Then crashed aluminum chloride (1.35 g, 10 mmol) was added at 0° C. in 15 minutes. The dark mixture was stirred at 0° C. to room temperature for 2 hours. The mixture was poured into ice-water (20 mL). The mixture was extracted with dichloromethane (30 mL×3). The combined organic layer was washed with brine (20 mL) and dried over sodium sulfate, filtered. The filtration was concentrated in vacuum to give the crude product as a pale yellow solid. The crude product was purified by chromatography to give Compound 20-3 as a white solid (800 mg, 87%, petrol ether/ethyl acetate=100/1-50/1). MS m/z 199[M+1]$^+$. $^1$H NMR (400 MHz, CDCl$_3$) δ 8.09-8.07 (d, J=8.8 Hz 1H), 7.75-7.31 (d, J=8.0 Hz 1H), 7.47-7.41 (m, 2H), 7.36-7.34 (d, J=8.8 Hz 1H), 4.15 (s, 3H), 3.80 (s, 2H).

Preparation of methyl 2-(1-(1-(8-methoxy-1,2-dihydroacenaphthylen-1-yl)piperidin-4-yl)-2-oxoindolin-3-yl)acetate (Compound 20-5)

To a sealed tube containing 8-methoxyacenaphthylen-1(2H)-one (Compound 20-3) (200 mg, 1.01 mmol), methyl 2-(2-oxo-1-(piperidin-4-yl)indolin-3-yl)acetate (Compound 20-4) (291 mg, 1.01 mmol) in tetrahydrofuran (5 mL) was added Titanium ethoxide (1.14 g, 5 mmol). The mixture was heated to 130° C. for 8 h under microwave conditions, then sodium cyanoborohydride (372 mg, 6 mmol) was added to the mixture and continued to heat to 100° C. for 1 hour under microwave conditions, The mixture was quenched with water (5 mL) and extracted with ethyl acetate (5 mL×3), the combined organic layer was washed with brine, dried over sodium sulfate, filtered and concentrated. The crude product was purified by column chromatography (dichloromethane: methanol=20:1) to give the target compound (80 mg, 17%) as a white solid. (ESI): m/z 471.1 [M+H]$^+$.

Preparation of 2-(3-hydroxy-1-(1-(8-methoxy-1,2-dihydroacenaphthylen-1-yl)piperidin-4-yl)-2-oxoindolin-3-yl)-N-methylacetamide (Compound 8)

To a solution of methyl 2-(1-(1-(8-methoxy-1,2-dihydroacenaphthylen-1-yl) piperidin-4-yl)-2-oxoindolin-3-yl) acetate (Compound 20-5) (30 mg, 0.06 mmol) in tetrahydrofuran (THF, 1 mL) was added methylamine (40% w/w aqueous solution, 1 mL). The mixture was stirred overnight at room temperature and purified by reversed phase chromatography to give the desired product 2-(3-hydroxy-1-(1-(8-methoxy-1,2-dihydroacenaphthylen-1-yl)piperidin-4-yl)-2-oxoindolin-3-yl)-N-methylacetamide (Compound 8) (10 mg, 34%) as a white solid. MS(ESI) m/z: 470[M+H]$^+$, 1H NMR (400 MHz, CDCl3) δ: 7.74-7.72 (d, J=8.8 Hz, 1H), 7.59-7.57 (d, J=8.4 Hz, 1H), 7.39-7.37 (d, J=7.6 Hz, 1H), 7.35-7.30 (m, 3H), 7.25-7.23 (m, 1H), 7.17 (m, 1H), 7.06-7.03 (t, J=7.2, 8.0 Hz, 1H), 5.92-5.91 (m, 1H), 5.68 (s, 1H), 5.03-5.01 (m, 1H), 4.18-4.16 (m, 1H), 4.07 (s, 3H), 3.50-3.49 (m, 1H), 3.37-3.32 (m, 1H), 2.87-2.82 (m, 5H), 2.75-2.70 (m, 2H), 2.50-2.39 (m, 3H), 2.15-2.09 (m, 1H), 1.66-1.60 (m, 2H).

Example 12B: Preparation of Compounds 9, 10, 55 and 21-9

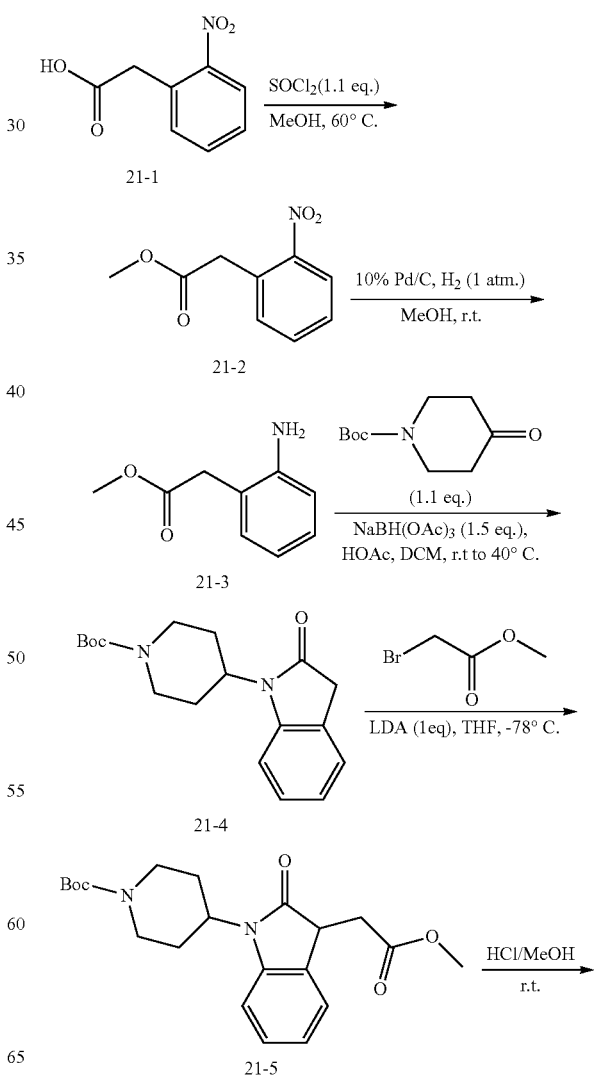

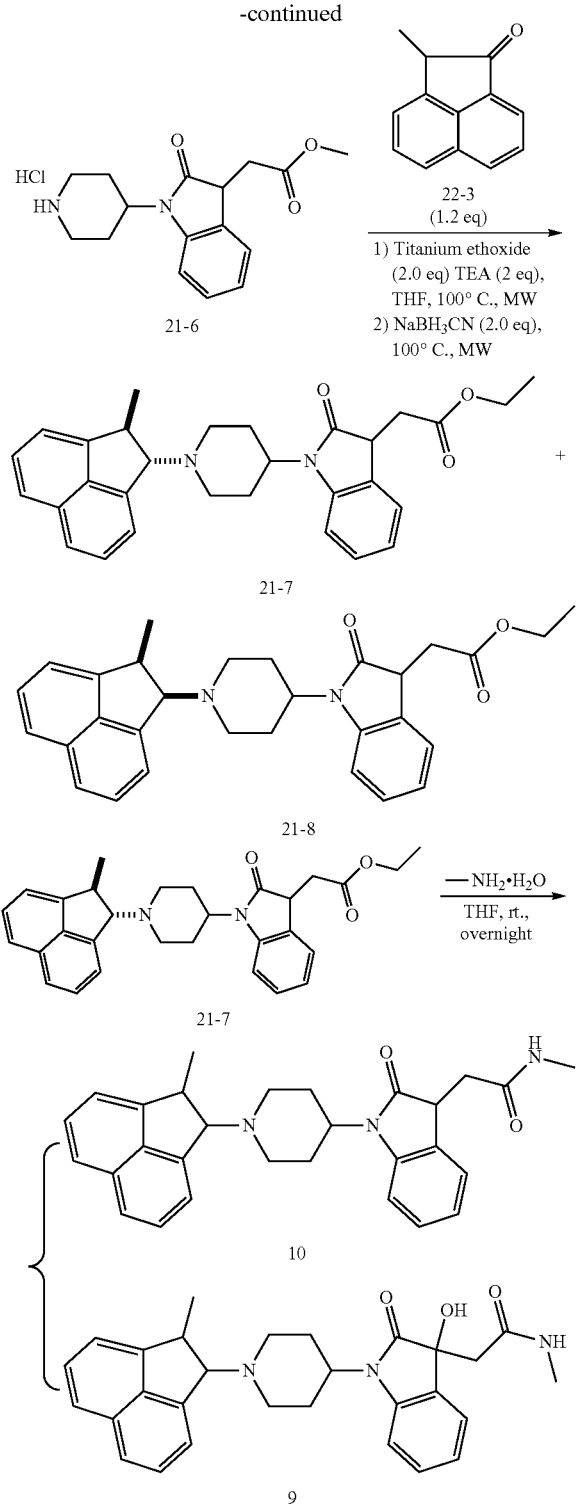

Preparation of methyl 2-(2-nitrophenyl)acetate
(Compound 21-2)

To a solution of 2-(2-nitrophenyl)acetic acid (Compound 21-1, 18.1 g, 100 mmol) in methanol (150 mL) at room temperature was dropwise added sulfurous dichloride (SOCl$_2$, 13.1 g, 110 mmol). The mixture was heated to 60° C. and stirred for 30 minutes. The reaction mixture was concentrated to give a pale yellow oil, diluted with ethyl acetate (200 mL), washed with NaHCO$_3$ (sat. aq., 150 mL×3), brine (100 mL×2), dried over anhydrous sodium sulfate, concentrated to give the desired product methyl 2-(2-nitrophenyl)acetate (Compound 21-2, 19.1 g, yield: 98%) as a pale yellow oil. MS (ESI): m/z: 196[M+H]$^+$. $^1$H NMR (400 MHz, CDCl$_3$) δ: 8.12 (dd, J=8.4, 1.2 Hz, 1H), 7.61-7.59 (m, 1H), 7.51-7.49 (m, 1H), 7.36 (d, J=7.6 Hz, 1H), 4.04 (s, 2H), 3.72 (s, 1H).

Preparation of methyl 2-(2-aminophenyl)acetate
(Compound 21-3)

A mixture of methyl 2-(2-nitrophenyl)acetate (Compound 21-2, 9.75 g, 50 mmol), 10% Pd/C (dry, 530 mg, 5 mmol) in methanol (100 mL) was stirred under H$_2$ (1 atm.) at room temperature overnight. The reaction mixture was filtered to remove Pd/C and the filtrate was concentrated to give the desired product methyl 2-(2-aminophenyl)acetate (Compound 21-3, 8.02 g, yield: 97%) as a pale yellow oil. MS (ESI): m/z: 166[M+H]$^+$. $^1$H NMR (400 MHz, DMSO-d$^6$) δ: 6.98-6.93 (m, 2H), 6.64 (d, J=8.0 Hz, 1H), 6.53-6.50 (m, 1H), 4.88 (s, 2H), 3.59 (s, 3H), 3.52 (s, 2H).

Preparation of tert-butyl 4-(2-oxoindolin-1-yl)piperidine-1-carboxylate (Compound 21-4)

A mixture of methyl 2-(2-aminophenyl)acetate (Compound 21-3, 3.30 g, 20 mmol), tert-butyl 4-oxopiperidine-1-carboxylate (4.38 g, 22 mmol), acetic acid (HOAc, 600 mg, 10 mmol) in dichloromethane (DCM, 80 mL) was stirred at room temperature for 2 h, then sodium triacetoxyborohydride (NaBH(OAc)$_3$, 6.36 g, 30 mmol) was added in portions and heated to 40° C., stirred overnight. The reaction mixture was cooled to room temperature and diluted with dichloromethane (DCM, 200 mL), washed with water (200 mL×2) and NaHCO$_3$ (sat. aq., 200 mL×2), dried over anhydrous sodium sulfate, concentrated to give the crude product, purified by flash column chromatography on silica gel (ethyl acetate/petroleum ether, 1/20-1/15-1/10 v/v) to give the desired product tert-butyl 4-(2-oxoindolin-1-yl) piperidine-1-carboxylate (Compound 21-4, 2.65 g, yield: 42%) as a pale yellow solid. MS (ESI): m/z: 261[M+H− 56]$^+$. $^1$H NMR (400 MHz, CDCl$_3$) δ: 7.26-7.22 (m, 2H), 7.05-6.99 (m, 2H), 4.46-4.38 (m, 1H), 4.28 (brs, 2H), 3.53 (s, 2H), 2.83 (brs, 2H), 2.38-2.28 (m, 2H), 1.72-1.66 (m, 2H), 1.50 (s, 9H).

Preparation of tert-butyl 4-(3-(2-methoxy-2-oxoethyl)-2-oxoindolin-1-yl)piperidine-1-carboxylate (Compound 21-5)

A solution of tert-butyl 4-(2-oxoindolin-1-yl)piperidine-1-carboxylate (Compound 21-4, 3.16 g, 10 mmol) in dry tetrahydrofuran (THF, 100 mL) was cooled to −78° C. by dry ice-acetone bath and lithium diisopropylamide (2 M in THF, 5 mL, 10 mmol) was added dropwise over 10 minutes, stirred for 1 hour at −78° C. A solution of methyl 2-bromoacetate (1.53 g, 10 mmol) in dry THF (10 mL) was added dropwise over 5 minutes. The reaction mixture was stirred for 4 hours at −78° C., quenched with NH$_4$Cl (sat. aq., 10 mL) at −78° C., and added acetic acid (HOAc, 1 mL) to make the reaction mixture neutral (pH=7), extracted with ethyl acetate (150 mL×3), combined organic layer was washed with brine (300 mL×2), dried over anhydrous sodium sulfate, concentrated to give the crude product, purified by flash column chromatography on silica gel (ethyl acetate/petroleum ether, 1/15-1/10 v/v) to give the desired product tert-butyl 4-(3-(2-methoxy-2-oxoethyl)-2-oxoindolin-1-yl)piperidine-1-carboxylate (Compound 21-5, 1.98 g, yield: 51%) as a pale yellow solid. MS (ESI): m/z: 333[M+H−56]$^+$. $^1$H NMR (400 MHz, CDCl$_3$) δ: 7.26~7.23 (m, 2H), 7.04~6.99 (m, 2H), 4.39 (s, 1H), 4.30 (d, J=12.8 Hz, 2H), 3.74~3.71 (m, 1H), 3.65 (s, 3H), 3.06 (d, $^1$J=12.8 Hz, $^2$J=4.4, 1H), 2.89~2.80 (m, 3H), 2.38~2.30 (m, 2H), 1.73 (d, J=12.8 Hz, 2H), 1.50 (s, 9H).

Preparation of methyl 2-(2-oxo-1-(piperidin-4-yl) indolin-3-yl)acetate HCl salt (Compound 21-6)

A mixture of tert-butyl 4-(3-(2-methoxy-2-oxoethyl)-2-oxoindolin-1-yl) piperidine-1-carboxylate (Compound 21-5, 3.88 g, 10 mmol) in 20 mL of methanol with hydrogen chloride was stirred overnight at room temperature. The solvent was removed under reduced pressure, the crude product was afford methyl 2-(2-oxo-1-(piperidin-4-yl)indolin-3-yl)acetate HCl salt (Compound 21-6, 3.90 g, yield: 97%) as a pale yellow solid. MS (ESI): m/z: 289[M+H]$^+$.

Preparation of ethyl 2-(1-(1-((1S,2R)-2-methyl-1,2-dihydroacenaphthylen-1-yl)piperidin-4-yl)-2-oxoindolin-3-yl)acetate (Compound 21-7) and ethyl 2-(1-(1-((1R,2R)-2-methyl-1,2-dihydroacenaphthylen-1-yl)piperidin-4-yl)-2-oxoindolin-3-yl)acetate (Compound 21-8)

To a solution of methyl 2-(2-oxo-1-(piperidin-4-yl)indolin-3-yl)acetate HCl salt (Compound 21-6, 648 mg 2.0 mmol) in dry tetrahydrofuran (8 mL) were added triethylamine (404 mg, 4.0 mmol), 2-methylacenaphthylen-1(2H)-one (Compound 22-3, 437 mg 2.4 mmol) and tetraisopropyl titanate (912 mg, 4.0 mmol). The mixture was stirred at 100° C. for 4 h under microwave condition, then sodium cyanoborohydride (252 mg, 4.0 mmol) was added, the resulting mixture was stirred at 100° C. for another 1.5 h. After completion, the reaction was quenched with water, filtered and concentrated. The residue was diluted with dichloromethane (50 mL) and washed with water (30 mL), brine (30 mL×2), dried over anhydrous sodium sulfate, concentrated to give the crude product, purified by prep-TLC (dichloromethane/methanol=20:1) to give ethyl 2-(1-(1-((1S,2R)-2-methyl-1,2-dihydroacenaphthylen-1-yl)piperidin-4-yl)-2-oxoindolin-3-yl)acetate (Compound 21-7, 100 mg, yield: 11%) (high polarity) as a pale yellow solid. MS (ESI): m/z: 469[M+H]$^+$.). $^1$H NMR (400 MHz, CDCl$_3$) δ: 7.73 (d, J=7.6 Hz, 2H), 7.66 (d, J=8.4 Hz, 2H), 7.59~7.50 (m, 3H), 7.30~7.22 (m, 4H), 7.02 (t, J=7.2 Hz, 1H), 4.47 (s, 1H), 4.31 (s, 1H), 4.18~4.28 (m, 2H), 3.75 (t, 2H), 3.09~3.05 (m, 2H), 2.86~2.76 (m, 2H), 2.56 (d, J=16 Hz, 2H), 2.48 (t, J=8.0 Hz, 2H), 1.70 (t, J=32.8 Hz, 2H), 1.52 (d, J=7.6 Hz, 3H), 1.18 (dd, J=7.2, 12.0 Hz, 3H). and ethyl 2-(1-(1-((1R,2R)-2-methyl-1,2-dihydroacenaphthylen-1-yl) piperidin-4-yl)-2-oxoindolin-3-yl)acetate (Compound 21-8, 50 mg, yield: 5.5%) (low polarity) as a pale yellow solid. MS (ESI): m/z: 469[M+H]$^+$.). $^1$H NMR (400 MHz, CDCl$_3$) δ: 7.73 (d, J=8.0 Hz, 1H), 7.64 (d, J=8.4 Hz, 1H), 7.55-7.46 (m, 3H), 7.27-7.23 (m, 3H), 7.12 (dd, J=2.4, 8.0 Hz, 1H), 7.01 (t, J=7.6 Hz, 1H), 4.67 (d, J=7.6 Hz, 1H), 4.15-4.07 (m, 3H), 3.87-3.83 (m, 1H), 3.73-3.71 (m, 1H), 3.20-3.14 (m, 2H), 3.06-3.01 (m, 1H), 2.84-2.79 (m, 1H), 2.59-2.56 (m, 1H), 2.33-2.30 (m, 1H), 2.16 (d, J=11.6 Hz, 1H), 1.78 (d, J=10.0 Hz, 1H), 1.62 (d, J=6.0 Hz, 1H), 1.53 (s, 1H), 1.36 (d, J=10.4 Hz, 1H), 1.20-1.14 (m, 3H).

Preparation of N-methyl-2-(1-(1-(2-methyl-1,2-dihydroacenaphthylen-1-yl)piperidin-4-yl)-2-oxoindolin-3-yl)acetamide (Compound 10) and 2-(3-hydroxy-1-(1-(2-methyl-1,2-dihydroacenaphthylen-1-yl)piperidin-4-yl)-2-oxoindolin-3-yl)-N-methylacetamide (Compound 9)

To a solution of 2-(1-(1-((1S,2R)-2-methyl-1,2-dihydroacenaphthylen-1-yl) piperidin-4-yl)-2-oxoindolin-3-yl) acetate (Compound 21-7, 187 mg, 0.4 mmol) in tetrahydrofuran (1.5 mL) was added methylamine solution (5.0 mL) (40%), the mixture was stirred at room temperature overnight in a sealed tube. After completion, the solvent was removed, the residue was extracted with dichloromethane (20 mL×3), washed with brine (30 mL×3), dried over anhydrous sodium sulfate, concentrated to give the crude product, purified by prep-TLC (dichloromethane/methanol=20:1) to give N-methyl-2-(1-(1-(2-methyl-1,2-dihydroacenaphthylen-1-yl)piperidin-4-yl)-2-oxoindolin-3-yl) acetamide (Compound 10, 23 mg, 13%) as an off-white solid MS (ESI): m/z: 454[M+H]$^+$. $^1$H NMR (400 MHz, CDCl$_3$) δ: 7.73 (d, J=7.6 Hz, 1H), 7.66 (d, J=8.4 Hz, 1H), 7.58-7.49 (m, 3H), 7.31-7.27 (m, 3H), 7.20 (d, J=7.6 Hz, 1H), 7.05 (t, J=7.6 Hz, 1H), 6.60 (s, 1H), 4.47 (s, 1H), 4.26 (s, 1H), 3.84-3.81 (m, 1H), 3.74 (d, J=5.6 Hz, 1H), 3.08 (d, J=6.0 Hz, 1H), 2.88-2.82 (m, 4H), 2.76 (s, 1H), 2.62-2.43 (m, 5H), 1.74-1.71 (m, 2H), 1.51 (d, J=7.6 Hz, 3H), and 2-(3-hydroxy-1-(1-(2-methyl-1,2-dihydroacenaphthylen-1-yl)piperidin-4-yl)-2-oxoindolin-3-yl)-N-methylacetamide (Compound 9, 4 mg, 2%) as an off-white solid MS (ESI): m/z: 470[M+H]$^+$. $^1$H NMR (400 MHz, CDCl$_3$) δ: 7.71 (d, J=7.6 Hz, 1H), 7.64 (d, J=7.6 Hz, 1H), 7.57-7.48 (m, 3H), 7.38 (d, J=7.2 Hz, 1H), 7.31 (t, J=8.0 Hz, 2H), 7.18 (s, 1H), 7.05 (t, J=7.6 Hz, 1H), 5.87 (s, 1H), 5.65 (d, J=16.0 Hz, 1H), 4.44 (s, 1H), 4.19 (s, 1H), 3.71 (s, 1H), 3.05 (s, 1H), 2.86 (d, J=4.8 Hz, 3H), 2.73 (dd, J=14.8, 3.2 Hz, 2H), 2.52-2.37 (m, 5H), 1.70 (d, J=7.2 Hz, 2H), 1.49 (d, J=6.8 Hz, 3H).

Preparation of N-methyl-2-(1-(1-((2S)-2-methyl-1,2-dihydroacenaphthylen-1-yl)piperidin-4-yl)-2-oxoindolin-3-yl)acetamide (Compound 54) and 2-(3-hydroxy-1-(1-((2S)-2-methyl-1,2-dihydroacenaphthylen-1-yl)piperidin-4-yl)-2-oxoindolin-3-yl)-N-methylacetamide (Compound 55)

To a solution of 2-(1-(1-((1R,2R)-2-methyl-1,2-dihydroacenaphthylen-1-yl) piperidin-4-yl)-2-oxoindolin-3-yl) acetate (Compound 21-8, 187 mg, 0.4 mmol) in tetrahydrofuran (1.5 mL) was added methylamine solution (5.0 mL) (40%), the mixture was stirred at room temperature overnight in a sealed tube. After completion, the solvent was removed, the residue was extracted with dichloromethane (20 mL×3), washed with brine (30 mL×3), dried over anhydrous sodium sulfate, concentrated to give the crude product, purified by prep-TLC (dichloromethane/methanol=20:1) to give N-methyl-2-(1-(1-((2S)-2-methyl-1,2-dihydroacenaphthylen-1-yl)piperidin-4-yl)-2-oxoindolin-3-yl)acetamide (Compound 54, 60 mg, 33%) as an off-white solid. MS (ESI): m/z: 454[M+H]$^+$. $^1$H NMR (400 MHz, CDCl$_3$) δ: 7.73 (d, J=8.0 Hz, 1H), 7.64 (d, J=8.0 Hz, 1H), 7.55-7.45 (m, 3H), 7.29-7.24 (m, 3H), 7.10 (d, J=7.6 Hz, 1H), 7.03 (t, J=7.6 Hz, 1H), 6.63 (s, 1H), 4.67 (d, J=8.0 Hz, 1H), 4.06 (m, 1H), 3.87-3.77 (m, 2H), 3.23 (d, J=9.6 Hz, 1H), 3.13 (t, J=11.6 Hz, 2H), 2.86-2.79 (m, 4H), 2.60-2.52 (m, 2H), 2.29-2.60 (m, 1H), 2.15 (d, J=11.2 Hz, 1H), 1.73 (s, 1H), 1.61 (d, J=7.2 Hz, 3H), 1.51 (t, J=11.6 Hz, 1H), 1.33 (t, J=12.0 Hz, 1H), and 2-(3-hydroxy-1-(1-((2S)-2-methyl-1,2-dihydroacenaphthylen-1-yl)piperidin-4-yl)-2-oxoindolin-3-yl)-N-methylacetamide (Compound 55, 23 mg, 12%) as an off-white solid. MS (ESI): m/z: 470[M+H]$^+$. $^1$H NMR (400 MHz, CDCl$_3$) δ: 7.72 (d, J=8.0 Hz, 1H), 7.63 (d, J=8.0 Hz, 1H), 7.48 (m, 3H), 7.37 (d, J=7.2 Hz, 1H), 7.27 (d, J=8.8 Hz, 1H), 7.27-7.24 (m, 1H), 7.09-7.02 (m, 2H), 6.01-5.99 (m, 1H), 4.65 (d, J=7.6 Hz, 1H), 4.00-3.98 (m, 1H), 3.86-3.82 (m, 1H), 3.19 (d, J=10.0 Hz, 1H), 2.85 (t, J=4.8 Hz, 3H), 2.71 (t, J=17.6 Hz, 1H), 2.51-2.46 (m, 1H), 2.44-2.42 (m, 1H), 2.26-2.22 (m, 1H), 2.13 (s, 1H), 1.76-1.73 (m, 1H), 1.60 (d, J=7.2 Hz, 3H), 1.47-1.45 (m, 1H), 1.31 (t, J=7.2 Hz, 1H).

Example 13: Preparation of 2-methylacenaphthylen-1(2H)-one

Scheme 22.

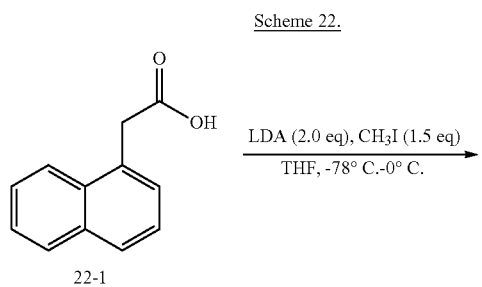

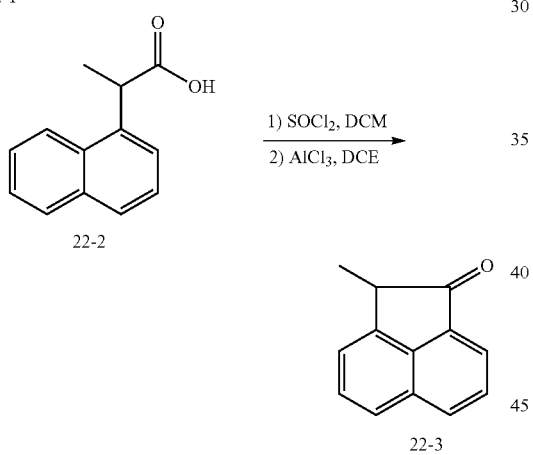

Preparation of 2-(naphthalen-1-yl)propanoic acid (Compound 22-2)

To a stirred −78° C. solution of LiN($^i$Pr)$_2$ (60 mL, 120 mmol) in dry THF (50 mL) under Ar, was added 2-(naphthalen-1-yl)acetic acid (Compound 22-1, 11.16 g, 60 mmol) in dry THF (50 mL) dropwise over 15 min. The solution was stirred at 0° C. for 2 hours and recooled to −78° C., and a single portion of iodomethane (12.78 g, 90 mmol) was added. After the mixture was stirred overnight at room temperature, the reaction was quenched with water. Then the mixture was concentrated in vacuo, and the residue was dissolved in water, extracted with ethyl ether (100 mL×2). The combined organic layer was dried over sulfate sodium, concentrated in vacuo, then the residue was recrystallized from petroleum ether to give crude 2-(naphthalen-1-yl)propanoic acid (Compound 22-2, 10.39 g, yield: 86%) as a light yellow solid. MS (ESI): m/z: 201 [M+H]$^+$.

Preparation of 2-methylacenaphthylen-1(2H)-one (Compound 22-3)

To a solution of Compound 22-2 (10.38 g, 51.9 mmol) in dichloromethane (50 mL), was added thionyl chloride (12.35 g, 103.8 mmol). After addition, the mixture was stirred at room temperature for 2 hours. Then dichloromethane and thionyl chloride were removed under reduced pressure, and the residue was dissolved in 1,2-dichloroethane (50 mL). Aluminum chloride (13.81 g, 103.8 mmol) was added to the mixture in portions. After stirred at 35° C. for 2 hours, the mixture was poured onto ice water and acidified with concentrated hydrochloric acid to pH 1-2, then filtered. The filtrate was extracted with dichloromethane (200 mL) and the organic layer was dried over sulfate sodium, then concentrated in vacuo. The residue was purified by flash chromatography (dichloromethane:petrol ether=1:40 to 1:20) to give (2-methylacenaphthylen-1(2H)-one (Compound 22-3, 2.06 g, yield: 22%). MS (ESI): m/z: 183 [M+H]$^+$. $^1$H NMR (400 MHz, CDCl$_3$) δ: 8.09 (d, J=8.0 Hz, 1H), 7.95 (d, J=6.8 Hz, 1H), 7.80 (d, J=8.4 Hz, 1H), 7.72-7.69 (m, 1H), 7.63~7.59 (m, 1H), 7.44 (d, J=6.4 Hz, 1H), 3.73 (q, 1H), 1.55 (d, J=7.6 Hz, 1H).

Example 14A: Preparation of Compound 11

Scheme 23A.

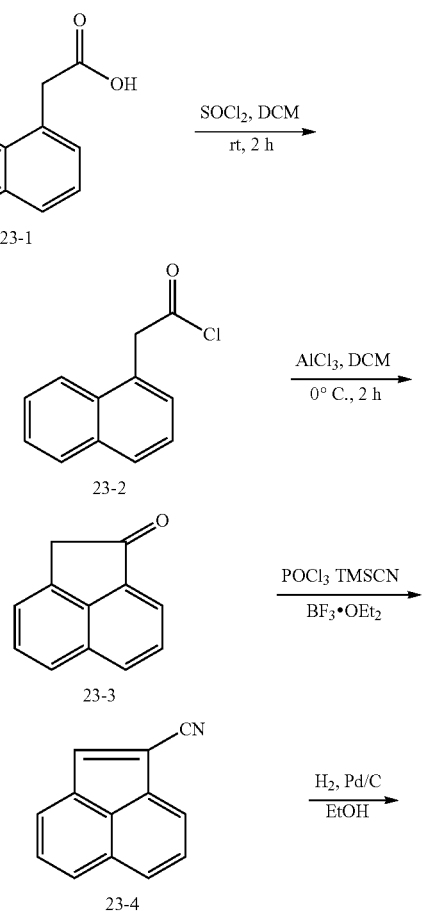

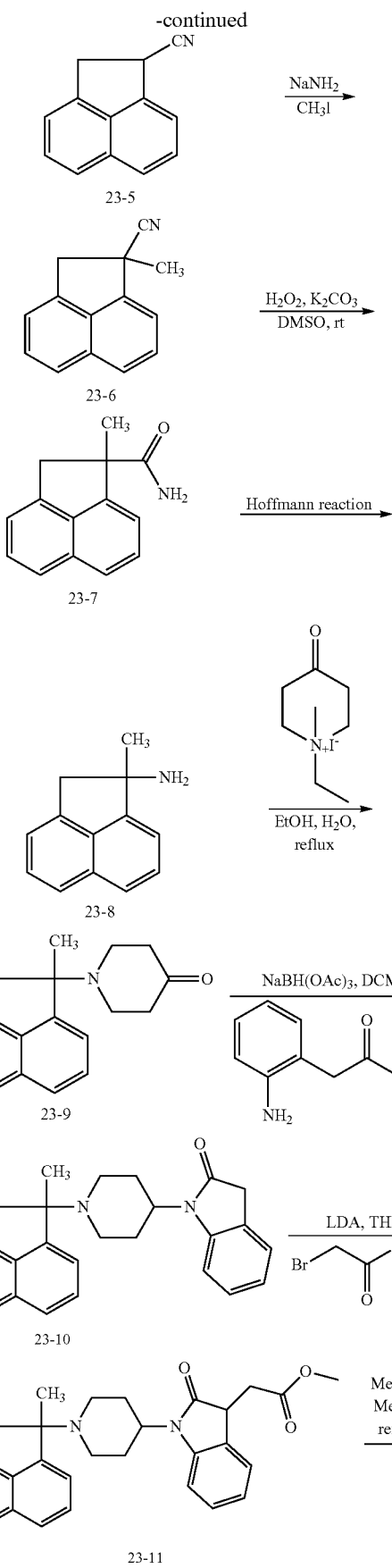

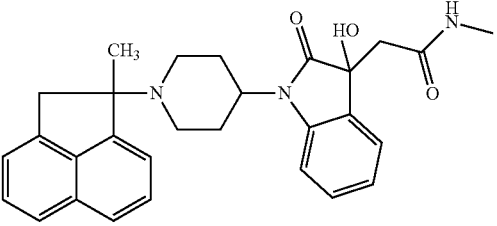

Preparation of 2-(naphthalen-1-yl) acetyl chloride (Compound 23-2)

To a solution of Compound 23-1 (100 g, 0.53 mol) in 150 mL of CH$_2$Cl$_2$ was added (42 mL 0.583 mol) of SOCl$_2$ dropwise over 30 min at 0° C. After stirring at room temperature for 2 h, the solution was vacuum-concentrated and the crude Compound 23-2 was used for the next step without further purification.

Preparation of acenaphthylen-1(2H)-one (Compound 23-3)

To a solution of Compound 23-2 (108.1 g, 0.53 mol) in 500 mL of CH$_2$Cl$_2$ was added AlCl$_3$ (150 g, 1.12 mol) in portions at 0° C. After the mixture was stirred at room temperature for 2 h, the reaction was poured into 500 mL ice-water carefully. Then it was extracted with CH$_2$Cl$_2$ (800 mL×4). The combined organic layer was concentrated under reduced pressure to afford a crude oil. Flash chromatography on silica gel afforded 46 g of Compound 23-3 as a yellow solid (51% yield for two steps). ESIMS (m/z): 168 [M+H]$^+$.

Preparation of acenaphthylene-1-carbonitrile (Compound 23-4)

To a stirred 25° C. mixture of (33.6 g 0.0.2 mol) of Compound 23-3 and 36 mL (0.27 mol) of Me3SiCN was added ten drops of BF3.OEt2 by dropwise. The mixture was heated to 60° C. and another ten drops of BF3.OEt2 was added, followed by 120 mL of anhydrous pyridine and 36 mL (0.39 mol) of POCl$_3$. The mixture was then heated at 100° C. for 1 h, cooled, poured onto 300 mL of ice-water, and extracted with EtOAc. The combined extracts were washed with 1 M HCl and saturated brine, dried over NaSO$_4$. The organic layer were dried over anhydrous sodium sulfate and evaporated in vacuum to afford the crude product. The crude product was purified by chromatography silica gel (ethyl acetate:petroleum ether=1:20 to 1:10) to obtained acenaphthylene-1-carbonitrile Compound 23-4 (22 g, yield 62%) as a yellow powder. ESIMS (m/z): 177 [M−26]$^+$ Preparation of 1,2-dihydroacenaphthylene-1-carbonitrile (Compound 23-5)

To a solution of Compound 23-4 (21.24 g, 120 mmol) in ethanol (200 mL) under nitrogen was added palladium, 10 wt. % on activated carbon (10.3 g). The reaction mixture was deoxygenated under vacuum and then hydrogenated at room temperature overnight. After the reaction completed, the reaction mixture was filtered through a pad of celite and washed with EtOH (50 mL×2). The filtrate was concentrated to give the desired product Compound 23-5 (19.2 g, yield: 90%) as yellow oil. This crude product was used for the next step without further purification. ESIMS (m/z): 179[M−26]+

Preparation of 1-methyl-1,2-dihydroacenaphthylene-1-carbonitrile (Compound 23-6)

To a solution of Compound 23-5 (15.2 g, 85 mmol) dissolved in toluene (50 mL) was added sodium amide (4.96 g, 127 mmol) and MeI (7.92 mL, 127 mmol) at room temperature. The reaction mixture was stirred at 45° C. under nitrogen overnight. After the reaction completed, the reaction mixture was partitioned between ethyl acetate (50 mL) and brine (40 mL). The aqueous layer was extracted with ethyl acetate (80 mL×3) and the combined organic phased were dried with anhydrous sodium sulfate, filtrated and concentrated, the residue layers was purified by flash chromatography to give the desired product Compound 23-6 (6.2 g, yield: 38%) as a light yellow oil. ESIMS (m/z): [M−26]+ 1H NMR (400 MHz, DMSO) δ 8.26 (d, J=7.9 Hz, 1H), 7.96-7.90 (m, 2H), 7.83-7.78 (m, 1H), 7.70-7.65 (m, 1H), 7.55 (d, J=6.8 Hz, 1H), 3.88 (s, 2H), 1.23 (s, 3H).

Preparation of 1-methyl-1,2-dihydroacenaphthylene-1-carboxamide (Compound 23-7)

To a solution of Compound 23-6 (6.2 g, 32 mmol) and K$_2$CO$_3$ (13.3 g, 96 mmol) dissolved in DMSO (10 mL) was added H$_2$O$_2$ (64 mmol, 3.74 mL) at room temperature. The reaction mixture was stirred at ambient temperature for 2 h. After the reaction completed, the reaction mixture was partitioned between ethyl acetate (50 mL) and brine (40 ml). The aqueous layer was extracted with ethyl acetate (80 mL×3) and the combined organic phased were concentrated to give Compound 23-7 (6.34 g, yield: 94%) as a white solid which can be used without further purification. ESIMS (m/z): 211 [M+1]+

Preparation of 1-methyl-1,2-dihydroacenaphthylen-1-amine (Compound 23-8)

To a solution of Compound 23-7 (6.32 g, 1.30 mmol) in a mixture of 80 mL of CH$_3$CN and 80 mL of H$_2$O was added [Bis(trifluoroacetoxy)iodo]benzene (19.4 g 1.45 mmol) portionwise at 0° C. Then the mixture was stirred at room temperature for 3 h, and made basic using saturated sodium bicarbonate solution after the reaction completed. The aqueous layer was extracted with ethyl acetate (3×80 mL) and the combined organic phase was concentrated to give crude yellow oil. Compound 23-8 (3.2 g, yield: 58%) was obtained after a silica gel chromatography. ESIMS (m/z): 183[M−16]+

Preparation of 1-(1-methyl-1,2-dihydroacenaphthylen-1-yl)piperidin-4-one (Compound 23-9)

To a solution of Compound 23-8 (3.2 g, 18 mmol) and K$_2$CO$_3$ (3.8 g, 27 mmol) in 100 mL EtOH was added 1-ethyl-1-methyl-4-oxopiperidin-1-ium iodide (14.5 g, 54 mmol) that was dissolved in 6 mL of H$_2$O at 60° C. Then the mixture was stirred at 80° C. for 6 h, and the reaction was cooled to room temperature and extracted with ethyl acetate (80 mL×3). The combined organic phase was concentrated and purified by silica gel chromatography to give Compound 23-9 (2.8 g, yield: 60%) as a pale yellow oil. ESIMS (m/z): 265[M−98]+ or 265[M+18]+

Preparation of 1-(1-(1-methyl-1,2-dihydroacenaphthylen-1-yl)piperidin-4-yl)indolin-2-one (Compound 23-10)

To a solution of 1-(1-methyl-1,2-dihydroacenaphthylen-1-yl)piperidin-4-one Compound 23-9 (132.68 mg, 0.5 mmol) and methyl 2-(2-aminophenyl)acetate (247.49 mg, 1.5 mmol) in 15 mL of dichloromethane was added acetic acid (150.0 mg, 2.5 mmol). The mixture was stirred for 1.5 h at room temperature. Sodium triacetoxyborohydride (316.5 mg, 1.5 mmol) was added into the mixture and stirred for 2 h at room temperature. Then the reaction mixture was heated to 30° C. and stirred overnight. The mixture was washed with water (20 mL×2), and sat. sodium carbonate (20 mL×2), brine (20 mL×2). The organic layer were dried over anhydrous sodium sulfate and evaporated in vacuum to afford the crude product. The crude product was purified by silica gel chromatography (ethyl acetate:petroleum ether=1:5 to 1:2) to obtain 1-(1-(1-methyl-1,2-dihydroacenaphthylen-1-yl)piperidin-4-yl)indolin-2-one (Compound 23-10, 101.5 mg, yield 53%) as a white solid. ESIMS (m/z): 382 [M+H]+.

Preparation of methyl 2-(1-(1-(1-methyl-1,2-dihydroacenaphthylen-1-yl)piperidin-4-yl)-2-oxoindolin-3-yl)acetate (Compound 23-11)

To a solution of 1-(1-(1-methyl-1,2-dihydroacenaphthylen-1-yl)piperidin-4-yl)indolin-2-one (Compound 23-10, 99.45 mg, 0.26 mmol) in 8 mL of tetrahydrofuran was added lithium diisopropylamide (0.17 mL, 0.34 mmol) at −78° C. over 30 min. A solution of methyl 2-bromoacetate (51.68 mg, 0.34 mmol) in 1 mL of tetrahydrofuran was added into the mixture at −70° C. The reaction mixture was stirred for 3 h at −70° C. Then 20 ml, solution of sat. Ammonium chloride was added slowly and stirred for 10 min at 0° C. The organic layer were separated and washed with solution of sat. Ammonium chloride (15 mL×2). The organic layer were dried over anhydrous sodium sulfate and evaporated in vacuum to afford the crude product. The crude product was purified by silica gel chromatography (ethyl acetate:petroleum ether=1:5 to 1:1) to obtained methyl 2-(1-(1-(1-methyl-1,2-dihydroacenaphthylen-1-yl)piperidin-4-yl)-2-oxoindolin-3-yl)acetate (Compound 23-11, 65 mg, yield 55%) as a white solid. ESIMS (m/z): 454[M+H]+.

Synthesis of Compound 11

The solution of methyl 2-(1-(1-(1-methyl-1,2-dihydroacenaphthylen-1-yl)piperidin-4-yl)-2-oxoindolin-3-yl)acetate (Compound 23-11, 63.5 mg, 0.14 mmol) in 2 mL of methylamine methanol was stirred for overnight at 80° C. in a sealed tube. After removed the solvent, the residue was purified with silica gel column chromatography (dichloromethane:methanol=10:1) to afford Compound 11 as white solid (21 mg, yield 33%). ESIMS (m/z): 469 [M+H]+. 1H NMR (400 MHz, MeOD) δ 7.87 (d, J=8.1 Hz, 1H), 7.72-7.65 (m, 2H), 7.64-7.59 (m, 1H), 7.56-7.50 (m, 1H), 7.39 (d, J=6.9 Hz, 1H), 7.25-7.17 (m, 2H), 6.99-6.93 (m, 2H), 4.22-4.12 (m, J=12.0 Hz, 1H), 4.03 (d, J=18.6 Hz, 1H), 3.76 (d, J=10.7 Hz, 1H), 3.50 (d, J=18.6 Hz, 1H), 3.19-3.10 (m, 1H), 2.98-2.90 (m, 1H), 2.87-2.74 (m, 3H), 2.74-2.65 (m, 1H), 2.36 (d, J=3.6 Hz, 3H), 2.02-1.87 (m, 5H), 1.26-1.18 (m, 1H).

Example 14B: Preparation of Compound 80

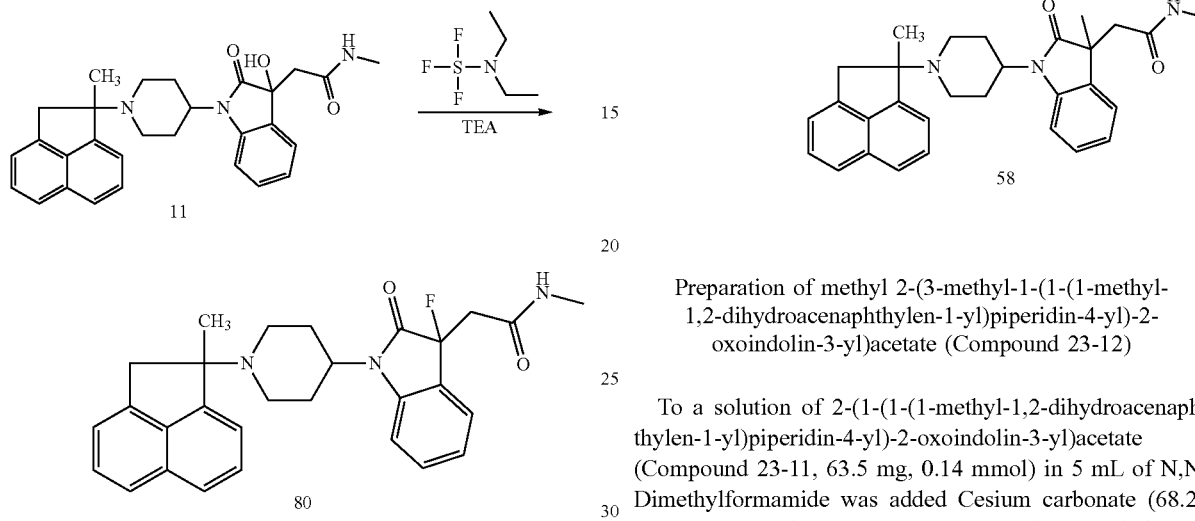

To a solution of 2-(3-hydroxy-1-(1-(1-methyl-1,2-dihydroacenaphthylen-1-yl)piperidin-4-yl)-2-oxoindolin-3-yl)-N-methylacetamide (Compound 11, 50.0 mg, 0.11 mmol) in dichloromethane was added triethylamine (22.2 mg, 0.22 mmol) and diethylaminosulfurtrifluoride (17.7 mg, 0.11 mmol). The mixture was stirred at room temperature for 0.5 h, then the mixture was washed with water, saturated sodium carbonate, and brine. The organic phase was dried over NaSO$_4$ and filtered. HPLC purification yielded 2-(3-fluoro-1-(1-(1-methyl-1,2-dihydroacenaphthylen-1-yl)piperidin-4-yl)-2-oxoindolin-3-yl)-N-methylacetamide (Compound 80, 13 mg, 22%). ESIMS m/z 471.1 [M+l]$^+$, $^1$H NMR (400 MHz, MeOD) δ 7.87 (d, J=8.1 Hz, 1H), 7.71-7.67 (m, 2H), 7.64-7.60 (m, 1H), 7.55-7.51 (m, 1H), 7.39 (d, J=6.9 Hz, 1H), 7.28-7.34 (m, 2H), 6.98-7.03 (m, 2H), 4.20-4.14 (m, 1H), 4.00-4.05 (m, 1H), 3.75-3.78 (m, 1H), 3.48-3.53 (m 1H), 3.15-3.10 (m, 2H), 2.95-2.67 (m, 4H), 237-2.38 (m, 3H), 2.00-1.92 (m, 5H), 1.19-1.23 (m, 1H).

Example 14C: Preparation of Compound 58

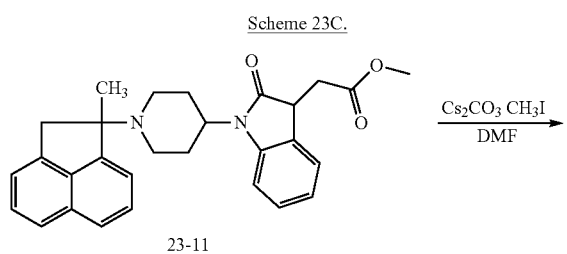

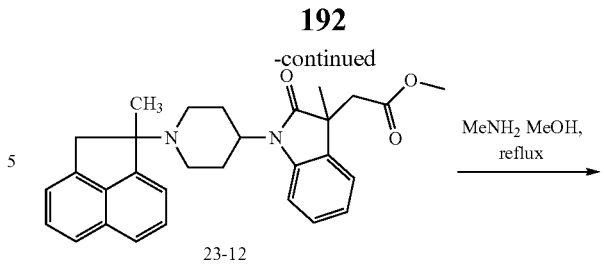

Preparation of methyl 2-(3-methyl-1-(1-(1-methyl-1,2-dihydroacenaphthylen-1-yl)piperidin-4-yl)-2-oxoindolin-3-yl)acetate (Compound 23-12)

To a solution of 2-(1-(1-(1-methyl-1,2-dihydroacenaph-thylen-1-yl)piperidin-4-yl)-2-oxoindolin-3-yl)acetate (Compound 23-11, 63.5 mg, 0.14 mmol) in 5 mL of N,N-Dimethylformamide was added Cesium carbonate (68.25 mg, 0.21 mmol) at 0° C. over 10 min. A solution of iodomethane (29.61 mg, 0.21 mmol) in 0.5 mL of N,N-Dimethylformamide was added into the mixture at 0° C. The reaction mixture was stirred for 1 h at room temperature. Then the reaction mixture were washed with water (15 mL×2) and extracted with EA (5 mL×3). The organic layer were dried over anhydrous sodium sulfate and evaporated in vacuum to afford the crude product. The crude product was purified by silica gel column chromatography to obtained methyl methyl 2-(3-methyl-1-(1-(1-methyl-1,2-dihydroace-naphthylen-1-yl)piperidin-4-yl)-2-oxoindolin-3-yl)acetate (Compound 23-12, 49.1 mg, yield 75%) as a white solid. ESIMS (m/z): 468 [M+H]$^+$.

Preparation of Compound 58

The solution of methyl 2(3-methyl-1-(1-(1-methyl-1,2-dihydroacenaphthylen-1-yl)piperidin-4-yl)-2-oxoindolin-3-yl)acetate (Compound 23-12, 46.8 mg, 0.1 mmol) in 1.5 mL of methylamine methanol was stirred for overnight at 80° C. in a sealed tube. After removed the solvent, the residue was purified with silica gel column chromatography (dichloromethane:methanol=20:1) to yield Compound 58 as white solid (19 mg, yield: 41%). ESIMS (m/z): 467 (M+H)$^+$. $^1$H NMR (400 MHz, MeOD) δ 7.87 (d, J=8.1 Hz, 1H), 7.69 (t, J=8.0 Hz, 2H), 7.62 (t, J=7.6 Hz, 1H), 7.53 (t, J=7.6 Hz, 1H), 7.40 (d, J=6.9 Hz, 1H), 7.16-7.09 (m, 2H), 7.00 (d, J=7.9 Hz, 1H), 6.92 (t, J=7.4 Hz, 1H), 4.27-4.18 (m, 1H), 4.04 (d, J=18.6 Hz, 1H), 3.77 (d, J=11.0 Hz, 1H), 3.50 (d, J=18.6 Hz, 1H), 3.19-3.11 (m, 1H), 3.02-2.64 (m, 5H), 2.32 (d, J=2.9 Hz, 3H), 2.02-1.89 (m, 5H), 1.26-1.14 (m, 4H).

Compound 58 was purified by chiral HPLC to yield Compound 174, Compound 175, Compound 176, Compound 177, and Compound 178.

Compound 174

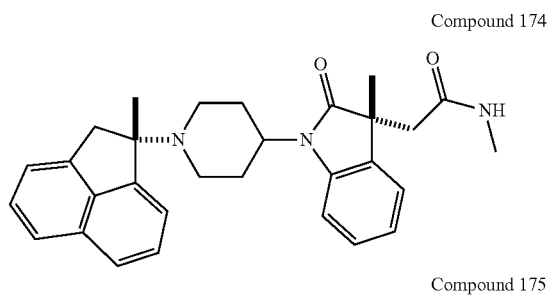

Compound 175

Compound 176

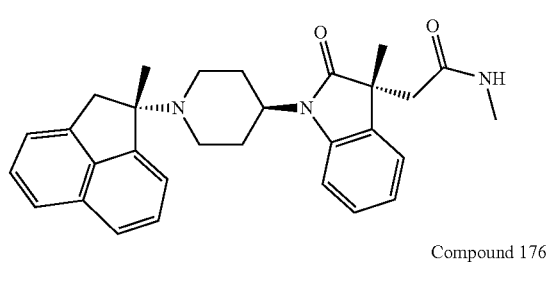

Compound 177

Compound 178

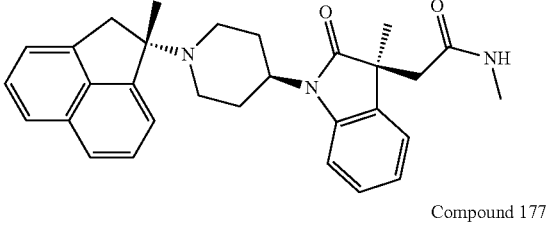

Example 15: Preparation of Compound 24-3

Scheme 24.

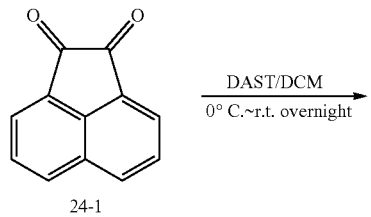

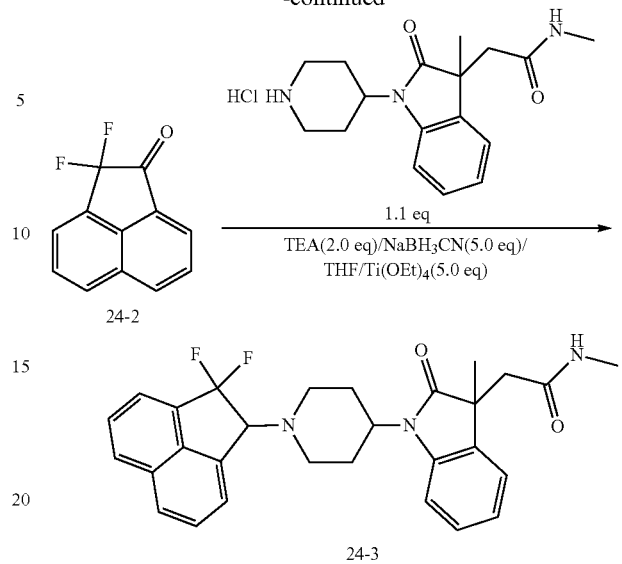

Preparation of 2,2-Difluoroacenaphthylen-1(2H)-one (Compound 24-2)

To a solution of acenaphthylene-1,2-dione (Compound 24-1, 0.6 g, 3.29 mmol) in 10 mL of dichloromethane was added diethylaminosulfur trifluoride (1.06 g, 6.59 mmol) slowly at 0° C. The reaction mixture was stirred at 0° C. for 1 h and warmed slowly to room temperature and stirred overnight. The reaction mixture was quenched with water, extracted with dichloromethane (50 mL×3) and washed with brine. The combined organic layers was dried over sodium sulfate and concentrated in vacuum. The crude product was purified by chromatography silica gel (petroleum ether:ethyl acetate=40:1) to obtain 2,2-difluoroacenaphthylen-1(2H)-one (Compound 24-2, 0.33 g, Yield 49%) as a yellow solid. MS(ESI): m/z 205 [M+H]$^+$.

Preparation of Compounds 60, 61 and 62

To a solution of methyl 2-(2-oxo-1-(piperidin-4-yl)indoin-3-yl)acetate hydrochloride (428 mg, 1.32 mmol) in 20 mL of tetrahydrofuran was added triethylamine (242 mg, 2.4 mmol), the mixture was stirred at room temperature for 15 min, then 2,2-difluoroacenaphthylen-1(2H)-one (Compound 24-2, 245 mg, 1.2 mmol) and titanium ethoxide (821 mg, 3.6 mmol) were added in, the resulting mixture reacted in microwave reactor at 120° C. for 5 h. Then sodium cyanoborohydride (377 mg, 6 mmol) was added in, the mixture reacted in microwave reactor at 120° C. for 1 h. The reaction mixture was quenched with water, extracted with ethyl acetate (25 mL×3) and washed with brine. The combined organic layers were dried over sodium sulfate and concentrated in vacuum. The crude product was purified by RP-HPLC to afford 2-(1-(1-(2,2-difluoro-1,2-dihydroacenaphthylen-1-yl)piperidin-4-yl)-3-methyl-2-oxoindolin-3-yl)-N-methylacetamide (Compound 24-3, 20 mg, Yield 3%), which was further purified by chiral-HPLC to obtained 2-((R)-1-((S)-2,2-difluoro-1,2-dihydroacenaphthylen-1-yl) piperidin-4-yl)-3-methyl-2-oxoindolin-3-yl)-N-methylacetamide (Compound 60) (4.1 mg, purity 85%) as a colorless liquid, MS(ESI): m/z 490 [M+H]$^+$. $^1$HNMR (400 MHz, CDCl$_3$) δ 7.986-7.968 (d, J=7.2 Hz, 1H), 7.854~7.834 (d, J=8.0 Hz, 1H), 7.742~7.651 (m, 3H), 7.613~7.588 (d, J=10 Hz, 1H), 7.294~7.275 (t, J=7.6 Hz, 2H), 7.224~7.195 (m, 1H), 7.105~7.068 (t, J=14.8 Hz, 1H), 6.262 (s, 1H), 4.965~4.908 (m, 1H), 4.290~4.269 (t, J=8.4 Hz, 1H), 3.309~3.224 (m, 2H), 3.083~3.066 (d, J=6.8 Hz, 1H), 2.938~2.817 (m, 4H), 2.780 (s, 1H), 2.463~2.402 (m, 1H), 1.814 (s, 1H), 1.796~1.719 (m, 1H), 1.465 (s, 3H).

2-((S)-1-(1-((S)-2,2-difluoro-1,2-dihydroacenaphthylen-1-yl)piperidin-4-yl)-3-methyl-2-oxoindolin-3-yl)-N-methylacetamide (Compound 61) (2.63 mg, purity 74%) as a colorless liquid, MS(ESI): m/z 490 [M+H]$^+$. $^1$HNMR (400 MHz, CDCl$_3$) δ 7.987~7.969 (d, J=7.2 Hz, 1H), 7.853~7.833 (d, J=8.0 Hz, 1H), 7.725~7.649 (m, 3H), 7.602~7.586 (d, J=6.4 Hz, 1H), 7.314 (s, 2H), 7.224~7.204 (d, J=78.0 Hz, 1H), 7.106~7.070 (t, J=14.4 Hz, 1H), 6.270 (s, 1H), 4.965~4.908 (m, 1H), 4.301 (s, 1H), 3.316~3.189 (m, 2H), 2.915~2.838 (m, 2H), 2.815~2.778 (m, 1H), 2.671~2.572 (m, 5H), 2.496~2.432 (m, 1H), 1.822~1.791 (d, J=12.4 Hz, 1H), 1.647~1.617 (d, J=12 Hz, 1H), 1.421 (s, 3H).

2-((R)-1-(1-((R)-2,2-difluoro-1,2-dihydroacenaphthylen-1-yl)piperidin-4-yl)-3-methyl-2-oxoindolin-3-yl)-N-methylacetamide (Compound 62) (3.25 mg, purity 100%) as a white solid. MS(ESI): m/z 490 [M+H]$^+$. $^1$HNMR (400 MHz, CDCl$_3$) δ 7.99~27.973 (d, J=7.6 Hz, 1H), 7.858~7.837 (d, J=8.4 Hz, 1H), 7.727~7.659 (m, 3H), 7.614~7.597 (d, J=6.8 Hz, 1H), 7.313 (s, 2H), 7.215~7.197 (d, J=7.2 Hz, 1H), 7.106~7.069 (m, 1H), 6.249 (s, 1H), 4.967~4.910 (m, 1H), 4.303 (s, 1H), 3.288~3.234 (m, 2H), 2.913~2.861 (m, 2H), 2.818~2.781 (m, 1H), 2.693~2.634 (m, 5H), 2.433~2.402 (m, 1H), 1.806~1.776 (d, J=12 Hz, 1H), 1.662~1.630 (d, J=12.8 Hz, 1H), 1.422 (s, 3H).

Example 16A: Preparation of Compound 63

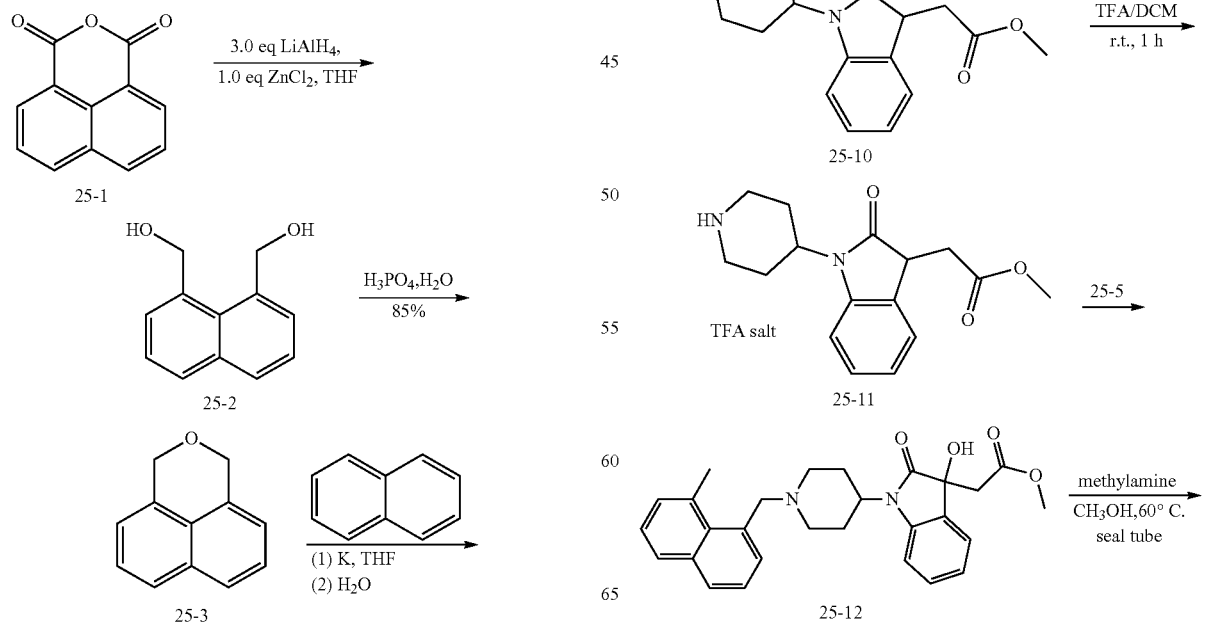

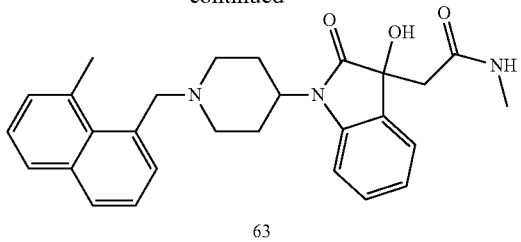

63

Preparation of Compound 25-1

Dry tetrahydrofuran (400 mL), Lithium aluminum hydride (4.55 g, 120 mmol) and zinc(II) chloride (8.18 g, 60 mmol) were added into a 1 L round-bottom flask, then 1,8-Naphthalic anhydride (Compound 25-1, 19.8 g, 100 mmol) was added slowly at room temperature. After 6 hours, 5 mL water was added followed by 10 mL 15% sodium hydroxide and 15 mL water at −10° C. The mixture was filtered, extracted with ethyl acetate, washed with brine and then dried over anhydrous sodium sulfate. After the solvent was evaporated, the crude product was recrystallized with ether and ethyl acetate (10/1) to give naphthalene-1,8-diyldimethanol (Compound 25-2) as white crystals 13.5 g (69%, yield). MS (ESI): m/z: 171 [M−17]$^+$. $^1$H NMR (400 MHz, CD$_3$OH) δ: 7.86 (dd, J=8.4 Hz, J=1.2 Hz, 2H), 7.62 (dd, J=6.8 Hz, J=1.2 Hz, 2H), 7.45 (q, J=7.2 Hz, 2H), 5.24 (s, 4H).

Preparation of Compound 25-3

A solution of naphthalene-1,8-diyldimethanol (Compound 25-2, 11 g, 58 mmol) in phosphoric acid (120 mL, 50%) was stirred at 100° C. for one hour, cooled to room temperature, extracted with dichloromethane, washed with water, saturated sodium bicarbonate and brine, dried over dried over anhydrous sodium sulfate, and evaporated to yield Compound 25-3 as a white solid (9.2 g, 92%). MS (ESI): m/z: 171 [M+H]$^+$. $^1$H NMR (400 MHz, DMSO-d$_6$) δ: 7.79 (d, J=8.0 Hz, 2H), 7.46 (t, J=8.0 Hz, 2H), 7.25 (d, J=6.8 Hz, 2H), 5.01 (s, 4H).

Preparation of Compound 25-4

A 500 mL 4-neck flask was charged with potassium (5.86 g, 0.15 mol) and tetrahydrofuran (200 mL). The suspension was heated to 60° C. for 10 min and then stirred at room temperature. To the reaction mixture was added naphthalene (0.4 g, 3 mmol), then the suspension was stirred at room temperature for 10 min and then cooled to −20° C. to afford a blue suspension. A solution of 1H, 3H-benzo[de]isochromene (5.1 g, 30 mmol) in tetrahydrofuran (100 mL) was slowly added. After stirring for 5 hours at −15° C., the suspension was warmed with stirring to 0° C., and then allowed to stand without stirring. The solution was decanted and the decanted solution was carefully treated with water (10 mL). The mixture was extracted with ethyl acetate, washed with brine and dried over anhydrous sodium sulfate, evaporated to give the crude product which was purified on silica gel (ethyl acetate in petro ether, 10% v/v) to yield Compound 25-4 as a white solid (3 g, 58%). $^1$H NMR (400 MHz, DMSO-d$_6$) δ: 7.81 (dd, J=8.0 Hz, J=1.2 Hz, 1H), 7.75 (dd, J=7.6 Hz, J=1.6 Hz, 1H), 7.59 (d, J=6.8 Hz, 1H), 7.42 (t, J=7.6 Hz, 1H), 7.37-7.31 (m, 2H), 5.28 (t, J=5.6 Hz, 1H), 5.05 (d, J=5.6 Hz, 2H), 2.94 (s, 3H).

Preparation of Compound 25-5

To a solution of compound (8-methylnaphthalen-1-yl) methanol (Compound 25-4, 52 mg, 0.3 mmol) in dichloromethane (2 mL) was added sulfurous dichloride (72 mg, 0.6 mmol) dropwise at 0° C. The reaction mixture was stirred at 0° C. for 1 hr. The mixture was evaporated at 10° C. to afford crude Compound 25-5. The compound was used for the next step without further purification.

Preparation of Compound 25-7

To a solution of 2-(2-nitrophenyl) acetic acid (Compound 25-6, 18.1 g, 100 mmol) in methanol (150 ml) at room temperature was added sulfurous dichloride (SOCl$_2$, 13.1 g, 110 mmol) dropwise. The mixture was heated to 60° C. and stirred for 30 minutes. The reaction mixture was concentrated to give a pale yellow oil, diluted with ethyl acetate, washed with NaHCO$_3$, brine, dried over anhydrous sodium sulfate, concentrated to give the desired product methyl 2-(2-nitrophenyl)acetate (Compound 25-7, 19.1 g, yield: 98%) as a pale yellow oil. MS (ESI): m/z: 196[M+H]$^+$. $^1$H NMR (400 MHz, CDCl$_3$) δ: 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 1H).

Preparation of Compound 25-8

A mixture of methyl 2-(2-nitrophenyl)acetate (Compound 25-7, 9.75 g, 50 mmol), 10% Pd/C (dry, 530 mg, 5 mmol) in methanol (100 ml) was stirred under H$_2$ (1 atm.) at room temperature overnight. The reaction mixture was filtered and the filtrate was concentrated to give the desired product methyl 2-(2-aminophenyl)acetate (Compound 25-8, 8.02 g, yield: 97%) as a pale yellow oil. MS (ESI): m/z: 166[M+H]$^+$. $^1$H NMR (400 MHz, DMSO-d6) δ: 6.94 (m, 2H), 6.64 (d, 1H, J=8.0 Hz), 6.51 (m, 1H), 4.88 (s, 2H), 3.59 (s, 3H), 3.52 (s, 2H).

Preparation of Compound 25-9

A mixture of methyl 2-(2-aminophenyl)acetate (Compound 25-8, 3.30 g, 20 mmol), tert-butyl 4-oxopiperidine-1-carboxylate (4.38 g, 22 mmol), acetic acid (600 mg, 10 mmol) in dichloromethane (80 ml) was stirred at room temperature for 2 h, then sodium triacetoxyborohydride (6.36 g, 30 mmol) was added in portions. The reaction was and heated to 40° C. and stirred overnight. The reaction mixture was cooled to room temperature and diluted with dichloromethane, washed with water and sodium bicarbonate, dried over anhydrous sodium sulfate, concentrated to give the crude product. Purification by flash column chromatography on silica gel (ethyl acetate in petroleum ether) yielded tert-butyl 4-(2-oxoindolin-1-yl)piperidine-1-carboxylate (Compound 25-9, 2.65 g, yield: 42%) as a pale yellow solid. MS (ESI): m/z: 261[M+H−56]$^+$. $^1$H NMR (400 MHz, CDCl$_3$) δ: 7.24 (m, 2H), 7.01 (m, 2H), 4.41 (m, 1H), 4.28 (br s, 2H), 3.53 (s, 2H), 2.83 (br s, 2H), 2.32 (m, 2H), 1.70 (m, 2H), 1.50 (s, 9H).

Preparation Compound 25-10

A solution of tert-butyl 4-(2-oxoindolin-1-yl) piperidine-1-carboxylate (Compound 25-9, 3.16 g, 10 mmol) in dry tetrahydrofuran (100 ml) was cooled to −78° C. and lithium diisopropylamide (2 M in tetrahydrofuran, 5 mL, 10 mmol) was added dropwise over 10 minutes. The reaction was stirred for 1 hour at −78° C. A solution of methyl 2-bromoacetate (1.53 g, 10 mmol) in dry tetrahydrofuran (10 mL) was added dropwise over 5 minutes. The reaction mixture was stirred for 4 hours at −78° C., quenched with ammonium chloride (sat. aq., 10 mL) at −78° C., and neutralized with 1 mL acetic acid (1 mL). The solution was extracted with ethyl acetate and the combined organic layer was washed with brine, dried over anhydrous sodium sulfate, and concentrated to give the crude product. Flash column chromatography on silica gel (ethyl acetate in petroleum ether) yielded tert-butyl 4-(3-(2-methoxy-2-oxoethyl)-2-oxoindolin-1-yl) piperidine-1-carboxylate (Compound 25-10, 1.98 g, yield: 51%) as a pale yellow solid. MS (ESI): m/z: 333[M+H−56]$^+$. $^1$H NMR (400 MHz, CDCl$_3$) δ: 7.24 (m, 2H), 7.01 (m, 2H), 4.39 (m, 1H), 4.30 (d, 2H, J=12.8 Hz), 3.73 (m, 1H), 3.65 (s, 3H), 3.06 (dd, 1H, J=4.4, 12.8 Hz), 2.84 (m, 3H), 2.34 (m, 2H), 1.73 (d, 2H, J=12.8 Hz), 1.50 (s, 9H).

Preparation of Compound 25-11

To a solution of tert-butyl 4-(3-(2-methoxy-2-oxoethyl)-2-oxoindolin-1-yl) piperidine-1-carboxylate (Compound 25-10, 3.88 g, 10 mmol) in dry dichloromethane (100 ml) was added trifluoroacetic acid (5.70 g, 50 mmol), the mixture was stirred for 1 hour at room temperature and concentrated to yield methyl 2-(2-oxo-1-(piperidin-4-yl)indolin-3-yl)acetate (Compound 25-11, TFA salt 3.90 g, yield: 97%) as a pale yellow syrup. MS (ESI): m/z: 289[M+H]$^+$.

Preparation Compound 25-12

To a solution of methyl 2-(2-oxo-1-(piperidin-4-yl)indolin-3-yl)acetate trifluoroacetic acid salt (Compound 25-11, 80 mg, 0.2 mmol) in N,N-dimethylformamide (3 mL) was added triethylamine (91 mg, 0.9 mmol). The mixture was stirred at room temperature for 10 min. Then to the mixture was added sodium iodide (5 mg, 0.03 mmol) and a solution of 1-(chloromethyl)-8-methylnaphthalene (Compound 25-5, 58 mg). The reaction mixture was stirred at room temperature overnight, then the mixture was poured into ice-water, extracted with dichloromethane, washed with brine, dried, concentrated, and purified by TLC to yield Compound 25-12 (16 mg, yield 12%) as a white solid. MS (ESI): m/z: 459[M+H]$^+$.

Preparation of Compound 63

A solution of methyl 2-(3-hydroxy-1-(1-((8-methylnaphthalen-1-yl)methyl) piperidin-4-yl)-2-oxoindolin-3-yl)acetate (Compound 25-12, 16 mg, 0.1 mmol) in methylamine/ethanol (2 mL, 35%) was heated to 80° C. in a sealed tube and stirred for 2 hours. The mixture was concentrated in vacuum and purified by TLC to yield 2-(3-hydroxy-1-(1-((8-methylnaphthalen-1-yl)methyl)piperidin-4-yl)-2-oxoindolin-3-yl)-N-methylacetamide (Compound 63, 7 mg, 44%) as a pale yellow solid. MS: m/z 458 [M+1]$^+$, $^1$H NMR (400 MHz, CDCl$_3$) δ: 7.79 (dd, J=2.0 Hz, J=7.2 Hz, 1H), 7.72 (t, J=4.4 Hz, 1H), 7.37-7.33 (m, 5H), 7.23 (dd, J=0.8 Hz, J=7.6 Hz, 1H), 7.00-7.04 (m, 2H), 5.92 (q, J=4.6 Hz, 1H), 5.63 (br s, 1H), 4.27-4.19 (m, 1H), 3.99 (q, J=13.6 Hz, 2H), 3.12 (s, 3H), 3.02 (d, J=10.2 Hz, 2H), 2.84 (d, J=4.9 Hz, 3H), 2.70 (d, J=14.6 Hz, 1H), 2.47 (d, J=14.9 Hz, 1H), 2.26-2.42 (m, 2H), 2.07-2.22 (m, 2H), 1.59-1.70 (m, 2H).

Example 16B: Preparation of Compounds 64 and 65

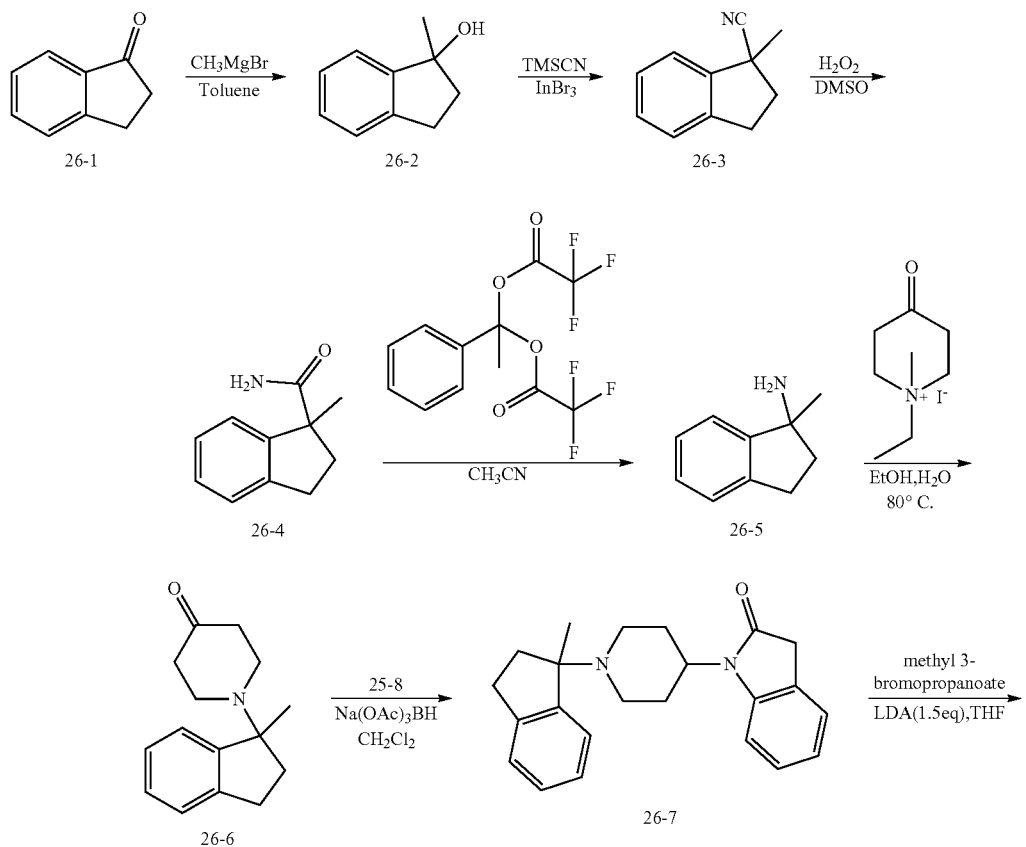

Scheme 26.

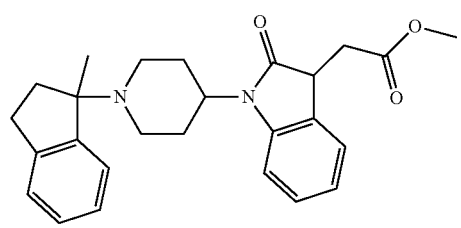

26-8

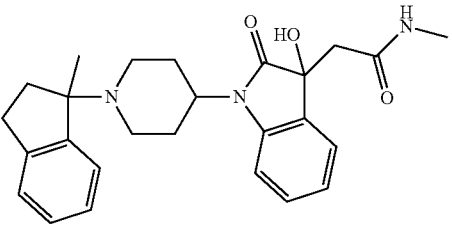

64

CH3I/K2CO3/DMF ↓       THF/CH3NH2/H2O →

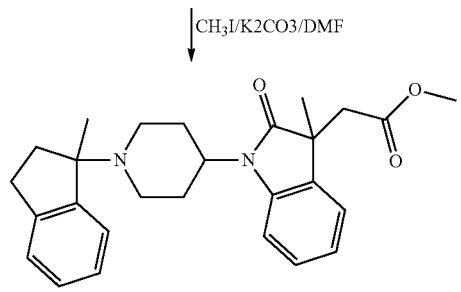

26-9

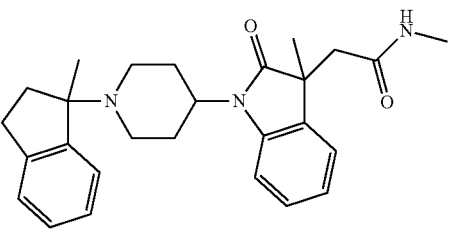

65

CH3NH2/CH3OH →

Preparation of Compound 26-2

Compound 26-1 (2.64 g, 20 mmol, 1.0 eq) was dissolved in ethyl ether (40 ml) and the system was cooled to 0° C. Then CH$_3$MgBr (1M in ethyl ether, 26 ml, 26 mmol) was added over 30 mins and the mixture was stirred for 2 hours. The reaction was quenched with NH$_4$Cl solution and extracted with ethyl acetate. The combined organic layers were dried over Na$_2$SO$_4$, filtered and condensed, and the residue was purified on silica gel (200-300 m, petrol/ethyl ester=2:1, Rf=0.2) to yield Compound 26-2 (2.13 g, 72%) as a solid. ESI/MS: 132 (M−17+1).

Preparation of Compound 26-3

TMSCN (4.28 g, 43.2 mmol) and InBr$_3$ (354 mg, 1.00 mmol) were dissolved in DCM (15 mL) and stirred for 5 mins. Compound 26-2 (2.13 g, 14.4 mmol) was added and the mixture was stirred at room temperature for 2 hours. The reaction was condensed and purified on silica gel (petrol/ethyl ester=20/1) to yield Compound 26-3 (1.18 g, 50%) as an oil. ESI/MS: 132 [M−17+H]$^+$.

Preparation of Compound 26-4

Compound 26-3 (1.18 g, 7.50 mmol) was dissolved in DMSO (5 ml) and potassium carbonate (1.03 g, 7.50 mmol) was added. H$_2$O$_2$ (1.00 ml, 29.41 mmol) was added dropwise. The reaction mixture was quenched with water and extracted with ethyl acetate. The combined organic layers were dried, filtered and condensed to yield Compound 26-4 (2.01 g, 152%) which was used without further purification. ESI/MS: 176 [M+H]$^+$.

Preparation of Compound 26-5

Compound 26-4 (2.01 g, 7.50 mmol, 1.0 equiv.) was dissolved in acetonitrile (15 mL) and water (3 mL). Ditrifluoroacet-idiobenzene (6.45 g, 15.00 mmol) was added in portions at room temperature. The mixture was stirred for 12 hours and monitored by LCMS. Upon completion, the solution was quenched with sodium hydroxide and extracted with ethyl acetate. The combined organic layer was washed with water, dried with anhydrous Na$_2$SO$_4$, and condensed. The residue was purified on silica gel (DCM/methanol) to yield Compound 26-5 (0.76 g, 69%) as an oil. ESI/MS: 132 [M−16+H]$^+$.

Preparation of Compound 26-6

A mixture of Compound 26-5 (0.76 g, 5.70 mmol) and sodium hydroxide (0.45 g, 11.40 mmol) were mixed in ethanol (3.0 mL), the mixture was heated to 80° C. Then 1-ethyl-1-methyl-4-oxopiperidinium iodide (4.45 g, 17.10 mmol) in water (1.0 mL) was added. The reaction was stirred at reflux for 2 hours and monitored by LCMS. Upon completion, the solution was extracted with DCM, the combined organic layer was washed with water, dried over anhydrous Na$_2$SO$_4$, and condensed. The residue was purified on silica gel (DCM/methanol) to yield Compound 26-6 (500 mg, 38%). ESI/MS: 132 (fragment).

Preparation of Compound 26-7

A solution of Compound 26-6 (500 mg, 2.18 mmol, 1.0 equiv.) in DCM (10 mL) was mixed with methyl 2-(2-aminophenyl)acetate (1.08 g, 6.55 mmol) and acetic acid (650 mg, 10.90 mmol). The mixture was stirred at room temperature for 2 hours, then NaBH(OAc)$_3$ (1.47 g, 6.54 mmol) was added in portions. The reaction mixture was stirred at room temperature for two days and monitored by LCMS. Upon completion, the reaction was quenched with water and extracted with ethyl acetate. The combined organic layers were dried with Na$_2$SO$_4$, filtered and condensed. The residue was purified on silica gel (petrol/ethyl acetate) to yield Compound 26-7 (452 mg, 60%) as a solid. ESI/MS: 347 [M+H]$^+$.

Preparation of Compound 26-8

Compound 26-7 (450 mg, 1.30 mmol) was dissolved in THF (5 mL), the mixture was cooled to −78° C. and LDA (1.0 ml, 2.00 mmol) was added dropwise. The mixture was stirred for 1 hour, then a methyl 3-bromopropanoate (200 mg, 1.32 mmol) solution in THF (1.0 mL) was added dropwise. The reaction mixture was stirred for 6 hours, and monitored by LCMS. The reaction mixture was quenched with saturated ammonium chloride solution and extracted with ethyl acetate. The combined organic layers were dried with anhydrous sodium sulfite, filtered and condensed to yield crude Compound 26-8 (500 mg, 93.6%) which was used without further purification. ESI/MS: 419 [M+H]⁺.

Preparation of Compound 64

Compound 26-8 (42 mg, 0.10 mmol, 1.0 equiv.) was dissolved in THF (2 mL) and methyl amine solution (aq, 33%, 1 ml) was added. The mixture was heated to reflux for 3 hours in a sealed tube and monitored by LCMS. Upon completion, the reaction was quenched with water and extracted with ethyl acetate. The combined organic layers were dried with Na₂SO₄, filtered and condensed. The residue was purified by HPLC to yield Compound 64 (16 mg, 37%). ESI/MS: 434 [M+H]⁺. 1H NMR (400 MHz, CD3OD): 7.19-7.23 (m, 4H), 7.10-7.12 (m, 3H), 6.92-6.96 (m, 1H), 4.01-4.04 (m, 1H), 3.27-3.30 (m, 1H), 2.73-2.86 (m, 5H), 2.26-2.48 (m+s, 6H), 2.12-2.19 (m, 2H), 1.50-1.76 (m, 3H), 1.40 (s, 3H).

Preparation of Compound 26-9

Compound 26-8 (450 mg, 1.07 mmol, 1.0 equiv.) was dissolved in DMF (5 mL) and iodomethane (303 mg, 2.14 mmol) was charged followed by K₂CO₃ (148 mg, 1.07 mmol). The solution was stirred at room temperature for 1 hour tube and monitored by LCMS. Upon completion, the reaction was quenched with water and extracted with ethyl acetate. The combined organic layers were dried with Na₂SO₄, filtered and condensed, and the residue was purified on silica gel (petrol/ethyl acetate) to yield Compound 26-9 (360 mg, 78%). ESI/MS: 433 [M+H]⁺.

Preparation of Compound 65

Compound 26-9 (360.0 mg, 0.83 mmol, 1.0 equiv.) was dissolved in methylamine solution (2.0 mL, 30%) in a sealed tube. The mixture was heated to reflux for 6 hours, and the reaction was monitored by LCMS. The mixture was condensed and extracted with ethyl acetate. The combined organic layers were dried with anhydrous sodium sulfite, filtered and condensed, and the residue was purified on silica gel (DCM: Methanol) to yield Compound 65 (120 mg, 33%) as a solid. ESI/MS: 432 [M+H]⁺. 1H NMR (SEP-0375093, 400 MHz, MeOD): 7.20-7.25 (m, 2H), 7.10-7.15 (m, 5H), 6.89-6.93 (m, 1H), 4.06-4.13 (m, 1H), 3.28-3.29 (m, 1H), 2.64-2.89 (m, 6H), 2.20-2.30 (m+s, 5H), 2.12-2.19 (m, 2H), 1.50-1.76 (m, 3H), 1.40 (s, 3H), 1.21 (s, 3H).

Example 16C: Chiral Separation of Compound 65

Compound 65 was separated using chiral chromatography into four isomers:

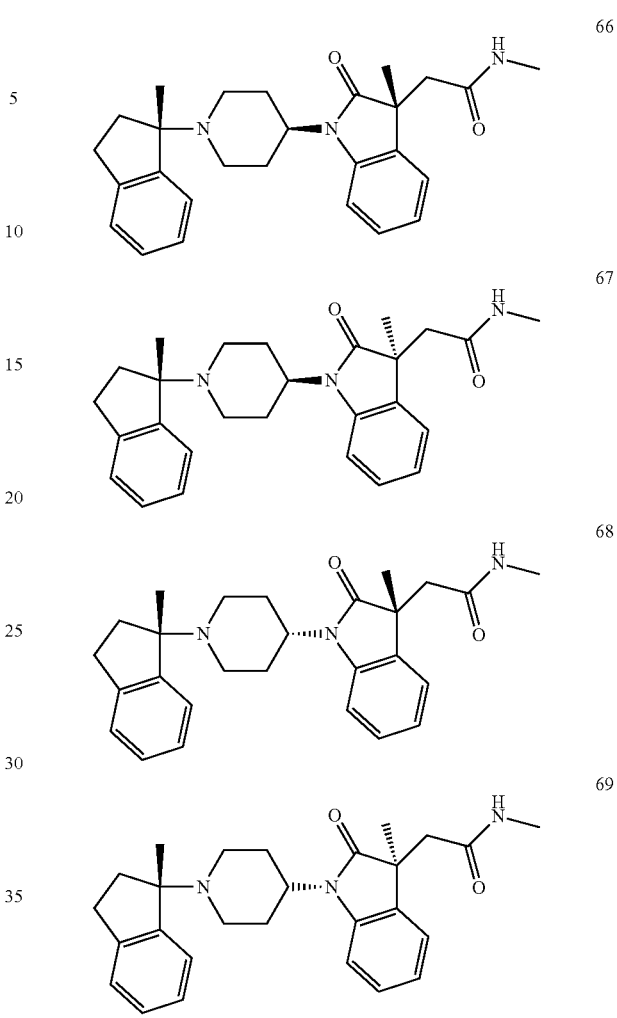

Compound 66 (15 mg): 1H NMR (400 MHz, MeOD): 7.24-7.29 (m, 2H), 7.18-7.23 (m, 5H), 6.98-7.02 (m, 1H), 4.13-4.18 (m, 1H), 3.37-3.40 (m, 1H), 2.81-2.96 (m, 3H), 2.69-2.77 (m, 3H), 2.25-2.59 (m+s, 5H), 2.22-2.24 (m, 2H), 1.66-1.76 (m, 3H), 1.50 (s, 3H), 1.23-1.25 (m, 4H).

Compound 67 (16 mg): 1H NMR (400 MHz, MEOD): 7.24-7.30 (m, 2H), 7.08-7.15 (m, 5H), 6.89-6.92 (m, 1H), 4.08-4.09 (m, 1H), 3.27-3.31 (m, 1H), 2.81-2.86 (m, 3H), 2.72-2.79 (m, 2H), 2.32-2.46 (m+s, 5H), 2.11-2.20 (m, 2H), 1.68-1.76 (m, 2H), 1.50-1.51 (m, 1H), 1.48 (s, 3H), 1.25-1.26 (m, 4H).

Compound 68 (25 mg): 1H NMR (400 MHz, MeOD): 7.30-7.37 (m, 2H), 7.20-7.25 (m, 5H), 6.99-7.02 (m, 1H), 4.17-4.19 (m, 1H), 3.34-3.41 (m, 1H), 2.87-2.97 (m, 3H), 2.70-2.82 (m, 2H), 2.42-2.57 (m+s, 5H), 2.25-2.31 (m, 2H), 1.80-1.86 (m, 2H), 1.63-1.65 (m, 1H), 1.48 (s, 3H), 1.25-1.26 (m, 4H).

Compound 69 (26 mg): 1H NMR (400 MHz, MEOD,): 7.24-7.34 (m, 2H), 7.18-7.25 (m, 5H), 6.99-7.02 (m, 1H), 4.17-4.19 (m, 1H), 3.34-3.41 (m, 1H), 2.87-2.97 (m, 3H), 2.73-2.82 (m, 2H), 2.42-2.69 (m+s, 5H), 2.22-2.29 (m, 2H), 1.80-1.85 (m, 3H), 1.50 (s, 3H), 1.25-1.26 (m, 4H).

Example 16D: Preparation of Compounds 70 and 71

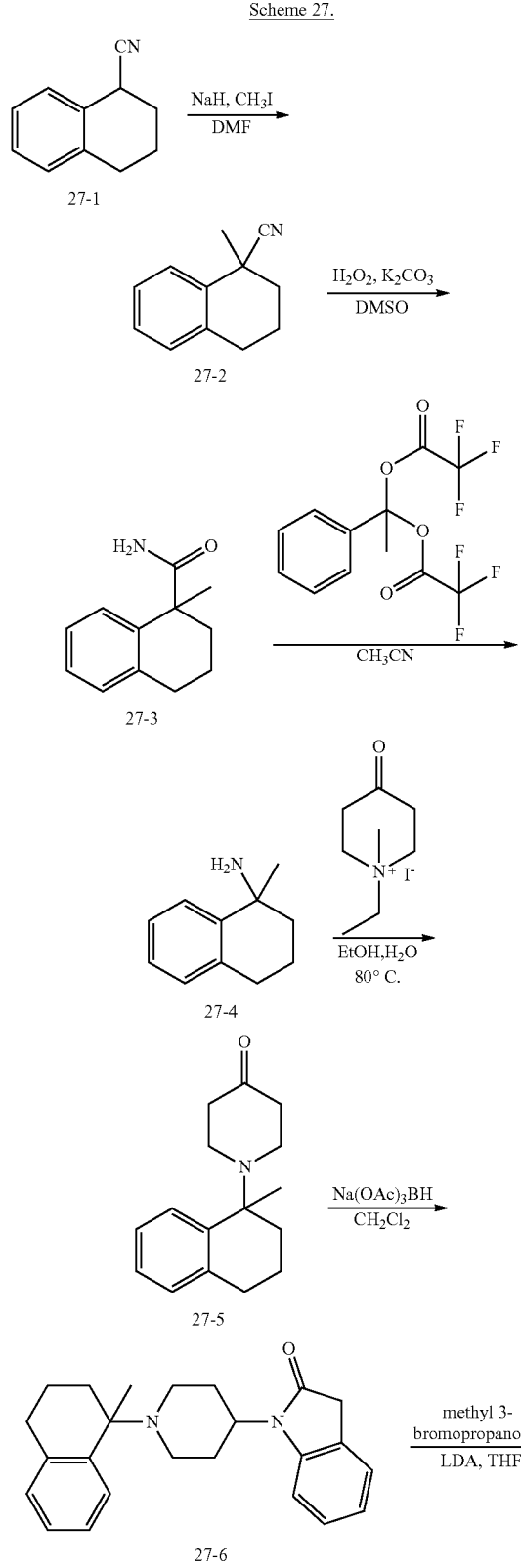

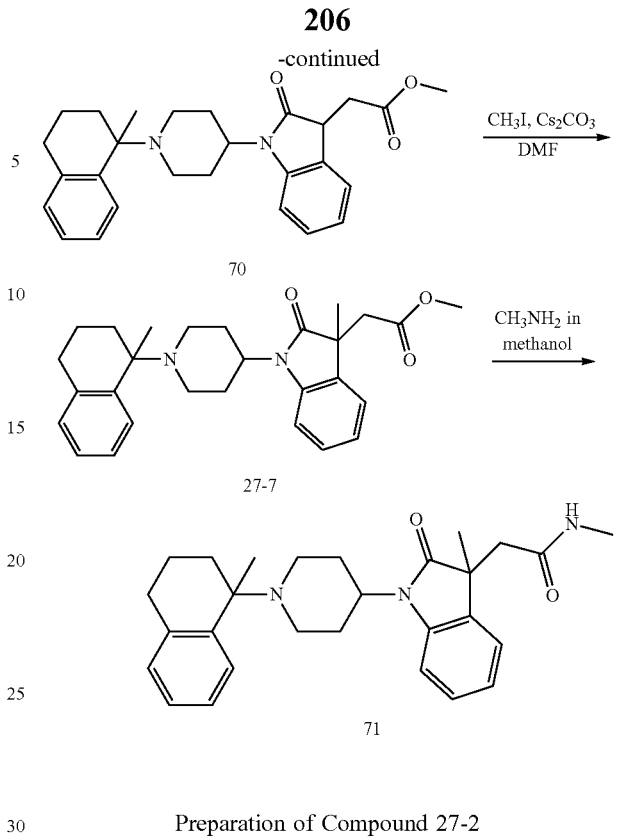

Preparation of Compound 27-2

To a mixture of 1,2,3,4-tetrahydronaphthalene-1-carbonitrile (Compound 27-1, 7.85 g, 50 mmol) in DMF (80 mL) was added NaH (2.16 g, 150 mmol) in portions at 0° C., then the mixture was stirred at room temperature for 1 hour. CH$_3$I (14.2 g, 100 mmol) was added dropwise and the reaction mixture was stirred at room temperature overnight. Water was added, and the mixture was extracted with ethyl acetate, dried and concentrated to yield crude Compound 27-2 (6.5 g) which was used without further purification. (MS (ESI): m/z 172 [M+H]$^+$.

Preparation of Compound 27-3

To a solution of 1-methyl-1,2,3,4-tetrahydronaphthalene-1-carbonitrile (Compound 27-2, 5 g, 29 mmol) and K$_2$CO$_3$ (12 g, 87 mmol) in DMSO (100 mL) was added H$_2$O$_2$ (30%, 80 mL) dropwise, then the mixture was stirred at room temperature for 5 hours. Water was added, and the mixture was extracted with ethyl acetate, dried and concentrated to give the crude product. The crude product was purified by reverse gel (eluted from water to 75:25 water:acetonitrile, 0.1% NH$_3$H$_2$O) to yield 1-methyl-1,2,3,4-tetrahydronaphthalene-1-carboxamide (Compound 27-3, 2.42 g, 44%) as a brown oil. (MS (ESI): m/z 190 [M+H]$^+$

Preparation of Compound 27-4

To a mixture of 1-methyl-1,2,3,4-tetrahydronaphthalene-1-carboxamide (Compound 27-3, 2.1 g, 11.1 mmol) in water/acetonitrile (40 mL/40 mL) stirred at 0° C. was added [Bis(trifluoroacetoxy) iodo]benzene (7.17 g, 16.6 mmol) in one portion, and the resulting mixture was stirred at room temperature overnight. Water was added and the solution was extracted with dichloromethane. The aqueous phase was neutralized with ammonium hydroxide (until pH=7) and then extracted with dichloromethane. The organic phase was dried and condensed to give the crude product. The crude product was purified by reverse gel (water to 90:10 water/acetonitrile, 0.1% TFA) to yield 1-(1-methyl-1,2,3,4-tetrahydronaphthalen-1-yl)piperidin-4-one (Compound 27-4, 1.31 g, yield: 73%) as a black oil. (MS (ESI): m/z 144 [M+H]$^+$ Preparation of Compound 27-5

A mixture of 1-methyl-1,2,3,4-tetrahydronaphthalen-1-amine (1.315 g, 8 mmol) and potassium carbonate (280 mg, 2 mmol) in ethanol (3 mL) was stirred at 80° C., then 1-ethyl-1-methyl-4-oxopiperidinium iodide (5.5 g, 20 mmol) in water (3 mL) was added dropwise. The mixture was stirred at 80° C. for 6 hours, then water was added and the solution was extracted with dichloromethane. The organic phase was dried and concentrated and the crude product was purified by silica gel (petroleum ether: ethyl acetate) to yield 1-(1-methyl-1,2,3,4-tetrahydronaphthalen-1-yl) piperidin-4-one (Compound 27-5, 1.03 g, yield: 49%) as a white solid. (MS (ESI): m/z 262[M+H]$^+$)

Preparation of Compound 27-6

To a mixture of 1-(1-methyl-1,2,3,4-tetrahydronaphthalen-1-yl) piperidin-4-one (Compound 27-5, 810 mg, 3.3 mmol) and methyl 2-(2-aminophenyl)acetate (3.32 g, 20 mmol) in dichloromethane (20 mL) was added sodium triacetoxyborohydride (3.53 g, 16.7 mmol) and acetic acid (2 mL). The resulting mixture was stirred at room temperature overnight, then water was added and the aqueous phase was adjusted pH to 8 and extracted with ethyl acetate. The organic layer was dried and concentrated, and the residue was purified by silica gel (petroleum ether:ethyl acetate) to yield 1-(1-(1-methyl-1,2,3,4-tetrahydronaphthalen-1-yl) piperidin-4-yl) indolin-2-one (Compound 27-6, 596 mg, yield: 49.6%) as an off-white solid. (MS (ESI): m/z 361[M+H]$^+$)

Preparation of Compound 70

To a mixture of 1-(1-(1-methyl-1,2,3,4-tetrahydronaphthalen-1-yl) piperidin-4-yl) indolin-2-one (Compound 27-6, 596 mg, 1.6 mmol) in dry tetrahydrofuran (15 mL) was added lithium diisopropylamide (2M in tetrahydrofuran, 1.24 mL, 2.48 mmol) dropwise at −78° C. After 30 mins, methyl 3-bromopropanoate (278 mg, 1.8 mmol) was added and the resulting mixture was stirred at −78° C. for 6 hours. Upon completion, the reaction was quenched with water and extracted with dichloromethane (20 mL×3), dried and concentrated to yield methyl 2-(1-(1-(1-methyl-1,2,3,4-tetrahydronaphthalen-1-yl) piperidin-4-yl)-2-oxoindolin-3-yl)acetate (Compound 70). (MS (ESI): m/z 433[M+H]$^+$). 1H NMR (400 MHz, CDCl3) δ 7.73 (d, J=7.9 Hz, 1H), 7.29 (t, J=7.8 Hz, 1H), 7.25-7.14 (m, 3H), 7.10 (t, J=7.3 Hz, 1H), 7.01 (t, J=8.1 Hz, 2H), 4.27-4.20 (m, 1H), 3.79-3.70 (m, 1H), 3.65 (d, J=7.2 Hz, 3H), 3.35 (d, J=8.1 Hz, 1H), 3.06 (dt, J=16.8, 4.5 Hz, 1H), 2.85-2.71 (m, 3H), 2.63 (dd, J=10.7, 2.7 Hz, 1H), 2.52-2.37 (m, 2H), 2.32-2.18 (m, 2H), 2.03-1.89 (m, 2H), 1.83-1.76 (m, 2H), 1.69-1.64 (m, 1H), 1.60 (s, 1H), 1.42 (s, 3H).

Preparation of Compound 27-8

To a mixture of methyl 2-(1-(1-(1-methyl-1,2,3,4-tetrahydronaphthalen-1-yl) piperidin-4-yl)-2-oxoindolin-3-yl) acetate (Compound 70, 577 mg, 1.33 mmol) and cesium carbonate (870 mg, 2.67 mmol) in dimethylformamide (5 mL) was added iodomethane (342 mg, 2.4 mmol). The mixture was stirred at room temperature for 3 hours. Upon completion, water was added and the mixture was extracted with ethyl acetate. The organic layer was dried and concentrated, and the residue was purified by TLC to yield methyl 2-(3-methyl-1-(1-(1-methyl-1,2,3,4-tetrahydronaphthalen-1-yl) piperidin-4-yl)-2-oxoindolin-3-yl)acetate (Compound 27-8, 150 mg, yield: 25%) as a white solid. (MS (ESI): m/z 447 [M+H]$^+$)

Preparation of Compound 71

A mixture of methyl 2-(3-methyl-1-(1-(1-methyl-1,2,3,4-tetrahydronaphthalen-1-yl) piperidin-4-yl)-2-oxoindolin-3-yl)acetate (Compound 27-8, 150 mg, 0.33 mmol) in methylamine (1 mL) was heated to 90° C. for 12 hours under microwave irradiation. Upon completion, the mixture was purified by HPLC to yield Compound 71 (50 mg, yield: 33%) as a white solid. (MS (ESI): m/z 445 [M+H]$^+$)

Example 16E: Chiral Separation of Compound 71

Compound 71 was separated using chiral chromatography into four isomers:

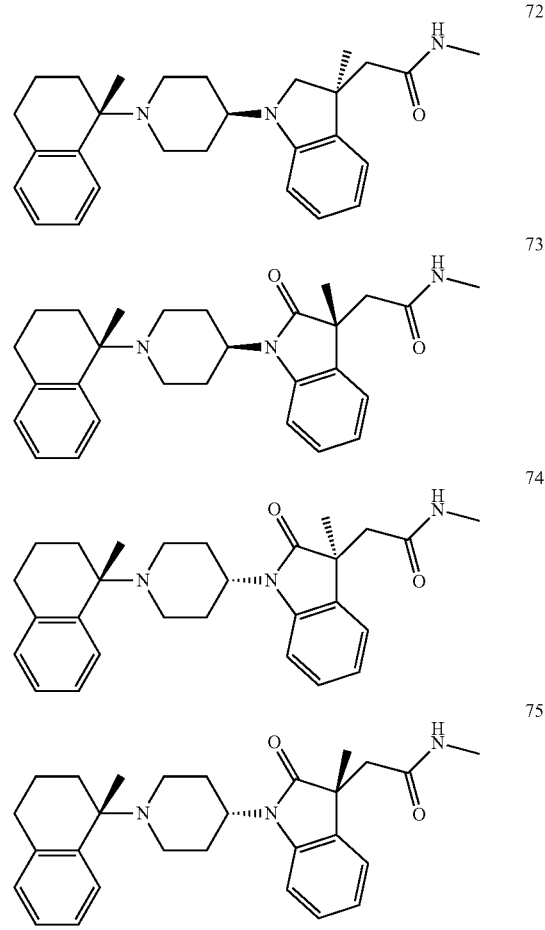

Compound 72: (400 MHz, CDCl$_3$): δ 7.77-7.75 (d, J=8 Hz, 1H), 7.32-7.27 (m, 2H), 7.20-7.17 (m, 2H), 7.14-7.04 (m, 3H), 6.22-6.21 (m, 1H), 4.21 (s, 1H), 3.39-3.37 (m, 1H), 2.80-2.74 (m, 3H), 2.67-2.62 (m, 5H), 2.53-2.42 (m, 2H), 2.35-2.23 (m, 2H), 2.02-1.92 (m, 2H), 1.82-1.52 (m, 2H), 1.68-1.52 (m, 2H), 1.44 (s, 3H), 1.42 (s, 3H).

Compound 73: (400 MHz, CDCl$_3$): δ 7.76-7.74 (d, J=8 Hz, 1H), 7.32-7.27 (m, 2H), 7.20-7.17 (m, 2H), 7.14-7.04 (m, 3H), 6.30-6.29 (m, 1H), 4.21 (s, 1H), 3.39-3.37 (m, 1H), 2.79-2.74 (m, 3H), 2.67-2.62 (m, 5H), 2.53-2.42 (m, 2H), 2.35-2.23 (m, 2H), 2.02-1.92 (m, 2H), 1.82-1.52 (m, 2H), 1.68-1.52 (m, 2H), 1.44 (s, 3H), 1.42 (s, 3H).

Compound 74: (1.98 mg, yellow solid); (400 MHz, CDCl$_3$): δ 7.76-7.74 (d, J=8 Hz, 1H), 7.32-7.27 (m, 2H), 7.20-7.17 (m, 2H), 7.14-7.04 (m, 3H), 6.29-6.28 (m, 1H), 4.21 (s, 1H), 3.39-3.37 (m, 1H), 2.79-2.74 (m, 3H), 2.67-2.62 (m, 5H), 2.53-2.42 (m, 2H), 2.35-2.23 (m, 2H), 2.02-1.92 (m, 2H), 1.82-1.52 (m, 2H), 1.68-1.52 (m, 2H), 1.44 (s, 3H), 1.42 (s, 3H).

Compound 75: (1.91 mg, white solid); (400 MHz, CDCl$_3$): δ 7.77-7.75 (d, J=8 Hz, 1H), 7.32-7.27 (m, 2H), 7.23-7.19 (m, 2H), 7.14-7.05 (m, 3H), 6.32-6.31 (m, 1H), 4.23-4.21 (m, 1H), 3.39-3.37 (d, J=8 Hz, 1H), 2.81-2.75 (m, 3H), 2.70-2.63 (m, 5H), 2.53-2.40 (m, 2H), 2.34-2.20 (m, 2H), 2.05-1.93 (m, 2H), 1.85-1.77 (m, 2H), 1.71-1.52 (m, 2H), 1.44 (s, 3H), 1.42 (s, 3H).

Example 17A: Preparation of Compound 57

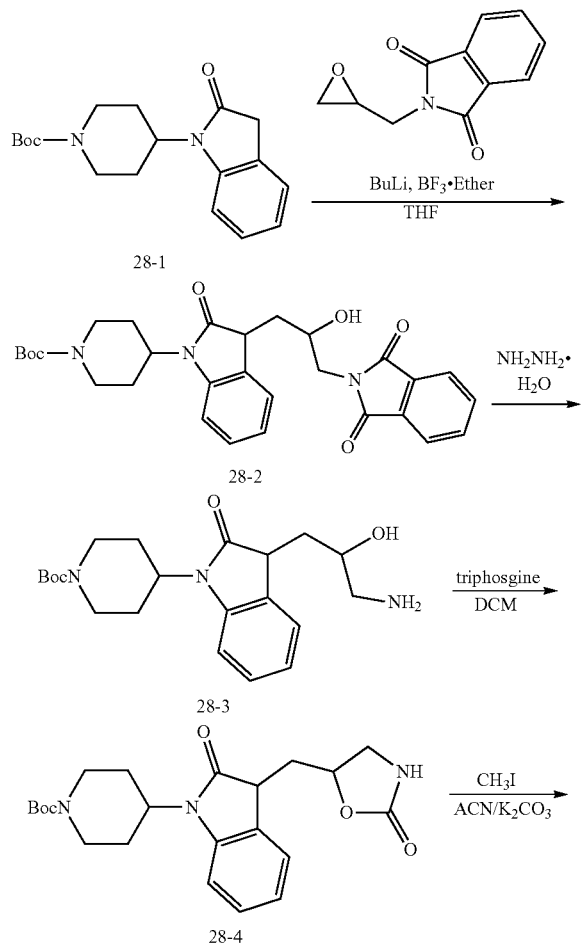

Scheme 28A.

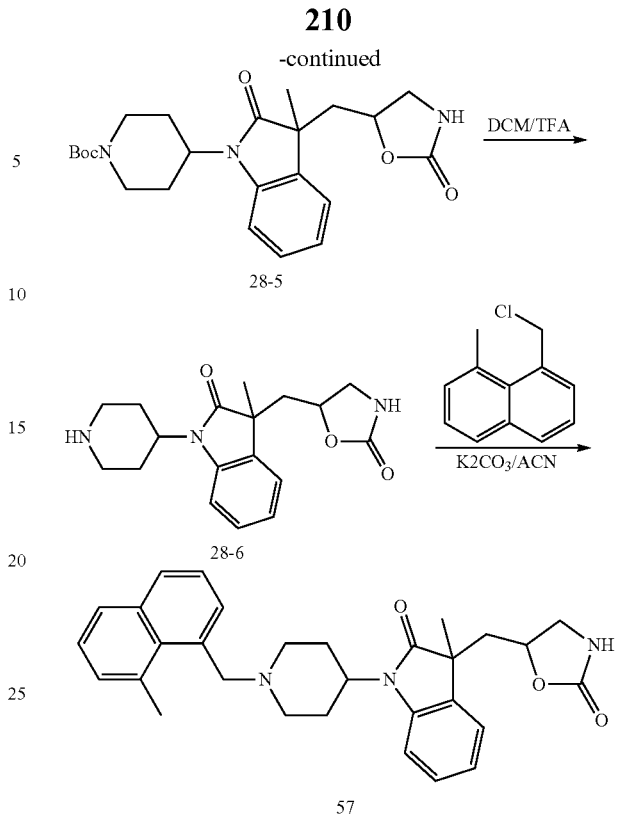

Preparation of Compound 28-2

Compound 28-1 (1.58 g, 5 mmol, 1.0 eq) was dissolved in THF (5 mL) and the system was cooled to −78° C. Then BuLi (2.5M in hexane, 3 mL, 7.5 mmol) was dropped and the mixture was stirred for 10 min followed with BF3.Et2O (1.06 g, 7.5 mmol) was added. The mixture was stirred for 15 min, then 2-(oxiran-2-ylmethyl) isoindoline-1,3-dione (1.02 g, 5.00 mmol) solution in THF (5 mL) was dropped within 5 min. Then the mixture was stirred at −78° C. for another 2 hrs and allowed to warm RT overnight. The reaction was quenched with NH4Cl solution and extracted with ethyl ester for three times (20 mL×3). The combined organic layers were dried with Na2SO4. After filtered and condensed, the residue was purified with silicon column (200-300 m, petrol/ethyl ester=2:1, Rf=0.2). Compound 28-2 (600 mg, 23%) was obtained as solid. ESI/MS: 420 (M−100+H).

Preparation of Compound 28-3

Compound 28-2 (0.60 g, 1.15 mmol) was dissolved in ethanol (5 mL) and hydrazine (85%, 1.0 mL) was charged, the mixture was stirred at RT for 2 h, monitored by LCMS and compound 1-3 formed. The reaction was purified with reverse phase column (TFA 0.1%, acetonitrile/H2O=25%) and Compound 28-3 (400 mg, 88%) was obtained as solid after lyophilized. ESI/MS: 390 [M+H]$^+$.

Preparation of Compound 28-4

Compound 28-3 (0.40 g, 1.03 mmol) was dissolved in DCM (5 mL) and TEA (0.31 g, 3.09 mL) was charged. The system was cooled to 0° C. and triphosgene (101 mg, 0.34 mmol) was charged. The mixture was stirred for 2 hrs, monitored by LCMS and Compound 28-3 disappeared. The reaction was quenched with NaHCO3 solution and extracted with DCM. After condensed and the residue was purified with reverse phase column (TFA 0.1%, acetonitrile/H2O=33%) and Compound 28-4 (200 mg, 47%) was obtained as solid after lyophilized. ESI/MS: 316 [M−100+H]+.

Preparation of Compound 28-5

A mixture of Compound 1-4 (0.10 g, 0.24 mmol, 1.0 equiv.), K2CO3 (0.066 g, 0.48 mmol) and acetonitrile (5 mL) was stirred at room temperature, then CH3I (0.07 g, 0.48 mmol) was charged. The mixture was stirred at RT for 12 hrs. Then LCMS indicated that it is completed. The solution was quenched with water and extracted with ethyl ester (10 mL×3), the combined organic layer was washed with water and dried with anhydrous Na2SO4. After condensed, the crude Compound 28-5 (80 mg, 77%) was obtained and used for next without further purification. ESI/MS: 330 [M−100+H]+.

Preparation of Compound 28-6

A mixture of Compound 28-5 (80.0 mg, 0.18 mmol, 1.0 equiv.), TFA (0.5 mL) and DCM (3.0 mL) was stirred at room temperature for 2 hrs. Then LCMS indicated that it is completed. The solution was quenched with NaHCO3 solution and extracted with ethyl ester (10 mL×3), the combined organic layer was washed with water and dried with anhydrous Na2SO4. After condensed, the crude Compound 28-6 (40 mg, 66%) was obtained and used for next without further purification. ESI/MS: 330 [M+H]+.

Preparation of Compound 57

A solution of Compound 28-6 (40.00 mg, 0.12 mmol, 1.0 equiv.) in acetonitrile (5 mL) was mixed with K2CO3 (42.0 mg) and stirred at RT for 12 hrs. Then LCMS indicated that the reaction is completed. Quenched with water and extracted with ethyl ester (10 mL×3), the combined organic layers were dried with Na2SO4. After filtered and condensed, the residue was purified with reverse phase column (TFA 0.1%, Acetonitrile/H2O=35%), and Compound 57 (15 mg, 26%) was obtained. ESI/MS: 484 [M+H]+. 1H NMR (400 MHz, MEOD): 8.12 (m, 1H), 7.91 (m, 1H), 7.75 (m, 1H), 7.49-7.60 (m, 3H), 7.21-7.34 (m, 2H), 7.12-7.19 (m, 2H), 5.06 (s, 2H), 4.52-4.88 (m, 2H), 3.61-3.64 (m, 2H), 3.29-3.40 (m, 3H), 3.10-3.15 (m, 1H), 2.99 (s, 3H), 2.71-2.78 (m, 2H), 2.05-2.40 (m, H), 1.80-1.85 (m, 3H).

Example 17B: Preparation of Compounds 56 and 76

Scheme 28B.

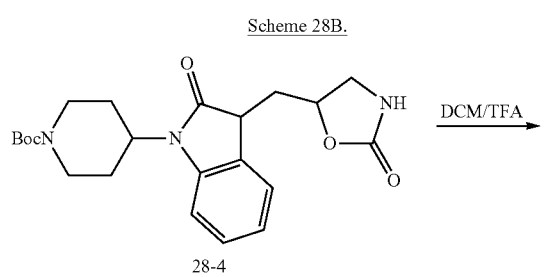

28-4

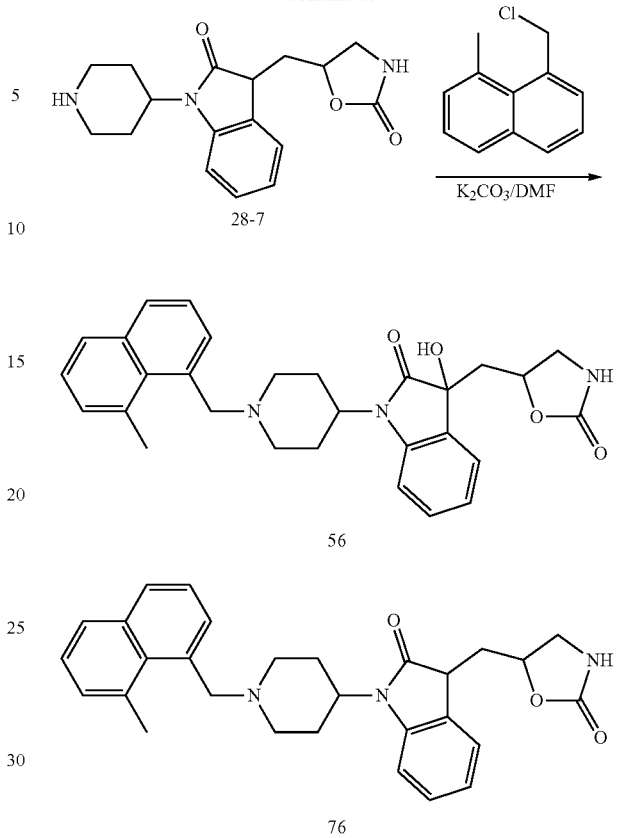

28-7

56

76

Preparation of Compound 28-7

A mixture of Compound 28-4 (100 mg, 0.24 mmol, 1.0 equiv.), TFA (0.5 mL) and DCM (3.0 mL) was stirred at room temperature for 2 hrs. Then LCMS indicated that it is completed. The solution was quenched with NaHCO3 solution and extracted with ethyl ester (10 mL×3). The combined organic layer was washed with water and dried with anhydrous Na2SO4. After condensed, crude Compound 28-7 (60 mg, 79%) was obtained and used for next without further purification. ESI/MS: 316 [M+H]+.

Preparation of Compounds 56 and 76

A solution of Compound 28-7 (31.5 mg, 0.10 mmol, 1.0 equiv.) and 1-(chloromethyl)-8-methylnaphthalene (18.8 mg, 0.10 mmol) in DMF (3 mL) were mixed with K2CO3 (13.8 mg, 0.10 mmol) and stirred at RT for 12 hrs. Then LCMS indicated that the reaction is completed. Quenched with water and extracted with ethyl ester (10 mL×3), the combined organic layers were dried with Na2SO4. After filtered and condensed, the residue was purified with reverse phase column (TFA 0.1%, Acetonitrile/H2O=29%), and Compound 56 (8.0 mg, 16%) and Compound 76 (5.0 mg, 10%) were obtained. Compound 56: ESI/MS, 486 [M+H]+. 1H NMR (400 MHz, CD3OD): 7.99-8.01 (m, 1H), 7.76-7.78 (m, 1H), 7.62-7.63 (m, 1H), 7.41-7.49 (m, 1H), 7.36-7.39 (m, 2H), 7.22-7.32 (m, 2H), 7.01-7.06 (m, 2H), 4.97 (s, 2H), 4.31-4.35 (m, 1H), 3.96-3.98 (m, 1H), 3.42-3.53 (m, 3H), 3.32-3.39 (m, 2H), 3.02-3.06 (m, 1H), 2.87 (s, 3H), 2.59-2.68 (m, 2H), 2.17-2.43 (m, 2H), 1.87-2.03 (m, 2H). SEP-0373242: ESI/MS, 470 [M+H]+. Compound 76: ESI/MS, 470 [M+H]$^+$, $^1$H NMR (400 MHz, CD3OD): 8.07-8.09 (m, 1H), 7.87-7.89 (m, 1H), 7.73-7.74 (m, 1H), 7.46-7.60 (m, 3H), 7.27-7.37 (m, 2H), 7.09-7.17 (m, 2H), 5.08 (s, 2H), 4.92 (m, 1H), 4.46-4.50 (m, 2H), 3.53-3.64 (m, 4H), 3.34-3.38 (m, 2H), 3.16-3.20 (m, 1H), 2.98 (s, 3H), 2.72-2.78 (m, 2H), 2.38-2.41 (m, 2H), 1.87-2.03 (m, 2H)

Example 17C: Preparation of Compound 77

Scheme 28C.

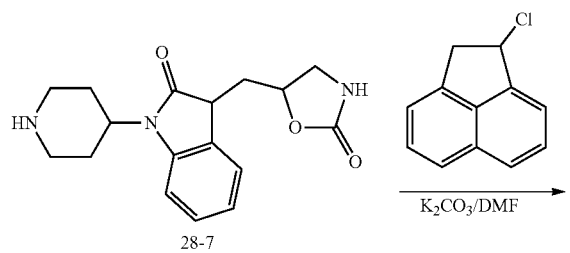

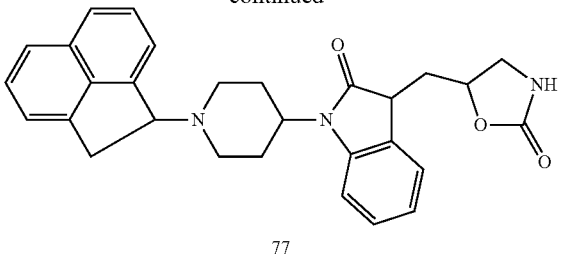

77

A solution of Compound 28-7 (25 mg, 0.08 mmol, 1.0 equiv.) and 1-chloro-1,2-dihydroacenaphthylene (18.0 mg, 0.10 mmol) in DMF (3 mL) were mixed with K2CO3 (13.8 mg, 0.10 mmol) and stirred at r.t. for 12 hrs. Then LCMS indicated that the reaction is completed. Quenched with water and extracted with ethyl ester (10 mL×3), the combined organic layers were dried with Na2SO4. After filtered and condensed, the residue was purified with reverse phase column (TFA 0.1%, Acetonitrile/H2O=30%) and Compound 77 (10.0 mg, 27%) was obtained. ESI/MS, 458 [M+H]$^+$. $^1$H NMR (400 MHz, CD3OD): 7.95-7.97 (m, 1H), 7.84-7.86 (m, 1H), 7.77-7.79 (m, 1H), 7.68-7.72 (m, 1H), 7.58-7.62 (m, 1H), 7.44-7.50 (m, 2H), 7.22-7.32 (m, 2H), 7.01-7.06 (m, 2H), 4.97 (s, 2H), 4.31-4.35 (m, 1H), 3.96-3.98 (m, 1H), 3.42-3.53 (m, 3H), 3.32-3.39 (m, 2H), 3.02-3.06 (m, 1H), 2.87 (s, 3H), 2.59-2.68 (m, 2H), 2.17-2.43 (m, 2H), 1.87-2.03 (m, 2H).

Example 17D: Preparation of Compound 12

Scheme 28D.

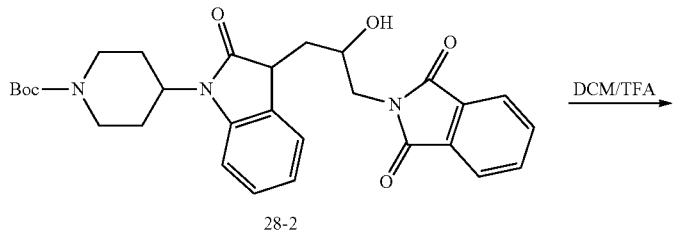

28-2

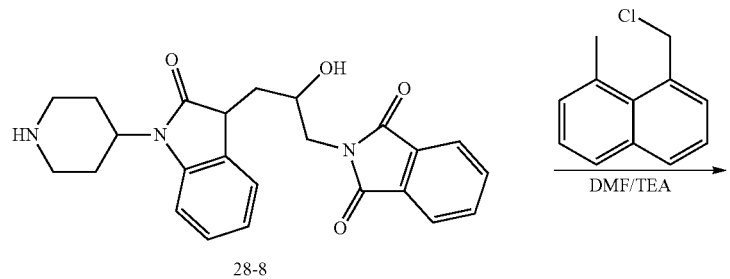

28-8

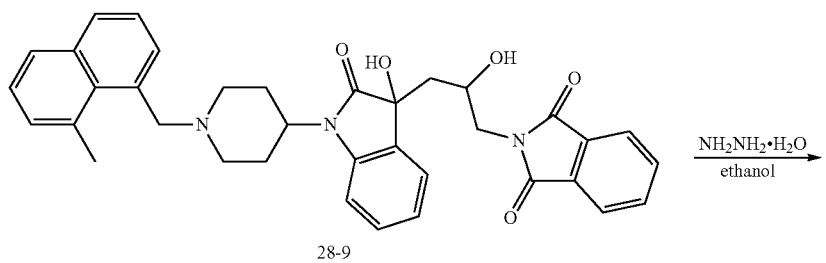

28-9

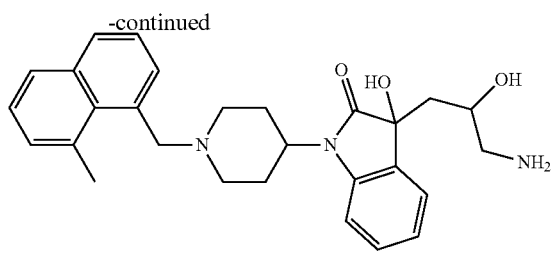

12

Preparation of Compound 28-8

A mixture of Compound 28-2 (620.00 mg, 1.19 mmol, 1.0 equiv.), TFA (1.0 mL) and DCM (5.0 mL) was stirred at room temperature for 2 hrs. Then LCMS indicated that it is completed. The solution was quenched with NaHCO3 solution and extracted with ethyl ester (50 mL×3), the combined organic layer was washed with water and dried with anhydrous Na2SO4. After condensed, Compound 28-8 (387 mg, 77%) was obtained and used for next without further purification. ESI/MS: 420 [M+H]+.

Preparation of Compound 28-9

A solution of Compound 28-8 (100.00 mg, 0.24 mmol, 1.0 equiv.) and 1-(chloromethyl)-8-methylnaphthalene (45.46 mg, 0.24 mmol) in DMF (3 mL) were mixed with TEA (101.00 mg, 1.00 mmol) and stirred at r.t. for 12 hrs. Then LCMS indicated that the reaction is completed. The reaction solution was purified with reverse phase column (TFA 0.1%, Acetonitrile/H2O=32%) and Compound 28-9 (30 mg, 21%) was obtained. ESI/MS: 590 [M+H]+.

Preparation of Compound 12

Compound 28-9 (30.0 mg, 0.05 mmol) was dissolved in ethanol (2 mL) and hydrazine (85%, 0.5 mL) was charged, the mixture was stirred at r.t. for 2 hrs, monitored by LCMS and the reaction was completed. The reaction was purified with reverse phase column (TFA 0.1%, acetonitrile/H2O=29%) and Compound 12 (12 mg, 52%) was obtained as solid after lyophilized. ESI/MS: 460 [M+H]+. 1H NMR (400 MHz, CD3OD): 8.05-8.09 (m, 1H), 7.85-7.87 (m, 1H), 7.72-7.74 (m, 1H), 7.50-7.57 (m, 1H), 7.41-7.49 (m, 2H), 7.33-7.39 (m, 1H), 7.29-7.31 (m, 1H), 7.08-7.18 (m, 2H), 5.08 (s, 2H), 4.35-4.46 (m, 1H), 3.58-3.60 (m, 2H), 3.34-3.37 (m, 2H), 2.93-3.12 (m, 1H), 2.97 (s, 3H), 2.66-2.79 (m, 3H), 2.16-2.20 (m, 1H), 1.87-2.07 (m, 3H), 1.25-1.27 (m, 1H).

Example 17E: Preparation of Compound 13

Scheme 28E.

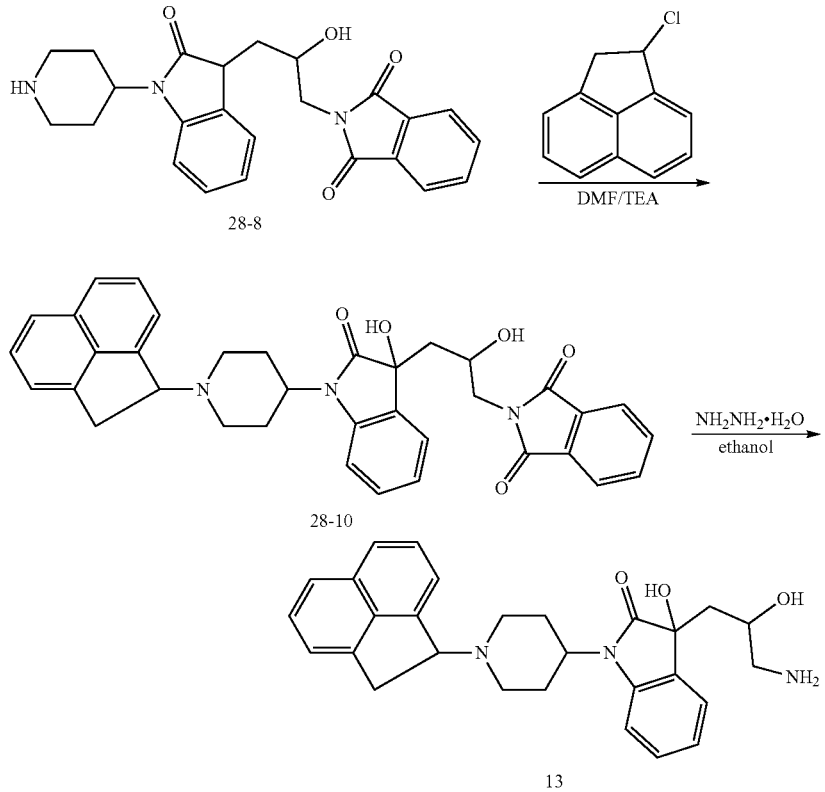

13

Preparation of Compound 28-10

A solution of compound 28-8 (100.00 mg, 0.24 mmol, 1.0 equiv.) and 1-chloro-1,2-dihydroacenaphthylene (135.60 mg, 0.72 mmol) in DMF (3 mL) were mixed with TEA (101.00 mg, 1.00 mmol) and stirred at r.t. for 12 hrs. Then LCMS indicated that the reaction is completed. The reaction solution was purified with reverse phase column (TFA 0.1%, Acetonitrile/H2O=33%) and compound 28-10 (36 mg, 25%) was obtained. ESI/MS: 588 [M+H]+.

Preparation of Compound 13

Compound 28-10 (36.0 mg, 0.06 mmol) was dissolved in ethanol (2 mL) and hydrazine (85%, 0.5 mL) was charged, the mixture was stirred at r.t. for 2 hrs, monitored by LCMS and the reaction was completed. The reaction was purified with reverse phase column (TFA 0.1%, acetonitrile/H2O=30%) and Compound 13 (11 mg, 40%) was obtained as solid after lyophilized. ESI/MS: 458 [M+H]+. 1H NMR (400 MHz, CD3OD): 7.94-7.96 (m, 1H), 7.87-7.89 (m, 1H), 7.76-7.78 (m, 1H), 7.67-7.71 (m, 1H), 7.57-7.61 (m, 1H), 7.48-7.49 (m, 1H), 7.39-7.43 (m, 1H), 7.32-7.35 (m, 1H), 7.23-7.26 (m, 1H), 7.09-7.14 (m, 1H), 5.59-5.60 (m, 1H), 4.39-4.81 (m, 1H), 3.87 (m, 2H), 3.30-3.43 (m, 1H), 3.24-3.28 (m, 1H), 3.11-3.13 (m, 1H), 3.05-3.08 (m, 1H), 2.93-2.97 (m, 2H), 2.71-2.87 (m, 3H), 2.17-2.23 (m, 1H), 1.87-2.08 (m, 3H), 1.25-1.26 (m, 1H).

Example 17F: Preparation of Compound 78

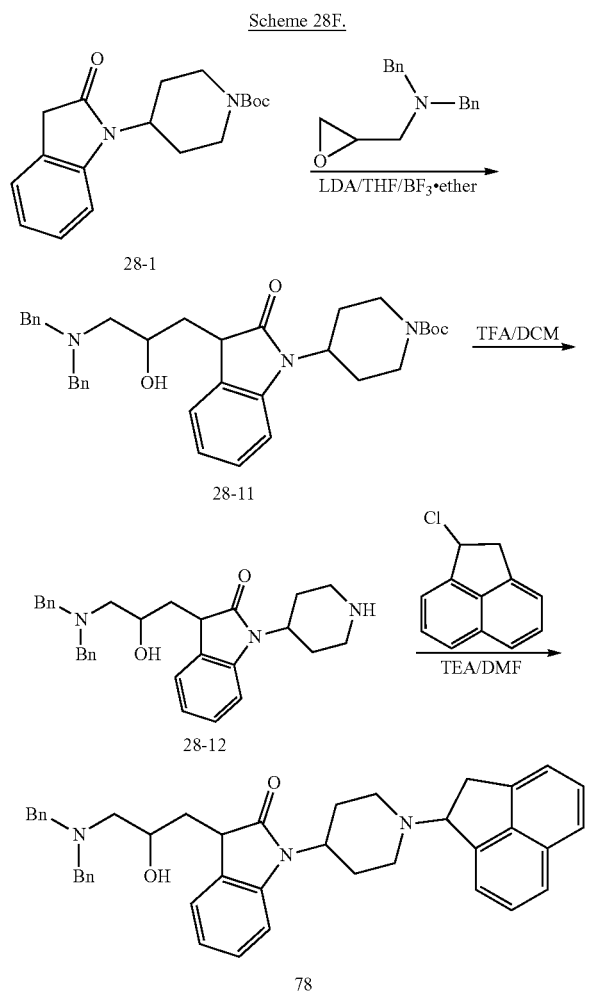

Preparation of Compound 28-11

Compound 28-1 (1.26 g, 4.00 mmol) was dissolved in anhydrous THF (20.00 mL), the system was cooled to −78° C. and LDA (4.00 mL, 8.00 mmol) was dropped. The mixture was stirred for 30 mins, then N, N-dibenzyl(oxiran-2-yl)methanamine (1.01 g, 4.00 mmol) solution in THF (10.00 mL) was dropped within 5 mins. The solution was stirred for 15 mins, then BF3.ether (0.85 g, 6.00 mmol) was charged, the mixture was stirred at −78° C. for 2 h, then allowed to warm room temperature overnight. Then the reaction was quenched with saturated NH4Cl solution and extracted with ethyl ester for three times. The combined organic layers were dried with anhydrous sodium sulfite. After filtered and condensed, the residue was purified with silicon column (petrol/ethyl ester=1:1), and Compound 28-11 (0.52 g, 23%) was obtained as orange solid. ESI/MS, 570 [M+H]+.

Preparation of Compound 28-12

A mixture of Compound 28-11 (510.00 mg, 0.90 mmol, 1.0 equiv.), TFA (1.0 mL) and DCM (5.0 mL) was stirred at room temperature for 2 h. Then LCMS indicated that it is completed. The solution was quenched with NaHCO3 solution and extracted with ethyl ester (50 mL×3), the combined organic layer was washed with water and dried with anhydrous Na2SO4. After condensed, Compound 28-12 (295 mg, 70%) was obtained and used for next without further purification. ESI/MS: 470 [M+H]+.

Preparation of Compound 78

A solution of Compound 28-12 (116.00 mg, 0.20 mmol, 1.0 equiv.) and 1-chloro-1,2-dihydroacenaphthylene (75.60 mg, 0.40 mmol) in DMF (3 mL) were mixed with TEA (80.00 mg, 0.80 mmol) and stirred at r.t. for 12 hrs. Then LCMS indicated that the reaction is completed. The reaction solution was purified with reverse phase column (TFA 0.1%, Acetonitrile/H2O=31%) and Compound 78 (12 mg, 10%) was obtained. ESI/MS: 622 [M+H]+. 1H NMR (400 MHz, CD3OD): 7.94-7.96 (m, 1H), 7.83-7.85 (m, 1H), 7.76-7.78 (m, 1H), 7.67-7.71 (m, 1H), 7.57-7.61 (m, 1H), 7.46-7.52 (m, 11H), 7.05-7.28 (m, 4H), 5.58-5.60 (m, 1H), 4.31-4.49 (m, 6H), 3.86-3.88 (m, 2H), 3.30-3.34 (m, 2H), 3.01-3.07 (m, 3H), 2.83-2.88 (m, 3H), 1.78-1.96 (m, 5H).

Example 18: Preparation of Compound 79

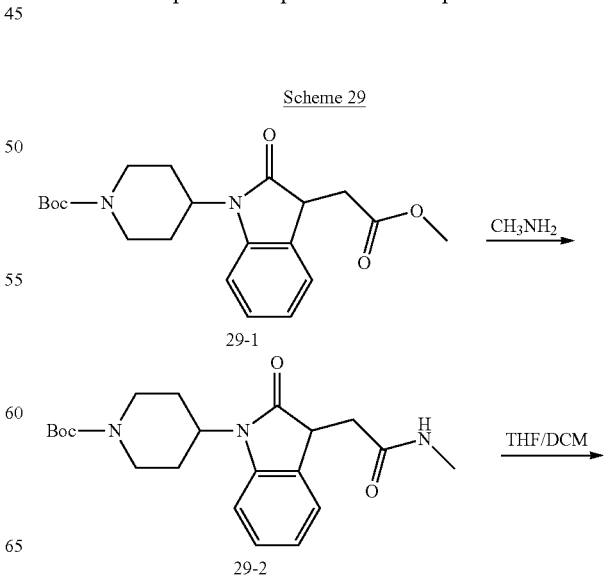

-continued

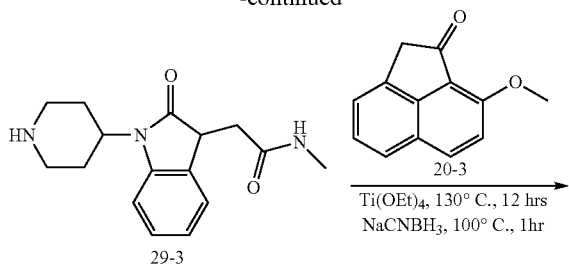

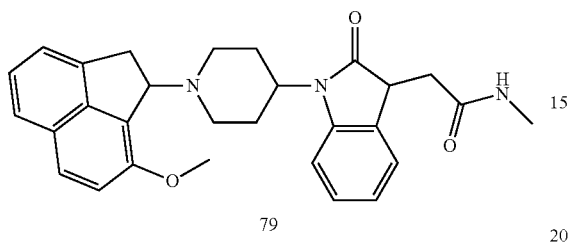

Preparation of Compound 29-2

A solution of tert-butyl 4-(3-(2-methoxy-2-oxoethyl)-2-oxoindolin-1-yl)piperidine-1-carboxylate (Compound 29-1, 388 mg, 1 mmol) in methylamine alcohol solution (2 mL) was heated to 80° C. for 3 hrs. After cooling, the solvent was removed and the crude tert-butyl 4-(3-(2-(methylamino)-2-oxoethyl)-2-oxoindolin-1-yl)piperidine-1-carboxylate (Compound 29-2, 370 mg) was used in next step without purification. MS (ESI): m/z 388 [M+H]$^+$ Preparation of Compound 29-3

To a solution of tert-butyl 4-(3-(2-(methylamino)-2-oxoethyl)-2-oxoindolin-1-yl) piperidine-1-carboxylate (Compound 29-2, 370 mg, 0.95 mmol) in dichloromethane (5 mL) was added trifluoroacetic acid (1 mL) and the mixture was stirred at room temperature for 2 hrs. Sodium bicarbonate solution was added to adjust pH to 8.0-9.0, then the mixture was extracted with dichloromethane. The combined organic layer was washed with brine, dried over sodium sulfate, filtered and concentrated. The crude product was purified by column chromatography (dichloromethane:methanol=5:1) to yield N-methyl-2-(2-oxo-1-(piperidin-4-yl)indolin-3-yl) acetamide (Compound 29-3, 150 mg) as a white solid. MS (ESI): m/z 288 [M+H]$^+$.

Preparation of Compound 79

To a sealed tube containing 8-methoxyacenaphthylen-1 (2H)-one (Compound 20-3, 99 mg, 0.5 mmol), N-methyl-2-(2-oxo-1-(piperidin-4-yl)indolin-3-yl)acetamide (Compound 29-3, 144 mg, 0.5 mmol) in tetrahydrofuran (3 mL) was added titanium ethoxide (570 mg, 2.5 mmol). The mixture was heated to 130° C. for 8 hrs under microwave conditions, then sodium cyanoborohydride (186 mg, 3 mmol) was added to the mixture and continued to heat to 100° C. for 1 hour under microwave conditions. The mixture was quenched with water and extracted with ethyl acetate. The combined organic layer was washed with brine, dried over sodium sulfate, filtered and concentrated. The crude product was purified by column chromatography (dichloromethane:methanol=20:1) to yield 2-(1-(1-(8-methoxy-1,2-dihydroacenaphthylen-1-yl)piperidin-4-yl)-2-oxoindolin-3-yl)-N-methylacetamide (Compound 79, 30 mg, 13%) as a white solid. MS (ESI): m/z 470 [M+H]$^+$. $^1$H NMR (400 MHz, CDCl3) δ 7.74-7.72 (d, J=8.4 Hz, 1H), 7.60-7.57 (d, J=8.4 Hz, 1H), 7.35-7.19 (m, 6H), 7.06-7.02 (t, J$_1$=7.2 Hz, J$_2$=8.0 Hz, 1H), 6.59 (s, 1H), 5.05-5.03 (m, 1H), 4.26-4.23 (m, 1H), 4.08-4.07 (d, J=4.0 Hz, 3H), 3.82-3.80 (m, 1H), 3.54-3.49 (m, 1H), 3.38-3.34 (m, 1H), 2.91-2.81 (m, 6H), 2.75-2.67 (m, 1H), 2.62-2.55 (m, 1H), 2.47-2.41 (m, 2H), 2.19-2.11 (m, 1H), 1.64-1.61 (m, 2H).

Example 19A: Preparation of 6b,7a-Dihydroacenaphtho[1,2-b]oxirene (Compound 30-2)

Scheme 30A.

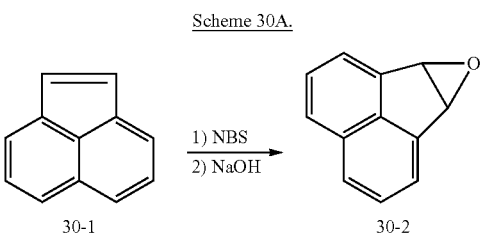 [SMILES: C1=Cc2cccc3cccc1c23 ; c1cc2c3c(cccc3c1)C1OC21]

To a solution of acenaphthylene (Compound 30-1, 20 g, 132 mmol) in dimethyl sulfoxide (150 mL) and water (20 mL) was added N-bromosuccinimide (28.0 g, 158 mmol) slowly. The mixture was stirred at room temperature for 2 hours. After completion, the solution was extracted with diethyl ether, the combined organic layer was washed with brine, dried over anhydrous sodium sulfate, and concentrated. The residue was dissolved in diethyl ether and sodium hydroxide (26.4 g, 660 mmol) was added portionwise. The mixture was stirred at room temperature overnight. After completion, the reaction mixture was washed with brine, dried over anhydrous sodium sulfate, and concentrated to yield 6b,7a-dihydroacenaphtho[1,2-b]oxirene (Compound 30-2, 22 g, yield: 99%) as a yellow solid. MS (ESI): m/z 169 [M+H]$^+$. $^1$H-NMR (400 MHz, DMSO): δ 4.89 (s, 2H), 7.46 (t, J=8.0 Hz, 2H), 7.63 (t, J=6.7 Hz, 2H), 7.74 (d, J=8.4 Hz, 2H).

Example 19B: Preparation of 1-methyl-6b,7a-dihydroacenaphtho[1,2-b]oxirene (Compound 30-9)

Scheme 30B.

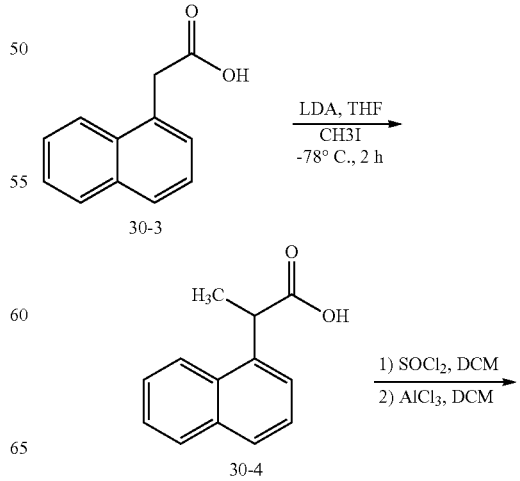

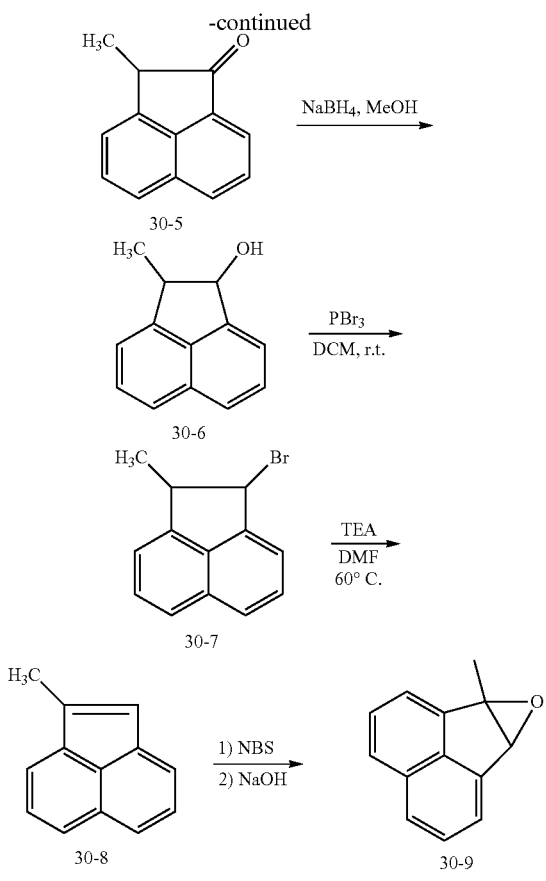

Preparation of Compound 30-4

To a stirred −78° C. solution of 200 mL (400 mmol) of LiN(iPr)$_2$ in 800 mL of dry THF under Ar was added 37.24 g (200 mmol) of 1-naphthylacetic acid in 200 mL of dry THF dropwise over 25 min. The solution was stirred at 0° C. for 1 h and recooled to −78° C., and a single portion of 18.75 mL (301 mmol) of MeI was added. After the mixture was stirred overnight at room temperature, the reaction was quenched with water; the mixture was vacuum-concentrated, and the residue was dissolved in water. Extraction with Et$_2$O both before and after acidification to give 2-(naphthalen-1-yl)propanoic acid as a white solid (Compound 30-4, 38.38 g yield: 96%). MS (ESI): m/z 201 [M+H]$^+$.

Preparation of Compound 30-5

To a stirred 25° C. suspension of 2-(naphthalen-1-yl) propanoic acid (Compound 30-4, 38.38 g, 191.8 mmol) in 650 mL of dry dichloromethane under Ar was added 17.9 mL (250 mmol) of thionyl chloride dropwise over 30 min. After stirring at 25° C. for 3.5 h, the solution was vacuum-concentrated. To the residue, stirred in 550 mL of dry dichloromethane under Ar at 0° C., was added 44.5 g (334 mmol) of AlCl$_3$ in portions. After the mixture was stirred overnight at room temperature, the reaction was quenched at −78° C. by dropwise addition of 200 mL of 4 N HCl. The organic layer combined with the dichloromethane extracts of the aqueous layer yielded a crude oil. Flash chromatography on silica gel afforded 2-methylacenaphthylen-1(2H)-one (Compound 30-5, 27 g, yield 77%) as a colorless oil. MS (ESI): m/z 183 [M+H]$^+$.

Preparation of Compound 30-6

To a solution of 2-methylacenaphthylen-1(2H)-one (Compound 30-5, 14.0 g, 77 mmol) in methanol (120 mL) was added sodium borohydride (3.80 g, 100 mmol) slowly. The resulting mixture was stirred at room temperature for 1.5 hours. After completion, the reaction was quenched with water, then the solvent was removed, the residue was dissolved in dichloromethane and water, extracted with dichloromethane. The combined organic layer was washed with brine, dried over anhydrous sodium sulfate, and concentrated to give the crude product 2-methyl-1,2-dihydroacenaphthylen-1-ol (Compound 30-6, 14.2 g, yield 100%). as a white solid. MS (ESI): m/z 167 [M−17(—OH)]$^+$.

Preparation of Compound 30-7

To a solution of 2-methyl-1,2-dihydroacenaphthylen-1-ol (Compound 30-6, 14.2 g, 77 mmol) in dichloromethane (100 mL) was added phosphorus tribromide (41.7 g, 154 mmol). The mixture was stirred at room temperature for 3 hours. After completion, the reaction was quenched with water and adjusted to pH=8 with aqueous sodium bicarbonate. The mixture was extracted with dichloromethane and the combined organic layer was washed with brine, dried over anhydrous sodium sulfate, and concentrated to give the crude product 1-bromo-2-methyl-1,2-dihydroacenaphthylene (Compound 30-7, 18.9 g, yield 100%) as a brown oil.

Preparation of Compound 30-8

To a solution of 1-bromo-2-methyl-1,2-dihydroacenaphthylene (Compound 30-7, 18.9 g, 77 mmol) in N, N-dimethylformamide (80 ml) was added triethylamine (15.6 g, 154 mmol) slowly. The mixture was stirred at 60° C. overnight. After completion, the solution was extracted with ethyl acetate/petrol ether and the combined organic layer was washed with brine, dried over anhydrous sodium sulfate, and concentrated to give the crude product 1-methyl-acenaphthylene (Compound 30-8, 10.7 g, yield 90%) as a yellow oil, which was purified using silica gel. MS (ESI): m/z 167 [M+H]$^+$.

Preparation of Compound 30-9

To a solution of 1-methylacenaphthylene (Compound 30-8, 498 mg, 3.0 mmol) in dimethyl sulfoxide (5 mL) and water (2 mL) was added N-bromosuccinimide (641 mg, 3.6 mmol) slowly. The mixture was stirred at room temperature for 3 hours. After completion, the solution was extracted with diethyl ether and the combined organic layer was washed with brine, dried over anhydrous sodium sulfate, and concentrated. The residue was dissolved in diethyl ether and sodium hydroxide (282 mg, 7.05 mmol) was added in one portion. The mixture was stirred at room temperature overnight. After completion, the reaction mixture was washed with brine, dried over anhydrous sodium sulfate, and concentrated to yield 1-methyl-6b,7a-dihydroacenaphtho[1,2-b]oxirene (Compound 30-9, 160 mg, yield 37%) as a brown oil. MS (ESI): m/z 183 [M+H]$^+$. $^1$H-NMR (400 MHz, DMSO): δ 2.04 (s, 3H), 4.76 (s, 1H), 7.46-7.54 (m, 2H), 7.59-7.64 (m, 2H), 7.77 (d, J=8.4 Hz, 2H).

Example 19C: Preparation of Compound 86

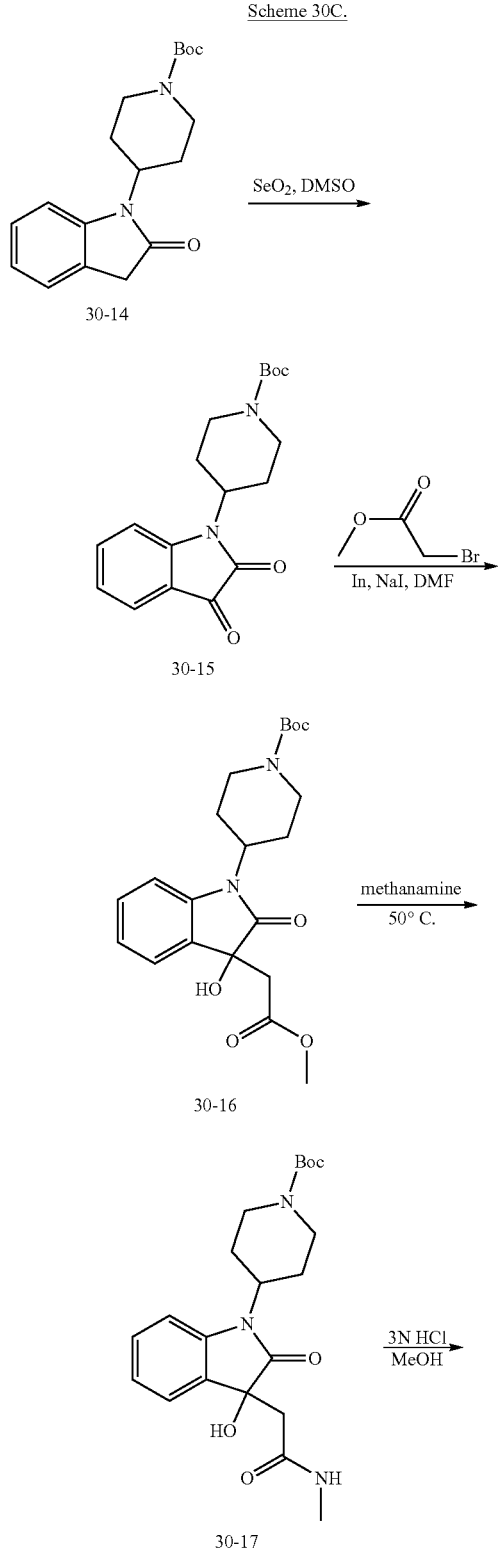

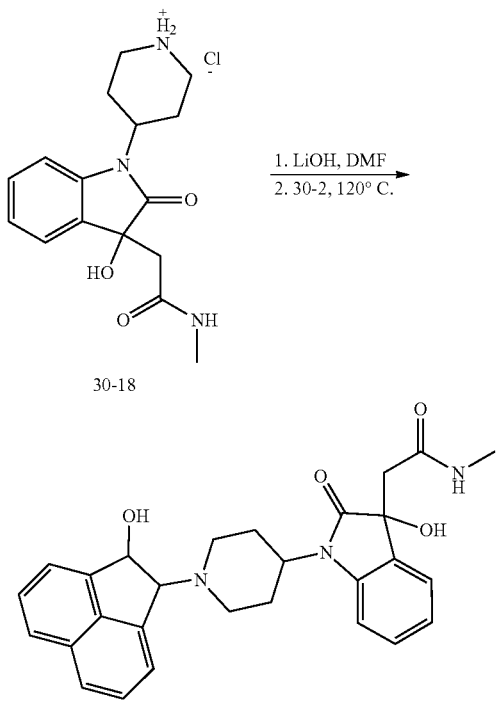

Preparation of Compound 30-15

A mixture of tert-butyl 4-(2-oxoindolin-1-yl)piperidine-1-carboxylate (Compound 30-14, 12.6 g, 40 mmol, 1.0 eq) and selenium dioxide (8.9 g, 80 mmol, 2.0 eq) in dimethylsulfoxide (120 mL) was heated to 60° C. with stirring 1 hour. Upon completion, the mixture was filtered, poured into water, and extracted with ethyl acetate. The organic layer was washed with brine, dried and concentrated in vacuo to give crude product. Recrystallization from ethyl acetate in petroleum ether yielded tert-butyl 4-(2,3-dioxoindolin-1-yl)piperidine-1-carboxylate (Compound 30-15, 12.2 g, yield 93%) as a yellow solid. MS (ESI): m/z 275 [M−56+H]+.

Preparation of Compound 30-16

To a mixture of tert-butyl 4-(2,3-dioxoindolin-1-yl)piperidine-1-carboxylate (Compound 30-15, 11.3 g, 34.2 mmol, 1.0 eq) in N, N-dimethylformamide (120 mL) was added methyl 2-bromoacetate (7.8 g, 51.4 mmol, 1.5 eq), In powder (7.8 g, 68.4 mmol, 2.0 eq) and NaI (7.7 g, 51.4 mmol, 1.5 eq) under nitrogen. The mixture was heated to 25° C. with stirring for overnight. Upon completion, the mixture was quenched with 50 mL of 1N aqueous hydrochloride and extracted with ethyl acetate. The organic layer was washed with brine, dried and concentrated in vacuo to give crude product. Recrystallization from ethyl acetate yielded tert-butyl 4-(3-hydroxy-3-(2-methoxy-2-oxoethyl)-2-oxoindolin-1-yl)piperidine-1-carboxylate (Compound 30-16, 6.4 g, yield 46%) as an off-white solid. MS (ESI): m/z 349 [M−56+H]+.

Preparation of Compound 30-17

A mixture of tert-butyl 4-(3-hydroxy-3-(2-methoxy-2-oxoethyl)-2-oxoindolin-1-yl)piperidine-1-carboxylate (Compound 30-16, 10.2 g, 25.2 mmol, 1.0 eq) and methanamine in alcohol (30%, 100 mL) was heated to 50° C. with stirring for 3 hours. Upon completion, the mixture was evaporated in vacuo and the residue was purified by silica gel chromatography (methanol in dichloromethane) to yield tert-butyl 4-(3-hydroxy-3-(2-(methylamino)-2-oxoethyl)-2-oxoindolin-1-yl) piperidine-1-carboxylate (Compound 30-17, 9.04 g, yield 89%) as an off-white solid. MS (ESI): m/z 348 [M−56+H]$^+$.

Preparation of Compound 30-18

A mixture of tert-butyl 4-(3-hydroxy-3-(2-(methylamino)-2-oxoethyl)-2-oxoindolin-1-yl)piperidine-1-carboxylate (Compound 30-17, 9.1 g, 22.6 mmol, 1.0 eq) in 3 N hydrochloride in methanol (80 mL) was stirred at r.t. for 3 hours. Upon completion, the mixture was evaporated in vacuo to yield 4-(3-Hydroxy-3-(2-(methylamino)-2-oxoethyl)-2-oxoindolin-1-yl)piperidinium hydrochloride (Compound 30-18, 8.8 g, yield 100%) as an off-white solid. MS (ESI): m/z 304 [M+H]$^+$.

Preparation of Compound 86

A mixture of 4-(3-hydroxy-3-(2-(methylamino)-2-oxoethyl)-2-oxoindolin-1-yl) piperidinium hydrochloride (Compound 30-18, 8.8 g, 22.6 mmol, 1.0 eq) and lithium hydroxide (949 mg, 22.6 mmol, 1.0 eq) in dimethyl formamide (80 mL) was stirred at 40° C. for 1 hour, then Compound 30-2 (7.6 g, 45.2 mmol, 2.0 eq) was added and the mixture was heated to 120° C. with stirring for 1 hour. Upon completion, the mixture was poured into water and extracted with dichloromethane. The organic layer was washed with brine, dried and concentrated in vacuo to yield the crude product which was purified by silica gel chromatography (methanol in dichloromethane), then by reverse flash in 0.1% aqueous ammonia to yield 2-(3-hydroxy-1-(1-((1S,2S)-2-hydroxy-1,2-dihydroacenaphthylen-1-yl) piperidin-4-yl)-2-oxoindolin-3-yl)-N-methylacetamide (Compound 86, 3.4 g, yield 49.8%) as a white solid. MS (ESI): m/z 472 [M+H]$^+$. $^1$H-NMR (400 MHz, CDCl$_3$): δ 7.80-7.63 (t, J=7.2 Hz, 2H), 7.61-7.55 (m, 4H), 7.42-7.40 (d, J=7.2 Hz, 1H), 7.32-7.28 (t, J=8.0 Hz, 1H), 7.24 (s, 1H), 7.09-7.05 (t, J=7.2 Hz, 1H), 5.99-5.98 (d, J=4.4 Hz, 1H), 5.77-5.74 (d, J=12.4 Hz, 2H), 4.72 (s, 1H), 4.26 (s, 1H), 3.13-3.11 (d, J=9.6 Hz, 1H), 2.93-2.50 (m, 11H), 1.77-1.68 (m, 2H).

Compound 86 was separated using chiral chromatography into four isomers, Compound 87, Compound 88, Compound 89 and Compound 90:

Compound 87

Compound 88

Compound 89

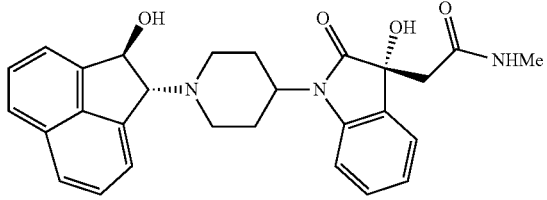

Compound 90

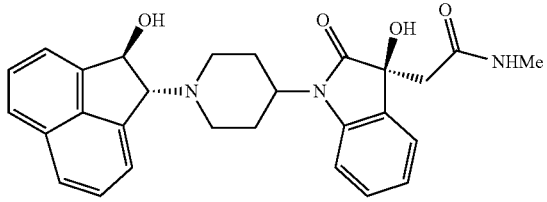

Example 19D: Preparation of Compound 91

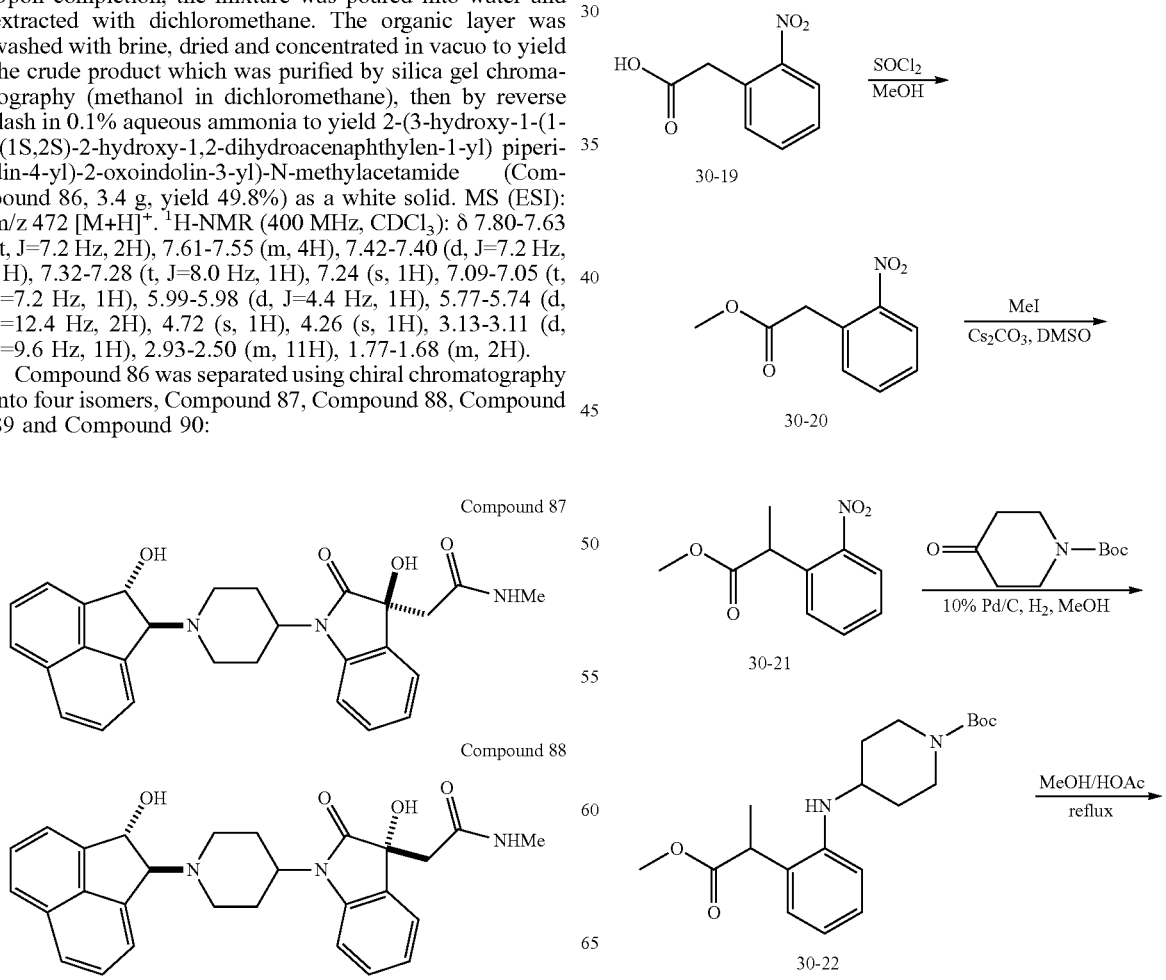

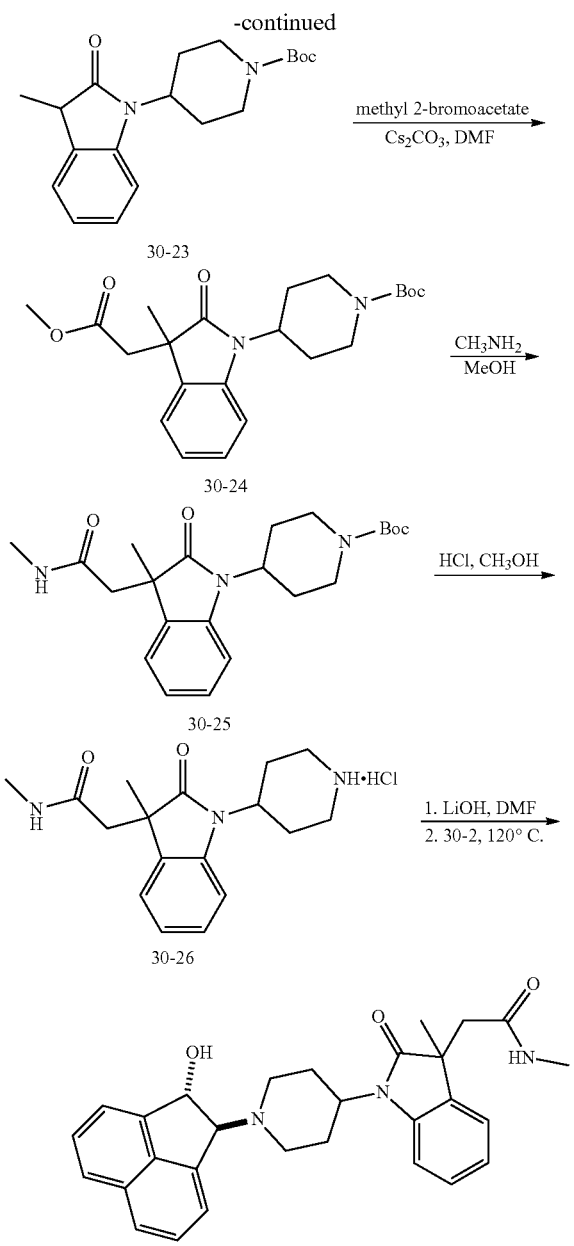

Preparation of Compound 30-20

To a solution of 2-(2-nitrophenyl)acetic acid (Compound 30-19, 18.1 g, 100 mmol) in methanol (150 mL) at room temperature was added sulfurous dichloride (13.1 g, 110 mmol) dropwise. The mixture was heated to 60° C. and stirred for 30 minutes. The reaction mixture was concentrated to give a pale yellow oil, then diluted with ethyl acetate, washed with NaHCO$_3$ and brine. The organic layer was dried over anhydrous sodium sulfate and concentrated to yield methyl 2-(2-nitrophenyl)acetate (Compound 30-20, 19.1 g, yield 98%) as a pale yellow oil. MS (ESI): m/z 196 [M+H]$^+$.

Preparation of Compound 30-21

To a solution of methyl 2-(2-nitrophenyl)acetate (Compound 30-20, 19 g, 97 mmol) in methylsulfinylmethane (200 mL) was added iodomethane (20.7 g, 146 mmol) at room temperature. The mixture was stirred at room temperature for 30 minutes. Then to the mixture was added cesium carbonate (63 g, 195 mmol), and the mixture was stirred at room temperature overnight. The mixture was poured into water and diluted with ethyl acetate. The organic layer was washed with water and brine, dried over anhydrous sodium sulfate, and concentrated to give crude product which was purified on silica gel (ethyl acetate in petroleum ether) to afford methyl 2-(2-nitrophenyl)propanoate (Compound 30-21, 18.7 g, yield 92%) as a colorless oil. MS (ESI): m/z 210 [M+H]$^+$.

Preparation of Compound 30-22

To a solution of methyl 2-(2-nitrophenyl)propanoate (Compound 30-21, 6.0 g, 28.7 mmol) in methanol (100 ml) was added tert-butyl 4-oxopiperidine-1-carboxylate (10.85 g, 54.5 mmol) and Pd/C (10%) (0.6 g) at room temperature. The mixture was stirred at room temperature for overnight under hydrogen atmosphere. The mixture was filtered to yield a methanol solution of tert-butyl 4-(2-(1-methoxy-1-oxopropan-2-yl)phenylamino)piperidine-1-carboxylate (Compound 30-22) which was used without further purification. MS (ESI): m/z 210 [M+H]$^+$.

Preparation of Compound 30-23

To a mixture of tert-butyl 4-(2-(1-methoxy-1-oxopropan-2-yl)phenylamino)piperidine-1-carboxylate (Compound 30-22) in methanol was added acetic acid (10 mL). The mixture was stirred at reflux for 1 hour. The mixture was concentrated and the residue was poured into water and the solution was adjusted to pH 7 with aqueous sodium carbonate. The mixture was extracted with ethyl acetate and the organic layer was washed with brine, dried over anhydrous sodium sulfate, and concentrated. Purification on silica gel (ethyl acetate in petroleum ether) yielded tert-butyl 4-(3-methyl-2-oxoindolin-1-yl)piperidine-1-carboxylate (Compound 30-23, 5.77 g, yield 61%) as a white solid. MS (ESI): m/z 331 [M+H]$^+$. $^1$H NMR (400 MHz, CDCl$_3$) δ 7.26-7.21 (m, 1H), 7.05 (d, J=7.2, 1H), 7.49 (t, J=6.8 Hz, 1H), 4.45-4.38 (m, 1H), 4.31-4.27 (m, 1H), 3.41 (q, J=7.6 Hz, 1H), 2.83 (t, J=14.4 Hz, 2H), 2.37-2.27 (m, 2H), 1.73-1.67 (m, 2H), 1.50 (s, 9H), 1.47 (d, J=7.6 Hz, 3H).

Preparation of Compound 30-24

To the mixture of tert-butyl 4-(3-methyl-2-oxoindolin-1-yl)piperidine-1-carboxylate (Compound 30-23, 5.77 g, 17.5 mmol) in N,N-dimethylformamide (100 mL) was added methyl 2-bromoacetate (2.94 g, 19.3 mmol). The mixture was stirred at room temperature for 30 minutes. To the mixture was added cesium carbonate (11.4 g, 35 mmol). The mixture was stirred at room temperature for 2 hours. The mixture was poured into water and extracted with ethyl acetate. The organic layer was washed with brine, dried over anhydrous sodium sulfate, and concentrated. The residue was purified on silica-gel (ethyl acetate in petroleum ether) to yield tert-butyl 4-(3-(2-methoxy-2-oxoethyl)-3-methyl-2-oxoindolin-1-yl)piperidine-1-carboxylate w (Compound 30-24, 3.8 g, yield 54%) as a white solid. MS (ESI): m/z 403 [M+H]$^+$.

Preparation of Compound 30-25

A mixture of tert-butyl 4-(3-(2-methoxy-2-oxoethyl)-3-methyl-2-oxoindolin-1-yl)piperidine-1-carboxylate (Compound 30-24, 11.5 g, 28.6 mmol) in methylamine (33% in methanol, 200 mL) was stirred at 50° C. overnight. Another portion of methylamine (33% in methanol, 150 mL) was added and the reaction was stirred at 50° C. overnight. The mixture was cooled and concentrated under reduced pressure to yield tert-butyl 4-(3-methyl-3-(2-(methylamino)-2-oxoethyl)-2-oxoindolin-1-yl)piperidine-1-carboxylate (Compound 30-25, 10.0 g, yield: 86.9%) as a brown oil. MS (ESI): m/z 346 [M−56+H]$^+$.

Preparation of Compound 30-26

A mixture of tert-butyl 4-(3-methyl-3-(2-(methylamino)-2-oxoethyl)-2-oxoindolin-1-yl)piperidine-1-carboxylate (Compound 30-25, 10.0 g, 24.9 mmol) in hydrogen chloride/methanol (150 mL, 3.6 N) was stirred at room temperature for 2.0 h. The mixture was concentrated to yield N-methyl-2-(3-methyl-2-oxo-1-(piperidin-4-yl)indolin-3-yl)acetamide hydrogen chloride salt (Compound 30-26, 9.0 g, yield 100%) as a brown oil which was used without further purification. MS (ESI): m/z 302 [M+H]$^+$.

Preparation of Compound 91

A mixture of N-methyl-2-(3-methyl-2-oxo-1-(piperidin-4-yl)indolin-3-yl)acetamide hydrogen chloride salt (Compound 30-26, 337 mg, 1.0 mmol) and lithium hydroxide (50.4 mg, 1.2 mmol) in dimethyl formamide (3.0 mL) was stirred at 40° C. with stirring for 1 hour, then 6b,7a-dihydroacenaphtho[1,2-b]oxirene (Compound 30-2, 336 g, 2.0 mmol) was added and the mixture was heated to 120° C. with stirring for 5 hours. Upon completion, the mixture was poured into water and extracted with dichloromethane. The organic layer was washed with brine, dried and concentrated in vacuo. The residue was purified by HPLC to afford 2-(1-(1-((1S,2S)-2-hydroxy-1,2-dihydroacenaphthylen-1-yl)piperidin-4-yl)-3-methyl-2-oxoindolin-3-yl)-N-methylacetamide (Compound 91, 10 mg, yield 2.1%). MS (ESI): m/z 470 [M+H]$^+$. $^1$H-NMR (400 MHz, DMSO) δ 7.77 (d, J=8.3 Hz, 2H), 7.54-7.64 (m, 3H), 7.45-7.52 (m, 2H), 7.10-7.26 (m, 3H), 6.94 (t, J=7.1 Hz, 1H), 5.74 (s, 1H), 5.57 (d, J=4.6 Hz, 1H), 4.54 (s, 1H), 4.03-4.15 (m, 1H), 3.01 (d, J=10.2 Hz, 1H), 2.53-2.76 (m, 5H), 2.41-2.48 (m, 2H), 2.33 (d, J=4.1 Hz, 3H), 1.53-1.70 (m, 2H), 1.18 (s, 3H).

Example 19E: Preparation of Compound 93

Scheme 30E:

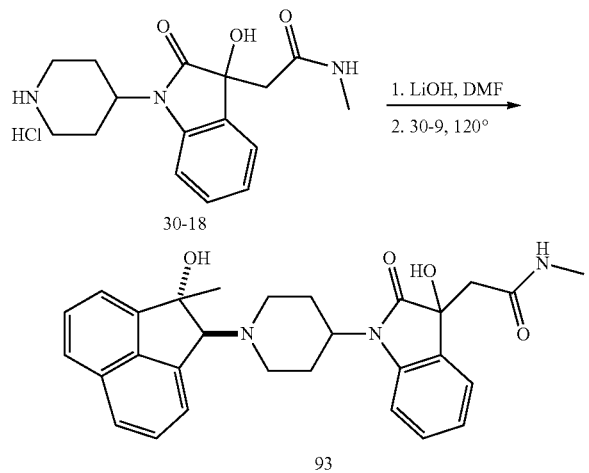

93

A mixture of 4-(3-hydroxy-3-(2-(methylamino)-2-oxoethyl)-2-oxoindolin-1-yl) piperidinium hydrochloride (Compound 30-18, 300 mg, 0.88 mmol) and lithium hydroxide (45 mg, 1.1 mmol) in dimethyl formamide (3.0 mL) was stirred at 40° C. for 1 hour, then 1-methyl-6b,7a-dihydroacenaphtho[1,2-b]oxirene (Compound 30-9, 400 mg, 2.2 mmol) was added and the mixture was heated to 120° C. with stirring for 1 hour. Upon completion, the mixture was poured into water and extracted with dichloromethane. The organic layer was washed with brine, dried and concentrated in vacuo. Purification by HPLC yielded 2-(3-hydroxy-1-(1-((1S,2S)-2-hydroxy-2-methyl-1,2-dihydroacenaphthylen-1-yl)piperidin-4-yl)-2-oxoindolin-3-yl)-N-methylacetamide (Compound 93, 130 mg, yield 49.8%) as a white solid. MS: m/z 486 (M+H+). 1H-NMR (400 MHz, DMSO) δ 7.68-7.80 (m, 3H), 7.48-7.62 (m, 3H), 7.41 (d, J=6.7 Hz, 1H), 7.21-7.28 (m, 2H), 7.08 (d, J=7.6 Hz, 1H), 6.95 (t, J=7.2 Hz, 1H), 6.07 (s, 1H), 5.36 (s, 1H), 4.44-4.51 (m, 1H), 3.87-4.01 (m, 1H), 3.23 (d, J=9.0 Hz, 1H), 3.08 (t, J=11.0 Hz, 1H), 2.64-2.80 (m, 2H), 2.40-2.47 (m, 1H), 2.35 (s, 3H), 2.15-2.29 (m, 2H), 1.95-2.09 (m, 1H), 1.62-1.74 (m, 4H), 1.36-1.48 (m, 1H).

Example 19F: Preparation of Compound 94

Scheme 30F:

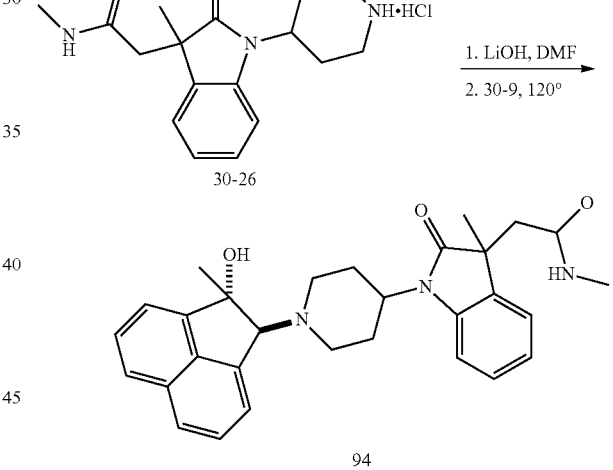

94

A mixture of N-methyl-2-(3-methyl-2-oxo-1-(piperidin-4-yl)indolin-3-yl)acetamide hydrogen chloride salt (Compound 30-26, 300 mg, 0.9 mmol) and lithium hydroxide (44.6 mg, 1.06 mmol) in dimethyl formamide (3.0 mL) was stirred at 40° C. for 1 hour, then 1-methyl-6b,7a-dihydroacenaphtho[1,2-b]oxirene (Compound 30-9, 400 g, 2.2 mmol) was added and the mixture was heated to 120° C. with stirring for 5 hours. Upon completion, the mixture was poured into water and extracted with dichloromethane. The organic layer was washed with brine, dried and concentrated in vacuo. Purification by HPLC afforded 2-(1-(1-((1S,2S)-2-hydroxy-2-methyl-1,2-dihydroacenaphthylen-1-yl)piperidin-4-yl)-3-methyl-2-oxoindolin-3-yl)-N-methylacetamide (Compound 94, 200 mg, yield 46.0%). MS (ESI): m/z 484 [M+H]$^+$. $^1$H-NMR (400 MHz, DMSO) δ 7.73-7.80 (m, 2H), 7.49-7.64 (m, 4H), 7.42 (d, J=7.0 Hz, 1H), 7.20 (t, J=9.5 Hz, 2H), 7.10 (d, J=7.8 Hz, 1H), 6.94 (t, J=7.3 Hz, 1H), 5.34 (s, 1H), 4.48 (s, 1H), 3.94-4.06 (m, 1H), 3.24 (d, J=10.3 Hz, 1H), 3.09 (t, J=11.3 Hz, 1H), 2.67 (dd, J=15.4, 3.6 Hz, 1H), 2.56 (dd, J=14.9, 4.3 Hz, 1H), 2.38-2.48 (m, 1H), 2.33 (t, J=4.6 Hz, 3H), 2.19-2.30 (m, 2H), 1.96-2.06 (m, 1H), 1.63-1.74 (m, 4H), 1.38-1.48 (m, 1H), 1.13-1.20 (m, 3H).

Example 20A: Preparation of Compound 95

Scheme 31A:

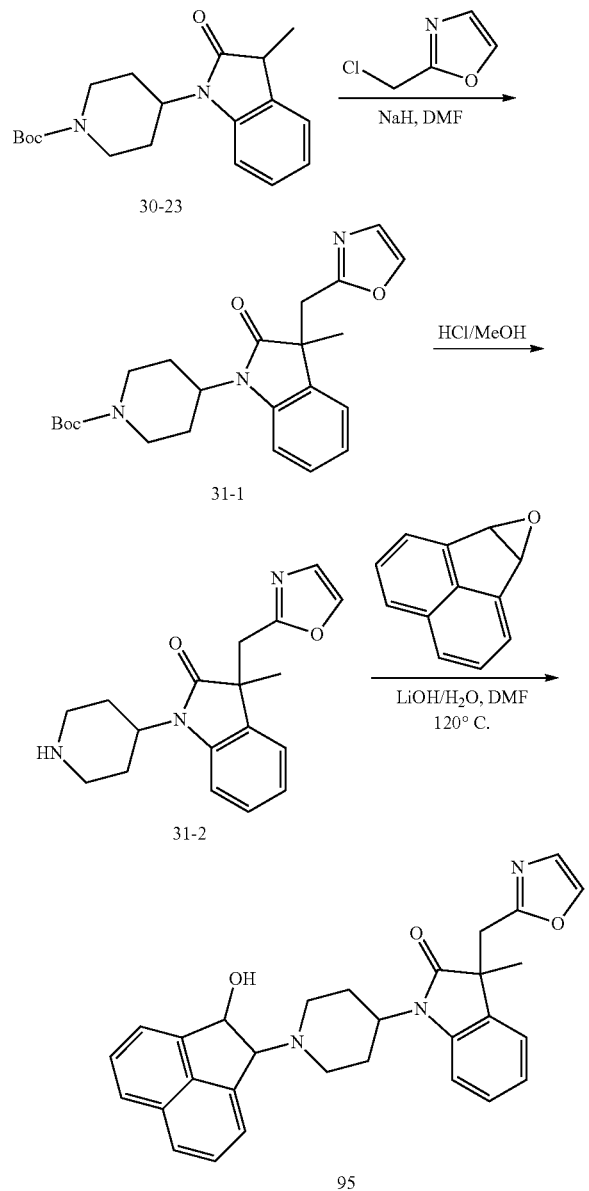

added and the aqueous layer was extracted with ethyl acetate. The combined organic layer was washed with brine, dried over sodium sulfate and concentrated. The residue was purified by silica gel chromatography (dichloromethane/methanol) to yield tert-butyl-4-(3-methyl-3-(oxazol-2-ylmethyl)-2-oxoindolin-1-yl)piperidine-1-carboxylate (Compound 30-23, 0.26 g, 15.5% yield) as a yellow solid. $^1$H-NMR (400 MHz, CDCl$_3$): 7.40 (s, 1H), 7.20 (t, J=7.6 Hz, 1H), 7.13 (d, J=7.6 Hz, 1H), 7.01 (t, J=7.6 Hz, 1H), 6.95 (d, J=7.6 Hz, 1H), 6.88 (s, 1H), 4.39-4.43 (m, 1H), 4.27-4.33 (m, 2H), 3.26-3.36 (m, 2H), 2.75-2.93 (m, 2H), 2.27-2.35 (m, 2H), 1.69-1.72 (m, 2H), 1.52 (s, 9H), 1.51 (s, 3H). m/z 412.1[M+H]$^+$.

Preparation of Compound 31-2

A mixture of tert-butyl-4-(3-methyl-3-(oxazol-2-ylmethyl)-2-oxoindolin-1-yl) piperidine-1-carboxylate (Compound 31-2, 120 mg, 0.29 mmol) in a solution of hydrochloric acid in methanol (5 mL) was stirred at room temperature for 1 hour. The reaction mixture was concentrated in vacuum to give crude 3-methyl-3-(oxazol-2-ylmethyl)-1-(piperidin-4-yl) indolin-2-one (Compound 31-2, 90 mg) as a yellow oil. m/z 312.1 [M+H]$^+$.

Preparation of Compound 95

To a solution of 3-methyl-3-(oxazol-2-ylmethyl)-1-(piperidin-4-yl) indolin-2-one (Compound 31-2, 90 mg, 0.29 mmol) in N, N-dimethylformamide (5 mL) was added 6b,7a-dihydroacenaphtho[1,2-b]oxirene (97 mg, 0.58 mmol). The reaction mixture was heated to 120° C. and stirred for 1 hour. After cooling to room temperature, water was added and the aqueous layer was extracted with ethyl acetate. The combined organic layer was washed with brine, dried over sodium sulfate and concentrated. The resulting solid was purified by TLC (dichloromethane/methanol) to yield 1-(1-(2-hydroxy-1,2-dihydroacenaphthylen-1-yl)piperidin-4-yl)-3-methyl-3-(oxazol-2-ylmethyl)indolin-2-one (Compound 95, 60 mg, 44%) as a yellow solid. $^1$H-NMR (400 MHz, CDCl$_3$): 7.79 (t, J=8.0 Hz, 2H), 7.56-7.62 (m, 4H), 7.36 (d, J=7.2 Hz, 1H), 7.19-7.21 (m, 2H), 7.06-7.12 (s, 1H), 6.93-7.04 (m, 1H), 6.84 (d, J=8.4 Hz, 1H), 5.79 (s, 1H), 4.74 (s, 1H), 4.35 (s, 1H), 3.23-3.32 (m, 2H), 3.11-3.16 (m, 1H), 3.90-3.96 (s, 1H), 2.71-2.75 (m, 1H), 2.45-2.59 (m, 3H), 1.62-1.77 (m, 2H), 1.50 (s, 3H). m/z 480.2[M+H]$^+$.

Example 20B: Preparation of Compounds 96, 97 and 98

Scheme 31B:

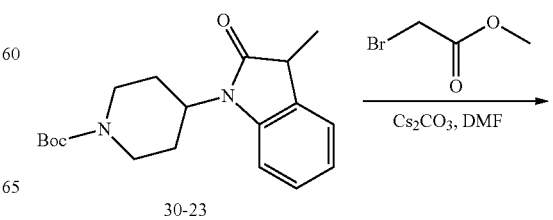

Preparation of Compound 31-1

To a solution of tert-butyl 4-(3-methyl-2-oxoindolin-1-yl) piperidine-1-carboxylate (Compound 30-23, 1.34 g, 4.06 mmol) in dimethyl formamide (20 mL) was added sodium hydride (0.19 g, 8.12 mmol) at 0° C. The mixture was stirred for 30 min, then a solution of 2-(chloromethyl)oxazole (0.95 g, 8.12 mmol) in dimethyl formamide was added and the resulting mixture was stirred at 0° C. for 30 min. Water was 233
-continued

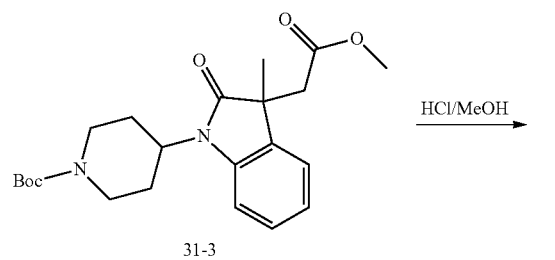

31-3

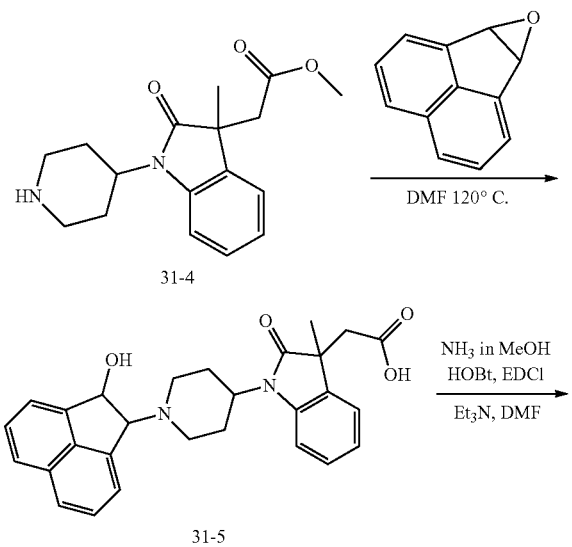

234
-continued

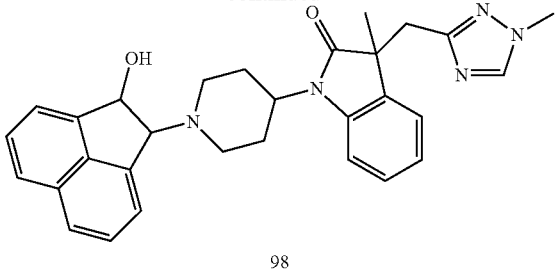

98

Preparation of Compound 31-3

To a solution of tert-butyl 4-(3-methyl-2-oxoindolin-1-yl) piperidine-1-carboxylate (Compound 30-23, 4.96 g, 15.0 mmol) in N,N-dimethylformamide (50 mL) was added cesium carbonate (9.77 g, 30.00 mmol). The reaction was stirred at ambient temperature for 30 min, then methyl 2-bromoacetate (3.44 g, 22.5 mmol) was added. The reaction was stirred at ambient temperature for 1 hour. Water was added and the aqueous layer was extracted with ethyl acetate. The combined organics were washed with brine, dried over anhydrous sodium sulfate, filtered and concentrated. The resulting solid was purified by silica gel chromatography (petroleum ether/ethyl acetate) to provide tert-butyl4-(3-(2-methoxy-2-oxoethyl)-3-methyl-2-oxoindolin-1-yl) piperidine-1-carboxylate (Compound 31-3, 4.76 g, 11.71 mmol) as a white solid. m/z 347.2 (M−56+1)$^+$.

Preparation of Compound 31-4

To a solution of tert-butyl 4-(3-(2-methoxy-2-oxoethyl)-3-methyl-2-oxoindolin-1-yl) piperidine-1-carboxylate (Compound 31-3, 0.80 g, 2.0 mmol) was added a solution of hydrochloric acid in methanol. The reaction was stirred at ambient temperature for 30 min. The reaction mixture was concentrated and the residue was adjusted pH=8 with a saturated solution of sodium bicarbonate. The aqueous was extracted with dichloromethane, and the combined organic phase was dried over sodium sulfate and concentrated to provide methyl 2-(3-methyl-2-oxo-1-(piperidin-4-yl)indolin-3-yl)acetate (Compound 31-4, 576 mg, 95%) as a white solid. m/z 303.2[M+H]$^+$.

Preparation of Compound 31-5

To a solution of methyl 2-(3-methyl-2-oxo-1-(piperidin-4-yl) Indolin-3-yl)acetate (Compound 31-4, 574 mg, 1.89 mmol) in dimethyl formamide (20 mL) was added 6b,7a-dihydroacenaphtho[1,2-b]oxirene (0.64 g, 3.78 mmol). The reaction mixture was heated to 120° C. and stirred for 1 hour. After cooling to room temperature, water was added and the aqueous layer was extracted with dichloromethane. The combined organic phase was washed with brine, dried over sodium sulfate and concentrated to provide 2-(1-(1-(2-hydroxy-1,2-dihydroacenaphthylen-1-yl)piperidin-4-yl)-3-methyl-2-oxoindolin-3-yl)acetic acid (Compound 31-5, 670 mg, 77%) as a yellow solid. m/z 457.3[M+H]$^+$.

Preparation of Compound 31-6

To a solution of 2-(1-(1-(2-hydroxy-1,2-dihydroacenaphthylen-1-yl) piperidin-4-yl)-3-methyl-2-oxoindolin-3-yl) acetic acid (Compound 31-5, 670 mg, 1.47 mmol) in dichlo-

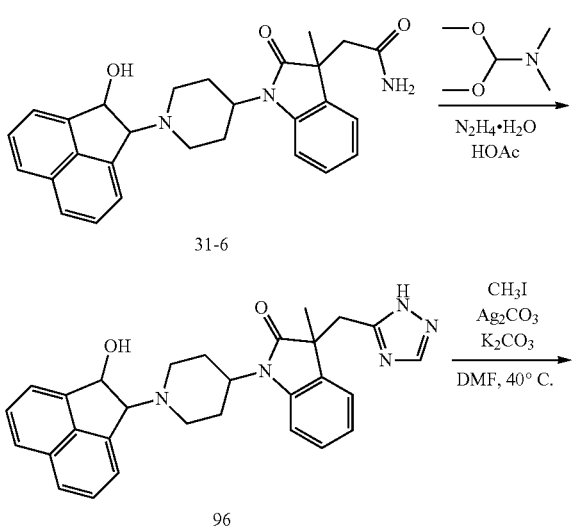

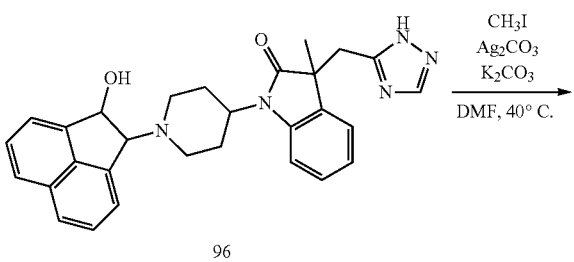

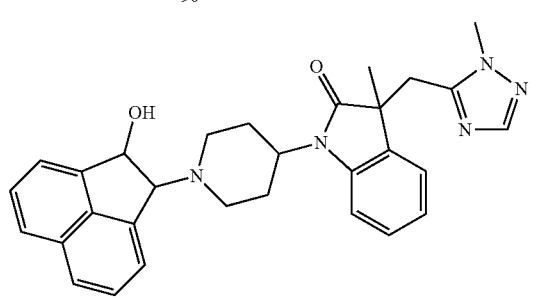

romethane (20 mL) was added 1-ethyl-3-(3-dimethylaminopropyl)carbodiimide hydrochloride (0.56 g, 2.94 mmol), 1-hydroxybenzotriazole (0.4 g, 2.94 mmol), triethylamine (0.45 g, 4.41 mmol) and a solution of ammonia in tetrahydrofuran (20 mL). The reaction mixture was heated to 35° C. and stirred for 12 hours. The reaction mixture was washed with saturated sodium bicarbonate, and the organic phase was washed with brine and dried over sodium sulfate and concentrated to provide 2-(1-(1-(2-hydroxy-1,2-dihydroacenaphthylen-1-yl) piperidin-4-yl)-3-methyl-2-oxoindolin-3-yl)acetamide (Compound 31-6, 648 mg, 1.28 mmol) as a yellow solid. m/z 456.1 [M+H]+.

Preparation of Compound 96

A mixture of 2-(1-(1-(2-hydroxy-1,2-dihydroacenaphthylen-1-yl) piperidin-4-yl)-3-methyl-2-oxoindolin-3-yl) acetamide (Compound 31-6, 548 mg, 1.21 mmol) in 1,1-dimethoxy-N,N-dimethylmethanamine (10 mL) was heated to 120° C. and stirred for 1.5 hour. The mixture was concentrated, then hydrazine hydrate (5 mL) and acetic acid (10 mL) was added. The mixture was heated to 90° C. and stirred for 1.5 hour. After cooling to room temperature, the reaction mixture was concentrated and the residue was adjusted pH=8 with a solution of sodium hydroxide (1 N). The aqueous layer was extracted with ethyl acetate, and the combined organic phase was washed with brine, dried over sodium sulfate and concentrated. The resulting solid was purified by silica gel chromatography (dichloromethane/methanol with 0.1% ammonium hydroxide) to provide 3-((1H-1,2,4-triazol-5-yl)methyl)-1-(1-(2-hydroxy-1,2-dihydroacenaphthylen-1-yl) piperidin-4-yl)-3-methylindolin-2-one (Compound 96, 0.3 g, 0.6 mmol) as a yellow solid. 1H-NMR (400 MHz, CDCl3): 7.72-7.80 (m, 3H), 7.47-7.54 (m, 4H), 7.14-7.20 (m, 2H), 7.10 (t, J=8.0 Hz, 1H), 7.01 (t, J=7.2 Hz, 1H), 5.70 (s, 1H), 4.69 (s, 1H), 4.13 (s, 1H), 3.32 (d, J=14.4 Hz, 1H), 3.15 (d, J=14.4 Hz, 1H), 2.98 (d, J=8.0 Hz, 1H), 2.88 (s, 1H), 2.38-2.57 (m, 4H), 1.50-1.59 (m, 2H), 1.40 (s, 3H). m/z 480.2[M+H]+.

Preparation of Compounds 97 and 98

To a solution of 3-((1H-1,2,4-triazol-5-yl)methyl)-1-(1-(2-hydroxy-1,2-dihydroacenaphthylen-1-yl)piperidin-4-yl)-3-methylindolin-2-one (Compound 96, 0.14 g, 0.3 mmol) in dimethyl formamide (10 mL) was added monosilver(I) monosilver(III) monooxide (0.10 g, 0.45 mmol), potassium carbonate (0.08 g, 0.6 mmol), and iodomethane (0.09 g, 0.6 mmol). The reaction mixture was heated to 40° C. and stirred for 12 hours. Water was added and the aqueous layer was extracted with ethyl acetate, and the combined organic layer was washed with brine, dried over sodium sulfate and concentrated. The resulting solid was purified by TLC (dichloromethane/methanol) to provide 1-(1-(2-hydroxy-1, 2-dihydroacenaphthylen-1-yl)piperidin-4-yl)-3-methyl-3-((1-methyl-1H-1,2,4-triazol-5-yl)methyl)indolin-2-one (Compound 97, 20 mg, 14%) and 1-(1-(2-hydroxy-1,2-dihydroacenaphthylen-1-yl)piperidin-4-yl)-3-methyl-3-((1-methyl-1H-1,2,4-triazol-3-yl)methyl)indolin-2-one (Compound 98, 10 mg, 7%) as yellow solids.

Compound 97: 1H-NMR (400 MHz, CDCl3): 7.77 (t, J=6.8 Hz, 2H), 7.52-7.60 (m, 5H), 7.19-7.21 (m, 2H), 7.09 (d, J=6.8 Hz, 1H), 7.01-7.04 (m, 1H), 5.75 (s, 1H), 4.72 (s, 1H), 4.22-4.27 (m, 1H), 3.60 (s, 3H), 3.22 (s, 2H), 3.07-3.18 (m, 1H), 2.91-2.96 (m, 1H), 2.36-2.67 (m, 4H), 1.49-1.68 (m, 5H). m/z 494.2[M+H]+.

Compound 98: 1H-NMR (400 MHz, CDCl3): 7.77-7.81 (m, 2H), 7.65 (d, J=4.0 Hz, 1H), 7.58-7.62 (m, 4H), 7.10-7.22 (m, 3H), 6.96 (t, J=7.2 Hz, 1H), 5.83 (s, 1H), 4.78 (s, 1H), 4.40-4.46 (m, 1H), 3.66 (s, 3H), 3.03-3.30 (m, 4H), 2.46-2.77 (m, 4H), 1.74-1.79 (m, 2H), 1.53 (s, 3H). m/z 494.4[M+H]+.

Example 20C: Preparation of Compound 99

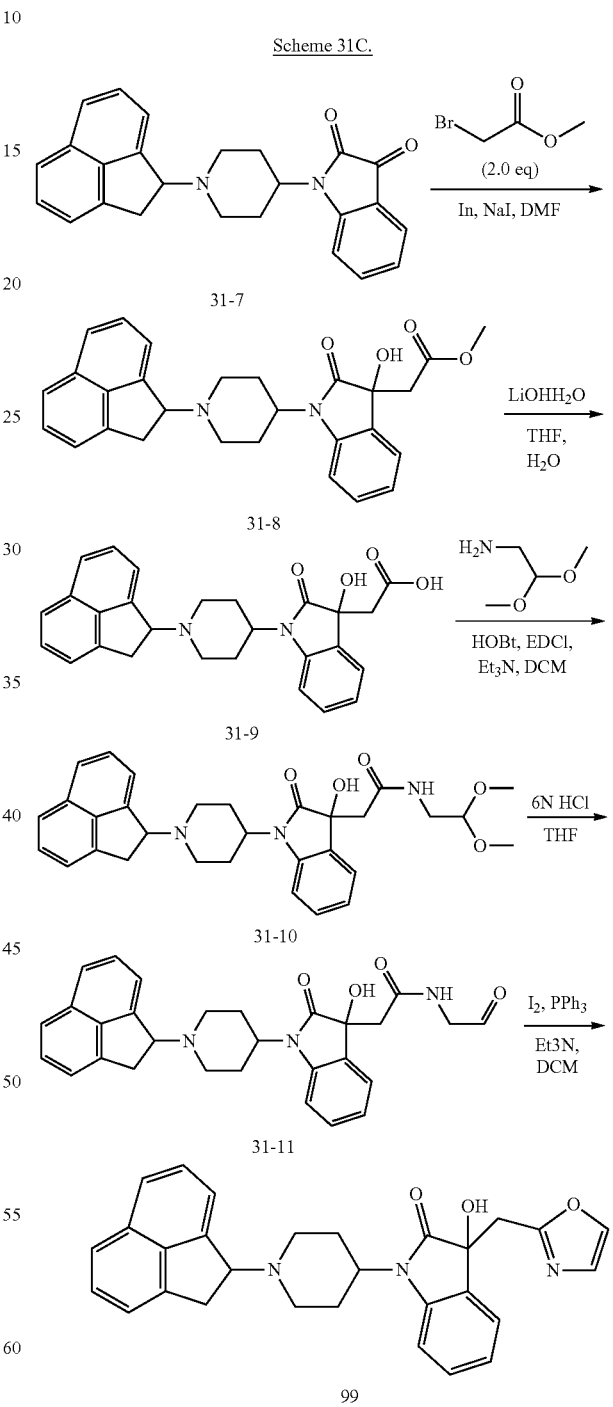

Scheme 31C.

Preparation of Compound 31-8

A mixture of 1-(1-(1,2-dihydroacenaphthylen-1-yl)piperidin-4-yl)indoline-2,3-dione (Compound 31-7, 500 mg, 1.31 mmol), indium (503 mg, 2.61 mmol), methyl 2-bromoacetate (398 mg, 2.61 mmol), sodium iodide (196 mg, 1.31 mmol) and N,N-dimethylformamide (8 mL) was stirred at room temperature for 16 hours. The mixture was poured into water and extracted with ethyl acetate. The organic phase was dried over sodium sulfate, filtered and the solvent removed under reduced pressure to yield the crude product which was purified by silica gel (dichloromethane/methanol) to give methyl 2-(1-(1-(1,2-dihydroacenaphthylen-1-yl)piperidin-4-yl)-3-hydroxy-2-oxoindolin-3-yl)acetate (Compound 31-8, 360 mg, 60% yield) as a yellow solid: MS (ESI): m/z 457.1 $[M+1]^+$.

Preparation of Compound 31-9

A solution of methyl 2-(1-(1-(1,2-dihydroacenaphthylen-1-yl)piperidin-4-yl)-3-hydroxy-2-oxoindolin-3-yl)acetate (Compound 31-8, 360 mg, 0.79 mmol) in tetrahydrofuran (10 mL) was added a solution of lithium hydroxide hydrate (166 mg, 3.95 mmol) in water (6 mL). The mixture was stirred at 40° C. for 3 hours. The mixture was cooled to 0° C. and the pH of the mixture was adjusted to 5 with 1 N hydrochloric acid. The mixture was extracted with ethyl acetate and the organic phase was dried over sodium sulfate, filtered and the solvent was removed to yield 2-(1-(1-(1,2-dihydroacenaphthylen-1-yl)piperidin-4-yl)-3-hydroxy-2-oxoindolin-3-yl)acetic acid (Compound 31-9, 320 mg, 92% yield) as a yellow solid: MS (ESI): m/z 443.1 $[M+1]^+$.

Preparation of Compound 31-10

To a solution of 2-(1-(1-(1,2-dihydroacenaphthylen-1-yl)piperidin-4-yl)-3-hydroxy-2-oxoindolin-3-yl)acetic acid (Compound 31-9, 320 mg, 0.72 mmol) in dichloromethane (8 mL) was added 1-hHydroxybenzotriazole (195 mg, 1.44 mmol), N1-((ethylimino)methylene)-N3,N3-dimethylpropane-1,3-diamine hydrochloride (275 mg, 1.44 mmol), triethylamine (219 mg, 2.17 mmol) and 2,2-dimethoxyethanamine (152 mg, 1.45 mmol). The mixture was stirred at room temperature for 16 hours. Aqueous sodium bicarbonate was added, the organic phase was separated and the aqueous layer was extracted with dichloromethane. The combined organic phase was dried over sodium sulfate, filtered and the solvent was removed under reduced pressure to give the crude product which was purified by TLC (dichloromethane/methanol) to yield 2-(1-(1-(1,2-dihydroacenaphthylen-1-yl)piperidin-4-yl)-3-hydroxy-2-oxoindolin-3-yl)-N-(2,2-dimethoxyethyl)acetamide (Compound 31-10, 300 mg, 78% yield) as a yellow solid: MS (ESI): m/z 530.1 $[M+1]^+$.

Preparation of Compound 31-11

A solution of 2-(1-(1-(1,2-dihydroacenaphthylen-1-yl)piperidin-4-yl)-3-hydroxy-2-oxoindolin-3-yl)-N-(2,2-dimethoxyethyl)acetamide (Compound 31-10, 300 mg, 0.57 mmol) in 6N hydrochloric acid (4 mL) and tetrahydrofuran (4 mL) was stirred at room temperature for 1 hour. Aqueous sodium bicarbonate was added, the organic phase was separated and the aqueous layer was extracted with dichloromethane. The combined organic phase was dried over sodium sulfate, filtered and the solvent was removed under reduced pressure to yield 2-(1-(1-(1,2-dihydroacenaphthylen-1-yl)piperidin-4-yl)-3-hydroxy-2-oxoindolin-3-yl)-N-(2-oxoethyl)acetamide (Compound 31-11, 260 mg, 95% yield) as a yellow solid: MS (ESI): m/z 484.1 $[M+1]^+$.

Preparation of Compound 99

A solution of 2-(1-(1-(1,2-dihydroacenaphthylen-1-yl)piperidin-4-yl)-3-hydroxy-2-oxoindolin-3-yl)-N-(2-oxoethyl)acetamide (Compound 31-11, 260 mg, 0.54 mmol) in dichloromethane (5 mL) was added a mixture of iodine (137 mg, 0.54 mmol), triphenylphosphine (141 mg, 0.54 mmol), and triethylamine (109 mg, 1.08 mmol). The resulting mixture was stirred at room temperature for 30 min. Aqueous sodium bicarbonate was added, the organic phase was separated and the aqueous layer was extracted with dichloromethane. The combined organic phase was dried over sodium sulfate, filtered and the solvent was removed under reduced pressure to give the crude product which was purified by HPLC to yield 1-(1-(1,2-dihydroacenaphthylen-1-yl)piperidin-4-yl)-3-hydroxy-3-(oxazol-2-ylmethyl)indolin-2-one (Compound 99, 18 mg, 7% yield) as a yellow solid: MS (ESI): m/z 466.1 $[M+1]^+$. $^1$H NMR (400 MHz, CDCl$_3$) δ 7.71-7.69 (m, 1H), 7.64-7.62 (m, 1H), 7.55-7.44 (m, 4H), 7.30-7.28 (m, 2H), 7.20-7.14 (m, 2H), 7.05-7.00 (m, 2H), 4.96 (m, 1H), 4.21-4.17 (m, 1H), 3.42-3.34 (m, 3H), 3.27-3.23 (m, 1H), 3.00-2.97 (m, 1H), 2.79-2.76 (m, 1H), 2.53-2.31 (m, 4H), 1.70-1.62 (m, 2H).

Example 20D: Preparation of Compound 100

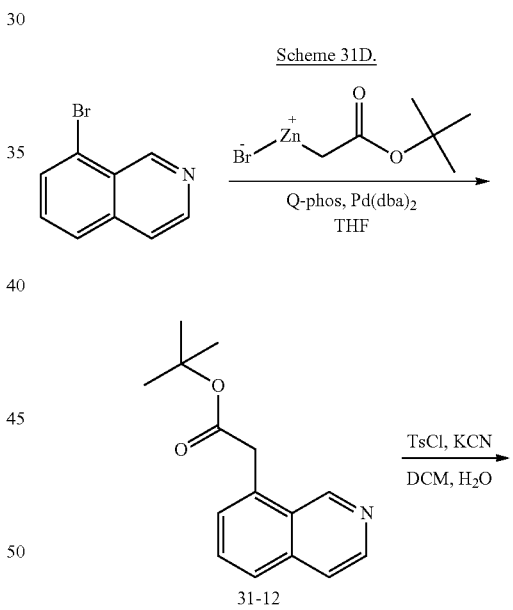

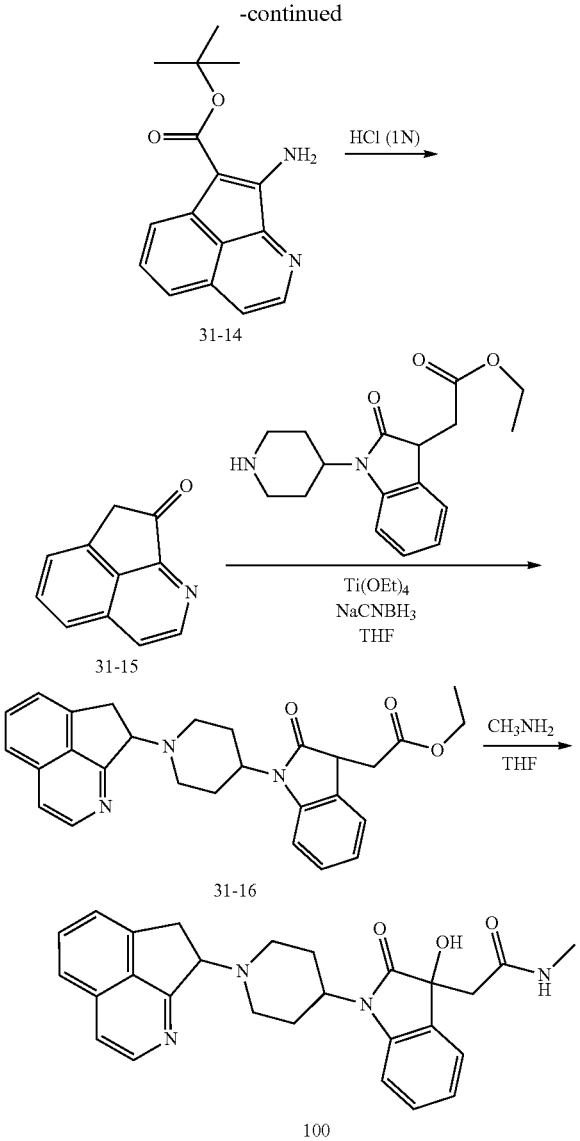

Preparation of Compound 31-12

To a suspension of 8-bromoisoquinoline (1.5 g, 7.3 mmol), Q-phos (52 mg, 0.073 mmol) and Pd(dba)2 (63 mg, 0.11 mmol) in dry THF (30 mL) was added 40 mL of (2-tert-butoxy-2-oxoethyl)zinc(II) bromide solution (20 ml, 0.5 M) under $N_2$. The resulting mixture was heated at 80° C. overnight. The solvent was evaporated under vacuum and the crude residue was diluted with ethyl acetate and washed with water. The combined organic layer was washed with brine, dried over $Na_2SO_4$ and the solvent was evaporated under vacuum to give a residue which was purified by silica gel chromatography to give tert-butyl 2-(isoquinolin-8-yl)acetate (Compound 31-12, 1.33 g, yield 75%) as a white solid. MS m/z 244[M+1]$^+$. $^1$H NMR (400 MHz, CDCl$_3$) δ 9.46 (s, 1H), 8.56-8.54 (d, J=5.6 Hz 1H), 7.76-7.74 (d, J=8.0 Hz 1H), 7.66-7.61 (m, 2H), 7.48-7.47 (d, J=6.8 Hz 1H), 4.07 (s, 2H), 1.42 (s, 9H).

Preparation of Compound 31-13

P-toluenesulfonyl chloride (1.58 g, 8.2 mmol) was added to a vigorously stirred solution of tert-butyl 2-(isoquinolin-8-yl)acetate (Compound 31-12, 1.33 g, 5.5 mmol) and KCN (1.07 g, 16.5 mmol) in $CH_2Cl_2/H_2O$, and the reaction mixture was stirred at 25° C. overnight. The reaction mixture was poured into water and extracted with $CH_2Cl_2$. The combined organic phases were dried over $Na_2SO_4$ and concentrated. Silica gel chromatography yielded tert-butyl 2-(1-cyano-2-tosyl-1,2-dihydroisoquinolin-8-yl)acetate (Compound 31-13, 800 mg, yield 34%) as a white solid. MS m/z 425[M+1]$^+$.

Preparation of Compound 31-14

A solution of tert-butyl 2-(1-cyano-2-tosyl-1,2-dihydroisoquinolin-8-yl)acetate (Compound 31-13, 800 mg, 1.88 mmol) in THF (20 mL) was added t-BuOK (1M in THF, 5.64 mL, 5.64 mmol) at 0° C., then the mixture was stirred at room temperature for 6 hours. The mixture was quenched with water and extracted with EtOAc. The combined organic layer was washed with water and brine, dried over $Na_2SO_4$, filtered and concentrated. Silica gel chromatography yielded tert-butyl tert-butyl8-aminocyclopenta[ij]isoquinoline-7-carboxylate (Compound 31-14, 257 mg, yield: 51%) as a white solid. MS m/z 269[M+1]$^+$.

Preparation of Compound 31-15

A solution of 8-aminocyclopenta[ij]isoquinoline-7-carboxylate (7-4) (Compound 31-14, 257 mg, 0.96 mmol) in dioxane and 1N HCl (9:1) (10 mL) was heated to reflux for 3 hours, then the mixture was diluted with EtOAc. A NaHCO$_3$ solution was added to adjust pH to 8, then the mixture was extracted with EtOAc. The combined organic layer was washed with water and brine, dried over $Na_2SO_4$, filtered and concentrated. Silica gel chromatography yielded cyclopenta[ij]isoquinolin-8(7H)-one (Compound 31-15, 100 mg, yield 62%) as a white solid. MS m/z 170 [M+1]$^+$.

Preparation of Compound 31-16

To a sealed tube containing cyclopenta[ij]isoquinolin-8(7H)-one (7-5) (Compound 31-15, 100 mg, 0.59 mmol) and ethyl 2-(2-oxo-1-(piperidin-4-yl)indolin-3-yl)acetate (267 mg, 0.89 mmol) in tetrahydrofuran (5 mL) was added titanium ethoxide (831 mg, 2.95 mmol). The mixture was heated to 130° C. for 8 hours under microwave conditions, then sodium cyanoborohydride (223 mg, 3.54 mmol) was added and the mixture was heated at 100° C. for 1 hour under microwave conditions. The mixture was quenched with water and extracted with ethyl acetate. The combined organic layer was washed with brine, dried over sodium sulfate, filtered and concentrated. The crude product was purified by silica gel chromatography to yield ethyl 2-(1-(1-(7,8-dihydrocyclopenta[ij]isoquinolin-8-yl) piperidin-4-yl)-2-oxoindolin-3-yl)acetate (Compound 31-16, 77 mg, 29%) as a white solid. (ESI): m/z 456[M+H].

Preparation of Compound 100

A solution of ethyl 2-(1-(1-(7,8-dihydrocyclopenta[ij]isoquinolin-8-yl) piperidin-4-yl)-2-oxoindolin-3-yl)acetate (Compound 31-16, 70 mg, 0.15 mmol) in THF (2 mL) was added aqueous CH$_3$NH$_2$ solution (1 mL), and the mixture was stirred at room temperature overnight. The solvent was removed and the crude product was purified by silica gel chromatography to yield 2-(1-(1-(7,8-dihydrocyclopenta[ij] isoquinolin-8-yl)piperidin-4-yl)-3-hydroxy-2-oxoindolin-3-yl)-N-methylacetamide (Compound 100, 28 mg, 40%) as a white solid. (ESI): m/z 457[M+H]. 1H NMR (400 MHz, CDCl3) δ: 8.55-8.54 (d, J=5.6 Hz, 1H), 7.75-7.71 (t, J$_1$=8.0 Hz, J$_2$=7.2 Hz, 1H), 7.64-7.62 (d, J=8.4 Hz, 1H), 7.51-7.50 (d, J=6.0 Hz, 1H), 7.46-7.44 (d, J=6.4 Hz, 1H), 7.41-7.39 (d, J=7.2 Hz, 1H), 7.31-7.29 (m, 1H), 7.27-7.23 (m, 1H), 7.07-7.04 (t, J$_1$=7.6 Hz, J$_2$=7.2 Hz, 1H), 6.05-6.03 (m, 1H), 5.81-5.70 (m, 1H), 4.89-4.87 (m, 1H), 4.27-4.23 (m, 1H), 3.57-3.45 (m, 2H), 3.13-3.07 (m, 1H), 2.88-2.87 (m, 4H), 2.78-2.74 (m, 1H), 2.57-2.35 (m, 4H), 1.77-1.68 (m, 3H).

Example 20E: Preparation of Compound 101

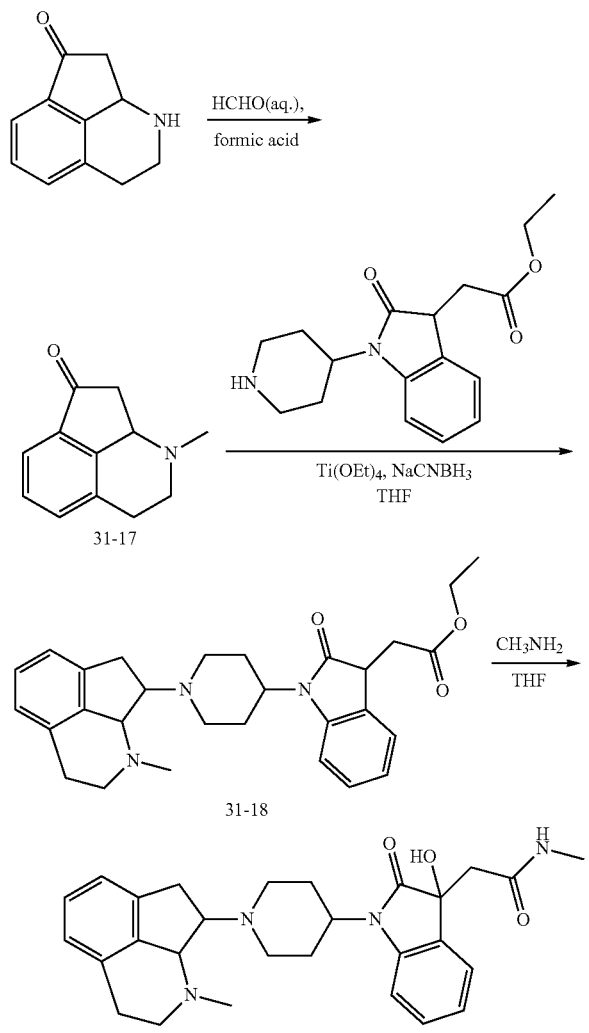

Preparation of Compound 31-17

To a solution of 2,3,8,8a-tetrahydrocyclopenta[ij]isoquinolin-7(1H)-one (519 mg, 3 mmol) in formic acid (5 mL) was added HCHO(aq.) (1 mL) and the mixture was heated to 80° C. for 16 hours. Upon completion, the reaction mixture was cooled, NaHCO$_3$ solution was added to adjust pH to 8 and the mixture was extracted with DCM. The combined organic layer was washed with brine, dried over sodium sulfate, filtered and concentrated. The crude product was purified by silica gel chromatography to yield 1-methyl-2,3,8,8a-tetrahydrocyclopenta[ij]isoquinolin-7(1H)-one (Compound 31-17, 368 mg, 66%) as a yellow solid. MS m/z 188 [M+l]$^+$.

Preparation of Compound 31-18

To a sealed tube containing 1-methyl-2,3,8,8a-tetrahydrocyclopenta[ij]isoquinolin-7(1H)-one (Compound 31-17, 187 mg, 1 mmol) and ethyl 2-(2-oxo-1-(piperidin-4-yl)indolin-3-yl)acetate (151 mg, 0.5 mmol) in tetrahydrofuran (3 mL) was added titanium ethoxide (570 mg, 2.5 mmol). The mixture was heated to 130° C. for 8 hours under microwave conditions, then sodium cyanoborohydride (186 mg, 3 mmol) was added and the mixture was heated to 100° C. for 1 hour under microwave conditions. The mixture was quenched with water and extracted with ethyl acetate. The combined organic layer was washed with brine, dried over sodium sulfate, filtered and concentrated. The crude product was purified by silica gel chromatography to yield ethyl 2-(1-(1-(1-methyl-1,2,3,7,8,8a-hexahydrocyclopenta[ij]iso-quinolin-8-yl) piperidin-4-yl)-2-oxoindolin-3-yl)acetate (Compound 31-18, 36 mg, 15%) as a white solid. (ESI): m/z 474[M+H].

Preparation of Compound 101

To a solution of ethyl 2-(1-(1-(1-methyl-1,2,3,7,8,8a-hexahydrocyclopenta[ij]iso-quinolin-8-yl)piperidin-4-yl)-2-oxoindolin-3-yl)acetate (Compound 31-18, 36 mg, 0.08 mmol) in tetrahydrofuran (THF, 1 mL) was added methylamine (40% w/w aqueous solution, 1 mL). The mixture was stirred overnight at room temperature and purified by reversed phase chromatography to yield 2-(3-hydroxy-1-(1-(1-methyl-1,2,3,7,8,8a-hexahydrocyclopenta[ij]isoquinolin-8-yl)piperidin-4-yl)-2-oxoindolin-3-yl)-N-methylacetamide (Compound 101, 7 mg, 19%) as a white solid. MS(ESI) m/z: 475[M+1]$^+$ $^1$H NMR (400 MHz, CDCl$_3$) δ: 7.42-7.40 (d, J=7.6 Hz, 1H), 7.35-7.31 (t, J$_1$=8.0 Hz, J$_2$=8.0 Hz, 1H), 7.22-7.19 (m, 3H), 7.10-7.00 (m, 2H), 6.07-6.03 (m, 1H), 4.46-4.44 (m, 1H), 4.23-4.19 (m, 1H), 3.14-3.00 (m, 4H), 2.87-2.75 (m, 6H), 2.72-2.67 (m, 1H), 2.64-2.50 (m, 3H), 2.47-2.24 (m, 5H), 2.22-2.17 (m, 1H), 1.92-1.60 (m, 4H).

Example 21: Preparation of Compound 102

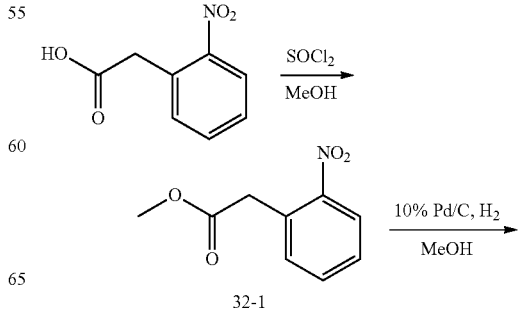

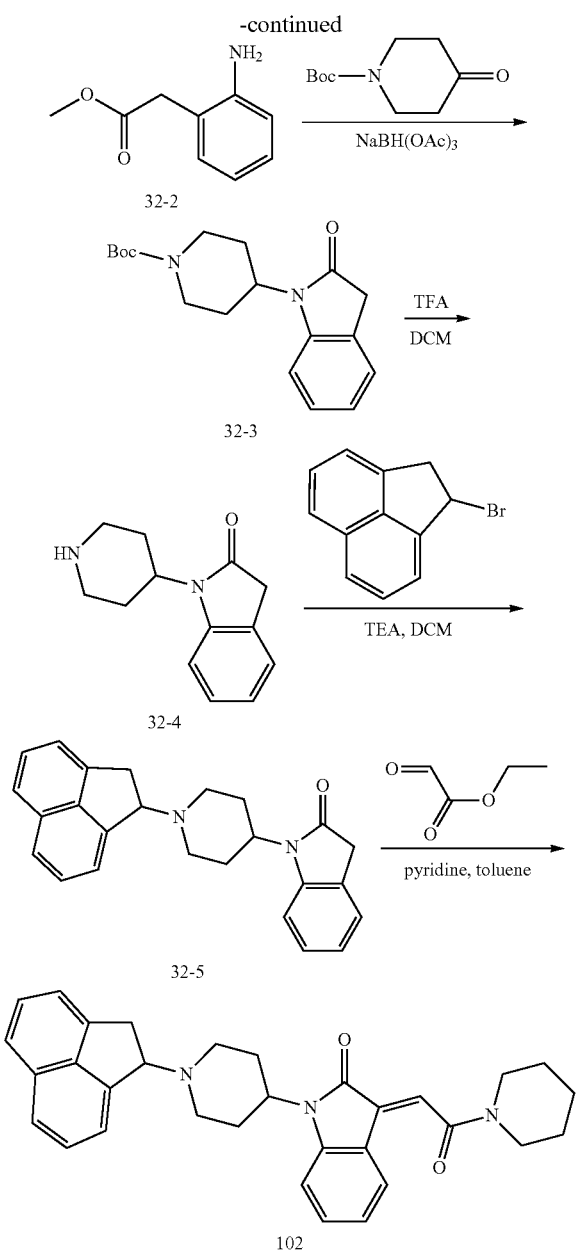

Preparation of Compound 32-1

To a solution of 2-(2-nitrophenyl)acetic acid (18.1 g, 100 mmol) in methanol (150 mL) at room temperature was added sulfurous dichloride (13.1 g, 110 mmol) dropwise. The mixture was heated to 60° C. and stirred for 30 minutes. The reaction mixture was concentrated to give a pale yellow oil, diluted with ethyl acetate, washed with NaHCO₃ and brine, dried over anhydrous sodium sulfate, and concentrated to yield methyl 2-(2-nitrophenyl)acetate (Compound 32-1, 19.1 g, yield: 98%) as a pale yellow oil. MS (ESI): m/z 196 [M+H]⁺. ¹H NMR (400 MHz, CDCl₃) δ 8.12 (dd, 1H, J=8.4, 1.2 Hz), 7.61 (m, 1H), 7.49 (m, 1H), 7.36 (d, 1H, J=7.6 Hz), 4.04 (s, 2H), 3.72 (s, 1H).

Preparation of Compound 32-2

A mixture of methyl 2-(2-nitrophenyl)acetate (Compound 32-1, 9.75 g, 50 mmol), palladium on activated carbon 10% Pd (530 mg, 5 mmol) in methanol (100 mL) was stirred under hydrogen (1 atm.) at room temperature overnight. The reaction mixture was filtered and the filtrate was concentrated to yield methyl 2-(2-aminophenyl)acetate (Compound 32-2, 8.02 g, yield: 97%) as a pale yellow oil. MS (ESI): m/z 166 [M+H]⁺. ¹H NMR (400 MHz, DMSO-d6) δ 6.94 (m, 2H), 6.64 (d, 1H, J=8.0 Hz), 6.51 (m, 1H), 4.88 (s, 2H), 3.59 (s, 3H), 3.52 (s, 2H).

Preparation of Compound 32-3

A mixture of methyl 2-(2-aminophenyl)acetate (Compound 32-2, 3.30 g, 20 mmol), tert-butyl 4-oxopiperidine-1-carboxylate (4.38 g, 22 mmol) and acetic acid (HOAc, 600 mg, 10 mmol) in dichloromethane (80 mL) was stirred at room temperature for 2 h, then sodium triacetoxyborohydride (6.36 g, 30 mmol) was added in portions and heated to 40° C., stirred overnight. The reaction mixture was cooled to room temperature and diluted with dichloromethane, washed with water and sodium bicarbonate, dried over anhydrous sodium sulfate, and concentrated to give the crude product. Purification by silica gel chromatography yielded tert-butyl 4-(2-oxoindolin-1-yl)piperidine-1-carboxylate (Compound 32-3, 2.65 g, yield: 42%) as a pale yellow solid. MS (ESI): m/z 261 [M+H−56]⁺. ¹H NMR (400 MHz, CDCl₃) δ 7.24 (m, 2H), 7.01 (m, 2H), 4.41 (m, 1H), 4.28 (br s, 2H), 3.53 (s, 2H), 2.83 (br s, 2H), 2.32 (m, 2H), 1.70 (m, 2H), 1.50 (s, 9H).

Preparation of Compound 32-4

Trifluoroacetic acid (11.2 g, 99 mmol) was added to a solution of tert-butyl 4-(3-(2-methoxy-2-oxoethyl)-2-oxoindolin-1-yl)piperidine-1-carboxylate (Compound 32-3, 6.27 g, 19.8 mmol) in dry dichloromethane (100 mL). The mixture was stirred for 1 hour at room temperature and concentrated to yield methyl 2-(2-oxo-1-(piperidin-4-yl)indolin-3-yl)acetate TFA salt (Compound 32-4, 12 g, yield 99%) as a pale yellow oil. MS (ESI): m/z 217 [M+H]⁺.

Preparation of Compound 32-5

To a mixture of 2-(2-oxo-1-(piperidin-4-yl)indolin-3-yl) acetate TFA salt (Compound 32-4, 12 g, 19.8 mmol) and triethylamine (10.0 g, 99 mmol) in N,N-dimethylmethanamide (50 mL) was added 1-bromo-1,2-dihydroacenaphthylene (5.09 g, 21.7 mmol). The resulting mixture was stirred at room temperature for 5 h. The mixture was diluted with ethyl acetate and washed with water and brine, dried over anhydrous sodium sulfate and concentrated to give the crude product which was purified by silica gel chromatography to yield 1-(1-(1,2-dihydroacenaphthylen-1-yl)piperidin-4-yl) indolin-2-one (Compound 32-5, 5.78 g, yield: 79%) as a green solid. MS (ESI): m/z 369 [M+H]⁺.

Preparation of Compound 102

A mixture of 1-(1-(1,2-dihydroacenaphthylen-1-yl)piperidin-4-yl)indolin-2-one (Compound 32-5, 1.0 g, 2.7 mmol), ethyl 2-oxoacetate (50% in toluene, 0.83 mL, 4.1 mmol) and pyridine (462 mg, 5.4 mmol) in methanol (30 mL) was stirred at reflux for 3 h. The resulting mixture was cooled and concentrated. The residue was purified by HPLC to yield (E)-1-(1-(1,2-dihydroacenaphthylen-1-yl)piperidin-4-yl)-3-(2-oxo-2-(piperidin-1-yl)ethylidene)indolin-2-one (Compound 102, 440 mg, yield 33%) as an orange solid. MS (ESI): m/z 492 [M+H]⁺. ¹H NMR (400 MHz, CDCl₃) δ

7.71~7.62 (m, 3H), 7.57~7.52 (m, 2H), 7.46 (t, 1H, J=7.6 Hz), 7.30~7.26 (m, 2H), 7.18 (s, 1H), 7.13 (d, 1H, J=7.6 Hz), 4.97 (t, 1H, J=5.2 Hz), 4.28~4.22 (m, 1H), 3.73 (m, 2H), 3.48~3.40 (m, 4H), 3.00 (d, 1H, J=11.2 Hz), 2.79 (d, 1H, J=10 Hz), 2.56~2.33 (m, 4H), 1.72~1.59 (m, 8H).

Example 22A: Preparation of Compounds 104, 105, 106 and 107

Scheme 33A.

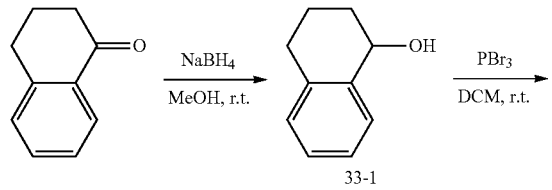

33-1

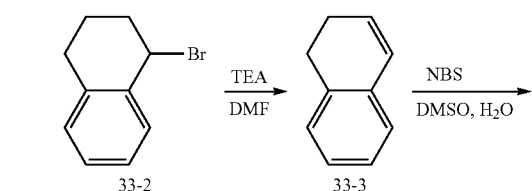

33-2        33-3

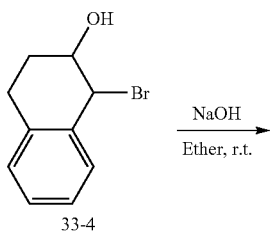

33-4

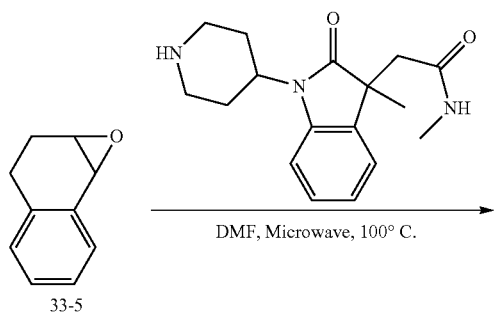

33-5

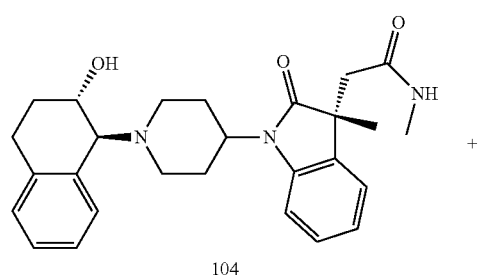

104

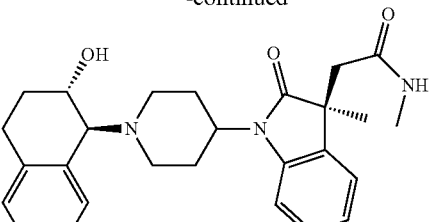

105

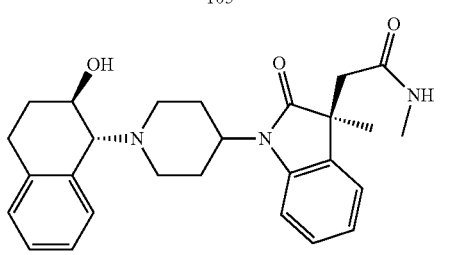

106

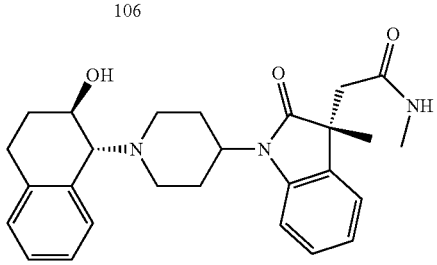

107

Preparation of Compound 33-1

To a solution of 3,4-dihydronaphthalen-1(2H)-one (7.3 g, 50 mmol) in MeOH (80 mL) was added sodium borohydride (2.85 g, 75 mmol). The resulting mixture was stirred at room temperature for 1.5 hours. After completion, the reaction was quenched with water, then the solvent was removed and the residue was dissolved in dichloromethane and water. The aqueous layer was extracted with dichloromethane and the combined organic layer was washed with brine, dried over anhydrous sodium sulfate, and concentrated to give the crude product 1,2,3,4-tetrahydronaphthalen-1-ol (Compound 33-1, 7.3 g, yield: 99%) as a white oil. MS (ESI): m/z: 131 [M−17(—OH)]⁺.

Preparation of Compound 33-2

To a solution of 1,2,3,4-tetrahydronaphthalen-1-ol (Compound 33-1, 7.3 g, 50 mmol) in dichloromethane (80 mL) was added phosphorus tribromide (26.7 g, 100 mmol). The mixture was stirred at room temperature for 3 hours. After completion, the reaction was quenched with water and adjusted to pH=8 with sodium bicarbonate aqueous. The mixture was extracted with dichloromethane and the combined organic layer was washed with brine, dried over anhydrous sodium sulfate, and concentrated to give the crude product 1-bromo-1,2,3,4-tetrahydronaphthalene (Compound 33-2, 7.0 g, yield: 70%) as a yellow oil. MS (ESI): m/z: 131 [M−78(—Br)]⁺.

Preparation of Compound 33-3

To a solution of 1-bromo-1,2,3,4-tetrahydronaphthalene (Compound 33-2, 7.0 g, 33.5 mmol) in N, N-dimethylformamide (60 mL) was added triethylamine (10.1 g, 100.5 mmol) slowly. The mixture was stirred at 60° C. overnight. After completion, the solution was extracted with EtOAc/PE, and the combined organic layer was washed with brine, dried over anhydrous sodium sulfate, and concentrated to give the crude product 1,2-dihydronaphthalene (Compound 33-3, 4.0 g, yield: 90%) as a dark-yellow oil.

Preparation of Compound 33-4

To a solution of 1,2-dihydronaphthalene (Compound 33-3, 390 mg, 3.0 mmol) in dimethyl sulfoxide (5 mL) and water (1 mL) was added N-bromosuccinimide (641 mg, 3.6 mmol) slowly. The mixture was stirred at room temperature for 3 hours. After completion, the solution was extracted with diethyl ether and the combined organic layer was washed with brine, dried over anhydrous sodium sulfate, and filtered to give a solution which was used in next step directly.

Preparation of Compound 33-5

To a solution of 1-bromo-1,2,3,4-tetrahydronaphthalen-2-ol (Compound 33-4) in diethyl ether (60 mL) was added sodium hydroxide (600 mg, 15 mmol). The mixture was stirred at room temperature overnight. After completion, the solution was extracted with EtOAc, and the combined organic layer was washed with brine, dried over anhydrous sodium sulfate, and concentrated to give the crude product 1a,2,3,7b-tetrahydronaphtho[1,2-b]oxirene (Compound 33-5) as a yellow oil. (160 mg, yield: 37%) MS (ESI): m/z: 147 [M+H]⁺.

Preparation of Compounds 104, 105, 106 and 107

To a solution of N-methyl-2-(3-methyl-2-oxo-1-(piperidin-4-yl)indolin-3-yl) acetamide HCl salt (337 mg, 1.0 mmol) in N, N-dimethylformamide (5 mL) was added lithium hydroxide hydrate (84 mg, 2.0 mmol). The mixture was stirred at room temperature for 30 min, then the compound 1a,2,3,7b-tetrahydronaphtho[1,2-b]oxirene (Compound 33-5, 292 mg, 2.0 mmol) was added. The resulting mixture was stirred at 100° C. for 2 hours under microwave. After completion, the mixture was purified by HPLC to give the product which was purified by chiral-HPLC to give the target compounds:

2-((R)-1-(1-((1S,2S)-2-hydroxy-1,2,3,4-tetrahydronaphthalen-1-yl)piperidin-4-yl)-3-methyl-2-oxoindolin-3-yl)-N-methylacetamide (Compound 104, 14 mg, yield: 3.2%) as a white solid. MS (ESI): m/z: 448 [M+H]⁺. ¹H NMR (400 MHz, MeOD) δ: 7.74 (d, 1H, J=7.6 Hz), 7.28-7.02 (m, 8H), 4.21-4.16 (m, 2H), 3.76 (d, 1H, J=6.8 Hz), 3.12-3.09 (m, 2H), 2.84-2.81 (m, 3H), 2.74 (d, 2H, J=14.4 Hz), 2.65-2.58 (m, 2H), 2.47 (s, 3H), 2.40-2.37 (m, 1H), 2.10-2.06 (m, 1H), 1.86-1.71 (m, 3H), 1.31 (s, 3H).

2-((S)-1-(1-((1S,2S)-2-hydroxy-1,2,3,4-tetrahydronaphthalen-1-yl)piperidin-4-yl)-3-methyl-2-oxoindolin-3-yl)-N-methylacetamide (Compound 105, (20 mg, yield: 4.5%) as a white solid. MS (ESI): m/z: 448 [M+H]⁺. ¹H NMR (400 MHz, MeOD) δ: 7.74 (d, 1H, J=8.0 Hz), 7.30-7.02 (m, 8H), 4.22-4.16 (m, 2H), 3.76 (d, 1H, J=7.2 Hz), 3.13-3.09 (m, 2H), 2.84-2.73 (m, 5H), 2.64-2.57 (m, 2H), 2.48 (s, 3H), 2.42-2.39 (m, 1H), 2.10-2.06 (m, 1H), 1.86-1.81 (m, 2H), 1.65 (d, 1H, J=12.0 Hz), 1.31 (s, 3H).

2-((S)-1-(1-((1R,2R)-2-hydroxy-1,2,3,4-tetrahydronaphthalen-1-yl)piperidin-4-yl)-3-methyl-2-oxoindolin-3-yl)-N-methylacetamide (Compound 106, 13 mg, yield: 3.0%) as a white solid. MS (ESI): m/z: 448 [M+H]⁺. ¹H NMR (400 MHz, MeOD) δ: 7.74 (d, 1H, J=8.0 Hz), 7.29-7.02 (m, 8H), 4.22-4.15 (m, 2H), 3.77 (d, 1H, J=7.2 Hz), 3.13-3.10 (m, 2H), 2.84-2.73 (m, 5H), 2.65-2.56 (m, 2H), 2.48 (s, 3H), 2.42-2.38 (m, 1H), 2.10-2.06 (m, 1H), 1.86-1.81 (m, 2H), 1.66 (d, 1H, J=11.6 Hz), 1.30 (s, 3H).

2-((R)-1-(1-((1R,2R)-2-hydroxy-1,2,3,4-tetrahydronaphthalen-1-yl)piperidin-4-yl)-3-methyl-2-oxoindolin-3-yl)-N-methylacetamide (Compound 107, 14 mg, yield: 3.2%) as a white solid. MS (ESI): m/z: 448 [M+H]⁺. ¹H NMR (400 MHz, MeOD) δ: 7.74 (d, 1H, J=7.6 Hz), 7.30-7.02 (m, 8H), 4.22-4.16 (m, 2H), 3.77 (d, 1H, J=7.2 Hz), 3.13-3.10 (m, 2H), 2.85-2.73 (m, 5H), 2.65-2.59 (m, 2H), 2.47 (s, 3H), 2.40-2.36 (m, 1H), 2.10-2.06 (m, 1H), 1.86-1.71 (m, 3H), 1.31 (s, 3H).

Example 22B: Preparation of Compounds 108 and 109

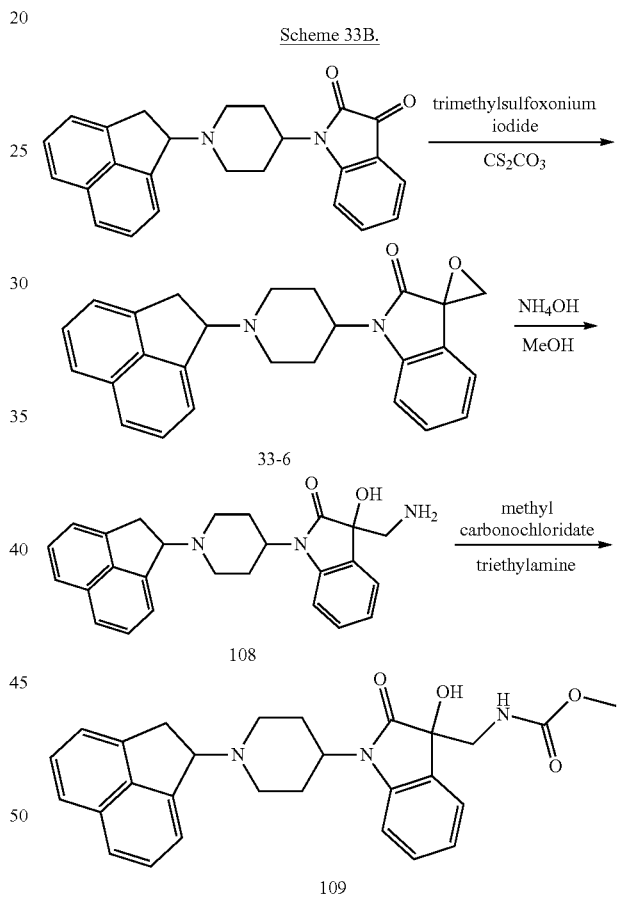

Preparation of Compound 33-6

A mixture of trimethylsulfoxonium iodide (86 mg, 0.39 mmol) and cesium carbonate (128 mg, 0.39 mmol) in acetonitrile (20 mL) was stirred at 50° C. for 1 h. 1-(1-(1, 2-dihydroacenaphthylen-1-yl)piperidin-4-yl)indoline-2,3-dione (100 mg, 0.26 mmol) was added. The resulting mixture was stirred at 50° C. for 1 h. The mixture was cooled and filtrated. The filtrate was concentrated to yield 1-(1-(1, 2-dihydroacenaphthylen-1-yl)piperidin-4-yl)spiro[indoline-3,2'-oxiran]-2-one (Compound 33-6, 95 mg, yield: 92%) as a white solid, which was used in the next step without further purification. MS (ESI): m/z: 397 [M+H]⁺.

Preparation of Compound 108

To a solution of 1-(1-(1,2-dihydroacenaphthylen-1-yl)piperidin-4-yl)spiro[indoline-3,2'-oxiran]-2-one (Compound 33-6, 95 mg, 0.24 mmol) in methanol (5 mL) was added ammonium hydroxide (28% solution, 4 mL). The resulting mixture was stirred at 50° C. for 2 h. The mixture was cooled and concentrated. The residue was purified by HPLC to give 3-(aminomethyl)-1-(1-(1,2-dihydroacenaphthylen-1-yl)piperidin-4-yl)-3-hydroxyindolin-2-one (Compound 108, 45 mg, yield: 45%). MS (ESI): m/z: 414 [M+H]$^+$. $^1$H NMR (400 MHz, CDCl$_3$) δ: 7.73 (d, 1H, J=8.0 Hz), 7.65 (d, 1H, J=8.0 Hz), 7.55 (t, 1H, J=7.2 Hz), 7.51~7.46 (m, 2H), 7.33 (t, 2H, J=6.0 Hz), 7.28 (t, 1H, J=8.0 Hz), 7.14 (d, 1H, J=7.6 Hz), 7.01 (t, 1H, J=6.8 Hz), 4.94 (m, 1H), 4.02 (m, 1H), 3.37 (m, 3H), 2.94 (m, 1H), 2.83~2.73 (m, 2H), 2.54 (m, 1H), 2.44~2.26 (m, 4H), 1.63~1.49 (m, 4H).

Preparation of Compound 109

To a solution of 3-(aminomethyl)-1-(1-(1,2-dihydroacenaphthylen-1-yl)piperidin-4-yl)-3-hydroxyindolin-2-one (Compound 108, 115 mg, 0.27 mmol) in dichloromethane (5 mL) was added triethylamine (56 mg, 0.55 mmol). The mixture was stirred at room temperature for 30 minutes. Methyl carbonochloridate (29 mg, 0.31 mmol) was added. The resulting mixture was stirred at room temperature for 2 h. The mixture was diluted with dichloromethane and washed with water and brine, dried over anhydrous sodium sulfate and concentrated. The residue was purified by pre-HPLC to give the designed product methyl(1-(1-(1,2-dihydroacenaphthylen-1-yl)piperidin-4-yl)-3-hydroxy-2-oxoindolin-3-yl)methylcarbamate (Compound 109, 55 mg, yield: 42%). MS (ESI): m/z: 472 [M+H]$^+$. $^1$H NMR (400 MHz, CDCl$_3$) δ: 7.73 (m, 1H), 7.64 (d, 1H, J=8.0 Hz), 7.56~7.43 (m, 4H), 7.34~7.30 (m, 2H), 7.20 (d, 1H, J=8.0 Hz), 7.09 (t, 1H, J=7.6 Hz), 5.54 (br s, 1H), 4.95 (m, 1H), 4.14 (m, 1H), 3.75~3.66 (m, 4H), 3.45~3.41 (m, 3H), 2.98 (m, 1H), 2.80 (m, 1H), 2.62~2.42 (m, 4H), 2.31 (t, 1H, J=11.2 Hz), 1.66 (m, 2H).

Example 23A: Preparation of Compounds 110, 111, 112, 113, and 114

Scheme 34A.

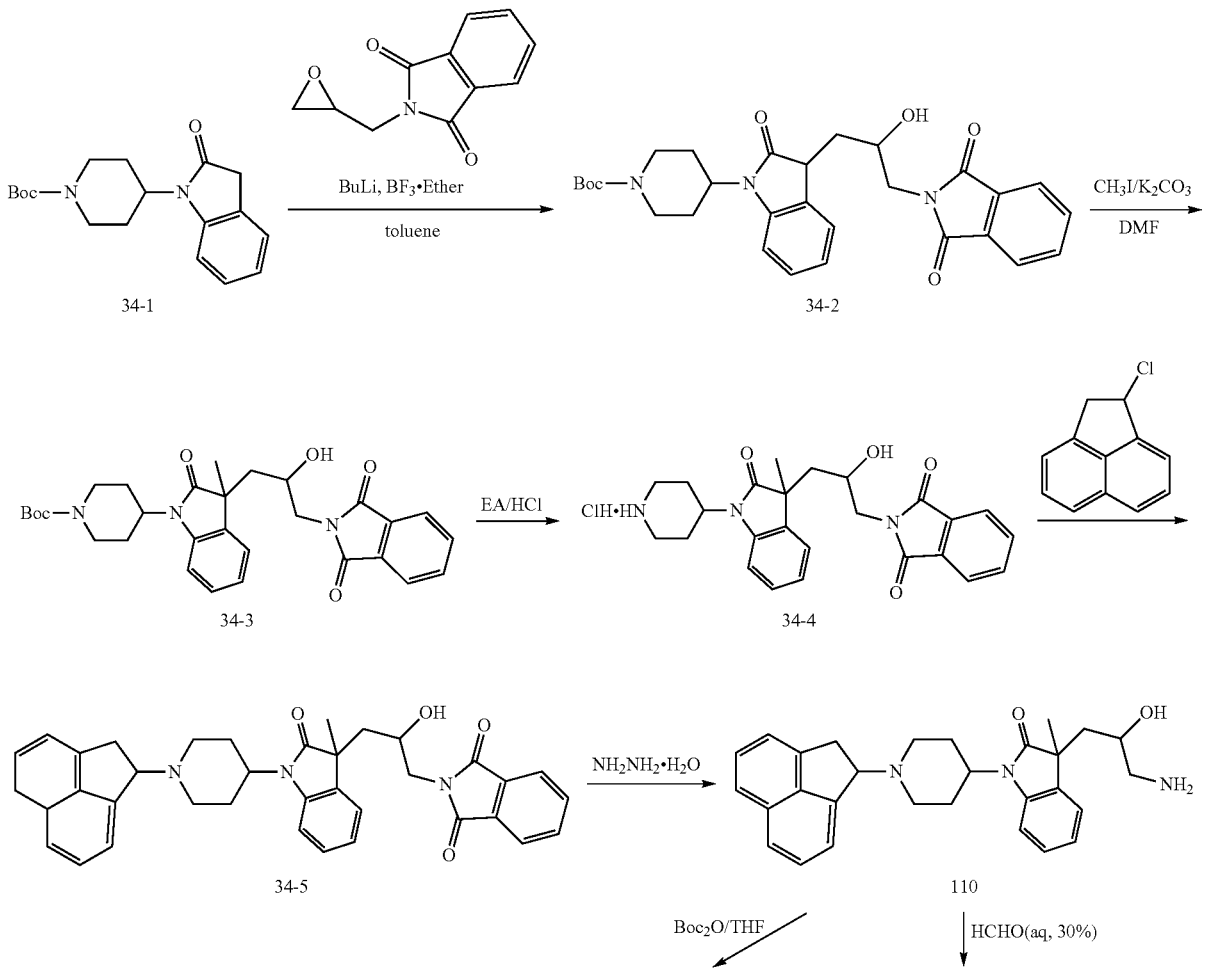

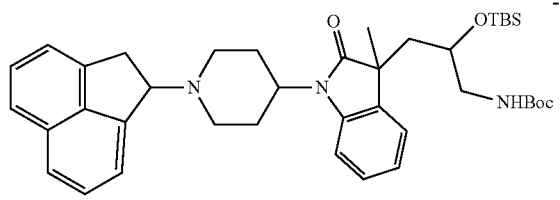

34-6

TBDMSCl
imidazole/DMF ↓

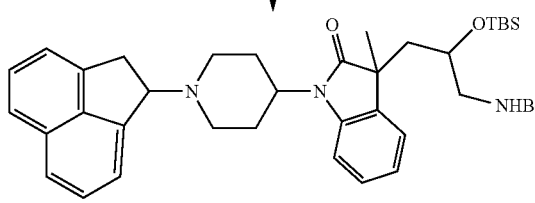

34-7

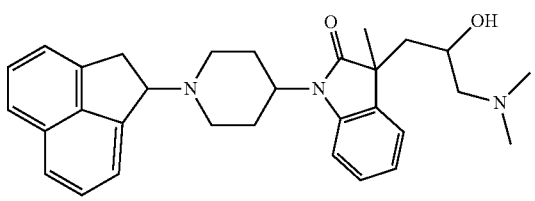

113

NaH/
DMF
CH₃I →

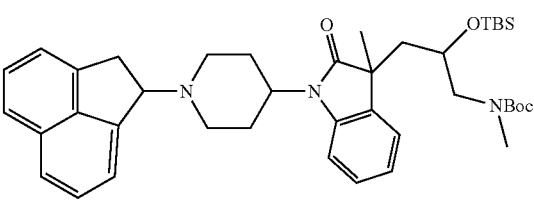

34-8

CF₃COOH | DCM ↓

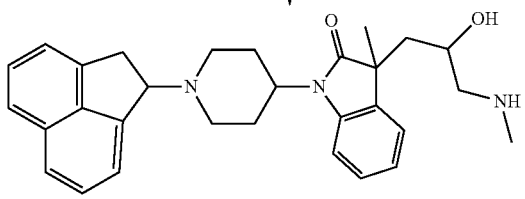

114

Preparation of Compound 34-2

Compound 34-1 (1.58 g, 5 mmol, 1.0 eq) was dissolved in toluene (15 mL) and the solution was cooled to −78° C. BuLi (2.5 M in hexane, 3 mL, 7.5 mmol) was added dropwise and the mixture was stirred for 10 mins, then BF₃·Et₂O (1.06 g, 7.5 mmol) was added. The mixture was stirred for 15 mins, then 2-(oxiran-2-ylmethyl) isoindoline-1,3-dione (1.02 g, 5.00 mmol) in toluene (10 mL) was added dropwise over 5 mins. The mixture was stirred at −78° C. for another 2 hours then stirred at room temperature overnight. The reaction was quenched with NH₄Cl solution and extracted with ethyl acetate. The combined organic layers were dried over Na₂SO₄, filtered and condensed. The residue was purified on silica gel to yield Compound 34-2 (800 mg, 31%). ESI/MS: 420 (M−100+1).

Preparation of compound 34-3

A solution of Compound 34-2 (0.80 g, 1.15 mol) and iodomethane (0.32 g, 2.30 mmol) in DMF was charged with potassium carbonate (15 9 mg, 1.15 mmol). The mixture was stirred at room temperature for 2 hours. The mixture was quenched with water and extracted with ethyl acetate. The combined organic layers were dried with anhydrous sodium sulfite, filtered and condensed. The residue was purified with silica gel to yield Compound 34-3 (0.46 g, 75%). ESI/MS: 434 (M−100+1).

Preparation of compound 34-4

Compound 34-3 (0.46 g, 0.86 mmol) was dissolved in EtOAc/HCl (5.0 mL, 2.3 mmol/mL). The mixture was stirred for 2 hours, and a solid precipitated. The solid was collected and Compound 34-4 (0.35 g, 86%) was obtained as yellow solid. ESI/MS: 434 (M+1).

Preparation of compound 34-5

To a mixture of Compound 34-4 (0.35 g, 0.73 mmol, 1.0 equiv.), K₂CO₃ (0.066 g, 0.48 mmol) in acetonitrile (5 mL) was added NaI (0.22 g, 1.46 mmol) and 1-chloro-1,2-dihydroacenaphthylene (0.27 g, 1.46 mmol). The mixture was stirred at room temperature for 12 hours. Upon completion, the mixture was quenched with water and extracted with ethyl acetate. The combined organic layer was washed with water, dried over anhydrous Na₂SO₄ and condensed. The residue was purified on silica gel to yield Compound 34-5 (0.33 g, 75%). ESI/MS: 586 (M+1).

Preparation of Compound 110

Compound 34-5 (0.33 g, 0.56 mmol, 1.0 equiv.) was dissolved in ethanol (10 ml) and hydrazine (85%, 2 ml) was charged. The mixture was stirred at room temperature for 2 h. The solution was condensed and extracted with DCM, and the combined organic layers were dried with anhydrous Na2SO4, filtered and condensed to obtain crude product (230 mg, 90%). A portion of the crude was purified by HPLC to yield Compound 110 (20 mg, 70%). ESI/MS: 456 (M+1). 1H NMR (400 MHz, CDCl3): δ 7.70-7.72 (d, J=8.0 Hz, 1H), 7.58-7.63 (m, 2H), 7.51-7.55 (m, 1H), 7.44-7.47 (m, 1H), 7.25-7.32 (m, 4H), 7.06-7.10 (m, 1H), 4.98-5.01 (m, 1H), 4.17-4.23 (m, 1H), 3.45-3.49 (m, 2H), 3.32-3.34 (m, 1H), 3.04-3.07 (m, 1H), 2.74-2.78 (m, 1H), 2.32-2.63 (m, 5H), 2.01-2.06 (m, 2H), 1.60-1.73 (m, 2H), 1.36 (s, 3H).

Preparation of Compounds 111 and 112

Compound 111 (10 mg) and Compound 112 (12 mg) were obtained using the same sequence as the synthesis of Compound 110, but using (R)-2-(oxiran-2-ylmethyl)isoindoline-1,3-dione. Compound 111: 1H NMR (400 MHz, CDCl3): δ 7.70-7.72 (d, J=8.0 Hz, 1H), 7.59-7.63 (m, 2H), 7.52-7.55 (m, 1H), 7.44-7.48 (m, 1H), 7.24-7.32 (m, 4H), 7.03-7.07 (m, 1H), 4.92-5.01 (m, 1H), 4.18-4.19 (m, 1H), 3.46-3.49 (m, 2H), 3.03-3.15 (m, 2H), 2.75-2.78 (m, 1H), 2.39-2.60 (m, 5H), 2.06-2.12 (m, 1H), 1.93-1.98 (m, 1H), 1.58-1.65 (m, 2H), 1.36 (s, 3H). Compound 112: 1H NMR (400 MHz, CDCl3): δ 7.70-7.72 (d, J=8.0 Hz, 1H), 7.58-7.63 (m, 2H), 7.51-7.55 (m, 1H), 7.44-7.47 (m, 1H), 7.25-7.32 (m, 4H), 7.06-7.10 (m, 1H), 4.98-5.01 (m, 1H), 4.17-4.23 (m, 1H), 3.45-3.49 (m, 2H), 3.32-3.34 (m, 1H), 3.04-3.07 (m, 1H), 2.74-2.78 (m, 1H), 2.32-2.63 (m, 5H), 1.95-2.06 (m, 2H), 1.60-1.73 (m, 2H), 1.36 (s, 3H).

Preparation of Compound 113

A solution of Compound 110 (20.00 mg, 0.04 mmol, 1.0 equiv.) and formaldehyde (aq, 30%, 0.1 mL) in methanol (3 mL) was stirred at room temperature for 0.5 hour. Then NaBH$_4$ (7.6 mg, 0.2 mmol) was charged with stirring for 2 hours. Upon completion, the reaction was quenched with water and extracted with ethyl acetate. The combined organic layers were dried over Na$_2$SO$_4$, filtered and condensed. The residue was purified by TLC to yield Compound 113 (10 mg, 47%). ESI/MS: 484 (M+1). 1H NMR (400 MHz, CDCl3): δ 7.70-7.72 (d, J=8.0 Hz, 1H), 7.58-7.63 (m, 2H), 7.51-7.55 (m, 1H), 7.44-7.47 (m, 1H), 7.23-7.31 (m, 4H), 7.03-7.07 (m, 1H), 4.97-4.99 (m, 1H), 4.18-4.19 (m, 1H), 3.44-3.52 (m, 2H), 3.17-3.20 (m, 1H), 3.02-3.07 (m, 1H), 2.74-2.76 (m, 1H), 2.38-2.58 (m, 4H), 2.01-2.18 (m, 9H), 1.67-1.69 (m, 2H), 1.30 (s, 3H).

Preparation of Compound 34-6

Compound 110 (180 mg, 0.40 mmol) was dissolved in THF (5 mL) and triethylamine (60 mg, 0.60 mmol) was charged. Boc$_2$O (87 mg, 0.40 mmol) was added and the mixture was stirred at room temperature for 2 hours. The reaction was condensed and Compound 34-6 (220 mg, 99%) was used without further purification. ESI/MS: 556 (M+1)

Preparation of Compound 34-7

Compound 34-6 (220 mg, 0.40 mmol) was dissolved in DMF (5 mL) and imidazole (68 mg, 1.0 mmol) was charged. TBDMSCl (90 mg, 0.60 mmol) was added and the mixture was stirred at room temperature for 12 hours. The reaction was quenched with water and extracted with ethyl acetate. The organic layer was dried over anhydrous sodium sulfate, filtered and condensed. The residue was purified on silica gel to yield compound 34-7 (200 mg, 74%). ESI/MS: 670 (M+1)

Preparation of Compound 34-8

Compound 34-7 (200 mg, 0.30 mmol) was dissolved in DMF (10 mL) and sodium hydrogen (60% in mineral oil, 24 mg, 0.60 mmol) was charged. The mixture was stirred at room temperature for 30 mins. Iodomethane (83 mg, 0.60 mmol) was added and the mixture was stirred at room temperature for 2 hours. The mixture was quenched with water and extracted with ethyl acetate. The organic layer was dried over anhydrous sodium sulfate, filtered and condensed to yield Compound 34-8 (216 mg, 105%) which was used without further purification. ESI/MS: 684 (M+1).

Preparation of Compound 114

Compound 34-8 (216 mg, 0.30 mmol) was dissolved in DCM (3.0 mL) and TFA (0.5 mL) was charged. The mixture was stirred at room temperature for 1 hour. The solution was condensed and the residue was neutralized with sodium bicarbonate to pH=8 and extracted with ethyl acetate. The residue was purified with HPLC to yield Compound 114 (50 mg, 36%). ESI/MS: 470 (M+1). MS (ESI) m/z 470 (M+H+) 1H NMR (400 MHz, CDCl$_3$): δ 7.92 (d, J=8.0 Hz, 1H), 7.81 (d, J=7.2 Hz, 1H), 7.74 (d, J=8.4 Hz, 1H), 7.67 (t, J=7.6 Hz, 1H), 7.57 (t, J=8.0 Hz, 1H), 7.47 (d, J=6.4 Hz, 1H), 7.30-7.22 (m, 3H), 7.08 (t, J=6.4 Hz, 1H), 5.57 (m, 1H), 4.43 (m, 1H), 3.84 (m, 3H), 3.59 (m, 1H), 3.41 (m, 1H), 3.33 (m, 1H), 3.06 (m, 1H), 2.78 (m, 3H), 2.68 (m, 1H), 2.56 (s, 3H), 2.00 (m, 4H), 1.33 (s, 3H).

Example 23B: Preparation of Compound 115

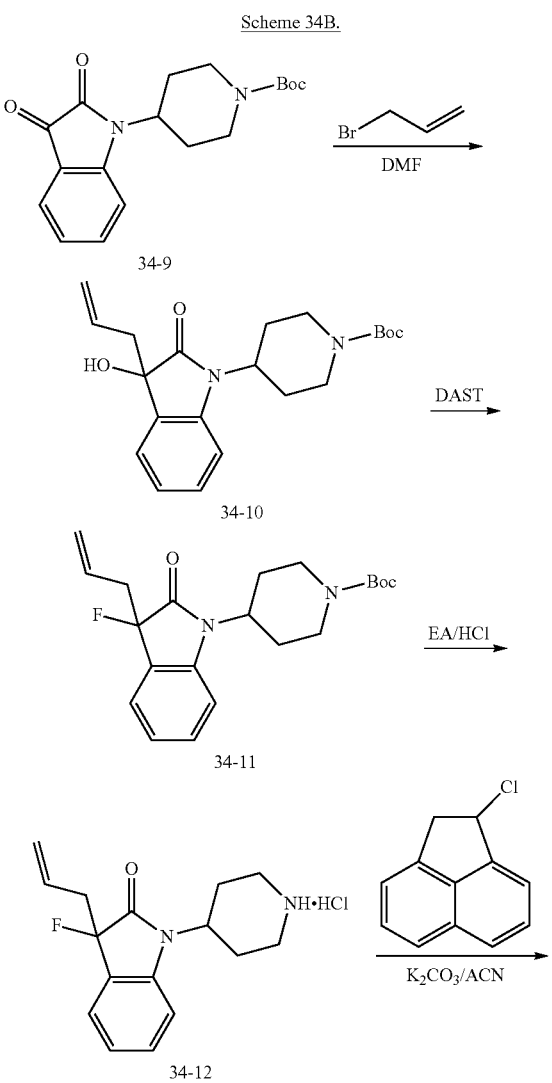

255

-continued

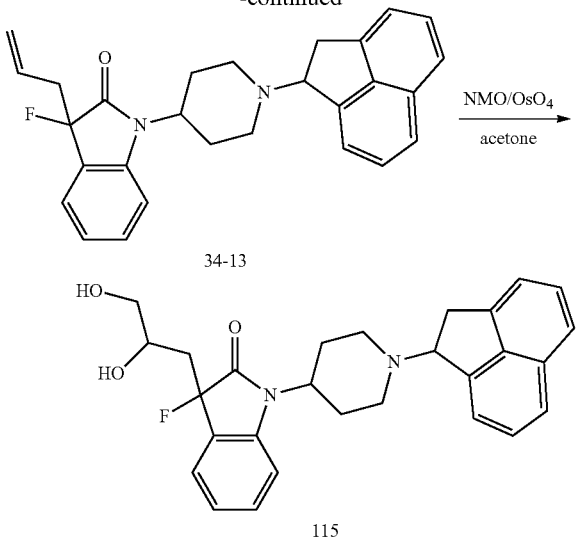

34-13

115

Preparation of Compound 34-10

Compound 34-9 (200 mg, 0.61 mmol) was dissolved in DMF (3.0 mL) and In powder (138 mg, 1.22 mmol) was charged followed with allylbromide (76 mg, 0.62 mmol). The mixture was stirred at room temperature for 6 hours. The reaction was quenched with water and extracted with ethyl acetate. The combined organic layers were dried over anhydrous sodium sulfate, filtered and condensed to yield Compound 34-10 (223 mg, 98%). ESI/MS: 373 (M+1)

Preparation of Compound 34-11

Compound 34-10 (223 mg, 0.60 mmol) was dissolved in DCM (10.0 mL) and DAST (193 mg, 1.20 mmol) was charged. The mixture was stirred at room temperature for 2 hours. Upon completion, the reaction was quenched with ammonium chloride solution and extracted with ethyl acetate. The combined organic layers were dried, filtered and condensed, to yield Compound 34-11 (160 mg, 71%). ESI/MS: 375 (M+1).

Preparation of 34-12

Compound 34-11 (160 mg, 0.43 mmol) was dissolved in EtOAc/HCl (2.33 mmol/mL, 5.0 mL). The mixture was stirred at room temperature for 2 hours. The reaction mixture was condensed and extracted with ethyl acetate. The aqueous layer was neutralized to pH=8 and extracted with ethyl acetate. The combined organic layers were dried over anhydrous sodium sulfate, filtered and condensed, to yield Compound 34-12 (100 mg, 85%). ESI/MS: 275 (M+1)

Preparation of Compound 34-13

A mixture of Compound 34-12 (100 mg, 0.36 mmol, 1.0 equiv.), K$_2$CO$_3$ (66 mg, 0.48 mmol) and acetonitrile (5 mL) was stirred at room temperature. NaI (110 mg, 0.73 mmol) and 1-chloro-1,2-dihydroacenaphthylene (135 mg, 0.73 mmol) were added and the mixture was stirred at room temperature for 12 hours. Upon completion, the mixture was quenched with water and extracted with ethyl acetate. The organic layer was washed with water and dried over anhy-

256 drous Na$_2$SO$_4$ and condensed. The residue was purified by TLC to yield Compound 34-13 (76 mg, 49%). ESI/MS: 427 (M+1).

Preparation of Compound 115

Compound 34-13 (75 mg, 0.18 mmol) was dissolved in acetone/water (4:1, 5 mL), then NMO (41 mg, 0.36 mmol) was charged followed with OsO$_4$ (5 mg, 0.02 mmol). The mixture was stirred at room temperature for 2 hours. The solution was condensed and extracted with ethyl acetate. The combined organic layers were dried over anhydrous sodium sulfate, filtered and condensed. The residue was purified by reverse phase chromatography to yield Compound 115 (10 mg, 12%). ESI/MS: 461 (M+1). 1H NMR (400 MHz, CDCl$_3$): δ 7.72-7.74 (d, J=8.0 Hz, 1H), 7.61-7.65 (m, 2H), 7.54-7.57 (m, 1H), 7.41-7.51 (m, 3H), 7.29-7.34 (m, 2H), 7.12-7.16 (m, 1H), 5.01-5.02 (m, 1H), 4.16-4.18 (m, 1H), 3.73-3.75 (m, 2H), 3.34-3.56 (m, 3H), 3.06-3.09 (m, 2H), 2.77-2.80 (m, 1H), 2.40-2.58 (m, 5H), 2.35-2.38 (m, 1H), 1.70-1.77 (m, 2H), 1.30 (s, 3H).

Example 24: Preparation of Compounds 118 and 119

Scheme 35.

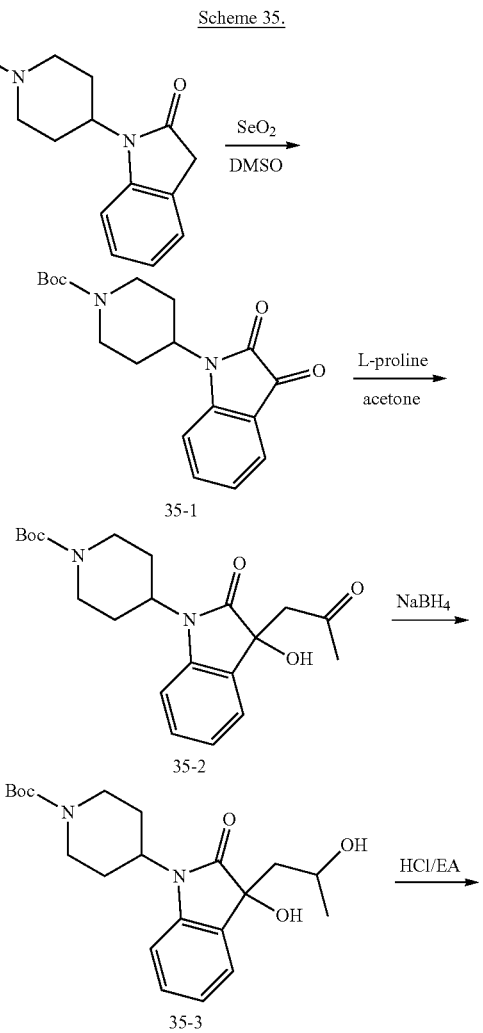

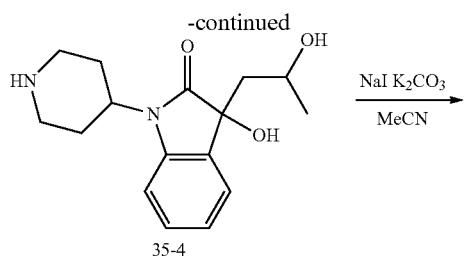

35-4

[Structure: Compound 118]

118

[Structure: Compound 119]

119

Preparation of Compound 35-1

A mixture of tert-Butyl 4-(2-oxoindolin-1-yl) piperidine-1-carboxylate 1-1 (3.0 g, 9.48 mmol) and selenium dioxide (2.63 g, 23.70 mmol) were suspended in dimethyl sulfoxide and the mixture was stirred at 50° C. for 2 hours. Upon completion, the reaction mixture was filtered under reduced pressure. EtOAc and water were added to the filtrate, the layers were separated and the aqueous phase was washed with EtOAc. The combined organic layers were washed with brine, dried over anhydrous $Na_2SO_4$, filtered and concentrated to yield Tert-butyl 4-(2,3-dioxoindolin-1-yl)piperidine-1-carboxylate (Compound 35-1, 3.12 g, 98%) as an orange solid which was used without further purification. MS (ESI): m/z 353.1 (M+Na)$^+$.

Preparation of Compound 35-2

A solution of tert-butyl 4-(2,3-dioxoindolin-1-yl)piperidine-1-carboxylate (Compound 35-1, 1.0 mg, 3.03 mmol) and L-proline (210 mg, 1.82 mmol) in acetone (30 mL) was stirred at room temperature overnight. Upon completion, the solvent was removed under reduced pressure to give the crude product which was purified by silica gel chromatography to yield tert-butyl 4-(3-hydroxy-2-oxo-3-(2-oxopropyl)indolin-1-yl)piperidine-1-carboxylate (Compound 35-2, 1.1 g, 93%) as a brown oil. MS (ESI): m/z 411.1 (M+23)$^+$.

Preparation of Compound 35-3

To a solution of MeOH (40 mL) was added tert-butyl 4-(3-hydroxy-2-oxo-3-(2-oxopropyl)indolin-1-yl)piperidine-1-carboxylate (Compound 35-2, 1.10 g, 2.83 mmol) and sodium borohydride (210 mg, 5.66 mmol) and the solution was stirred at room temperature for 2 hours. The solvent was removed under reduced pressure, then water (15 mL) was added to the residue and the mixture was extracted with DCM. The combined the organic phases were washed with brine, dried over anhydrous $Na_2SO_4$, filtered, and concentrated to yield tert-butyl 4-(3-hydroxy-3-(2-hydroxypropyl)-2-oxoindolin-1-yl)piperidine-1-carboxylate (Compound 35-3, 1.2 g) as a light yellow oil which was used without further purification. MS (ESI): m/z 413.1 (M+23)$^+$.

Preparation of Compound 35-4

To a solution of HCl/EtOAc (3.0 M) (30 mL) was added tert-butyl 4-(3-hydroxy-3-(2-hydroxypropyl)-2-oxoindolin-1-yl)piperidine-1-carboxylate (Compound 35-3, 1.2 g, 3.07 mmol). After addition, the solution was stirred at room temperature for 2 hours, then the solvent was removed under reduced pressure to yield 3-hydroxy-3-(2-hydroxypropyl)-1-(piperidin-4-yl) indolin-2-one hydrochloride (Compound 35-4, 1.16 g) as a light brown solid which was used without further purification. MS (ESI): m/z 292.1 (M+1)+.

Preparation of Compound 35-5

A mixture of 3-hydroxy-3-(2-hydroxypropyl)-1-(piperidin-4-yl) indolin-2-one hydrochloride (Compound 35-4, 70 mg, 0.21 mmol), 1-chloro-1,2-dihydroacenaphthylene (80 mg, 0.42 mmol) NaI (50 mg, 0.32 mmol) and $K_2CO_3$ (90 mg, 0.63 mmol) in MeCN (8 mL) was stirred at 45° C. overnight. Upon completion, the solvent was evaporated under reduced pressure, water was added to the residue, and the mixture was extracted with EtOAc. The combined organic layers were washed with brine, dried over $Na_2SO_4$, and concentrated to give the crude product which was purified by HPLC to yield Compound 118 (15 mg) and Compound 119 (12 mg). MS (ESI): m/z 443.1

Compound 118: $^1$H-NMR (400 MHz, MeOD): δ 7.74 (d, J=8.0 Hz, 1H), 7.64 (t, J=8.4 Hz, 2H), 7.56 (t, J=7.2 Hz, 1H), 7.50~7.47 (dd, J$^1$=6.8 Hz, J$^2$=1.2 Hz, 1H), 7.36~7.31 (m, 4H), 7.11~7.07 (m, 1H), 5.02 (q, J=3.6 Hz, 1H), 4.19~4.11 (m, 1H), 3.57~3.44 (m, 3H), 3.09~3.06 (m, 1H), 2.81~2.77 (dd, J$^1$=7.6 Hz, J$^2$=2.8 Hz, 1H), 2.65~2.38 (m, 4H), 2.26~2.19 (m, 1H), 2.07~1.96 (dd, J$^1$=6.8 Hz, J$^2$=2.8 Hz, 1H), 1.76~1.68 (m, 2H).

Compound 119: $^1$H-NMR (400 MHz, MeOD): δ 7.74 (d, J=8.0 Hz, 1H), 7.64 (t, J=8.4 Hz, 2H), 7.56 (t, J=7.2 Hz, 1H), 7.50~7.47 (dd, J$^1$=6.4 Hz, J$^2$=1.2 Hz, 1H), 7.44~7.42 (dd, J$^1$=6.4 Hz, J$^2$=0.8 Hz, 1H), 7.37~7.29 (m, 3H), 7.14~7.10 (m, 1H), 5.03 (q, J=3.6 Hz, 1H), 4.20~4.13 (m, 1H), 3.99~3.91 (m, 1H), 3.57~3.44 (m, 2H), 3.08 (d, J=12.4 Hz, 1H), 2.79 (d, J=9.2 Hz, 1H), 2.6~2.41 (m, 4H), 2.08~1.92 (m, 2H), 1.75~1.66 (m, 2H), 2.18 (d, J=6.4 Hz, 3H)).

Example 25A: Preparation of Compounds 120 and 121

Scheme 36A.

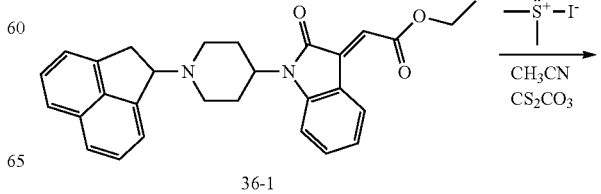

36-1

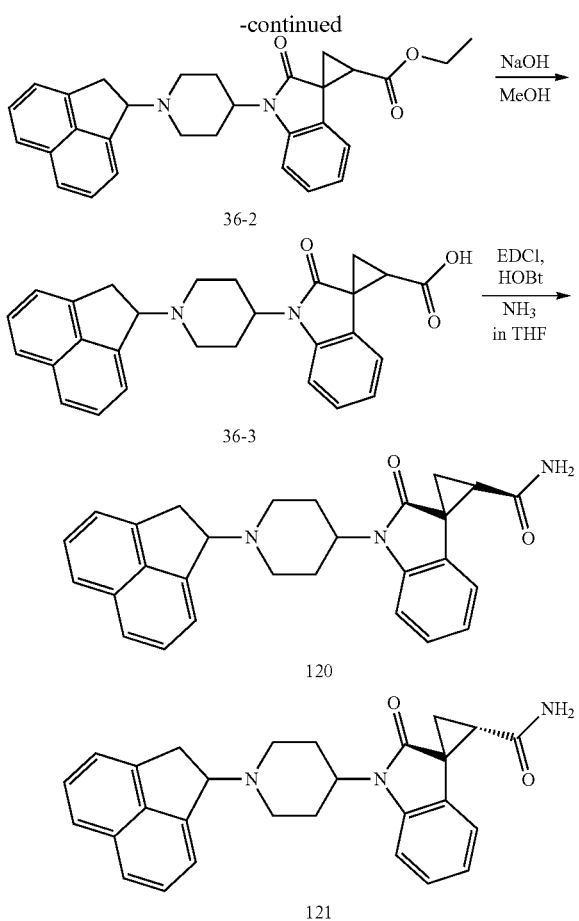

36-2

36-3

120

121

Preparation of Compound 36-2

To a solution of (E)-ethyl 2-(1-(1-(1,2-dihydroacenaphthylen-1-yl) piperidin-4-yl)-2-oxoindolin-3-ylidene)acetate (Compound 36-1, 1.36 g, 3 mmol) and cesium carbonate (8 mmol, 2.60 g) was added trimethylsulfoxoniumiodide (1.65 g, 7.5 mmol). The reaction mixture was stirred at 60° C. for 3 h. The mixture was extracted with ethyl acetate and concentrated under reduced pressure to afford a brown oil which was purified by silica gel chromatography to yield Ethyl 1'-(1-(1,2-dihydroacenaphthylen-1-yl)piperidin-4-yl)-2'-oxospiro[cyclopropane-1,3'-indoline]-2-carboxylate (Compound 36-2, 1.02 g, 72% yield) as a white solid. MS (ESI): m/z 467.1 [M+H]$^+$.

Preparation of Compound 36-3

2.5 mL of sodium hydroxide (2 M) was added to a solution of Compound 36-2 (1 mmol, 467 mg) in 20 mL methanol. The mixture was refluxed for 3 h, then cooled to ambient temperature and acidified to pH=2 with 1M HCl. The solution was extracted ethyl acetate and the organic phase was washed with brine dried over sodium sulfate. The mixture was filtered and the solvent was evaporated to yield 1'-(1-(1,2-dihydroacenaphthylen-1-yl)piperidin-4-yl)-2'-oxospiro[cyclopropane-1,3'-indoline]-2-carboxylic acid (401 mg, 91%) as a white solid. ESI-MS [M+H]$^+$=439.2

Preparation of Compound 120 and Compound 121

1'-(1-(1,2-dihydroacenaphthylen-1-yl)piperidin-4-yl)-2'-oxospiro[cyclopropane-1,3'-indoline]-2-carboxylic acid (Compound 36-3, 401 mg, 0.9 mmol) was dissolved in 30 mL of ammonia in tetrahydrofuran solution (2 M). Then N-(3-dimethylaminopropyl)-N'-ethylcarbodiimide hydrochloride (155 mg, 1 mmol) and 1-hydroxybenzotriazole (27 mg, 0.2 mmol) were added and the reaction was stirred overnight at ambient temperature. Water and ethyl acetate were added to the reaction mixture and the phases were separated. The aqueous phase was washed twice with ethyl acetate. The combined organic phases were dried over sodium sulfate, filtered and concentrated to provide a pale yellow oil. The pale yellow oil was purified by HPLC to yield Compound 120 (102 mg, yield 25%) and Compound 120 (92 mg, yield 23%). ESI-MS [M+H]$^+$=438.3

Compound 120: $^1$H NMR (400 MHz, DMSO) δ 7.98 (d, J=8.2 Hz, 1H), 7.86-7.79 (m, 2H), 7.74-7.69 (m, 1H), 7.63-7.59 (m, 1H), 7.52-7.48 (m, 2H), 7.26 (d, J=3.9 Hz, 2H), 7.08-7.00 (m, 2H), 6.96 (s, 1H), 5.63 (d, J=6.1 Hz, 1H), 4.53 (s, 1H), 3.91-3.75 (m, 2H), 3.58-3.33 (m, 2H), 3.25-3.04 (m, 2H), 2.80-2.58 (m, 3H), 2.01 (dd, J=8.1, 4.1 Hz, 1H), 1.92-1.77 (m, 3H).

Compound 121: $^1$H NMR (400 MHz, DMSO) δ 7.74 (d, J=7.8 Hz, 2H), 7.66 (d, J=8.2 Hz, 1H), 7.56 (t, J=7.4 Hz, 1H), 7.49 (dd, J=13.8, 6.9 Hz, 2H), 7.36-7.30 (m, 2H), 7.24 (d, J=4.1 Hz, 2H), 7.12 (s, 1H), 6.96-6.91 (m, 1H), 5.02-4.92 (m, 1H), 4.13 (t, J=12.2 Hz, 1H), 3.45-3.37 (m, 2H), 2.95 (s, 1H), 2.63-2.32 (m, 6H), 1.97 (dd, J=7.4, 3.8 Hz, 1H), 1.74-1.52 (m, 3H).

Example 25B: Preparation of Compounds 122 and 123

Scheme 36B.

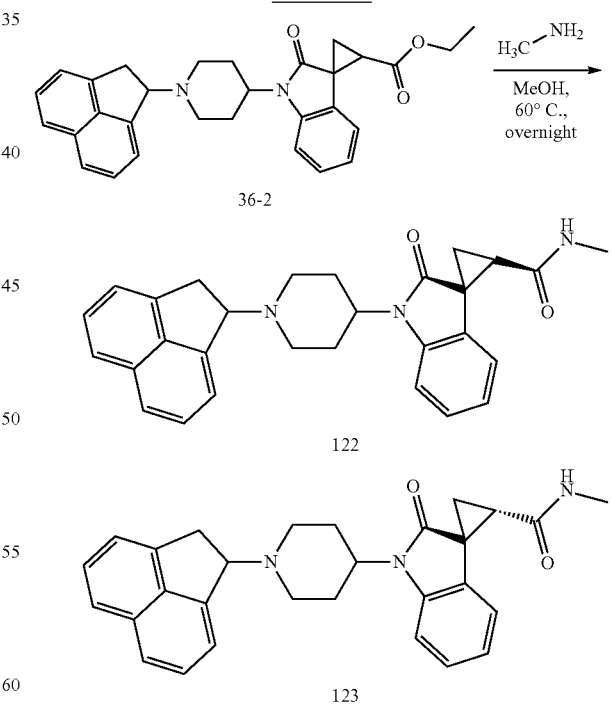

36-2

122

123

5 mL methyl amine (2 M, methanol solution) was added to a solution of Compound 36-2 (1 mmol, 467 mg) in 20 ml of methanol and the mixture was refluxed overnight. The solution was cooled to ambient temperature then extracted with ethyl acetate. The organic phase was washed with brine and dried over sodium sulfate. The mixture was filtered and the solvent was evaporated under reduced pressure to produce a pale yellow oil. The pale yellow oil was purified by HPLC to yield Compound 122 (73 mg, yield 16%) and Compound 123 (62 mg, yield 14%). ESI-MS [M+H]$^+$=452.2

Compound 122: $^1$H NMR (400 MHz, MeOD) δ 7.71 (d, J=7.9 Hz, 1H), 7.64-7.51 (m, 3H), 7.46 (t, J=7.5 Hz, 1H), 7.39-7.24 (m, 3H), 7.06-6.96 (m, 2H), 5.00 (s, 1H), 4.35-4.18 (m, 1H), 3.56-3.39 (m, 2H), 3.10-3.03 (m, 1H), 2.84-2.74 (m, 5H), 2.65-2.37 (m, 4H), 2.22-2.11 (m, 1H), 1.95-1.84 (m, 1H), 1.76-1.48 (m, 2H).

Compound 123: $^1$H NMR (400 MHz, MeOD) δ 7.71 (d, J=8.0 Hz, 1H), 7.60 (dd, J=11.2, 7.6 Hz, 2H), 7.56-7.51 (m, 1H), 7.48-7.43 (m, 1H), 7.31 (d, J=6.4 Hz, 2H), 7.25 (dd, J=13.4, 7.3 Hz, 2H), 6.95 (t, J=7.5 Hz, 1H), 4.99 (dd, J=7.1, 3.4 Hz, 1H), 4.32-4.12 (m, 1H), 3.55-3.39 (m, 2H), 3.04 (d, J=10.7 Hz, 1H), 2.85-2.71 (m, 1H), 2.67-2.63 (m, 3H), 2.63-2.49 (m, 4H), 2.47-2.34 (m, 1H), 2.13 (dd, J=7.4, 4.3 Hz, 1H), 1.82 (dd, J=8.7, 4.3 Hz, 1H), 1.66 (dd, J=24.4, 11.8 Hz, 2H).

Using the methods similar to those described herein, the following compounds were prepared:

| No. | Structure | Data |
|---|---|---|
| 124 | (structure) | MS (ESI): m/z 432 [M + H]$^+$. 1H NMR (400 MHz, CDCl$_3$): 7.74 (d, J = 7.6 Hz, 1H), 7.33-7.30 (m, 2H), 7.21-7.17 (m, 2H), 7.11 (t, J = 7.2 Hz, 1H), 7.05 (t, J = 7.6 Hz, 2H), 6.68 (brs, 1H), 4.23 (m, 1H), 3.83 (m, 1H), 3.36 (d, J = 8.0 Hz, 1H), 2.85 (m, 4H), 2.73 (m, 2H), 2.64 (m, 2H), 2.43 (m, 2H), 2.24 (m, 2H), 2.01(m, 2H), 1.78 (m, 2H), 1.67 (m, 1H), 1.54 (m, 1H), 1.44 (s, 3H). |
| 125 | (structure) | MS (ESI): m/z 442 [M + H]$^+$. 1H NMR (400 MHz, CDCl$_3$): 7.81-7.78 (dd, J$_1$ = 7.6 Hz, J$_2$ = 0.8 Hz, 1H), 7.72 (t, J = 4.8 Hz, 1H), 7.40-7.33 (m, 4H), 7.28(d, J$_1$ = 7.6 Hz, 1H), 7.21 (t, J = 4.8 Hz, 1H), 7.05-6.99(m, 2H), 6.57 (brs, 1H), 4.33-4.25 (m, 1H), 3.99 (s, 2H), 3.81 (t, J = 6.4 Hz, 1H), 3.14(s, 3H), 3.03(d, J = 11.6 Hz, 2H), 2.82 (m, 4H), 2.57(dd, J$_1$ = 15.2 Hz, J$_2$ = 6.4 Hz, 1H), 2.41-2.32 (m, 2H), 2.16 (t, J = 16.4 Hz, 2H), 1.65-1.63(m, 2H). |
| 126 | (structure) | MS (ESI): m/z 470 [M + H]$^+$. 1H NMR (400 MHz, CDCl3): 7.74-7.72 (d, J = 8.4 Hz, 1H), 7.60-7.57 (d, J = 8.4 Hz, 1H), 7.35-7.19 (m, 6H), 7.06-7.02 (t, J$_1$ = 7.2 Hz, J$_2$ = 8.0 Hz, 1H), 6.59 (s, 1H), 5.05-5.03 (m, 1H), 4.26-4.23 (m, 1H), 4.08-4.07 (d, J = 4.0 Hz, 3H), 3.82-3.80 (m, 1H), 3.54-3.49 (m, 1H), 3.38-3.34 (m, 1H), 2.91-2.81 (m, 6H), 2.75-2.67 (m, 1H), 2.62-2.55 (m, 1H), 2.47-2.41 (m, 2H), 2.19-2.11 (m, 1H), 1.64-1.61 (m, 2H). |

-continued

| No. | Structure | Data |
|---|---|---|
| 127 | 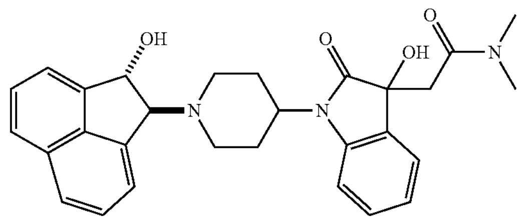 [SMILES: CN(C)C(=O)CC1(O)C(=O)N(C2CCN([C@H]3c4cccc5cccc(c45)[C@@H]3O)CC2)c2ccccc21] | MS (ESI): m/z 486.1 [M + 1]⁺.<br>¹H NMR (400 MHz, CDCl3): 7.77-7.74 (m, 2H), 7.59-7.49 (m, 5H), 7.26-7.20 (m, 2H), 7.05-7.01 (m, 1H), 6.42 (bs, 1H), 5.74 (s, 1H), 4.69 (s, 1H), 4.29-4.23 (m, 1H), 3.10-3.07 (m, 1H), 2.99-2.46 (m, 14H), 1.76-1.67 (m, 2H). |
| 128 | 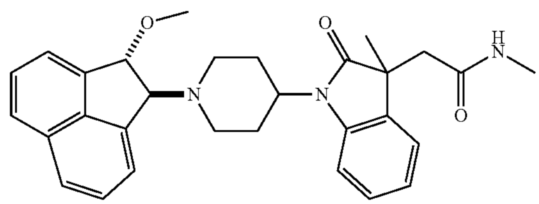 [SMILES: CNC(=O)CC1(C)C(=O)N(C2CCN([C@H]3c4cccc5cccc(c45)[C@@H]3OC)CC2)c2ccccc21] | MS (ESI): m/z 484.3[M + H]⁺.<br>¹H-NMR (400 MHz, CDCl₃): 7.75-7.81 (m, 2 H), 7.53-7.60 (m, 4H), 7.26-7.29 (m, 2H), 7.20 (d, J = 8.0 Hz, 1H), 7.07 (t, J = 7.2 Hz, 1H), 6.23 (s, 1H), 5.38 (s, 1H), 4.77 (s, 1H), 4.25-4.28 (m, 1H), 3.64 (s, 3H), 3.06 (d, J = 6.8 Hz, 1H), 2.76-2.84 (m, 2H), 2.46-2.66 (m, 8H), 1.75 (s, 1 H), 1.67 (d, J = 12.4 Hz, 1 H), 1.41 (s, 3H). MS |
| 129 | 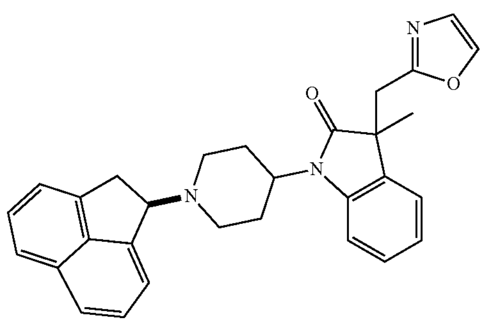 | MS (ESI): m/z 464.2[M + H]⁺.<br>¹H-NMR (400 MHz, CDCl₃): 7.72-7.74 (m, 1 H), 7.66 (d, J = 8.4 Hz, 1 H), 7.53-7.58 (m, 2H), 7.49 (t, J = 7.6 Hz, 1H), 7.32-7.37 (m, 2H), 7.22 (t, J = 7.2 Hz, 1H), 7.09-7.18 (m, 2H), 7.01 (t, J = 7.2 Hz, 1H), 6.85 (d, J = 9.2 Hz, 1H), 5.01 (s, 1 H), 4.12 (s, 1H), 3.45 (s, 2H), 3.22-3.33 (m, 2H), 3.03 (s, 1H), 2.80 (s, 1 H), 2.40-2.55 (m, 4H), 1.52-1.70 (m, 2H), 1.50 (s, 3H). |
| 130 | 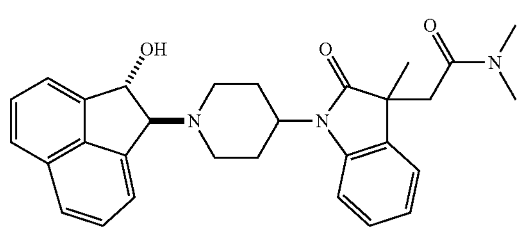 [SMILES: CN(C)C(=O)CC1(C)C(=O)N(C2CCN([C@H]3c4cccc5cccc(c45)[C@@H]3O)CC2)c2ccccc21] | MS (ESI): m/z 484.1 [M + 1]⁺.<br>¹H NMR (400 MHz, CDCl3): 7.80-7.76 (m, 2H), 7.61-7.54 (m, 4H), 7.27-7.15 (m, 3H), 7.02-6.98 (m, 1H), 5.80 (bs, 1H, 4.74 (s, 1H), 4.39 (m, 1H), 3.18-3.13 (m, 1H), 3.03-2.92 (m, 6H), 2.80-2.58 (m, 7H), 1.95-1.74 (m, 3H), 1.36 (s, 3H). |
| 131 | 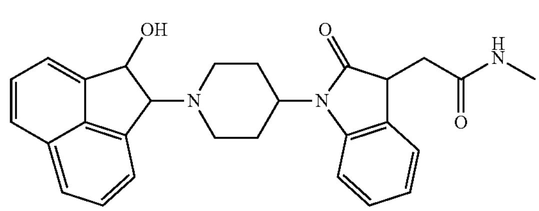 [SMILES: CNC(=O)CC1C(=O)N(C2CCN(C3c4cccc5cccc(c45)C3O)CC2)c2ccccc21] | MS (ESI): m/z 456 [M + 1]⁺.<br>1H NMR (400 MHz, CDCl3): 7.81-7.77(t, J₁ = 7.2 Hz, J₂ = 8.0 Hz, 2H), 7.62-7.54(m, 4H), 7.32-7.30(m, 2H), 7.26-7.23(m, 1H), 7.08-7.04(t, J₁ = 7.6 Hz, J₂ = 7.6 Hz, 1H), |

| No. | Structure | Data |
|---|---|---|
| | | 6.54(s, 1H), 5.78(s, 1H), 4.73 (s, 1H), 4.32(m, 1H), 3.86-3.82(m, 1H), 3.16-3.13(m, 1H), 3.00-2.97(m, 1H), 2.89-2.84(m, 3H), 2.75-2.50(m, 6H), 1.72(m, 3H). |
| 132 | 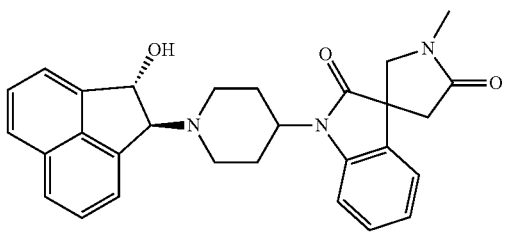 [SMILES: CN1CC2(CC1=O)C(=O)N(C1CCN([C@H]3c4cccc5cccc(c45)[C@@H]3O)CC1)c1ccccc12] | MS (ESI): m/z 468 [M + 1]$^+$. 1H NMR (400 MHz, CDCl3): 7.81-7.77(t, $J_1$ = 6.8 Hz, $J_2$ = 7.6 Hz, 2H), 7.62-7.55(m, 4H),7.30-7.28(m, 2H), 7.28-7.27(m, 1H), 7.10-7.06(m, 1H), 5.78(s, 1H), 4.74(s, 1H), 4.34-4.33(m, 1H), 3.82-3.79(d, J = 9.6 Hz, 1H), 3.41-3.39(d, J = 9.6 Hz, 1H), 3.15-3.12(m, 1H), 3.00-2.97(m, 5H), 2.74-2.57(m, 3H), 2.54-2.50(m, 2H), 1.78-1.70(m, 3H). |
| 133 | 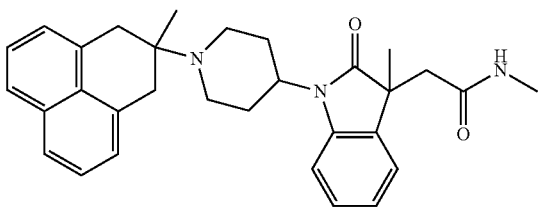 [SMILES: CNC(=O)CC1(C)C(=O)N(C2CCN(C3(C)Cc4cccc5cccc(c45)C3)CC2)c2ccccc21] | MS (ESI): m/z 482.0 [M + 1]$^+$. $^1$H-NMR (400 MHz, CDCl$_3$): 7.73 (d, J = 8.0 Hz, 2H), 7.41 (t, J = 7.2 Hz, 2H), 4.23 (d, J = 6.8 Hz, 3H), 7.16 (t, J = 7.6 Hz, 1H), 7.04 (t, J = 7.6 Hz, 1H), 6.75 (s, 1H), 6.25 (s, 1H), 4.28 (s, 1 H), 3.26-3.37 (m, 4H), 3.15 (d, J = 15.6 Hz, 2H), 2.77 (d, J = 14.4 Hz, 1H), 2.66 (d, J = 4.8 Hz, 3H), 2.62 (d, J = 14.4 Hz, 1H), 2.35-2.42 (m, 2H), 2.02-2.19 (m, 2H), 1.63-1.76 (m, 2H), 1.39 (s, 3H), 1.08 (s, 3H). |
| 134 | 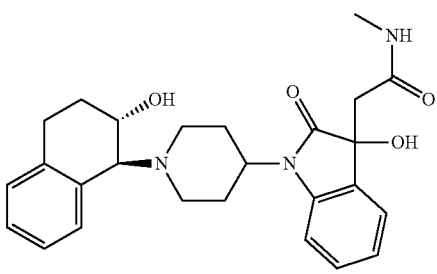 [SMILES: CNC(=O)CC1(O)C(=O)N(C2CCN([C@H]3c4ccccc4CC[C@@H]3O)CC2)c2ccccc21] | MS (ESI): m/z 450 [M + H]$^+$. 1H NMR (400 MHz, MeOD): 7.72(d, 1H, J = 5.2 Hz), 7.28(t, 2H, J = 6.4 Hz), 7.20(t, 1H, J = 7.6 Hz), 7.12(t, 2H, J = 5.2 Hz), 7.06(d, 1H, J = 7.6 Hz), 6.97(t, 1H, J = 7.6 Hz), 6.09(s, 1H), 4.76(d, 1H, J = 5.2 Hz), 4.02(m, 2H), 3.63(d, 1H, J = 6.8 Hz), 3.13-3.03(m, 2H), 2.79-2.68(m, 4H), 2.54-2.45(m, 2H), 2.41-2.37(m, 4H), 2.19-2.13(m, 1H), 1.94-1.91(m, 1H), 1.75-1.62(m, 2H), 1.55(t, 1H, J = 12.4 Hz). |

| No. | Structure | Data |
|---|---|---|
| 135 | 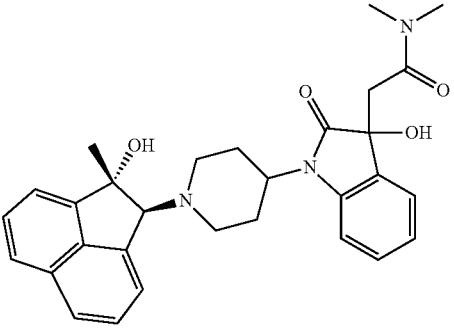 | MS (ESI): m/z 450 [M + H]⁺. ¹H NMR (400 MHz, MeOD): 7.77(d, 2H, J = 8.4 Hz), 7.62-7.55(m, 3H), 7.47(d, 1H, J = 6.8 Hz), 7.37-7.29(m, 2H), 7.17(d, 1H, J = 7.6 Hz), 7.04(t, 1H, J = 6.4 Hz), 4.58(s, 1H), 4.03(m, 1H), 3.36-3.28(m, 2H), 3.20(t, 1H, J = 11.2 Hz), 3.10(s, 1H), 3.06(d, 3H, J = 5.2 Hz), 2.74(d, 3H, J = 6.0 Hz), 2.65(m, 1H), 2.41-2.32(m, 2H), 2.04-2.03(m, 1H), 1.90-1.84(m, 4H), 1.56(t, 1H, J = 13.6 Hz). |
| 136 | 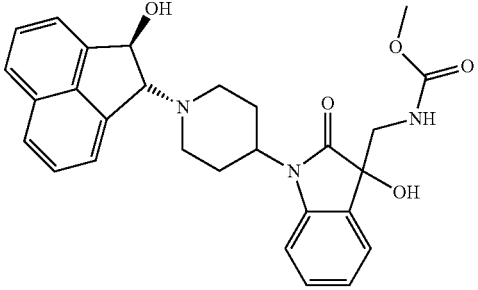 | MS (ESI): m/z 488 [M + 1]⁺. ¹H NMR (400 MHz, MeOD): 7.75-7.82 (m, 2H), 7.52-7.65 (m, 4H), 7.26-7.44 (m, 3H), 7.09 (t, J = 7.6 Hz, 2H), 5.75 (d, J = 2.1 Hz, 1H), 4.67 (d, J = 2.2 Hz, 1H), 4.12-4.27 (m, 1H), 3.42-3.64 (m, 5H), 3.21 (d, J = 10.4 Hz, 1H), 2.40-2.89 (m, 5H), 1.79 (t, J = 11.6 Hz, 1H), 1.62-1.71 (m, 1H). |
| 137 | 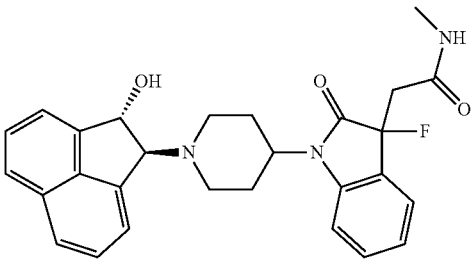 [SMILES: CNC(=O)CC1(F)C(=O)N(C2CCN([C@H]3c4cccc5cccc(c45)[C@@H]3O)CC2)c2ccccc21] | MS (ESI): m/z 474 [M + H]⁺. ¹H NMR (400 MHz, MeOD): 7.79~7.76 (m, 2H), 7.62~7.54 (m, 2H), 7.46~7.40 (m, 2H), 7.30 (d, 1H, J = 8.4 Hz), 7.10 (t, 1H, J = 7.6 Hz), 5.75 (m, 1H), 4.68 (m, 1H), 4.22~4.16 (m, 1H), 3.24~3.19 (m, 3H), 2.84~2.80 (m, 2H), 2.65~2.61 (m, 1H), 2.53~2.45 (m, 5H), 1.90 (m, 1H), 1.71 (m, 1H). |
| 138 | 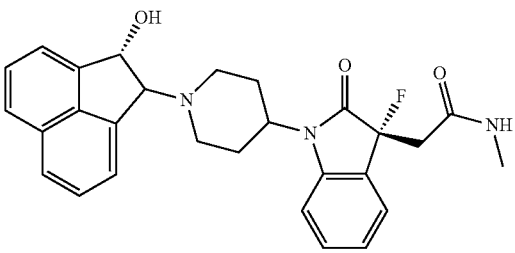 [SMILES: CNC(=O)C[C@]1(F)C(=O)N(C2CCN(C3c4cccc5cccc(c45)[C@@H]3O)CC2)c2ccccc21] | Chiral HPLC (column AD-H) of Compound 137, RT = 2.52 min. MS (ESI): m/z: 474 [M + H]⁺. ¹H NMR (400 MHz, MeOD) δ: 7.79-7.76 (m, 2H), 7.62-7.55 (m, 4H), 7.46-7.41 (m, 2H), 7.30 (d, J = 7.6 Hz, 1H), 7.10 (t, J = 7.6 Hz, 1H), 5.75 (s, 1H), 4.68 (s, 1H), 4.22-4.16 (m, 1H), 3.24-3.20 (m, 3H), 2.84-2.80 (m, 2H), 2.71-2.65 (m, 1H), 2.53-2.45 (m, 5H), 1.88 (d, J = 12.4 Hz, 1H), 1.78-1.76 (m, 1H). |

| No. | Structure | Data |
|-----|-----------|------|
| 139 | 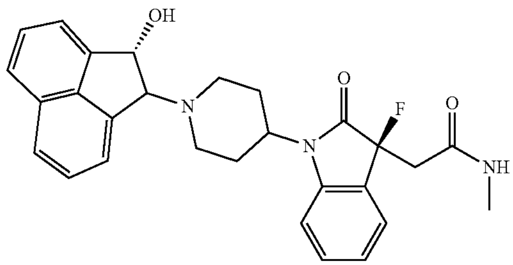 [SMILES: CNC(=O)C[C@@]1(F)C(=O)N(C2CCN(C3c4cccc5cccc(c45)[C@@H]3O)CC2)c2ccccc21] | Chiral HPLC (column AD-H) of Compound 137, RT = 2.92 min. MS (ESI): m/z: 474 [M + H]⁺. ¹H NMR (400 MHz, MeOD) δ: 7.80-7.77 (m, 2H), 7.62-7.55 (m, 4H), 7.46-7.41 (m, 2H), 7.30 (d, J = 8.4 Hz, 1H), 7.10 (t, J = 7.6 Hz, 1H), 5.75 (s, 1H), 4.68 (s, 1H), 4.22-4.16 (m, 1H), 3.24-3.20 (m, 3H), 2.84-2.80 (m, 2H), 2.69-2.62 (m, 1H), 2.53-2.45 (m, 5H), 1.92 (d, J = 12.4 Hz, 1H), 1.73-1.71 (m, 1H). |
| 140 | 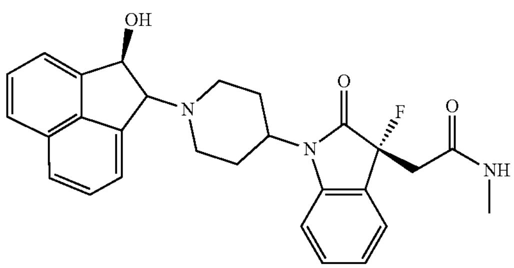 [SMILES: CNC(=O)C[C@]1(F)C(=O)N(C2CCN(C3c4cccc5cccc(c45)[C@H]3O)CC2)c2ccccc21] | Chiral HPLC (column AD-H), RT = 4.36 min. MS (ESI): m/z: 474 [M + H]⁺. ¹H NMR (400 MHz, MeOD) δ: 7.80-7.77 (m, 2H), 7.62-7.55 (m, 4H), 7.46-7.41 (m, 2H), 7.30 (d, J = 8.0 Hz, 1H), 7.11 (t, J = 7.6 Hz, 1H), 5.75 (s, 1H), 4.68 (s, 1H), 4.19 (m, 1H), 3.24-3.20 (m, 3H), 2.84-2.80 (m, 2H), 2.69-2.62 (m, 1H), 2.53-2.45 (m, 5H), 1.90 (d, J = 10.4 Hz, 1H), 1.77-1.76 (m, 1H). |
| 141 | 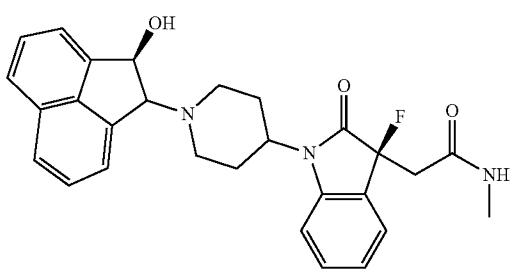 [SMILES: CNC(=O)C[C@@]1(F)C(=O)N(C2CCN(C3c4cccc5cccc(c45)[C@H]3O)CC2)c2ccccc21] | Chiral HPLC (column AD-H), RT = 5.51 min. MS (ESI): m/z: 474 [M + H]⁺. ¹H NMR (400 MHz, MeOD) δ: 7.80-7.77 (m, 2H), 7.62-7.55 (m, 4H), 7.46-7.41 (m, 2H), 7.30 (d, J = 8.4 Hz, 1H), 7.11 (t, J = 7.6 Hz, 1H), 5.75 (s, 1H), 4.68 (s, 1H), 4.19 (m, 1H), 3.22-3.20 (m, 3H), 2.82 (t, J = 11.2 Hz, 2H), 2.65-2.61 (m, 1H), 2.53-2.47 (m, 5H), 1.90 (d, J = 4.0 Hz, 1H), 1.72-1.70 (m, 1H). |
| 142 | 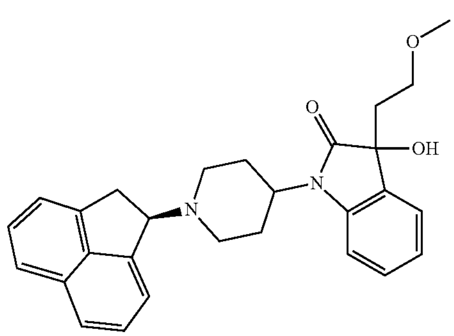 [SMILES: COCCC1(O)C(=O)N(C2CCN([C@@H]3Cc4cccc5cccc3c45)CC2)c2ccccc21] | MS (ESI): m/z 443 [M + H]⁺. ¹H NMR (400 MHz, CDCl₃): 7.63 (m, 1H), 7.57 (d, J = 8.4 Hz, 1H), 7.45 (m, 1H), 7.39 (t, J = 8.0 Hz, 1H), 7.30 (d, J = 7.6 Hz, 1H), 7.22-7.19 (m, 3H), 7.09 (m, 1H), 6.99 (t, J = 8.0 Hz, 1H), 4.90 (m, 1H), 4.13 (m, 2H), 3.64 (m, 1H), 3.44 (m, 1H), 3.35 (m, 1H), 3.25 (s, 3H), 2.91 (m, 1H), 2.72 (m, 1H), 2.44-2.31 (m, 4H), 1.94 (m, 1H), 1.56 (m, 4H). |

| No. | Structure | Data |
|---|---|---|
| 143 | 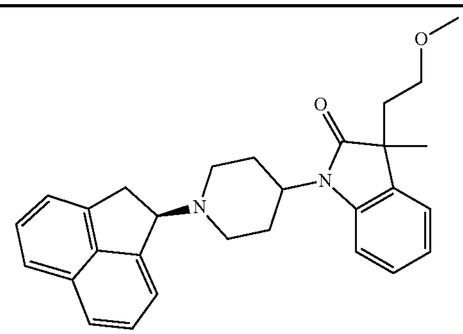 | MS (ESI): m/z 441.1 [M + H]+. 1H NMR (400 MHz, CDCl3): 7.73-7.67 (m, 1H), 7.63 (d, J = 8.2 Hz, 1H), 7.57-7.51 (m, 2H), 7.46 (t, J = 7.5 Hz, 1H), 7.30 (d, J = 6.8 Hz, 1H), 7.25-7.19 (m, 2H), 7.18-7.14 (m, 1H), 7.02 (dd, J = 15.1, 7.8 Hz, 1H), 4.98 (t, J = 5.4 Hz, 1H), 4.36-4.15 (m, 1H), 3.43 (d, J = 5.1 Hz, 2H), 3.10-2.96 (m, 6H), 2.76 (s, 1H), 2.60-2.25 (m, 5H), 1.96-1.87 (m, 1H), 1.74-1.58 (m, 2H), 1.34 (s, 3H). |
| 144 | 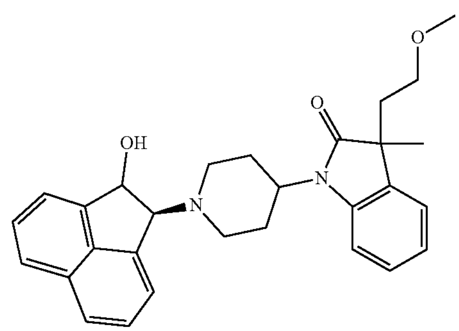 [SMILES: COCCC1(C)C(=O)N(C2CCN([C@H]3c4cccc5cccc(c45)C3O)CC2)c2ccccc21] | MS (ESI): m/z 457.0 [M + H]+. 1H NMR (400 MHz, DMSO): 7.77 (d, J = 8.1 Hz, 2H), 7.61-7.55 (m, 2H), 7.48 (t, J = 5.9 Hz, 2H), 7.34-7.22 (m, 2H), 7.18 (d, J = 7.7 Hz, 1H), 7.02 (t, J = 7.3 Hz, 1H), 5.74 (d, J = 6.6 Hz, 1H), 5.58 (s, 1H), 4.54 (s, 1H), 4.08 (s, 1H), 3.07-2.78 (m, 6H), 2.80-2.55 (m, 2H), 2.49-2.25 (m, 3H), 2.14-2.05 (m, 1H), 2.02-1.89 (m, 1H), 1.62 (d, J = 11.0 Hz, 1H), 1.53 (d, J = 10.8 Hz, 1H), 1.23 (s, 1H). |
| 145 | 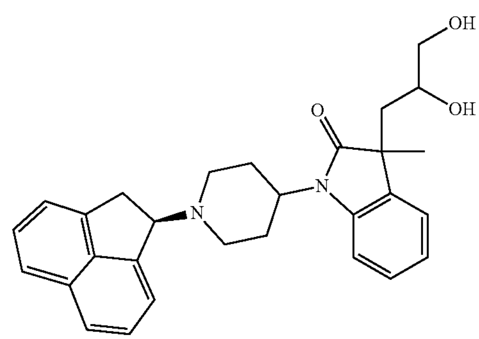 [SMILES: CC1(CC(O)CO)C(=O)N(C2CCN([C@@H]3Cc4cccc5cccc3c45)CC2)c2ccccc21] | MS (ESI): m/z 457.1 [M + H]+. 1H NMR (400 MHz, MeOD): 7.99 (d, J = 8.2 Hz, 1H), 7.86 (d, J = 7.0 Hz, 1H), 7.81 (d, J = 8.2 Hz, 1H), 7.72 (t, J = 7.6 Hz, 1H), 7.63 (t, J = 7.6 Hz, 1H), 7.52 (d, J = 6.9 Hz, 1H), 7.36-7.25 (m, 2H), 7.13-7.07 (m, 2H), 5.60 (d, J = 6.3 Hz, 1H), 4.36 (s, 1H), 3.99-3.83 (m, 2H), 3.60 (d, J = 10.7 Hz, 1H), 3.53-3.42 (m, 2H), 3.28 (d, J = 5.6 Hz, 2H), 3.17-3.03 (m, 2H), 3.01-2.79 (m, 2H), 2.13-1.95 (m, 4H), 1.31 (s, 3H). |
| 146 | 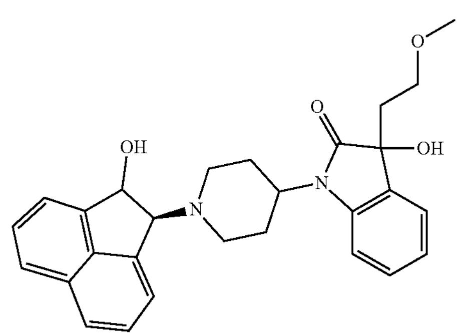 [SMILES: COCCC1(O)C(=O)N(C2CCN([C@H]3c4cccc5cccc(c45)C3O)CC2)c2ccccc21] | MS (ESI): m/z 459 [M + H]+. 1H NMR (400 MHz, CDCl3): 7.75 (t, J = 7.2 Hz, 2H), 7.55 (m, 4H), 7.36 (d, J = 7.2 Hz, 1H), 7.22 (m, 2H), 7.04 (t, J = 7.6 Hz, 1H), 5.73 (s, 1H), 4.70 (s, 1H), 4.23 (m, 1H), 3.62 (m, 1H), 3.47 (m, 1H), 3.27 (s, 3H), 3.01 (m, 2H), 2.59 (m, 4H), 2.29 (m, 1H), 2.03 (m, 1H), 1.66 (m, 2H). |

| No. | Structure | Data |
|---|---|---|
| 147 | 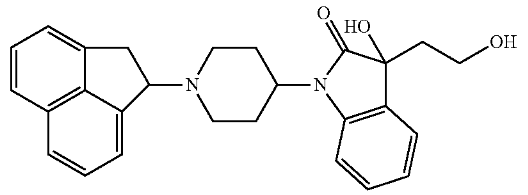 [SMILES: O=C1N(C2CCN(C3Cc4cccc5cccc3c45)CC2)c2ccccc2C1(O)CCO] | MS (ESI): m/z 429 [M + H]⁺. ¹H NMR (400 MHz, CDCL3): 7.68 (m, 1H), 7.60 (d, J = 8.0 Hz, 1H), 7.51 (m, 2H), 7.44 (t, J = 8.0 Hz, 1H), 7.38 (d, J = 7.2 Hz, 1H), 7.26 (m, 2H), 7.19 (d, J = 8.0 Hz, 1H), 7.04 (t, J = 7.6 Hz, 1H), 5.27 (s, 1H), 4.90 (m, 1H), 4.13 (m, 1H), 3.86 (m, 2H), 3.39 (m, 2H), 2.93 (m, 1H), 2.76 (m, 1H), 2.50 (m, 3H), 2.28 (m, 2H), 2.03 (m, 1H), 1.63 (m, 2H). |
| 148 | 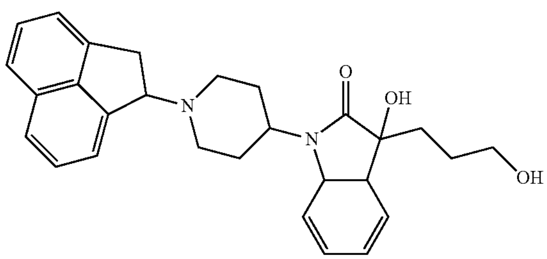 [SMILES: O=C1N(C2CCN(C3Cc4cccc5cccc3c45)CC2)C2C=CC=CC2C1(O)CCCO] | MS (ESI): m/z 427.1 [M + H]⁺. ¹H NMR (400 MHz, CDCl₃): 7.71-7.70 (m, 1H), 7.64-7.60 (m, 1H), 7.54-7.43 (m, 3H), 7.40-7.39 (m, 1H), 7.31-7.27 (m, 2H), 7.22-7.18 (m, 1H), 7.09-7.06 (m, 1H), 4.97 (s, 1H), 4.16-4.13 (m, 1H), 4.00 (bs, 1H), 3.70-3.58 (m, 2H), 3.42 (bs, 2H), 3.00-2.98 (m, 1H), 2.79 (bs, 1H), 2.53-2.31 (m, 4H), 2.05-1.99 (m, 2H), 1.70-1.58 (m, 2H), 1.52-1.46 (m, 1H). |
| 149 | 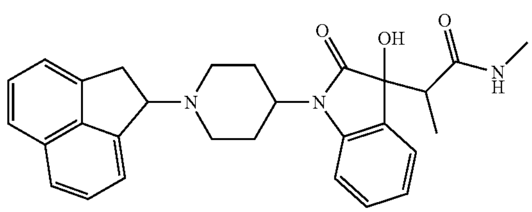 [SMILES: CNC(=O)C(C)C1(O)C(=O)N(C2CCN(C3Cc4cccc5cccc3c45)CC2)c2ccccc21] | MS (ESI): m/z 470 [M + H]⁺. ¹H NMR (400 MHz, CDCl₃): 7.73-7.71 (m, 1H), 7.65 (d, 1H, J = 8.0 Hz), 7.55-7.47 (m, 3H), 7.38 (d, 1H, J = 7.2 Hz), 7.32-7.28 (m, 2H), 7.18 (br s, 1H), 7.11-7.04 (m, 1H), 6.74-6.28 (m, 1H), 4.98 (s, 1H), 4.19-4.11 (m, 1H), 3.43 (s, 1H), 3.13-2.80 (m, 6H), 2.53-2.32 (m, 4H), 1.71-1.65 (m, 2H), 1.33-1.26 (m, 1H), 1.05-0.89 (m, 3H). |
| 150 | 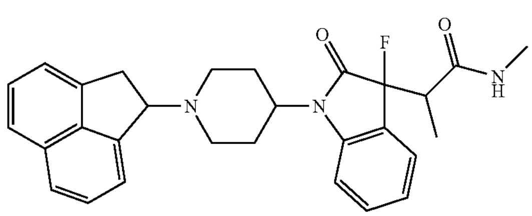 [SMILES: CNC(=O)C(C)C1(F)C(=O)N(C2CCN(C3Cc4cccc5cccc3c45)CC2)c2ccccc21] | MS (ESI): m/z 472 [M + H]⁺. ¹H NMR (400 MHz, CDCl₃): 7.70 (d, 1H, J = 6.8 Hz), 7.63 (d, 1H, J = 8.4 Hz), 7.55-7.42 (m, 4H), 7.36 (t, 1H, J = 7.6 Hz), 7.29 (d, 1H, J = 6.8 Hz), 7.14-7.12 (m, 1H), 7.07 (t, 1H, J = 7.6 Hz), 4.97 (m, 1H), 4.13 (m, 1H), 3.41 (s, 2H), 3.31-3.14 (m, 1H), 3.02-2.99 (m, 1H), 2.90 (d, 2H, J = 4.8 Hz), 2.79-2.78 (m, 2H), 2.50-2.31 (m, 4H), 1.73-1.66 (m, 3H), 1.15 (d, 1H, J = 7.6 Hz), 0.87 (d, 2H, J = 6.8 Hz). |

-continued

| No. | Structure | Data |
|---|---|---|
| 151 | 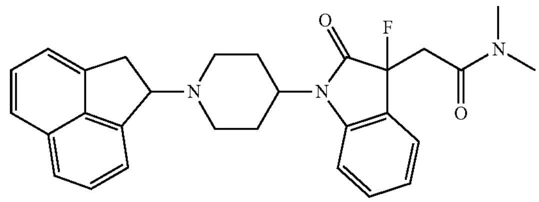 [SMILES: CN(C)C(=O)CC1(F)C(=O)N(C2CCN(C3Cc4cccc5cccc3c45)CC2)c2ccccc21] | MS (ESI): m/z 472.0 [M + H]$^+$. $^1$H-NMR (400 MHz, CDCl3): 7.72 (d, J = 8.0 Hz, 1H), 7.65 (d, J = 8.0 Hz, 1H), 7.47-7.55 (m, 3 H), 7.31-7.39 (m, 3H), 7.20 (d, J = 7.2 Hz, 1H), 7.05 (t, J = 7.6 Hz, 1H), 5.0 (s, 1H), 4.22 (s, 1H), 3.43 (d, J = 8.0 Hz, 4H), 3.04 (s, 4H), 2.79 (s, 4 H), 2.41-2.59 (m, 4H), 1.62-1.91 (m, 2H). |
| 152 | 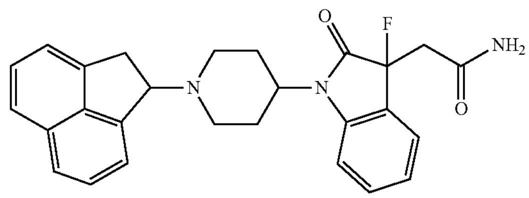 [SMILES: NC(=O)CC1(F)C(=O)N(C2CCN(C3Cc4cccc5cccc3c45)CC2)c2ccccc21] | MS (ESI): m/z 440.0 [M + H]$^+$. $^1$H-NMR (400 MHz, CD3OD): 7.73 (d, J = 8.0 Hz, 1H), 7.63 (t, J = 8.0 Hz, 2H), 7.55 (t, J = 8.0 Hz, 1H), 7.48 (t, J = 7.6 Hz, 2H), 7.41 (t, J = 7.6 Hz, 1H), 7.33 (d, J = 6.8 Hz, 1H), 7.28 (d, J = 8.0 Hz, 1H), 7.10 (t, J = 7.6 Hz, 1H), 4.99 (s, 1H), 4.09-4.15 (m, 1H), 3.48-3.54 (m, 2H), 3.20-3.39 (m, 2H), 3.06 (d, J = 14.0 Hz, 1H), 2.76 (d, J = 14.0 Hz, 1H), 2.41-2.61 (m, 4 H), 1.72-1.81 (m, 2H). |
| 153 | 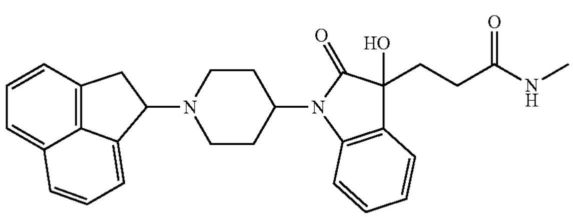 [SMILES: CNC(=O)CCC1(O)C(=O)N(C2CCN(C3Cc4cccc5cccc3c45)CC2)c2ccccc21] | MS (ESI): m/z 470 [M + 1]$^+$. $^1$H NMR (400 MHz, CDCl$_3$): 7.75-7.72 (m, 1H), 7.67-7.65 (d, J = 8.0 Hz, 1H), 7.56-7.55 (m, 1H), 7.51-7.47 (t, J$_1$ = 7.2 Hz, J$_2$ = 8.0 Hz, 1H), 7.41-7.40 (d, J = 7.2 Hz, 1H), 7.33-7.31 (m, 2H), 7.21 (s,1H), 7.10-7.07 (t, J$_1$ = 8.0 Hz, J$_2$ = 7.2 Hz, 1 H), 5.70-5.69 (m, 1H), 5.19-5.15 (m, 1H), 5.00 (s, 1H), 5.03-5.01 (m, 1H), 4.21 (m, 1H), 3.51-3.46 (m, 2H), 3.04-3.01 (m, 1H), 2.83-2.82 (m, 3H), 2.75-2.68 (m, 1H), 2.55-2.50 (m, 2H), 2.40-5-2.03 (m, 4H), 1.68-1.62 (m, 4H). |
| 154 | 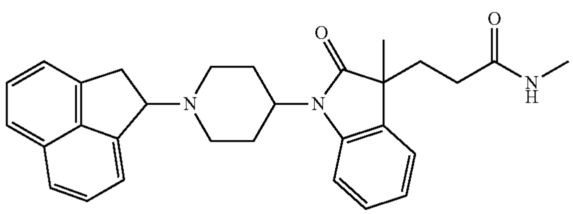 [SMILES: CNC(=O)CCC1(C)C(=O)N(C2CCN(C3Cc4cccc5cccc3c45)CC2)c2ccccc21] | MS (ESI): m/z 468 [M + 1]+. $^1$H NMR (400 MHz, CDCl$_3$): 7.74-7.72 (m, 1H), 7.67-7.65 (d, J = 8.0 Hz, 1H), 7.58-7.55 (m, 2H), 7.51-7.47 (t, J$_1$ = 7.2 Hz, J$_2$ = 8.0 Hz, 1H), 7.34-7.32 (d, J = 6.8 Hz, 1H), 7.26-7.21 (m, 3H), 7.09-7.05 (t, J$_1$ = 7.6 Hz, J$_2$ = 7.2 Hz, 1H), 5.30 (s, 1H), 5.00 (s, 1H), 4.29 (m, 1H), 3.46-3.45 (m, 2H), 3.05-3.02 (m, 1H), 2.82-2.80 (m, 1H), 2.70-2.68 (m, 3H), 2.55-2.38 (m, 4H), 2.21-5-2.13 (m, 2H), 1.90-1.83 (m, 1H), 1.75-1.63 (m, 3H), 1.37 (s, 3H). |

| No. | Structure | Data |
|---|---|---|
| 155 | 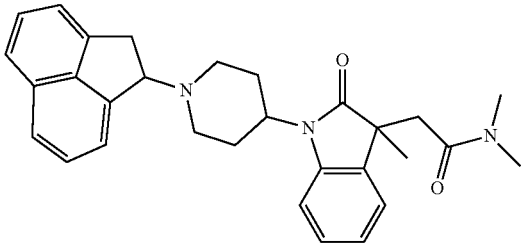 [SMILES: CN(C)C(=O)CC1(C)C(=O)N(C2CCN(C3Cc4cccc5cccc3c45)CC2)c2ccccc21] | MS (ESI): m/z 468.1 [M + H]+. $^1$H NMR (400 MHz, MeOD): 7.69 (d, J = 8.0 Hz, 1H), 7.62-7.57 (m, 2H), 7.54-7.50 (m, 1H), 7.46-7.43 (m, 1H), 7.30-7.25 (m, 2H), 7.21-7.17 (m, 2H), 6.99-6.95 (m, 1H), 4.91-4.87 (m, 1H), 4.20-4.15 (m, 1H), 3.50-3.42 (m, 2H), 3.22-3.18 (m, 1H), 3.05-2.92 (m, 5H), 2.76-2.66 (m, 4H), 2.61-2.36 (m, 4H), 1.82-1.72 (m, 2H), 1.24 (s, 3H). |
| 156 | 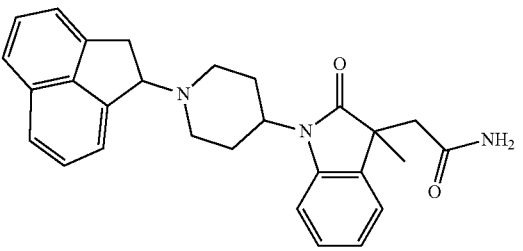 [SMILES: CC1(CC(N)=O)C(=O)N(C2CCN(C3Cc4cccc5cccc3c45)CC2)c2ccccc21] | MS (ESI): m/z 440.1 [M + H]+. $^1$H NMR (400 MHz, CDCl3): 7.72-7.70 (m, 1H), 7.65-7.63 (m, 1H), 7.54-7.53 (m, 2H), 7.49-7.45 (m, 1H), 7.31-7.23 (m, 4H), 7.07-7.03 (m, 1H), 6.22 (bs, 1H), 5.21 (bs, 1H), 4.99 (m, 1H), 4.29-4.24 (m, 1H), 3.44 (s, 2H), 3.00 (m, 1H), 2.85-2.81 (m, 2H), 2.67-2.63 (m, 1H), 2.56-2.32 (m, 4H), 1.73-1.69 (m, 2H), 1.40 (s, 3H). |
| 157 | 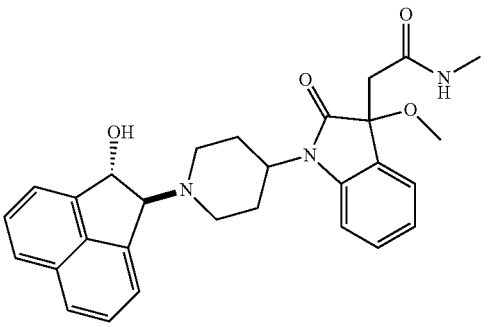 [SMILES: CNC(=O)CC1(OC)C(=O)N(C2CCN([C@H]3c4cccc5cccc(c45)[C@@H]3O)CC2)c2ccccc21] | MS (ESI): m/z 486[M + H]+. $^1$H-NMR (400 MHz, CDCl$_3$): 7.80-7.76(t, J = 8.0 Hz, 2H), 7.61-7.53(m, 4H), 7.32-7.24(m, 3H), 7.12-7.08(t, J = 7.2 Hz, 1H), 6.71-6.70(d, J = 4.8 Hz, 1H), 5.76(s, 1H), 4.73(s, 1H), 4.32(m, 1H), 3.22-3.10(m, 2H), 3.02(s, 3H), 2.95-2.93(d, J = 9.2 Hz, 1H), 2.88-2.81(m, 4H), 2.74-2.46(m, 5H), 1.78-1.67(m, 2H). |
| 158 | 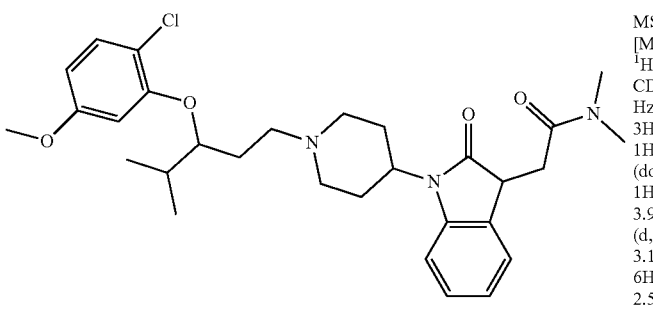 | MS (ESI): m/z 542 [M + H]+. $^1$H-NMR (400 MHz, CDCl$_3$): 7.36 (d, J = 8.0 Hz, 1H), 7.25-7.17 (m, 3H), 6.99 (t, J = 7.6 Hz, 1H), 6.78 (m, 1H), 6.40 (dd, J$_1$ = 8.8, J$_2$ = 2.8 Hz, 1H), 4.36-4.25 (m, 2H), 3.93-3.91 (m, 1H), 3.76 (d, J = 2.4 Hz, 3H), 3.14-3.11 (m, 2H), 2.99 (s, 6H), 2.92 (m, 1H), 2.70-2.50 (m, 5H), 2.17-1.95 (m, 3H), 1.87 (m, 2H), 1.69 (m, 2H), 1.01-0.98 (m, 6H). |

| No. | Structure | Data |
|---|---|---|
| 159 | 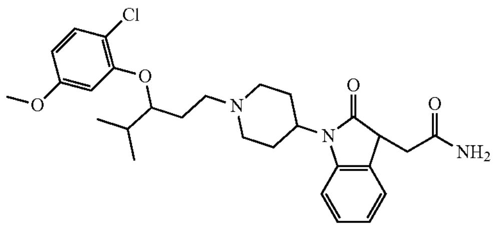 [SMILES: COc1ccc(Cl)c(OC(CCN2CCC(N3C(=O)C(CC(N)=O)c4ccccc43)CC2)C(C)C)c1] | MS (ESI): m/z: 514 [M + H]+. ¹H NMR (400 MHz, CDCl₃): 7.33 (d, J = 7.6 Hz, 1H), 7.28-7.17 (m, 3H), 7.05 (t, J = 7.2 Hz, 1H), 6.79 (m, 1H), 6.54 (br s, 1H), 6.41 (dd, J₁ = 8.8, J₂ = 2.4 Hz, 1H), 5.50 (brs, 1H), 4.34-4.25 (m, 2H), 3.82 (t, J = 6.4 Hz, 1H), 3.77 (s, 3H), 3.09 (d, J = 11.2 Hz, 1H), 2.95-2.88 (m, 2H), 2.68-2.55 (m, 1H), 2.38 (m, 4H), 2.15-1.97 (m, 3H), 1.88-1.81 (m, 2H), 1.73-1.62 (m, 2H), 1.02-0.99 (m, 6H). |
| 160 | 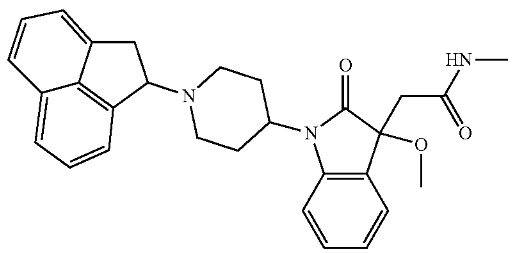 [SMILES: CNC(=O)CC1(OC)C(=O)N(C2CCN(C3Cc4cccc5cccc3c45)CC2)c2ccccc21] | MS (ESI): m/z: 470 [M + H]+. ¹H NMR (400 MHz, CDCl₃) δ 7.72-7.69 (m, 1H), 7.65-7.62 (m, 1H), 7.56-7.45 (m, 3H), 7.36-7.28 (m, 3H), 7.19 (d, J = 7.6 Hz, 1H), 7.09 (t, J = 7.6 Hz, 1H), 6.69 (brs, 1H), 4.98 (t, J = 5.6 Hz, 1H), 4.25-4.19 (m, 1H), 3.42 (d, J = 5.2 Hz, 2H), 3.07-2.97 (m, 4H), 2.87-2.79 (m, 5H), 2.65 (d, J = 14.8 Hz, 1H), 2.57-2.35 (m, 4H), 1.73-1.63 (m, 2H). |
| 161 | 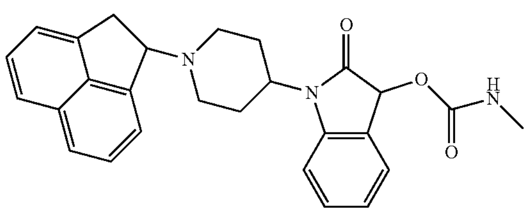 [SMILES: CNC(=O)OC1C(=O)N(C2CCN(C3Cc4cccc5cccc3c45)CC2)c2ccccc21] | MS (ESI): m/z: 442 [M + H]+. ¹H NMR (400 MHz, CDCl₃): 7.71-7.69 (m, 1H), 7.63 (d, J = 8.0 Hz, 1H), 7.55-7.50 (m, 2H), 7.48-7.41 (m, 2H), 7.33-7.29 (m, 2H), 7.18-7.16 (m, 1H), 7.03 (t, J = 7.6 Hz, 1H), 5.82 (d, J = 4.8 Hz, 1H), 4.97 (m, 1H), 4.84-4.83 (m, 1H), 4.25-4.19 (m, 1H), 3.41 (s, 2H), 3.00 (m, 1H), 2.84 (d, J = 5.2 Hz, 3H), 2.79 (m, 1H), 2.57-2.35 (m, 4H), 1.70-1.65 (m, 2H). |
| 162 | 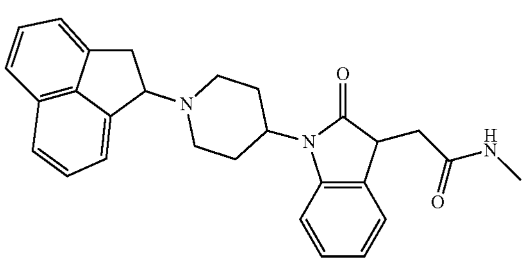 [SMILES: CNC(=O)CC1C(=O)N(C2CCN(C3Cc4cccc5cccc3c45)CC2)c2ccccc21] | MS (ESI): m/z: 440 [M + H]+. ¹H NMR (400 MHz, CDCl₃): 7.71-7.69 (m, 1H), 7.62 (d, J = 8.4 Hz, 1H), 7.53-7.52 (m, 2H), 7.48-7.44 (m, 1H), 7.30-7.24 (m, 3H), 7.18 (d, J = 7.6 Hz, 1H), 7.05-7.01 (m, 1H), 6.58 (m, 1H), 4.99-4.96 (m, 1H), 4.27-4.19 (m, 1H), 3.82-3.80 (m, 1H), 3.42 (d, J = 5.2 Hz, 2H), 3.02-2.98 (m, 1H), 2.86-2.77 (m, 5H), 2.59-2.52 (m, 5H), 1.72-1.60 (m, 2H). |

| No. | Structure | Data |
|---|---|---|
| 163 | 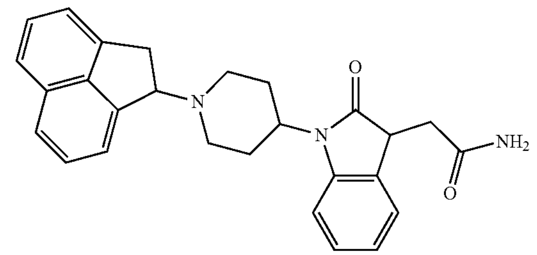 [SMILES: NC(=O)CC1C(=O)N(C2CCN(C3Cc4cccc5cccc3c45)CC2)c2ccccc21] | MS (ESI): m/z: 426 [M + H]+. 1H NMR (400 MHz, CDCl3): 7.72-7.70 (m, 1H), 7.63 (d, J = 8.4 Hz, 1H), 7.56-7.53 (m, 2H), 7.49-7.45 (m, 1H), 7.33-7.28 (m, 3H), 7.22-7.20 (m, 1H), 7.06-7.03 (m, 1H), 6.53 (br s, 1H), 5.43 (br s, 1H), 4.99 (s, 1H), 4.26 (t, J = 12.0 Hz, 1H), 3.81 (t, J = 6.4 Hz, 1H), 3.43 (d, J = 2.8 Hz, 2H), 3.01 (m, 1H), 3.00-2.80 (m, 2H), 2.54-2.32 (m, 5H), 1.70 (m, 2H). |
| 164 | 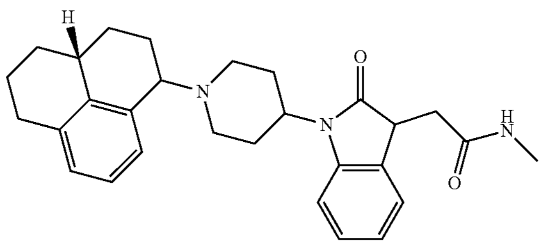 [SMILES: CNC(=O)CC1C(=O)N(C2CCN(C3CC[C@H]4CCCc5cccc3c54)CC2)c2ccccc21] | MS (ESI): m/z: 458 [M + H]+. 1H NMR (400 MHz, CDCl3): 7.62-7.58 (m, 1H), 7.32-7.24 (m, 2H), 7.17-7.13 (m, 2H), 7.06-6.98 (m, 2H), 6.63-6.60 (m, 1H), 4.25 (brs, 1H), 3.97 (brs, 1H), 3.82 (t, J = 6.4 Hz, 1H), 3.06-3.01 (m, 1H), 2.88-2.76 (m, 7H), 2.62-2.56 (m, 2H), 2.40-2.24 (m, 2H), 2.04-2.00 (m, 2H), 1.94-1.87 (m, 2H), 1.86-1.60 (m, 4H), 1.42-1.25(m, 4H). |
| 165 | 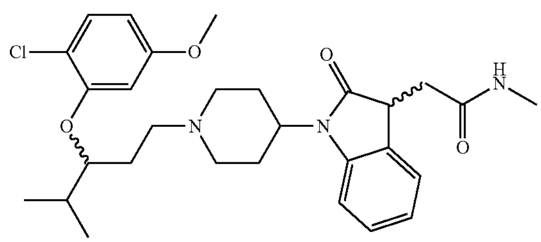 [SMILES: CNC(=O)CC1C(=O)N(C2CCN(CCC(Oc3cc(OC)ccc3Cl)C(C)C)CC2)c2ccccc21] | MS (ESI): m/z: 528 [M + H]+. 1H NMR (400 MHz, CDCl3): 7.30-7.19 (m, 4H), 7.03 (t, J = 7.2 Hz, 1H), 6.80 (q, J = 4.4 Hz, 1H), 6.63 (brs, 1H), 6.41 (dd, J1 = 8.8 Hz, J2 = 2.8 Hz, 1H), 4.30-4.26 (m, 2H), 3.83 (t, J = 6.4 Hz, 1H), 3.76 (s, 3H), 3.11-3.08 (d, J = 6.0 Hz, 1H), 2.95-2.92 (d, J = 12.0 Hz, 1H), 2.88-2.82 (m, 4H), 2.61-2.45 (m, 5H), 2.13-1.99 (m, 3H), 1.87-1.85 (m, 2H), 1.70-1.66 (m, 2H), 1.02-0.99 (t, J = 7.6 Hz, 6H). |
| 166 | 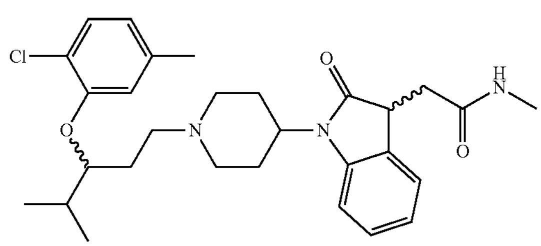 [SMILES: CNC(=O)CC1C(=O)N(C2CCN(CCC(Oc3cc(C)ccc3Cl)C(C)C)CC2)c2ccccc21] | MS (ESI): m/z: 512 [M + H]+. 1H NMR (400 MHz, CDCl3): 7.30-7.20 (m, 3H), 7.14-7.12 (d, J = 8.0 Hz, 1H), 7.05-7.02 (t, J = 7.6 Hz, 1H), 6.90-6.89 (d, J = 4.8 Hz, 1H), 6.70-6.66 (d, J = 8.0 Hz, 1H), 6.54 (brs, 1H), 4.30-4.28 (m, 2H), 3.84-3.81 (t, J = 6.0 Hz, 1H), 3.13-3.11 (d, J = 8.8Hz, 1H), 2.99-2.97 (m, 1H), 2.88-2.83 (d, J = 6.0 Hz, 4H), 2.62-2.47 (m, 5H), 2.33 (s, 3H), 2.17-1.97 (m, 3H), 1.88~1.87 (m, 2H), 1.75-1.66 (m, 2H), 1.02-0.99 (t, J = 6.8 Hz, 6H). |

| No. | Structure | Data |
|---|---|---|
| 167 | 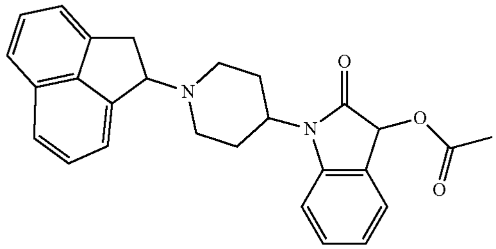 [SMILES: CC(=O)OC1C(=O)N(C2CCN(C3Cc4cccc5cccc3c45)CC2)c2ccccc21] | MS (ESI): m/z: 427 [M + H]⁺.<br>¹H NMR (400 MHz, CDCl₃): 7.71 (d, J = 6.4 Hz, 1H), 7.63 (d, J = 8.0 Hz, 1H), 7.56-7.52 (m, 2H), 7.47 (t, J = 7.6 Hz, 1H), 7.36-7.29 (m, 3H), 7.18 (d, J = 8.0 Hz, 1H), 7.04 (t, J = 7.2 Hz, 1H), 5.88 (d, J = 4.4 Hz, 1H), 4.98 (t, J = 5.2 Hz, 1H), 4.20 (m, 1H), 3.42 (d, J = 4.4 Hz, 2H), 2.99 (s, 1H), 2.78 (m, 1H), 2.54-2.34 (m, 4H), 2.18 (s, 3H), 1.72 (m, 2H). |
| 168 | 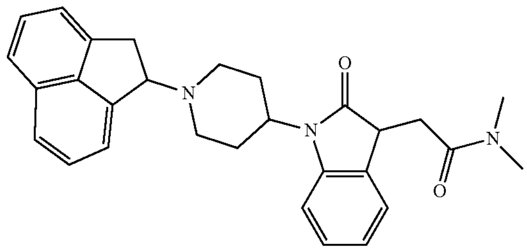 [SMILES: CN(C)C(=O)CC1C(=O)N(C2CCN(C3Cc4cccc5cccc3c45)CC2)c2ccccc21] | MS (ESI): m/z: 454 [M + H]⁺.<br>¹H NMR (400 MHz, CDCl₃): 7.70 (t, J = 4.0 Hz, 1H), 7.63 (d, J = 7.6 Hz, 1H), 7.54 (m, 2H), 7.46 (m, 1H), 7.36 (d, J = 6.8 Hz, 1H), 7.30 (d, J = 7.6 Hz, 1H), 7.25-7.21 (m, 2H), 7.01-6.97 (m, 1H), 4.99 (t, J = 4.8 Hz, 1H), 4.29 (m, 1H), 3.94-3.92 (m, 1H), 3.43 (d, J = 4.4 Hz, 2H), 3.13-3.08 (m, 2H), 2.98 (s, 6H), 2.80 (m, 1H), 2.68-2.32 (m, 5H), 1.70-1.66 (m, 2H). |
| 169 | 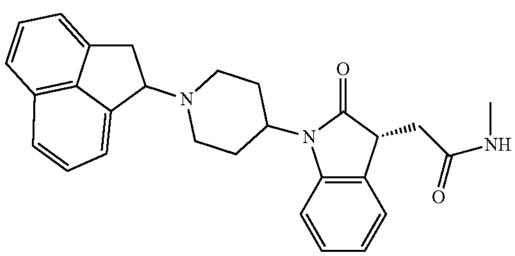 [SMILES: CNC(=O)C[C@H]1C(=O)N(C2CCN(C3Cc4cccc5cccc3c45)CC2)c2ccccc21] | |
| 170 | 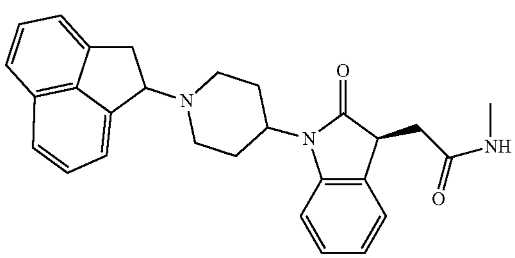 [SMILES: CNC(=O)C[C@@H]1C(=O)N(C2CCN(C3Cc4cccc5cccc3c45)CC2)c2ccccc21] | |
| 171 | 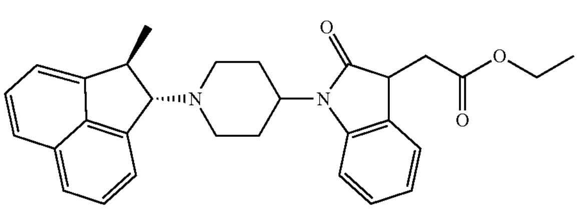 [SMILES: CCOC(=O)CC1C(=O)N(C2CCN([C@@H]3c4cccc5cccc(c45)[C@H]3C)CC2)c2ccccc21] | MS (ESI): m/z: 469 [M + H]⁺.<br>¹H NMR (400 MHz, CDCl₃): 7.73 (d, J = 7.6 Hz, 1H), 7.66 (d, J = 8.4 Hz, 1H), 7.59-7.50 (m, 3H), 7.30-7.22 (m, 4H), 7.02 (t, J = 7.2 Hz, 1H), 4.47 (s, 1H), 4.31 (s, 1H), 4.18-4.28 (m, 2H), 3.75 (t, 2H), 3.09-3.05 (m, 2H), 2.86-2.76 (m, 2H), 2.56 (d, J = 16 Hz, 2H), 2.48 (t, J = 8.0 Hz, 2H), |

| No. | Structure | Data |
|---|---|---|
| 172 | 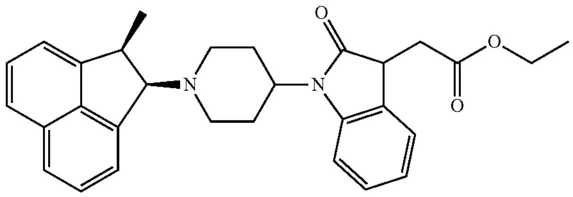 [SMILES: CCOC(=O)CC1C(=O)N(C2CCN([C@H]3c4cccc5cccc(c45)[C@H]3C)CC2)c2ccccc21] | MS (ESI): m/z: 469 [M + H]⁺. $^1$H NMR (400 MHz, CDCl$_3$): 7.73 (d, J = 8.0 Hz, 1H), 7.64 (d, J = 8.4 Hz, 1H), 7.55-7.46 (m, 3H), 7.27-7.23 (m, 3H), 7.12 (dd, J$_1$ = 8.0 Hz, J$_2$ = 2.4 Hz, 1H), 7.01 (t, J = 7.6 Hz, 1H), 4.67 (d, J = 7.6 Hz, 1H), 4.15-4.07 (m, 3H), 3.87-3.83 (m, 1H), 3.73-3.71 (m, 1H), 3.20-3.14 (m, 2H), 3.06-3.01 (m, 1H), 2.84-2.79 (m, 1H), 2.59-2.56 (m, 1H), 2.33-2.30 m, 1H), 2.16 (d, J = 11.6 Hz, 1H), 1.78 (d, J = 10.0 Hz, 1H), 1.62 (d, J = 6.0 Hz, 3H), 1.53 (s, 1H), 1.36 (d, J = 10.4 Hz, 1H), 1.20-1.14 (m, 3H). |
| | | 1.70 (t, J = 32.8 Hz, 2H), 1.52 (d, J = 7.6 Hz, 3H), 1.18 (dd, J$_1$ = 12.0 Hz, J$_2$ = 7.2 Hz, 3H) |
| 173 | 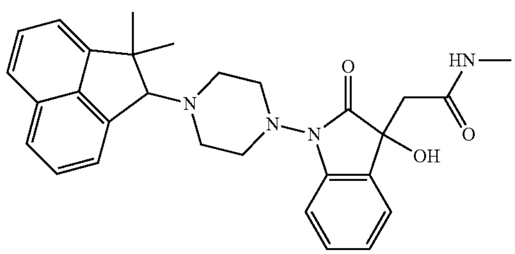 [SMILES: CNC(=O)CC1(O)C(=O)N(N2CCN(C3c4cccc5cccc(c45)C3(C)C)CC2)c2ccccc21] | MS (ESI): m/z: 484 [M + H]⁺. 1H NMR (400 MHz, CDCl$_3$): 7.72 (d, J = 7.6 Hz, 1H), 7.63 (d, J = 7.6 Hz, 1H), 7.55 (m, 3H), 7.36 (d, J = 7.6 Hz, 1H), 7.30 (m, 1H), 7.19(d, J = 6.4 Hz, 1H), 7.08-7.01 (m, 2H), 5.96 (brs, 1H), 5.60 (m, 1H), 4.24 (s, 1H), 4.03 (brs, 1H), 3.15 (m, 2H), 2.85-2.83 (m, 3H), 2.68 (m, 1H), 2.54 (m, 2H), 2.25 (m, 3H), 1.74 (m, 2H), 1.57 (s, 3H), 1.33 (s, 3H) |

Example 26: In Vitro Assays cAMP Assay on CHO Cells Expressing the Human NOP/MOP Receptors cAMP assays on HEK cells expressing human NOP ("NOP assay") or CHO cells expressing μ-opioid receptor ("MOR assay") were conducted according to standard protocols, for example, see Carra et al. (*J. Pharm and Exp. Therapeutics*, 312:3, 1114-1123 (2005)). The data for various compounds of the invention in the NOP assay and MOR assays are presented below in Table 2. For each assay, values indicated as "A" represent an EC50 of less than 100 nM; values indicated as "B" represent an EC50 of between 100 nM and 1 μM; values indicated as "C" represent an EC50 of greater than 1 μM to 5 μM; values indicated as "D" represent an EC50 of greater than 5 μM.

TABLE 2

| Cmpd. No. | NOP EC50 | MOR EC50 |
|---|---|---|
| 2 | A | B |
| 3 | A | A |
| 4 | A | C |
| 5 | A | A |
| 6 | A | A |
| 7 | A | B |
| 8 | A | A |
| 9 | A | A |
| 10 | A | B |
| 11 | A | A |
| 12 | C | D |
| 13 | A | B |
| 19 | A | A |
| 20 | A | B |
| 24 | A | B |
| 27 | A | B |
| 32 | A | B |
| 33 | B | A |
| 34 | A | B |
| 35 | A | B |
| 36 | A | B |
| 39 | B | C |
| 40 | B | B |
| 41 | A | A |
| 43 | B | D |

TABLE 2-continued

| Cmpd. No. | NOP EC50 | MOR EC50 |
|---|---|---|
| 44 | B | B |
| 45 | A | A |
| 46 | A | A |
| 47 | B | B |
| 48 | A | B |
| 49 | B | B |
| 50 | D | D |
| 51 | A | A |
| 52 | A | B |
| 54 | A | B |
| 55 | A | B |
| 56 | C | C |
| 57 | D | B |
| 58 | A | A |
| 59 | A | A |
| 60 | B | B |
| 61 | B | A |
| 63 | A | C |
| 64 | A | A |
| 65 | A | |
| 66 | A | A |
| 67 | A | A |
| 68 | A | |
| 69 | A | |
| 70 | A | A |
| 71 | A | A |
| 72 | A | A |
| 73 | A | C |
| 74 | A | A |
| 75 | B | A |
| 76 | C | B |
| 77 | A | B |
| 78 | D | D |
| 79 | D | D |
| 80 | A | C |
| 86 | A | B |
| 87 | A | B |
| 88 | A | B |
| 89 | A | B |
| 90 | B | C |
| 91 | A | A |
| 93 | B | C |
| 94 | B | B |
| 95 | D | D |
| 96 | D | D |
| 97 | D | D |
| 98 | D | D |
| 99 | D | D |
| 100 | D | D |
| 101 | D | D |
| 102 | D | D |
| 104 | D | D |
| 105 | D | D |
| 106 | D | D |
| 107 | D | D |
| 108 | D | D |
| 109 | D | D |
| 110 | B | B |
| 111 | D | D |
| 112 | D | D |
| 113 | D | D |
| 114 | D | D |
| 115 | D | D |
| 118 | D | D |
| 119 | D | D |
| 120 | A | A |
| 121 | A | B |
| 122 | C | B |
| 123 | A | A |
| 124 | A | A |
| 125 | A | C |
| 126 | A | A |
| 127 | A | B |
| 128 | A | A |
| 129 | D | D |
| 130 | A | B |
| 131 | A | B |
| 132 | A | B |
| 133 | D | A |
| 134 | B | B |
| 135 | D | D |
| 136 | D | D |
| 137 | D | D |
| 138 | D | D |
| 139 | D | D |
| 140 | D | D |
| 141 | D | D |
| 142 | D | D |
| 143 | A | A |
| 144 | A | A |
| 145 | D | D |
| 146 | D | D |
| 147 | D | D |
| 148 | D | D |
| 149 | A | A |
| 150 | A | A |
| 151 | A | B |
| 152 | A | A |
| 153 | A | A |
| 154 | A | A |
| 155 | A | B |
| 156 | A | A |
| 157 | A | B |
| 158 | B | B |
| 159 | A | A |
| 160 | A | A |
| 161 | A | B |
| 162 | A | A |
| 163 | A | A |
| 164 | A | A |
| 165 | A | A |
| 166 | A | B |
| 167 | A | B |
| 168 | A | B |
| 169 | A | A |
| 170 | A | A |
| 171 | B | B |
| 172 | B | B |
| 173 | B | B |
| 174 | A | A |
| 175 | A | A |
| 176 | A | A |
| 177 | A | A |
| 178 | A | A |
| 179 | A | B |
| 180 | A | B |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated by reference herein in their entireties. Citation or identification of any reference in this application is not an admission that such reference is available as prior art to this application. The full scope of the disclosure is better understood with reference to the appended claims.

What is claimed:

1. A compound of formula (I):

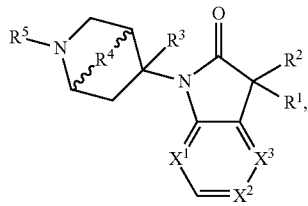

or a pharmaceutically acceptable salt thereof, wherein:
$X^1$, $X^2$ and $X^3$ are each independently —CH=;
$R^1$ is halo, hydroxyl, cyano, $C_{1-6}$ alkyl, $C_{2-6}$ alkenyl, $C_{1-6}$ haloalkyl, $C_{1-6}$ alkoxy, —O—C(O)—$C_{1-6}$ alkyl, —C(O)—O—$C_{1-6}$ alkyl, —C(O)—$NR^6$—$C_{1-6}$ alkyl, —$NR^6$—C(O)—$C_{1-6}$ alkyl, —$C_{1-6}$ alkyl-C(O)—$NR^6$—$C_{1-6}$ alkyl, —$C_{1-6}$ alkyl-$NR^6$—C(O)—$C_{1-6}$ alkyl, —$C_{1-6}$ alkyl-$NR^6$—C(O)—O—$C_{1-6}$ alkyl, —$C_{1-6}$ alkyl-C(O)—O—$C_{1-6}$ alkyl, —O—C(O)—$NR^6$—$C_{1-6}$ alkyl, $C_{3-7}$ cycloalkyl, $C_{3-7}$ cycloalkylalkyl, aryl, heteroaryl, aralkyl, heteroaralkyl, heterocyclyl or heterocyclylalkyl, wherein each alkyl, alkenyl, alkoxy, cycloalkyl, aryl, heteroaryl and heterocyclyl is substituted with 0-3 occurrences of $R^7$;
$R^2$ is halo, hydroxyl, $C_{1-6}$ alkyl, $C_{1-6}$ haloalkyl or $C_{1-6}$ alkoxy;
$R^3$ is hydrogen, hydroxyl, halo, $C_{1-6}$ alkyl, $C_{1-6}$ alkoxy, cyano, alkoxyalkyl or $C_{1-6}$ haloalkyl;
$R^4$ is absent;
$R^5$ is $C_{3-20}$ cycloalkyl substituted with 0-3 occurrences of $R^7$;
each $R^6$ is independently hydrogen or $C_{1-6}$ alkyl;
each $R^7$ is independently halo, cyano, $N(R^8)_2$, —C(O)—$N(R^8)_2$, hydroxyl, $C_{1-6}$ alkyl, $C_{1-6}$ alkoxy, $C_{3-7}$ cycloalkyl, aryl, aryloxy, heteroaryl, heteroaryloxy or heterocyclyl, wherein each alkyl, alkoxy, cycloalkyl, aryl, aryloxy, heteroaryl, heteroaryloxy or heterocyclyl is substituted with 0-3 occurrences of $R^9$;
each $R^8$ is independently hydrogen, $C_{1-6}$ alkyl, C(O)—$C_{1-6}$ alkyl, aryl, or benzyl;
or alternatively, two $R^8$ groups taken together with the nitrogen to which they are attached form a heterocyclyl; and
each $R^9$ is independently halo, $C_{1-6}$ alkyl, $C_{1-6}$ alkoxy or $C_{1-6}$ haloalkyl.

2. The compound of claim 1, or a pharmaceutically acceptable salt thereof, wherein $R^1$ is —$NR^6$—C(O)—$C_{1-6}$ alkyl, —$C_{1-6}$ alkyl-C(O)—$NR^6$—$C_{1-6}$ alkyl or —O—C(O)—$NR^6$—$C_{1-6}$ alkyl.

3. The compound of claim 2, or a pharmaceutically acceptable salt thereof, wherein $R^1$ is —$CH_2$—C(O)—NH—$CH_3$ or —$CH_2$—C(O)—$N(CH_3)_2$.

4. The compound of claim 1, or a pharmaceutically acceptable salt thereof, wherein $R^1$ is $C_{1-6}$ alkyl substituted with 0-3 occurrences of $R^7$.

5. The compound of claim 4, or a pharmaceutically acceptable salt thereof, wherein:
$R^1$ is $C_{1-6}$ alkyl substituted with 1-2 occurrences of $R^7$; and
$R^7$ is —OH, —$NH_2$, —NH—$CH_3$, —$N(CH_3)_2$, —C(O)—$NH_2$, $C_{1-6}$ alkoxy, heterocyclyl, or heteroalkyl, wherein each heterocyclyl and heteroaryl is substituted with 0-3 occurrences of $R^9$.

6. The compound of claim 1, or a pharmaceutically acceptable salt thereof, wherein $R^2$ is hydroxyl, $C_{1-6}$ alkyl, halo or $C_{1-6}$ alkoxy.

7. The compound of claim 1, or a pharmaceutically acceptable salt thereof, wherein $R^5$ is 2,3-dihydroindenyl, 1,2,3,4-tetrahydronaphthyl, or 1,2-dihydroacenaphthyl, each substituted with 0-3 occurrences of $R^7$.

8. The compound of claim 1, wherein $R^3$ is hydrogen.

9. The compound of claim 1, wherein the compound is selected from a compound of formula (III):

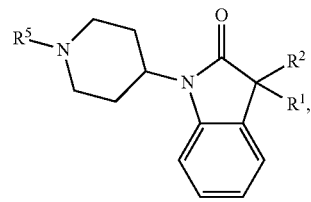

or a pharmaceutically acceptable salt thereof.

10. The compound of claim 1, wherein the compound is selected from a compound of formula (IV):

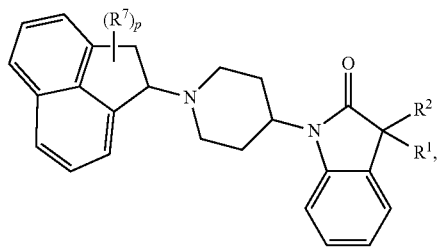

or a pharmaceutically acceptable salt thereof, wherein p is 0-3.

11. The compound of claim 10, wherein the compound is selected from a compound of formula (IVa):

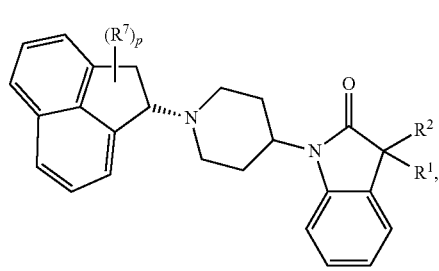

or a pharmaceutically acceptable salt thereof, wherein p is 0-3.

12. The compound of claim 10, wherein the compound is selected from a compound of formula (IVb):

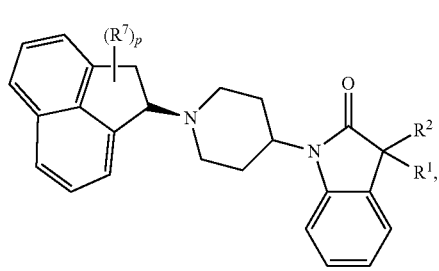

or a pharmaceutically acceptable salt thereof, wherein p is 0-3.

13. The compound of claim 1, wherein the compound is selected from a compound of formula (V):

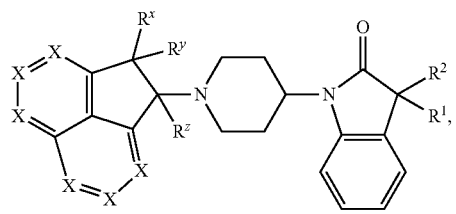

or a pharmaceutically acceptable salt thereof, wherein:
  each X is independently —CH= or —N=;
  $R^x$ and $R^y$ are each independently hydrogen, fluoro, $C_{1-6}$ alkyl, $C_{1-6}$ alkoxy or hydroxyl; and
  $R^z$ is hydrogen or $C_{1-6}$ alkyl.

14. The compound of claim 1, wherein the compound is selected from the group consisting of:

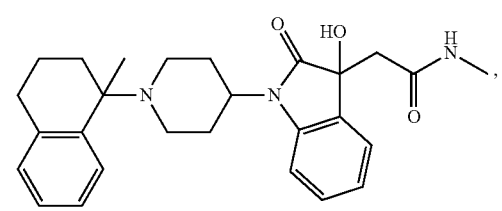

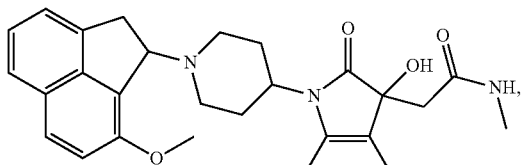

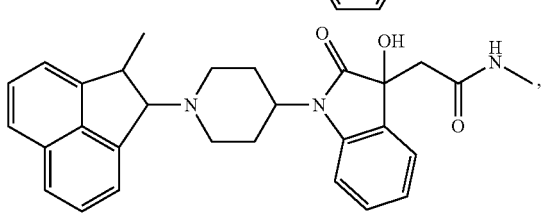

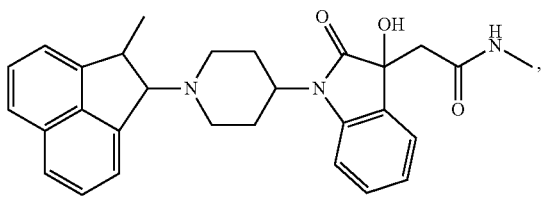

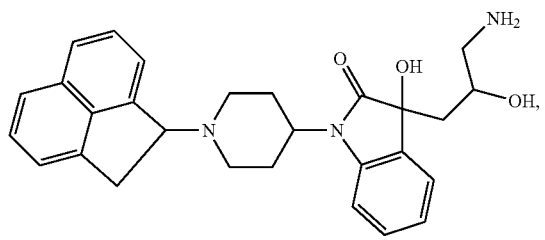

-continued

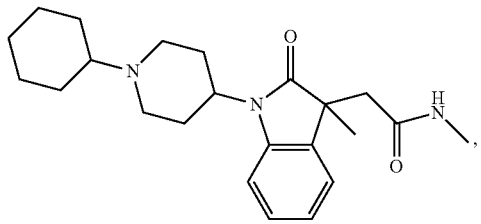

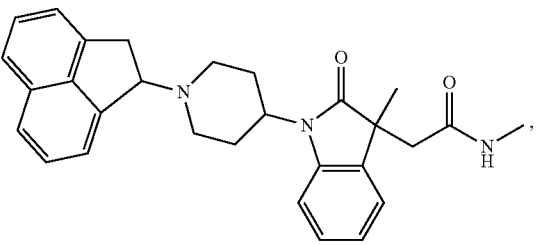

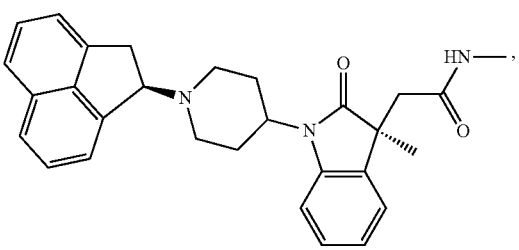

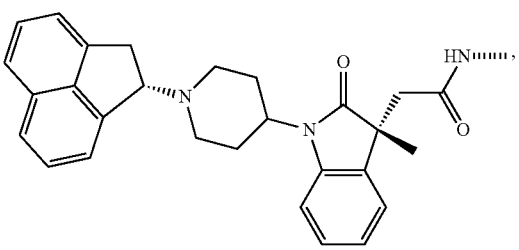

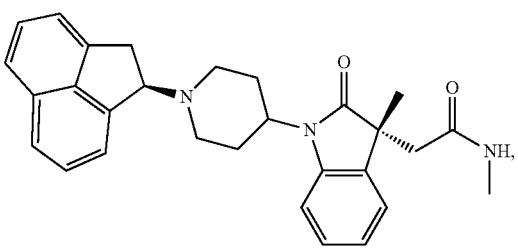

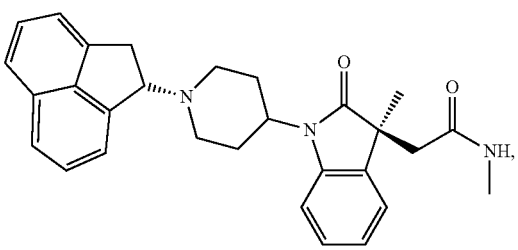

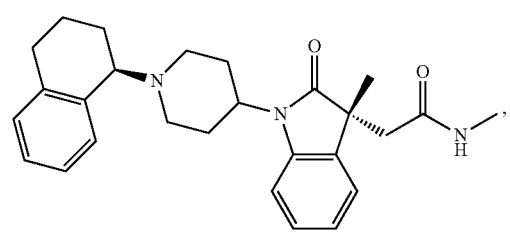

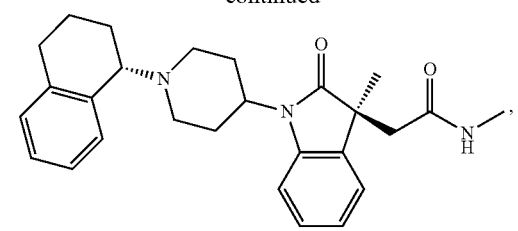
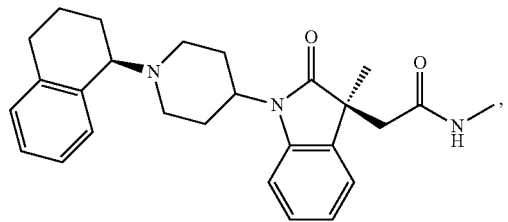
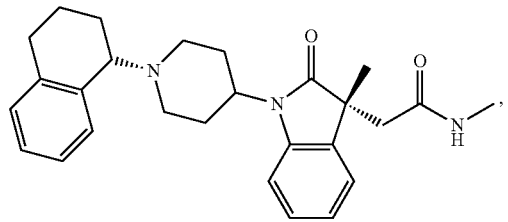
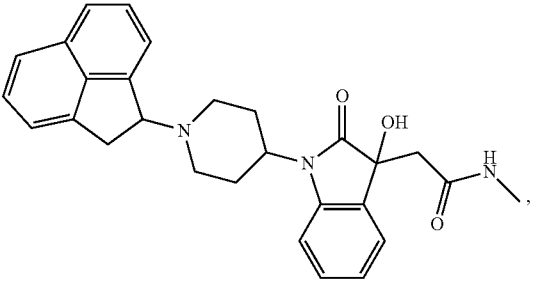
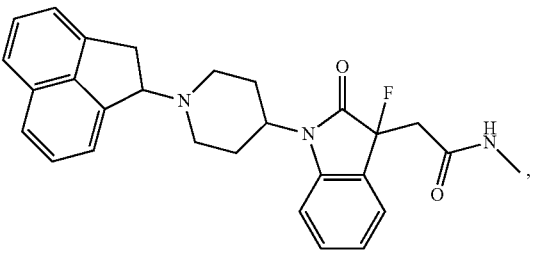
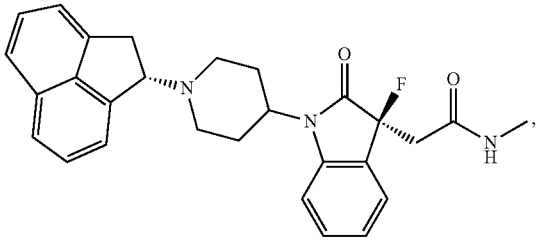
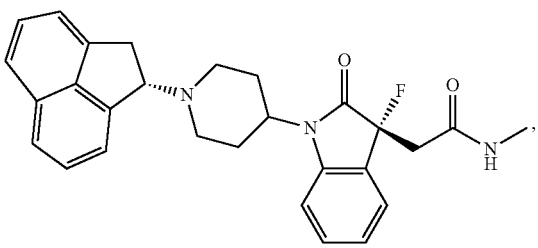
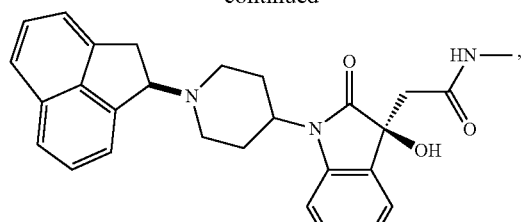
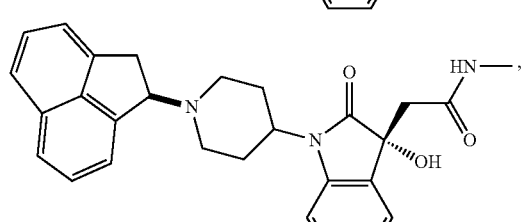
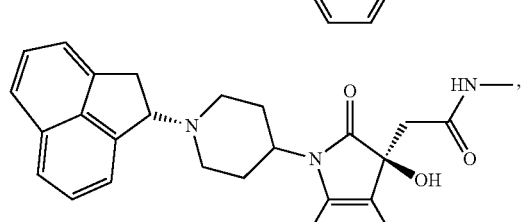
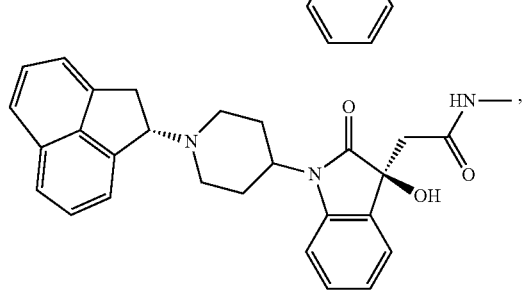
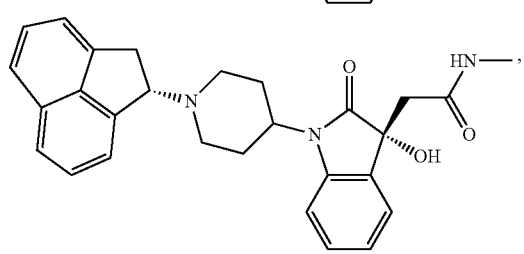
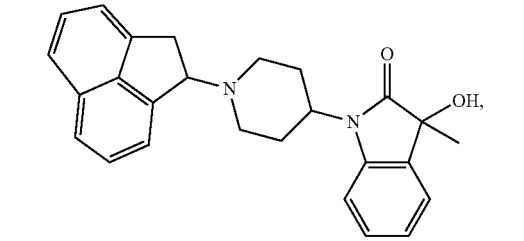
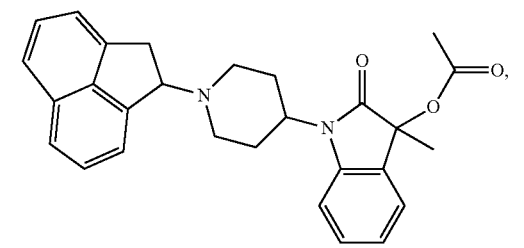

-continued
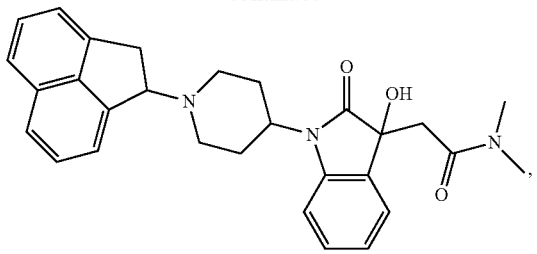
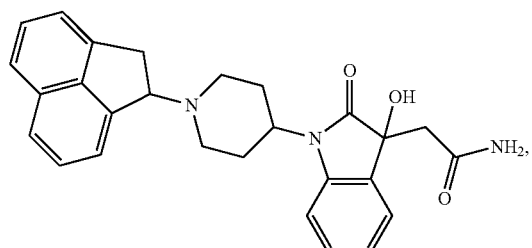
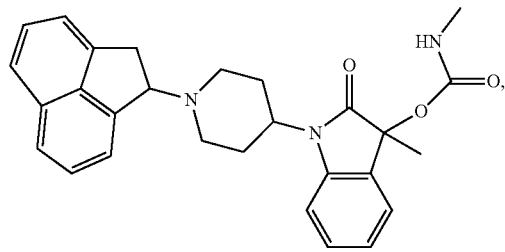
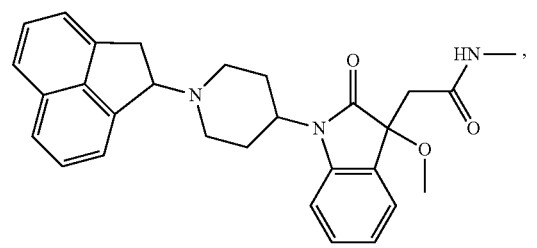
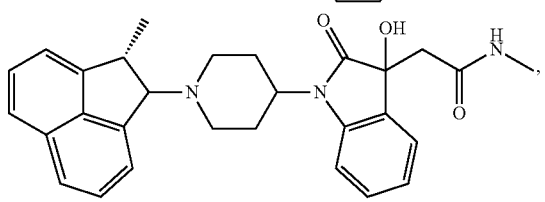
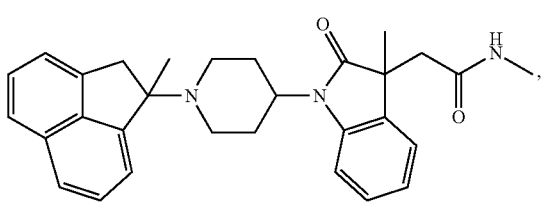
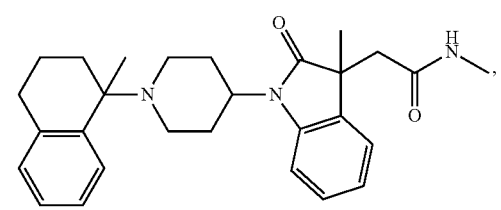
-continued
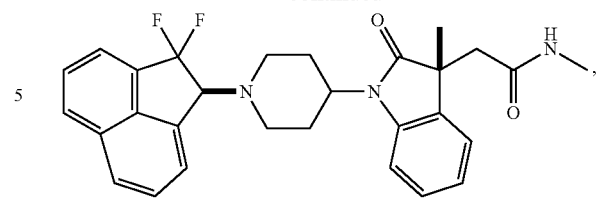
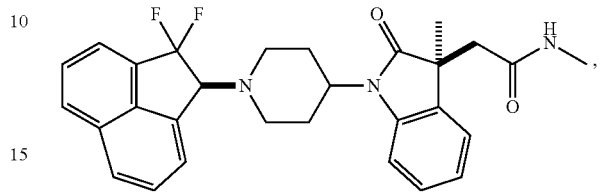
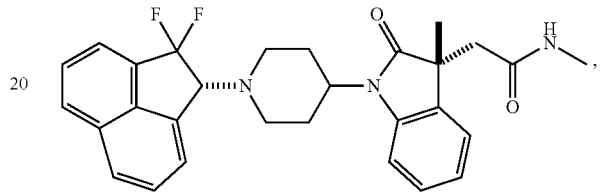
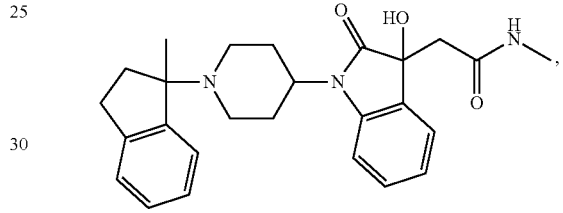
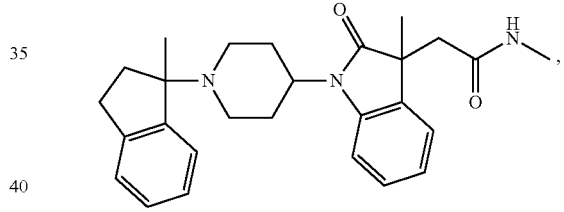
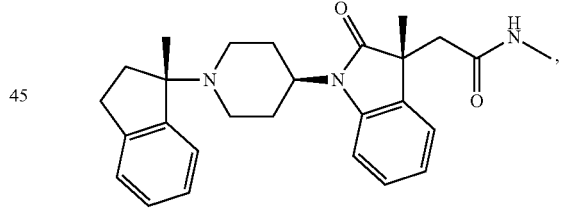
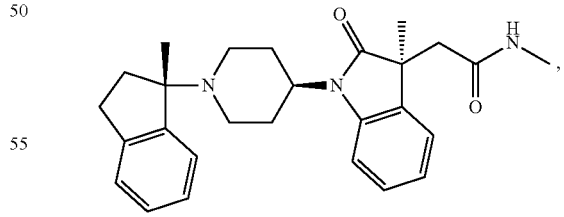
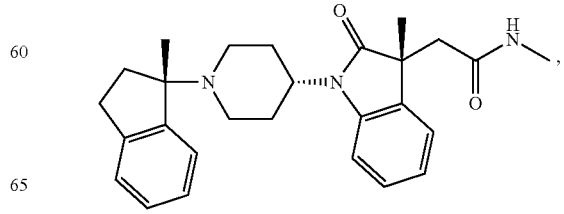

297
-continued
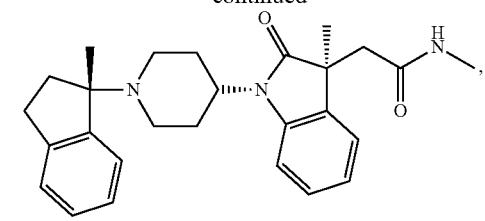
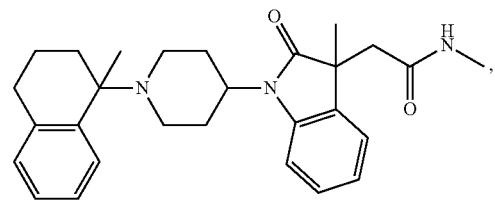
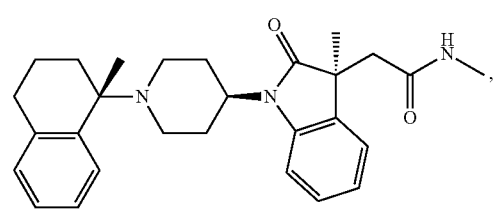
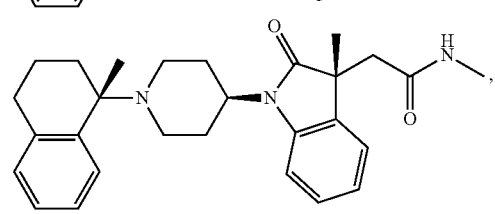
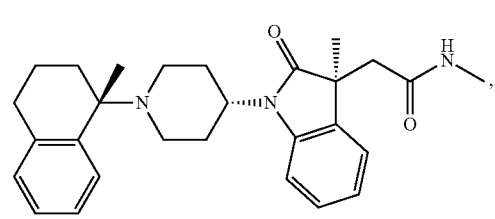
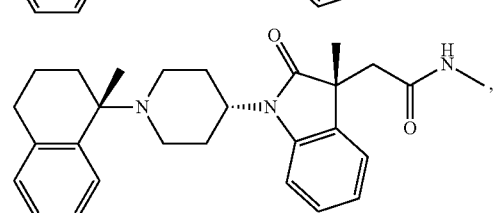
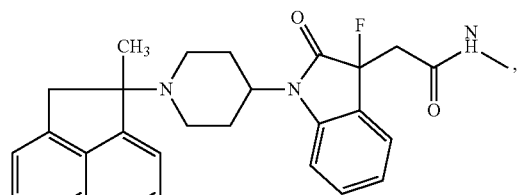
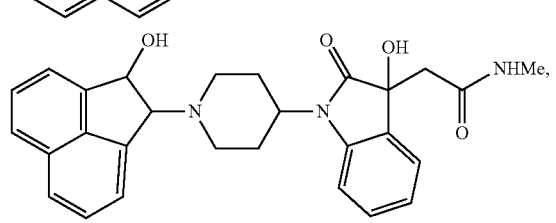
298
-continued
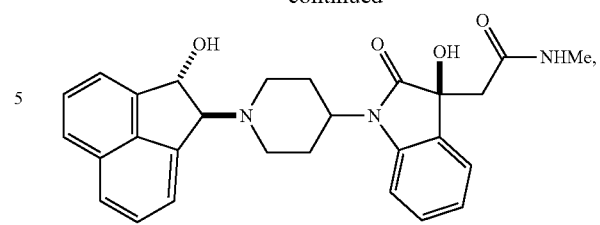
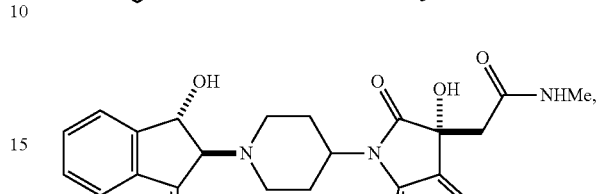
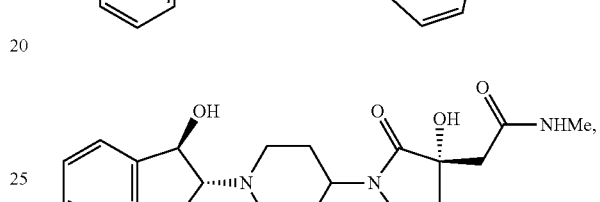
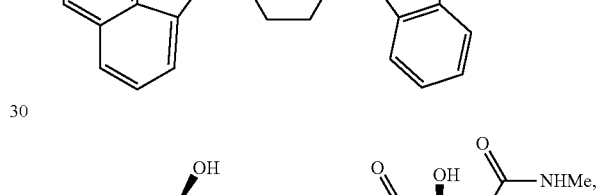
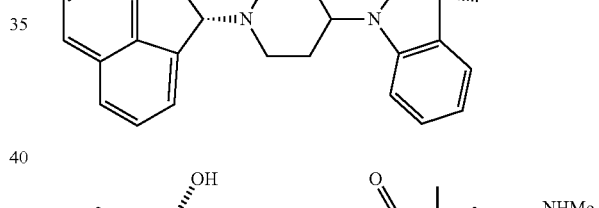
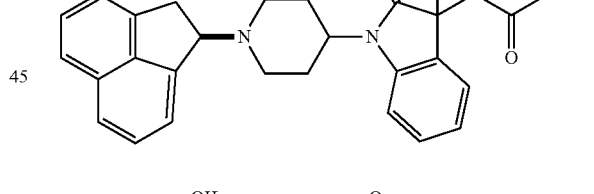
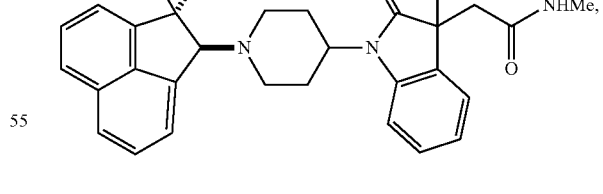
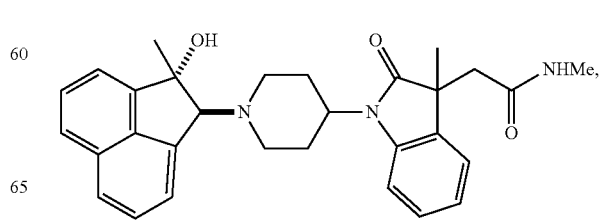

299
-continued
300
-continued
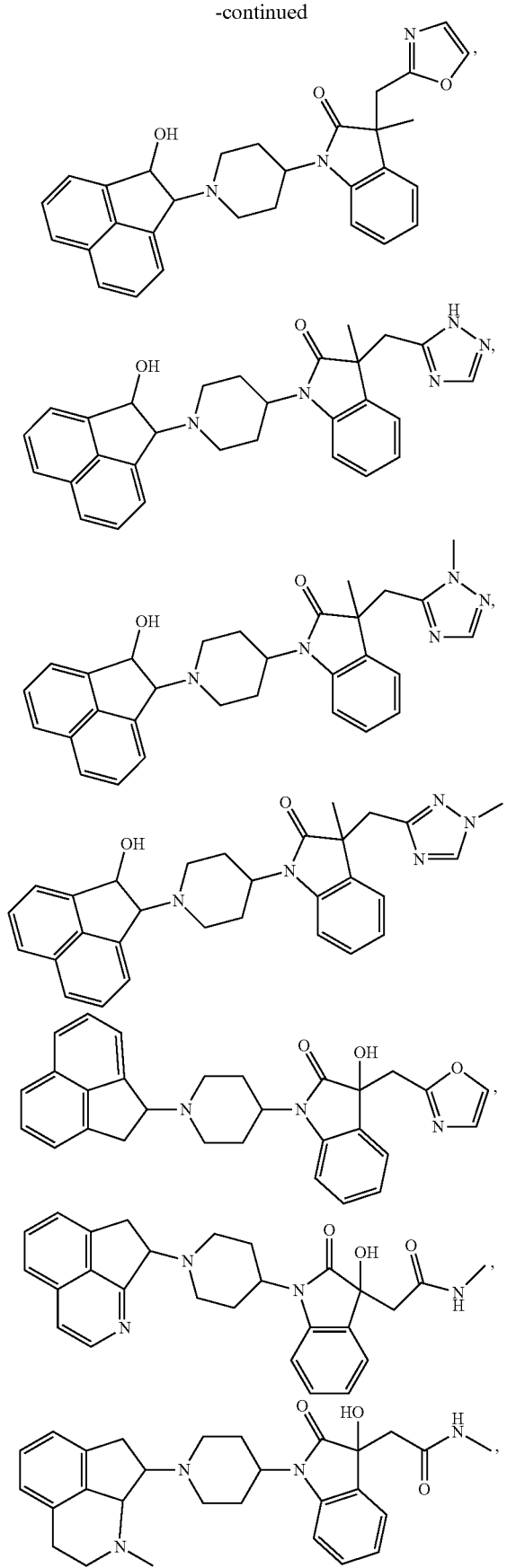
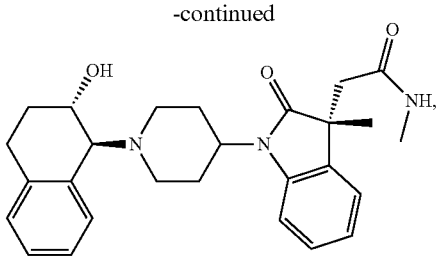
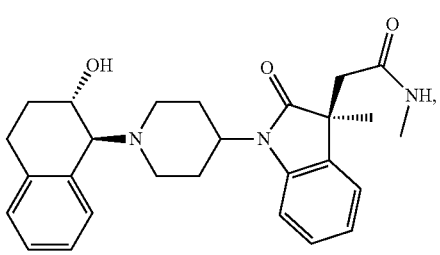
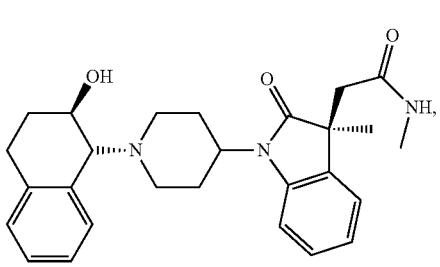
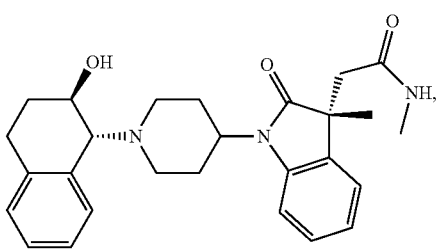
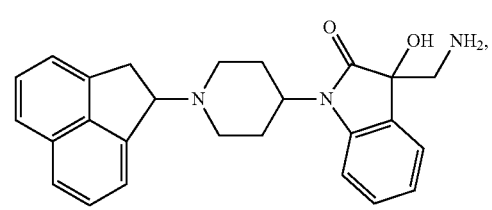
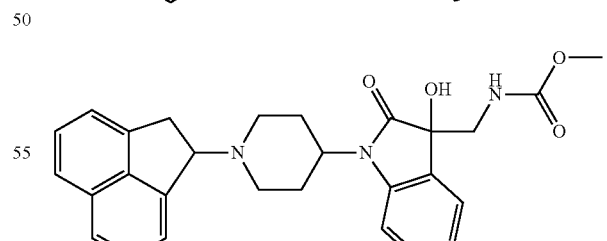
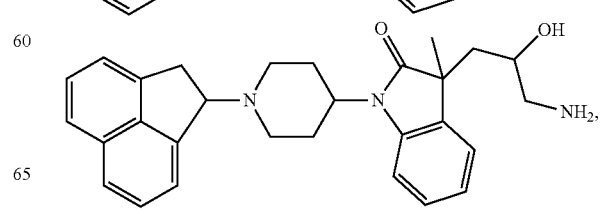

301
-continued
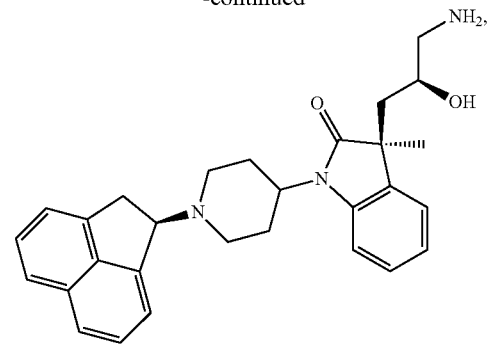
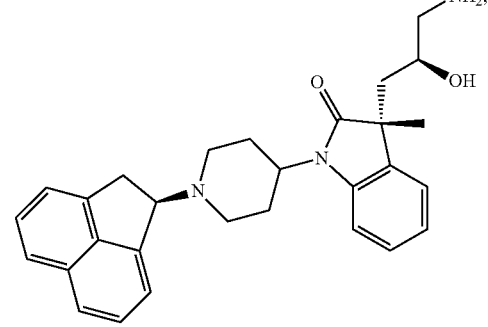
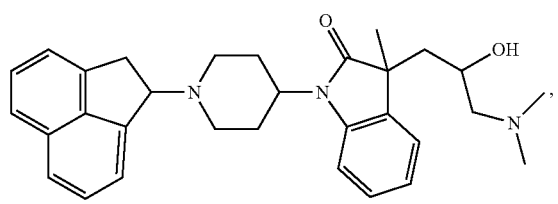
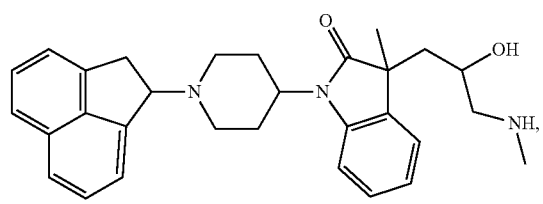
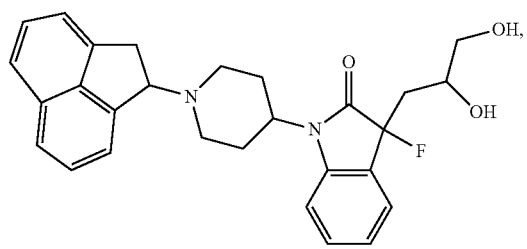
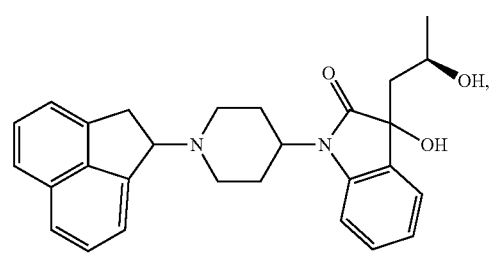
302
-continued
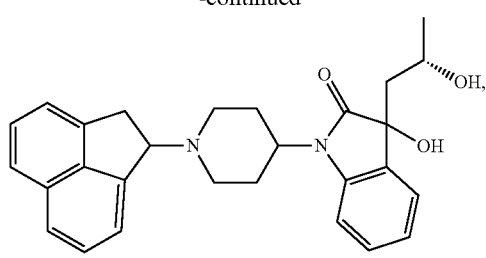
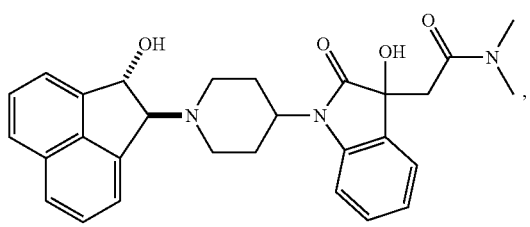
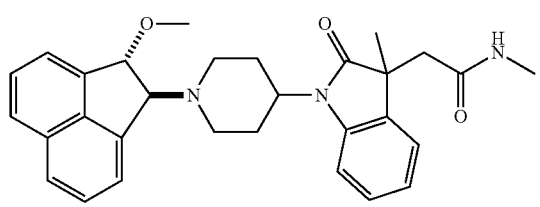
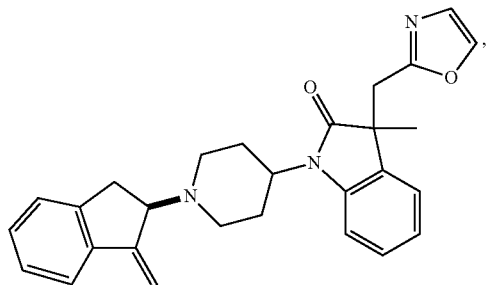
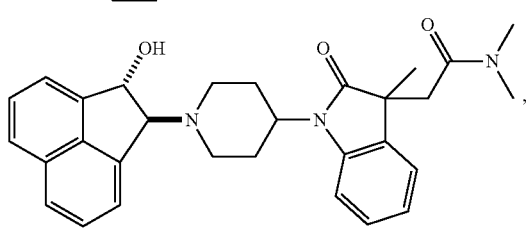
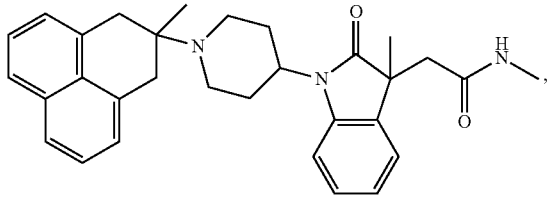
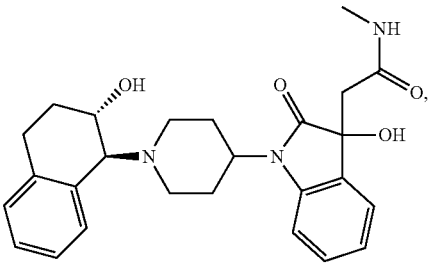

303
-continued
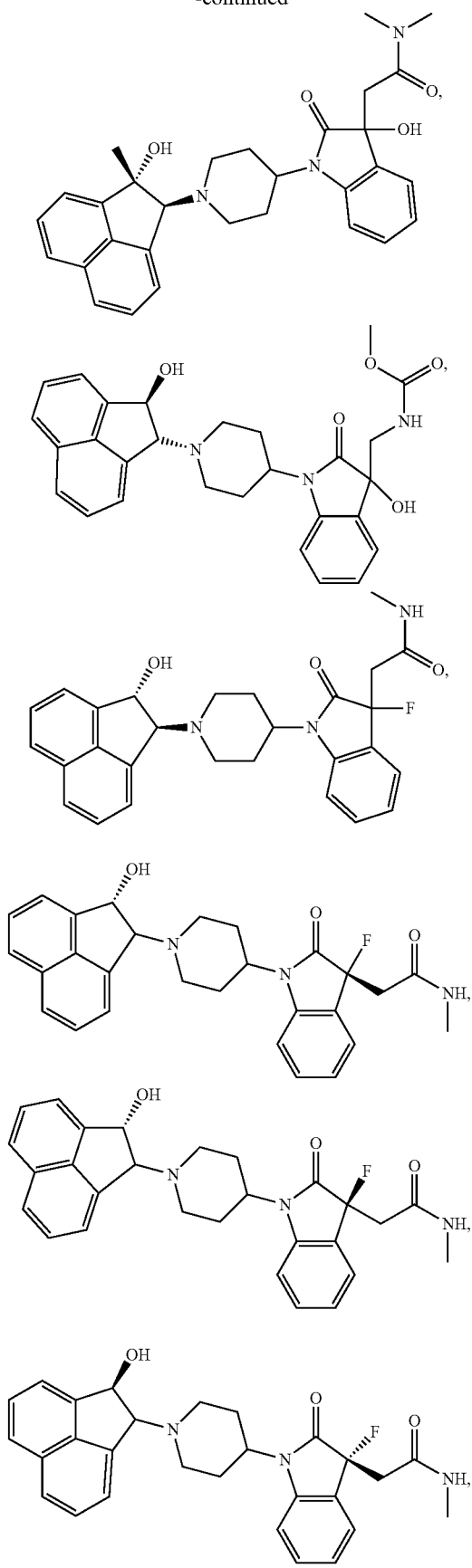
304
-continued
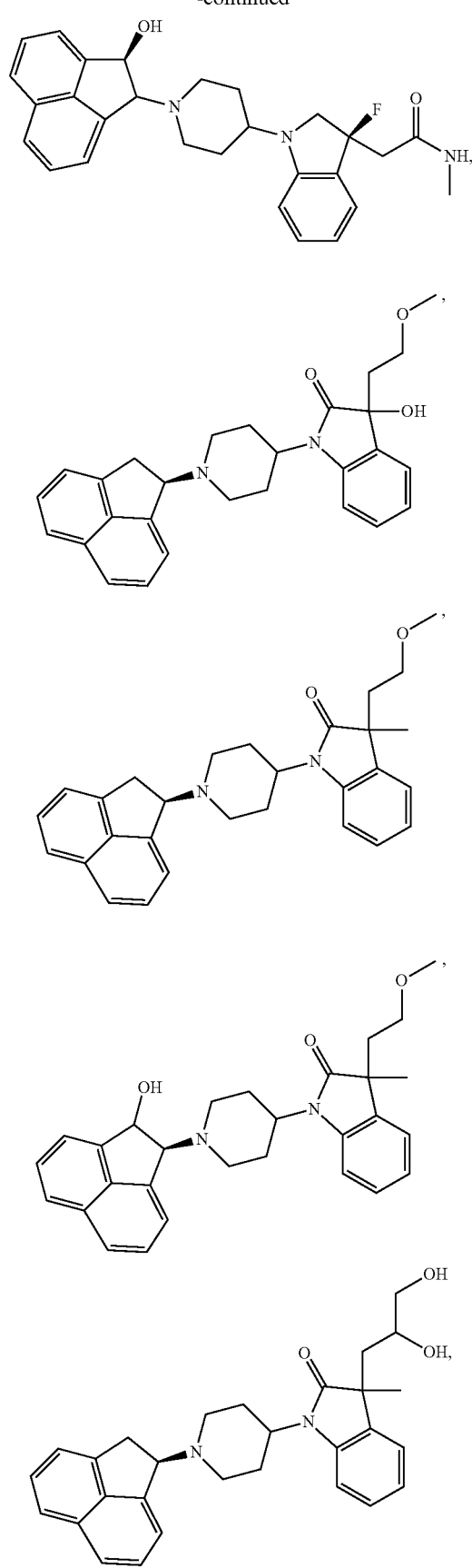

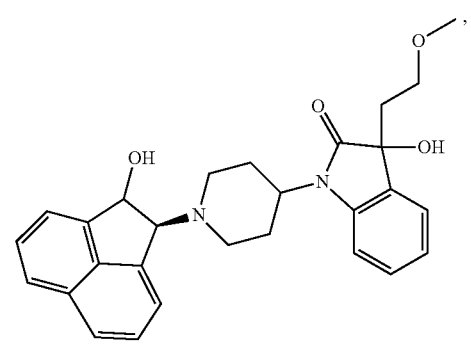
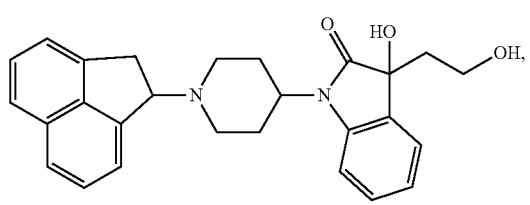
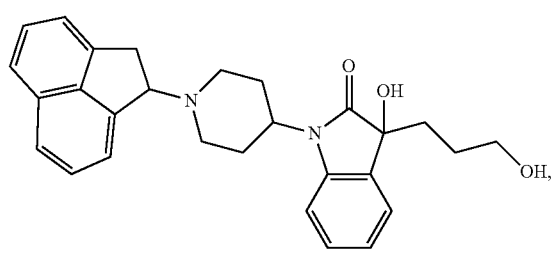
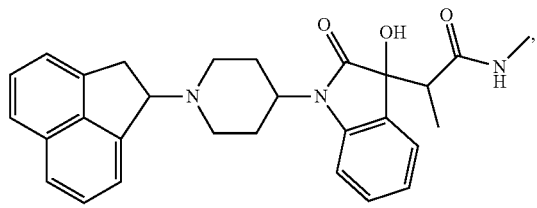
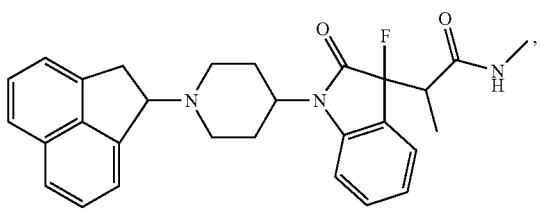
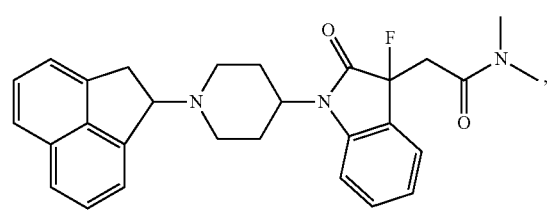
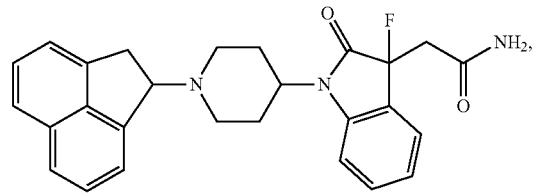
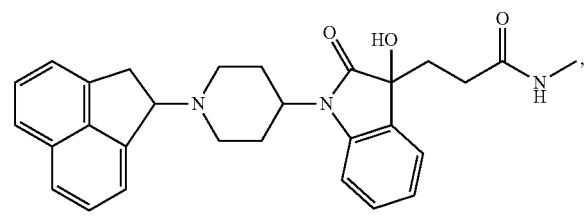
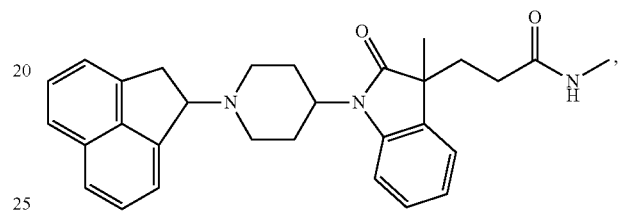
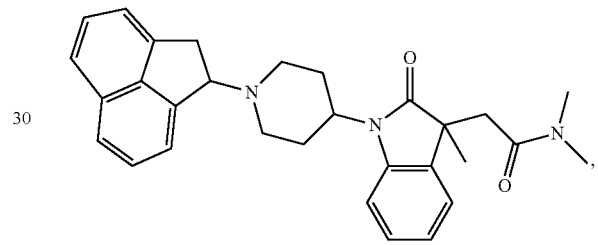
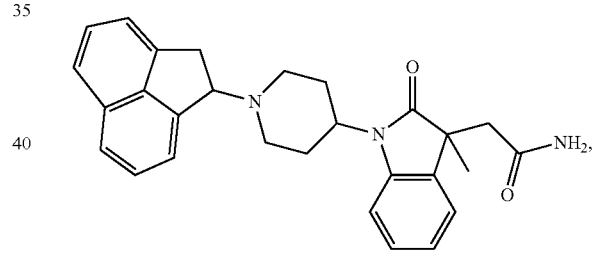
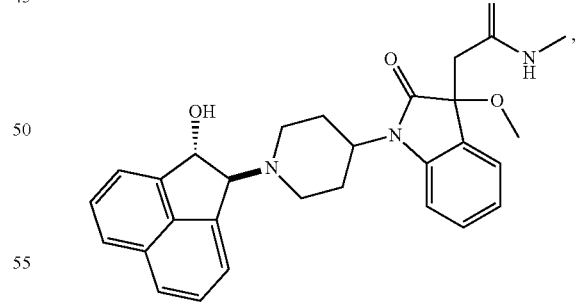
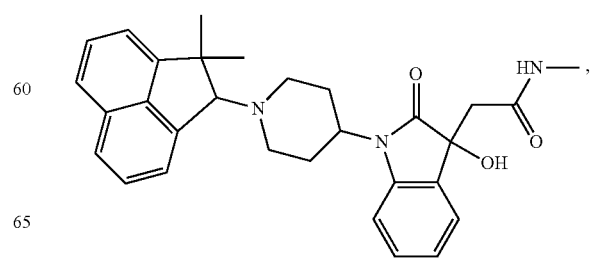

-continued

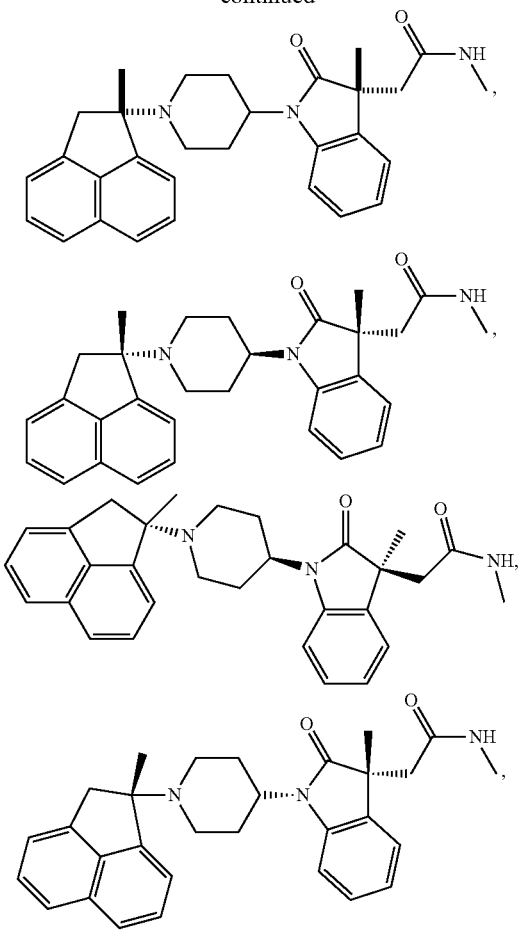

-continued

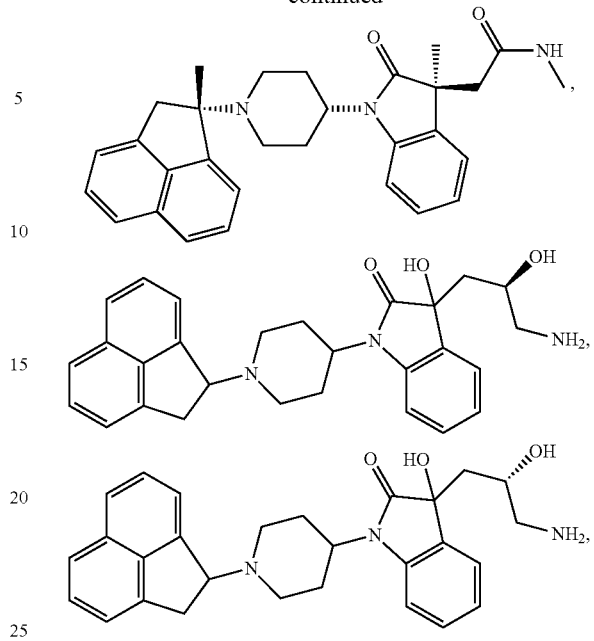

or a pharmaceutically acceptable salt thereof.

15. A pharmaceutical composition comprising a compound of claim 1, or a pharmaceutically acceptable salt thereof, and a pharmaceutically acceptable excipient or carrier.

16. A method of treating a neurological disorder selected from psychosis or schizophrenia, comprising administering to a subject a therapeutically or prophylactically effective amount of the compound of claim 1, or a pharmaceutically acceptable salt thereof.

* * * * *

UNITED STATES PATENT AND TRADEMARK OFFICE
CERTIFICATE OF CORRECTION

PATENT NO. : 9,884,844 B2
APPLICATION NO. : 14/758681
DATED : February 6, 2018
INVENTOR(S) : Fang et al.

Page 1 of 3

It is certified that error appears in the above-identified patent and that said Letters Patent is hereby corrected as shown below:

On the Title Page

In the Assignee (73):
Delete "Sunovion Pharmaceuticals, Inc." and insert -- Sunovion Pharmaceuticals Inc. --

In the Claims

Column 291, Line 52:

Claim 14, Delete " 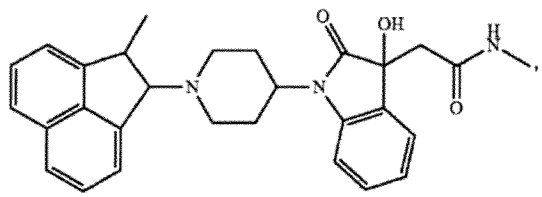 " and insert

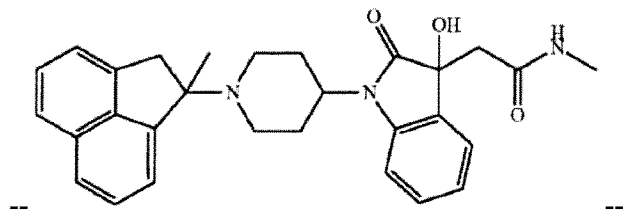

-- --

Signed and Sealed this
Thirteenth Day of November, 2018

Andrei Iancu
*Director of the United States Patent and Trademark Office*

CERTIFICATE OF CORRECTION (continued)
U.S. Pat. No. 9,884,844 B2

Column 294, Line 30:

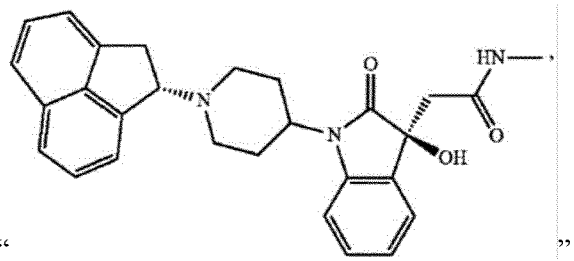

Claim 14, Delete " "

Column 296, Line 1:

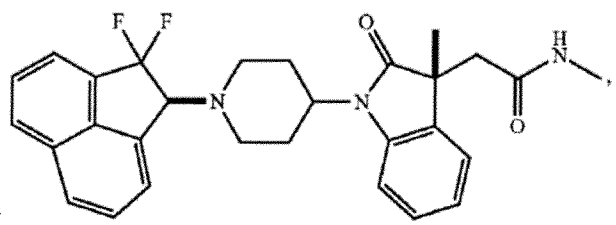

Claim 14, Delete " " and insert

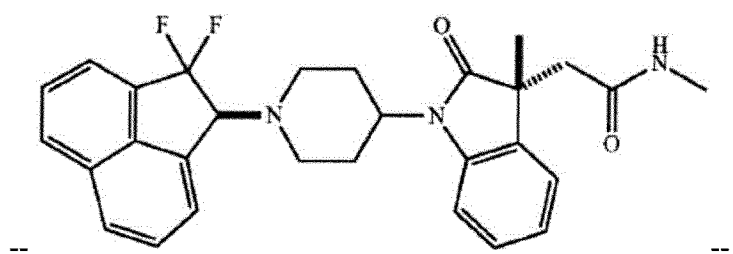

-- --

Column 298, Line 1:

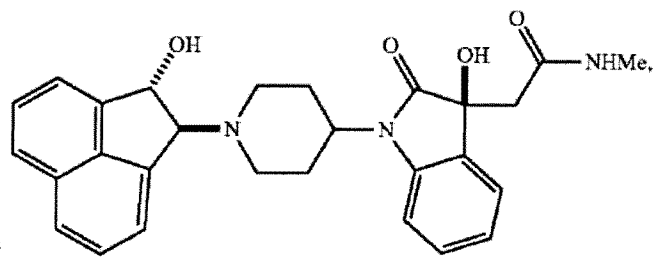

Claim 14, Delete " " and insert

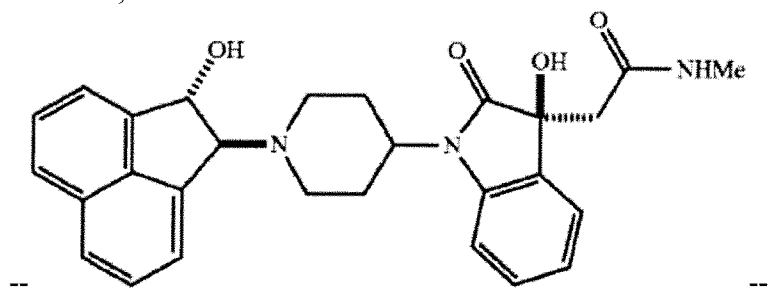

-- --

CERTIFICATE OF CORRECTION (continued)
U.S. Pat. No. 9,884,844 B2

Column 303, Line 40:

Claim 14, Delete " 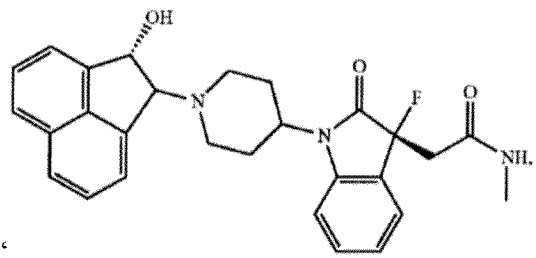 " and insert

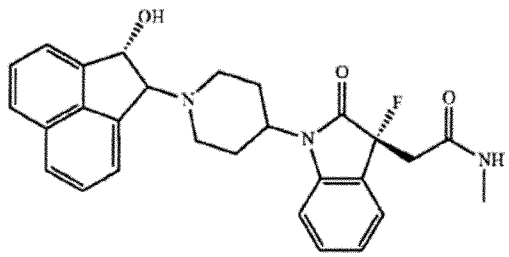

-- --

Column 304, Line 1:

Claim 14, Delete " 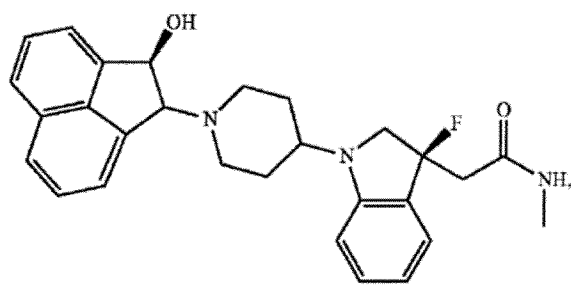 " and insert

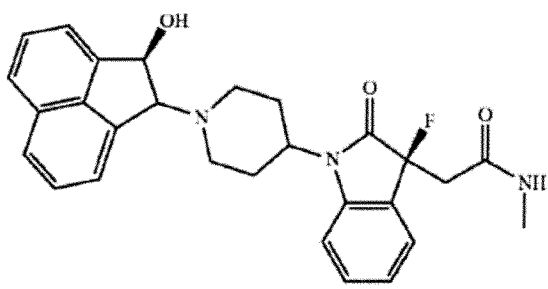

-- --

Column 306, Line 56:

Claim 14, after Line 55, insert -- 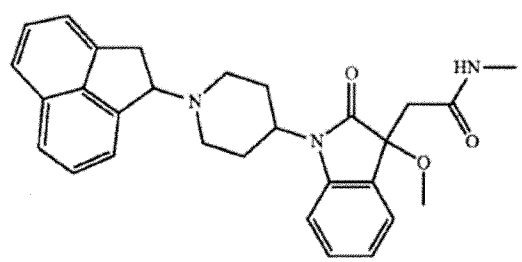 --